United States Patent
Wahhab et al.

(10) Patent No.: US 10,981,931 B2
(45) Date of Patent: Apr. 20, 2021

(54) LIBRARIES OF HETEROARYL-CONTAINING MACROCYCLIC COMPOUNDS AND METHODS OF MAKING AND USING THE SAME

(71) Applicant: CYCLENIUM PHARMA INC., Sherbrooke (CA)

(72) Inventors: Amal Wahhab, Laval (CA); Helmut Thomas, Sherbrooke (CA); Luc Richard, Laval (CA); Mark L. Peterson, Sherbrooke (CA); Dwight MacDonald, Pointe-Claire (CA); Daniel Dubé, Saint-Lazare (CA)

(73) Assignee: CYCLENIUM PHARMA INC., Sherbrooke (CA)

( * ) Notice: Subject to any disclaimer, the term of this patent is extended or adjusted under 35 U.S.C. 154(b) by 48 days.

(21) Appl. No.: 16/521,904

(22) Filed: Jul. 25, 2019

(65) Prior Publication Data
US 2020/0157116 A1    May 21, 2020

Related U.S. Application Data

(63) Continuation of application No. 15/761,371, filed as application No. PCT/CA2016/000232 on Sep. 14, 2016, now Pat. No. 10,407,442.

(60) Provisional application No. 62/222,995, filed on Sep. 24, 2015.

(51) Int. Cl.
| | |
|---|---|
| *C07D 498/00* | (2006.01) |
| *C07D 497/00* | (2006.01) |
| *C07D 497/02* | (2006.01) |
| *C07D 498/08* | (2006.01) |
| *C40B 40/04* | (2006.01) |
| *C07D 498/02* | (2006.01) |
| *G01N 33/50* | (2006.01) |
| *C40B 50/00* | (2006.01) |
| *C40B 30/04* | (2006.01) |
| *C40B 30/06* | (2006.01) |

(52) U.S. Cl.
CPC ......... *C07D 498/00* (2013.01); *C07D 497/00* (2013.01); *C07D 497/02* (2013.01); *C07D 498/02* (2013.01); *C07D 498/08* (2013.01); *C40B 40/04* (2013.01); *G01N 33/5008* (2013.01); *C40B 30/04* (2013.01); *C40B 30/06* (2013.01); *C40B 50/00* (2013.01)

(58) Field of Classification Search
CPC combination set(s) only.
See application file for complete search history.

(56) References Cited

U.S. PATENT DOCUMENTS

| | | |
|---|---|---|
| 10,407,442 B2 | 9/2019 | Wahhab et al. |
| 2006/0161007 A1 | 7/2006 | M. Martin et al. |

FOREIGN PATENT DOCUMENTS

| | | |
|---|---|---|
| CA | 2284459 | 4/2001 |
| WO | 2004078682 | 9/2004 |
| WO | 2005012331 | 2/2005 |
| WO | 2005012332 | 2/2005 |
| WO | 2007003525 | 1/2007 |
| WO | 2011146336 | 11/2011 |
| WO | 2012062777 | 5/2012 |
| WO | 2014182839 | 11/2014 |
| WO | 2015150557 | 10/2015 |
| WO | 2017021823 | 2/2017 |
| WO | 2017049383 | 3/2017 |
| WO | 2017062777 | 4/2017 |
| WO | 2017197488 | 11/2017 |

OTHER PUBLICATIONS

Amr et al., "Synthesis of Some New Chiral Tricyclic and Macrocyclic Pyridine Derivatives as Antimicrobial Agents", National Research Centre, Dokiki, Cairo Egypt, Z. Naturforsch. 58b, 861-868 (2003).
Mann et al., "New Oxazole-Based Peptidominetics: Useful Building Blocks for the Synthesis of Orthogonally Protected Macrocyclic Scaffolds", Organic Letters (Sep. 2, 2003), vol. 5, No. 24 pp. 4567-4570.
Qi et al., "Design and Synthesis of Polyoxazole-based Macrocycles Tethered with a Phosphonate Group", Chin. J. Chem. (Jun. 13, 2014), 32 pp. 585-591.
Marsault et al., "Efficient parallel synthesis of macrocyclic peptidomimetics", Bioorganic & Medicinal Chemistry Letter, vol. 18, Issue 16 (Aug. 15, 2008), pp. 4731-4735).
Di Francesco et al., "Novel Macrocyclic Inhibitors of Hepatitis C NS3/4A Protease Featuring a 2-Amino-1,3-thiazole as a P4 Carbamate Replacement", Journal of Medicinal Chemistry, vol. 52, No. 22, Nov. 26, 2009, pp. 7014-7028.
Bertram et al., "Synthesis of Libraries of Thiazole, Oxazole and Imidazole-Based Cyclic Peptides from Azole-Based Amino Acis. A New Synthetic Approach to Bistratamides and Didmolamides", Organic & Biomolecular Chemistry, vol. 5, No. 10, Jan. 1, 2007, p. 1541.
David et al., "Synthesis of sansalvamide a peptidomimetics: triazole, oxazole, thiazole, and pseudoproline containing compounds", Tetrahedron (2012) 1029-1051.

*Primary Examiner* — Jeremy C Flinders
(74) *Attorney, Agent, or Firm* — Bereskin & Parr LLP/S.E.N.C.R.L., s.r.l.

(57) ABSTRACT

The present disclosure relates to novel macrocyclic compounds and libraries thereof containing heteroaryl moieties that are useful as research tools for drug discovery efforts. The present disclosure also relates to methods of preparing these compounds and libraries and methods of using these libraries, such as in high throughput screening. In particular, these libraries are useful for evaluation of bioactivity at existing and newly identified pharmacologically relevant targets, including G protein-coupled receptors, nuclear receptors, enzymes, ion channels, transporters, transcription factors, protein-protein interactions and nucleic acid-protein interactions. As such, these libraries can be applied to the search for new pharmaceutical agents for the treatment and prevention of a range of medical conditions.

4 Claims, No Drawings

LIBRARIES OF HETEROARYL-CONTAINING MACROCYCLIC COMPOUNDS AND METHODS OF MAKING AND USING THE SAME

CROSS-REFERENCE TO RELATED APPLICATIONS

The present application is a continuation of U.S. patent application Ser. No. 15/761,371 filed on Mar. 19, 2018, that is a 35 USC 371 national stage entry of PCT/CA2016/000232 filed on Sep. 14, 2016 and which claims priority to U.S. provisional application No. 62/222,995 filed on Sep. 24, 2015. These documents are hereby incorporated herein by reference in their entirety.

FIELD OF THE DISCLOSURE

The present document relates to the field of medicinal chemistry. More particularly, it relates to novel macrocyclic compounds and libraries thereof containing heteroaryl moieties that are useful as research tools for drug discovery efforts. The present disclosure also relates to methods of preparing these compounds and libraries and methods of using these libraries, such as in high throughput screening. In particular, these libraries are useful for evaluation of bioactivity at existing and newly identified pharmacologically relevant targets, including G protein-coupled receptors, nuclear receptors, enzymes, ion channels, transporters, transcription factors, protein-protein interactions and nucleic acid-protein interactions. As such, these libraries can be applied to the search for new pharmaceutical agents for the treatment and prevention of a range of medical conditions.

BACKGROUND OF THE DISCLOSURE

From its start in the 1990's, high throughput screening (HTS) of chemical compound libraries has become an essential part of the drug discovery process with the successful generation of many lead molecules, clinical candidates and marketed pharmaceuticals (Curr. Opin. Chem. Biol. 2001, 5, 273-284; Curr. Opin. Chem. Biol. 2003, 7, 308-325; J. Biomol. Screen. 2006, 11, 864-869; Drug Disc. Today 2006, 11, 277-279; Nat. Rev. Drug Disc. 2011, 10, 188-195). Current collections of molecules for HTS, however, often are overpopulated by compounds related to known pharmaceutical agents, with a continuing need to expand chemical diversity and improve the content of screening collections (Curr. Opin. Chem. Biol. 2010, 14, 289-298; Drug Disc. Today 2013, 18, 298-304). Indeed, the diversity of molecular structures available in the library collections utilized for HTS has been identified as an area that needs to be dramatically improved (Curr. Opin. Chem. Biol. 2010, 14, 289-298; Biochem. Pharmacol. 2009, 78, 217-223; Curr. Med. Chem. 2009, 16, 4374-4381). Whereas the initial efforts at building screening libraries focused primarily on numbers of compounds, the focus has shifted to providing higher quality molecules (Fut. Med. Chem. 2014, 6, 497-502) that permit more complete sampling of "chemical space". Fortunately, given the estimated vastness of this space (J. Chem. Info. Model. 2007, 47, 342-353), significant opportunity exists for finding and exploring new or under-explored compound classes for desirable biological activity.

As an additional consideration, HTS has traditionally varied considerably in success rate depending on the type of target being interrogated, with certain target classes identified as being particularly challenging, for example protein-protein interactions (PPI). To address such intractable targets, a wider range of compounds and chemotypes will need to be explored. This situation has been exacerbated as advances in genomics and proteomics have led to the identification and characterization of large numbers of new potential pharmacological targets (Nat. Rev. Drug Disc. 2002, 1, 727-730; Drug Disc. Today 2005, 10, 1607-1610; Nat. Biotechnol. 2006, 24, 805-815), many of which fall into these difficult classes.

Recently, macrocycles have been identified as an under-explored class of biologically relevant synthetic molecules that possess properties amenable to these more difficult targets (Nat. Rev. Drug Disc. 2008, 7, 608-624; J. Med. Chem. 2011, 54, 1961-2004; Fut. Med. Chem. 2012, 4, 1409-1438; Molecules 2013, 18, 6230-6268; J. Med. Chem. 2014, 57, 278-295; Curr. Pharm. Design 2016, 22, 4086-4093). Although such structures are widespread in natural products, considerable challenges of synthetic accessibility have to date limited their presence in screening collections.

The interest in macrocycles originates in part from their ability to bridge the gap between traditional small molecules and biomolecules such as proteins, nucleotides and antibodies. They are considered to fill an intermediate chemical space between these two broad classes, but possessing favorable features of each: the high potency and exceptional selectivity of biomolecules with the ease of manufacturing and formulation, favorable drug-like properties and attractive cost-of-goods of small molecules. Hence, macrocycles provide a novel approach to addressing targets on which existing screening collections have not proven effective.

Indeed, macrocycles display dense functionality in a rather compact structural framework, but still occupy a sufficiently large topological surface area to enable interaction at the disparate binding sites often present in PPI and other difficult targets. In addition, macrocycles possess defined conformations, which can preorganize interacting functionality into appropriate regions of three-dimensional space, thereby permitting high selectivity and potency to be achieved even in early stage hits. Interestingly, spatial or shape diversity in the design of libraries has been identified as an important factor for broad biological activity (J. Chem. Info. Comput. Sci. 2003, 43, 987-1003).

Although cyclic peptide libraries of both synthetic and biosynthetic origin have been prepared and studied in some depth (J. Comput. Aided. Mol. Des. 2002, 16, 415-430; Curr. Opin. Struct. Biol. 2013, 23, 571-580), libraries of macrocyclic non-peptidic or semi-peptidic structures remain more problematic to construct and their bioactivity only perfunctorily investigated (J. Med. Chem. 2011, 54, 1961-2004; Macrocycles in Drug Discovery, J. Levin, ed., RSC Publishing, 2015, pp 398-486, ISBN 978-1-84973-701-2).

Thiazoles, oxazoles and, to a lesser extent, imidazoles have been found to be common structural features of natural products, particularly those of marine origin (Marine Drugs. 2010, 8, 2755-2780; Nat. Prod. Rep. 2011, 28, 1143-1191; Nat. Prod. Rep. 2013, 30, 869-915). In fact, many such products contain multiple azole rings. In addition, compounds containing the thiazole ring have been found to have significant pharmacological and therapeutic impact (Curr. Top. Med. Chem. 2016, 16, 284-2862). Further, the imidazole ring, partly from its presence in the natural amino acid histidine, plays a vital role in many biological interactions due to its unique combination of basic and aromatic character (Curr. Med. Chem. 2006, 13, 1-23; Med. Chem. Res. 2011, 20, 1119-1140).

However, the incorporation of these heteroaromatic components into the ring backbone of synthetic macrocycles and libraries, as well as assessment of bioactivity for the resulting molecules, have not been widely explored (Org. Lett. 2003, 5, 4567-4570; J. Med. Chem. 2009, 52, 7014-7028; J. Org. Chem. 2010, 75, 7939-7941; Intl. Pat. Appl. Publ. WO 2012/062777; Tetrahedron 2012, 68, 1029-1051; Chem. Biodivers. 2012, 9, 2473-2484; J. Org. Chem. 2012, 77, 11079-11090; Chem. Rec. 2013, 13, 539-548; Proc. Natl. Acad. Sci. USA 2013, 110, E3753-E3760; ACS Comb. Sci. 2014, 16, 71-77).

Hence, the macrocyclic compounds and libraries of the disclosure, which include these heteroaryl moieties, provide distinct structural scaffolds from those previously known. In that manner, they satisfy a significant need in the art for novel compounds and libraries that are useful in the search for new therapeutic agents for the prevention or treatment of a wide variety of disease states.

SUMMARY OF THE DISCLOSURE

According to one aspect, there are provided libraries of two or more macrocyclic compounds of formulas (Ia), (Ib), (Ic), (Id) and (Ie) and their salts as defined in the present disclosure.

According to another aspect, there are provided libraries comprising from two (2) to over ten thousand (10,000) macrocyclic compounds.

According to other aspects, there are provided libraries comprising discrete macrocyclic compounds and libraries comprising mixtures of macrocyclic compounds.

According to an additional aspect, it was found that such libraries can be useful for the identification of macrocyclic compounds that modulate a biological target.

According to still other aspects, there are provided libraries dissolved in a solvent and libraries distributed in one or more multiple sample holders.

According to yet another aspect, there are provided kits comprising the libraries as defined in the present disclosure and one or more multiple sample holders.

According to a further aspect, there are provided macrocyclic compounds and their pharmaceutically acceptable salts as defined in the present disclosure.

According to one more aspect, there is provided a process for preparing macrocyclic compounds and libraries thereof as defined in the present disclosure.

It was found that such libraries of macrocyclic compounds are useful as research tools in drug discovery efforts for new therapeutic agents to treat or prevent a range of diseases.

BRIEF DESCRIPTION OF THE SCHEMES

Further features and advantages of the disclosure will become more readily apparent from the following description of specific embodiments as illustrated by way of examples in the schemes found in the last few pages of the description wherein:

Scheme 1 shows a general synthetic scheme for the synthesis of macrocyclic compounds for the libraries of the present disclosure.

Scheme 2 shows a synthetic scheme for a representative library of macrocyclic compounds of formula (Ib) of the present disclosure.

Scheme 3 shows a synthetic scheme for a representative library of macrocyclic compounds of formula (Ic) of the present disclosure.

Scheme 4 shows a synthetic scheme for a representative library of macrocyclic compounds of formula (Ia) of the present disclosure.

Scheme 5 shows a synthetic scheme for a representative library of macrocyclic compounds of formula (Ie) of the present disclosure.

Scheme 6 shows a synthetic scheme for another representative library of macrocyclic compounds of formula (Ie) of the present disclosure.

Scheme 7 shows a synthetic scheme for a third representative library of macrocyclic compounds of formula (Ie) of the present disclosure.

Scheme 8 shows a synthetic scheme for a representative library of macrocyclic compounds of formula (Id) of the present disclosure.

DETAILED DESCRIPTION OF THE DISCLOSURE

The inventors have discovered new macrocyclic compounds, specifically incorporating heteroaryl components in the ring skeleton, and libraries thereof that are useful as research tools for the discovery of new pharmaceutical agents for a range of diseases. In particular, they include oxazole, thiazole and imidazole rings. Processes for preparing these compounds and libraries have also been developed and comprise part of this disclosure.

Therefore, in a first aspect, the disclosure relates to libraries comprising at least two macrocyclic compounds selected from the group consisting of compounds of formula (Ia), formula (Ib), formula (Ic), formula (Id), formula (Ie) and salts thereof:

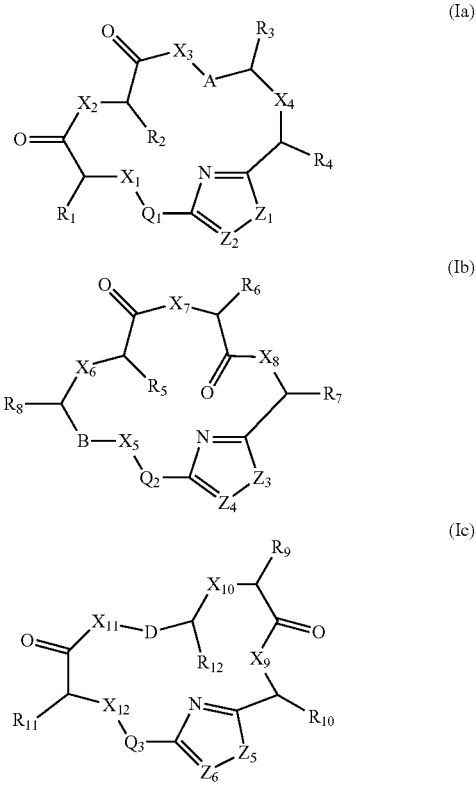

-continued

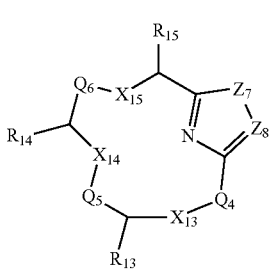
(Id)

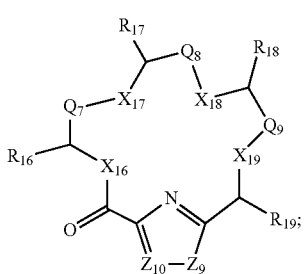
(Ie)

wherein:
$Q_1$, $Q_2$, $Q_3$, $Q_4$, $Q_5$, $Q_6$, $Q_7$, $Q_8$ and $Q_8$ are independently selected from the group consisting of $CH_2$ or $C=O$, wherein in formula (Id) at least one of $Q_4$, $Q_5$ and $Q_6$ is $CH_2$ and wherein in formula (Ie) at least one of $Q_7$, $Q_8$ and $Q_9$ is $CH_2$;

$X_1$, $X_5$, $X_{12}$, $X_{13}$, $X_{14}$, $X_{15}$, $X_{17}$, $X_{18}$ and $X_{19}$ are, when $Q_1$, $Q_2$, $Q_3$, $Q_4$, $Q_5$, $Q_6$, $Q_7$, $Q_8$ and $Q_9$, respectively, are $C=O$, independently selected from the group consisting of O and $NR_{20a}$, where $R_{20a}$ is selected from the group consisting of hydrogen, $C_1$-$C_{20}$ alkyl, $C_3$-$C_{15}$ cycloalkyl, $C_2$-$C_{14}$ heterocycle, $C_6$-$C_{15}$ aryl, $C_4$-$C_{14}$ heteroaryl, sulfonyl and $C_1$-$C_6$ alkyl substituted with hydroxy, alkoxy, amino, mercapto, carboxy, carboxyalkyl, carboxyaryl, amido, amidino, guanidino, $C_3$-$C_{15}$ cycloalkyl, $C_2$-$C_{14}$ heterocycle, $C_6$-$C_{15}$ aryl or $C_4$-$C_{14}$ heteroaryl;

when $X_1$, $X_{12}$, $X_{13}$, $X_{14}$, $X_{15}$, $X_{17}$, $X_{18}$ or $X_{19}$ are $NR_{20a}$, $X_1$, $X_{12}$, $X_{13}$, $X_{14}$, $X_{15}$, $X_{17}$, $X_{18}$ and $X_{19}$ can also form an optionally substituted four, five, six or seven-membered ring together with, respectively, $R_1$, $R_{11}$, $R_{13}$, $R_{14}$, $R_{15}$, $R_{17}$, $R_{18}$ and $R_{19}$;

when $Q_1$, $Q_2$, $Q_3$, $Q_4$, $Q_5$, $Q_6$, $Q_7$, $Q_8$ and $Q_9$, are $CH_2$, $X_1$, $X_5$, $X_{12}$, $X_{13}$, $X_{14}$, $X_{15}$, $X_{17}$, $X_{18}$ and $X_{19}$, respectively, can also be independently selected from the group consisting of $S(O)_{q1}$ and $NR_{20b}$, where q1 is 0-2; and $R_{20b}$ is selected from the group consisting of formyl, acyl, amino acyl, amido, amidino, carboxyalkyl, carboxyaryl and sulfonamido, and that $X_5$ can also be N and form, together with B, an optionally substituted four, five, six or seven-membered ring;

$X_2$, $X_3$, $X_7$, $X_8$, $X_9$, $X_{11}$ and $X_{16}$ are independently selected from the group consisting of O and $NR_{21}$, where $R_{21}$ is selected from the group consisting of hydrogen, $C_1$-$C_{20}$ alkyl, $C_3$-$C_{15}$ cycloalkyl, $C_2$-$C_{14}$ heterocycle, $C_6$-$C_{15}$ aryl, $C_4$-$C_{14}$ heteroaryl, sulfonyl and $C_1$-$C_6$ alkyl substituted with hydroxy, alkoxy, amino, mercapto, carboxy, carboxyalkyl, carboxyaryl, amido, amidino, guanidino, $C_3$-$C_{15}$ cycloalkyl, $C_2$-$C_{14}$ heterocycle, $C_6$-$C_{15}$ aryl or $C_4$-$C_{14}$ heteroaryl, when $X_2$, $X_7$, $X_8$, $X_9$ or $X_{16}$ are $NR_{21}$, $X_2$, $X_7$, $X_8$, $X_9$ and $X_{16}$ can also form an optionally substituted four, five, six or seven-membered ring together with, respectively, $R_2$, $R_6$, $R_7$, $R_{10}$ and $R_{16}$, and wherein $X_3$ and $X_8$ can also independently be N and form, together with A and D, respectively, an optionally substituted four, five, six or seven-membered ring;

$X_4$, $X_6$ and $X_{10}$ are independently selected from the group consisting of O, $S(O)_{q2}$ and $NR_{22}$, where q2 is 0-2 and $R_{22}$ is selected from the group consisting of hydrogen, $C_1$-$C_{20}$ alkyl, $C_3$-$C_{15}$ cycloalkyl, $C_2$-$C_{14}$ heterocycle, $C_6$-$C_{15}$ aryl, $C_4$-$C_{14}$ heteroaryl, formyl, acyl, amino acyl, carboxyalkyl, carboxyaryl, amido, amidino, sulfonyl, sulfonamido and $C_1$-$C_6$ alkyl substituted with hydroxy, alkoxy, amino, mercapto, carboxy, carboxyalkyl, carboxyaryl, amido, amidino, guanidino, $C_3$-$C_{15}$ cycloalkyl, $C_2$-$C_{14}$ heterocycle, $C_6$-$C_{15}$ aryl or $C_4$-$C_{14}$ heteroaryl, when $X_4$ or $X_6$ are $NR_{22}$, $X_4$ and $X_6$ can also form an optionally substituted four, five, six or seven-membered ring together with, respectively, $R_4$ and $R_5$;

$Z_1$, $Z_3$, $Z_5$, $Z_7$ and $Z_9$ are independently selected from the group consisting of O, S and $NR_{23}$ where $R_{23}$ is selected from the group consisting of hydrogen, $C_1$-$C_{20}$ alkyl, $C_3$-$C_{15}$ cycloalkyl, $C_2$-$C_{14}$ heterocycle, $C_6$-$C_{15}$ aryl, $C_4$-$C_{14}$ heteroaryl, formyl, acyl, amino acyl, carboxyalkyl, carboxyaryl, amido, amidino, sulfonyl, sulfonamido and $C_1$-$C_8$ alkyl substituted with $C_3$-$C_{15}$ cycloalkyl, $C_6$-$C_{15}$ aryl, or $C_4$-$C_{14}$ heteroaryl;

$Z_2$, $Z_4$, $Z_6$, $Z_8$ and $Z_{10}$ are independently selected from the group consisting of N, $N^+$—$O^-$ and $CR_{24}$ where $R_{24}$ is selected from the group consisting of hydrogen, halogen, amino, nitro, carboxy, carboxyalkyl, carboxyaryl, trifluoromethyl, $C_1$-$C_{20}$ alkyl, $C_3$-$C_{15}$ cycloalkyl, $C_2$-$C_{14}$ heterocycle, $C_6$-$C_{15}$ aryl, $C_4$-$C_{14}$ heteroaryl;

$R_1$, $R_2$, $R_4$, $R_5$, $R_6$, $R_7$, $R_9$, $R_{10}$, $R_{11}$, $R_{13}$, $R_{14}$, $R_{15}$, $R_{16}$, $R_{17}$, $R_{18}$ and $R_{19}$ are independently selected from the group consisting of:

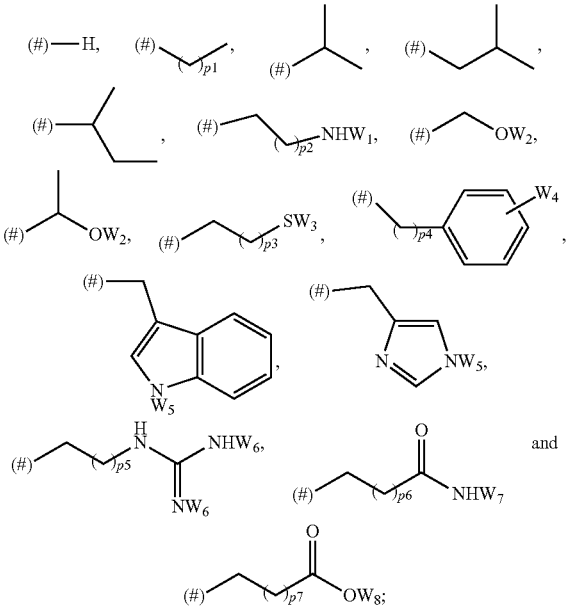

where (#) indicates the site of bonding of the group to the remainder of the structure; p1, p2, p3, p4 and p5 are independently 0-5; p6 and p7 are independently 0-6;

$W_1$ is selected from the group consisting of hydrogen, $C_1$-$C_{20}$ alkyl, $C_3$-$C_{15}$ cycloalkyl, $C_2$-$C_{14}$ heterocycle, $C_6$-$C_{15}$ aryl, $C_4$-$C_{14}$ heteroaryl, formyl, acyl, amino acyl, amido, carboxyalkyl, carboxyaryl, amidino, sulfonyl, sulfonamido and $C_1$-$C_8$ alkyl substituted with $C_3$-$C_{15}$ cycloalkyl, $C_6$-$C_{15}$ aryl or $C_4$-$C_{14}$ heteroaryl;

$W_2$ is selected from the group consisting of hydrogen, $C_1$-$C_{20}$ alkyl, $C_3$-$C_{15}$ cycloalkyl, $C_2$-$C_{14}$ heterocycle, $C_6$-$C_{15}$ aryl, $C_4$-$C_{14}$ heteroaryl, acyl, amino acyl and $C_1$-$C_8$ alkyl substituted with $C_3$-$C_{15}$ cycloalkyl, $C_6$-$C_{15}$ aryl or $C_4$-$C_{14}$ heteroaryl;

$W_3$ and $W_8$ are independently selected from the group consisting of hydrogen, $C_1$-$C_{20}$ alkyl, $C_3$-$C_{15}$ cycloalkyl, $C_2$-$C_{14}$ heterocycle, $C_6$-$C_{15}$ aryl, $C_4$-$C_{14}$ heteroaryl and $C_1$-$C_8$ alkyl substituted with $C_3$-$C_{15}$ cycloalkyl, $C_6$-$C_{15}$ aryl or $C_4$-$C_{14}$ heteroaryl;

$W_4$ is selected from the group consisting of hydrogen, halogen, trifluoromethyl, hydroxy and methyl;

$W_5$ is selected from the group consisting of hydrogen, $C_1$-$C_{20}$ alkyl, $C_3$-$C_{15}$ cycloalkyl, $C_2$-$C_{14}$ heterocycle, $C_6$-$C_{15}$ aryl, $C_4$-$C_{14}$ heteroaryl, formyl, acyl, carboxyalkyl, carboxyaryl, amido, amidino, sulfonyl, sulfonamido and $C_1$-$C_8$ alkyl substituted with $C_3$-$C_{15}$ cycloalkyl, $C_6$-$C_{15}$ aryl or $C_4$-$C_{14}$ heteroaryl;

$W_6$ is selected from the group consisting of hydrogen, $C_1$-$C_{20}$ alkyl, $C_3$-$C_{15}$ cycloalkyl, $C_2$-$C_{14}$ heterocycle, $C_6$-$C_{15}$ aryl, $C_4$-$C_{14}$ heteroaryl, acyl, carboxyalkyl, carboxyaryl, amido and sulfonyl; and $W_7$ is selected from the group consisting of hydrogen, $C_1$-$C_{20}$ alkyl, $C_3$-$C_{15}$ cycloalkyl, $C_2$-$C_{14}$ heterocycle, $C_6$-$C_{15}$ aryl, $C_4$-$C_{14}$ heteroaryl, sulfonyl and $C_1$-$C_8$ alkyl substituted with $C_3$-$C_{15}$ cycloalkyl, $C_6$-$C_{15}$ aryl or $C_4$-$C_{14}$ heteroaryl;

wherein $R_1$, $R_{11}$, $R_{13}$, $R_{14}$, $R_{15}$, $R_{17}$, $R_{18}$ and $R_{19}$, when $X_1$, $X_{12}$, $X_{13}$, $X_{14}$, $X_{15}$, $X_{17}$, $X_{18}$ or $X_{19}$ are $NR_{20a}$, can also form an optionally substituted four, five, six or seven-membered ring together with $NR_{20a}$, wherein $R_2$, $R_6$, $R_7$, $R_{10}$ and $R_{16}$, when $X_2$, $X_7$, $X_8$, $X_9$ or $X_{16}$, respectively, are $NR_{21}$, can also form an optionally substituted four, five, six or seven-membered ring together with $NR_{21}$, wherein $R_4$ and $R_5$, when $X_4$ or $X_6$, respectively, are $NR_{22}$, can also form an optionally substituted four, five, six or seven-membered ring together with $NR_{22}$;

$R_3$, $R_8$ and $R_{12}$ are independently selected from the group consisting of hydrogen, $C_1$-$C_6$ alkyl and $C_6$-$C_{15}$ aryl; and A, B and D are independently selected from the group consisting of:

$(X)-(CH_2)_{n1a}-(C)$, $(X)-(CH_2)_{n1b}-X_{20}-(CH_2)_{n1c}-(C)$,

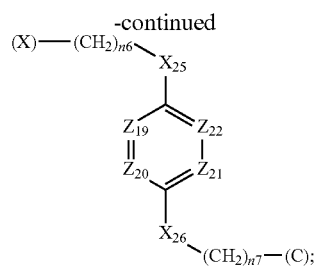

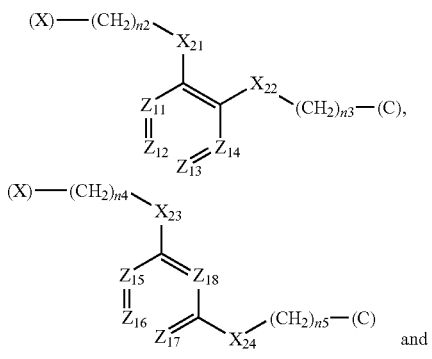

-continued

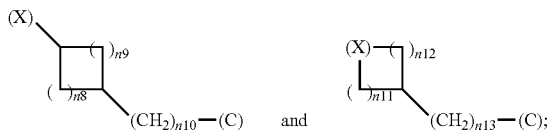

when $X_3$, $X_5$, or $X_8$ is N, A, B and D, respectively, can also be independently selected from the group consisting of:

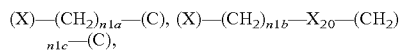

wherein n1a is 0-5; n1b and n1c are independently 1-3; n2, n3, n4, n5, n6, n7, n10 and n13 are independently 0-4; n8, n9, n11 and n12 are independently 0-4, wherein the sum of n8 and n9 is at least 2 and the sum of n11 and n12 is at least 2;

$X_{20}$ is selected from O, $NR_{26}$, CH=CH and C≡C, where $R_{26}$ is selected from the group consisting of hydrogen, $C_1$-$C_4$ alkyl, acyl and sulfonyl;

$X_{21}$, $X_{22}$, $X_{23}$, $X_{24}$, $X_{25}$ and $X_{26}$ are independently selected from the group consisting of $(CH_2)_{m1}$, O, $S(O)_{q3}$ and $NR_{27}$, where m1 is 0-4, q3 is 0-2 and $R_{27}$ is selected from the group consisting of hydrogen, $C_1$-$C_4$ alkyl, acyl and sulfonyl;

$Z_{11}$, $Z_{12}$, $Z_{13}$, $Z_{14}$, $Z_{15}$, $Z_{16}$, $Z_{17}$, $Z_{18}$, $Z_{19}$, $Z_{20}$, $Z_{21}$ and $Z_{22}$ are independently selected from the group consisting of N, $N^+$—$O^-$ and $CR_{28}$, where $R_{28}$ is selected from hydrogen, hydroxy, alkoxy, amino, amido, amidino, guanidino, halogen, cyano, nitro, carboxy, carboxyalkyl, carboxyaryl, trifluoromethyl, $C_1$-$C_{20}$ alkyl, $C_3$-$C_{15}$ cycloalkyl, $C_2$-$C_{14}$ heterocycle, $C_6$-$C_{15}$ aryl, $C_4$-$C_{14}$ heteroaryl, wherein in the group of $Z_{11}$, $Z_{12}$, $Z_{13}$ and $Z_{14}$, three or less within that group are N; wherein in the group of $Z_{15}$, $Z_{16}$, $Z_{17}$ and $Z_{18}$, three or less within that group are N; and wherein in the group of $Z_{19}$, $Z_{20}$, $Z_{21}$ and $Z_{22}$, three or less within that group are N; and (X) indicates the site or sites of bonding to $X_3$ of formula (Ia) for A, to $X_5$ of formula (Ib) for B, and to $X_{11}$ of formula (Ic) for D, and (C) indicates the site of bonding to $CHR_3$ of formula (Ia) for A, to $CHR_8$ of formula (Ib) for B and to $CHR_{12}$ of formula (Ic) for D.

In one embodiment, the libraries of the present disclosure may be comprised of at least two macrocyclic compounds selected from only one of formula (Ia), formula (Ib), formula (Ic), formula (Id) and formula (Ie), from two of said formulas, from three of said formulas, from four of said formula or from all five of said formulas.

In further embodiments, the libraries of the present disclosure may comprise as few as two (2) to more than ten thousand (10,000) such macrocyclic compounds.

In another embodiment, A in formula (Ia), B in formula (Ib) and D in formula (Ic) are independently selected from the group consisting of:

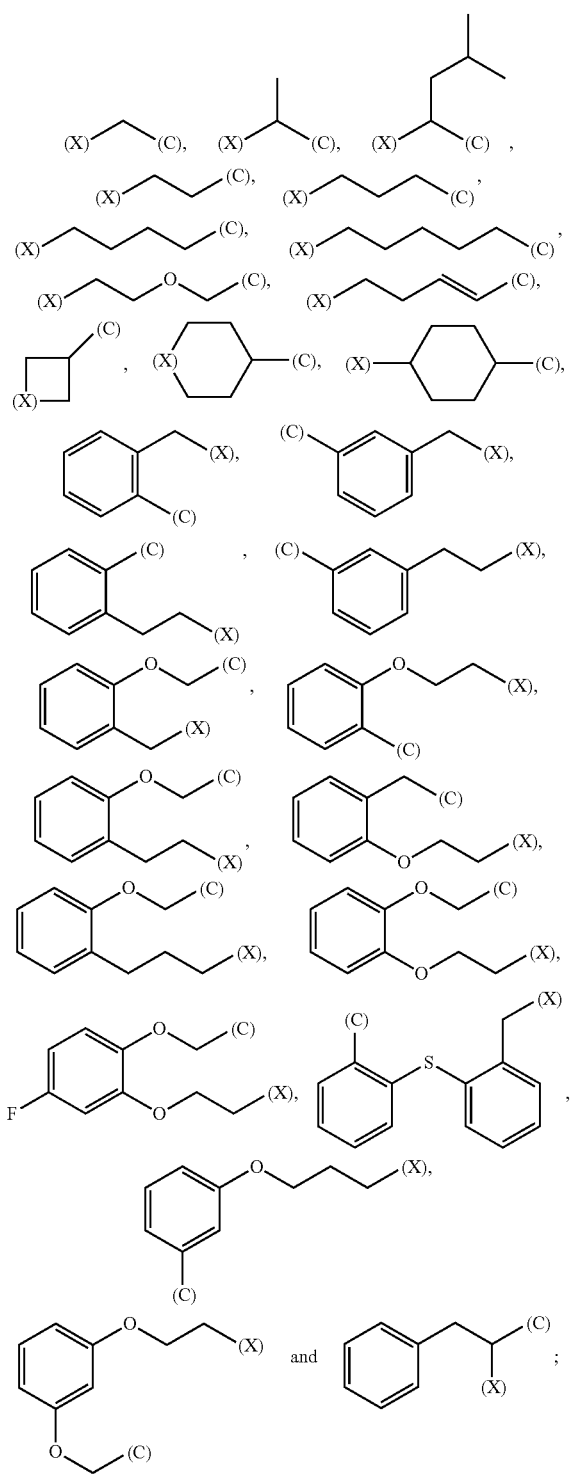

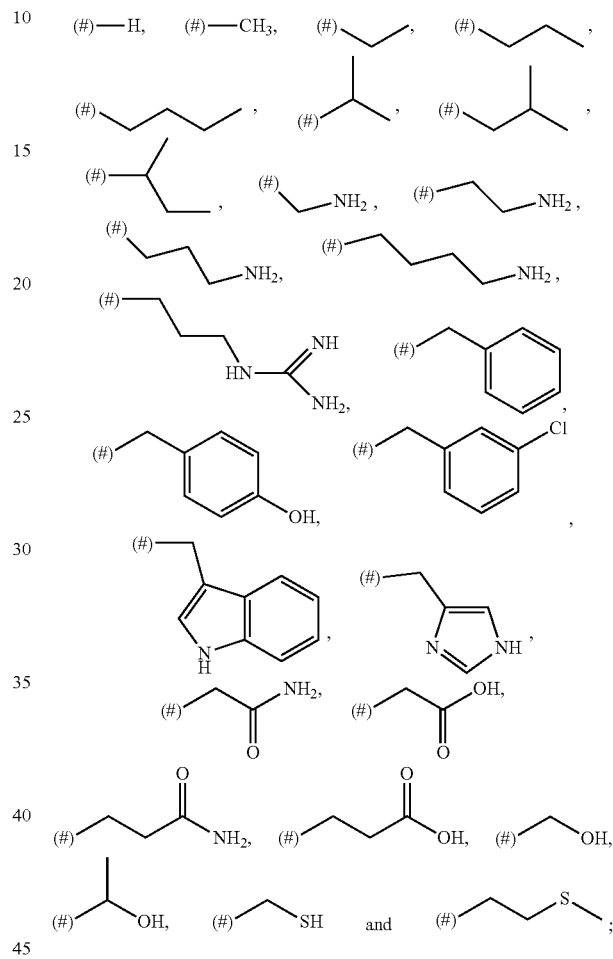

where (X) indicates the site of bonding to $X_3$ of formula (Ia) for A, to $X_5$ of formula (Ib) for B, and to $X_{11}$ of formula (Ic) for D, and (C) indicates the site of bonding to $CHR_3$ of formula (Ia) for A, to $CHR_8$ of formula (Ib) for B and to $CHR_{12}$ of formula (Ic) for D.

In an additional embodiment, $Z_1$, $Z_3$, $Z_5$, $Z_7$ and $Z_9$ are independently selected from the group consisting of O and S; and $Z_2$, $Z_4$, 4, $Z_8$ and $Z_{10}$ are CH.

In other embodiments, $Z_{11}$, $Z_{12}$, $Z_{13}$, $Z_{14}$, $Z_{15}$, $Z_{16}$, $Z_{17}$, $Z_{18}$, $Z_{19}$, $Z_{20}$, $Z_{21}$ and $Z_{22}$ are independently $CR_{27}$ and $R_{27}$ is selected from the group consisting of hydrogen or halogen.

In still a further embodiment, $R_1$, $R_2$, $R_4$, $R_5$, $R_6$, $R_7$, $R_9$, $R_{10}$, $R_{11}$, $R_{13}$, $R_{14}$, $R_{15}$, $R_{16}$, $R_{17}$, $R_{18}$ and $R_{19}$ are independently selected from the group consisting of:

where (#) indicates the site of bonding of the group to the remainder of the structure.

In yet another embodiment, $R_3$, $R_8$ and $R_{12}$ are independently selected from the group consisting of hydrogen, methyl or phenyl.

In more embodiments, $X_1$, $X_2$, $X_3$, $X_4$, $X_5$, $X_6$, $X_7$, $X_8$, $X_9$, $X_{10}$, $X_{11}$, $X_{12}$, $X_{13}$, $X_{14}$, $X_{15}$, $X_{16}$, $X_{17}$, $X_{18}$ and $X_{19}$ are independently selected from selected from the group consisting of NH and $NCH_3$.

In a further embodiment, $X_{21}$, $X_{22}$, $X_{23}$, $X_{24}$, $X_{25}$ and $X_{26}$ are independently selected from selected from the group consisting of $CH_2$, $CH_2CH_2$, O, NH and $NCH_3$.

In an additional embodiment, the library is comprised of macrocyclic compounds selected from those with structures 1-1334 as defined herein.

In yet an another embodiment, the library is comprised of macrocyclic compounds selected from those with structures 1335-1467 as defined herein.

In a preferred embodiment, the library can be synthesized as discrete individual macrocyclic compounds utilizing techniques as described herein.

In still another embodiment, the library is synthesized as mixtures of at least two macrocyclic compounds.

In further embodiments, the macrocyclic compounds in the library are provided as solids (powders, salts, crystals, amorphous material and so on), syrups or oils as they are obtained from the preparation methods described in the disclosure.

In a different embodiment, the macrocyclic compounds in the library are provided dissolved in an appropriate organic, aqueous or mixed solvent, solvent system or buffer.

In a preferred embodiment, the organic solvent used to dissolve the macrocyclic compounds in the library is DMSO. The resulting concentration of the compound in DMSO may be between 0.001 and 100 mM.

In an embodiment relating to the use of the libraries, the macrocyclic compounds are distributed into at least one multiple sample holder, such as a microtiter plate or a miniaturized chip. For most uses, this distribution is done in an array format compatible with the automated systems used in HTS.

In a related embodiment, this distribution may be done as single, discrete compounds in each sample of the at least one multiple sample holder or as mixtures in each sample of the at least one multiple sample holder.

In a further embodiment, at least one multiple sample holder is a microtiter plate containing 96, 384, 1536, 3456, 6144 or 9600 wells, which are the sizes typically used in HTS, although other numbers of wells may be utilized for specialized assays or equipment.

In another aspect, the disclosure relates to kits comprising a library of macrocyclic compounds as described herein and at least one multiple sample holder.

In an embodiment, the one multiple sample holder in the kit is a microtiter plate containing 96, 384, 1536, 3456, 6144 or 9600 wells or a miniaturized chip.

In other embodiments, the library in the kit is distributed as individual compounds in each sample of the at least one multiple sample holder or as more than one compound in each sample of the at least one multiple sample holder In an additional aspect, the disclosure relates to macrocyclic compounds represented by formula (Ia), formula (Ib), formula (Ic), formula (Id) and formula (Ie) and salts thereof.

In a particular embodiment, macrocyclic compounds with structures 1-1334 as defined in the disclosure and their pharmaceutically acceptable salts are provided.

In another particular embodiment, macrocyclic compounds with structures 1335-1467 as defined in the disclosure and their pharmaceutically acceptable salts are provided.

In a further aspect, the disclosure relates to methods of using the libraries of macrocyclic compounds of formula (Ia), formula (Ib), formula (Ic), formula (Id) and formula (Ie) and their salts for the identification of specific compounds that modulate a biological target by contacting the compounds of the libraries with said target. This is most often done using HTS assays, but may also be done in low or medium throughput assays. The libraries of the disclosure may be tested in these assays in whole or in part and may be tested separately or at the same time as tests of other compounds and libraries.

In an embodiment, the biological target is selected from any known class of pharmacological targets, including enzymes, G protein-coupled receptors (GPCR), nuclear receptors, ion channels, transporters, transcription factors, protein-protein interactions and nucleic acid-protein interactions. Enzymes include, but are not limited to, proteases, kinases, esterases, amidases, dehydrogenases, endonucleases, hydrolases, lipases, phosphatases, convertases, synthetases and transferases. Since HTS assays have been developed for all of these target classes, the nature of the target is not a limiting factor in the use of the libraries of the present disclosure. Further, given this level of experience, it is within the scope of those skilled in the art to develop such assays for new targets that are identified and characterized for use in drug discovery programs.

In a further embodiment, the modulation in the method of using the libraries is agonism, antagonism, inverse agonism, activation, inhibition or partial variants of each of these types of activities as may be of interest depending on the specific target and the associated disease state.

In other embodiments, the modulation and biological target being investigated in the method of using the libraries may have relevance for the treatment and prevention of a broad range of medical conditions. As such, the libraries of the present disclosure have wide applicability to the discovery of new pharmaceutical agents.

In a further embodiment, there is provided the use of the libraries according to the present disclosure or at least one compound according the present disclosure for identification of compounds that modulate a biological target. For example, the identification is conducted in a high throughput fashion. For example, the biological target is an enzyme, a G protein-coupled receptor, a nuclear receptor, an ion channel, a transporter, a transcription factor, a protein-protein interaction or a nucleic acid-protein interaction. For example, the modulation is agonism, antagonism, activation, inhibition or inverse agonism.

In an additional aspect, the disclosure provides a process for preparing the macrocyclic compounds of formula (Ia), formula (Ib), formula (Ic), formula (Id) and formula (Ie) and libraries of such macrocyclic compounds.

In a particular embodiment, the process involves the following steps:
  synthesis of the individual multifunctional, protected building blocks;
  assembly of from three to six building blocks in a sequential manner with cycles of selective deprotection of a reactive functionality followed by attachment, wherein one of the building blocks contains an oxazole, thiazole or imidazole ring;
  selective deprotection of two reactive functional groups of the assembled building block structure followed by cyclization;
  removal of all remaining protecting groups from the cyclized products; and
  optionally, purification.

In another embodiment applicable to libraries, the process further comprises distribution of the final macrocycle compounds into a format suitable for screening.

In an additional embodiment, one or more of the above steps are performed on the solid phase. In particular, the assembly of the building blocks is preferentially conducted on the solid phase.

In further embodiments, the attachment of each individual building block is performed using a reaction independently selected from amide bond formation, reductive amination, Mitsunobu reaction and its variants, such as the Fukuyama-Mitsunobu reaction, and nucleophilic substitution.

Unless otherwise defined, all technical and scientific terms used herein have the same meaning as commonly understood by one of ordinary skill in the art to which this disclosure belongs.

The term "alkyl" refers to straight or branched chain saturated or partially unsaturated hydrocarbon groups having from 1 to 20 carbon atoms, in some instances 1 to 8 carbon atoms. Examples of alkyl groups include, but are not limited to, methyl, ethyl, isopropyl, tert-butyl, 3-hexenyl, and 2-butynyl. By "unsaturated" is meant the presence of 1, 2 or 3 double or triple bonds, or a combination of the two. Such alkyl groups may also be optionally substituted as described below.

When a subscript is used with reference to an alkyl or other hydrocarbon group defined herein, the subscript refers to the number of carbon atoms that the group may contain. For example, "$C_2$-$C_4$ alkyl" indicates an alkyl group with 2, 3 or 4 carbon atoms.

The term "cycloalkyl" refers to saturated or partially unsaturated cyclic hydrocarbon groups having from 3 to 15 carbon atoms in the ring, in some instances 3 to 7, and to alkyl groups containing said cyclic hydrocarbon groups. Examples of cycloalkyl groups include, but are not limited to, cyclopropyl, cyclopropylmethyl, cyclopentyl, cyclohexyl, 2-(cyclohexyl)ethyl, cycloheptyl, and cyclohexenyl. Cycloalkyl as defined herein also includes groups with multiple carbon rings, each of which may be saturated or partially unsaturated, for example decalinyl, [2.2.1]-bicycloheptanyl or adamantanyl. All such cycloalkyl groups may also be optionally substituted as described below.

The term "aromatic" refers to an unsaturated cyclic hydrocarbon group having a conjugated pi electron system that contains 4n+2 electrons where n is an integer greater than or equal to 1. Aromatic molecules are typically stable and are depicted as a planar ring of atoms with resonance structures that consist of alternating double and single bonds, for example benzene or naphthalene.

The term "aryl" refers to an aromatic group in a single or fused carbocyclic ring system having from 6 to 15 ring atoms, in some instances 6 to 10, and to alkyl groups containing said aromatic groups. Examples of aryl groups include, but are not limited to, phenyl, 1-naphthyl, 2-naphthyl and benzyl. Aryl as defined herein also includes groups with multiple aryl rings which may be fused, as in naphthyl and anthracenyl, or unfused, as in biphenyl and terphenyl. Aryl also refers to bicyclic or tricyclic carbon rings, where one of the rings is aromatic and the others of which may be saturated, partially unsaturated or aromatic, for example, indanyl or tetrahydronaphthyl (tetralinyl). All such aryl groups may also be optionally substituted as described below.

The term "heterocycle" or "heterocyclic" refers to non-aromatic saturated or partially unsaturated rings or ring systems having from 3 to 15 atoms, in some instances 3 to 7, with at least one heteroatom in at least one of the rings, said heteroatom being selected from O, S or N. Each ring of the heterocyclic group can contain one or two O atoms, one or two S atoms, one to four N atoms, provided that the total number of heteroatoms in each ring is four or less and each ring contains at least one carbon atom. The fused rings completing the heterocyclic groups may contain only carbon atoms and may be saturated or partially unsaturated. The N and S atoms may optionally be oxidized and the N atoms may optionally be quaternized. Examples of non-aromatic heterocycle groups include, in a non-limitative manner, pyrrolidinyl, tetrahydrofuranyl, morpholinyl, thiomorpholinyl, piperidinyl, piperazinyl, thiazolidinyl, isothiazolidinyl, and imidazolidinyl. All such heterocyclic groups may also be optionally substituted as described below.

The term "heteroaryl" refers to an aromatic group in a single or fused ring system having from 5 to 15 ring atoms, in some instances 5 to 10, which have at least one heteroatom in at least one of the rings, said heteroatom being selected from O, S or N. Each ring of the heteroaryl group can contain one or two O atoms, one or two S atoms, one to four N atoms, provided that the total number of heteroatoms in each ring is four or less and each ring contains at least one carbon atom. The fused rings completing the bicyclic or tricyclic groups may contain only carbon atoms and may be saturated, partially unsaturated or aromatic. In structures where the lone pair of electrons of a nitrogen atom is not involved in completing the aromatic pi electron system, the N atoms may optionally be quaternized or oxidized to the N-oxide. Heteroaryl also refers to alkyl groups containing said cyclic groups. Examples of monocyclic heteroaryl groups include, but are not limited to pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, and triazinyl. Examples of bicyclic heteroaryl groups include, but are not limited to indolyl, benzothiazolyl, benzoxazolyl, benzothienyl, quinolinyl, tetrahydroisoquinolinyl, isoquinolinyl, benzimidazolyl, benzopyranyl, indolizinyl, benzofuranyl, isobenzofuranyl, chromonyl, coumarinyl, benzopyranyl, cinnolinyl, quinoxalinyl, indazolyl, purinyl, pyrrolopyridinyl, furopyridinyl, thienopyridinyl, dihydroisoindolyl, and tetrahydroquinolinyl. Examples of tricyclic heteroaryl groups include, but are not limited to carbazolyl, benzindolyl, phenanthrollinyl, acridinyl, phenanthridinyl, and xanthenyl. All such heteroaryl groups may also be optionally substituted as described below.

The term "alkoxy" or "alkoxyl" refers to the group —$OR_a$, wherein $R_a$ is alkyl, cycloalkyl or heterocyclic. Examples include, but are not limited to methoxy, ethoxy, tert-butoxy, cyclohexyloxy and tetrahydropyranyloxy.

The term "aryloxy" refers to the group —$OR_b$ wherein $R_b$ is aryl or heteroaryl. Examples include, but are not limited to phenoxy, benzyloxy and 2-naphthyloxy.

The term "acyl" refers to the group —C(=O)—$R_c$ wherein $R_c$ is alkyl, cycloalkyl, heterocyclic, aryl or heteroaryl. Examples include, but are not limited to, acetyl, benzoyl and furoyl.

The term "amino acyl" indicates an acyl group that is derived from an amino acid as later defined.

The term "amino" refers to an —$NR_dR_e$ group wherein $R_d$ and $R_e$ are independently selected from the group consisting of hydrogen, alkyl, cycloalkyl, heterocyclic, aryl and heteroaryl. Alternatively, $R_d$ and $R_e$ together form a heterocyclic ring of 3 to 8 members, optionally substituted with unsubstituted alkyl, unsubstituted cycloalkyl, unsubstituted heterocyclic, unsubstituted aryl, unsubstituted heteroaryl, hydroxy, alkoxy, aryloxy, acyl, amino, amido, carboxy, carboxyalkyl, carboxyaryl, mercapto, sulfinyl, sulfonyl, sulfonamido, amidino, carbamoyl, guanidino or ureido, and optionally containing one to three additional heteroatoms selected from O, S or N.

The term "amido" refers to the group —C(=O)—$NR_fR_g$ wherein $R_f$ and $R_g$ are independently selected from the group consisting of hydrogen, alkyl, cycloalkyl, heterocyclic, aryl and heteroaryl. Alternatively, $R_f$ and $R_g$ together form a heterocyclic ring of 3 to 8 members, optionally substituted with unsubstituted alkyl, unsubstituted cycloalkyl, unsubstituted heterocyclic, unsubstituted aryl, unsubstituted heteroaryl, hydroxy, alkoxy, aryloxy, acyl, amino, amido, carboxy, carboxyalkyl, carboxyaryl, mercapto, sulfinyl, sulfonyl, sulfonamido, amidino, carbamoyl, guanidino or ureido, and optionally containing one to three additional heteroatoms selected from O, S or N.

The term "amidino" refers to the group —C(=$NR_h$)$NR_iR_j$ wherein $R_h$ is selected from the group consisting of hydrogen, alkyl, cycloalkyl, heterocyclic, aryl and heteroaryl; and $R_i$ and $R_j$ are independently selected from the group consisting of hydrogen, alkyl, cycloalkyl, heterocyclic, aryl and heteroaryl. Alternatively, $R_i$ and $R_j$ together form a heterocyclic ring of 3 to 8 members, optionally substituted with unsubstituted alkyl, unsubstituted cycloalkyl, unsubstituted heterocyclic, unsubstituted aryl, unsubstituted heteroaryl, hydroxy, alkoxy, aryloxy, acyl, amino, amido, carboxy, carboxyalkyl, carboxyaryl, mercapto, sulfinyl, sulfonyl, sulfonamido, amidino, carbamoyl, guanidino or ureido, and optionally containing one to three additional heteroatoms selected from O, S or N.

The term "carboxyalkyl" refers to the group —$CO_2R_k$, wherein $R_k$ is alkyl, cycloalkyl or heterocyclic.

The term "carboxyaryl" refers to the group —$CO_2R_m$, wherein $R_m$ is aryl or heteroaryl.

The term "oxo" refers to the bivalent group =O, which is substituted in place of two hydrogen atoms on the same carbon to form a carbonyl group.

The term "mercapto" refers to the group —$SR_n$ wherein $R_n$ is hydrogen, alkyl, cycloalkyl, heterocyclic, aryl or heteroaryl.

The term "sulfinyl" refers to the group —$S(=O)R_p$ wherein $R_p$ is alkyl, cycloalkyl, heterocyclic, aryl or heteroaryl.

The term "sulfonyl" refers to the group —$S(=O)_2$—$R_{q1}$ wherein $R_{q1}$ is alkyl, cycloalkyl, heterocyclic, aryl or heteroaryl.

The term "aminosulfonyl" refers to the group —$NR_{q2}$—$S(=O)_2$—$R_{q3}$ wherein $R_{q2}$ is hydrogen, alkyl, cycloalkyl, heterocyclic, aryl or heteroaryl; and $R_{q3}$ is alkyl, cycloalkyl, heterocyclic, aryl or heteroaryl.

The term "sulfonamido" refers to the group —$S(=O)_2$—$NR_rR_s$ wherein $R_r$ and $R_s$ are independently selected from the group consisting of hydrogen, alkyl, cycloalkyl, heterocyclic, aryl or heteroaryl. Alternatively, $R_r$ and $R_s$ together form a heterocyclic ring of 3 to 8 members, optionally substituted with unsubstituted alkyl, unsubstituted cycloalkyl, unsubstituted heterocyclic, unsubstituted aryl, unsubstituted heteroaryl, hydroxy, alkoxy, aryloxy, acyl, amino, amido, carboxy, carboxyalkyl, carboxyaryl, mercapto, sulfinyl, sulfonyl, sulfonamido, amidino, carbamoyl, guanidino or ureido, and optionally containing one to three additional heteroatoms selected from O, S or N.

The term "carbamoyl" refers to a group of the formula —$N(R_t)$—$C(=O)$—$OR_u$ wherein $R_t$ is selected from hydrogen, alkyl, cycloalkyl, heterocyclic, aryl or heteroaryl; and $R_u$ is selected from alkyl, cycloalkyl, heterocyclic, aryl or heteroaryl.

The term "guanidino" refers to a group of the formula —$N(R_v)$—$C(=NR_w)$—$NR_xR_y$ wherein $R_v$, $R_w$, $R_x$ and $R_y$ are independently selected from hydrogen, alkyl, cycloalkyl, heterocyclic, aryl or heteroaryl. Alternatively, $R_x$ and $R_y$ together form a heterocyclic ring or 3 to 8 members, optionally substituted with unsubstituted alkyl, unsubstituted cycloalkyl, unsubstituted heterocyclic, unsubstituted aryl, unsubstituted heteroaryl, hydroxy, alkoxy, aryloxy, acyl, amino, amido, carboxy, carboxyalkyl, carboxyaryl, mercapto, sulfinyl, sulfonyl, sulfonamido, amidino, carbamoyl, guanidino or ureido, and optionally containing one to three additional heteroatoms selected from O, S or N.

The term "ureido" refers to a group of the formula —$N(R_z)$—$C(=O)$—$NR_{aa}R_{bb}$ wherein $R_z$, $R_{aa}$ and $R_{bb}$ are independently selected from hydrogen, alkyl, cycloalkyl, heterocyclic, aryl or heteroaryl. Alternatively, $R_{aa}$ and $R_{bb}$ together form a heterocyclic ring of 3 to 8 members, optionally substituted with unsubstituted alkyl, unsubstituted cycloalkyl, unsubstituted heterocyclic, unsubstituted aryl, unsubstituted heteroaryl, hydroxy, alkoxy, aryloxy, acyl, amino, amido, carboxy, carboxyalkyl, carboxyaryl, mercapto, sulfinyl, sulfonyl, sulfonamido, amidino, carbamoyl, guanidino or ureido, and optionally containing one to three additional heteroatoms selected from O, S or N.

The expression "optionally substituted" is intended to indicate that the specified group is unsubstituted or substituted by one or more suitable substituents, unless the optional substituents are expressly specified, in which case the term indicates that the group is unsubstituted or substituted with the specified substituents. As defined above, various groups may be unsubstituted or substituted (i.e., they are optionally substituted) unless indicated otherwise herein (e.g., by indicating that the specified group is unsubstituted).

The term "substituted" when used with the terms alkyl, cycloalkyl, heterocyclic, aryl and heteroaryl refers to an alkyl, cycloalkyl, heterocyclic, aryl or heteroaryl group having one or more of the hydrogen atoms of the group replaced by substituents independently selected from unsubstituted alkyl, unsubstituted cycloalkyl, unsubstituted heterocyclic, unsubstituted aryl, unsubstituted heteroaryl, hydroxy, alkoxy, aryloxy, acyl, amino, amido, carboxy, carboxyalkyl, carboxyaryl, halo, oxo, mercapto, sulfinyl, sulfonyl, sulfonamido, amidino, carbamoyl, guanidino, ureido and groups of the formulas —$NR_{cc}C(=O)R_{dd}$, —$NR_{ee}C(=NR_{ff})R_{gg}$, —$OC(=O)NR_{hh}R_{ii}$, —$OC(=O)R_{jj}$, —$OC(=O)OR_{kk}$, —$NR_{mm}SO_2R_{nn}$, or —$NR_{pp}SO_2NR_{qq}R_{rr}$ wherein $R_{cc}$, $R_{dd}$, $R_{ee}$, $R_{ff}$, $R_{gg}$, $R_{hh}$, $R_{ii}$, $R_{jj}$, $R_{mm}$, $R_{pp}$, $R_{qq}$ and $R_{rr}$ are independently selected from hydrogen, unsubstituted alkyl, unsubstituted cycloalkyl, unsubstituted heterocyclic, unsubstituted aryl or unsubstituted heteroaryl; and wherein $R_{kk}$ and $R_{nn}$ are independently selected from unsubstituted alkyl, unsubstituted cycloalkyl, unsubstituted heterocyclic, unsubstituted aryl or unsubstituted heteroaryl. Alternatively, $R_{gg}$ and $R_{hh}$, $R_{ii}$ and $R_{kk}$ or $R_{pp}$ and $R_{qq}$ together form a heterocyclic ring of 3 to 8 members, optionally substituted with unsubstituted alkyl, unsubstituted cycloalkyl, unsubstituted heterocyclic, unsubstituted aryl, unsubstituted heteroaryl, hydroxy, alkoxy, aryloxy, acyl, amino, amido, carboxy, carboxyalkyl, carboxyaryl, mercapto, sulfinyl, sulfonyl, sulfonamido, amidino, carbamoyl, guanidino or ureido, and optionally containing one to three additional heteroatoms selected from O, S or N. In addition, the term "substituted" for aryl and heteroaryl groups includes as an option having one of the hydrogen atoms of the group replaced by cyano, nitro or trifluoromethyl.

A substitution is made provided that any atom's normal valency is not exceeded and that the substitution results in a stable compound. Generally, when a substituted form of a group is present, such substituted group is preferably not further substituted or, if substituted, the substituent comprises only a limited number of substituted groups, in some instances 1, 2, 3 or 4 such substituents.

When any variable occurs more than one time in any constituent or in any formula herein, its definition on each occurrence is independent of its definition at every other occurrence. Also, combinations of substituents and/or variables are permissible only if such combinations result in stable compounds.

A "stable compound" or "stable structure" refers to a compound that is sufficiently robust to survive isolation to a useful degree of purity and formulation into an efficacious therapeutic agent.

The term "amino acid" refers to the common natural (genetically encoded) or synthetic amino acids and common derivatives thereof, known to those skilled in the art. When applied to amino acids, "standard" or "proteinogenic" refers to the genetically encoded 20 amino acids in their natural configuration. Similarly, when applied to amino acids, "non-standard," "unnatural" or "unusual" refers to the wide selection of non-natural, rare or synthetic amino acids such as those described by Hunt, S. in *Chemistry and Biochemistry of the Amino Acids*, Barrett, G. C., ed., Chapman and Hall: New York, 1985.

The term "amino acid side chain" refers to any side chain from a standard or unnatural amino acid, and is denoted $R_{AA}$. For example, the side chain of alanine is methyl, the side chain of valine is isopropyl and the side chain of tryptophan is 3 indolylmethyl.

The term "activator" refers to a compound that increases the normal activity of a protein, receptor, enzyme, interaction, or the like.

The term "agonist" refers to a compound that duplicates at least some of the effect of the endogenous ligand of a protein, receptor, enzyme, interaction, or the like.

The term "antagonist" refers to a compound that reduces at least some of the effect of the endogenous ligand of a protein, receptor, enzyme, interaction, or the like.

The term "inhibitor" refers to a compound that reduces the normal activity of a protein, receptor, enzyme, interaction, or the like.

The term "inverse agonist" refers to a compound that reduces the activity of a constitutively-active receptor below its basal level.

The term "library" refers to a collection of chemical compounds.

The term "modulator" refers to a compound that imparts an effect on a biological or chemical process or mechanism. For example, a modulator may increase, facilitate, upregulate, activate, inhibit, decrease, block, prevent, delay, desensitize, deactivate, down regulate, or the like, a biological or chemical process or mechanism. Accordingly, a modulator can be an "agonist" or an "antagonist." Exemplary biological processes or mechanisms affected by a modulator include, but are not limited to, enzyme binding, receptor binding and hormone release or secretion. Exemplary chemical processes or mechanisms affected by a modulator include, but are not limited to, catalysis and hydrolysis.

The term "peptide" refers to a chemical compound comprising at least two amino acids covalently bonded together using amide bonds.

The term "peptidomimetic" refers to a chemical compound designed to mimic a peptide, but which contains structural differences through the addition or replacement of one of more functional groups of the peptide in order to modulate its activity or other properties, such as solubility, metabolic stability, oral bioavailability, lipophilicity, permeability, etc. This can include replacement of the peptide bond, side chain modifications, truncations, additions of functional groups, etc. When the chemical structure is not derived from the peptide, but mimics its activity, it is often referred to as a "non-peptide peptidomimetic."

The term "peptide bond" refers to the amide [—C(=O)—NH—] functionality with which individual amino acids are typically covalently bonded to each other in a peptide.

The term "protecting group" refers to any chemical compound that may be used to prevent a potentially reactive functional group, such as an amine, a hydroxyl or a carboxyl, on a molecule from undergoing a chemical reaction while chemical change occurs elsewhere in the molecule. A number of such protecting groups are known to those skilled in the art and examples can be found in *Protective Groups in Organic Synthesis*, T. W. Greene and P. G. Wuts, eds., John Wiley & Sons, New York, 4$^{th}$ edition, 2006, 1082 pp, ISBN 9780471697541. Examples of amino protecting groups include, but are not limited to, phthalimido, trichloroacetyl, benzyloxycarbonyl, tert butoxycarbonyl, and adamantyl-oxycarbonyl. In some embodiments, amino protecting groups are carbamate amino protecting groups, which are defined as an amino protecting group that when bound to an amino group forms a carbamate. In other embodiments, amino carbamate protecting groups are allyloxycarbonyl (Alloc), benzyloxycarbonyl (Cbz), 9 fluorenylmethoxycarbonyl (Fmoc), tert-butoxycarbonyl (Boc) and α,α dimethyl-3,5 dimethoxybenzyloxycarbonyl (Ddz). For a recent discussion of newer nitrogen protecting groups see: *Tetrahedron* 2000, 56, 2339-2358. Examples of hydroxyl protecting groups include, but are not limited to, acetyl, tert-butyldimethylsilyl (TBDMS), trityl (Trt), tert-butyl, and tetrahydropyranyl (THP). Examples of carboxyl protecting groups include, but are not limited to, methyl ester, tert-butyl ester, benzyl ester, trimethylsilylethyl ester, and 2,2,2-trichloroethyl ester. A protecting group is herein designated as PG, with a subscript if more than one is present in the same molecule.

The term "solid phase chemistry" refers to the conduct of chemical reactions where one component of the reaction is covalently bonded to a polymeric material (solid support as defined below). Reaction methods for performing chemistry on solid phase have become more widely known and established outside the traditional fields of peptide and oligonucleotide chemistry (*Solid-Phase Synthesis: A Practical Guide*, F. Albericio, ed., CRC Press, 2000, 848 pp, ISBN: 978-0824703592; *Organic Synthesis on Solid Phase*, 2$^{nd}$ edition, Florencio Zaragoza Dörwald, Wiley-VCH, 2002, 530 pp, ISBN: 3-527-30603-X; *Solid-Phase Organic Synthesis: Concepts, Strategies, and Applications*, P. H. Toy, Y. Lam, eds., Wiley, 2012, 568 pp, ISBN: 978-0470599143).

The term "solid support," "solid phase" or "resin" refers to a mechanically and chemically stable polymeric matrix utilized to conduct solid phase chemistry. This is denoted by "Resin," "P—" or the following symbol:

Examples of appropriate polymer materials include, but are not limited to, polystyrene, polyethylene, polyethylene glycol (PEG, including, but not limited to, ChemMatrix® (Matrix Innovation, Quebec, Quebec, Canada; J. Comb. Chem. 2006, 8, 213-220)), polyethylene glycol grafted or covalently bonded to polystyrene (also termed PEG-polystyrene, TentaGel™, Rapp, W.; Zhang, L.; Bayer, E. In Innovations and Perspectives in Solid Phase Synthesis. Peptides, Polypeptides and Oligonucleotides; Epton, R., ed.; SPCC Ltd.: Birmingham, UK; p 205), polyacrylate (CLEAR™), polyacrylamide, polyurethane, PEGA [polyethyleneglycol poly(N,N dimethyl-acrylamide) co-polymer, Tetrahedron Lett. 1992, 33, 3077-3080], cellulose, etc. These materials can optionally contain additional chemical agents to form cross-linked bonds to mechanically stabilize the structure, for example polystyrene cross-linked with divinylbenezene (DVB, usually 0.1-5%, preferably 0.5-2%). This solid support can include as non-limiting examples aminomethyl polystyrene, hydroxymethyl polystyrene, benzhydrylamine polystyrene (BHA), methylbenzhydrylamine (MBHA) polystyrene, and other polymeric backbones containing free chemical functional groups, most typically, $NH_2$ or —OH, for further derivatization or reaction. The term is also meant to include "Ultraresins" with a high proportion ("loading") of these functional groups such as those prepared from polyethyleneimines and cross-linking molecules (J. Comb. Chem. 2004, 6, 340-349). At the conclusion of the synthesis, resins are typically discarded, although they have been shown to be able to be recycled (Tetrahedron Lett. 1975, 16, 3055).

In general, the materials used as resins are insoluble polymers, but certain polymers have differential solubility depending on solvent and can also be employed for solid phase chemistry. For example, polyethylene glycol can be utilized in this manner since it is soluble in many organic solvents in which chemical reactions can be conducted, but it is insoluble in others, such as diethyl ether. Hence, reactions can be conducted homogeneously in solution, then the product on the polymer precipitated through the addition of diethyl ether and processed as a solid. This has been termed "liquid-phase" chemistry.

The term "linker" when used in reference to solid phase chemistry refers to a chemical group that is bonded covalently to a solid support and is attached between the support and the substrate typically in order to permit the release (cleavage) of the substrate from the solid support. However, it can also be used to impart stability to the bond to the solid support or merely as a spacer element. Many solid supports are available commercially with linkers already attached.

Abbreviations used for amino acids and designation of peptides follow the rules of the IUPAC-IUB Commission of Biochemical Nomenclature in J. Biol. Chem. 1972, 247, 977-983. This document has been updated: Biochem. J., 1984, 219, 345-373; Eur. J. Biochem., 1984, 138, 9-37; 1985, 152, 1; Int. J. Pept. Prot. Res., 1984, 24, following p 84; J. Biol. Chem., 1985, 260, 14-42; Pure Appl. Chem. 1984, 56, 595-624; Amino Acids and Peptides, 1985, 16, 387-410; and in *Biochemical Nomenclature and Related Documents*, $2^{nd}$ edition, Portland Press, 1992, pp 39-67. Extensions to the rules were published in the JCBN/NC-IUB Newsletter 1985, 1986, 1989; see *Biochemical Nomenclature and Related Documents*, $2^{nd}$ edition, Portland Press, 1992, pp 68-69.

The expression "compound(s) and/or composition(s) of the present disclosure" as used in the present document refers to compounds of formulas (Ia), (Ib), (Ic), (Id) and (Ie) presented in the disclosure, isomers thereof, such as stereoisomers (for example, enantiomers, diastereoisomers, including racemic mixtures) or tautomers, or to pharmaceutically acceptable salts, solvates, hydrates and/or prodrugs of these compounds, isomers of these latter compounds, or racemic mixtures of these latter compounds, and/or to composition (s) made with such compound(s) as previously indicated in the present disclosure. The expression "compound(s) of the present disclosure" also refers to mixtures of the various compounds or variants mentioned in the present paragraph.

It is to be clear that the present disclosure includes isomers, racemic mixtures, pharmaceutically acceptable salts, solvates, hydrates and prodrugs of compounds described therein and mixtures comprising at least two of such entities.

The macrocyclic compounds comprising the libraries of the disclosure may have at least one asymmetric center. Where the compounds according to the present document possess more than one asymmetric center, they may exist as diastereomers. It is to be understood that all such isomers and mixtures thereof in any proportion are encompassed within the scope of the present disclosure. It is to be understood that while the stereochemistry of the compounds of the present disclosure may be as provided for in any given compound listed herein, such compounds of the disclosure may also contain certain amounts (for example less than 30%, less than 20%, less than 10%, or less than 5%) of compounds of the present disclosure having alternate stereochemistry.

The expression "pharmaceutically acceptable" means compatible with the treatment of subjects such as animals or humans.

The expression "pharmaceutically acceptable salt" means an acid addition salt or basic addition salt which is suitable for or compatible with the treatment of subjects such as animals or humans.

The expression "pharmaceutically acceptable acid addition salt" as used herein means any non-toxic organic or inorganic salt of any compound of the present disclosure, or any of its intermediates. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluenesulfonic and methanesulfonic acids. Either the mono or di-acid salts can be formed, and such salts may exist in either a hydrated, solvated or substantially anhydrous form. In general, the acid addition salts of the compounds of the present disclosure are more soluble in water and various hydrophilic organic solvents, and generally demonstrate higher melting points in comparison to their free base forms. The selection of the appropriate salt will be known to one skilled in the art. Other non-pharmaceutically acceptable salts, e.g. oxalates, may be used, for example, in the isolation of the compounds of the present disclosure, for laboratory use, or for subsequent conversion to a pharmaceutically acceptable acid addition salt.

The term "pharmaceutically acceptable basic addition salt" as used herein means any non-toxic organic or inorganic base addition salt of any acid compound of the disclosure, or any of its intermediates. Acidic compounds of the disclosure that may form a basic addition salt include, for example, where $CO_2H$ is a functional group. Illustrative inorganic bases which form suitable salts include lithium, sodium, potassium, calcium, magnesium or barium hydroxide. Illustrative organic bases which form suitable salts include aliphatic, alicyclic or aromatic organic amines such as methylamine, trimethylamine and picoline or ammonia. The selection of the appropriate salt will be known to a person skilled in the art. Other non-pharmaceutically acceptable basic addition salts, may be used, for example, in the isolation of the compounds of the disclosure, for laboratory use, or for subsequent conversion to a pharmaceutically acceptable acid addition salt.

The formation of a desired compound salt is achieved using standard techniques. For example, the neutral compound is treated with an acid or base in a suitable solvent and the formed salt is isolated by filtration, extraction or any other suitable method.

The formation of a desired compound salt is achieved using standard techniques. For example, the neutral compound is treated with an acid or base in a suitable solvent and the formed salt is isolated by filtration, extraction or any other suitable method.

The term "solvate" as used herein means a compound of the present disclosure, wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate". The formation of solvates of the compounds of the present disclosure will vary depending on the compound and the solvate. In general, solvates are formed by dissolving the compound in the appropriate solvent and isolating the solvate by cooling or using an antisolvent. The solvate is typically dried or azeotroped under ambient conditions.

The terms "appropriate" and "suitable" mean that the selection of the particular group or conditions would depend on the specific synthetic manipulation to be performed and the identity of the molecule but the selection would be well within the skill of a person trained in the art. All process steps described herein are to be conducted under conditions suitable to provide the product shown. A person skilled in the art would understand that all reaction conditions, including, for example, reaction solvent, reaction time, reaction temperature, reaction pressure, reactant ratio and whether or not the reaction should be performed under an anhydrous or inert atmosphere, can be varied to optimize the yield of the desired product and it is within their skill to do so.

Compounds of the present disclosure include prodrugs. In general, such prodrugs will be functional derivatives of these compounds which are readily convertible in vivo into the compound from which it is notionally derived. Prodrugs of the compounds of the present disclosure may be conventional esters formed with available hydroxy, or amino group. For example, an available OH or nitrogen in a compound of the present disclosure may be acylated using an activated acid in the presence of a base, and optionally, in inert solvent (e.g. an acid chloride in pyridine). Some common esters which have been utilized as prodrugs are phenyl esters, aliphatic ($C_8$-$C_{24}$) esters, acyloxymethyl esters, carbamates and amino acid esters. In certain instances, the prodrugs of the compounds of the present disclosure are those in which one or more of the hydroxy groups in the compounds is masked as groups which can be converted to hydroxy groups in vivo. Conventional procedures for the selection and preparation of suitable prodrugs are described, for example, in "Design of Prodrugs" ed. H. Bundgaard, Elsevier, 1985.

Compounds of the present disclosure include radiolabeled forms, for example, compounds labeled by incorporation within the structure $^2H$, $^3H$, $^{14}C$, $^{15}N$, or a radioactive halogen such as $^{125}I$. A radiolabeled compound of the compounds of the present disclosure may be prepared using standard methods known in the art.

The term "subject" as used herein includes all members of the animal kingdom including human.

The expression a "therapeutically effective amount", "effective amount" or a "sufficient amount" of a compound or composition of the present disclosure is a quantity sufficient to, when administered to the subject, including a mammal, for example a human, effect beneficial or desired results, including clinical results, and, as such, an "effective amount" or synonym thereto depends upon the context in which it is being applied. For example, in the context of treating cancer, for example, it is an amount of the compound or composition sufficient to achieve such treatment of the cancer as compared to the response obtained without administration of the compound or composition. The amount of a given compound or composition of the present disclosure that will correspond to an effective amount will vary depending upon various factors, such as the given drug or compound, the pharmaceutical formulation, the route of administration, the type of disease or disorder, the identity of the subject or host being treated, and the like, but can nevertheless be routinely determined by one skilled in the art. Also, as used herein, a "therapeutically effective amount", "effective amount" or a "sufficient amount" of a compound or composition of the present disclosure is an amount which inhibits, suppresses or reduces a cancer (e.g., as determined by clinical symptoms or the amount of cancerous cells) in a subject as compared to a control.

As used herein, and as well understood in the art, "treatment" or "treating" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" or "treating" can also mean prolonging survival as compared to expected survival if not receiving treatment.

"Palliating" a disease or disorder, means that the extent and/or undesirable clinical manifestations of a disorder or a disease state are lessened and/or time course of the progression is slowed or lengthened, as compared to not treating the disorder.

The expression "derivative thereof" as used herein when referring to a compound means a derivative of the compound that has a similar reactivity and that could be used as an alternative to the compound in order to obtain the same desired result.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

Further features and advantages of the macrocyclic compounds and libraries of the present disclosure will become more readily apparent from the following description of synthetic methods, analytical procedures and methods of use.

1. Synthetic Methods

A. General Synthetic Information

Reagents and solvents were of reagent quality or better and were used as obtained from various commercial suppliers unless otherwise noted. For certain reagents, a source may be indicated if the number of suppliers is limited. Solvents, such as DMF, DCM, DME and THF, are of DriSolv®, OmniSolv® (EMD Millipore, Darmstadt, Germany), or an equivalent synthesis grade quality except for (i) deprotection, (ii) resin capping reactions and (iii) washing. NMP used for coupling reactions is of analytical grade. DMF was adequately degassed by placing under vacuum for a minimum of 30 min prior to use. Ether refers to diethyl ether. Amino acids, Boc-, Fmoc- and Alloc-protected and side chain-protected derivatives, including those of N-methyl and unnatural amino acids, were obtained from commercial suppliers, including AAPPTec (Louisville, Ky., USA), Advanced ChemTech (part of CreoSalus, Louisville, Ky.), AstaTech (Bristol, Pa., USA), Bachem (Bubendorf, Switzerland), Chem-Impex International (Wood Dale, Ill., USA), Iris Biotech (Marktredwitz, Germany), Novabiochem (EMD Millipore), PepTech (Bedford, Mass., USA), or synthesized through standard methodologies known to those in the art. Amino alcohols were obtained commercially or synthesized from the corresponding amino acids or amino esters using established procedures from the literature (for example Tet. Lett. 1992, 33, 5517-5518; J. Org. Chem. 1993, 58, 3568-3571; Lett. Pept. Sci. 2003, 10, 79-82; Ind. J. Chem. 2006, 45B, 1880-1886; Synth. Comm. 2011, 41, 1276-1281). Hydroxy acids were obtained from commercial suppliers or synthesized from the corresponding amino acids as described in the literature (Tetrahedron 1989, 45, 1639-1646; Tetrahedron 1990, 46, 6623-6632; J. Org. Chem. 1992, 57, 6239-6256; J. Am. Chem. Soc. 1999, 121, 6197-6205; Org. Lett. 2004, 6, 497-500; Chem. Comm. 2015, 51, 2828-2831). The synthesis of thiazole, imidazole and oxazole-containing amino acids are carried out as described in the literature (J. Pept. Sci. 1999, 5, 392-398; Org. Lett. 2006, 8, 2417-2420; ACS Comb. Sci. 2014, 16, 1-4; ACS Comb. Sci. 2014, 16, 39-45) and in Examples 1I, 1M, 1N, 1O, 1P and 1Q. Resins for solid phase synthesis were obtained from commercial suppliers, including AAPTech, Novabiochem and Rapp Polymere (Tubingen, Germany). Analytical TLC was performed on pre-coated plates of silica gel, for example 60F254 (0.25 mm thickness) containing a fluorescent indicator.

NMR spectra were recorded on a Bruker 400 MHz or 500 MHz spectrometer and are referenced internally with respect to the residual proton signals of the solvent. Additional structural information or insight about the conformation of the molecules in solution can be obtained utilizing appropriate two-dimensional NMR techniques known to those skilled in the art.

HPLC analyses were performed on a Waters Alliance system running at 1 mL/min using a Zorbax SB-C18 (4.6 mm×30 mm, 2.5 µm), an Xterra MS C18 column (4.6 mm×50 mm, 3.5 µm), or comparable. A Waters 996 PDA provided UV data for purity assessment. Data was captured and processed utilizing the instrument software package. MS spectra were recorded on a Waters ZQ or Platform II system.

Preparative HPLC purifications were performed on deprotected macrocycles using the following instrumentation configuration (or comparable): Waters 2767 Sample Manager, Waters 2545 Binary Gradient Module, Waters 515 HPLC Pumps (2), Waters Flow Splitter, 30-100 mL, 5000:1, Waters 2996 Photodiode Detector, Waters Micromass ZQ., on an Atlantis Prep C18 OBD (19×100 mm, 5 µm), an XTerra MS C18 column (19×100 mm, 5 µm). The mass spectrometer, HPLC, and mass-directed fraction collection are controlled via MassLynx software version 4.0 with FractionLynx. Fractions shown by MS analysis to contain the desired pure product were evaporated under reduced pressure, usually on a centrifugal evaporator system [Genevac (SP Scientific), SpeedVac™ (Thermo Scientific, Savant) or comparable] or, alternatively, lyophilized. Compounds were then analyzed by LC-MS-UV analysis for purity assessment and identity confirmation. Automated medium pressure chromatographic purifications were performed on a Biotage Isolera system with disposable silica or C18 cartridges. Solid phase extraction was performed utilizing PoraPak™ (Sigma-Aldrich (Supelco), St. Louis, Mo., USA), SiliaSep™, SiliaPrep™ and SiliaPrepX™ (SiliCycle, Quebec, Quebec, Canada) or comparable columns, cartridges, plates or media as appropriate for the compound being purified.

The expression "concentrated/evaporated/removed under reduced pressure or in vacuo" indicates evaporation utilizing a rotary evaporator under either water aspirator pressure or the stronger vacuum provided by a mechanical oil vacuum pump as appropriate for the solvent being removed or, for multiple samples simultaneously, evaporation of solvent utilizing a centrifugal evaporator system. "Flash chromatography" refers to the method described as such in the literature (J. Org. Chem. 1978, 43, 2923.) and is applied to chromatography on silica gel (230-400 mesh, EMD Millipore or equivalent) used to remove impurities, some of which may be close in $R_f$ to the desired material.

The majority of the synthetic procedures described herein are for the solid phase (i.e. on resin), since this is more appropriate for creating the libraries of the present disclosure, but it will be appreciated by those in the art that these same transformations can also be modified to be applicable to traditional solution phase processes as well. The major modifications are the substitution of a standard aqueous organic work-up process for the successive resin washing steps and the use of lower equivalents for reagents versus the solid phase.

The following synthetic methods will be referenced elsewhere in the disclosure by using the number 1 followed by the letter referring to the method or procedure, i.e. Method 1F for Fmoc deprotection.

B. General Methods for Synthesis of Libraries of Macrocyclic Compounds

Different synthetic strategies, including solution and solid phase techniques, are employed to prepare the libraries of macrocyclic compounds of the disclosure. An outline of the general strategy for the synthesis of the libraries of compounds of the disclosure is provided in Scheme 1. It will be appreciated by those skilled in the art that for the synthesis of larger libraries, the use of solid phase procedures typically will be preferable and more efficient. Further, the macrocyclic compounds can be made in mixtures or as discrete compounds. In either case, the utilization of specific strategies for tracking the synthesis can be advantageous, such as the use of tagging methodologies (i.e. radiofrequency, color-coding or specific chemical functionality, for a review, see J. Receptor Signal Transduction Res. 2001, 21, 409-445) and sequestration of resin containing a single compound using a polypropylene mesh "tea" bag (Proc. Natl. Acad. Sci. USA 1985, 82, 5131-5135) or flow-through capsule (MiniKan™, Biotechnol. Bioengineer. 2000, 71, 44-50), which permit the simultaneous transformation of multiple different individual compounds in the same reaction vessel. For mixtures, such tags can also be effectively used to facilitate "deconvolution" or the identification of the active structure(s) from a mixture that was found to be a hit during screening.

The construction of the macrocyclic compounds of the library involves the following phases: (i) synthesis of the individual multifunctional, appropriately protected, building blocks, including elements for interaction at biological targets and fragments for control and definition of conformation, as well as moieties that can perform both functions; (ii) assembly of the building blocks, typically in a sequential manner with cycles of selective deprotection and attachment, although this step could also be performed in a convergent manner, utilizing standard chemical transformations as well as those described in more detail in the General/Standard Procedures and Examples herein, such as amide bond formation, reductive amination, Mitsunobu reaction and its variants, and nucleophilic substitution reactions; (iii) selective deprotection of two functional groups followed by cyclization of the assembled linear compounds, which can involve one or more steps, to form the macrocyclic structures; (iv) optionally, selective removal of one or more protecting groups can be performed, then the macrocycle further reacted with one or more additional building blocks to extend the structure at the unprotected functional group(s); and (v) removal of all remaining protecting groups, if necessary, and, optionally, purification to provide the desired final macrocycles.

The assembly reactions require protection of functional groups to avoid side reactions. Even though amino acids are only one of the types of building blocks employed, the well-established strategies of peptide chemistry have utility for the macrocyclic compounds and libraries of the disclosure as well (Meth. Mol. Biol. 2005, 298, 3-24). In particular, these include the Fmoc/tBu strategy (Int. J. Pept. Prot. Res. 1990, 35, 161-214) and the Boc/Bzl strategy (Meth. Mol. Biol. 2013, 1047, 65-80), although those in the art will appreciate that other orthogonal strategies may be necessary, for example the use of allyl-based protecting groups, to enable selective reaction at a particular site in multi-functional building blocks.

For solid phase processes, the cyclization can be conducted with the linear precursor on the resin after the two reacting groups are selectively deprotected and the appropriate reagents for cyclization added. This is followed by cleavage from the resin, which may also cleave the side chain protecting groups with the use of appropriate conditions. However, it is also possible to cyclize concomitant with resin cleavage if a special linker that facilitates this so-called "cyclization-release" process (Comb. Chem. HTS 1998, 1, 185-214) is utilized. Alternatively, the assembled linear precursor can be cleaved from the resin and then cyclized in solution. This requires the use of a resin that permits removal of the bound substrate without concomitant protecting group deprotection. For Fmoc strategies, 2-chlorotrityl resin (Tetrahedron Lett. 1989, 30, 3943-3946; Tetrahedron Lett. 1989, 30, 3947-3950) and derivatives are effective for this purpose, while for Boc approaches, an oxime resin has been similarly utilized (J. Org. Chem. 1980, 45, 1295-1300). Alternatively, a resin can be used that is specially activated for facile cleavage only after precursor assembly, but is otherwise quite stable, termed a "safety-catch" linker or resin (Bioorg. Med. Chem. 2005, 13, 585-599). For cyclization in solution phase, the assembled linear precursor is selectively deprotected at the two reacting functional groups, then subjected to appropriate reaction conditions for cyclization.

Upon isolation and characterization, the library compounds can be stored individually in the form thus obtained (solids, syrups, liquids) or dissolved in an appropriate solvent, for example DMSO. If in solution, the compounds can also be distributed into an appropriate array format for ease of use in automated screening assays, such as in microplates or on miniaturized chips. Prior to use, the library compounds, as either solids or solutions, are typically stored at low temperature to ensure the integrity of the compounds is maintained over time. As an example, libraries are stored at or below −70° C. as 10 mM solutions in 100% DMSO, allowed to warm to ambient temperature and diluted with buffer, first to a working stock solution, then further to appropriate test concentrations for use in HTS or other assays.

C. General Methods for Solid Phase Chemistry

These methods can be equally well applied for the combinatorial synthesis of mixtures of compounds or the parallel synthesis of multiple individual compounds to provide the libraries of macrocyclic compounds of the present disclosure. In the event of combinatorial synthesis of mixtures, it is necessary to include some type of encoding or tracking mechanism in order to deconvolute the data obtained from HTS of the libraries so that the identity of the active compound obtained can be ascertained (Curr. Opin. Biotechnol. 1995, 6, 632-639; Curr. Opin. Drug Discov. Develop. 2002, 5, 580-593; Curr. Opin. Chem. Biol. 2003, 7, 374-379).

For solid phase chemistry, the solvent choice is important not just to solubilize reactants as in solution chemistry, but also to swell the resin to be able to access all the reactive sites thereon. Certain solvents interact differently with the polymer matrix depending on its nature and can affect this swelling property. As an example, polystyrene (with DVB cross-links) swells best in nonpolar solvents such as DCM and toluene, while shrinking when exposed to polar solvents like alcohols. In contrast, other resins such as PEG (for example, ChemMatrix) and PEG-grafted ones (for example, TentaGel), maintain their swelling even in polar solvents. For the reactions of the present disclosure, appropriate choices can be made by one skilled in the art. In general, polystyrene-DVB resins are employed with DMF, DCM and NMP common solvents. The volume of the reaction solvent required is generally 3-5 mL per 100 mg resin. When the term "appropriate amount of solvent" is used in the synthesis methods, it refers to this quantity. The recommended quantity of solvent roughly amounts to a 0.2 M solution of building blocks (amino acids, hydroxy acids, amino alcohols, diacids, diamines, and derivatives thereof, typically used at 5 eq relative to the initial loading of the resin). Reaction stoichiometry was determined based upon the "loading" (represents the number of active functional sites, provided by the supplier, typically as mmol/g) of the starting resin.

The reaction can be conducted in any appropriate vessel, for example round bottom flasks, solid phase reaction vessels equipped with a fritted filter and stopcock, or Teflon-capped jars. The vessel size should be such that there is adequate space for the solvent, and that there is sufficient room for the resin to be effectively agitated taking into account that certain resins can swell significantly when treated with organic solvents. The solvent/resin mixture should fill about 60% of the vessel. Agitations for solid phase chemistry could be performed manually or with an orbital shaker (for example, Thermo Scientific, Forma Models 416 or 430) at 150-200 rpm, except for those reactions where scale makes use of mild mechanical stirring more suitable to ensure adequate mixing, a factor which is generally accepted as important for a successful reaction on resin.

The volume of solvent used for the resin wash is a minimum of the same volume as used for the reaction, although more is generally used to ensure complete removal of excess reagents and other soluble residual by-products (minimally 0.05 mL/mg resin). Each of the resin washes specified in the General/Standard Procedures and Examples should be performed for a duration of at least 5 min with agitation (unless otherwise specified) in the order listed. The number of washings is denoted by "nx" together with the solvent or solution, where n is an integer. In the case of mixed solvent washing systems, they are listed together and denoted solvent 1/solvent 2. After washing, the expression "dried in the usual manner" and analogous expressions mean that the resin is dried first in a stream of air or nitrogen for 20 min-1 h, using the latter if there is concern over oxidation of the substrate on the resin, and subsequently under vacuum (oil pump usually) until full dryness is attained (minimum 2 h to overnight (o/n)).

The general and specific synthetic methods and procedures utilized for representative macrocyclic compounds disclosed and utilized herein are presented below. Although the methods described may indicate a specific protecting group, other suitable protection known in the art may also be employed.

D. General Procedure for Loading of First Building Block to Resin

Certain resins can be obtained with the first building block, in particular amino acid building blocks, already attached. For other cases on the solid support, the building blocks can be attached using methods known in the art. As an example, the following procedure is followed for 2-chlorotrityl chloride resin.

Prewash the resin with DCM (2×), then dry in the usual manner. In a suitable reaction vessel, dissolve Fmoc-$BB_1$ (2 eq) in DCM (0.04 mL/mg resin) and add DIPEA (4 eq.), agitate briefly, then add the resin. Agitate o/n on an orbital shaker, remove the solvent, wash with DMF (2×), then, cap any remaining reactive sites using MeOH/DIPEA/DCM (2:1:17) (3×). The resin is then washed sequentially with DCM (1×), iPrOH (1×), DCM (2×), ether (1×), then dried in the usual manner.

In the case of solution phase chemistry, the first building block is typically used as a suitably protected derivative with one functional group free for subsequent reaction.

E. Standard Procedure for Monitoring the Progress of Reactions on the Solid Phase Since methods usually employed for monitoring reaction progress (TLC, direct GC or HPLC) are not available for solid phase reactions, it is necessary to perform the following in order to determine the progress of such a transformation. A small amount of resin (a few beads is usually sufficient) is removed from the reaction vessel, then washed successively with DMF (2×), iPrOH (1×), DCM (2×), ether (1×), dried, then treated with 200 µL 20% hexafluoroisopropanol (HFIP)/DCM, for 10-20 min, and concentrated with a stream of air or nitrogen. To the crude residue obtained, add 200-400 µL MeOH (or use DMSO or THF to solubilize fully protected intermediate compounds), filter through a 45 µm HPLC filter, or a plug of cotton, and analyze the filtrate by HPLC or HPLC-MS.

F. General Procedure for Fmoc Deprotection In an appropriate vessel, a solution of 20% piperidine (Pip) in DMF (0.04 mL/mg resin) was prepared. The resin was added to the solution and the mixture agitated for 30 min. The reaction solution was removed, then this treatment repeated. After this, the resin was washed sequentially with: DMF (2×), iPrOH (1×), DMF (1×), iPrOH (1×), DCM (2×), ether (1×), then the resin dried in the usual manner.

Note that when N-alkylated-amino acids are present in the $BB_1$ position, to minimize the potential of diketopiperazine formation, 50% Pip/DMF is used for Fmoc-deprotection of $BB_2$ and the procedure modified as follows: Add the solution to the resin and agitate for only 5-7 min, remove the solvent, add DMF, agitate quickly and remove the solvent, then resume the remaining washes as described above.

G General Procedure for Attachment of Amines to Acids

To an appropriate reaction vessel, add the acid building block (2.5-3.5 eq), coupling agent (2.5-3.5 eq) and NMP (0.04 mL/mg resin), followed by DIPEA (5-7 eq). Agitate the mixture vigorously for a few seconds and then add the amine-containing resin. Alternatively, separately prepare a solution of the coupling agent (3.5 eq) in NMP, then add this solution to the acid building block (2.5-3.5 eq) and agitate vigorously. Add DIPEA (5-7 eq), agitate a few seconds, then add the resin. HATU (1-[Bis(dimethylamino)methylene]-1H-1,2,3-triazolo[4,5-b]pyridinium 3-oxid hexafluorophosphate) and DEPBT (3-(diethoxyphosphoryloxy)-1,2,3-benzotriazin-4(3H)-one) are the typical coupling agents employed, although many other suitable ones are known and could also be utilized (Chem. Rev. 2011, 111, 6557-6602). Agitate the reaction mixture o/n, remove the solution and, if deprotection will be done immediately, wash the resin sequentially with: DMF (2×), iPrOH (1×), DMF (2×), then dry. If deprotection will not be performed immediately, wash sequentially with DMF (2×); iPrOH (1×); DMF (1×); iPrOH (1×), DCM (2×), ether (1×), then dry in the usual manner.

For attachment of $BB_3$ and beyond, utilize 5 eq of acid building block and coupling agent with 10 eq of DIPEA. If the acid building block is one known to require repeated treatment for optimal results, for example N-alkylated and other hindered amino acids, use half of the indicated equivalents for each of the two treatments.

Although the above describes the amine on resin and the acid as the new building block added, it will be appreciated by those in the art that the reverse can also be performed in a similar manner, with the acid component on the solid phase and the amine being the added component.

In addition to the use of acids as building blocks, it is also possible to utilize Fmoc acid fluorides (formed from the acid using cyanuric fluoride, J. Am. Chem. Soc. 1990, 112, 9651-9652) and Fmoc acid chlorides (formed from the acid using triphosgene, J. Org. Chem. 1986, 51, 3732-3734) as alternatives for particularly difficult attachments.

H General Procedure for Oxidation of Alcohol Building Blocks to Aldehydes.

A number of different oxidation methods can be utilized to convert alcohols to aldehydes for use in the attachment of building blocks by reductive amination. The following lists the most appropriate methods for the compounds of the present disclosure, and the types of building blocks on which they are applied, 1) $MnO_2$ oxidation (see Example 1L for additional details) used for benzylic aldehydes.

2) Swern oxidation (DMSO, oxalyl chloride) used for both benzylic and alkyl aldehydes. (Synthesis 1981, 165-185)

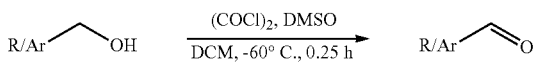

3) Pyridine•$SO_3$ (see Example 1K for additional details) used for both benzylic and alkyl aldehydes.

4) Dess-Martin Periodinane (DMP, 1,1,1-Triacetoxy-1,1-dihydro-1,2-benziodoxol-3(1H)-one) used for alkyl aldehydes (J. Am. Chem. Soc., 1991, 113, 7277-7287)

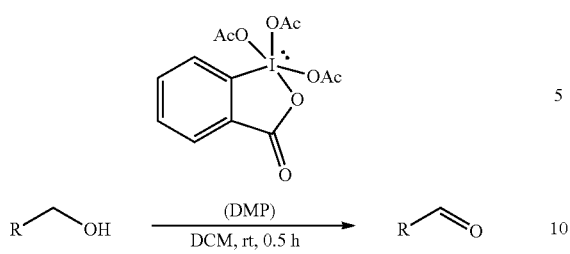

The following are structures of representative aldehyde building blocks of the present disclosure formed by oxidation of the corresponding alcohols or prepared as described in the Examples.

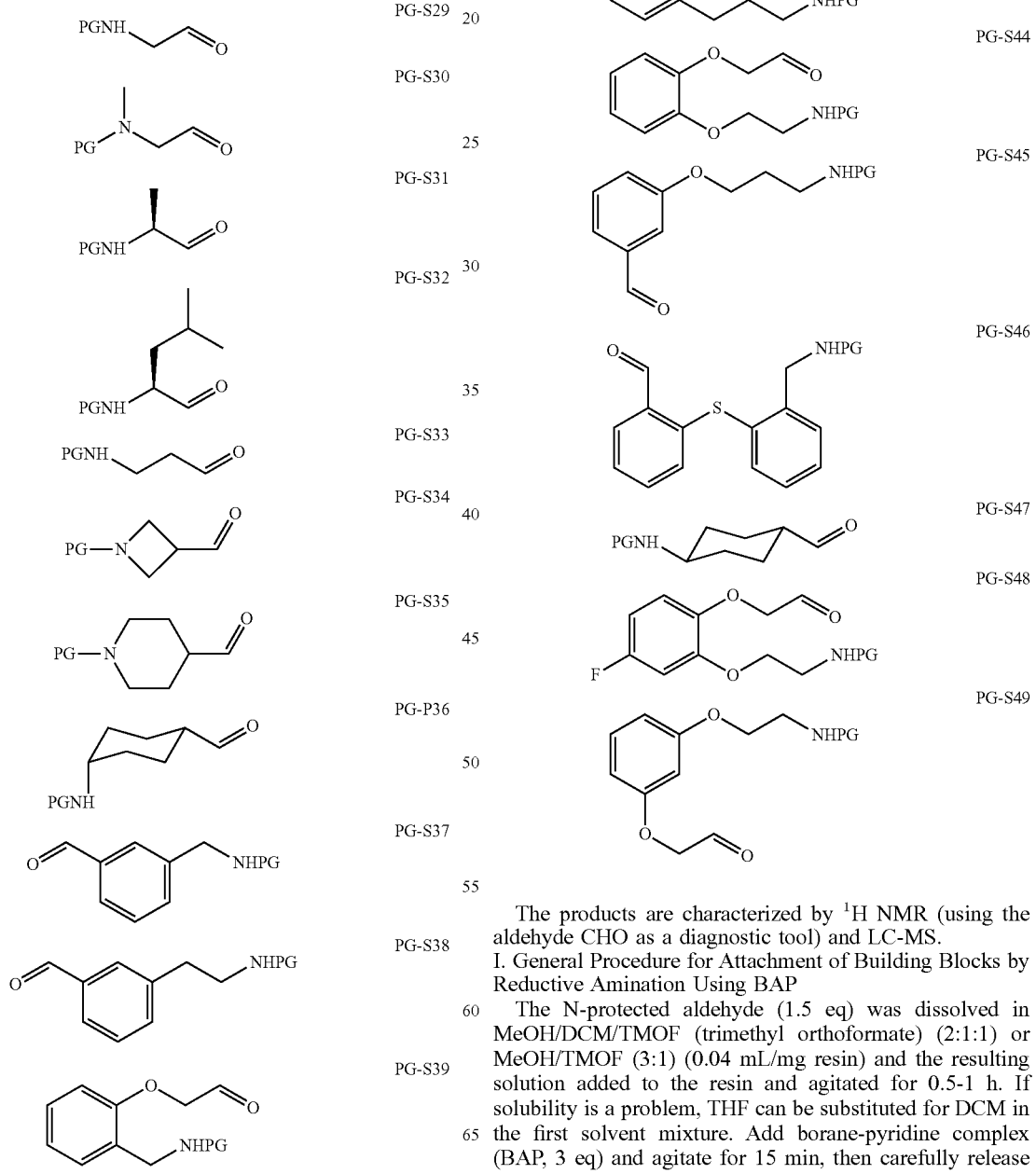

The products are characterized by $^1$H NMR (using the aldehyde CHO as a diagnostic tool) and LC-MS.

I. General Procedure for Attachment of Building Blocks by Reductive Amination Using BAP The N-protected aldehyde (1.5 eq) was dissolved in MeOH/DCM/TMOF (trimethyl orthoformate) (2:1:1) or MeOH/TMOF (3:1) (0.04 mL/mg resin) and the resulting solution added to the resin and agitated for 0.5-1 h. If solubility is a problem, THF can be substituted for DCM in the first solvent mixture. Add borane-pyridine complex (BAP, 3 eq) and agitate for 15 min, then carefully release built-up pressure and continue agitation o/n. If the reaction is not complete, add more BAP (2 eq) and agitate again o/n. After removal of the solvent, the resin was washed sequentially with DMF (2×), THF (1×), iPrOH (1×), DCM (1×), THF/MeOH (3:1, 1×), DCM/MeOH (3:1, 1×), DCM (2×), ether (1×), then dried in the usual manner.

For alkyl aldehydes, the quantity of reactants can be adjusted slightly to 1.4-1.5 eq of aldehyde and 2-3 eq of BAP in MeOH/DCM/TMOF (2:1:1). However, note that the reaction often does require up to 3 eq of reducing agent to go to completion with hindered amines. For benzylic aldehydes, add 3 eq of BAP in a mixture of 3:1 of MeOH/TMOF. If the reaction is not complete, add another 2 eq of BAP and agitate again o/n. Certain amino acids, such as Gly, undergo double alkylation easily (for such cases use Nos-Gly and attach the building block using Method 1L), while hindered amino acids such as Aib do not proceed to completion. In the latter instance, monitor reaction closely before proceeding to Fmoc deprotection and, if not complete, perform a second treatment.

J. General Procedure for Attachment of Building Blocks by Reductive Amination Using Sodium Triacetoxyborohydride As an alternative method, found particularly useful for benzylic aldehydes, sodium triacetoxyborohydride can be employed in the reductive amination process as follows. Dissolve 1.5-3 eq of the aldehyde in DCM (0.4 mL/mg resin), add the amine-containing resin, then agitate for 2 h. To the mixture, add NaBH(OAc)$_3$ (4-5 eq) and agitate o/n. Once the reaction is complete, remove the solvent, then wash the resin sequentially with DMF (2×), THF (1×), iPrOH (1×), DCM (1×), THF/MeOH (3:1, 1×), DCM/MeOH (3:1, 1×), DCM (2×), ether (1×) and dry in the usual manner. Please note that if the reductive amination is not complete, such as is often encountered with Pro or N-alkyl amino acids, additional aldehyde must be included as part of the second treatment.

K. General Procedure for Attachment of Building Blocks by Reductive Amination Using Sequential Sodium Cyanoborohydride and BAP Treatment For certain benzylic aldehydes, a sequential Borch and BAP reduction process can be beneficial as described in the following. In the first step, the Fmoc-protected aldehyde (3 eq) in NMP/TMOF (1:1) containing 0.5% glacial acetic acid) (0.4 mL/mg resin) is added to the resin in an appropriate reaction vessel and agitate for 30 min. To the mixture, add NaBH$_3$CN (10 eq), agitate for 10 min, then release pressure and continue agitation o/n. Remove the solvent and wash the resin sequentially with: DMF (2×), iPrOH (1×), DMF (1×), iPrOH (1×), DCM (2×), ether (1×). If in-process QC (Method 1E) shows incomplete reaction, proceed to suspend the resin in MeOH/DCM/TMOF (2:1:1), add BAP (2-3 eq) and agitate for 4 h. Remove the solvent and wash the resin sequentially with: DMF (2×), THF (1×), iPrOH (1×), DCM (1×), THF/MeOH (3:1, 1×), DCM/MeOH (3:1, 1×), DCM (2×), ether (1×), then dry in the usual manner. For building blocks containing a pyridine moiety, use MeOH/DCM (1:1), no TMOF, for the second treatment.

Reductive amination conditions and reagents for representative building blocks are as follows:

| Aldehyde Building Block(s) | Conditions and reagents |
|---|---|
| PG-S30 | 3 eq aldehyde, MeOH/DCM/TMOF 2:1:1, 3 eq BAP |
| PG-S31, PG-S32 and any amino aldehyde derived from an amino acid | 2-3 eq aldehyde, MeOH/DCM/TMOF 2:1:1, 3 eq BAP |
| PG-S37 | 1.5-2 eq aldehyde NaBH(OAc)$_3$/DCM |
| PG-S38 | 1.5 eq aldehyde, MeOH/TMOF 3:1, 3 eq BAP, followed by NaBH(OAc)$_3$, or NaBH(OAc)$_3$/DCM |
| PG-S43 | 1.5 eq aldehyde, MeOH/DCM/TMOF 2:1:1, 2 eq BAP |
| PG-S46 | 1.5 eq aldehyde, MeOH/TMOF 3:1, 3 eq. BAP or NaBH(OAc)$_3$ |
| PG-S49 | 1.5 eq aldehyde, MeOH/DCM/TMOF 2:1:1, 2 eq BAP |
| Pyridine-containing building blocks | 3 eq aldehyde, MeOH/DCM/TMOF (2:1:1), 2-3 eq BAP |

Although the above procedures for reductive amination describe the amine being the resin component and the aldehyde as the new building block added, it will be appreciated by those in the art that the reverse can also be performed in a similar manner, with the aldehyde component on the solid phase and the amine being the added component.

L. Standard Procedure for Building Block Attachment Using Mitsunobu Reaction.

Step 1L-1. Prepare a solution of HATU (5 eq), or other appropriate coupling agent, in NMP (0.04 mL/mg resin), monitoring the pH and adjusting to maintain around pH 8, then add to the nosyl-containing building block (5 eq, see Method 1M below) and agitate vigorously. To this solution, add DIPEA (10 eq), agitate briefly, then add to resin and agitate o/n. Use 50% of the indicated quantities if a repeat treatment is planned or anticipated. Upon completion, if the next step will be conducted immediately, wash the resin sequentially with DMF (2×), i-PrOH (1×), DMF (2×), then proceed. Otherwise, wash with DMF (2×); i-PrOH (1×); DMF (1×); DCM (2×), the last wash cycle can be alternatively done as DCM (1×), ether (1×), then dry the resin in the usual manner.

Step 1L-2. Dissolve the reactant hydroxy component (alcohol, phenol) (5 eq) in THF (0.04 mL/mg resin, 0.2 M) and add PPh$_3$-DIAD adduct (5 eq, see Method 1O below) and very briefly agitate (10-15 sec). Alternatively, prepare a solution of PPh$_3$ (5 eq) and alcohol (5 eq) in THF, cool to 0° C. and add DIAD (5 eq) dropwise. Stir for 15 min at 0° C., add nosyl-containing resin and agitate o/n. Filter the resin and wash sequentially with: THF (2×), toluene (1×), EtOH (1×), toluene (1×), THF (1×), iPrOH (1×), THF (1×), THF/MeOH (3:1, 1×), DCM/MeOH (3:1, 1×), DCM (2×), then dry the resin in the usual manner. Note that the order of addition is important for best results.

The Mitsunobu reaction is used preferentially to attach the following building blocks (note that some may require a second treatment): PG-S7, PG-S8, PG-S9, PG-S10, PG-S13, PG-S15.

The above procedure describes the building block being attached as its 2-nitrobenzenesulfonyl-derivative (Nos, nosyl) and then Fukuyama-Mitsunobu reaction conditions (Tet. Lett. 1995, 36, 6373-6374) used for attachment of the next building block. However, the building block can also be attached as its Fmoc, Boc or other N-protected derivative. In those cases, that protection must first be removed using the appropriate method, then the nosyl group installed and the alkyation executed as described in Method 1P below. Other sulfonamides containing electron-withdrawing substituents can also be utilized for this transformation, including, but not limited to, the 4-nitro-benzenesulfonyl, 2,4-dinitrobenzenesulfonyl (Tet. Lett. 1997, 38, 5831-5834) and Bts (benzothiazolylsulfonyl) (J. Am. Chem. Soc. 1996, 118, 9796-9797; Bioorg. Med. Chem. Lett. 2008, 18, 4731-4735) groups.

Further, although the above procedure describes the nosylated amine being on the resin and the hydroxy/phenol-containing component being present on the new building block added, it will be appreciated by those in the art that the reverse arrangement can also be utilized in an analogous manner, with the hydroxy/phenol-containing component on the solid phase and the nosylated amine being present on the added building block.

M. Standard Procedure for Nosyl Protection.

The amine substrate was added to a solution of 2-nitrobenzenesulfonyl chloride (Nos-Cl, 4 eq) and 2,4,6-collidine (10 eq) in NMP (0.04 mL/mg resin), then the reaction agitate for 1-2 h. The solution was removed and the resin washed sequentially with: DMF(2×), iPrOH (1×), DMF (1×), iPrOH (1×), DMF (2×), iPrOH (1×), DCM (2×), ether (1×). For protection of primary amines, Nos-Cl (1 eq) and 2,4,6-collidine (2.5 eq) in NMP (0.04 mL/mg resin) were used with agitation for 30-45 min. With more hindered amines, a second treatment might be required.

N. Standard Procedure for Nosyl Deprotection

A solution of 2-mercaptoethanol (10 eq), DBU (1,8-diazabicyclo[5.4.0.]undec-7-ene, 5 eq) in NMP (0.04 mL/mg resin) was prepared and added to the resin, then the mixture agitated for 8-15 min. The longer reaction time will be required for more hindered substrates. The resin was filtered and washed with NMP, then the treatment repeated. The resin was again filtered and washed sequentially with: DMF (2×), iPrOH (1×), DMF (1×), iPrOH (1×), DMF (1×), DCM (1×), iPrOH (1×), DCM (2×), ether (1×).

O. Standard Procedure for the Synthesis of PPh$_3$-DIAD Adduct.

This reagent was prepared in a manner essentially as described in WO 2004/111077. In a round bottom flask under nitrogen, DIAD (1 eq) was added dropwise to a solution of PPh$_3$ (1 eq) in THF (0.4 M) at 0° C., then the reaction stirred for 30 min at that temperature. The solid precipitate was collected on a medium porosity glass-fritted filter, wash the solid with cold THF (DriSolv grade or equivalent) to remove any color, then with anhydrous ether. The resulting white powder was dried under vacuum and stored under nitrogen in the freezer. It is removed shortly before an intended use.

P. Standard Procedure for N-Alkylation conditions (Tet. Lett. 1995, 36, 6373-6374). The nosyl group is then removed using Method 1N, then the next building block is added or, if the building block assembly is concluded, the precursor is cleaved from the resin (or the appropriate functionality on the first building block is deprotected if solution phase) and subjected to the macrocyclization reaction (Method 1R).

As an example utilized in the disclosure, certain N-methyl amino acids are not available commercially, while others are difficult to access or expensive. However, this procedure, using methanol (MeOH) as the alcohol components permits the installation of an N-methyl group on a nitrogen prior to its reaction with another building block.

Q. General Procedure for Cleavage from 2-Chlorotrityl Resin.

Add a solution of 20% HFIP (hexafluoro-2-propanol) in DCM (0.03 mL/mg resin) to the resin and agitate for 2 h. Filter the resin and wash it with 20% HFIP in DCM (0.01 mL/mg resin, 2×) and DCM (0.01 mL/mg resin, 1×). The filtrate is evaporated to dryness under vacuum.

R. General Procedure for Macrocyclization.

A solution of DEPBT (1.0-1.2 eq) and DIPEA (2.0-2.4 eq) in 25% NMP/THF (0.03 mL/mg original resin) is prepared and added to the residue from the previous step. In certain cases where compounds may be poorly soluble, dissolve the residue first in NMP, then add DEPBT and DIPEA in THF to the solution. The crude reaction mixture is filtered through one or more solid phase extraction (SPE) cartridges (for example PoraPak, PS-Trisamine, Si-Triamine, Si-Carbonate), then further purified by flash chromatography or preparative HPLC.

S. Standard Procedures for Final Protecting Group Deprotection

The method of deprotection depends on the nature of the protecting groups on the side chains of the macrocycle(s) being deprotected using the following guidelines.

1) For removal of Boc and tBu groups only, the following mixtures are utilized: 50% TFA,/3% triisopropylsilane (TIPS)/47% DCM or 50% TFA/45% DCM/5% H$_2$O (2 mL/cpd), agitate for 2 h, then concentrate in vacuo. For building blocks containing a double bond, 50% TFA/45% DCM/5% H$_2$O should be used as the cleavage solution to avoid reduction of the alkene.

2) For removal of tBu esters/ethers and trityl groups, utilize 75% TFA/22% DCM/3% TIPS (2 mL/cpd), agitate for 2 h, then concentrate in vacuo. Alternatively, 75% 4N

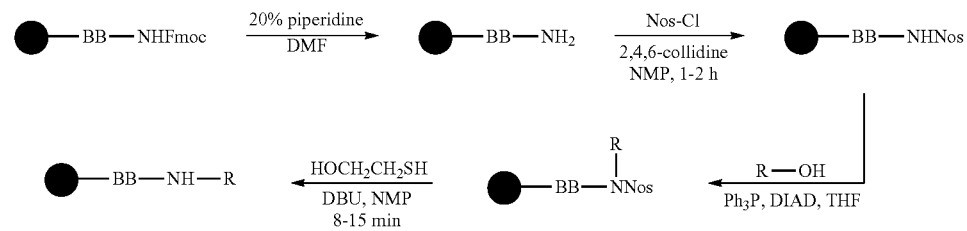

If the building block is attached as its Fmoc (depicted), Boc or other N-protected derivative, first remove that protection using the appropriate deprotection method, and execute installation of the nosyl group using Method 1M. With the Nos group in place, use the procedure of Step 1K-2 above to alkylate the nitrogen under Fukuyama-Mitsunobu HCl/dioxane/20% DCM/5% H$_2$O mixture can be employed, which works particularly well to ensure complete Ser(But) deprotection. Also, if the macrocycle does not contain Thr, Ser, His, Asn or Gln building block components, 75% TFA/20% DCM/5% H$_2$O (2 mL/cpd) can be used as an alternative cleavage mixture.

3) For removal of Pbf groups, use a mixture of 91% TFA/2% DCM/5% H₂O/2% TIPS (2 mL/cpd), agitate for 2 h protected from ambient light, then concentrate in vacuo.
4) Triethylsilane (TES) can also be used for the above deprotection procedures in place of TIPS, but should not be used with compounds containing Trp as it can reduce the indole moiety.

T. Standard Procedure for Reactions of Side Chain Functionalities on Solid Phase Using orthogonal protecting groups on side chains permits selective deprotection and reaction of the liberated group(s) in order to further diversify the library of macrocyclic compounds. Representative groups that can be derivatized with one or more of the procedures below are amines, alcohols, phenols and acids. This is typically performed while the structure is still bound to the resin and prior to cyclization. The following are representative types of transformations that have been performed:

1) With Acid Chlorides
Prepare a solution of acid chloride (3.5 eq) in THF, 2,4,6-collidine (5 eq) and add the substrate on resin, agitate at rt o/n. The reaction mixture becomes milky after about 5 min. After o/n, remove the solution and wash the resin with: DMF (2×), DCM (1×), iPrOH (1×), DMF (1×), DCM (2×), ether (1×), then dry in the usual manner.

2) With Sulfonyl Chlorides
Add the sulfonyl chloride (4 eq for aryl sulfonyl chlorides and 8 eq for alkyl sulfonyl chlorides) to the suspension of the resin and collidine (2.5× sulfonyl chloride eq) in NMP, then agitate for 1-2 h. Remove the solution, wash the resin sequentially with DMF (2×), iPrOH (1×), DMF (1×), DCM (2×), ether (1×), then dry the resin in the usual manner.

3) With Carboxylic Acids
To a solution of carboxylic acid (5 eq), DIPEA (10 eq), HATU (5 eq) in NMP, add the resin and agitate o/n. Remove the solution, wash the resin sequentially with DMF (2×), iPrOH (1×), DMF (1×), DCM (2×), ether (1×), then dry the resin in the usual manner.

4) Reductive Amination
The standard procedures (Methods 1I, 1J and 1K) described above are employed for reductive amination, except only 1 eq of the aldehyde is used to avoid double alkylation side products.

5) With Amines
Prepare a solution of 6-Cl-HOBt (1 eq), EDAC (3-(((ethylimino)-methylene)amino)-N,N-dimethylpropan-1-amine hydrochloride, 5 eq.), and DIPEA (1 eq) in NMP. Add the resin and agitate for 15 min. To this is added the amine (5 eq) and the reaction mixture agitated o/n. Remove the solutions and wash the resin sequentially with DMF (2×); iPrOH (1×); DMF (1×); DCM (2×), ether (1×), then dry in the usual manner.

U. Standard Procedure for Boc Protection

Di-tert-butyl dicarbonate (5 eq) was added to the amine substrate on resin and triethylamine (5 eq) in DCM (0.04 mL/mg resin), then the mixture agitated for 4 h. The solvent was removed and the resin washed sequentially with DMF (2×), iPrOH (1×), DMF (1×), DCM (2×), ether (1×), then dried the resin in the usual manner. An analogous method can be utilized in solution phase.

V. Standard Procedure for Boc Deprotection

The Boc-containing substrate on resin was treated with 25% TFA in DCM (0.04 mL/mg resin) and agitated for 30 min. The resin was washed sequentially with DMF (2×); iPrOH (1×); DMF (1×); DCM (2×), ether (1×), then dried in the usual manner.

W. Standard Procedures for Alloc Deprotection

Suspend the resin in DCM and bubble nitrogen gas through the mixture for 10 min, then add phenylsilane (PhSiH₃) (10-24 eq) and bubble nitrogen through the suspension again for 5 min. Add Pd(PPh₃)₄ (0.1 eq) and maintain the nitrogen flow for a further 5 min, then agitate the reaction for 4 h protected from light. Remove the solvent and wash the resin sequentially with: DMF (2×), iPrOH (1×), DCM (1×), DMF (1×), 0.5% sodium diethylthiocarbamate in DMF (3×), DMF (1×), iPrOH (1×), DMF (1×), DCM (2×), ether (1×), then dry in the usual manner.

X. Standard Procedure for Ally Ester Deprotection

Bubble nitrogen through the resin in DCM for 5 min, then evacuate and flush with nitrogen (3×) and bubble nitrogen through for a further 5 min. Add phenylsilane (10-24 eq), bubble nitrogen for 5 min, then add Pd(PPh₃)₄ (0.1 eq) and keep bubbling nitrogen through for a further 5 min. Close the reaction vessel, and agitate for 5 h protected from light. Remove the solution and wash the resin sequentially with: DMF (2×); iPrOH (1×); DCM (1×); DMF (1×); 0.5% sodium diethylthiocarbamate in DMF (3×); DMF (1×); iPrOH (1×); DMF (1×); DCM (2×); ether (1×) and dry in the usual manner.

Y. Standard Procedure for Ally Ether Deprotection

Bubble nitrogen through the resin in DCM for 5 min, then evacuate and flush with nitrogen (3×) and bubble nitrogen through for a further 5 min. Add phenylsilane (24 eq), bubble nitrogen for 5 min, then add Pd(PPh₃)₄ (0.10-0.25 eq) and keep bubbling nitrogen through for a further 5 min, close the reaction vessel and agitate at rt for 16 h (o/n) protected from light. Remove the solution and wash the resin sequentially with: DMF (2×); iPrOH (1×); DCM (1×); DMF (1×); 0.5% sodium diethylthiocarbamate in DMF (3×); DMF (1×); iPrOH (1×); DMF (1×); DCM (2×); ether (1×), then dry in the usual manner.

2. Analytical Methods

The following methods for qualitative and quantitative analysis and characterization of the macrocyclic compounds comprising the libraries of the disclosure are routinely performed both for monitoring reaction progress as well as to assess the final products obtained. These analytical methods will be referenced elsewhere in the disclosure by using the number 2 followed by the letter referring to the method or procedure, i.e. Method 2B for preparative purification.

A. Standard HPLC Methods for Purity Analysis

Column: Zorbax SB-C18, 4.6 mm×30 mm, 2.5 µm

Solvent A: Water+0.1% TFA

Solvent B: CH₃CN+0.1% TFA

UV Monitoring at λ=220, 254, 280 nm

Gradient Method A1

| Time (min) | Flow (mL/min) | % A | % B |
|---|---|---|---|
| 0 | 2 | 95 | 5 |
| 2.3 | 2 | 0 | 100 |
| 2.32 | 2 | 0 | 100 |
| 4 | 2 | 0 | 100 |

Gradient Method A2

| Time (min) | Flow (mL/min) | % A | % B |
|---|---|---|---|
| 0 | 2 | 95 | 5 |
| 0.5 | 2 | 95 | 5 |
| 5 | 2 | 0 | 100 |
| 7 | 2 | 0 | 100 |

The following methods are employed for preparative HPLC purification of the macrocyclic compounds comprising the libraries of the disclosure.

B. Standard HPLC Methods for Preparative Purification

Column: Atlantis Prep C18 OBD, 19 mm×100 mm, 5 μm
Solvent A: Aqueous Buffer (10 mM ammonium formate, pH 4)
Solvent B: MeOH Gradient Method P1

| Time (min) | Flow (mL/min) | % A | % B | Curve |
|---|---|---|---|---|
| 0 | 30 | 89 | 11 | — |
| 2 | 30 | 89 | 11 | 6 |
| 8 | 30 | 2 | 98 | 6 |
| 9.7 | 30 | 2 | 98 | 6 |
| 10 | 30 | 50 | 50 | 6 |

Gradient Method P2

| Time (min) | Flow (mL/min) | % A | % B | Curve |
|---|---|---|---|---|
| 0 | 30 | 80 | 20 | — |
| 2 | 30 | 80 | 20 | 6 |
| 8 | 30 | 2 | 98 | 6 |
| 9.7 | 30 | 2 | 98 | 6 |
| 10 | 30 | 50 | 50 | 6 |

Gradient Method P3

| Time (min) | Flow (mL/min) | % A | % B | Curve |
|---|---|---|---|---|
| 0 | 30 | 70 | 30 | — |
| 2 | 30 | 70 | 30 | 6 |
| 8 | 30 | 2 | 98 | 6 |
| 9.7 | 30 | 2 | 98 | 6 |
| 10 | 30 | 50 | 50 | 6 |

Gradient Method P4

| Time (min) | Flow (mL/min) | % A | % B | Curve |
|---|---|---|---|---|
| 0 | 30 | 60 | 40 | — |
| 2 | 30 | 60 | 40 | 6 |
| 8 | 30 | 2 | 98 | 6 |
| 9.7 | 30 | 2 | 98 | 6 |
| 10 | 30 | 50 | 50 | 6 |

Gradient Method P5

| Time (min) | Flow (mL/min) | % A | % B | Curve |
|---|---|---|---|---|
| 0 | 30 | 89 | 11 | — |
| 2 | 30 | 89 | 11 | 6 |
| 12 | 30 | 2 | 98 | 6 |
| 14.7 | 30 | 2 | 98 | 6 |
| 15 | 30 | 70 | 30 | 6 |

Gradient Method P6

| Time (min) | Flow (mL/min) | % A | % B | Curve |
|---|---|---|---|---|
| 0 | 30 | 80 | 20 | — |
| 2 | 30 | 80 | 20 | 6 |
| 12 | 30 | 2 | 98 | 6 |
| 14.7 | 30 | 2 | 98 | 6 |
| 15 | 30 | 70 | 30 | 6 |

Gradient Method P7

| Time (min) | Flow (mL/min) | % A | % B | Curve |
|---|---|---|---|---|
| 0 | 30 | 89 | 11 | — |
| 2 | 30 | 89 | 11 | 6 |
| 11.7 | 30 | 2 | 98 | 6 |
| 12 | 30 | 89 | 11 | 6 |

Gradient Method P8

| Time (min) | Flow (mL/min) | % A | % B | Curve |
|---|---|---|---|---|
| 0 | 30 | 89 | 11 | — |
| 3 | 30 | 89 | 11 | 6 |
| 11.7 | 30 | 2 | 98 | 6 |
| 12 | 30 | 89 | 11 | 6 |

Typically, methods P5, P6, P7 and P8 are used if a sample requires additional purification after the initial purification run.

Note that lower flow rates (i.e. 20-25 mL/min) can be utilized with concomitant lengthening of the gradient run time.

The use of ammonium formate buffer results in the macrocyclic compounds, typically, being obtained as their formate salt forms.

3. Methods of Use

The libraries of macrocyclic compounds of the present disclosure are useful for application in high throughput screening (HTS) on a wide variety of targets of therapeutic interest. The design and development of appropriate HTS assays for known, as well as newly identified, targets is a process well-established in the art (Methods Mol. Biol. 2009, 565, 1-32; Mol. Biotechnol. 2011, 47, 270-285) and such assays have been found to be applicable to the interrogation of targets from any pharmacological target class. These include G protein-coupled receptors (GPCR), nuclear receptors, enzymes, ion channels, transporters, protein-protein interactions and nucleic acid-protein interactions. Methods for HTS of these target classes are known to those skilled in the art (*High Throughput Screening in Drug Discovery*, J. Hüser, ed., Wiley-VCH, 2006, pp 343, ISBN 978-3-52731-283-2; High Throughput Screening: Methods and Protocols, 2$^{nd}$ edition, W. P. Janzen, P. Bernasconi, eds., Springer, 2009, pp 268, ISBN 978-1-60327-257-5; Cell-Based Assays for High-Throughput Screening: Methods and Protocols, P. A. Clemons, N. J. Tolliday, B. K. Wagner, eds., Springer, 2009, pp 211, ISBN 978-1-60327-545-3). These methods can be utilized to identify modulators of any type, including agonists, activators, inhibitors, antagonists, and inverse agonists. The Examples describe representative HTS assays in which libraries of the present disclosure are useful. The targets include an enzyme, a G protein-coupled receptor and a protein-protein interaction. Prior to use, the libraries are typically stored at or below −70° C. as 10 mM stock solutions in 100% DMSO, then diluted to an appropriate test concentration, for example 10 μM in buffer.

The libraries of compounds of the present disclosure are thus used as research tools for the identification of bioactive hits from HTS that in turn serve to initiate drug discovery efforts directed towards new therapeutic agents for the prevention and treatment of a range of medicalconditions. As used herein, "treatment" is not necessarily meant to imply cure or complete abolition of the disorder or symptoms associated therewith.

Further embodiments of the present disclosure will now be described with reference to the following Examples. It should be appreciated that these Examples are for the purposes of illustrating embodiments of the present disclosure, and do not limit the scope of the disclosure.

Example 1

Preparation of Building Blocks

Protected building blocks S1, S2, S3, S4, S5, S6, S7 and S8 were prepared by N-protection of the readily commercially available materials 2-aminoethanol, 2-methylaminoethanol, L-alaninol, L-leucinol, 3-aminopropan-1-ol, 4-aminobutan-1-ol, 5-aminopentan-1-ol, 6-aminohexan-1-ol, respectively, with methods and conditions known to those in the art, for example Boc$_2$O and K$_2$CO$_3$ for N-Boc derivatives, and Fmoc-OSu (as shown in Example 1A) or Fmoc-Cl and base for N-Fmoc derivatives. Similarly, protected derivatives of S9, S11, S12, S13, S14, S15, S16, S23, S24 and S28 can be prepared directly from the commercially available starting materials indicated:

S9: 2-(2-aminoethoxy)ethanol (Alfa Aesar (Ward Hill, Mass.), Cat. No. L18897);
S11: 3-(Hydroxymethyl)azetidine (SynQuest Laboratories (Alachua, Fla.), Cat. No. 4H56-1-NX);
S12: 4-piperidinyl-methanol (Alfa Aesar Cat. No. 17964);
S13: [2-(Aminomethyl)phenyl]methanol (Ark Pharm (Libertyville, Ill.) Cat. No. AK138281, as HCl salt);
S14: [3-(Aminomethyl)phenyl]methanol (Combi-Blocks (San Diego, Calif.) Cat. No. QB-3285);
S15: 2-(2-aminoethyl)benzoic acid (Ark Pharm Cat. No. AK100976);
S16: 3-(2-aminoethyl)benzoic acid (Ark Pharm Cat. No. AK100975);
S23: 2-[2-(aminomethyl)phenylthio]benzyl alcohol (Aldrich (Milwaukee, Wis.), Cat. No. 346314);
S24: cis-4-aminocyclohexyl methanol (Enamine (Monmouth Junction, NJ), Cat. No. EN300-105832);
S28: trans-4-aminocyclohexyl methanol (Enamine), Cat. No. EN300-106767);

Building blocks S10 and S21 were synthesized as described in the literature (J. Med. Chem. 2006, 49, 7190-7197, Supplementary Information; compounds 4g and 4b, respectively).

Structures of representative amino alcohol building blocks of the present disclosure, presented as their N-protected derivatives, the usual species utilized, are:

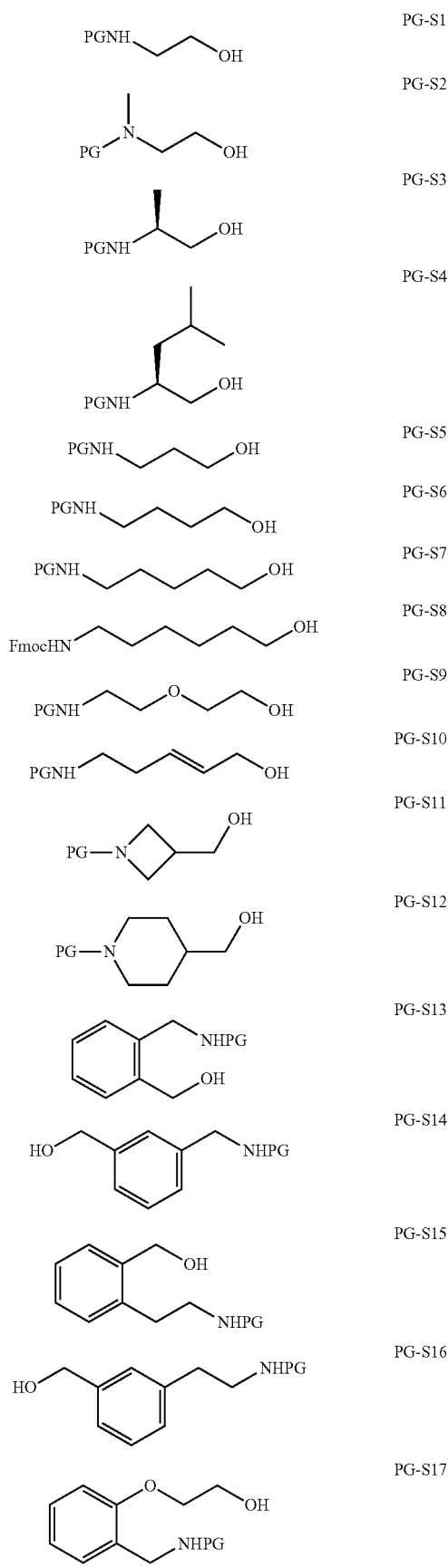

-continued

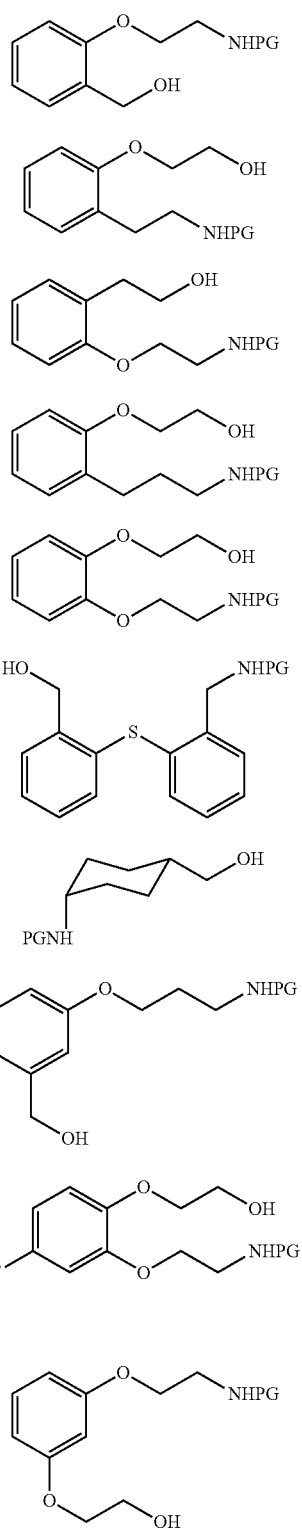

PG-S18
PG-S19
PG-S20
PG-S21
PG-S22
PG-S23
PG=S24
PG-S25
PG-S26
PG-S27
PG-S28

A. Representative Procedure for Fmoc Protection

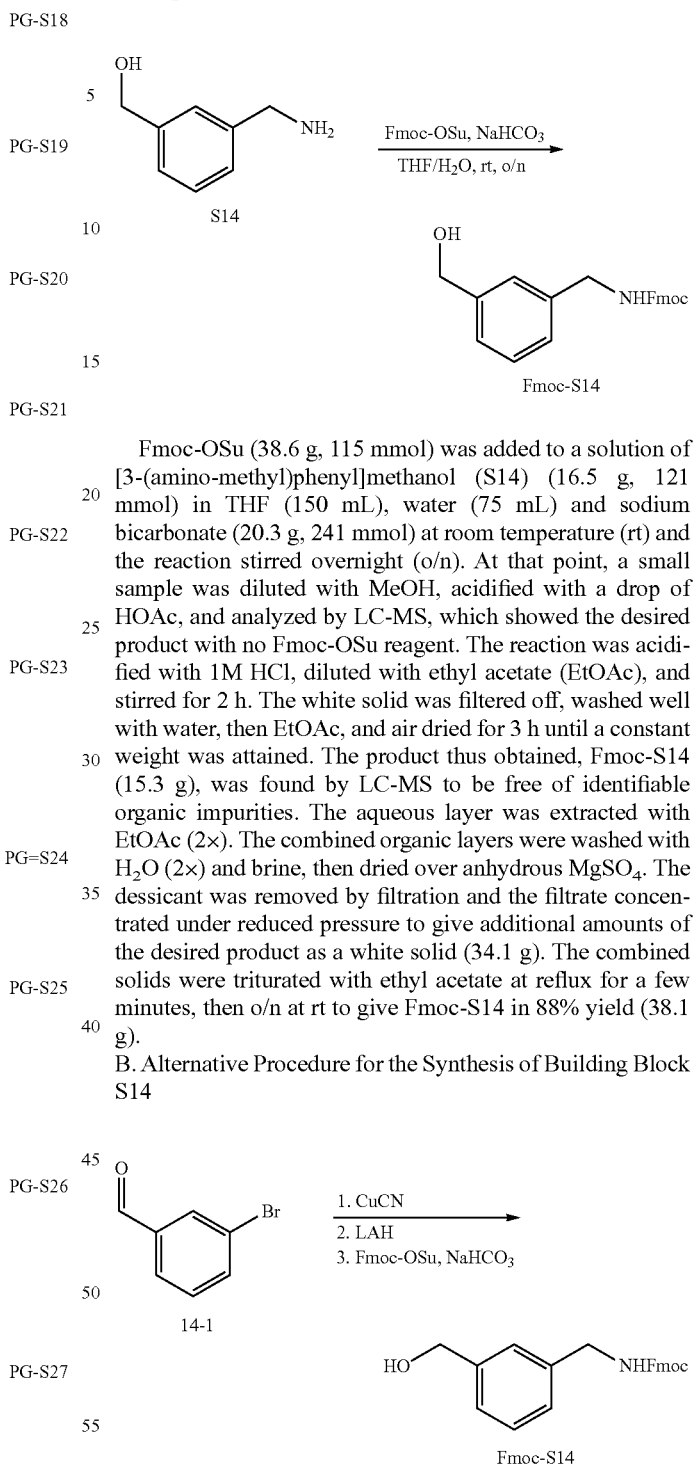

Fmoc-OSu (38.6 g, 115 mmol) was added to a solution of [3-(amino-methyl)phenyl]methanol (S14) (16.5 g, 121 mmol) in THF (150 mL), water (75 mL) and sodium bicarbonate (20.3 g, 241 mmol) at room temperature (rt) and the reaction stirred overnight (o/n). At that point, a small sample was diluted with MeOH, acidified with a drop of HOAc, and analyzed by LC-MS, which showed the desired product with no Fmoc-OSu reagent. The reaction was acidified with 1M HCl, diluted with ethyl acetate (EtOAc), and stirred for 2 h. The white solid was filtered off, washed well with water, then EtOAc, and air dried for 3 h until a constant weight was attained. The product thus obtained, Fmoc-S14 (15.3 g), was found by LC-MS to be free of identifiable organic impurities. The aqueous layer was extracted with EtOAc (2×). The combined organic layers were washed with $H_2O$ (2×) and brine, then dried over anhydrous $MgSO_4$. The dessicant was removed by filtration and the filtrate concentrated under reduced pressure to give additional amounts of the desired product as a white solid (34.1 g). The combined solids were triturated with ethyl acetate at reflux for a few minutes, then o/n at rt to give Fmoc-S14 in 88% yield (38.1 g).

B. Alternative Procedure for the Synthesis of Building Block S14

Conversion of 3-bromobenzaldehyde (14-1) to the nitrile was accomplished through nucleophilic aromatic substitution with copper(I) cyanide. Subsequent reduction of both the carbonyl and nitrile with lithium aluminum hydride (LAH) provided the amino alcohol after appropriate work-up, which was then protected with Fmoc using standard conditions (Example 1A). The corresponding Boc derivative is accessed by substituting $Boc_2O$ and $K_2CO_3$ in the last step.

C. Standard Procedure for the Synthesis of Building Blocks S15 and S16

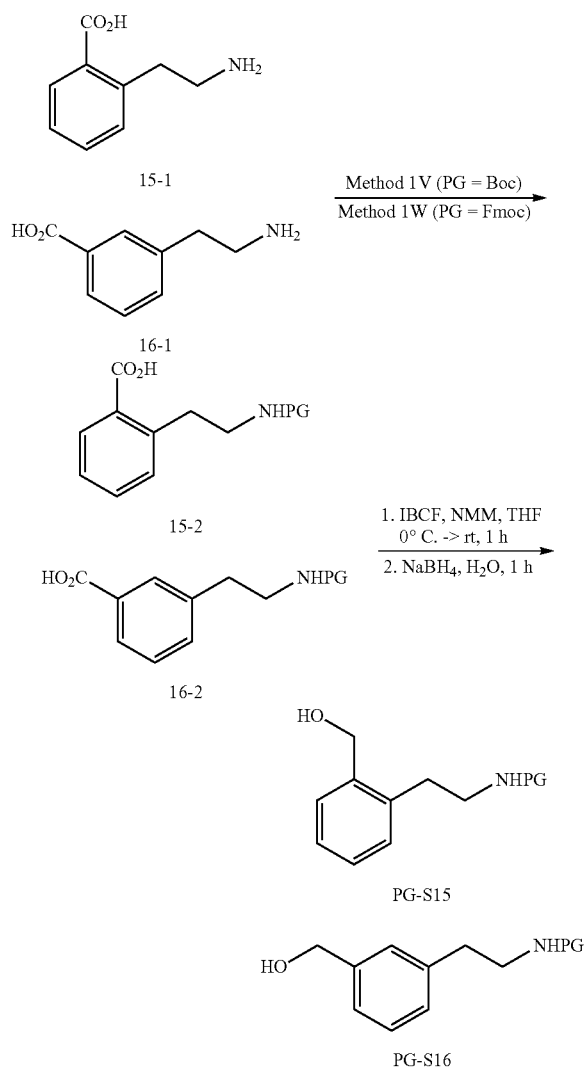

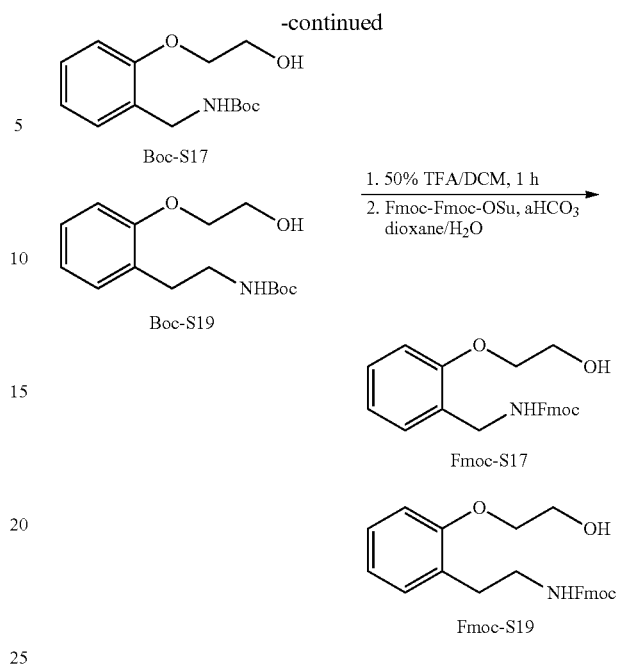

Analogous procedures are utilized to access protected derivatives of S15 and S16 starting, respectively, from 2-(2-aminoethyl)benzoic acid (15-1, Ark Pharm, Cat. No. AK-32693) and 3-(2-aminoethyl)benzoic acid (16-1, Ark Pharm, Cat. No. AK-34290). The amine is protected with Boc (Method 1U) or Fmoc (Method 1W, Example 1A) in the standard manner to provide 15-2 and 16-2. The acid was then reduced to the alcohol through the mixed anhydride (see Example 1I) to yield PG-S15 and PG-S16.

D. Standard Procedure for the Synthesis of Protected Building Blocks S17 and S19

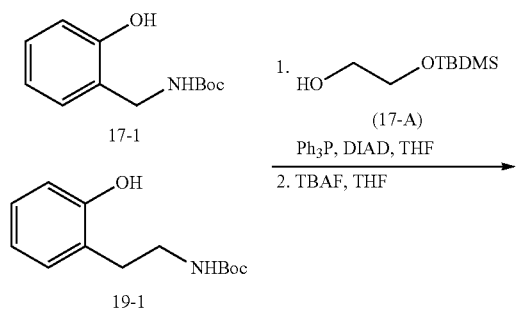

An identical strategy is employed for the preparation of the protected building blocks of S17 and S19. The former begins from 2-(2-aminomethyl)-phenol (Combi-Blocks Cat. No. A-3525, as HCl salt), while the latter proceeds from 2-(2-aminoethyl)phenol (Ark Pharm Cat. No. 114741). The amine of each is protected with Boc in the usual manner ($Boc_2O$, $Na_2CO_3$) to give 17-1 and 19-1, respectively. For each, the free phenol is then derivatized using a Mitsunobu reaction with triphenylphosphine and diisopropylazodicarboxylate (DIAD) along with the mono-t-butyldimethylsilyl (TBDMS) ether of ethylene glycol (17-A), followed by removal of the silyl protecting group with tetrabutylammonium fluoride (TBAF, 1 M in THF) to give Boc-S17 and Boc-S19. These can be converted into the corresponding Fmoc analogues through the deprotection-protection sequence shown.

As an alternative approach to these two molecules, the phenol can be alkylated via a substitution reaction utilizing base (for example $K_2CO_3$, NaH) and a suitable derivative of 17-A containing a leaving group (i.e. halide, mesylate, tosylate, triflate) in place of the hydroxyl, which can be prepared from 17-A using procedures known to those in the art.

E. Standard Procedure for the Synthesis of Protected Building Blocks S18 and S20

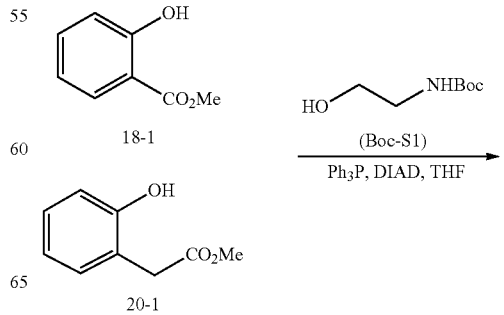

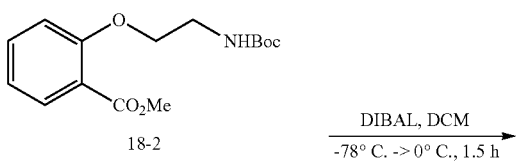

18-2

DIBAL, DCM
-78° C. -> 0° C., 1.5 h

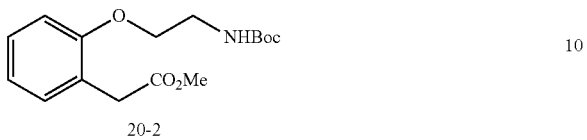

20-2

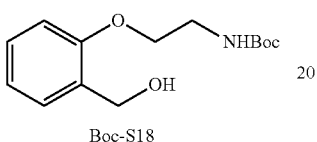

Boc-S18

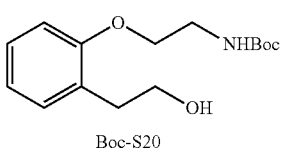

Boc-S20

An essentially identical strategy is utilized for the synthesis of the protected building blocks S18 and S20. The former starts from methyl salicylate (18-1), while the latter initiates from methyl 2-(2-hydroxyphenyl)acetate (20-1, Ark Pharm Cat. No. AK-76378). Reaction of the phenol of these two materials with Boc-2-aminoethanol (Boc-S1) under Mitsunobu conditions gives 18-2 and 20-2, respectively. Reduction of the ester group with diisobutylaluminum hydride (DIBAL) provides the Boc-protected target compounds. Conversion of the protecting group from Boc to Fmoc can be effected as already described to give Fmoc-S17 and Fmoc-S19.

F. Standard Procedure for the Synthesis of Building Block S22 and S27

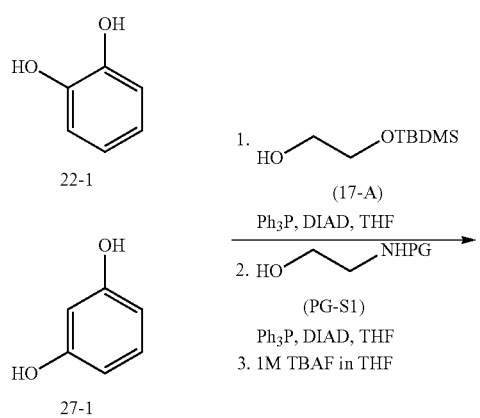

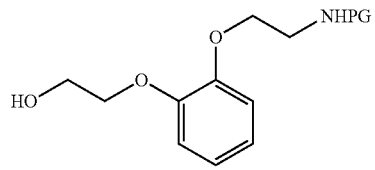

PG-S22

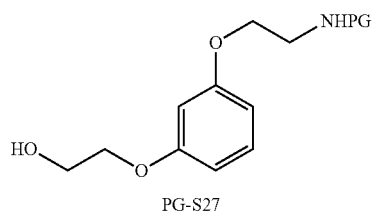

PG-S27

The two phenols of catechol (22-1) or resorcinol (27-1) were sequentially reacted under Mitsunobu conditions, first with 1 eq of the mono-protected diol 17-A, followed by 1 eq of an appropriate N-protected-2-amino-ethanol (PG-S1). Material that does not react fully can be extracted with aqueous base (hence, the PG chosen must be compatible with such conditions). Standard deprotection of the silyl ether with 1 M TBAF in THF provides PG-S22 and PG-527. The N-protecting group can be interchanged as already described if necessary.

G. Standard Procedure for the Synthesis of Building Block S25

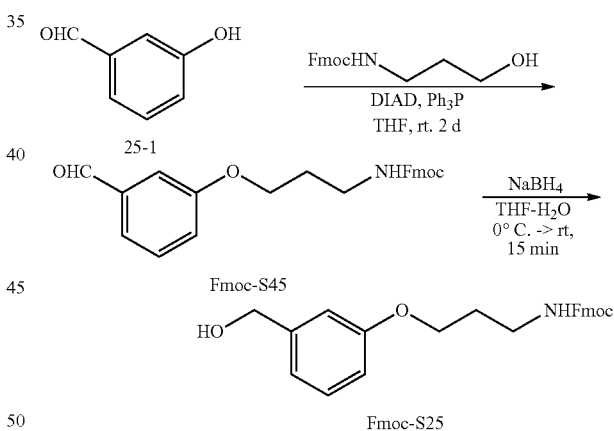

To a solution of 3-hydroxybenzaldehyde (25-1, 100 mg, 0.819 mmol), Ph$_3$P (215 mg, 0.819 mmol) and Fmoc-3-amino-1-propanol (Fmoc-55, 256 mg, 0.860 mmol) in THF (30 mL) at rt was added dropwise DIAD (0.159 mL, 0.819 mmol). The mixture was stirred at rt for 2 d, then evaporated in vacuo and the residue purified by flash chromatography (hexanes:EtOAc: 95:5 to 50:50 over 14 min). Product-containing fractions were concentrated under reduced pressure to leave the desired coupled product, Fmoc-545, as a white solid, $^1$H NMR and MS consistent with structure. Reduction of the aldehyde with sodium borohydride under standard conditions provided Fmoc-525.

H. Standard Procedure for the Synthesis of Building Block S26

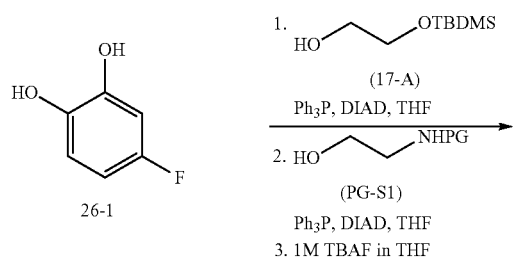

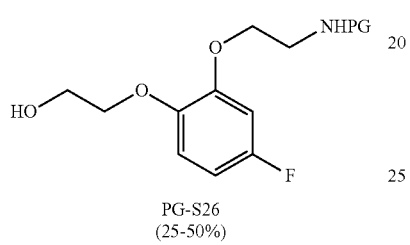

PG-S26
(25-50%)

In a manner analogous to that described above for PG-S22 and PG-S27, the two phenol moieties of 4-fluoro-catechol (26-1, Fluorochem Cat. No. 306910) were sequentially reacted under Mitsunobu conditions, first with 17-A, then with PG-S1. Although the initial conversion is regioselective for the phenol para to the fluorine substituent, the first reaction uses only a single equivalent of 17-A to minimize formation of side products. Standard deprotection of the silyl ether with 1 M TBAF in THF provides PG-526.

I. Standard Procedure for the Synthesis of Oxazole Amino Acids

The synthetic approach followed that described in the literature by Nefzi (ACS Comb. Sci. 2014, 16, 39-45) and shown above for a generic oxazole amino acid. Standard coupling of the Boc-protected amino acid I-1 with L-serine methyl ester provided the dipeptide (I-2). Cyclization to form the oxazole (I-3) was effected using the two step literature method through the intermediate oxazoline (Org. Lett. 2000, 2, 1165-1168). Subsequent cleavage of the methyl ester and acidification provided the oxazole amino acid (I-4). The Boc derivatives thus obtained could be converted to the corresponding Fmoc derivatives (I-5) using standard transformations. Representative compounds prepared using this methodology are shown below along with the overall yields from I-1 to I-5. $^1$H NMR and LC-MS were consistent with the indicated structures.

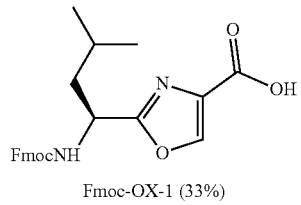

Fmoc-OX-1 (33%)

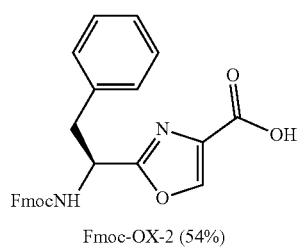

Fmoc-OX-2 (54%)

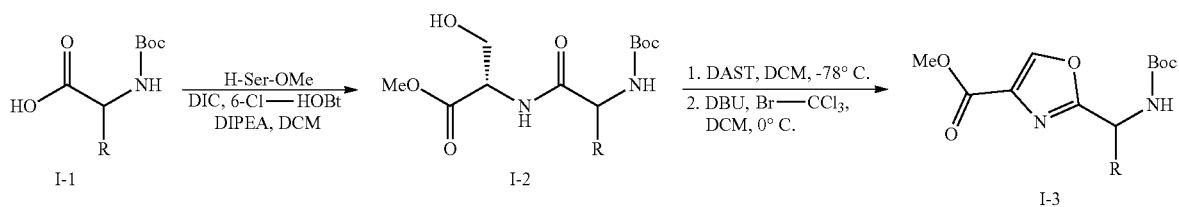

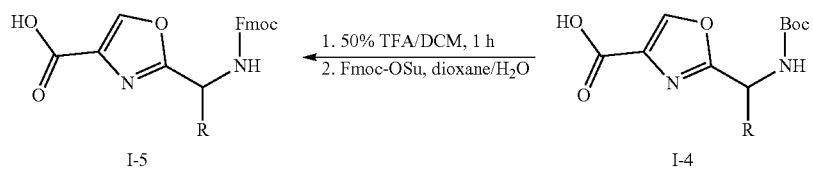

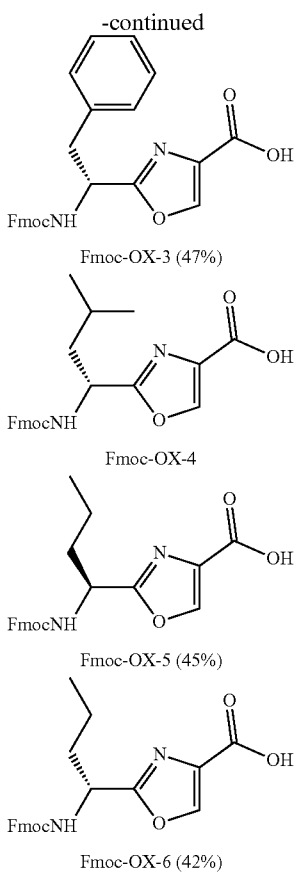

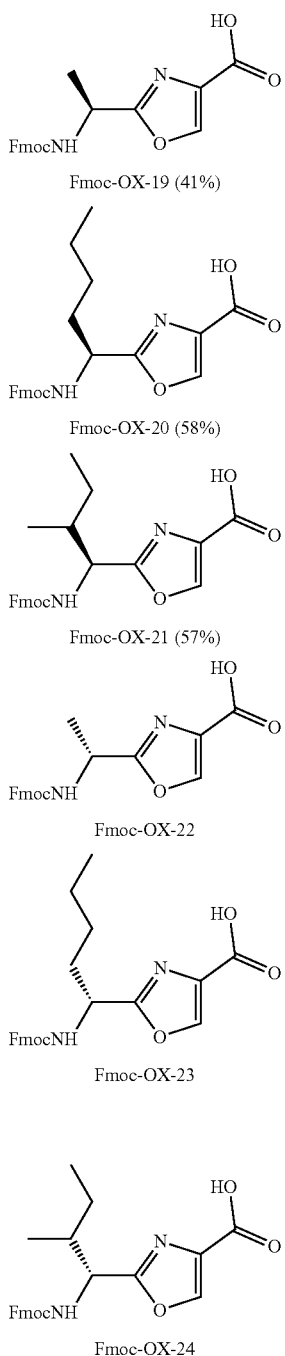

40° C. for 16 h. LC/MS of a sample showed the desired product. The solvent was removed under reduced pressure, then EtOAc added to the residue followed by aqueous NaHCO₃(sat.). The organic layer was separated, washed with water, then with 1N HCl, followed by brine (2×), dried over MgSO4, filtered and concentrated leaving the product as a clear oil (7.66 g, 83%). This procedure in conjunction with the other steps in the standard process led to the following oxazole building blocks in the yields indicated. The corresponding enantiomers are accessed similarly starting from the appropriate Fmoc-D-amino acids.

An improved procedure (Org. Proc. Res. Develop. 2009, 13, 310-314) has been applied to the first step with better yields for certain derivatives as described for a representative amino acid substrate.

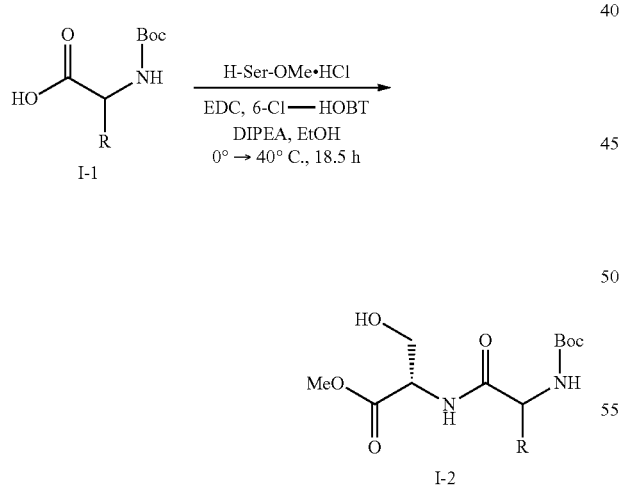

To a solution of Boc-Ala (6 g, 31.7 mmol), H-Ser-OMe.HCl (5.08 g, 32.7 mmol), and 6-Cl-HOBt (1.613 g, 9.51 mmol) in EtOH (81 mL) was added DIPEA (11.60 ml, 66.6 mmol) and the mixture cooled in an ice-bath under nitrogen. EDC (1-Ethyl-3-(3-dimethylaminopropyl)carbodiimide hydrochloride, 6.69 g, 34.9 mmol) was added to the cold reaction mixture. The reaction was stirred for 1.5 h in the ice-bath, then for 1 h at rt after which it was heated to

J. Representative Procedure for the Reduction of Acid Building Blocks to Alcohols

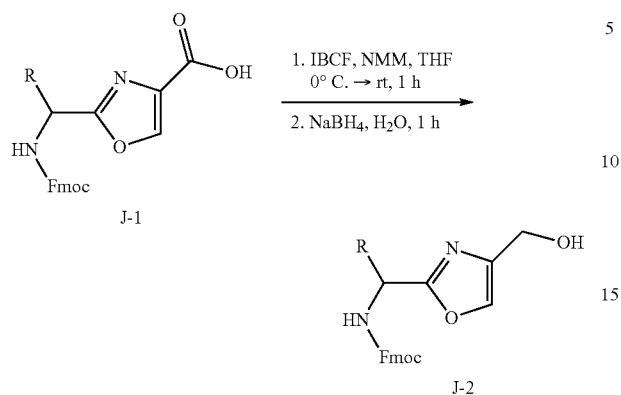

As an example of the transformation of amino acid building blocks (J-1) to the corresponding amino alcohol (J-2) components, a solution of Fmoc-OX-1 (6.55 g, 15.6 mmol) in THF (100 mL) under nitrogen was cooled in an ice-salt bath, then isobutyl chloroformate (IBCF, 2.04 mL, 15.6 mmol) and 4-methylmorpholine (NMM, 1.71 mL, 15.6 mmol) added dropwise simultaneously via syringes over 5 min. The mixture was stirred at 0° C. for 30 min, then at rt for another 30 min. The white precipitate that formed was filtered into a 500 mL flask through a pre-washed Celite® pad and rinsed with anhydrous ether (71.4 mL). The flask was placed under nitrogen in an ice-bath, and a mixture of sodium borohydride (0.884 g, 23.4 mmol) in water (10 mL) added in one shot with the neck of the flask left open. Significant gas evolution was observed and the reaction mixture formed a suspension. More water (20 mL) was added, the ice-bath removed, and the reaction stirred rapidly with monitoring by LC-MS and TLC. After 1 h at ambient temperature, LC-MS analysis indicated that the reaction was complete. More water was then added and the organic layer extracted with EtOAc (2×150 mL). The combined organic layers were washed sequentially with 1 M citric acid, NaHCO$_3$ (sat.), water, brine, and dried over anhydrous MgSO$_4$. The mixture was filtered and the filtrate concentrated under reduced pressure to give Fmoc-OX-7 in 71.4% yield (4.52 g). The product was sufficiently pure to be used without further purification for subsequent reactions. Other non-limiting examples of the compounds from this transformation are shown below:

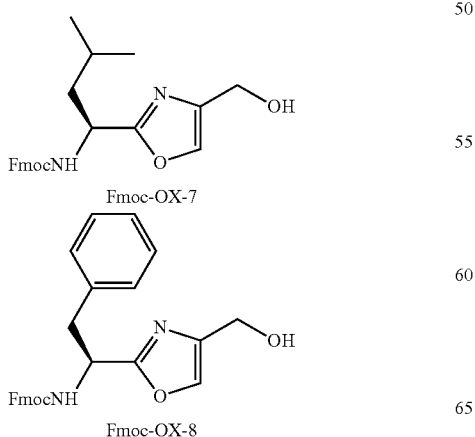

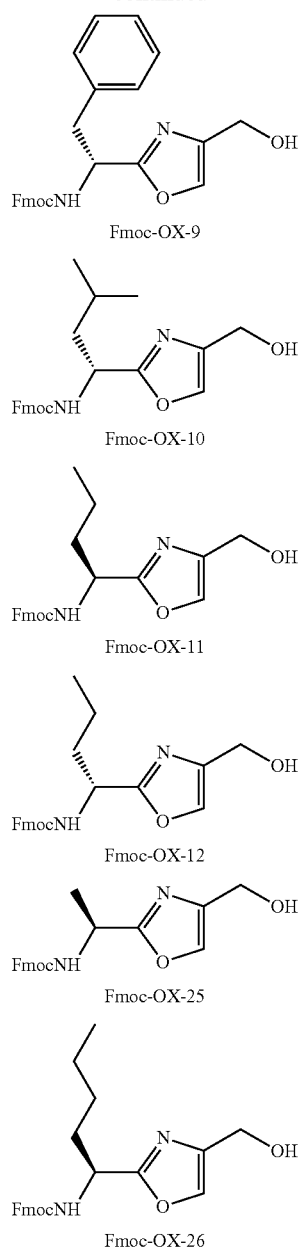

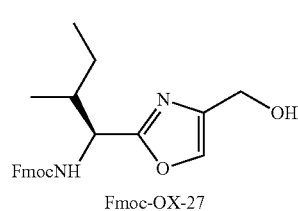

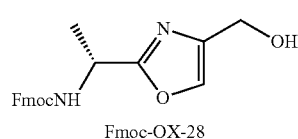

-continued

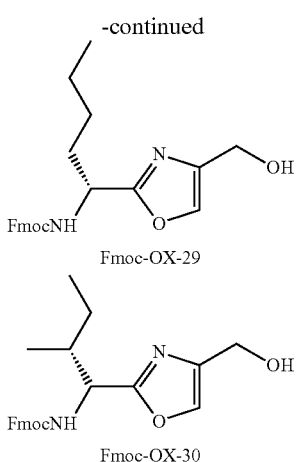

Fmoc-OX-29

Fmoc-OX-30

This same procedure can be utilized for the transformation of standard protected amino acid derivatives into the corresponding alcohols.

Alternatively, the N-protected amino acid ester can be reduced directly to the N-protected amino alcohol, for example with lithium borohydride or DIBAL, which can provide a more efficient route to these building blocks in certain cases.

K. Representative Procedure for the Oxidation of Alcohol Building Blocks to Aldehydes Using Pyridine Sulfur Trioxide Complex

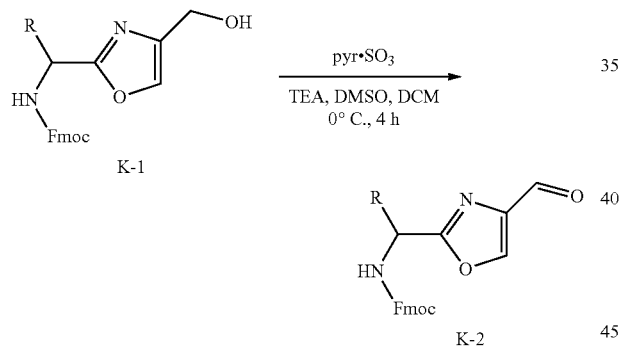

The following procedure is provided as an example of the transformation of amino alcohol building blocks such as K-1 to the corresponding amino aldehyde components (K-2) for use in a reductive amination attachment procedure. In a 250 mL round-bottomed flask was dissolved Fmoc-OX-7 (3.95 g, 9.72 mmol) in CH$_2$Cl$_2$ (46.3 mL) and DMSO (10 mL). Triethylamine (TEA, 5.42 mL, 38.9 mmol) was added and the solution cooled to 0° C. under nitrogen. Pyridine sulfur trioxide complex (pyr.SO$_3$, 4.64 g, 29.2 mmol) was added as a solution in DMSO (15.8 mL) over 20 min and the reaction monitored by TLC and LC-MS until complete. After 4 h, the reaction was cooled to 0° C. in an ice-bath, EtOAc/ether (1:1, 150 mL) was added, and the organic layer washed with saturated NaHCO$_3$ (1×150 mL). More water was added as necessary to dissolve any insoluble material. The aqueous layer was extracted with EtOAc/ether (1:1, 3×150 mL). The organic extracts were combined and washed sequentially with 1M KHSO$_4$ (1×150 mL), saturated NH$_4$Cl (2×120 mL), water (200 mL), brine (2×200 mL), dried over anhydrous MgSO$_4$, filtered and the filtrate concentrated under reduced pressure to give Fmoc-OX-13 in 95% yield (3.72 g) as a clear semi-solid. The product thus obtained was acceptable for use in the further transformations without further purification. Other non-limiting examples of the compounds from this transformation, with selected yields, are shown below:

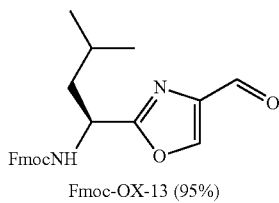

Fmoc-OX-13 (95%)

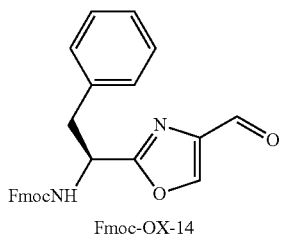

Fmoc-OX-14

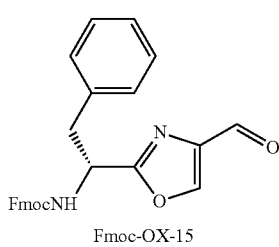

Fmoc-OX-15

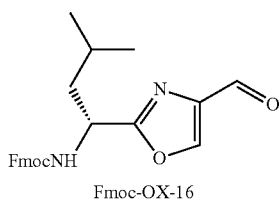

Fmoc-OX-16

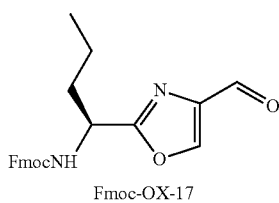

Fmoc-OX-17

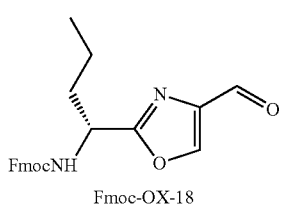

Fmoc-OX-18

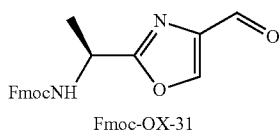

Fmoc-OX-31

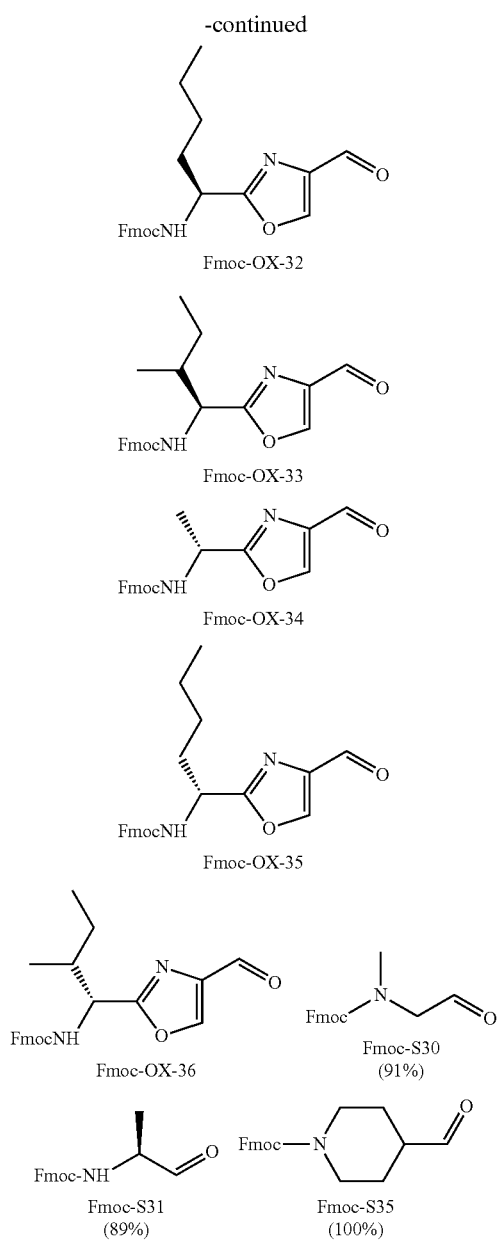

L. Representative Procedure for the Oxidation of Building Blocks to Aldehydes with Manganese Dioxide

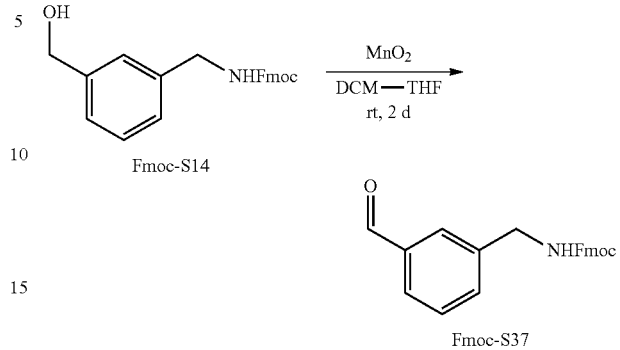

Fmoc-S14 (38 g, 106 mmol) was suspended in DCM (151 mL) and THF (151 mL). Manganese dioxide (Strem (Newburyport, Mass., USA) Cat. No. 25-1360, 92 g, 1.06 mol) was added and the reaction agitated o/n on an orbital shaker at 200 rpm. A small sample was filtered through MgSO$_4$ with THF and analyzed by LC-MS, which indicated 87% conversion. More MnO$_2$ (23.0 g, 264 mmol) was added and the reaction agitated for 16 h more, at which time the reaction was found to have progressed to 90% conversion. Another quantity of MnO$_2$ (23.0 g, 264 mmol) was added and agitation continued for another 16 h, after which LC-MS indicated complete reaction. The reaction mixture was filtered through MgSO$_4$ with filter-paper on top, and the trapped solids rinsed with THF. The residual MnO$_2$ was agitated with THF, filtered and washed with THF. The filtrate was passed again through MgSO$_4$ and several layers of filter-paper and the filtrate was pale yellow with no MnO$_2$. Evaporation of the filtrate under reduced pressure left a light yellow solid. The solid was triturated with ether, heated to reflux and allowed to cool slowly with stirring. After stirring for 4 h, the white solid that formed was filtered to give Fmoc-537 as a white solid (28.6 g, 80 mmol, 76.0% yield). $^1$H-NMR and LC-MS were consistent with the expected product. The MnO$_2$ was washed again with THF (300 mL) with agitation o/n, followed by filtration and concentration of the filtrate in vacuo to give 1.0 g of crude product which was combined with 2.0 g recovered from the mother liquor of the above trituration and this combined solid triturated with ether. A second crop of the desired product was isolated as an off white solid (1.60 g, 4.48 mmol, 4.2% additional yield).

M. Standard Procedures for the Synthesis of Oxazole and Thiazole Amino Acids

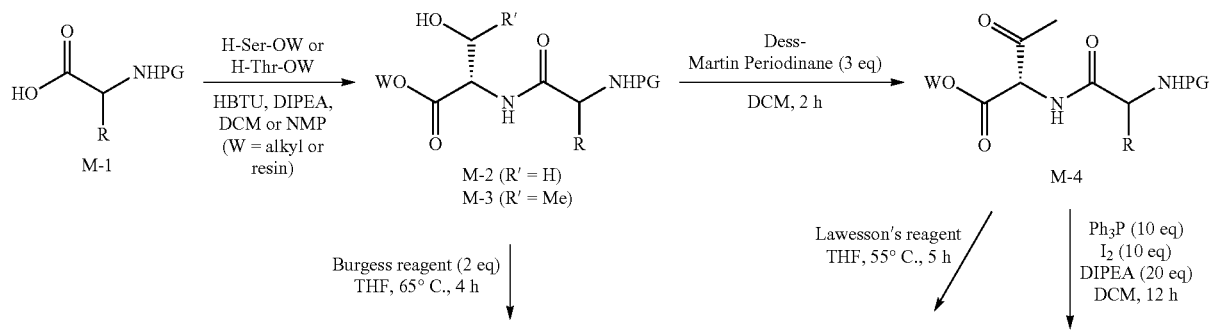

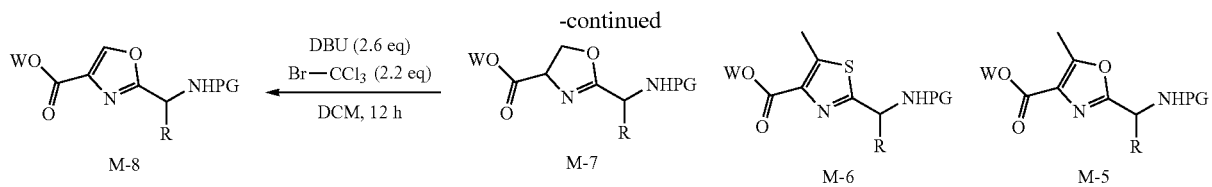

Variations of the routes as described in the literature procedure (Org. Lett. 2006, 8, 2417-2420) permit both oxazole and thiazole-containing building blocks to be accessed from a common intermediate. In the first instance, the dipeptide (M-3), from standard coupling of an N-protected amino acid (AA) to carboxy-protected Thr, was oxidized to the ketone M-4, which underwent cyclodehydration to either the oxazole (M-5) or the thiazole (M-6) using the reagents indicated. In contrast, the AA-Ser dipeptide (M-3) was treated with Burgess reagent to effect cyclodehydration to the oxazoline (M-7), which could then be further oxidized to the oxazole (M-8). The two-step process proved to be more efficient with this substrate.

N. Standard Procedure for the Synthesis of Thiazole Amino Acids

Step 1N-3. In anhydrous EtOH (30 mL/mmol) were dissolved N-3 (1 eq), 3-bromo-2-oxo-propionic acid (bromopyruvic acid, 1.5 eq), and $CaCO_3$ (5.5 eq) and the resulting mixture stirred under an inert atmosphere at rt for 24 h. Upon reaction completion, water and ethyl acetate were added and the organic layer washed sequentially with water and 5% $H_2SO_4$ (aq), then dried over anhydrous $MgSO_4$. The solution was filtered, the filtrate evaporated in vacuo, and the resulting residue purified by crystallization from an appropriate solvent or solvent mixture to give the desired product (N-4).

The protected thiazole amino acids (N-4) can be converted to their corresponding alcohols and aldehydes in a manner similar to those described for the oxazole amino acids in Examples 1J and 1K.

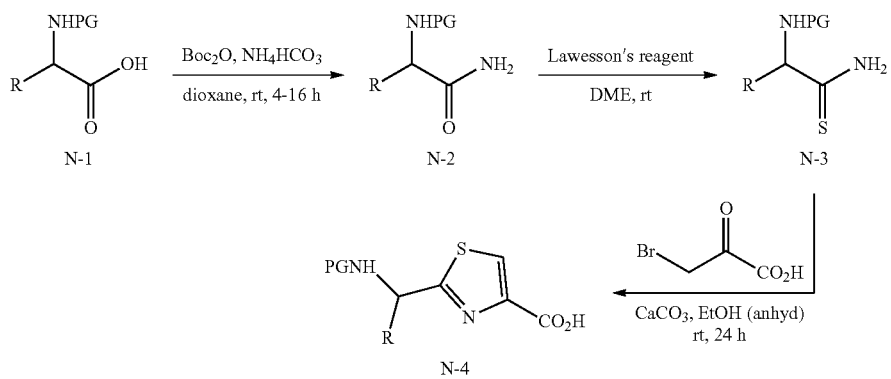

Step 1N-1. Construction of protected thiazole building blocks (N4) was performed based upon the literature method (J. Pept. Sci. 1999, 5, 392-398) starting from the N-protected amino acid (N-1) and utilizing a Hantzsch cyclocondensation as the key step. To a stirred solution of N-1 (1 eq), pyridine (0.05 mL/eq) and di-t-butyl-dicarbonate ($Boc_2O$, 1.3 eq) in an appropriate solvent (10-15 mL) was added ammonium hydrogen carbonate (1.25 eq) and the mixture stirred for 4-16 h. Upon completion, EtOAc or a mixture of $CHCl_3$:1-propanol (9:1) was added and the organic layer washed with water and 5% $H_2SO_4$ (aq), then dried over anhydrous $MgSO_4$. The solution was filtered, the filtrate evaporated in vacuo, and the resulting product triturated with ether. Alternatively, the reaction mixture was diluted with water (30-40 mL), then stirred until crystallization was completed. The solid amide (N-2) was collected by filtration, washed with water, dried in vacuo and recrystallized if necessary.

Step 1N-2. Lawesson's reagent (0.75 mmol/mmol of N-2) and a solution of N-2 (1 eq) in dimethoxyethane (DME, 20 mL/mmol) was stirred at rt) until the starting material was consumed as indicated by TLC or HPLC. The solvent was evaporated in vacuo and the residue recrystallized from an appropriate solvent to yield the intermediate thioamide (N-3).

O. Standard Procedure for the Synthesis of Trifunctional Thiazole Amino Acids

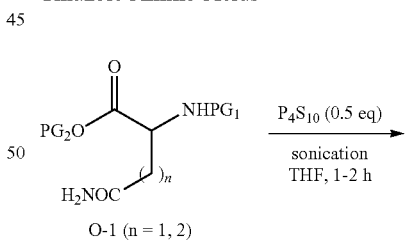

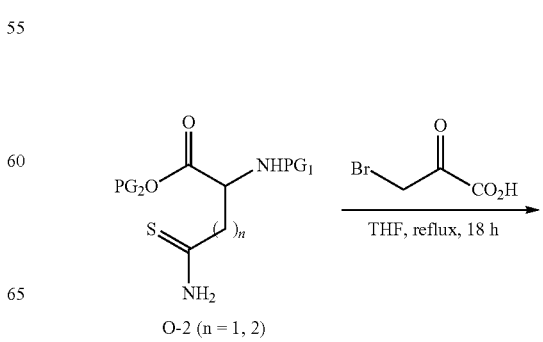

-continued

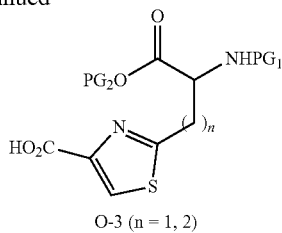

O-3 (n = 1, 2)

An analogous strategy to that of Example 1N can be employed as illustrated to construct trifunctional thiazole building blocks from protected derivatives of Asn and Gln (ACS Comb. Sci. 2014, 16, 1-4). With the appropriate orthogonal protection strategy in place, these compounds can be subjected to attachment of the next building block or cyclization through any of the three reactive groups.

Step 1O-1. The (bis)protected amino acid (O-1, 1 eq) is dissolved in THF (9 mL/mmol), then phosphorous pentasulfide (0.5 eq) added quickly. The reaction vessel is sealed and the mixture placed in a sonicating bath for 1-2 h until TLC indicates the conversion is complete. Ice is added to the bath to cool the exothermic reaction. The yellow precipitate that forms is separated by filtration and discarded. The filtrate is concentrated in vacuo and the residue purified by flash chromatography using 100% DCM or DCM followed by EtOAc to provide the desired thioamide (O-2) in 70-80% yield.

Step 1O-2. To O-2 (1 eq) in THF (3 mL/mmol) is added bromopyruvic acid (1.1 eq) and the reaction brought to reflux in a heating bath and maintained for 18 h. After cooling to rt, the solvent is removed in vacuo, then the residue dissolved in DCM and filtered through a pad of charcoal to remove the dark color. The filtrate is evaporated under reduced pressure and the crude product purified by flash chromatography. The product thus obtained is recrystallized to provide O-3 as a white solid in 50-55% yield.

P. Standard Procedure for the Synthesis of Thiazole and Imidazole Amino Acids

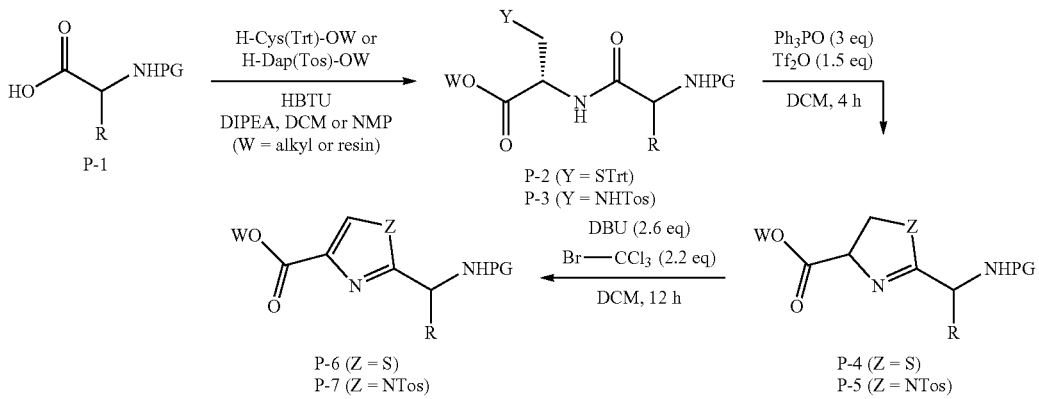

Based upon the literature report (Org. Lett. 2006, 8, 2417-2420), similar processes can be employed to prepare thiazole and imidazole building blocks either in solution or on solid phase. Formation of the dipeptide (P-2, P-3) under standard conditions is followed by cyclodehydration to the thiazoline (P-4) or imidazoline (P-5) using bis(triphenyl) oxodiphosphonium trifluoro-methanesulfonate generated in situ from triphenylphosphine oxide and triflic anhydride. Oxidation with BrCCl$_3$/DBU then provided the thiazole (P-6) or imidazole (P-7) products.

Q. Standard Procedure for the Synthesis of Imidazole Amino Acids

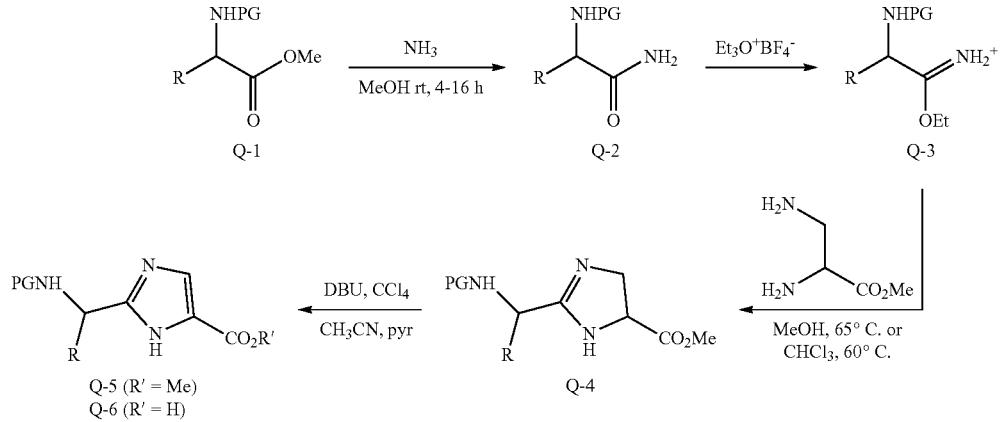

The N-protected amino acid amide (Q-2) was prepared using well-established methodology from the corresponding ester (Q-1), then the imidazole amino acid ester (Q-5) synthesized based upon the literature method (J. Pept. Sci. 1999, 5, 392-398). Treatment with Meerwein's Reagent (triethyloxonium tetrafluoroborate) or the analogous hexafluorophosphate provides the O-alkylated intermediate (Q-3), an excess (1.3 eq) of which is reacted with L-2,3-diaminopropionic acid methyl ester (1 eq, as its HCl salt) in refluxing MeOH or CHCl$_3$ (4 mL/mmol) to yield the imidazoline (Q-4). Oxidation of Q-4 is conducted by adding DBU (3 eq) in a mixture of CCl$_4$ (5 mL/mmol), pyridine (3 mL/mmol) and acetonitrile (5 mL/mmol). After 3 h at rt, the solvent is removed in vacuo and the residue dissolved in EtOAc. The organic is extracted with 0.5 N HCl, then the aqueous phase back-extracted with EtOAc (2×). The combined organic phase is washed with brine, dried over anhydrous MgSO$_4$. The dessicant is removed by filtration, the filtrate evaporated in vacuo, and the residue recrystallized. Cleavage of the methyl ester with a method compatible with the other protecting groups of Q-5 gives the imidazole amino acid Q-6.

The imidazole amino acids can be converted to their corresponding alcohols and aldehydes in a similar manner to those described for the oxazole amino acids (Examples 1J and 1K), although protection of the imidazole NH with a Boc, Trt or other appropriate removable moiety is required to minimize side reactions.

R. Standard Procedure for the Synthesis of Building Block S50

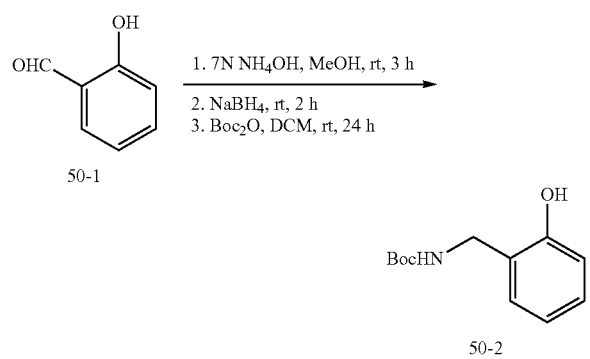

Step S50-1. To a solution of 2-hydroxybenzaldehyde (50-1, 10.0 g, 82 mmol) in MeOH (100 mL) at rt was added 7 N ammonium hydroxide (29.2 mL, 205 mmol) in MeOH. The solution turned yellow in color. The homogeneous solution was stirred at rt for 3 h at which time TLC showed a new, more polar product. Solid sodium borohydride (1.73 g, 45.7 mmol) was added to the reaction in small portions and stirring continued at rt for 2 h. The reaction was quenched with 10% NaOH, then the methanol evaporated in vacuo. The resulting aqueous solution was diluted with EtOAc (50 mL) and the layers separated. The organic layer was washed with 10% HCl (3×). The aqueous washes were combined with the original aqueous layer and the pH adjusted to 9 with 10% NaOH. A white solid formed, which was isolated by filtration, washed and dried in air. This material was treated with Boc$_2$O (19.0 mL, 82.0 mmol) in DCM and stirred at rt for 24 h. The reaction mixture was diluted with water, extracted with EtOAc, the organic layers dried over MgSO$_4$, filtered, then evaporated in vacuo to leave an oil that was purified by flash chromatography (hexanes:EtOAc, 9:1 to 1:1) to give 50-2 as a colorless oil (65% yield).

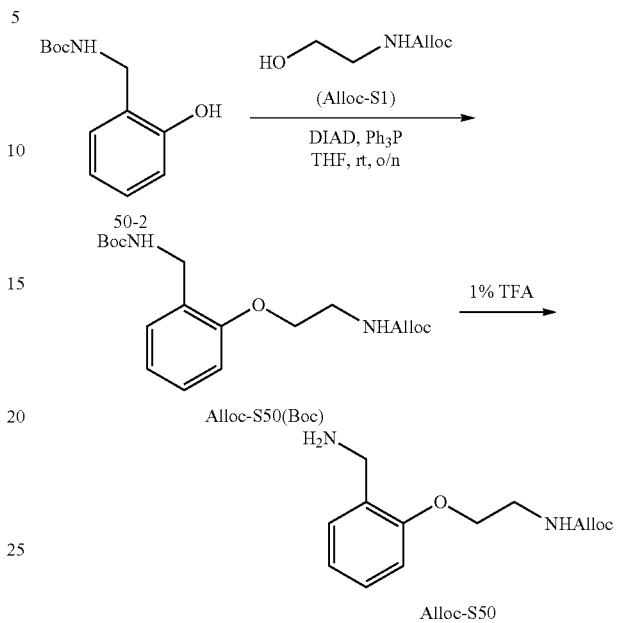

Step S50-2. To a solution of 50-2 (3.86 g, 17.29 mmol) and Alloc-S1 (3.76 g, 25.9 mmol) in THF (200 mL) at rt was added Ph$_3$P (6.80 g, 25.9 mmol), then DIAD (5.04 mL, 25.9 mmol). The mixture was stirred at rt o/n at which point TLC indicated reaction completion. The solvent was evaporated in vacuo and the residue purified by flash chromatography (100 g silica, hexanes:EtOAc: 90:10 to 70:30 over 13 min) to give two fractions. The main fraction contained primarily the desired product, while the minor fraction was contaminated with a significant amount of solid hydrazine by-product. The minor fraction was triturated with an ether/hexane mixture, then filtered. The residue from concentration in vacuo of the mother liquors from this filtration were combined with the major fraction and subjected to a second flash chromatography (hexanes:EtOAc: 90:10 to 60:40 over 14 min) to give the diprotected product, Alloc-S50(Boc), as a colorless oil (46% yield). This was treated with 1% TFA to remove the Boc group, which provided Alloc-S50.

S. Alternative Procedure for the Synthesis of Building Block S50

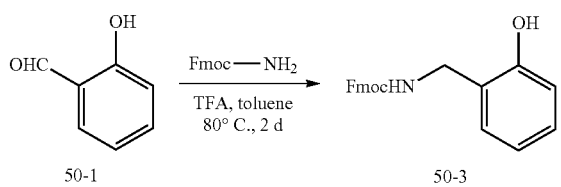

To 2-hydroxybenzaldehyde (50-1, 605 mg, 4.96 mmol) and (9H-fluoren-9-yl)methyl carbamate (593 mg, 2.48 mmol) in toluene (30 mL) was added TFA (0.955 mL, 12.4 mmol). The mixture was stirred at 80° C. for 2 d, then allowed to cool to rt, evaporated in vacuo and the residue purified by flash chromatography (hexanes:EtOAc: 95:5 to 50:50 over 14 min). Product-containing fractions were concentrated under reduced pressure to leave 50-3 as a solid, $^1$H NMR and LC-MS consistent with structure, 0.39 mg, estimated 46% yield.

As another alternative, 2-(aminomethyl) phenol is commercially available (Matrix Scientific Cat. No. 009264; Apollo Scientific Cat. No. OR12317; Oakwood Cat. No. 023454) and can be protected with Fmoc using standard methods (Method 1W, Example 1A).

Analogously as described for 50-2, 50-3 can be converted into Alloc-S50 by a reaction sequence involving Mitsunobu coupling followed by standard Fmoc deprotection (Method 1F).

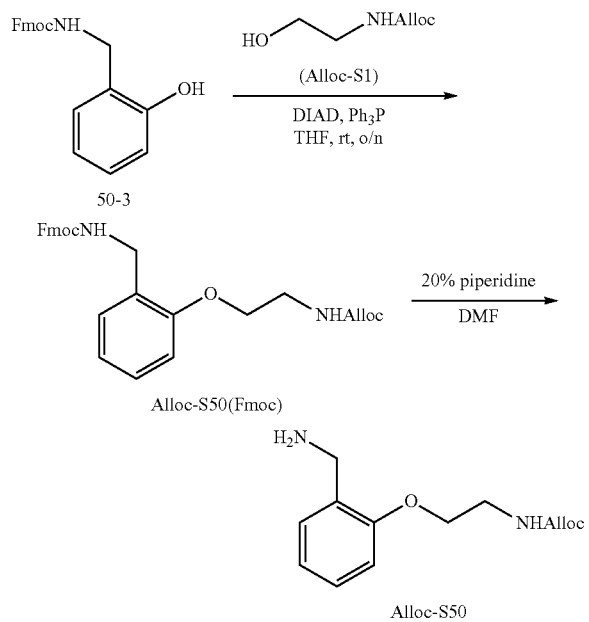

T. Standard Procedure for the Synthesis of Building Block S51

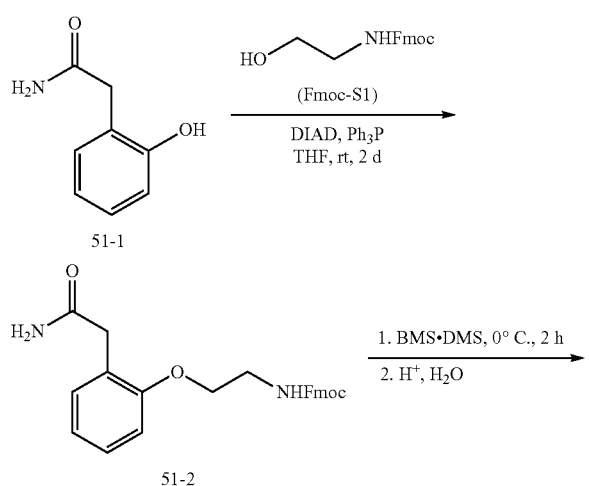

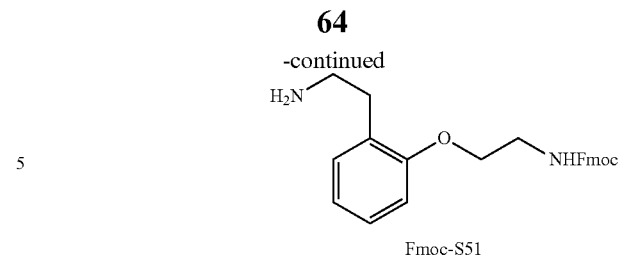

To a solution of 2-(2-hydroxyphenyl)acetamide (50-1, Fluorochem Cat. No. 375417, 50.0 mg, 0.331 mmol), Ph$_3$P (104 mg, 0.397 mmol) and Fmoc-2-aminoethanol (Fmoc-S1, 122 mg, 0.430 mmol) in THF (4 mL) at rt was added DIAD (0.077 ml, 0.397 mmol) dropwise. The mixture was stirred at rt overnight, then evaporated in vacuo and the residue purified by flash chroatography. The intermediate amide 51-2 was then treated with borane-dimethyl sulfide at 0° C. for 2 h, then quenched carefully with water, followed by dilute acid. The product Fmoc-S51 was isolated after standard work-up. Use of other appropriate nitrogen protecting groups on 2-aminoethanol provides alternative protected derivatives of S51.

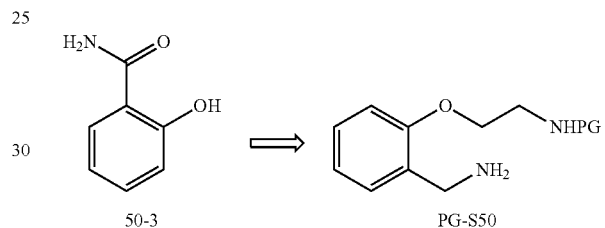

In a similar manner, various protected derivatives of S50 can be accessed starting from salicylamide (50-3) as an alternative route to these materials.

U. Standard Procedure for the Synthesis of Building Block S52

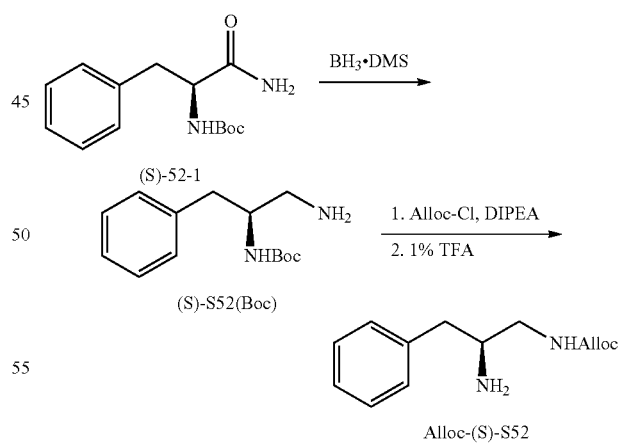

Boc-L-phenylalaninamide ((S)-52-1), purchased from commercial suppliers or prepared from the unprotected precursor by treatment with Boc$_2$O under standard conditions, was reduced with borane-dimethyl sulfide to give the mono-protected diamine (S)—S52(Boc). The primary amine was protected in the usual manner with an Alloc group, then the Boc group removed using standard conditions to yield Alloc-(S)—S52. The enantiomer was synthesized similarly from D-phenylalaninamide. Such a procedure is also applicable to the synthesis of other diamines from α-N-protected amino acid amides.

Example 2

Synthesis of a Representative Library of Macrocyclic Compounds of Formula (Ib)

The synthetic scheme presented in Scheme 2 was followed to prepare the library of macrocyclic compounds 1-289 on solid support. The oxazole amino acid ($BB_1$) was loaded onto the resin (Method 1D), then the next two building blocks ($BB_2$, $BB_3$) sequentially coupled (Method 1G) after removal of the Fmoc protection (Method 1F) on the preceding building block. The final building block ($BB_4$) was attached using reductive amination (Methods 1I or 1J) followed by selective N-terminal deprotection (Method 1F and macrocyclization (Method 1R). The side chain protecting groups were then removed (Method 1S) and the resulting crude product purified by preparative HPLC (Method 2B). The amounts of each macrocycle obtained, their HPLC purity and confirmation of their identity by mass spectrometry (MS) are provided in Table 1A. The individual structures of the compounds thus prepared are presented in Table 1B.

TABLE 1A

| Cpd | $BB_1$ | $BB_2$ | $BB_3$ | $BB_4$ | Wt (mg)[1] | Purity[2] | MS (M + H) |
|---|---|---|---|---|---|---|---|
| 1 | Fmoc-OX-1 | Fmoc-D-Trp(Boc) | Fmoc-Ala | Fmoc-S33 | 6.7 | 100 | 557 |
| 2 | Fmoc-OX-1 | Fmoc-D-Tyr(But) | Fmoc-Ala | Fmoc-S33 | 5.9 | 100 | 534 |
| 3 | Fmoc-OX-1 | Fmoc-Trp(Boc) | Fmoc-Ala | Fmoc-S33 | 6.0 | 100 | 557 |
| 4 | Fmoc-OX-1 | Fmoc-Tyr(But) | Fmoc-Ala | Fmoc-S33 | 6.9 | 97 | 534 |
| 5 | Fmoc-OX-1 | Fmoc-D-Trp(Boc) | Fmoc-Asn(Trt) | Fmoc-S33 | 12.0 | 100 | 600 |
| 6 | Fmoc-OX-1 | Fmoc-D-Tyr(But) | Fmoc-Asn(Trt) | Fmoc-S33 | 10.7 | 98 | 577 |
| 7 | Fmoc-OX-1 | Fmoc-Trp(Boc) | Fmoc-Asn(Trt) | Fmoc-S33 | 9.1 | 100 | 600 |
| 8 | Fmoc-OX-1 | Fmoc-Tyr(But) | Fmoc-Asn(Trt) | Fmoc-S33 | 10.1 | 100 | 577 |
| 9 | Fmoc-OX-1 | Fmoc-D-Trp(Boc) | Fmoc-Asp(OBut) | Fmoc-S33 | 8.6 | 100 | 601 |
| 10 | Fmoc-OX-1 | Fmoc-D-Tyr(But) | Fmoc-Asp(OBut) | Fmoc-S33 | 9.8 | 100 | 578 |
| 11 | Fmoc-OX-1 | Fmoc-Trp(Boc) | Fmoc-Asp(OBut) | Fmoc-S33 | 7.2 | 100 | 601 |
| 12 | Fmoc-OX-1 | Fmoc-Tyr(But) | Fmoc-Asp(OBut) | Fmoc-S33 | 6.4 | 100 | 578 |
| 13 | Fmoc-OX-1 | Fmoc-D-Trp(Boc) | Fmoc-D-Ala | Fmoc-S33 | 6.5 | 100 | 557 |
| 14 | Fmoc-OX-1 | Fmoc-D-Tyr(But) | Fmoc-D-Ala | Fmoc-S33 | 6.8 | 100 | 534 |
| 15 | Fmoc-OX-1 | Fmoc-Trp(Boc) | Fmoc-D-Ala | Fmoc-S33 | 5.0 | 100 | 557 |
| 16 | Fmoc-OX-1 | Fmoc-Tyr(But) | Fmoc-D-Ala | Fmoc-S33 | 5.7 | 100 | 534 |
| 17 | Fmoc-OX-1 | Fmoc-D-Trp(Boc) | Fmoc-D-Asn(Trt) | Fmoc-S33 | 10.9 | 100 | 600 |
| 18 | Fmoc-OX-1 | Fmoc-D-Tyr(But) | Fmoc-D-Asn(Trt) | Fmoc-S33 | 13.5 | 97 | 577 |
| 19 | Fmoc-OX-1 | Fmoc-Trp(Boc) | Fmoc-D-Asn(Trt) | Fmoc-S33 | 9.3 | 100 | 600 |
| 20 | Fmoc-OX-1 | Fmoc-Tyr(But) | Fmoc-D-Asn(Trt) | Fmoc-S33 | 9.7 | 100 | 577 |
| 21 | Fmoc-OX-1 | Fmoc-D-Trp(Boc) | Fmoc-D-Asp(OBut) | Fmoc-S33 | 9.5 | 100 | 601 |
| 22 | Fmoc-OX-1 | Fmoc-D-Tyr(But) | Fmoc-D-Asp(OBut) | Fmoc-S33 | 13.9 | 100 | 578 |
| 23 | Fmoc-OX-1 | Fmoc-Trp(Boc) | Fmoc-D-Asp(OBut) | Fmoc-S33 | 6.6 | 100 | 601 |
| 24 | Fmoc-OX-1 | Fmoc-Tyr(But) | Fmoc-D-Asp(OBut) | Fmoc-S33 | 6.2 | 100 | 578 |
| 25 | Fmoc-OX-1 | Fmoc-D-Trp(Boc) | Fmoc-D-His(Trt) | Fmoc-S33 | 11.7 | 98 | 623 |
| 26 | Fmoc-OX-1 | Fmoc-D-Tyr(But) | Fmoc-D-His(Trt) | Fmoc-S33 | 11.4 | 98 | 600 |
| 27 | Fmoc-OX-1 | Fmoc-Trp(Boc) | Fmoc-D-His(Trt) | Fmoc-S33 | 8.3 | 100 | 623 |
| 28 | Fmoc-OX-1 | Fmoc-Tyr(But) | Fmoc-D-His(Trt) | Fmoc-S33 | 8.2 | 100 | 600 |
| 29 | Fmoc-OX-1 | Fmoc-D-Trp(Boc) | Fmoc-D-Lys(Boc) | Fmoc-S33 | 8.3 | 100 | 614 |
| 30 | Fmoc-OX-1 | Fmoc-D-Tyr(But) | Fmoc-D-Lys(Boc) | Fmoc-S33 | 7.0 | 100 | 591 |
| 31 | Fmoc-OX-1 | Fmoc-Trp(Boc) | Fmoc-D-Lys(Boc) | Fmoc-S33 | 6.4 | 100 | 614 |
| 32 | Fmoc-OX-1 | Fmoc-Tyr(But) | Fmoc-D-Lys(Boc) | Fmoc-S33 | 7.2 | 100 | 591 |
| 33 | Fmoc-OX-1 | Fmoc-D-Trp(Boc) | Fmoc-D-Nva | Fmoc-S33 | 7.9 | 100 | 585 |
| 34 | Fmoc-OX-1 | Fmoc-D-Tyr(But) | Fmoc-D-Nva | Fmoc-S33 | 6.1 | 100 | 562 |
| 35 | Fmoc-OX-1 | Fmoc-Trp(Boc) | Fmoc-D-Nva | Fmoc-S33 | 6.4 | 100 | 585 |
| 36 | Fmoc-OX-1 | Fmoc-Tyr(But) | Fmoc-D-Nva | Fmoc-S33 | 6.7 | 100 | 562 |
| 37 | Fmoc-OX-1 | Fmoc-D-Trp(Boc) | Fmoc-D-Phe | Fmoc-S33 | 12.5 | 100 | 633 |
| 38 | Fmoc-OX-1 | Fmoc-D-Tyr(But) | Fmoc-D-Phe | Fmoc-S33 | 10.4 | 100 | 610 |
| 39 | Fmoc-OX-1 | Fmoc-Trp(Boc) | Fmoc-D-Phe | Fmoc-S33 | 7.2 | 100 | 633 |
| 40 | Fmoc-OX-1 | Fmoc-Tyr(But) | Fmoc-D-Phe | Fmoc-S33 | 11.4 | 100 | 610 |
| 41 | Fmoc-OX-1 | Fmoc-D-Trp(Boc) | Fmoc-D-Pro | Fmoc-S33 | 12.3 | 100 | 583 |
| 42 | Fmoc-OX-1 | Fmoc-D-Tyr(But) | Fmoc-D-Pro | Fmoc-S33 | 11.9 | 100 | 560 |
| 43 | Fmoc-OX-1 | Fmoc-Trp(Boc) | Fmoc-D-Pro | Fmoc-S33 | 10.3 | 99 | 583 |
| 44 | Fmoc-OX-1 | Fmoc-Tyr(But) | Fmoc-D-Pro | Fmoc-S33 | 9.6 | 100 | 560 |
| 45 | Fmoc-OX-1 | Fmoc-D-Trp(Boc) | Fmoc-D-Ser(But) | Fmoc-S33 | 8.7 | 100 | 573 |
| 46 | Fmoc-OX-1 | Fmoc-D-Tyr(But) | Fmoc-D-Ser(But) | Fmoc-S33 | 8.5 | 100 | 550 |
| 47 | Fmoc-OX-1 | Fmoc-Trp(Boc) | Fmoc-D-Ser(But) | Fmoc-S33 | 6.4 | 100 | 573 |
| 48 | Fmoc-OX-1 | Fmoc-Tyr(But) | Fmoc-D-Ser(But) | Fmoc-S33 | 6.4 | 100 | 550 |
| 49 | Fmoc-OX-1 | Fmoc-Ala | Fmoc-D-Trp(Boc) | Fmoc-S33 | 7.1 | 100 | 557 |
| 50 | Fmoc-OX-1 | Fmoc-Asn(Trt) | Fmoc-D-Trp(Boc) | Fmoc-S33 | 11.1 | 100 | 600 |
| 51 | Fmoc-OX-1 | Fmoc-D-Ala | Fmoc-D-Trp(Boc) | Fmoc-S33 | 8.1 | 100 | 557 |
| 52 | Fmoc-OX-1 | Fmoc-Dap(Boc) | Fmoc-D-Trp(Boc) | Fmoc-S33 | 7.3 | 100 | 572 |
| 53 | Fmoc-OX-1 | Fmoc-D-Asn(Trt) | Fmoc-D-Trp(Boc) | Fmoc-S33 | 11.5 | 95 | 600 |
| 54 | Fmoc-OX-1 | Fmoc-D-Dap(Boc) | Fmoc-D-Trp(Boc) | Fmoc-S33 | 8.5 | 100 | 572 |
| 55 | Fmoc-OX-1 | Fmoc-D-Gln(Trt) | Fmoc-D-Trp(Boc) | Fmoc-S33 | 11.0 | 96 | 614 |
| 56 | Fmoc-OX-1 | Fmoc-D-Glu(OBut) | Fmoc-D-Trp(Boc) | Fmoc-S33 | 8.8 | 97 | 615 |
| 57 | Fmoc-OX-1 | Fmoc-D-His(Trt) | Fmoc-D-Trp(Boc) | Fmoc-S33 | 8.5 | 100 | 623 |
| 58 | Fmoc-OX-1 | Fmoc-D-Ile | Fmoc-D-Trp(Boc) | Fmoc-S33 | 8.2 | 100 | 599 |
| 59 | Fmoc-OX-1 | Fmoc-D-Lys(Boc) | Fmoc-D-Trp(Boc) | Fmoc-S33 | 9.1 | 100 | 614 |
| 60 | Fmoc-OX-1 | Fmoc-D-Nva | Fmoc-D-Trp(Boc) | Fmoc-S33 | 8.6 | 100 | 585 |
| 61 | Fmoc-OX-1 | Fmoc-D-Phe | Fmoc-D-Trp(Boc) | Fmoc-S33 | 9.4 | 97 | 633 |

TABLE 1A-continued

| Cpd | BB$_1$ | BB$_2$ | BB$_3$ | BB$_4$ | Wt (mg)[1] | Purity[2] | MS (M + H) |
|---|---|---|---|---|---|---|---|
| 62 | Fmoc-OX-1 | Fmoc-D-Pro | Fmoc-D-Trp(Boc) | Fmoc-S33 | 4.1 | 100 | 583 |
| 63 | Fmoc-OX-1 | Fmoc-D-Ser(But) | Fmoc-D-Trp(Boc) | Fmoc-S33 | 6.1 | 100 | 573 |
| 64 | Fmoc-OX-1 | Fmoc-D-Trp(Boc) | Fmoc-D-Trp(Boc) | Fmoc-S33 | 6.1 | 100 | 672 |
| 65 | Fmoc-OX-1 | Fmoc-D-Tyr(But) | Fmoc-D-Trp(Boc) | Fmoc-S33 | 9.1 | 96 | 649 |
| 66 | Fmoc-OX-1 | Fmoc-D-Val | Fmoc-D-Trp(Boc) | Fmoc-S33 | 8.4 | 100 | 585 |
| 67 | Fmoc-OX-1 | Fmoc-Glu(OBut) | Fmoc-D-Trp(Boc) | Fmoc-S33 | 7.4 | 100 | 615 |
| 68 | Fmoc-OX-1 | Fmoc-Sar | Fmoc-D-Trp(Boc) | Fmoc-S33 | 7.2 | 100 | 557 |
| 69 | Fmoc-OX-1 | Fmoc-His(Trt) | Fmoc-D-Trp(Boc) | Fmoc-S33 | 7.9 | 100 | 623 |
| 70 | Fmoc-OX-1 | Fmoc-Ile | Fmoc-D-Trp(Boc) | Fmoc-S33 | 7.0 | 100 | 599 |
| 71 | Fmoc-OX-1 | Fmoc-Lys(Boc) | Fmoc-D-Trp(Boc) | Fmoc-S33 | 7.2 | 97 | 614 |
| 72 | Fmoc-OX-1 | Fmoc-Nva | Fmoc-D-Trp(Boc) | Fmoc-S33 | 7.3 | 100 | 585 |
| 73 | Fmoc-OX-1 | Fmoc-Phe | Fmoc-D-Trp(Boc) | Fmoc-S33 | 9.1 | 100 | 633 |
| 74 | Fmoc-OX-1 | Fmoc-Pro | Fmoc-D-Trp(Boc) | Fmoc-S33 | 5.1 | 100 | 583 |
| 75 | Fmoc-OX-1 | Fmoc-Ser(But) | Fmoc-D-Trp(Boc) | Fmoc-S33 | 8.4 | 100 | 573 |
| 76 | Fmoc-OX-1 | Fmoc-Trp(Boc) | Fmoc-D-Trp(Boc) | Fmoc-S33 | 9.8 | 100 | 672 |
| 77 | Fmoc-OX-1 | Fmoc-Tyr(But) | Fmoc-D-Trp(Boc) | Fmoc-S33 | 11.5 | 100 | 649 |
| 78 | Fmoc-OX-1 | Fmoc-Val | Fmoc-D-Trp(Boc) | Fmoc-S33 | 8.9 | 100 | 585 |
| 79 | Fmoc-OX-1 | Fmoc-Ala | Fmoc-D-Tyr(But) | Fmoc-S33 | 7.2 | 100 | 534 |
| 80 | Fmoc-OX-1 | Fmoc-Asn(Trt) | Fmoc-D-Tyr(But) | Fmoc-S33 | 11.9 | 100 | 577 |
| 81 | Fmoc-OX-1 | Fmoc-D-Ala | Fmoc-D-Tyr(But) | Fmoc-S33 | 8.8 | 100 | 534 |
| 82 | Fmoc-OX-1 | Fmoc-Dap(Boc) | Fmoc-D-Tyr(But) | Fmoc-S33 | 5.7 | 100 | 549 |
| 83 | Fmoc-OX-1 | Fmoc-D-Asn(Trt) | Fmoc-D-Tyr(But) | Fmoc-S33 | 11.7 | 100 | 577 |
| 84 | Fmoc-OX-1 | Fmoc-D-Dap(Boc) | Fmoc-D-Tyr(But) | Fmoc-S33 | 7.2 | 100 | 549 |
| 85 | Fmoc-OX-1 | Fmoc-D-Gln (Trt) | Fmoc-D-Tyr(But) | Fmoc-S33 | 10.2 | 96 | 591 |
| 86 | Fmoc-OX-1 | Fmoc-D-Glu(OBut) | Fmoc-D-Tyr(But) | Fmoc-S33 | 10.1 | 97 | 592 |
| 87 | Fmoc-OX-1 | Fmoc-D-His(Trt) | Fmoc-D-Tyr(But) | Fmoc-S33 | 8.2 | 100 | 600 |
| 88 | Fmoc-OX-1 | Fmoc-D-Ile | Fmoc-D-Tyr(But) | Fmoc-S33 | 10.0 | 98 | 576 |
| 89 | Fmoc-OX-1 | Fmoc-D-Lys(Boc) | Fmoc-D-Tyr(But) | Fmoc-S33 | 8.2 | 100 | 591 |
| 90 | Fmoc-OX-1 | Fmoc-D-Nva | Fmoc-D-Tyr(But) | Fmoc-S33 | 9.0 | 100 | 562 |
| 91 | Fmoc-OX-1 | Fmoc-D-Phe | Fmoc-D-Tyr(But) | Fmoc-S33 | 10.7 | 97 | 610 |
| 92 | Fmoc-OX-1 | Fmoc-D-Pro | Fmoc-D-Tyr(But) | Fmoc-S33 | 3.8 | 100 | 560 |
| 93 | Fmoc-OX-1 | Fmoc-D-Ser(But) | Fmoc-D-Tyr(But) | Fmoc-S33 | 6.7 | 100 | 550 |
| 94 | Fmoc-OX-1 | Fmoc-D-Trp(Boc) | Fmoc-D-Tyr(But) | Fmoc-S33 | 9.4 | 100 | 649 |
| 95 | Fmoc-OX-1 | Fmoc-D-Tyr(But) | Fmoc-D-Tyr(But) | Fmoc-S33 | 10.5 | 95 | 626 |
| 96 | Fmoc-OX-1 | Fmoc-D-Val | Fmoc-D-Tyr(But) | Fmoc-S33 | 9.3 | 100 | 562 |
| 97 | Fmoc-OX-1 | Fmoc-Glu(OBut) | Fmoc-D-Tyr(But) | Fmoc-S33 | 9.3 | 100 | 592 |
| 98 | Fmoc-OX-1 | Fmoc-Sar | Fmoc-D-Tyr(But) | Fmoc-S33 | 7.8 | 100 | 534 |
| 99 | Fmoc-OX-1 | Fmoc-His(Trt) | Fmoc-D-Tyr(But) | Fmoc-S33 | 5.9 | 100 | 600 |
| 100 | Fmoc-OX-1 | Fmoc-Ile | Fmoc-D-Tyr(But) | Fmoc-S33 | 7.4 | 100 | 576 |
| 101 | Fmoc-OX-1 | Fmoc-Lys(Boc) | Fmoc-D-Tyr(But) | Fmoc-S33 | 5.6 | 100 | 591 |
| 102 | Fmoc-OX-1 | Fmoc-Nva | Fmoc-D-Tyr(But) | Fmoc-S33 | 7.7 | 100 | 562 |
| 103 | Fmoc-OX-1 | Fmoc-Phe | Fmoc-D-Tyr(But) | Fmoc-S33 | 9.8 | 100 | 610 |
| 104 | Fmoc-OX-1 | Fmoc-Pro | Fmoc-D-Tyr(But) | Fmoc-S33 | 3.7 | 100 | 560 |
| 105 | Fmoc-OX-1 | Fmoc-Ser(But) | Fmoc-D-Tyr(But) | Fmoc-S33 | 13.4 | 100 | 550 |
| 106 | Fmoc-OX-1 | Fmoc-Trp(Boc) | Fmoc-D-Tyr(But) | Fmoc-S33 | 9.7 | 100 | 649 |
| 107 | Fmoc-OX-1 | Fmoc-Tyr(But) | Fmoc-D-Tyr(But) | Fmoc-S33 | 13.9 | 100 | 626 |
| 108 | Fmoc-OX-1 | Fmoc-Val | Fmoc-D-Tyr(But) | Fmoc-S33 | 9.8 | 100 | 562 |
| 109 | Fmoc-OX-1 | Fmoc-D-Trp(Boc) | Fmoc-D-Val | Fmoc-S33 | 9.0 | 95 | 585 |
| 110 | Fmoc-OX-1 | Fmoc-D-Tyr(But) | Fmoc-D-Val | Fmoc-S33 | 2.7 | 100 | 562 |
| 111 | Fmoc-OX-1 | Fmoc-Trp(Boc) | Fmoc-D-Val | Fmoc-S33 | 5.5 | 100 | 585 |
| 112 | Fmoc-OX-1 | Fmoc-Tyr(But) | Fmoc-D-Val | Fmoc-S33 | 9.4 | 96 | 562 |
| 113 | Fmoc-OX-1 | Fmoc-D-Trp(Boc) | Fmoc-Sar | Fmoc-S33 | 5.8 | 100 | 557 |
| 114 | Fmoc-OX-1 | Fmoc-D-Tyr(But) | Fmoc-Sar | Fmoc-S33 | 9.0 | 100 | 534 |
| 115 | Fmoc-OX-1 | Fmoc-Trp(Boc) | Fmoc-Sar | Fmoc-S33 | 9.4 | 97 | 557 |
| 116 | Fmoc-OX-1 | Fmoc-Tyr(But) | Fmoc-Sar | Fmoc-S33 | 5.9 | 100 | 534 |
| 117 | Fmoc-OX-1 | Fmoc-D-Trp(Boc) | Fmoc-His(Trt) | Fmoc-S33 | 7.8 | 100 | 623 |
| 118 | Fmoc-OX-1 | Fmoc-D-Tyr(But) | Fmoc-His(Trt) | Fmoc-S33 | 4.8 | 100 | 600 |
| 119 | Fmoc-OX-1 | Fmoc-Trp(Boc) | Fmoc-His(Trt) | Fmoc-S33 | 6.7 | 100 | 623 |
| 120 | Fmoc-OX-1 | Fmoc-Tyr(But) | Fmoc-His(Trt) | Fmoc-S33 | 7.4 | 100 | 600 |
| 121 | Fmoc-OX-1 | Fmoc-D-Trp(Boc) | Fmoc-Lys(Boc) | Fmoc-S33 | 6.2 | 100 | 614 |
| 122 | Fmoc-OX-1 | Fmoc-D-Tyr(But) | Fmoc-Lys(Boc) | Fmoc-S33 | 6.7 | 100 | 591 |
| 123 | Fmoc-OX-1 | Fmoc-Trp(Boc) | Fmoc-Lys(Boc) | Fmoc-S33 | 6.5 | 100 | 614 |
| 124 | Fmoc-OX-1 | Fmoc-Tyr(But) | Fmoc-Lys(Boc) | Fmoc-S33 | 8.8 | 100 | 591 |
| 125 | Fmoc-OX-1 | Fmoc-D-Trp(Boc) | Fmoc-Nva | Fmoc-S33 | 7.1 | 100 | 585 |
| 126 | Fmoc-OX-1 | Fmoc-D-Tyr(But) | Fmoc-Nva | Fmoc-S33 | 8.1 | 100 | 562 |
| 127 | Fmoc-OX-1 | Fmoc-Trp(Boc) | Fmoc-Nva | Fmoc-S33 | 5.7 | 100 | 585 |
| 128 | Fmoc-OX-1 | Fmoc-Tyr(But) | Fmoc-Nva | Fmoc-S33 | 6.4 | 100 | 562 |
| 129 | Fmoc-OX-1 | Fmoc-D-Trp(Boc) | Fmoc-Phe | Fmoc-S33 | 9.9 | 100 | 633 |
| 130 | Fmoc-OX-1 | Fmoc-D-Tyr(But) | Fmoc-Phe | Fmoc-S33 | 9.6 | 100 | 610 |
| 131 | Fmoc-OX-1 | Fmoc-Trp(Boc) | Fmoc-Phe | Fmoc-S33 | 5.8 | 100 | 633 |
| 132 | Fmoc-OX-1 | Fmoc-Tyr(But) | Fmoc-Phe | Fmoc-S33 | 6.6 | 100 | 610 |
| 133 | Fmoc-OX-1 | Fmoc-D-Trp(Boc) | Fmoc-Pro | Fmoc-S33 | 8.7 | 100 | 583 |
| 134 | Fmoc-OX-1 | Fmoc-D-Tyr(But) | Fmoc-Pro | Fmoc-S33 | 9.5 | 100 | 560 |
| 135 | Fmoc-OX-1 | Fmoc-Trp(Boc) | Fmoc-Pro | Fmoc-S33 | 9.7 | 100 | 583 |
| 136 | Fmoc-OX-1 | Fmoc-Tyr(But) | Fmoc-Pro | Fmoc-S33 | 10.8 | 100 | 560 |
| 137 | Fmoc-OX-1 | Fmoc-D-Trp(Boc) | Fmoc-Ser(But) | Fmoc-S33 | 9.3 | 100 | 573 |
| 138 | Fmoc-OX-1 | Fmoc-D-Tyr(But) | Fmoc-Ser(But) | Fmoc-S33 | 7.8 | 100 | 550 |
| 139 | Fmoc-OX-1 | Fmoc-Trp(Boc) | Fmoc-Ser(But) | Fmoc-S33 | 6.7 | 100 | 573 |

TABLE 1A-continued

| Cpd | BB$_1$ | BB$_2$ | BB$_3$ | BB$_4$ | Wt (mg)[1] | Purity[2] | MS (M + H) |
|---|---|---|---|---|---|---|---|
| 140 | Fmoc-OX-1 | Fmoc-Tyr(But) | Fmoc-Ser(But) | Fmoc-S33 | 6.2 | 100 | 550 |
| 141 | Fmoc-OX-1 | Fmoc-Ala | Fmoc-Trp(Boc) | Fmoc-S33 | 6.7 | 100 | 557 |
| 142 | Fmoc-OX-1 | Fmoc-Asn(Trt) | Fmoc-Trp(Boc) | Fmoc-S33 | 4.4 | 100 | 600 |
| 143 | Fmoc-OX-1 | Fmoc-D-Ala | Fmoc-Trp(Boc) | Fmoc-S33 | 7.7 | 100 | 557 |
| 144 | Fmoc-OX-1 | Fmoc-Dap(Boc) | Fmoc-Trp(Boc) | Fmoc-S33 | 5.5 | 95 | 572 |
| 145 | Fmoc-OX-1 | Fmoc-D-Asn(Trt) | Fmoc-Trp(Boc) | Fmoc-S33 | 12.4 | 100 | 600 |
| 146 | Fmoc-OX-1 | Fmoc-D-Dap(Boc) | Fmoc-Trp(Boc) | Fmoc-S33 | 7.4 | 100 | 572 |
| 147 | Fmoc-OX-1 | Fmoc-D-Gln(Trt) | Fmoc-Trp(Boc) | Fmoc-S33 | 8.5 | 100 | 614 |
| 148 | Fmoc-OX-1 | Fmoc-D-Glu(OBut) | Fmoc-Trp(Boc) | Fmoc-S33 | 7.0 | 100 | 615 |
| 149 | Fmoc-OX-1 | Fmoc-D-His(Trt) | Fmoc-Trp(Boc) | Fmoc-S33 | 7.8 | 100 | 623 |
| 150 | Fmoc-OX-1 | Fmoc-D-Ile | Fmoc-Trp(Boc) | Fmoc-S33 | 8.0 | 100 | 599 |
| 151 | Fmoc-OX-1 | Fmoc-D-Lys(Boc) | Fmoc-Trp(Boc) | Fmoc-S33 | 5.4 | 100 | 614 |
| 152 | Fmoc-OX-1 | Fmoc-D-Nva | Fmoc-Trp(Boc) | Fmoc-S33 | 7.0 | 100 | 585 |
| 153 | Fmoc-OX-1 | Fmoc-D-Phe | Fmoc-Trp(Boc) | Fmoc-S33 | 9.0 | 100 | 633 |
| 154 | Fmoc-OX-1 | Fmoc-D-Pro | Fmoc-Trp(Boc) | Fmoc-S33 | 9.3 | 100 | 583 |
| 155 | Fmoc-OX-1 | Fmoc-D-Ser(But) | Fmoc-Trp(Boc) | Fmoc-S33 | 6.4 | 100 | 573 |
| 156 | Fmoc-OX-1 | Fmoc-D-Trp(Boc) | Fmoc-Trp(Boc) | Fmoc-S33 | 8.5 | 100 | 672 |
| 157 | Fmoc-OX-1 | Fmoc-D-Tyr(But) | Fmoc-Trp(Boc) | Fmoc-S33 | 8.4 | 100 | 649 |
| 158 | Fmoc-OX-1 | Fmoc-D-Val | Fmoc-Trp(Boc) | Fmoc-S33 | 8.0 | 100 | 585 |
| 159 | Fmoc-OX-1 | Fmoc-Glu(OBut) | Fmoc-Trp(Boc) | Fmoc-S33 | 6.3 | 100 | 615 |
| 160 | Fmoc-OX-1 | Fmoc-Sar | Fmoc-Trp(Boc) | Fmoc-S33 | 7.6 | 100 | 557 |
| 161 | Fmoc-OX-1 | Fmoc-His(Trt) | Fmoc-Trp(Boc) | Fmoc-S33 | 4.5 | 100 | 623 |
| 162 | Fmoc-OX-1 | Fmoc-Ile | Fmoc-Trp(Boc) | Fmoc-S33 | 6.4 | 100 | 599 |
| 163 | Fmoc-OX-1 | Fmoc-Lys(Boc) | Fmoc-Trp(Boc) | Fmoc-S33 | 4.6 | 100 | 614 |
| 164 | Fmoc-OX-1 | Fmoc-Nva | Fmoc-Trp(Boc) | Fmoc-S33 | 6.8 | 100 | 585 |
| 165 | Fmoc-OX-1 | Fmoc-Phe | Fmoc-Trp(Boc) | Fmoc-S33 | 7.3 | 100 | 633 |
| 166 | Fmoc-OX-1 | Fmoc-Pro | Fmoc-Trp(Boc) | Fmoc-S33 | 5.1 | 100 | 583 |
| 167 | Fmoc-OX-1 | Fmoc-Ser(But) | Fmoc-Trp(Boc) | Fmoc-S33 | 3.8 | 100 | 573 |
| 168 | Fmoc-OX-1 | Fmoc-Trp(Boc) | Fmoc-Trp(Boc) | Fmoc-S33 | 6.3 | 100 | 672 |
| 169 | Fmoc-OX-1 | Fmoc-Tyr(But) | Fmoc-Trp(Boc) | Fmoc-S33 | 5.6 | 100 | 649 |
| 170 | Fmoc-OX-1 | Fmoc-Val | Fmoc-Trp(Boc) | Fmoc-S33 | 7.6 | 100 | 585 |
| 171 | Fmoc-OX-1 | Fmoc-Ala | Fmoc-Tyr(But) | Fmoc-S33 | 4.8 | 100 | 534 |
| 172 | Fmoc-OX-1 | Fmoc-Ala | Fmoc-Tyr(But) | Fmoc-S31 | 3.5 | 100 | 472 |
| 173 | Fmoc-OX-1 | Fmoc-Asn(Trt) | Fmoc-Tyr(But) | Fmoc-S33 | 5.8 | 100 | 577 |
| 174 | Fmoc-OX-1 | Fmoc-Asn(Trt) | Fmoc-Tyr(But) | Fmoc-S31 | na | na | na |
| 175 | Fmoc-OX-1 | Fmoc-D-Ala | Fmoc-Tyr(But) | Fmoc-S33 | 7.3 | 100 | 534 |
| 176 | Fmoc-OX-1 | Fmoc-D-Ala | Fmoc-Tyr(But) | Fmoc-S31 | 3.6 | 100 | 472 |
| 177 | Fmoc-OX-1 | Fmoc-Dap(Boc) | Fmoc-Tyr(But) | Fmoc-S33 | 5.0 | 100 | 549 |
| 178 | Fmoc-OX-1 | Fmoc-D-Asn(Trt) | Fmoc-Tyr(But) | Fmoc-S33 | 12.4 | 100 | 577 |
| 179 | Fmoc-OX-1 | Fmoc-D-Asn(Trt) | Fmoc-Tyr(But) | Fmoc-S31 | 6.1 | 100 | 515 |
| 180 | Fmoc-OX-1 | Fmoc-D-Dap(Boc) | Fmoc-Tyr(But) | Fmoc-S33 | 6.2 | 100 | 549 |
| 181 | Fmoc-OX-1 | Fmoc-D-Gln(Trt) | Fmoc-Tyr(But) | Fmoc-S33 | 11.3 | 100 | 591 |
| 182 | Fmoc-OX-1 | Fmoc-D-Gln(Trt) | Fmoc-Tyr(But) | Fmoc-S31 | 7.4 | 100 | 529 |
| 183 | Fmoc-OX-1 | Fmoc-D-Glu(OBut) | Fmoc-Tyr(But) | Fmoc-S33 | 8.4 | 100 | 592 |
| 184 | Fmoc-OX-1 | Fmoc-D-Glu(OBut) | Fmoc-Tyr(But) | Fmoc-S31 | 4.4 | 100 | 530 |
| 185 | Fmoc-OX-1 | Fmoc-D-His(Trt) | Fmoc-Tyr(But) | Fmoc-S33 | 7.0 | 100 | 600 |
| 186 | Fmoc-OX-1 | Fmoc-D-His(Trt) | Fmoc-Tyr(But) | Fmoc-S31 | 5.9 | 100 | 538 |
| 187 | Fmoc-OX-1 | Fmoc-D-Ile | Fmoc-Tyr(But) | Fmoc-S33 | 8.3 | 100 | 576 |
| 188 | Fmoc-OX-1 | Fmoc-D-Lys(Boc) | Fmoc-Tyr(But) | Fmoc-S33 | 5.7 | 100 | 591 |
| 189 | Fmoc-OX-1 | Fmoc-D-Lys(Boc) | Fmoc-Tyr(But) | Fmoc-S31 | 3.4 | 100 | 529 |
| 190 | Fmoc-OX-1 | Fmoc-D-Nva | Fmoc-Tyr(But) | Fmoc-S33 | 7.9 | 100 | 562 |
| 191 | Fmoc-OX-1 | Fmoc-D-Nva | Fmoc-Tyr(But) | Fmoc-S31 | 4.1 | 100 | 500 |
| 192 | Fmoc-OX-1 | Fmoc-D-Phe | Fmoc-Tyr(But) | Fmoc-S33 | 9.0 | 100 | 610 |
| 193 | Fmoc-OX-1 | Fmoc-D-Phe | Fmoc-Tyr(But) | Fmoc-S31 | 4.6 | 100 | 548 |
| 194 | Fmoc-OX-1 | Fmoc-D-Pro | Fmoc-Tyr(But) | Fmoc-S33 | 8.4 | 100 | 560 |
| 195 | Fmoc-OX-1 | Fmoc-D-Pro | Fmoc-Tyr(But) | Fmoc-S31 | 5.2 | 100 | 498 |
| 196 | Fmoc-OX-1 | Fmoc-D-Ser(But) | Fmoc-Tyr(But) | Fmoc-S33 | 7.4 | 100 | 550 |
| 197 | Fmoc-OX-1 | Fmoc-D-Ser(But) | Fmoc-Tyr(But) | Fmoc-S31 | 4.0 | 100 | 488 |
| 198 | Fmoc-OX-1 | Fmoc-D-Trp(Boc) | Fmoc-Tyr(But) | Fmoc-S33 | 9.4 | 100 | 649 |
| 199 | Fmoc-OX-1 | Fmoc-D-Trp(Boc) | Fmoc-Tyr(But) | Fmoc-S31 | 5.4 | 100 | 587 |
| 200 | Fmoc-OX-1 | Fmoc-D-Tyr(But) | Fmoc-Tyr(But) | Fmoc-S33 | 9.1 | 100 | 626 |
| 201 | Fmoc-OX-1 | Fmoc-D-Tyr(But) | Fmoc-Tyr(But) | Fmoc-S31 | 5.3 | 100 | 564 |
| 202 | Fmoc-OX-1 | Fmoc-D-Val | Fmoc-Tyr(But) | Fmoc-S33 | 7.2 | 100 | 562 |
| 203 | Fmoc-OX-1 | Fmoc-D-Val | Fmoc-Tyr(But) | Fmoc-S31 | 4.1 | 100 | 500 |
| 204 | Fmoc-OX-1 | Fmoc-Glu(OBut) | Fmoc-Tyr(But) | Fmoc-S33 | 4.1 | 100 | 592 |
| 205 | Fmoc-OX-1 | Fmoc-Glu(OBut) | Fmoc-Tyr(But) | Fmoc-S31 | 5.7 | 100 | 530 |
| 206 | Fmoc-OX-1 | Fmoc-Sar | Fmoc-Tyr(But) | Fmoc-S33 | 7.1 | 100 | 534 |
| 207 | Fmoc-OX-1 | Fmoc-Sar | Fmoc-Tyr(But) | Fmoc-S31 | 2.2 | 100 | 472 |
| 208 | Fmoc-OX-1 | Fmoc-His(Trt) | Fmoc-Tyr(But) | Fmoc-S33 | 5.2 | 100 | 600 |
| 209 | Fmoc-OX-1 | Fmoc-His(Trt) | Fmoc-Tyr(But) | Fmoc-S31 | 9.2 | 100 | 538 |
| 210 | Fmoc-OX-1 | Fmoc-Ile | Fmoc-Tyr(But) | Fmoc-S33 | 8.8 | 100 | 576 |
| 211 | Fmoc-OX-1 | Fmoc-Lys(Boc) | Fmoc-Tyr(But) | Fmoc-S33 | 5.7 | 100 | 591 |
| 212 | Fmoc-OX-1 | Fmoc-Lys(Boc) | Fmoc-Tyr(But) | Fmoc-S31 | 5.4 | 100 | 529 |
| 213 | Fmoc-OX-1 | Fmoc-Nva | Fmoc-Tyr(But) | Fmoc-S33 | 8.9 | 100 | 562 |
| 214 | Fmoc-OX-1 | Fmoc-Nva | Fmoc-Tyr(But) | Fmoc-S31 | 5.3 | 100 | 500 |
| 215 | Fmoc-OX-1 | Fmoc-Phe | Fmoc-Tyr(But) | Fmoc-S33 | 6.5 | 100 | 610 |
| 216 | Fmoc-OX-1 | Fmoc-Phe | Fmoc-Tyr(But) | Fmoc-S31 | 7.3 | 100 | 548 |
| 217 | Fmoc-OX-1 | Fmoc-Pro | Fmoc-Tyr(But) | Fmoc-S33 | 4.2 | 100 | 560 |

TABLE 1A-continued

| Cpd | BB$_1$ | BB$_2$ | BB$_3$ | BB$_4$ | Wt (mg)[1] | Purity[2] | MS (M + H) |
|---|---|---|---|---|---|---|---|
| 218 | Fmoc-OX-1 | Fmoc-Pro | Fmoc-Tyr(But) | Fmoc-S31 | 2.4 | 100 | 498 |
| 219 | Fmoc-OX-1 | Fmoc-Ser(But) | Fmoc-Tyr(But) | Fmoc-S33 | 3.5 | 100 | 550 |
| 220 | Fmoc-OX-1 | Fmoc-Ser(But) | Fmoc-Tyr(But) | Fmoc-S31 | 5.1 | 100 | 488 |
| 221 | Fmoc-OX-1 | Fmoc-Trp(Boc) | Fmoc-Tyr(But) | Fmoc-S33 | 7.7 | 100 | 649 |
| 222 | Fmoc-OX-1 | Fmoc-Trp(Boc) | Fmoc-Tyr(But) | Fmoc-S31 | 6.6 | 100 | 587 |
| 223 | Fmoc-OX-1 | Fmoc-Tyr(But) | Fmoc-Tyr(But) | Fmoc-S33 | 7.4 | 100 | 626 |
| 224 | Fmoc-OX-1 | Fmoc-Tyr(But) | Fmoc-Tyr(But) | Fmoc-S31 | 7.1 | 100 | 564 |
| 225 | Fmoc-OX-1 | Fmoc-Val | Fmoc-Tyr(But) | Fmoc-S33 | 7.8 | 100 | 562 |
| 226 | Fmoc-OX-1 | Fmoc-Val | Fmoc-Tyr(But) | Fmoc-S31 | 5.6 | 100 | 500 |
| 227 | Fmoc-OX-1 | Fmoc-D-Trp(Boc) | Fmoc-Val | Fmoc-S33 | 8.6 | 100 | 585 |
| 228 | Fmoc-OX-1 | Fmoc-D-Tyr(But) | Fmoc-Val | Fmoc-S33 | 8.7 | 100 | 562 |
| 229 | Fmoc-OX-1 | Fmoc-Trp(Boc) | Fmoc-Val | Fmoc-S33 | 6.4 | 100 | 585 |
| 230 | Fmoc-OX-1 | Fmoc-Tyr(But) | Fmoc-Val | Fmoc-S33 | 6.5 | 100 | 562 |
| 231 | Fmoc-OX-1 | Fmoc-Arg(Pbf) | Fmoc-Tyr(But) | Fmoc-S33 | 2.5 | 100 | 619 |
| 232 | Fmoc-OX-1 | Fmoc-Arg(Pbf) | Fmoc-Trp(Boc) | Fmoc-S33 | 2.9 | 100 | 642 |
| 233 | Fmoc-OX-1 | Fmoc-Arg(Pbf) | Fmoc-D-Tyr(But) | Fmoc-S33 | 1.7 | 100 | 619 |
| 234 | Fmoc-OX-1 | Fmoc-Arg(Pbf) | Fmoc-D-Trp(Boc) | Fmoc-S33 | 2.2 | 100 | 642 |
| 235 | Fmoc-OX-1 | Fmoc-Arg(Pbf) | Fmoc-Tyr(But) | Fmoc-S31 | 0.6 | 85 | 557 |
| 236 | Fmoc-OX-1 | Fmoc-D-Arg(Pbf) | Fmoc-Tyr(But) | Fmoc-S33 | 5.3 | 100 | 619 |
| 237 | Fmoc-OX-1 | Fmoc-D-Arg(Pbf) | Fmoc-Trp(Boc) | Fmoc-S33 | 6.1 | 100 | 642 |
| 238 | Fmoc-OX-1 | Fmoc-D-Arg(Pbf) | Fmoc-D-Tyr(But) | Fmoc-S33 | 9.9 | 100 | 619 |
| 239 | Fmoc-OX-1 | Fmoc-D-Arg(Pbf) | Fmoc-D-Trp(Boc) | Fmoc-S33 | 9.4 | 100 | 642 |
| 240 | Fmoc-OX-1 | Fmoc-D-Arg(Pbf) | Fmoc-Tyr(But) | Fmoc-S31 | 3.7 | 100 | 557 |
| 241 | Fmoc-OX-1 | Fmoc-D-Trp(Boc) | Fmoc-Arg(Pbf) | Fmoc-S33 | 6.6 | 100 | 642 |
| 242 | Fmoc-OX-1 | Fmoc-D-Tyr(But) | Fmoc-Arg(Pbf) | Fmoc-S33 | 5.0 | 100 | 619 |
| 243 | Fmoc-OX-1 | Fmoc-Trp(Boc) | Fmoc-Arg(Pbf) | Fmoc-S33 | 6.0 | 100 | 642 |
| 244 | Fmoc-OX-1 | Fmoc-Tyr(But) | Fmoc-Arg(Pbf) | Fmoc-S33 | 8.6 | 100 | 619 |
| 245 | Fmoc-OX-1 | Fmoc-D-Trp(Boc) | Fmoc-D-Arg(Pbf) | Fmoc-S33 | 6.7 | 100 | 642 |
| 246 | Fmoc-OX-1 | Fmoc-D-Tyr(But) | Fmoc-D-Arg(Pbf) | Fmoc-S33 | 8.6 | 100 | 619 |
| 247 | Fmoc-OX-1 | Fmoc-Trp(Boc) | Fmoc-D-Arg(Pbf) | Fmoc-S33 | 8.5 | 100 | 642 |
| 248 | Fmoc-OX-1 | Fmoc-Tyr(But) | Fmoc-D-Arg(Pbf) | Fmoc-S33 | 6.6 | 100 | 619 |
| 249 | Fmoc-OX-5 | Fmoc-D-Val | Fmoc-D-Phe | Fmoc-S48 | na | na | na |
| 250 | Fmoc-OX-6 | Fmoc-D-Val | Fmoc-D-Phe | Fmoc-S48 | na | na | na |
| 251 | Fmoc-OX-5 | Fmoc-Val | Fmoc-D-Phe | Fmoc-S48 | na | na | na |
| 252 | Fmoc-OX-6 | Fmoc-Val | Fmoc-D-Phe | Fmoc-S48 | na | na | na |
| 253 | Fmoc-OX-5 | Fmoc-D-Ser(But) | Fmoc-D-Phe | Fmoc-S48 | na | na | na |
| 254 | Fmoc-OX-6 | Fmoc-D-Ser(But) | Fmoc-D-Phe | Fmoc-S48 | na | na | na |
| 255 | Fmoc-OX-5 | Fmoc-Ser(But) | Fmoc-D-Phe | Fmoc-S48 | na | na | na |
| 256 | Fmoc-OX-6 | Fmoc-Ser(But) | Fmoc-D-Phe | Fmoc-S48 | na | na | na |
| 257 | Fmoc-OX-5 | Fmoc-Dap(Boc) | Fmoc-D-Phe | Fmoc-S48 | na | na | na |
| 258 | Fmoc-OX-6 | Fmoc-Dap(Boc) | Fmoc-D-Phe | Fmoc-S48 | na | na | na |
| 259 | Fmoc-OX-5 | Fmoc-Ala | Fmoc-D-Phe | Fmoc-S48 | na | na | na |
| 260 | Fmoc-OX-6 | Fmoc-Ala | Fmoc-D-Phe | Fmoc-S48 | na | na | na |
| 261 | Fmoc-OX-5 | Fmoc-D-Ala | Fmoc-D-Phe | Fmoc-S48 | na | na | na |
| 262 | Fmoc-OX-6 | Fmoc-D-Ala | Fmoc-D-Phe | Fmoc-S48 | na | na | na |
| 263 | Fmoc-OX-5 | Fmoc-D-Val | Fmoc-Phe | Fmoc-S48 | na | na | na |
| 264 | Fmoc-OX-6 | Fmoc-D-Val | Fmoc-Phe | Fmoc-S48 | na | na | na |
| 265 | Fmoc-OX-5 | Fmoc-Val | Fmoc-Phe | Fmoc-S48 | na | na | na |
| 266 | Fmoc-OX-6 | Fmoc-Val | Fmoc-Phe | Fmoc-S48 | na | na | na |
| 267 | Fmoc-OX-5 | Fmoc-D-Val | Fmoc-D-Phe | Fmoc-S33 | na | na | na |
| 268 | Fmoc-OX-6 | Fmoc-D-Val | Fmoc-D-Phe | Fmoc-S33 | na | na | na |
| 269 | Fmoc-OX-5 | Fmoc-Val | Fmoc-D-Phe | Fmoc-S33 | na | na | na |
| 270 | Fmoc-OX-6 | Fmoc-Val | Fmoc-D-Phe | Fmoc-S33 | na | na | na |
| 271 | Fmoc-OX-5 | Fmoc-D-Ser(But) | Fmoc-D-Phe | Fmoc-S33 | na | na | na |
| 272 | Fmoc-OX-6 | Fmoc-D-Ser(But) | Fmoc-D-Phe | Fmoc-S33 | na | na | na |
| 273 | Fmoc-OX-5 | Fmoc-Ser(But) | Fmoc-D-Phe | Fmoc-S33 | na | na | na |
| 274 | Fmoc-OX-6 | Fmoc-Ser(But) | Fmoc-D-Phe | Fmoc-S33 | na | na | na |
| 275 | Fmoc-OX-5 | Fmoc-Dap(Boc) | Fmoc-D-Phe | Fmoc-S33 | na | na | na |
| 276 | Fmoc-OX-6 | Fmoc-Dap(Boc) | Fmoc-D-Phe | Fmoc-S33 | na | na | na |
| 277 | Fmoc-OX-5 | Fmoc-Ala | Fmoc-D-Phe | Fmoc-S33 | na | na | na |
| 278 | Fmoc-OX-6 | Fmoc-Ala | Fmoc-D-Phe | Fmoc-S33 | na | na | na |
| 279 | Fmoc-OX-5 | Fmoc-D-Ala | Fmoc-D-Phe | Fmoc-S33 | na | na | na |
| 280 | Fmoc-OX-6 | Fmoc-D-Ala | Fmoc-D-Phe | Fmoc-S33 | na | na | na |
| 281 | Fmoc-OX-5 | Fmoc-D-Val | Fmoc-Phe | Fmoc-S33 | na | na | na |
| 282 | Fmoc-OX-6 | Fmoc-D-Val | Fmoc-Phe | Fmoc-S33 | na | na | na |
| 283 | Fmoc-OX-5 | Fmoc-Val | Fmoc-Phe | Fmoc-S33 | na | na | na |
| 284 | Fmoc-OX-6 | Fmoc-Val | Fmoc-Phe | Fmoc-S33 | na | na | na |
| 285 | Fmoc-OX-5 | Fmoc-D-Dap(Boc) | Fmoc-D-Phe | Fmoc-S48 | na | na | na |
| 286 | Fmoc-OX-6 | Fmoc-D-Dap(Boc) | Fmoc-D-Phe | Fmoc-S48 | na | na | na |
| 287 | Fmoc-OX-5 | Fmoc-D-Dap(Boc) | Fmoc-D-Phe | Fmoc-S33 | na | na | na |
| 288 | Fmoc-OX-6 | Fmoc-D-Dap(Boc) | Fmoc-D-Phe | Fmoc-S33 | na | na | na |
| 289 | Fmoc-OX-6 | Fmoc-D-Ser(But) | Fmoc-D-Phe | Fmoc-S33 | na | na | na | na = not available

[1] All syntheses were carried out on the solid phase starting from 70-80 mg of 2-chlorotrityl chloride resin (typical loading 1.0 mmol/g).
[2] Purity is determined by analysis with LC-UV at 220 nm.

TABLE 1B

| Cpd | R₁ | R₂ | R₃ | R₄ | R₅ | R₆ |
|---|---|---|---|---|---|---|
| 1 | (S)- isobutyl(CH) | (R)- 1H-indol-3-ylmethyl(CH) | H | (S)—CH₃ | H | 3-methoxybenzyl(NH) |
| 2 | (S)- isobutyl(CH) | (R)- 4-hydroxybenzyl(CH) | H | (S)—CH₃ | H | 3-methoxybenzyl(NH) |
| 3 | (S)- isobutyl(CH) | (R)- 1H-indol-3-ylmethyl(CH) | H | (S)—CH₃ | H | 3-methoxybenzyl(NH) |
| 4 | (S)- isobutyl(CH) | (R)- 4-hydroxybenzyl(CH) | H | (S)—CH₃ | H | 3-methoxybenzyl(NH) |

TABLE 1B-continued

| Cpd | R₁ | R₂ | R₃ | R₄ | R₅ | R₆ |
|---|---|---|---|---|---|---|
| 5 | (S)- isobutyl (CH) | (R)- indol-3-ylmethyl (CH) | H | (S)- H₂NOC-CH₂-CH₂ (CH) | H | 3-(hydroxymethyl)benzyl (NH)(H₂C) |
| 6 | (S)- isobutyl (CH) | (R)- 4-hydroxybenzyl (CH) | H | (S)- H₂NOC-CH₂-CH₂ (CH) | H | 3-(hydroxymethyl)benzyl (NH)(H₂C) |
| 7 | (S)- isobutyl (CH) | (R)- indol-3-ylmethyl (CH) | H | (S)- H₂NOC-CH₂-CH₂ (CH) | H | 3-(hydroxymethyl)benzyl (NH)(H₂C) |
| 8 | (S)- isobutyl (CH) | (R)- 4-hydroxybenzyl (CH) | H | (S)- H₂NOC-CH₂-CH₂ (CH) | H | 3-(hydroxymethyl)benzyl (NH)(H₂C) |

TABLE 1B-continued

| Cpd | R$_1$ | R$_2$ | R$_3$ | R$_4$ | R$_5$ | R$_6$ |
|---|---|---|---|---|---|---|
| 9 | (S)- isobutyl(CH) | (R)- indol-3-ylmethyl(CH) | H | (S)- HO$_2$C-CH$_2$(CH) | H | 3-methoxybenzyl(NH)(H$_2$CO) |
| 10 | (S)- isobutyl(CH) | (R)- 4-hydroxybenzyl(CH) | H | (S)- HO$_2$C-CH$_2$(CH) | H | 3-methoxybenzyl(NH)(H$_2$CO) |
| 11 | (S)- isobutyl(CH) | (R)- indol-3-ylmethyl(CH) | H | (S)- HO$_2$C-CH$_2$(CH) | H | 3-methoxybenzyl(NH)(H$_2$CO) |
| 12 | (S)- isobutyl(CH) | (R)- 4-hydroxybenzyl(CH) | H | (S)- HO$_2$C-CH$_2$(CH) | H | 3-methoxybenzyl(NH)(H$_2$CO) |

TABLE 1B-continued

| Cpd | R₁ | R₂ | R₃ | R₄ | R₅ | R₆ |
|---|---|---|---|---|---|---|
| 13 | (S)- isobutyl (CH) | (R)- indolylmethyl (CH) | H | (R)-CH₃ | H | 3-methoxybenzyl (NH)(H₂C) |
| 14 | (S)- isobutyl (CH) | (R)- 4-hydroxybenzyl (CH) | H | (R)-CH₃ | H | 3-methoxybenzyl (NH)(H₂C) |
| 15 | (S)- isobutyl (CH) | (R)- indolylmethyl (CH) | H | (R)-CH₃ | H | 3-methoxybenzyl (NH)(H₂C) |
| 16 | (S)- isobutyl (CH) | (R)- 4-hydroxybenzyl (CH) | H | (R)-CH₃ | H | 3-methoxybenzyl (NH)(H₂C) |

TABLE 1B-continued

| Cpd | R₁ | R₂ | R₃ | R₄ | R₅ | R₆ |
|---|---|---|---|---|---|---|
| 17 | (S)-isobutyl(CH) | (R)-indol-3-ylmethyl(CH) | H | (R)-CH₂CH₂C(O)NH₂ | H | 3-(methyl)benzyl(NH) |
| 18 | (S)-isobutyl(CH) | (R)-4-hydroxybenzyl(CH) | H | (R)-CH₂CH₂C(O)NH₂ | H | 3-(methyl)benzyl(NH) |
| 19 | (S)-isobutyl(CH) | (S)-indol-3-ylmethyl(CH) | H | (R)-CH₂CH₂C(O)NH₂ | H | 3-(methyl)benzyl(NH) |
| 20 | (S)-isobutyl(CH) | (S)-4-hydroxybenzyl(CH) | H | (R)-CH₂CH₂C(O)NH₂ | H | 3-(methyl)benzyl(NH) |

TABLE 1B-continued

| Cpd | R₁ | R₂ | R₃ | R₄ | R₅ | R₆ |
|---|---|---|---|---|---|---|
| 21 | (S)- isobutyl(CH) | (R)- 3-indolylmethyl(CH) | H | (R)- HO₂C-CH₂-CH₂(CH) | H | 3-(H₂C)-phenyl-CH₂(NH) |
| 22 | (S)- isobutyl(CH) | (R)- 4-hydroxybenzyl(CH) | H | (R)- HO₂C-CH₂-CH₂(CH) | H | 3-(H₂C)-phenyl-CH₂(NH) |
| 23 | (S)- isobutyl(CH) | (S)- 3-indolylmethyl(CH) | H | (R)- HO₂C-CH₂-CH₂(CH) | H | 3-(H₂C)-phenyl-CH₂(NH) |
| 24 | (S)- isobutyl(CH) | (S)- 4-hydroxybenzyl(CH) | H | (R)- HO₂C-CH₂-CH₂(CH) | H | 3-(H₂C)-phenyl-CH₂(NH) |

TABLE 1B-continued

| Cpd | R₁ | R₂ | R₃ | R₄ | R₅ | R₆ |
|---|---|---|---|---|---|---|
| 25 | (S)- isobutyl (CH) | (R)- indol-3-ylmethyl (CH) | H | (R)- imidazol-4-ylmethyl (CH) | H | 3-methoxybenzyl (NH)(H₂C) |
| 26 | (S)- isobutyl (CH) | (R)- 4-hydroxybenzyl (CH) | H | (R)- imidazol-4-ylmethyl (CH) | H | 3-methoxybenzyl (NH)(H₂C) |
| 27 | (S)- isobutyl (CH) | (S)- indol-3-ylmethyl (CH) | H | (R)- imidazol-4-ylmethyl (CH) | H | 3-methoxybenzyl (NH)(H₂C) |
| 28 | (S)- isobutyl (CH) | (S)- 4-hydroxybenzyl (CH) | H | (R)- imidazol-4-ylmethyl (CH) | H | 3-methoxybenzyl (NH)(H₂C) |

TABLE 1B-continued

| Cpd | R$_1$ | R$_2$ | R$_3$ | R$_4$ | R$_5$ | R$_6$ |
|---|---|---|---|---|---|---|
| 29 | (S)-isobutyl | (R)-indol-3-ylmethyl (CH$_2$) | H | (R)-(CH$_2$)$_4$NH$_2$ | H | 3-methoxybenzyl (NH) |
| 30 | (S)-isobutyl | (R)-4-hydroxybenzyl (CH$_2$) | H | (R)-(CH$_2$)$_4$NH$_2$ | H | 3-methoxybenzyl (NH) |
| 31 | (S)-isobutyl | (S)-indol-3-ylmethyl (CH$_2$) | H | (R)-(CH$_2$)$_4$NH$_2$ | H | 3-methoxybenzyl (NH) |
| 32 | (S)-isobutyl | (S)-4-hydroxybenzyl (CH$_2$) | H | (R)-(CH$_2$)$_4$NH$_2$ | H | 3-methoxybenzyl (NH) |

TABLE 1B-continued

| Cpd | R₁ | R₂ | R₃ | R₄ | R₅ | R₆ |
|---|---|---|---|---|---|---|
| 33 | (S)- isobutyl | (R)- indol-3-ylmethyl (CH₂) | H | (R)- butyl (CH₂) | H | 3-(aminomethyl)benzyl |
| 34 | (S)- isobutyl | (R)- 4-hydroxybenzyl (CH₂) | H | (R)- butyl (CH₂) | H | 3-(aminomethyl)benzyl |
| 35 | (S)- isobutyl | (S)- indol-3-ylmethyl (CH₂) | H | (R)- butyl (CH₂) | H | 3-(aminomethyl)benzyl |
| 36 | (S)- isobutyl | (S)- 4-hydroxybenzyl (CH₂) | H | (R)- butyl (CH₂) | H | 3-(aminomethyl)benzyl |

TABLE 1B-continued

| Cpd | R₁ | R₂ | R₃ | R₄ | R₅ | R₆ |
|-----|-----|-----|-----|-----|-----|-----|
| 37 | (S)- isobutyl (CH) | (R)- indol-3-ylmethyl-CH₂ (CH) | H | (R)- benzyl (CH) | H | 3-methoxybenzyl (NH) |
| 38 | (S)- isobutyl (CH) | (R)- 4-hydroxybenzyl (CH) | H | (R)- benzyl (CH) | H | 3-methoxybenzyl (NH) |
| 39 | (S)- isobutyl (CH) | (S)- indol-3-ylmethyl-CH₂ (CH) | H | (R)- benzyl (CH) | H | 3-methoxybenzyl (NH) |
| 40 | (S)- isobutyl (CH) | (S)- 4-hydroxybenzyl (CH) | H | (R)- benzyl (CH) | H | 3-methoxybenzyl (NH) |

TABLE 1B-continued

| Cpd | R₁ | R₂ | R₃ | R₄ | R₅ | R₆ |
|---|---|---|---|---|---|---|
| 41 | (S)- isobutyl(CH) | (R)- 3-indolylmethyl(CH) | H | (R)- pyrrolidinyl(HC)(N) | H | 3-methoxybenzyl(H₂C)(NH) |
| 42 | (S)- isobutyl(CH) | (R)- 4-hydroxybenzyl(CH) | H | (R)- pyrrolidinyl(HC)(N) | H | 3-methoxybenzyl(H₂C)(NH) |
| 43 | (S)- isobutyl(CH) | (S)- 3-indolylmethyl(CH) | H | (R)- pyrrolidinyl(HC)(N) | H | 3-methoxybenzyl(H₂C)(NH) |
| 44 | (S)- isobutyl(CH) | (S)- 4-hydroxybenzyl(CH) | H | (R)- pyrrolidinyl(HC)(N) | H | 3-methoxybenzyl(H₂C)(NH) |

TABLE 1B-continued

| Cpd | R₁ | R₂ | R₃ | R₄ | R₅ | R₆ |
|---|---|---|---|---|---|---|
| 45 | (S)- isobutyl(CH) | (R)- indol-3-ylmethyl(CH) | H | (R)- hydroxyethyl(CH) | H | 3-methoxybenzyl(NH) |
| 46 | (S)- isobutyl(CH) | (R)- 4-hydroxybenzyl(CH) | H | (R)- hydroxyethyl(CH) | H | 3-methoxybenzyl(NH) |
| 47 | (S)- isobutyl(CH) | (S)- indol-3-ylmethyl(CH) | H | (R)- hydroxyethyl(CH) | H | 3-methoxybenzyl(NH) |
| 48 | (S)- isobutyl(CH) | (S)- 4-hydroxybenzyl(CH) | H | (R)- hydroxyethyl(CH) | H | 3-methoxybenzyl(NH) |

TABLE 1B-continued
| Cpd | R₁ | R₂ | R₃ | R₄ | R₅ | R₆ |
|---|---|---|---|---|---|---|
| 49 | (S)- 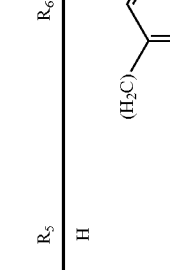 | (S)—CH₃ | H | (R)- 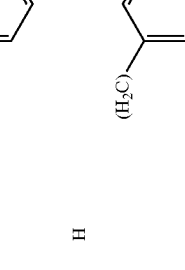 | H | 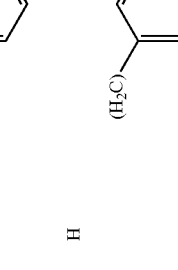 |
| 50 | (S)- 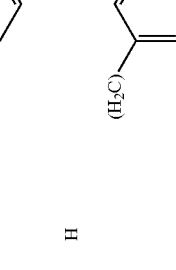 | (S)- H₂NOC—(CH) | H | (R)-  | H | 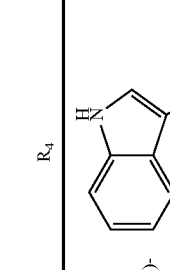 |
| 51 | (S)- 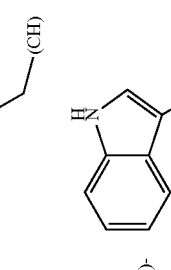 | (R)—CH₃ | H | (R)- 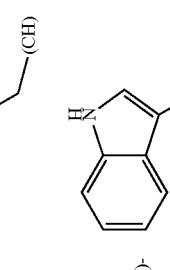 | H | 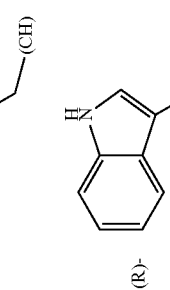 |
| 52 | (S)- 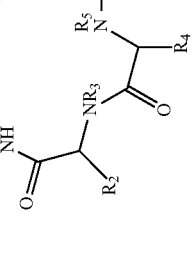 | (S)- H₂N—(CH) | H | (R)- 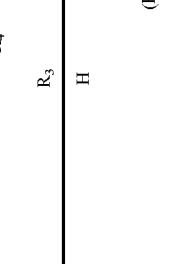 | H | 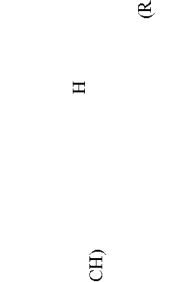 |

TABLE 1B-continued

| Cpd | R₁ | R₂ | R₃ | R₄ | R₅ | R₆ |
|---|---|---|---|---|---|---|
| 53 | (S)- isobutyl (CH) | (R)- H₂NOC-CH₂CH₂- (CH) | H | (R)- indol-3-ylmethyl (CH) | H | 3-methoxybenzyl (NH) |
| 54 | (S)- isobutyl (CH) | (R)- H₂N-CH₂CH₂- (CH) | H | (R)- indol-3-ylmethyl (CH) | H | 3-methoxybenzyl (NH) |
| 55 | (S)- isobutyl (CH) | (R)- H₂NOC-CH₂CH₂CH₂- (CH) | H | (R)- indol-3-ylmethyl (CH) | H | 3-methoxybenzyl (NH) |
| 56 | (S)- isobutyl (CH) | (R)- HO₂C-CH₂CH₂CH₂- (CH) | H | (R)- indol-3-ylmethyl (CH) | H | 3-methoxybenzyl (NH) |

TABLE 1B-continued

| Cpd | R₁ | R₂ | R₃ | R₄ | R₅ | R₆ |
|---|---|---|---|---|---|---|
| 57 | (S)-isobutyl | (R)-imidazolylmethyl | H | (R)-indolylmethyl | H | 3-(aminomethyl)benzyl |
| 58 | (S)-isobutyl | (R)-sec-butyl | H | (R)-indolylmethyl | H | 3-(aminomethyl)benzyl |
| 59 | (S)-isobutyl | (R)-4-aminobutyl | H | (R)-indolylmethyl | H | 3-(aminomethyl)benzyl |
| 60 | (S)-isobutyl | (R)-propyl | H | (R)-indolylmethyl | H | 3-(aminomethyl)benzyl |

TABLE 1B-continued

| Cpd | R₁ | R₂ | R₃ | R₄ | R₅ | R₆ |
|---|---|---|---|---|---|---|
| 61 | (S)- isobutyl (CH) | (R)- benzyl (CH) | H | (R)- indol-3-ylmethyl (CH) | H | 3-methoxybenzyl (NH)(H₂CO) |
| 62 | (S)- isobutyl (CH) | (R)- pyrrolidin-2-yl (HC)(N) | H | (R)- indol-3-ylmethyl (CH) | H | 3-methoxybenzyl (NH)(H₂CO) |
| 63 | (S)- isobutyl (CH) | (R)- 2-hydroxyethyl (HO)(CH) | H | (R)- indol-3-ylmethyl (CH) | H | 3-methoxybenzyl (NH)(H₂CO) |
| 64 | (S)- isobutyl (CH) | (R)- indol-3-ylmethyl (CH) | H | (R)- indol-3-ylmethyl (CH) | H | 3-methoxybenzyl (NH)(H₂CO) |

TABLE 1B-continued

| Cpd | R₁ | R₂ | R₃ | R₄ | R₅ | R₆ |
|---|---|---|---|---|---|---|
| 65 | (S)- isobutyl (CH) | (R)- 4-hydroxybenzyl (CH) | H | (R)- indol-3-ylmethyl (CH) | H | 3-methoxybenzyl (NH) |
| 66 | (S)- isobutyl (CH) | (R)- isopropyl (CH) | H | (R)- indol-3-ylmethyl (CH) | H | 3-methoxybenzyl (NH) |
| 67 | (S)- isobutyl (CH) | (S)- HO₂C-CH₂CH₂- (CH) | H | (R)- indol-3-ylmethyl (CH) | H | 3-methoxybenzyl (NH) |
| 68 | (S)- isobutyl (CH) | H | Me | (R)- indol-3-ylmethyl (CH) | H | 3-methoxybenzyl (NH) |

TABLE 1B-continued

| Cpd | R₁ | R₂ | R₃ | R₄ | R₅ | R₆ |
|---|---|---|---|---|---|---|
| 69 | (S)- isobutyl (CH) | (S)- imidazolylmethyl (CH) | H | (R)- indolylmethyl (CH) | H | 3-methylbenzyl (NH) |
| 70 | (S)- isobutyl (CH) | (S)- sec-butyl (CH) | H | (R)- indolylmethyl (CH) | H | 3-methylbenzyl (NH) |
| 71 | (S)- isobutyl (CH) | (S)- 4-aminobutyl (CH) | H | (R)- indolylmethyl (CH) | H | 3-methylbenzyl (NH) |
| 72 | (S)- isobutyl (CH) | (S)- propyl (CH) | H | (R)- indolylmethyl (CH) | H | 3-methylbenzyl (NH) |

TABLE 1B-continued
| Cpd | R₁ | R₂ | R₃ | R₄ | R₅ | R₆ |
|---|---|---|---|---|---|---|
| 73 | (S)- (CH) | (S)- (CH) | H | (R)- (CH) | H | (NH)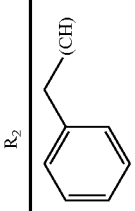(H₂C) |
| 74 | (S)- (CH) | (S)- (HC)(N) | H | (R)- (CH) | H | (NH)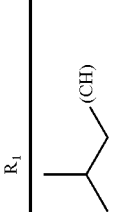(H₂C) |
| 75 | (S)- (CH) | (S)- HO(CH) | H | (R)- (CH) | H | (NH)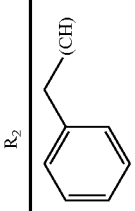(H₂C) |
| 76 | (S)- (CH) | (S)- 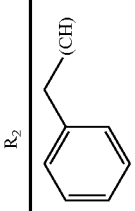(CH) | H | (R)- (CH) | H | (NH)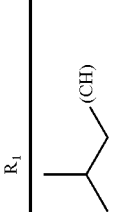(H₂C) |

TABLE 1B-continued

| Cpd | R₁ | R₂ | R₃ | R₄ | R₅ | R₆ |
|---|---|---|---|---|---|---|
| 77 | (S)- isobutyl (CH) | (S)- 4-hydroxybenzyl (CH) | H | (R)- indol-3-ylmethyl (CH) | H | 3-methoxybenzyl (NH)(H₂C) |
| 78 | (S)- isobutyl (CH) | (S)- isopropyl (CH) | H | (R)- indol-3-ylmethyl (CH) | H | 3-methoxybenzyl (NH)(H₂C) |
| 79 | (S)- isobutyl (CH) | (S)-CH₃ | H | (R)- 4-hydroxybenzyl (CH) | H | 3-methoxybenzyl (NH)(H₂C) |
| 80 | (S)- isobutyl (CH) | (S)- H₂NOC-CH₂CH₂ (CH) | H | (R)- 4-hydroxybenzyl (CH) | H | 3-methoxybenzyl (NH)(H₂C) |

TABLE 1B-continued

| Cpd | R₁ | R₂ | R₃ | R₄ | R₅ | R₆ |
|---|---|---|---|---|---|---|
| 81 | (S)- isobutyl (CH) | (R)—CH₃ | H | (R)- 4-hydroxybenzyl (CH) | H | 3-(H₂C)-benzyl (NH) |
| 82 | (S)- isobutyl (CH) | (S)- H₂N-ethyl (CH) | H | (R)- 4-hydroxybenzyl (CH) | H | 3-(H₂C)-benzyl (NH) |
| 83 | (S)- isobutyl (CH) | (R)- H₂NOC-ethyl (CH) | H | (R)- 4-hydroxybenzyl (CH) | H | 3-(H₂C)-benzyl (NH) |
| 84 | (S)- isobutyl (CH) | (R)- H₂N-ethyl (CH) | H | (R)- 4-hydroxybenzyl (CH) | H | 3-(H₂C)-benzyl (NH) |

TABLE 1B-continued

| Cpd | R₁ | R₂ | R₃ | R₄ | R₅ | R₆ |
|---|---|---|---|---|---|---|
| 85 | (S)- isobutyl(CH) | (R)- H₂NOC-propyl(CH) | H | (R)- 4-hydroxybenzyl(CH) | H | 3-(aminomethyl)benzyl (H₂C)(NH) |
| 86 | (S)- isobutyl(CH) | (R)- HO₂C-propyl(CH) | H | (R)- 4-hydroxybenzyl(CH) | H | 3-(aminomethyl)benzyl (H₂C)(NH) |
| 87 | (S)- isobutyl(CH) | (R)- imidazolylmethyl(CH) | H | (R)- 4-hydroxybenzyl(CH) | H | 3-(aminomethyl)benzyl (H₂C)(NH) |
| 88 | (S)- isobutyl(CH) | (R)- sec-butyl(CH) | H | (R)- 4-hydroxybenzyl(CH) | H | 3-(aminomethyl)benzyl (H₂C)(NH) |

TABLE 1B-continued

| Cpd | R₁ | R₂ | R₃ | R₄ | R₅ | R₆ |
|-----|----|----|----|----|----|----|
| 89 | (S)-isobutyl(CH) | (R)-4-aminobutyl(CH), H₂N- | H | (R)-4-hydroxybenzyl(CH), HO- | H | 3-(aminomethyl)benzyl (NH), (H₂C)- |
| 90 | (S)-isobutyl(CH) | (R)-propyl(CH) | H | (R)-4-hydroxybenzyl(CH), HO- | H | 3-(aminomethyl)benzyl (NH), (H₂C)- |
| 91 | (S)-isobutyl(CH) | (R)-benzyl(CH) | H | (R)-4-hydroxybenzyl(CH), HO- | H | 3-(aminomethyl)benzyl (NH), (H₂C)- |
| 92 | (S)-isobutyl(CH) | (R)-pyrrolidinyl(HC) | H | (R)-4-hydroxybenzyl(CH), HO- | H | 3-(aminomethyl)benzyl (NH), (H₂C)- |

TABLE 1B-continued

| Cpd | R₁ | R₂ | R₃ | R₄ | R₅ | R₆ |
|---|---|---|---|---|---|---|
| 93 | (S)-isobutyl(CH) | (R)-CH₂CH₂OH | H | (R)-4-hydroxybenzyl(CH) | H | 3-(CH₂)-benzyl(NH) |
| 94 | (S)-isobutyl(CH) | (R)-3-indolylmethyl(CH) | H | (R)-4-hydroxybenzyl(CH) | H | 3-(CH₂)-benzyl(NH) |
| 95 | (S)-isobutyl(CH) | (R)-4-hydroxybenzyl(CH) | H | (R)-4-hydroxybenzyl(CH) | H | 3-(CH₂)-benzyl(NH) |
| 96 | (S)-isobutyl(CH) | (R)-isobutyl(CH) | H | (R)-4-hydroxybenzyl(CH) | H | 3-(CH₂)-benzyl(NH) |

TABLE 1B-continued

| Cpd | R₁ | R₂ | R₃ | R₄ | R₅ | R₆ |
|---|---|---|---|---|---|---|
| 97 | (S)-isobutyl(CH) | (S)-HO₂C-propyl(CH) | H | (R)-4-hydroxybenzyl(CH) | H | 3-methoxybenzyl(NH) |
| 98 | (S)-isobutyl(CH) | H | Me | (R)-4-hydroxybenzyl(CH) | H | 3-methoxybenzyl(NH) |
| 99 | (S)-isobutyl(CH) | (S)-(1H-imidazol-4-yl)methyl(CH) | H | (R)-4-hydroxybenzyl(CH) | H | 3-methoxybenzyl(NH) |
| 100 | (S)-isobutyl(CH) | (S)-sec-butyl(CH) | H | (R)-4-hydroxybenzyl(CH) | H | 3-methoxybenzyl(NH) |

TABLE 1B-continued

| Cpd | R₁ | R₂ | R₃ | R₄ | R₅ | R₆ |
|---|---|---|---|---|---|---|
| 101 | (S)- isobutyl(CH) | (S)- 4-aminobutyl (CH) H₂N- | H | (R)- 4-hydroxybenzyl (CH) HO- | H | 3-(methylene)benzyl (H₂C)-(NH) |
| 102 | (S)- isobutyl(CH) | (S)- propyl (CH) | H | (R)- 4-hydroxybenzyl (CH) HO- | H | 3-(methylene)benzyl (H₂C)-(NH) |
| 103 | (S)- isobutyl(CH) | (S)- benzyl (CH) | H | (R)- 4-hydroxybenzyl (CH) HO- | H | 3-(methylene)benzyl (H₂C)-(NH) |
| 104 | (S)- isobutyl(CH) | (S)- pyrrolidinyl (HC)-(N) | H | (R)- 4-hydroxybenzyl (CH) HO- | H | 3-(methylene)benzyl (H₂C)-(NH) |

TABLE 1B-continued

| Cpd | R₁ | R₂ | R₃ | R₄ | R₅ | R₆ |
|-----|----|----|----|----|----|----|
| 105 | (S)- isobutyl(CH) | (S)- HOCH₂(CH) | H | (R)- 4-hydroxybenzyl(CH) | H | 3-(H₂C)benzyl(NH) |
| 106 | (S)- isobutyl(CH) | (S)- indol-3-ylmethyl(CH) | H | (R)- 4-hydroxybenzyl(CH) | H | 3-(H₂C)benzyl(NH) |
| 107 | (S)- isobutyl(CH) | (S)- 4-hydroxybenzyl(CH) | H | (R)- 4-hydroxybenzyl(CH) | H | 3-(H₂C)benzyl(NH) |
| 108 | (S)- isobutyl(CH) | (S)- isobutyl(CH) | H | (R)- 4-hydroxybenzyl(CH) | H | 3-(H₂C)benzyl(NH) |

TABLE 1B-continued

| Cpd | R₁ | R₂ | R₃ | R₄ | R₅ | R₆ |
|---|---|---|---|---|---|---|
| 109 | (S)- isobutyl (CH) | (R)- indol-3-ylmethyl (CH) | H | (R)- isopropyl (CH) | H | 3-(methoxy)benzyl (NH)(H₂C) |
| 110 | (S)- isobutyl (CH) | (R)- 4-hydroxybenzyl (CH) | H | (R)- isopropyl (CH) | H | 3-(methoxy)benzyl (NH)(H₂C) |
| 111 | (S)- isobutyl (CH) | (S)- indol-3-ylmethyl (CH) | H | (R)- isopropyl (CH) | H | 3-(methoxy)benzyl (NH)(H₂C) |
| 112 | (S)- isobutyl (CH) | (S)- 4-hydroxybenzyl (CH) | H | (R)- isopropyl (CH) | H | 3-(methoxy)benzyl (NH)(H₂C) |

TABLE 1B-continued

| Cpd | R₁ | R₂ | R₃ | R₄ | R₅ | R₆ |
|---|---|---|---|---|---|---|
| 113 | (S)- isobutyl (CH) | (R)- 3-indolylmethyl (CH) | H | H | Me | 3-methoxybenzyl (NH)(H₂C) |
| 114 | (S)- isobutyl (CH) | (R)- 4-hydroxybenzyl (CH) | H | H | Me | 3-methoxybenzyl (NH)(H₂C) |
| 115 | (S)- isobutyl (CH) | (S)- 3-indolylmethyl (CH) | H | H | Me | 3-methoxybenzyl (NH)(H₂C) |
| 116 | (S)- isobutyl (CH) | (S)- 4-hydroxybenzyl (CH) | H | H | Me | 3-methoxybenzyl (NH)(H₂C) |

TABLE 1B-continued

| Cpd | R₁ | R₂ | R₃ | R₄ | R₅ | R₆ |
|---|---|---|---|---|---|---|
| 117 | (S)- isobutyl (CH) | (R)- indolylmethyl (CH) | H | (S)- imidazolylmethyl (CH) | H | 3-methoxybenzyl (NH) |
| 118 | (S)- isobutyl (CH) | (R)- 4-hydroxybenzyl (CH) | H | (S)- imidazolylmethyl (CH) | H | 3-methoxybenzyl (NH) |
| 119 | (S)- isobutyl (CH) | (S)- indolylmethyl (CH) | H | (S)- imidazolylmethyl (CH) | H | 3-methoxybenzyl (NH) |
| 120 | (S)- isobutyl (CH) | (S)- 4-hydroxybenzyl (CH) | H | (S)- imidazolylmethyl (CH) | H | 3-methoxybenzyl (NH) |

TABLE 1B-continued

| Cpd | R₁ | R₂ | R₃ | R₄ | R₅ | R₆ |
|-----|----|----|----|----|----|----|
| 121 | (S)- isobutyl (CH) | (R)- indol-3-ylmethyl (CH) | H | (S)- 4-aminobutyl (CH), H₂N | H | 3-(methyl)benzyl (NH), (H₂C) |
| 122 | (S)- isobutyl (CH) | (R)- 4-hydroxybenzyl (CH), HO | H | (S)- 4-aminobutyl (CH), H₂N | H | 3-(methyl)benzyl (NH), (H₂C) |
| 123 | (S)- isobutyl (CH) | (S)- indol-3-ylmethyl (CH) | H | (S)- 4-aminobutyl (CH), H₂N | H | 3-(methyl)benzyl (NH), (H₂C) |
| 124 | (S)- isobutyl (CH) | (S)- 4-hydroxybenzyl (CH), HO | H | (S)- 4-aminobutyl (CH), H₂N | H | 3-(methyl)benzyl (NH), (H₂C) |

TABLE 1B-continued

| Cpd | R1 | R2 | R3 | R4 | R5 | R6 |
|---|---|---|---|---|---|---|
| 125 | (S)- isobutyl | (R)- CH2-indole | H | (S)- n-butyl | H | 3-methoxybenzyl (NH) |
| 126 | (S)- isobutyl | (R)- CH2-(4-hydroxyphenyl) | H | (S)- n-butyl | H | 3-methoxybenzyl (NH) |
| 127 | (S)- isobutyl | (S)- CH2-indole | H | (S)- n-butyl | H | 3-methoxybenzyl (NH) |
| 128 | (S)- isobutyl | (S)- CH2-(4-hydroxyphenyl) | H | (S)- n-butyl | H | 3-methoxybenzyl (NH) |

TABLE 1B-continued

| Cpd | R₁ | R₂ | R₃ | R₄ | R₅ | R₆ |
|-----|----|----|----|----|----|----|
| 129 | (S)- isobutyl(CH) | (R)- indolylmethyl(CH) | H | (S)- benzyl(CH) | H | 3-methoxybenzyl(NH) |
| 130 | (S)- isobutyl(CH) | (R)- 4-hydroxybenzyl(CH) | H | (S)- benzyl(CH) | H | 3-methoxybenzyl(NH) |
| 131 | (S)- isobutyl(CH) | (S)- indolylmethyl(CH) | H | (S)- benzyl(CH) | H | 3-methoxybenzyl(NH) |
| 132 | (S)- isobutyl(CH) | (S)- 4-hydroxybenzyl(CH) | H | (S)- benzyl(CH) | H | 3-methoxybenzyl(NH) |

TABLE 1B-continued

| Cpd | R₁ | R₂ | R₃ | R₄ | R₅ | R₆ |
|---|---|---|---|---|---|---|
| 133 | (S)-isobutyl | (R)-indol-3-ylmethyl | H | (S)-pyrrolidinyl | H | 3-(methoxy)benzyl (NH) |
| 134 | (S)-isobutyl | (R)-4-hydroxybenzyl | H | (S)-pyrrolidinyl | H | 3-(methoxy)benzyl (NH) |
| 135 | (S)-isobutyl | (S)-indol-3-ylmethyl | H | (S)-pyrrolidinyl | H | 3-(methoxy)benzyl (NH) |
| 136 | (S)-isobutyl | (S)-4-hydroxybenzyl | H | (S)-pyrrolidinyl | H | 3-(methoxy)benzyl (NH) |

TABLE 1B-continued
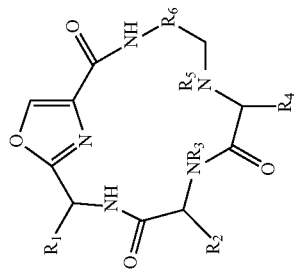
| Cpd | R₁ | R₂ | R₃ | R₄ | R₅ | R₆ |
|---|---|---|---|---|---|---|
| 137 | (S)- isobutyl (CH) | (R)- indol-3-ylmethyl (CH) | H | (S)- hydroxymethyl (CH) | H | 3-methoxybenzyl (NH)(H₂C) |
| 138 | (S)- isobutyl (CH) | (R)- 4-hydroxybenzyl (CH) | H | (S)- hydroxymethyl (CH) | H | 3-methoxybenzyl (NH)(H₂C) |
| 139 | (S)- isobutyl (CH) | (S)- indol-3-ylmethyl (CH) | H | (S)- hydroxymethyl (CH) | H | 3-methoxybenzyl (NH)(H₂C) |
| 140 | (S)- isobutyl (CH) | (S)- 4-hydroxybenzyl (CH) | H | (S)- hydroxymethyl (CH) | H | 3-methoxybenzyl (NH)(H₂C) |

TABLE 1B-continued

| Cpd | R₁ | R₂ | R₃ | R₄ | R₅ | R₆ |
|---|---|---|---|---|---|---|
| 141 | (S)- isobutyl (CH) | (S)-CH₃ | H | (S)- indol-3-ylmethyl (CH) | H | 3-methoxybenzyl (NH)(H₂C) |
| 142 | (S)- isobutyl (CH) | (S)- H₂NOC-CH₂ (CH) | H | (S)- indol-3-ylmethyl (CH) | H | 3-methoxybenzyl (NH)(H₂C) |
| 143 | (S)- isobutyl (CH) | (R)-CH₃ | H | (S)- indol-3-ylmethyl (CH) | H | 3-methoxybenzyl (NH)(H₂C) |
| 144 | (S)- isobutyl (CH) | (S)- H₂N-CH₂ (CH) | H | (S)- indol-3-ylmethyl (CH) | H | 3-methoxybenzyl (NH)(H₂C) |

TABLE 1B-continued

| Cpd | R₁ | R₂ | R₃ | R₄ | R₅ | R₆ |
|-----|----|----|----|----|----|----|
| 145 | (S)- isobutyl(CH) | (R)- H₂NOC-CH₂-(CH) | H | (S)- indol-3-ylmethyl(CH) | H | 3-methoxybenzyl (NH) |
| 146 | (S)- isobutyl(CH) | (R)- H₂N-CH₂-(CH) | H | (S)- indol-3-ylmethyl(CH) | H | 3-methoxybenzyl (NH) |
| 147 | (S)- isobutyl(CH) | (R)- H₂NOC-CH₂CH₂-(CH) | H | (S)- indol-3-ylmethyl(CH) | H | 3-methoxybenzyl (NH) |
| 148 | (S)- isobutyl(CH) | (R)- HO₂C-CH₂CH₂-(CH) | H | (S)- indol-3-ylmethyl(CH) | H | 3-methoxybenzyl (NH) |

TABLE 1B-continued

| Cpd | R₁ | R₂ | R₃ | R₄ | R₅ | R₆ |
|---|---|---|---|---|---|---|
| 149 | (S)- isobutyl (CH) | (R)- 4-methylimidazole (CH) | H | (S)- 3-indolylmethyl (CH) | H | 3-methoxybenzyl (NH) |
| 150 | (S)- isobutyl (CH) | (R)- sec-butyl (CH) | H | (S)- 3-indolylmethyl (CH) | H | 3-methoxybenzyl (NH) |
| 151 | (S)- isobutyl (CH) | (R)- 4-aminobutyl (CH) | H | (S)- 3-indolylmethyl (CH) | H | 3-methoxybenzyl (NH) |
| 152 | (S)- isobutyl (CH) | (R)- n-propyl (CH) | H | (S)- 3-indolylmethyl (CH) | H | 3-methoxybenzyl (NH) |

TABLE 1B-continued

| Cpd | R₁ | R₂ | R₃ | R₄ | R₅ | R₆ |
|---|---|---|---|---|---|---|
| 153 | (S)- isobutyl (CH) | (R)- benzyl (CH) | H | (S)- indol-3-ylmethyl (CH) | H | 3-methoxybenzyl (NH)(H₂C) |
| 154 | (S)- isobutyl (CH) | (R)- pyrrolidin-2-yl (HC)(N) | H | (S)- indol-3-ylmethyl (CH) | H | 3-methoxybenzyl (NH)(H₂C) |
| 155 | (S)- isobutyl (CH) | (R)- hydroxymethyl HO (CH) | H | (S)- indol-3-ylmethyl (CH) | H | 3-methoxybenzyl (NH)(H₂C) |
| 156 | (S)- isobutyl (CH) | (R)- indol-3-ylmethyl (CH) | H | (S)- indol-3-ylmethyl (CH) | H | 3-methoxybenzyl (NH)(H₂C) |

TABLE 1B-continued

| Cpd | R₁ | R₂ | R₃ | R₄ | R₅ | R₆ |
|---|---|---|---|---|---|---|
| 157 | (S)- isobutyl (CH) | (R)- 4-hydroxybenzyl (CH) | H | (S)- indol-3-ylmethyl (CH) | H | 3-(aminomethyl)benzyl (NH)(H₂C) |
| 158 | (S)- isobutyl (CH) | (R)- isopropyl (CH) | H | (S)- indol-3-ylmethyl (CH) | H | 3-(aminomethyl)benzyl (NH)(H₂C) |
| 159 | (S)- isobutyl (CH) | (S)- 2-carboxyethyl (CH) HO₂C | H | (S)- indol-3-ylmethyl (CH) | H | 3-(aminomethyl)benzyl (NH)(H₂C) |
| 160 | (S)- isobutyl (CH) | H | Me | (S)- indol-3-ylmethyl (CH) | H | 3-(aminomethyl)benzyl (NH)(H₂C) |

TABLE 1B-continued

| Cpd | R₁ | R₂ | R₃ | R₄ | R₅ | R₆ |
|---|---|---|---|---|---|---|
| 161 | (S)-isobutyl | (S)-imidazolylmethyl | H | (S)-indol-3-ylmethyl | H | 3-(aminomethyl)benzyl |
| 162 | (S)-isobutyl | (S)-sec-butyl | H | (S)-indol-3-ylmethyl | H | 3-(aminomethyl)benzyl |
| 163 | (S)-isobutyl | (S)-4-aminobutyl | H | (S)-indol-3-ylmethyl | H | 3-(aminomethyl)benzyl |
| 164 | (S)-isobutyl | (S)-n-propyl | H | (S)-indol-3-ylmethyl | H | 3-(aminomethyl)benzyl |

TABLE 1B-continued

| Cpd | R₁ | R₂ | R₃ | R₄ | R₅ | R₆ |
|---|---|---|---|---|---|---|
| 165 | (S)-isobutyl | (S)-benzyl | H | (S)-indol-3-ylmethyl | H | 3-(methyl)benzyl(NH) |
| 166 | (S)-isobutyl | (S)-pyrrolidinyl | H | (S)-indol-3-ylmethyl | H | 3-(methyl)benzyl(NH) |
| 167 | (S)-isobutyl | (S)-hydroxymethyl | H | (S)-indol-3-ylmethyl | H | 3-(methyl)benzyl(NH) |
| 168 | (S)-isobutyl | (S)-indol-3-ylmethyl | H | (S)-indol-3-ylmethyl | H | 3-(methyl)benzyl(NH) |

TABLE 1B-continued

| Cpd | R₁ | R₂ | R₃ | R₄ | R₅ | R₆ |
|---|---|---|---|---|---|---|
| 169 | (S)- isobutyl (CH) | (S)- 4-hydroxybenzyl (CH) | H | (S)- indol-3-ylmethyl (CH) | H | 3-methoxybenzyl (NH)(H₂C) |
| 170 | (S)- isobutyl (CH) | (S)- isopropyl (CH) | H | (S)- indol-3-ylmethyl (CH) | H | 3-methoxybenzyl (NH)(H₂C) |
| 171 | (S)- isobutyl (CH) | (S)- CH₃ | H | (S)- 4-hydroxybenzyl (CH) | H | 3-methoxybenzyl (NH)(H₂C) |
| 172 | (S)- isobutyl (CH) | (S)- CH₃ | H | (S)- 4-hydroxybenzyl (CH) | H | (S)- 1-(3-methoxyphenyl)ethyl (NH)(H₂C) |
| 173 | (S)- isobutyl (CH) | (S)- H₂NOC-CH₂CH₂ (CH) | H | (S)- 4-hydroxybenzyl (CH) | H | 3-methoxybenzyl (NH)(H₂C) |

TABLE 1B-continued
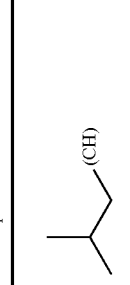
| Cpd | R₁ | R₂ | R₃ | R₄ | R₅ | R₆ |
|---|---|---|---|---|---|---|
| 174 | (S)- isobutyl(CH) | (S)- H₂NOC-(CH) | H | (S)- 4-hydroxybenzyl(CH) | H | (S)- CH(CH₃)(CH₂)(NH) |
| 175 | (S)- isobutyl(CH) | (R)-CH₃(CH) | H | (S)- 4-hydroxybenzyl(CH) | H | 3-methoxybenzyl(NH) |
| 176 | (S)- isobutyl(CH) | (R)-CH₃(CH) | H | (S)- 4-hydroxybenzyl(CH) | H | (S)- CH(CH₃)(CH₂)(NH) |
| 177 | (S)- isobutyl(CH) | (S)- H₂N-(CH) | H | (S)- 4-hydroxybenzyl(CH) | H | 3-methoxybenzyl(NH) |
| 178 | (S)- isobutyl(CH) | (R)- H₂NOC-(CH) | H | (S)- 4-hydroxybenzyl(CH) | H | 3-methoxybenzyl(NH) |

TABLE 1B-continued

| Cpd | R₁ | R₂ | R₃ | R₄ | R₅ | R₆ |
|---|---|---|---|---|---|---|
| 179 | (S)- isobutyl (CH) | (R)- H₂NOC-CH₂-(CH) | H | (S)- 4-hydroxybenzyl (CH) | H | (S)- CH(CH₃)-CH₂-(3-methoxyphenyl)(NH) |
| 180 | (S)- isobutyl (CH) | (R)- H₂N-CH₂-(CH) | H | (S)- 4-hydroxybenzyl (CH) | H | 3-methoxybenzyl (NH) |
| 181 | (S)- isobutyl (CH) | (R)- H₂NOC-CH₂CH₂-(CH) | H | (S)- 4-hydroxybenzyl (CH) | H | 3-methoxybenzyl (NH) |
| 182 | (S)- isobutyl (CH) | (R)- H₂NOC-CH₂CH₂-(CH) | H | (S)- 4-hydroxybenzyl (CH) | H | (S)- CH(CH₃)-CH₂-(3-methoxyphenyl)(NH) |
| 183 | (S)- isobutyl (CH) | (R)- HO₂C-CH₂CH₂-(CH) | H | (S)- 4-hydroxybenzyl (CH) | H | 3-methoxybenzyl (NH) |

TABLE 1B-continued

| Cpd | R₁ | R₂ | R₃ | R₄ | R₅ | R₆ |
|---|---|---|---|---|---|---|
| 184 | (S)- isobutyl (CH) | (R)- -(CH₂)₂-CO₂H | H | (S)- -CH₂-C₆H₄-OH (CH) | H | -(CH₂)-CH(CH₃)- (NH) |
| 185 | (S)- isobutyl (CH) | (R)- -CH₂-(4-imidazolyl) (CH) | H | (S)- -CH₂-C₆H₄-OH (CH) | H | -(CH₂)-(3-C₆H₄)- (NH) |
| 186 | (S)- isobutyl (CH) | (R)- -CH₂-(4-imidazolyl) (CH) | H | (S)- -CH₂-C₆H₄-OH (CH) | H | -(CH₂)-CH(CH₃)- (NH) |
| 187 | (S)- isobutyl (CH) | (R)- sec-butyl (CH) | H | (S)- -CH₂-C₆H₄-OH (CH) | H | -(CH₂)-(3-C₆H₄)- (NH) |
| 188 | (S)- isobutyl (CH) | (R)- -(CH₂)₄-NH₂ (CH) | H | (S)- -CH₂-C₆H₄-OH (CH) | H | -(CH₂)-(3-C₆H₄)- (NH) |

TABLE 1B-continued

| Cpd | R₁ | R₂ | R₃ | R₄ | R₅ | R₆ |
|---|---|---|---|---|---|---|
| 189 | (S)-isobutyl | (R)-4-aminobutyl | H | (S)-4-hydroxybenzyl | H | (R)-1-aminopropan-2-yl |
| 190 | (S)-isobutyl | (R)-propyl | H | (S)-4-hydroxybenzyl | H | 3-(aminomethyl)benzyl |
| 191 | (S)-isobutyl | (R)-propyl | H | (S)-4-hydroxybenzyl | H | (R)-1-aminopropan-2-yl |
| 192 | (S)-isobutyl | (R)-benzyl | H | (S)-4-hydroxybenzyl | H | 3-(aminomethyl)benzyl |
| 193 | (S)-isobutyl | (R)-benzyl | H | (S)-4-hydroxybenzyl | H | (R)-1-aminopropan-2-yl |

TABLE 1B-continued

| Cpd | R₁ | R₂ | R₃ | R₄ | R₅ | R₆ |
|---|---|---|---|---|---|---|
| 194 | (S)-isobutyl | (R)-pyrrolidinyl | H | (S)-4-hydroxybenzyl | H | 3-(aminomethyl)benzyl |
| 195 | (S)-isobutyl | (R)-pyrrolidinyl | H | (S)-4-hydroxybenzyl | H | (R)-1-aminopropyl |
| 196 | (S)-isobutyl | (R)-2-hydroxyethyl | H | (S)-4-hydroxybenzyl | H | 3-(aminomethyl)benzyl |
| 197 | (S)-isobutyl | (R)-2-hydroxyethyl | H | (S)-4-hydroxybenzyl | H | (R)-1-aminopropyl |
| 198 | (S)-isobutyl | (R)-1H-indol-3-ylmethyl | H | (S)-4-hydroxybenzyl | H | 3-(aminomethyl)benzyl |

TABLE 1B-continued

| Cpd | R₁ | R₂ | R₃ | R₄ | R₅ | R₆ |
|---|---|---|---|---|---|---|
| 199 | (S)- isobutyl (CH) | (R)- 1H-indol-3-ylmethyl-CH₂ (CH) | H | (S)- 4-hydroxybenzyl (CH) | H | (R)- 1-aminoethyl (H₂C)(NH) |
| 200 | (S)- isobutyl (CH) | (R)- 4-hydroxybenzyl (CH) | H | (S)- 4-hydroxybenzyl (CH) | H | 3-methoxybenzyl (NH) |
| 201 | (S)- isobutyl (CH) | (R)- 4-hydroxybenzyl (CH) | H | (S)- 4-hydroxybenzyl (CH) | H | (R)- 1-aminoethyl (H₂C)(NH) |
| 202 | (S)- isobutyl (CH) | (R)- isobutyl (CH) | H | (S)- 4-hydroxybenzyl (CH) | H | 3-methoxybenzyl (NH) |
| 203 | (S)- isobutyl (CH) | (R)- isobutyl (CH) | H | (S)- 4-hydroxybenzyl (CH) | H | (R)- 1-aminoethyl (H₂C)(NH) |

TABLE 1B-continued

[Structure: macrocyclic scaffold containing oxazole ring with substituents R1–R6 as depicted]

| Cpd | R1 | R2 | R3 | R4 | R5 | R6 |
|---|---|---|---|---|---|---|
| 204 | (S)- isobutyl (CH) | (S)- -CH2-CH2-CO2H (CH) | H | (S)- 4-hydroxybenzyl (CH) | H | 3-(aminomethyl)benzyl, (H2C)-C6H4-(CH2NH) |
| 205 | (S)- isobutyl (CH) | (S)- -CH2-CH2-CO2H (CH) | H | (S)- 4-hydroxybenzyl (CH) | H | (R)-1-aminopropan-2-yl, (H2C)-CH(NH)-CH3 |
| 206 | (S)- isobutyl (CH) | H | Me | (S)- 4-hydroxybenzyl (CH) | H | 3-(aminomethyl)benzyl, (H2C)-C6H4-(CH2NH) |
| 207 | (S)- isobutyl (CH) | H | Me | (S)- 4-hydroxybenzyl (CH) | H | (R)-1-aminopropan-2-yl, (H2C)-CH(NH)-CH3 |
| 208 | (S)- isobutyl (CH) | (S)- imidazol-4-ylmethyl (CH) | H | (S)- 4-hydroxybenzyl (CH) | H | 3-(aminomethyl)benzyl, (H2C)-C6H4-(CH2NH) |

TABLE 1B-continued

| Cpd | R₁ | R₂ | R₃ | R₄ | R₅ | R₆ |
|-----|----|----|----|----|----|----|
| 209 | (S)- isobutyl | (S)- CH₂-imidazole | H | (S)- CH₂-(4-hydroxyphenyl) | H | (S)- CH(CH₃)-(3-methoxyphenyl)-NH |
| 210 | (S)- isobutyl | (S)- sec-butyl (CH₂CH(CH₃)CH₂) | H | (S)- CH₂-(4-hydroxyphenyl) | H | CH₂-(3-methoxyphenyl)-NH |
| 211 | (S)- isobutyl | (S)- (CH₂)₄NH₂ | H | (S)- CH₂-(4-hydroxyphenyl) | H | CH₂-(3-methoxyphenyl)-NH |
| 212 | (S)- isobutyl | (S)- (CH₂)₄NH₂ | H | (S)- CH₂-(4-hydroxyphenyl) | H | (S)- CH(CH₃)-(3-methoxyphenyl)-NH |
| 213 | (S)- isobutyl | (S)- n-butyl | H | (S)- CH₂-(4-hydroxyphenyl) | H | CH₂-(3-methoxyphenyl)-NH |

TABLE 1B-continued

| Cpd | R₁ | R₂ | R₃ | R₄ | R₅ | R₆ |
|---|---|---|---|---|---|---|
| 214 | (S)-isobutyl | (S)-n-butyl | H | (S)-4-hydroxybenzyl | H | (S)-1-aminoethyl |
| 215 | (S)-isobutyl | (S)-benzyl | H | (S)-4-hydroxybenzyl | H | 3-(aminomethyl)benzyl |
| 216 | (S)-isobutyl | (S)-benzyl | H | (S)-4-hydroxybenzyl | H | (S)-1-aminoethyl |
| 217 | (S)-isobutyl | (S)-pyrrolidinyl | H | (S)-4-hydroxybenzyl | H | 3-(aminomethyl)benzyl |
| 218 | (S)-isobutyl | (S)-pyrrolidinyl | H | (S)-4-hydroxybenzyl | H | (S)-1-aminoethyl |

TABLE 1B-continued

| Cpd | R₁ | R₂ | R₃ | R₄ | R₅ | R₆ |
|---|---|---|---|---|---|---|
| 219 | (S)- isobutyl (CH) | (S)- 2-hydroxyethyl (CH₂OH) | H | (S)- 4-hydroxybenzyl (CH₂-C₆H₄-OH) | H | 3-(aminomethyl)benzyl (3-CH₂NH-C₆H₄-CH₂-) |
| 220 | (S)- isobutyl (CH) | (S)- 2-hydroxyethyl (CH₂OH) | H | (S)- 4-hydroxybenzyl (CH) | H | (S)- 1-aminopropan-2-yl (CH₃, NH) |
| 221 | (S)- isobutyl (CH) | (S)- indol-3-ylmethyl (CH) | H | (S)- 4-hydroxybenzyl (CH) | H | 3-(aminomethyl)benzyl |
| 222 | (S)- isobutyl (CH) | (S)- indol-3-ylmethyl (CH) | H | (S)- 4-hydroxybenzyl (CH) | H | (S)- 1-aminopropan-2-yl |
| 223 | (S)- isobutyl (CH) | (S)- 4-hydroxybenzyl (CH) | H | (S)- 4-hydroxybenzyl (CH) | H | 3-(aminomethyl)benzyl |

TABLE 1B-continued

| Cpd | R1 | R2 | R3 | R4 | R5 | R6 |
|---|---|---|---|---|---|---|
| 224 | (S)-isobutyl | (S)-4-hydroxybenzyl | H | (S)-4-hydroxybenzyl | H | (S)-methyl-CH2-NH |
| 225 | (S)-isobutyl | (S)-isobutyl | H | (S)-4-hydroxybenzyl | H | 3-methoxybenzyl-NH |
| 226 | (S)-isobutyl | (S)-isobutyl | H | (S)-4-hydroxybenzyl | H | (S)-methyl-CH2-NH |
| 227 | (S)-isobutyl | (R)-indol-3-ylmethyl | H | (S)-isobutyl | H | 3-methoxybenzyl-NH |
| 228 | (S)-isobutyl | (R)-4-hydroxybenzyl | H | (S)-isobutyl | H | 3-methoxybenzyl-NH |

TABLE 1B-continued

| Cpd | R₁ | R₂ | R₃ | R₄ | R₅ | R₆ |
|---|---|---|---|---|---|---|
| 229 | (S)- isobutyl | (S)- indol-3-ylmethyl | H | (S)- isobutyl | H | 3-methoxybenzyl (NH) |
| 230 | (S)- isobutyl | (S)- 4-hydroxybenzyl | H | (S)- isobutyl | H | 3-methoxybenzyl (NH) |
| 231 | (S)- isobutyl | (S)- guanidinopropyl | H | (S)- 4-hydroxybenzyl | H | 3-methoxybenzyl (NH) |
| 232 | (S)- isobutyl | (S)- guanidinopropyl | H | (S)- indol-3-ylmethyl | H | 3-methoxybenzyl (NH) |

TABLE 1B-continued

| Cpd | R₁ | R₂ | R₃ | R₄ | R₅ | R₆ |
|---|---|---|---|---|---|---|
| 233 | (S)- isobutyl (CH) | (S)- (CH₂)₃NHC(=NH)NH₂ | H | (R)- 4-hydroxybenzyl (CH₂) | H | 3-(aminomethyl)benzyl (CH₂) |
| 234 | (S)- isobutyl (CH) | (S)- (CH₂)₃NHC(=NH)NH₂ | H | (R)- indol-3-ylmethyl (CH₂) | H | 3-(aminomethyl)benzyl (CH₂) |
| 235 | (S)- isobutyl (CH) | (S)- (CH₂)₃NHC(=NH)NH₂ | H | (S)- 4-hydroxybenzyl (CH₂) | H | (R)-1-aminopropan-2-yl (CH₂) |
| 236 | (S)- isobutyl (CH) | (R)- (CH₂)₃NHC(=NH)NH₂ | H | (S)- 4-hydroxybenzyl (CH₂) | H | 3-(aminomethyl)benzyl (CH₂) |

TABLE 1B-continued

| Cpd | R₁ | R₂ | R₃ | R₄ | R₅ | R₆ |
|---|---|---|---|---|---|---|
| 237 | (S)- isobutyl (CH) | (R)- (CH₂)₃-NH-C(=NH)-NH₂ | H | (S)- indol-3-ylmethyl (CH) | H | 3-(aminomethyl)benzyl (CH₂) |
| 238 | (S)- isobutyl (CH) | (R)- (CH₂)₃-NH-C(=NH)-NH₂ | H | (R)- 4-hydroxybenzyl (CH) | H | 3-(aminomethyl)benzyl (CH₂) |
| 239 | (S)- isobutyl (CH) | (R)- (CH₂)₃-NH-C(=NH)-NH₂ | H | (R)- indol-3-ylmethyl (CH) | H | 3-(aminomethyl)benzyl (CH₂) |
| 240 | (S)- isobutyl (CH) | (R)- (CH₂)₃-NH-C(=NH)-NH₂ | H | (S)- 4-hydroxybenzyl (CH) | H | (1-aminoethyl) (CH₂) |

TABLE 1B-continued
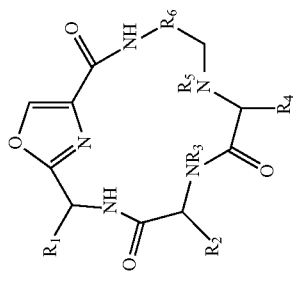
| Cpd | R₁ | R₂ | R₃ | R₄ | R₅ | R₆ |
|---|---|---|---|---|---|---|
| 241 | (S)- (CH) isobutyl | (R)- (CH) indolylmethyl | H | (S)- guanidinopropyl | H | (NH) (H₂C) 3-methoxybenzyl |
| 242 | (S)- (CH) isobutyl | (R)- (CH) 4-hydroxybenzyl | H | (S)- guanidinopropyl | H | (NH) (H₂C) 3-methoxybenzyl |
| 243 | (S)- (CH) isobutyl | (S)- (CH) indolylmethyl | H | (S)- guanidinopropyl | H | (NH) (H₂C) 3-methoxybenzyl |
| 244 | (S)- (CH) isobutyl | (S)- (CH) 4-hydroxybenzyl | H | (S)- guanidinopropyl | H | (NH) (H₂C) 3-methoxybenzyl |

TABLE 1B-continued
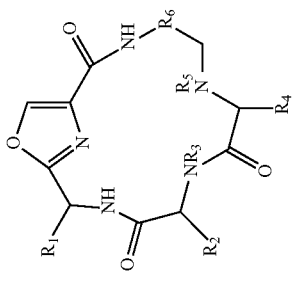
| Cpd | R₁ | R₂ | R₃ | R₄ | R₅ | R₆ |
|---|---|---|---|---|---|---|
| 245 | (S)-isobutyl | (R)-CH₂-(1H-indol-3-yl) | H | (R)-(CH₂)₄-NH-C(=NH)-NH₂ | H | (H₂C)-C₆H₄-(NH) (meta) |
| 246 | (S)-isobutyl | (R)-CH₂-(4-hydroxyphenyl) | H | (R)-(CH₂)₄-NH-C(=NH)-NH₂ | H | (H₂C)-C₆H₄-(NH) (meta) |
| 247 | (S)-isobutyl | (S)-CH₂-(1H-indol-3-yl) | H | (R)-(CH₂)₄-NH-C(=NH)-NH₂ | H | (H₂C)-C₆H₄-(NH) (meta) |
| 248 | (S)-isobutyl | (S)-CH₂-(4-hydroxyphenyl) | H | (R)-(CH₂)₄-NH-C(=NH)-NH₂ | H | (H₂C)-C₆H₄-(NH) (meta) |

TABLE 1B-continued

| Cpd | R₁ | R₂ | R₃ | R₄ | R₅ | R₆ |
|---|---|---|---|---|---|---|
| 249 | (S)- n-propyl (CH) | (R)- isopropyl (CH) | H | (R)- benzyl (CH) | H | (HN)-CH₂CH₂-O-(5-fluoro-2-(OCH₂-)phenyl) |
| 250 | (R)- n-propyl (CH) | (R)- isopropyl (CH) | H | (R)- benzyl (CH) | H | (HN)-CH₂CH₂-O-(5-fluoro-2-(OCH₂-)phenyl) |
| 251 | (S)- n-propyl (CH) | (S)- isopropyl (CH) | H | (R)- benzyl (CH) | H | (HN)-CH₂CH₂-O-(5-fluoro-2-(OCH₂-)phenyl) |

TABLE 1B-continued

| Cpd | R₁ | R₂ | R₃ | R₄ | R₅ | R₆ |
|---|---|---|---|---|---|---|
| 252 | (R)- propyl (CH) | (S)- isobutyl (CH) | H | (R)- benzyl (CH) | H | (HN)-CH₂CH₂-O-(2-fluoro-phenyl with OCH₂ at ortho) |
| 253 | (S)- propyl (CH) | (R)- HOCH₂ (CH) | H | (R)- benzyl (CH) | H | (HN)-CH₂CH₂-O-(2-fluoro-phenyl with OCH₂ at ortho) |
| 254 | (R)- propyl (CH) | (R)- HOCH₂ (CH) | H | (R)- benzyl (CH) | H | (HN)-CH₂CH₂-O-(2-fluoro-phenyl with OCH₂ at ortho) |

TABLE 1B-continued

| Cpd | R₁ | R₂ | R₃ | R₄ | R₅ | R₆ |
|---|---|---|---|---|---|---|
| 255 | (S)- -(CH)-CH₂CH₃ | (S)- HO-CH₂-(CH)- | H | (R)- -CH₂-C₆H₅ (CH) | H | (HN)-CH₂CH₂-O-(2-O-CH₂-,5-F-phenyl) |
| 256 | (R)- -(CH)-CH₂CH₃ | (S)- HO-CH₂-(CH)- | H | (R)- -CH₂-C₆H₅ (CH) | H | (HN)-CH₂CH₂-O-(2-O-CH₂-,5-F-phenyl) |
| 257 | (S)- -(CH)-CH₂CH₃ | (S)- H₂N-CH₂-(CH)- | H | (R)- -CH₂-C₆H₅ (CH) | H | (HN)-CH₂CH₂-O-(2-O-CH₂-,5-F-phenyl) |

TABLE 1B-continued
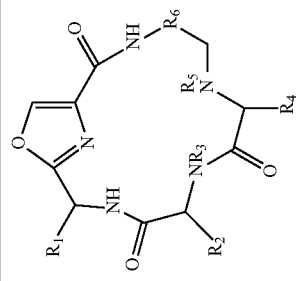
| Cpd | R₁ | R₂ | R₃ | R₄ | R₅ | R₆ |
|---|---|---|---|---|---|---|
| 258 | (R)- -(CH)-CH₂CH₂CH₃ | (S)- H₂N-CH₂CH₂-(CH)- | H | (R)- -(CH)-CH₂-C₆H₅ | H | (HN)-CH₂CH₂-O-(2-O-CH₂-, 5-F-phenyl) |
| 259 | (S)- -(CH)-CH₂CH₂CH₃ | (S)- -CH₃ | H | (R)- -(CH)-CH₂-C₆H₅ | H | (HN)-CH₂CH₂-O-(2-O-CH₂-, 5-F-phenyl) |
| 260 | (R)- -(CH)-CH₂CH₂CH₃ | (S)- -CH₃ | H | (R)- -(CH)-CH₂-C₆H₅ | H | (HN)-CH₂CH₂-O-(2-O-CH₂-, 5-F-phenyl) |

TABLE 1B-continued

| Cpd | R₁ | R₂ | R₃ | R₄ | R₅ | R₆ |
|---|---|---|---|---|---|---|
| 261 | (S)-CH₂CH₂CH₃ | (R)-CH₃ | H | (R)-CH₂-phenyl | H | (HN)-CH₂CH₂-O-(2-(OCH₂CH₂)-5-F-phenyl) |
| 262 | (R)-CH₂CH₂CH₃ | (R)-CH₃ | H | (R)-CH₂-phenyl | H | (HN)-CH₂CH₂-O-(2-(OCH₂CH₂)-5-F-phenyl) |
| 263 | (S)-CH₂CH₂CH₃ | (R)-CH(CH₃)₂ | H | (S)-CH₂-phenyl | H | (HN)-CH₂CH₂-O-(2-(OCH₂CH₂)-5-F-phenyl) |

TABLE 1B-continued

| Cpd | R₁ | R₂ | R₃ | R₄ | R₅ | R₆ |
|---|---|---|---|---|---|---|
| 264 | (R)- n-propyl (CH) | (R)- isopropyl (CH) | H | (S)- benzyl (CH) | H | (HN)-CH₂CH₂-O-(2-(OCH₂-),5-F-phenyl) |
| 265 | (S)- n-propyl (CH) | (S)- isopropyl (CH) | H | (S)- benzyl (CH) | H | (HN)-CH₂CH₂-O-(2-(OCH₂-),5-F-phenyl) |
| 266 | (R)- n-propyl (CH) | (S)- isopropyl (CH) | H | (S)- benzyl (CH) | H | (HN)-CH₂CH₂-O-(2-(OCH₂-),5-F-phenyl) |

TABLE 1B-continued
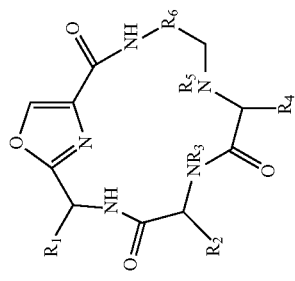
| Cpd | R₁ | R₂ | R₃ | R₄ | R₅ | R₆ |
|---|---|---|---|---|---|---|
| 267 | (S)- CH₂CH₂CH₃ | (R)- CH(CH₃)₂ | H | (R)- CH₂Ph | H | (NH)CH₂-C₆H₄-CH₃ (meta) |
| 268 | (R)- CH₂CH₂CH₃ | (R)- CH(CH₃)₂ | H | (R)- CH₂Ph | H | (NH)CH₂-C₆H₄-CH₃ (meta) |
| 269 | (S)- CH₂CH₂CH₃ | (S)- CH(CH₃)₂ | H | (R)- CH₂Ph | H | (NH)CH₂-C₆H₄-CH₃ (meta) |
| 270 | (R)- CH₂CH₂CH₃ | (S)- CH(CH₃)₂ | H | (R)- CH₂Ph | H | (NH)CH₂-C₆H₄-CH₃ (meta) |

TABLE 1B-continued

| Cpd | R₁ | R₂ | R₃ | R₄ | R₅ | R₆ |
|---|---|---|---|---|---|---|
| 271 | (S)- -(CH)-CH₂-CH₃ | (R)- HO-CH₂-(CH)- | H | (R)- -(CH)-CH₂-C₆H₅ | H | -CH₂-C₆H₄-(OCH₃)(NH) |
| 272 | (R)- -(CH)-CH₂-CH₃ | (R)- HO-CH₂-(CH)- | H | (R)- -(CH)-CH₂-C₆H₅ | H | -CH₂-C₆H₄-(OCH₃)(NH) |
| 273 | (S)- -(CH)-CH₂-CH₃ | (S)- HO-CH₂-(CH)- | H | (R)- -(CH)-CH₂-C₆H₅ | H | -CH₂-C₆H₄-(OCH₃)(NH) |
| 274 | (R)- -(CH)-CH₂-CH₃ | (S)- HO-CH₂-(CH)- | H | (R)- -(CH)-CH₂-C₆H₅ | H | -CH₂-C₆H₄-(OCH₃)(NH) |

TABLE 1B-continued

| Cpd | R₁ | R₂ | R₃ | R₄ | R₅ | R₆ |
|---|---|---|---|---|---|---|
| 275 | (S)- ⟨CH⟩~ | (S)- H₂N~⟨CH⟩ | H | (R)- ⟨CH⟩-benzyl | H | (H₂C)-(3-aminomethyl)phenyl (NH) |
| 276 | (R)- ⟨CH⟩~ | (S)- H₂N~⟨CH⟩ | H | (R)- ⟨CH⟩-benzyl | H | (H₂C)-(3-aminomethyl)phenyl (NH) |
| 277 | (S)- ⟨CH⟩~ | (S)—CH₃ | H | (R)- ⟨CH⟩-benzyl | H | (H₂C)-(3-aminomethyl)phenyl (NH) |
| 278 | (R)- ⟨CH⟩~ | (S)—CH₃ | H | (R)- ⟨CH⟩-benzyl | H | (H₂C)-(3-aminomethyl)phenyl (NH) |

TABLE 1B-continued

| Cpd | R₁ | R₂ | R₃ | R₄ | R₅ | R₆ |
|---|---|---|---|---|---|---|
| 279 | (S)-CH₂CH₂CH₃ | (R)-CH₃ | H | (R)-CH₂-phenyl | H | 3-(H₂C)-benzyl-(NH) |
| 280 | (R)-CH₂CH₂CH₃ | (R)-CH₃ | H | (R)-CH₂-phenyl | H | 3-(H₂C)-benzyl-(NH) |
| 281 | (S)-CH₂CH₂CH₃ | (R)-CH(CH₃)₂ | H | (S)-CH₂-phenyl | H | 3-(H₂C)-benzyl-(NH) |
| 282 | (R)-CH₂CH₂CH₃ | (R)-CH(CH₃)₂ | H | (S)-CH₂-phenyl | H | 3-(H₂C)-benzyl-(NH) |

TABLE 1B-continued

| Cpd | R₁ | R₂ | R₃ | R₄ | R₅ | R₆ |
|---|---|---|---|---|---|---|
| 283 | (S)- isobutyl(CH) | (S)- isobutyl(CH) | H | (S)- benzyl(CH) | H | 3-(methoxymethyl)benzyl (NH)(H₂C) |
| 284 | (R)- isobutyl(CH) | (S)- isobutyl(CH) | H | (S)- benzyl(CH) | H | 3-(methoxymethyl)benzyl (NH)(H₂C) |
| 285 | (S)- isobutyl(CH) | (R)- 2-aminoethyl H₂N(CH) | H | (R)- benzyl(CH) | H | 2-(2-(5-fluorophenoxy)ethoxy)ethyl (HN)(CH₂) |

TABLE 1B-continued

| Cpd | R₁ | R₂ | R₃ | R₄ | R₅ | R₆ |
|-----|-----|-----|-----|-----|-----|-----|
| 286 | (R)- propyl (CH) | (R)- H₂N-ethyl (CH) | H | (R)- benzyl (CH) | H | 2-(2-aminoethoxy)-4-fluoro-phenoxyethyl (HN-CH₂CH₂-O-C₆H₃(F)-O-CH₂CH₂-) |
| 287 | (S)- propyl (CH) | (R)- H₂N-ethyl (CH) | H | (R)- benzyl (CH) | H | 3-(aminomethyl)benzyl |
| 288 | (R)- propyl (CH) | (R)- H₂N-ethyl (CH) | H | (R)- benzyl (CH) | H | 3-(aminomethyl)benzyl |
| 289 | (R)- propyl (CH) | (R)- tBuO-ethyl (CH) | H | (R)- benzyl (CH) | H | 3-(aminomethyl)benzyl |

Example 3

Synthesis of a Representative Library of Macrocyclic Compounds of Formula (Ic)

The synthetic scheme presented in Scheme 3 was followed to prepare the library of macrocyclic compounds 301-597 on solid support. The first amino acid building block amino acid (BB$_1$) was loaded onto the resin (Method 1D), then, after removal of the Fmoc protection (Method 1F), the oxazole building block (BB$_2$) attached through amide bond formation (Method 1G) or reductive amination (Method 1J). The next amino acid building block (BB$_3$) was coupled (Method 1G) after Fmoc-deprotection (Method 1F) to extend the intermediate chain, then the last building block component added using reductive amination (Method 1I or 1J) to complete the cyclization precursor. N-Terminal Fmoc deprotection (Method 1F), macrocyclization (Method 1R) and removal of side chain protecting groups (Method 1S) gave the crude product after evaporation under reduced pressure. The quantities of each macrocycle obtained, their HPLC purity and confirmation of their identity by mass spectrometry (MS) after purification by preparative HPLC (Method 2B) are included in Table 2A. Individual compound structures are provided in Table 2B.

TABLE 2A

| Cpd | BB$_1$ | BB$_2$ | BB$_3$ | BB$_4$ | Wt (mg)[1] | Purity[2] | MS (M + H) |
|---|---|---|---|---|---|---|---|
| 301 | Fmoc-Ala | Fmoc-OX-1 | Fmoc-D-Trp(Boc) | Fmoc-S37 | 8.7 | 100 | 557 |
| 302 | Fmoc-Asn(Trt) | Fmoc-OX-1 | Fmoc-D-Trp(Boc) | Fmoc-S37 | 14.5 | 100 | 600 |
| 303 | Fmoc-D-Ala | Fmoc-OX-1 | Fmoc-D-Trp(Boc) | Fmoc-S37 | 8.4 | 100 | 557 |
| 304 | Fmoc-D-Asn(Trt) | Fmoc-OX-1 | Fmoc-D-Trp(Boc) | Fmoc-S37 | 13.9 | 100 | 600 |
| 305 | Fmoc-D-Gln(Trt) | Fmoc-OX-1 | Fmoc-D-Trp(Boc) | Fmoc-S37 | 9.6 | 100 | 614 |
| 306 | Fmoc-D-Glu(OBut) | Fmoc-OX-1 | Fmoc-D-Trp(Boc) | Fmoc-S37 | 7.7 | 100 | 615 |
| 307 | Fmoc-D-His(Trt) | Fmoc-OX-1 | Fmoc-D-Trp(Boc) | Fmoc-S37 | 10.4 | 100 | 623 |
| 308 | Fmoc-D-Lys(Boc) | Fmoc-OX-1 | Fmoc-D-Trp(Boc) | Fmoc-S37 | 8.2 | 100 | 614 |
| 309 | Fmoc-D-Nva | Fmoc-OX-1 | Fmoc-D-Trp(Boc) | Fmoc-S37 | 11.4 | 100 | 585 |
| 310 | Fmoc-D-Phe | Fmoc-OX-1 | Fmoc-D-Trp(Boc) | Fmoc-S37 | 10.8 | 100 | 633 |
| 311 | Fmoc-D-Pro | Fmoc-OX-1 | Fmoc-D-Trp(Boc) | Fmoc-S37 | 9.6 | 100 | 583 |
| 312 | Fmoc-D-Ser(But) | Fmoc-OX-1 | Fmoc-D-Trp(Boc) | Fmoc-S37 | 11.8 | 100 | 573 |
| 313 | Fmoc-D-Trp(Boc) | Fmoc-OX-1 | Fmoc-D-Trp(Boc) | Fmoc-S37 | 8.2 | 100 | 672 |
| 314 | Fmoc-D-Tyr(But) | Fmoc-OX-1 | Fmoc-D-Trp(Boc) | Fmoc-S37 | 10.8 | 100 | 649 |
| 315 | Fmoc-D-Val | Fmoc-OX-1 | Fmoc-D-Trp(Boc) | Fmoc-S37 | 9.3 | 100 | 585 |
| 316 | Fmoc-Gln(Trt) | Fmoc-OX-1 | Fmoc-D-Trp(Boc) | Fmoc-S37 | 11.2 | 100 | 614 |
| 317 | Fmoc-Glu(OBut) | Fmoc-OX-1 | Fmoc-D-Trp(Boc) | Fmoc-S37 | 7.3 | 100 | 615 |
| 318 | Fmoc-His(Trt) | Fmoc-OX-1 | Fmoc-D-Trp(Boc) | Fmoc-S37 | 6.3 | 100 | 623 |
| 319 | Fmoc-Lys(Boc) | Fmoc-OX-1 | Fmoc-D-Trp(Boc) | Fmoc-S37 | 7.2 | 100 | 614 |
| 320 | Fmoc-Nva | Fmoc-OX-1 | Fmoc-D-Trp(Boc) | Fmoc-S37 | 9.1 | 100 | 585 |
| 321 | Fmoc-Phe | Fmoc-OX-1 | Fmoc-D-Trp(Boc) | Fmoc-S37 | 11.9 | 100 | 633 |
| 322 | Fmoc-Pro | Fmoc-OX-1 | Fmoc-D-Trp(Boc) | Fmoc-S37 | 11.5 | 100 | 583 |
| 323 | Fmoc-Ser(But) | Fmoc-OX-1 | Fmoc-D-Trp(Boc) | Fmoc-S37 | 10.9 | 100 | 573 |
| 324 | Fmoc-Trp(Boc) | Fmoc-OX-1 | Fmoc-D-Trp(Boc) | Fmoc-S37 | 5.9 | 100 | 672 |
| 325 | Fmoc-Tyr(But) | Fmoc-OX-1 | Fmoc-D-Trp(Boc) | Fmoc-S31 | 1.1 | 100 | 587 |
| 326 | Fmoc-Val | Fmoc-OX-1 | Fmoc-D-Trp(Boc) | Fmoc-S37 | 8.6 | 100 | 585 |
| 327 | Fmoc-Ala | Fmoc-OX-1 | Fmoc-D-Tyr(But) | Fmoc-S37 | 8.6 | 100 | 534 |
| 328 | Fmoc-Asn(Trt) | Fmoc-OX-1 | Fmoc-D-Tyr(But) | Fmoc-S37 | 14.8 | 100 | 577 |
| 329 | Fmoc-D-Ala | Fmoc-OX-1 | Fmoc-D-Tyr(But) | Fmoc-S37 | 8.5 | 100 | 534 |
| 330 | Fmoc-D-Asn(Trt) | Fmoc-OX-1 | Fmoc-D-Tyr(But) | Fmoc-S37 | 12.7 | 100 | 577 |
| 331 | Fmoc-D-Gln(Trt) | Fmoc-OX-1 | Fmoc-D-Tyr(But) | Fmoc-S37 | 10.7 | 100 | 591 |
| 332 | Fmoc-D-Glu(OBut) | Fmoc-OX-1 | Fmoc-D-Tyr(But) | Fmoc-S37 | 6.5 | 100 | 592 |
| 333 | Fmoc-D-His(Trt) | Fmoc-OX-1 | Fmoc-D-Tyr(But) | Fmoc-S37 | 9.2 | 100 | 600 |
| 334 | Fmoc-D-Lys(Boc) | Fmoc-OX-1 | Fmoc-D-Tyr(But) | Fmoc-S37 | 8.3 | 100 | 591 |
| 335 | Fmoc-D-Nva | Fmoc-OX-1 | Fmoc-D-Tyr(But) | Fmoc-S37 | 10.0 | 100 | 562 |
| 336 | Fmoc-D-Phe | Fmoc-OX-1 | Fmoc-D-Tyr(But) | Fmoc-S37 | 9.9 | 100 | 610 |
| 337 | Fmoc-D-Pro | Fmoc-OX-1 | Fmoc-D-Tyr(But) | Fmoc-S37 | 10.0 | 100 | 560 |
| 338 | Fmoc-D-Ser(But) | Fmoc-OX-1 | Fmoc-D-Tyr(But) | Fmoc-S37 | 11.3 | 100 | 550 |
| 339 | Fmoc-D-Trp(Boc) | Fmoc-OX-1 | Fmoc-D-Tyr(But) | Fmoc-S37 | 8.6 | 100 | 649 |
| 340 | Fmoc-D-Tyr(But) | Fmoc-OX-1 | Fmoc-D-Tyr(But) | Fmoc-S37 | 11.9 | 100 | 626 |
| 341 | Fmoc-D-Val | Fmoc-OX-1 | Fmoc-D-Tyr(But) | Fmoc-S37 | 7.7 | 100 | 562 |
| 342 | Fmoc-Gln(Trt) | Fmoc-OX-1 | Fmoc-D-Tyr(But) | Fmoc-S37 | 9.7 | 100 | 591 |
| 343 | Fmoc-Glu(OBut) | Fmoc-OX-1 | Fmoc-D-Tyr(But) | Fmoc-S37 | 7.3 | 100 | 592 |
| 344 | Fmoc-His(Trt) | Fmoc-OX-1 | Fmoc-D-Tyr(But) | Fmoc-S37 | 6.8 | 100 | 600 |
| 345 | Fmoc-Lys(Boc) | Fmoc-OX-1 | Fmoc-D-Tyr(But) | Fmoc-S37 | 8.2 | 100 | 591 |
| 346 | Fmoc-Nva | Fmoc-OX-1 | Fmoc-D-Tyr(But) | Fmoc-S37 | 10.1 | 100 | 562 |
| 347 | Fmoc-Phe | Fmoc-OX-1 | Fmoc-D-Tyr(But) | Fmoc-S37 | 10.2 | 100 | 610 |
| 348 | Fmoc-Pro | Fmoc-OX-1 | Fmoc-D-Tyr(But) | Fmoc-S37 | 13.6 | 100 | 560 |
| 349 | Fmoc-Ser(But) | Fmoc-OX-1 | Fmoc-D-Tyr(But) | Fmoc-S37 | 10.9 | 100 | 550 |
| 350 | Fmoc-Trp(Boc) | Fmoc-OX-1 | Fmoc-D-Tyr(But) | Fmoc-S37 | 7.9 | 100 | 649 |
| 351 | Fmoc-Tyr(But) | Fmoc-OX-1 | Fmoc-D-Tyr(But) | Fmoc-S37 | 10.7 | 100 | 626 |
| 352 | Fmoc-Val | Fmoc-OX-1 | Fmoc-D-Tyr(But) | Fmoc-S37 | 10.1 | 100 | 562 |
| 353 | Fmoc-Ala | Fmoc-OX-1 | Fmoc-Trp(Boc) | Fmoc-S37 | 10.4 | 100 | 557 |
| 354 | Fmoc-Asn(Trt) | Fmoc-OX-1 | Fmoc-Trp(Boc) | Fmoc-S37 | 13.4 | 100 | 600 |
| 355 | Fmoc-D-Ala | Fmoc-OX-1 | Fmoc-Trp(Boc) | Fmoc-S37 | 8.3 | 100 | 557 |
| 356 | Fmoc-D-Asn(Trt) | Fmoc-OX-1 | Fmoc-Trp(Boc) | Fmoc-S37 | 17.6 | 100 | 600 |
| 357 | Fmoc-D-Gln(Trt) | Fmoc-OX-1 | Fmoc-Trp(Boc) | Fmoc-S37 | 10.5 | 100 | 614 |
| 358 | Fmoc-D-Glu(OBut) | Fmoc-OX-1 | Fmoc-Trp(Boc) | Fmoc-S37 | 6.9 | 100 | 615 |
| 359 | Fmoc-D-His(Trt) | Fmoc-OX-1 | Fmoc-Trp(Boc) | Fmoc-S37 | 7.3 | 100 | 623 |
| 360 | Fmoc-D-Lys(Boc) | Fmoc-OX-1 | Fmoc-Trp(Boc) | Fmoc-S37 | 6.8 | 100 | 614 |
| 361 | Fmoc-D-Nva | Fmoc-OX-1 | Fmoc-Trp(Boc) | Fmoc-S37 | 11.0 | 100 | 585 |

TABLE 2A-continued

| Cpd | BB$_1$ | BB$_2$ | BB$_3$ | BB$_4$ | Wt (mg)[1] | Purity[2] | MS (M + H) |
|---|---|---|---|---|---|---|---|
| 362 | Fmoc-D-Phe | Fmoc-OX-1 | Fmoc-Trp(Boc) | Fmoc-S37 | 11.8 | 100 | 633 |
| 363 | Fmoc-D-Pro | Fmoc-OX-1 | Fmoc-Trp(Boc) | Fmoc-S37 | 8.6 | 87 | 583 |
| 364 | Fmoc-D-Ser(But) | Fmoc-OX-1 | Fmoc-Trp(Boc) | Fmoc-S37 | 9.4 | 100 | 573 |
| 365 | Fmoc-D-Trp(Boc) | Fmoc-OX-1 | Fmoc-Trp(Boc) | Fmoc-S37 | 8.2 | 100 | 672 |
| 366 | Fmoc-D-Tyr(But) | Fmoc-OX-1 | Fmoc-Trp(Boc) | Fmoc-S37 | 12.3 | 95 | 649 |
| 367 | Fmoc-D-Val | Fmoc-OX-1 | Fmoc-Trp(Boc) | Fmoc-S37 | 6.7 | 100 | 585 |
| 368 | Fmoc-Gln(Trt) | Fmoc-OX-1 | Fmoc-Trp(Boc) | Fmoc-S37 | 22.7 | 100 | 614 |
| 369 | Fmoc-Glu(OBut) | Fmoc-OX-1 | Fmoc-Trp(Boc) | Fmoc-S37 | 7.5 | 100 | 615 |
| 370 | Fmoc-His(Trt) | Fmoc-OX-1 | Fmoc-Trp(Boc) | Fmoc-S37 | na | na | na |
| 371 | Fmoc-Lys(Boc) | Fmoc-OX-1 | Fmoc-Trp(Boc) | Fmoc-S37 | 8.2 | 100 | 614 |
| 372 | Fmoc-Nva | Fmoc-OX-1 | Fmoc-Trp(Boc) | Fmoc-S37 | 11.5 | 100 | 585 |
| 373 | Fmoc-Phe | Fmoc-OX-1 | Fmoc-Trp(Boc) | Fmoc-S37 | 10.7 | 100 | 633 |
| 374 | Fmoc-Pro | Fmoc-OX-1 | Fmoc-Trp(Boc) | Fmoc-S37 | 14.2 | 100 | 583 |
| 375 | Fmoc-Ser(But) | Fmoc-OX-1 | Fmoc-Trp(Boc) | Fmoc-S37 | 10.9 | 100 | 573 |
| 376 | Fmoc-Trp(Boc) | Fmoc-OX-1 | Fmoc-Trp(Boc) | Fmoc-S37 | 8.6 | 100 | 672 |
| 377 | Fmoc-Tyr(But) | Fmoc-OX-1 | Fmoc-Trp(Boc) | Fmoc-S37 | 13.0 | 100 | 649 |
| 378 | Fmoc-Val | Fmoc-OX-1 | Fmoc-Trp(Boc) | Fmoc-S37 | 11.2 | 100 | 585 |
| 379 | Fmoc-Ala | Fmoc-OX-1 | Fmoc-Tyr(But) | Fmoc-S37 | 11.0 | 100 | 534 |
| 380 | Fmoc-Asn(Trt) | Fmoc-OX-1 | Fmoc-Tyr(But) | Fmoc-S37 | 16.8 | 100 | 577 |
| 381 | Fmoc-D-Ala | Fmoc-OX-1 | Fmoc-Tyr(But) | Fmoc-S37 | 8.9 | 100 | 534 |
| 382 | Fmoc-D-Asn(Trt) | Fmoc-OX-1 | Fmoc-Tyr(But) | Fmoc-S37 | 15.0 | 100 | 577 |
| 383 | Fmoc-D-Gln(Trt) | Fmoc-OX-1 | Fmoc-Tyr(But) | Fmoc-S37 | 10.8 | 100 | 591 |
| 384 | Fmoc-D-Glu(OBut) | Fmoc-OX-1 | Fmoc-Tyr(But) | Fmoc-S37 | 6.7 | 100 | 592 |
| 385 | Fmoc-D-His(Trt) | Fmoc-OX-1 | Fmoc-Tyr(But) | Fmoc-S37 | 13.0 | 100 | 600 |
| 386 | Fmoc-D-Lys(Boc) | Fmoc-OX-1 | Fmoc-Tyr(But) | Fmoc-S37 | 10.1 | 100 | 591 |
| 387 | Fmoc-D-Nva | Fmoc-OX-1 | Fmoc-Tyr(But) | Fmoc-S37 | 13.3 | 100 | 562 |
| 388 | Fmoc-D-Phe | Fmoc-OX-1 | Fmoc-Tyr(But) | Fmoc-S37 | 12.8 | 100 | 610 |
| 389 | Fmoc-D-Pro | Fmoc-OX-1 | Fmoc-Tyr(But) | Fmoc-S37 | 11.3 | 100 | 560 |
| 390 | Fmoc-D-Ser(But) | Fmoc-OX-1 | Fmoc-Tyr(But) | Fmoc-S37 | 13.9 | 100 | 550 |
| 391 | Fmoc-D-Trp(Boc) | Fmoc-OX-1 | Fmoc-Tyr(But) | Fmoc-S37 | 7.2 | 100 | 649 |
| 392 | Fmoc-D-Tyr(But) | Fmoc-OX-1 | Fmoc-Tyr(But) | Fmoc-S37 | 12.8 | 100 | 626 |
| 393 | Fmoc-D-Val | Fmoc-OX-1 | Fmoc-Tyr(But) | Fmoc-S37 | 7.7 | 100 | 562 |
| 394 | Fmoc-Gln(Trt) | Fmoc-OX-1 | Fmoc-Tyr(But) | Fmoc-S37 | 19.0 | 100 | 591 |
| 395 | Fmoc-Glu(OBut) | Fmoc-OX-1 | Fmoc-Tyr(But) | Fmoc-S37 | 10.4 | 100 | 592 |
| 396 | Fmoc-His(Trt) | Fmoc-OX-1 | Fmoc-Tyr(But) | Fmoc-S37 | 10.2 | 100 | 600 |
| 397 | Fmoc-Lys(Boc) | Fmoc-OX-1 | Fmoc-Tyr(But) | Fmoc-S37 | 11.8 | 100 | 591 |
| 398 | Fmoc-Nva | Fmoc-OX-1 | Fmoc-Tyr(But) | Fmoc-S37 | 12.6 | 100 | 562 |
| 399 | Fmoc-Phe | Fmoc-OX-1 | Fmoc-Tyr(But) | Fmoc-S37 | 12.8 | 100 | 610 |
| 400 | Fmoc-Pro | Fmoc-OX-1 | Fmoc-Tyr(But) | Fmoc-S37 | 12.5 | 100 | 560 |
| 401 | Fmoc-Ser(But) | Fmoc-OX-1 | Fmoc-Tyr(But) | Fmoc-S37 | 16.4 | 100 | 550 |
| 402 | Fmoc-Trp(Boc) | Fmoc-OX-1 | Fmoc-Tyr(But) | Fmoc-S37 | 11.6 | 100 | 649 |
| 403 | Fmoc-Tyr(But) | Fmoc-OX-1 | Fmoc-Tyr(But) | Fmoc-S37 | 12.3 | 100 | 626 |
| 404 | Fmoc-Val | Fmoc-OX-1 | Fmoc-Tyr(But) | Fmoc-S37 | 9.8 | 100 | 562 |
| 405 | Fmoc-Arg(Pbf) | Fmoc-OX-1 | Fmoc-Tyr(But) | Fmoc-S37 | 7.8 | 100 | 619 |
| 406 | Fmoc-Arg(Pbf) | Fmoc-OX-1 | Fmoc-Trp(Boc) | Fmoc-S37 | 7.3 | 100 | 642 |
| 407 | Fmoc-Arg(Pbf) | Fmoc-OX-1 | Fmoc-D-Tyr(But) | Fmoc-S37 | 5.8 | 100 | 619 |
| 408 | Fmoc-Arg(Pbf) | Fmoc-OX-1 | Fmoc-D-Trp(Boc) | Fmoc-S37 | 7.1 | 100 | 642 |
| 409 | Fmoc-D-Arg(Pbf) | Fmoc-OX-1 | Fmoc-Tyr(But) | Fmoc-S37 | 7.7 | 100 | 619 |
| 410 | Fmoc-D-Arg(Pbf) | Fmoc-OX-1 | Fmoc-Trp(Boc) | Fmoc-S37 | 5.4 | 100 | 642 |
| 411 | Fmoc-D-Arg(Pbf) | Fmoc-OX-1 | Fmoc-D-Tyr(But) | Fmoc-S37 | 5.5 | 100 | 619 |
| 412 | Fmoc-D-Arg(Pbf) | Fmoc-OX-1 | Fmoc-D-Trp(Boc) | Fmoc-S37 | 5.7 | 100 | 642 |
| 413 | Fmoc-D-Trp(Boc) | Fmoc-OX-1 | Fmoc-Lys(Boc) | Fmoc-S35 | 0.7 | 100 | 592 |
| 414 | Fmoc-D-Tyr(But) | Fmoc-OX-1 | Fmoc-Lys(Boc) | Fmoc-S35 | 1.5 | 100 | 569 |
| 415 | Fmoc-Trp(Boc) | Fmoc-OX-1 | Fmoc-His(Trt) | Fmoc-S35 | 2.2 | 92 | 601 |
| 416 | Fmoc-Tyr(But) | Fmoc-OX-1 | Fmoc-His(Trt) | Fmoc-S35 | 3.4 | 67 | 578 |
| 417 | Fmoc-Phe | Fmoc-OX-1 | Fmoc-Trp(Boc) | Fmoc-S35 | 5.8 | 100 | 611 |
| 418 | Fmoc-D-Phe | Fmoc-OX-1 | Fmoc-Trp(Boc) | Fmoc-S35 | 2.8 | 100 | 611 |
| 419 | Fmoc-Val | Fmoc-OX-1 | Fmoc-Trp(Boc) | Fmoc-S35 | 5.5 | 72 | 563 |
| 420 | Fmoc-D-Val | Fmoc-OX-1 | Fmoc-Trp(Boc) | Fmoc-S35 | 1.5 | 100 | 563 |
| 421 | Fmoc-Ala | Fmoc-OX-1 | Fmoc-Trp(Boc) | Fmoc-S35 | 4.6 | 78 | 535 |
| 422 | Fmoc-D-Ala | Fmoc-OX-1 | Fmoc-Trp(Boc) | Fmoc-S35 | 2.6 | 100 | 535 |
| 423 | Fmoc-Ser(But) | Fmoc-OX-1 | Fmoc-Trp(Boc) | Fmoc-S35 | 7.3 | na | na |
| 424 | Fmoc-D-Ser(But) | Fmoc-OX-1 | Fmoc-Trp(Boc) | Fmoc-S35 | 3.4 | 100 | 551 |
| 425 | Fmoc-Leu | Fmoc-OX-1 | Fmoc-Trp(Boc) | Fmoc-S35 | 5.2 | 77 | 577 |
| 426 | Fmoc-D-Leu | Fmoc-OX-1 | Fmoc-Trp(Boc) | Fmoc-S35 | 1.9 | 100 | 577 |
| 427 | Fmoc-Gln(Trt) | Fmoc-OX-1 | Fmoc-Trp(Boc) | Fmoc-S35 | 4.0 | 54 | 592 |
| 428 | Fmoc-D-Gln(Trt) | Fmoc-OX-1 | Fmoc-Trp(Boc) | Fmoc-S35 | 2.3 | 100 | 592 |
| 429 | Fmoc-D-Trp(Boc) | Fmoc-OX-1 | Fmoc-D-Lys(Boc) | Fmoc-S35 | 3.0 | 100 | 592 |
| 430 | Fmoc-D-Tyr(But) | Fmoc-OX-1 | Fmoc-D-Lys(Boc) | Fmoc-S35 | 2.3 | 100 | 569 |
| 431 | Fmoc-Trp(Boc) | Fmoc-OX-1 | Fmoc-D-Lys(Boc) | Fmoc-S35 | 2.1 | 100 | 592 |
| 432 | Fmoc-Tyr(But) | Fmoc-OX-1 | Fmoc-D-Lys(Boc) | Fmoc-S35 | 2.1 | 100 | 569 |
| 433 | Fmoc-Phe | Fmoc-OX-1 | Fmoc-D-Lys(Boc) | Fmoc-S35 | 2.5 | 100 | 553 |
| 434 | Fmoc-D-Phe | Fmoc-OX-1 | Fmoc-D-Lys(Boc) | Fmoc-S35 | 2.4 | 100 | 553 |
| 435 | Fmoc-Val | Fmoc-OX-1 | Fmoc-D-Trp(Boc) | Fmoc-S35 | 2.0 | 92 | 563 |
| 436 | Fmoc-D-Val | Fmoc-OX-1 | Fmoc-D-Trp(Boc) | Fmoc-S35 | 4.8 | 100 | 563 |
| 437 | Fmoc-D-Trp(Boc) | Fmoc-OX-13 | Fmoc-D-Asn(Trt) | Fmoc-S37 | 8.4 | 100 | 586 |
| 438 | Fmoc-D-Tyr(But) | Fmoc-OX-13 | Fmoc-D-Asn(Trt) | Fmoc-S37 | 12.3 | 100 | 563 |
| 439 | Fmoc-Trp(Boc) | Fmoc-OX-13 | Fmoc-D-Asn(Trt) | Fmoc-S37 | 10.5 | 100 | 586 |

TABLE 2A-continued

| Cpd | BB$_1$ | BB$_2$ | BB$_3$ | BB$_4$ | Wt (mg)[1] | Purity[2] | MS (M + H) |
|---|---|---|---|---|---|---|---|
| 440 | Fmoc-Tyr(But) | Fmoc-OX-13 | Fmoc-D-Asn(Trt) | Fmoc-S37 | 12.3 | 100 | 563 |
| 441 | Fmoc-D-Trp(Boc) | Fmoc-OX-13 | Fmoc-D-Ser(But) | Fmoc-S37 | 7.7 | 100 | 559 |
| 442 | Fmoc-D-Tyr(But) | Fmoc-OX-13 | Fmoc-D-Ser(But) | Fmoc-S37 | 4.2 | 100 | 536 |
| 443 | Fmoc-Trp(Boc) | Fmoc-OX-13 | Fmoc-D-Ser(But) | Fmoc-S37 | 7.1 | 100 | 559 |
| 444 | Fmoc-Tyr(But) | Fmoc-OX-13 | Fmoc-D-Ser(But) | Fmoc-S37 | 6.4 | 100 | 536 |
| 445 | Fmoc-Phe | Fmoc-OX-13 | Fmoc-Asn(Trt) | Fmoc-S37 | 1.6 | 100 | 547 |
| 446 | Fmoc-D-Phe | Fmoc-OX-13 | Fmoc-D-Asn(Trt) | Fmoc-S37 | 2.8 | 96 | 547 |
| 447 | Fmoc-Lys(Boc) | Fmoc-OX-13 | Fmoc-Phe | Fmoc-S37 | 10.9 | 100 | 561 |
| 448 | Fmoc-D-Lys(Boc) | Fmoc-OX-13 | Fmoc-D-Phe | Fmoc-S37 | 2.5 | 89 | 561 |
| 449 | Fmoc-Ser(But) | Fmoc-OX-13 | Fmoc-Ala | Fmoc-S37 | 0.2 | 100 | 444 |
| 450 | Fmoc-D-Ser(But) | Fmoc-OX-13 | Fmoc-D-Ala | Fmoc-S37 | 0.4 | 100 | 444 |
| 451 | Fmoc-Ala | Fmoc-OX-13 | Fmoc-Tyr(But) | Fmoc-S37 | 0.9 | 100 | 520 |
| 452 | Fmoc-D-Ala | Fmoc-OX-13 | Fmoc-D-Tyr(But) | Fmoc-S37 | 2.8 | 100 | 520 |
| 453 | Fmoc-D-Trp(Boc) | Fmoc-OX-13 | Fmoc-Asn(Trt) | Fmoc-S37 | 1.4 | 96 | 586 |
| 454 | Fmoc-D-Tyr(But) | Fmoc-OX-13 | Fmoc-Asn(Trt) | Fmoc-S37 | 0.8 | 67 | 563 |
| 455 | Fmoc-Trp(Boc) | Fmoc-OX-13 | Fmoc-Asn(Trt) | Fmoc-S37 | 1.9 | 100 | 586 |
| 456 | Fmoc-Tyr(But) | Fmoc-OX-13 | Fmoc-Asn(Trt) | Fmoc-S37 | 3.0 | 91 | 563 |
| 457 | Fmoc-D-Trp(Boc) | Fmoc-OX-13 | Fmoc-Ser(But) | Fmoc-S37 | 2.1 | 100 | 559 |
| 458 | Fmoc-D-Tyr(But) | Fmoc-OX-13 | Fmoc-Ser(But) | Fmoc-S37 | 1.7 | 68 | 536 |
| 459 | Fmoc-Trp(Boc) | Fmoc-OX-13 | Fmoc-Ser(But) | Fmoc-S37 | 1.8 | 100 | 559 |
| 460 | Fmoc-Tyr(But) | Fmoc-OX-13 | Fmoc-Ser(But) | Fmoc-S37 | 1.3 | 100 | 536 |
| 461 | Fmoc-Lys(Boc) | Fmoc-OX-13 | Fmoc-Ser(But) | Fmoc-S37 | 3.6 | 100 | 501 |
| 462 | Fmoc-D-Lys(Boc) | Fmoc-OX-13 | Fmoc-Ser(But) | Fmoc-S37 | 4.1 | 100 | 501 |
| 463 | Fmoc-Phe | Fmoc-OX-13 | Fmoc-Sar | Fmoc-S37 | 2.0 | na | na |
| 464 | Fmoc-D-Phe | Fmoc-OX-13 | Fmoc-Sar | Fmoc-S37 | 2.3 | 95 | 504 |
| 465 | Fmoc-Lys(Boc) | Fmoc-OX-13 | Fmoc-Sar | Fmoc-S37 | 7.5 | 65 | 485 |
| 466 | Fmoc-D-Lys(Boc) | Fmoc-OX-13 | Fmoc-Sar | Fmoc-S37 | 7.4 | 100 | 485 |
| 467 | Fmoc-Ser(But) | Fmoc-OX-13 | Fmoc-Sar | Fmoc-S37 | 2.0 | 79 | 444 |
| 468 | Fmoc-D-Ser(But) | Fmoc-OX-13 | Fmoc-Sar | Fmoc-S37 | 1.6 | 100 | 444 |
| 469 | Fmoc-Ala | Fmoc-OX-13 | Fmoc-Sar | Fmoc-S37 | 1.4 | 100 | 428 |
| 470 | Fmoc-D-Ala | Fmoc-OX-13 | Fmoc-Sar | Fmoc-S37 | 2.2 | 100 | 428 |
| 471 | Fmoc-D-Trp(Boc) | Fmoc-OX-13 | Fmoc-Sar | Fmoc-S37 | 3.0 | 100 | 543 |
| 472 | Fmoc-D-Tyr(But) | Fmoc-OX-13 | Fmoc-Sar | Fmoc-S37 | 1.5 | 100 | 520 |
| 473 | Fmoc-Trp(Boc) | Fmoc-OX-13 | Fmoc-Sar | Fmoc-S37 | 2.6 | 90 | 543 |
| 474 | Fmoc-Tyr(But) | Fmoc-OX-13 | Fmoc-Sar | Fmoc-S37 | 1.2 | 91 | 520 |
| 475 | Fmoc-Dap(Boc) | Fmoc-OX-13 | Fmoc-Sar | Fmoc-S37 | 3.5 | 90 | 443 |
| 476 | Fmoc-D-Dap(Boc) | Fmoc-OX-13 | Fmoc-Sar | Fmoc-S37 | 4.0 | 87 | 443 |
| 477 | Fmoc-Arg(Pbf) | Fmoc-OX-13 | Fmoc-Sar | Fmoc-S37 | 2.1 | na | na |
| 478 | Fmoc-D-Arg(Pbf) | Fmoc-OX-13 | Fmoc-Sar | Fmoc-S37 | 1.3 | 100 | 513 |
| 479 | Fmoc-Dap(Boc) | Fmoc-OX-13 | Fmoc-Asn(Trt) | Fmoc-S37 | 2.5 | 100 | 486 |
| 480 | Fmoc-D-Dap(Boc) | Fmoc-OX-13 | Fmoc-D-Asn(Trt) | Fmoc-S37 | 3.9 | 100 | 486 |
| 481 | Fmoc-Arg(Pbf) | Fmoc-OX-13 | Fmoc-Phe | Fmoc-S37 | 2.1 | 100 | 589 |
| 482 | Fmoc-D-Arg(Pbf) | Fmoc-OX-13 | Fmoc-D-Phe | Fmoc-S37 | 2.2 | 90 | 589 |
| 483 | Fmoc-Val | Fmoc-OX-13 | Fmoc-Tyr(But) | Fmoc-S37 | 3.6 | 87 | 548 |
| 484 | Fmoc-D-Val | Fmoc-OX-13 | Fmoc-D-Tyr(But) | Fmoc-S37 | 4.5 | 100 | 548 |
| 485 | Fmoc-His(Trt) | Fmoc-OX-13 | Fmoc-Asn(Trt) | Fmoc-S37 | 2.0 | na | na |
| 486 | Fmoc-D-His(Trt) | Fmoc-OX-13 | Fmoc-Asn(Trt) | Fmoc-S37 | 1.9 | 79 | 537 |
| 487 | Fmoc-Pro | Fmoc-OX-13 | Fmoc-Asn(Trt) | Fmoc-S37 | 0.6 | 100 | 497 |
| 488 | Fmoc-D-Fmoc-Pro | Fmoc-OX-13 | Fmoc-Asn(Trt) | Fmoc-S37 | 0.8 | 100 | 497 |
| 489 | Fmoc-His(Trt) | Fmoc-OX-13 | Fmoc-Ser(But) | Fmoc-S37 | 1.4 | 90 | 510 |
| 490 | Fmoc-D-His(Trt) | Fmoc-OX-13 | Fmoc-Ser(But) | Fmoc-S37 | 1.3 | na | na |
| 491 | Fmoc-Pro | Fmoc-OX-13 | Fmoc-Ser(But) | Fmoc-S37 | 0.6 | 100 | 470 |
| 492 | Fmoc-D-Pro | Fmoc-OX-13 | Fmoc-Ser(But) | Fmoc-S37 | 0.7 | 100 | 470 |
| 493 | Fmoc-His(Trt) | Fmoc-OX-13 | Fmoc-D-Asn(Trt) | Fmoc-S37 | 3.1 | 100 | 537 |
| 494 | Fmoc-D-His(Trt) | Fmoc-OX-13 | Fmoc-D-Asn(Trt) | Fmoc-S37 | 3.2 | 100 | 537 |
| 495 | Fmoc-Pro | Fmoc-OX-13 | Fmoc-D-Asn(Trt) | Fmoc-S37 | 0.9 | 100 | 497 |
| 496 | Fmoc-D-Pro | Fmoc-OX-13 | Fmoc-D-Asn(Trt) | Fmoc-S37 | 0.9 | 100 | 497 |
| 497 | Fmoc-His(Trt) | Fmoc-OX-13 | Fmoc-D-Ser(But) | Fmoc-S37 | 2.1 | 100 | 510 |
| 498 | Fmoc-D-His(Trt) | Fmoc-OX-13 | Fmoc-D-Ser(But) | Fmoc-S37 | 1.9 | 100 | 510 |
| 499 | Fmoc-Pro | Fmoc-OX-13 | Fmoc-D-Ser(But) | Fmoc-S37 | 0.9 | 100 | 470 |
| 500 | Fmoc-D-Pro | Fmoc-OX-13 | Fmoc-D-Ser(But) | Fmoc-S37 | 0.7 | 100 | 470 |
| 501 | Fmoc-D-Trp(Boc) | Fmoc-OX-13 | Fmoc-Thr(But) | Fmoc-S37 | 3.0 | 100 | 573 |
| 502 | Fmoc-D-Tyr(But) | Fmoc-OX-13 | Fmoc-D-Thr(But) | Fmoc-S37 | 1.6 | 100 | 550 |
| 503 | Fmoc-Trp(Boc) | Fmoc-OX-13 | Fmoc-Thr(But) | Fmoc-S37 | 2.9 | 100 | 573 |
| 504 | Fmoc-Tyr(But) | Fmoc-OX-13 | Fmoc-D-Thr(But) | Fmoc-S37 | 2.5 | 82 | 550 |
| 505 | Fmoc-Lys(Boc) | Fmoc-OX-13 | Fmoc-Thr(But) | Fmoc-S37 | 7.3 | 100 | 515 |
| 506 | Fmoc-D-Lys(Boc) | Fmoc-OX-13 | Fmoc-D-Thr(But) | Fmoc-S37 | 10.3 | 100 | 515 |
| 507 | Fmoc-Phe | Fmoc-OX-13 | Fmoc-Thr(But) | Fmoc-S37 | 3.2 | 90 | 534 |
| 508 | Fmoc-D-Phe | Fmoc-OX-13 | Fmoc-D-Thr(But) | Fmoc-S37 | 0.9 | 100 | 534 |
| 509 | Fmoc-Dap(Boc) | Fmoc-OX-13 | Fmoc-Thr(But) | Fmoc-S37 | 2.5 | 100 | 473 |
| 510 | Fmoc-D-Dap(Boc) | Fmoc-OX-13 | Fmoc-D-Thr(But) | Fmoc-S37 | 3.3 | 100 | 473 |
| 511 | Fmoc-Arg(Pbf) | Fmoc-OX-13 | Fmoc-Thr(But) | Fmoc-S37 | 2.2 | 100 | 543 |
| 512 | Fmoc-D-Arg(Pbf) | Fmoc-OX-13 | Fmoc-D-Thr(But) | Fmoc-S37 | 2.7 | 100 | 543 |
| 513 | Fmoc-Val | Fmoc-OX-13 | Fmoc-Thr(But) | Fmoc-S37 | 4.2 | 100 | 486 |
| 514 | Fmoc-D-Val | Fmoc-OX-13 | Fmoc-D-Thr(But) | Fmoc-S37 | 8.6 | 97 | 486 |
| 515 | Fmoc-His(Trt) | Fmoc-OX-13 | Fmoc-Thr(But) | Fmoc-S37 | 2.0 | 100 | 524 |
| 516 | Fmoc-D-His(Trt) | Fmoc-OX-13 | Fmoc-D-Thr(But) | Fmoc-S37 | 2.6 | 100 | 524 |
| 517 | Fmoc-Pro | Fmoc-OX-13 | Fmoc-Arg(Pbf) | Fmoc-S37 | 0.3 | na | 539 |

TABLE 2A-continued

| Cpd | BB$_1$ | BB$_2$ | BB$_3$ | BB$_4$ | Wt (mg)[1] | Purity[2] | MS (M + H) |
|---|---|---|---|---|---|---|---|
| 518 | Fmoc-D-Pro | Fmoc-OX-13 | Fmoc-Arg(Pbf) | Fmoc-S37 | 0.2 | 100 | 539 |
| 519 | Fmoc-D-Trp(Boc) | Fmoc-OX-13 | Fmoc-Arg(Pbf) | Fmoc-S37 | 1.2 | 100 | 628 |
| 520 | Fmoc-D-Tyr(But) | Fmoc-OX-13 | Fmoc-Arg(Pbf) | Fmoc-S37 | 2.2 | 100 | 605 |
| 521 | Fmoc-Trp(Boc) | Fmoc-OX-13 | Fmoc-Arg(Pbf) | Fmoc-S37 | 1.4 | 100 | 628 |
| 522 | Fmoc-Tyr(But) | Fmoc-OX-13 | Fmoc-Arg(Pbf) | Fmoc-S37 | 1.9 | 89 | 605 |
| 523 | Fmoc-Phe | Fmoc-OX-13 | Fmoc-Arg(Pbf) | Fmoc-S37 | 1.6 | 87 | 589 |
| 524 | Fmoc-D-Phe | Fmoc-OX-13 | Fmoc-Arg(Pbf) | Fmoc-S37 | 1.0 | 100 | 589 |
| 525 | Fmoc-Val | Fmoc-OX-13 | Fmoc-Arg(Pbf) | Fmoc-S37 | 2.2 | 100 | 541 |
| 526 | Fmoc-D-Val | Fmoc-OX-13 | Fmoc-Arg(Pbf) | Fmoc-S37 | 2.6 | 100 | 541 |
| 527 | Fmoc-Ala | Fmoc-OX-13 | Fmoc-Arg(Pbf) | Fmoc-S37 | 0.6 | 100 | 513 |
| 528 | Fmoc-D-Ala | Fmoc-OX-13 | Fmoc-Arg(Pbf) | Fmoc-S37 | 0.8 | 100 | 513 |
| 529 | Fmoc-Ser(But) | Fmoc-OX-13 | Fmoc-Arg(Pbf) | Fmoc-S37 | 1.1 | 100 | 529 |
| 530 | Fmoc-D-Ser(But) | Fmoc-OX-13 | Fmoc-Arg(Pbf) | Fmoc-S37 | 1.2 | 100 | 529 |
| 531 | Fmoc-Pro | Fmoc-OX-13 | Fmoc-D-Arg(Pbf) | Fmoc-S37 | na | na | na |
| 532 | Fmoc-D-Pro | Fmoc-OX-13 | Fmoc-D-Arg(Pbf) | Fmoc-S37 | 0.3 | 100 | 539 |
| 533 | Fmoc-D-Trp(Boc) | Fmoc-OX-13 | Fmoc-D-Arg(Pbf) | Fmoc-S37 | 1.0 | 100 | 628 |
| 534 | Fmoc-D-Tyr(But) | Fmoc-OX-13 | Fmoc-D-Arg(Pbf) | Fmoc-S37 | 1.6 | 100 | 605 |
| 535 | Fmoc-Trp(Boc) | Fmoc-OX-13 | Fmoc-D-Arg(Pbf) | Fmoc-S37 | 0.8 | 100 | 628 |
| 536 | Fmoc-Tyr(But) | Fmoc-OX-13 | Fmoc-D-Arg(Pbf) | Fmoc-S37 | 1.3 | 100 | 605 |
| 537 | Fmoc-Phe | Fmoc-OX-13 | Fmoc-D-Arg(Pbf) | Fmoc-S37 | 1.4 | 100 | 589 |
| 538 | Fmoc-D-Phe | Fmoc-OX-13 | Fmoc-D-Arg(Pbf) | Fmoc-S37 | 1.7 | 100 | 589 |
| 539 | Fmoc-Val | Fmoc-OX-13 | Fmoc-D-Arg(Pbf) | Fmoc-S37 | 1.6 | 100 | 541 |
| 540 | Fmoc-D-Val | Fmoc-OX-13 | Fmoc-D-Arg(Pbf) | Fmoc-S37 | 1.8 | 100 | 541 |
| 541 | Fmoc-Ala | Fmoc-OX-13 | Fmoc-D-Arg(Pbf) | Fmoc-S37 | 0.4 | 100 | 513 |
| 542 | Fmoc-D-Ala | Fmoc-OX-13 | Fmoc-D-Arg(Pbf) | Fmoc-S37 | 0.5 | 100 | 513 |
| 543 | Fmoc-Ser(But) | Fmoc-OX-13 | Fmoc-D-Arg(Pbf) | Fmoc-S37 | 0.6 | 100 | 529 |
| 544 | Fmoc-D-Ser(But) | Fmoc-OX-13 | Fmoc-D-Arg(Pbf) | Fmoc-S37 | 1.3 | 100 | 529 |
| 545 | Fmoc-Phe | Fmoc-OX-13 | Fmoc-Asn(Trt) | Fmoc-S35 | 7.0 | 95 | 525 |
| 546 | Fmoc-D-Phe | Fmoc-OX-13 | Fmoc-D-Asn(Trt) | Fmoc-S35 | 6.2 | na | na |
| 547 | Fmoc-Lys(Boc) | Fmoc-OX-13 | Fmoc-Phe | Fmoc-S35 | 2.8 | 100 | 539 |
| 548 | Fmoc-Ser(But) | Fmoc-OX-13 | Fmoc-Ala | Fmoc-S35 | 1.3 | 100 | 422 |
| 549 | Fmoc-D-Ser(But) | Fmoc-OX-13 | Fmoc-D-Ala | Fmoc-S35 | 1.4 | 100 | 422 |
| 550 | Fmoc-Ala | Fmoc-OX-13 | Fmoc-Tyr(But) | Fmoc-S35 | 1.8 | 100 | 498 |
| 551 | Fmoc-D-Ala | Fmoc-OX-13 | Fmoc-D-Tyr(But) | Fmoc-S35 | 2.2 | 100 | 498 |
| 552 | Fmoc-D-Trp(Boc) | Fmoc-OX-13 | Fmoc-Asn(Trt) | Fmoc-S35 | na | na | na |
| 553 | Fmoc-D-Tyr(But) | Fmoc-OX-13 | Fmoc-Asn(Trt) | Fmoc-S35 | 4.9 | 86 | 541 |
| 554 | Fmoc-Trp(Boc) | Fmoc-OX-13 | Fmoc-Asn(Trt) | Fmoc-S35 | 5.0 | 100 | 564 |
| 555 | Fmoc-Tyr(But) | Fmoc-OX-13 | Fmoc-Asn(Trt) | Fmoc-S35 | 0.9 | 63 | 541 |
| 556 | Fmoc-D-Tyr(But) | Fmoc-OX-13 | Fmoc-Ser(But) | Fmoc-S35 | 4.9 | 89 | 514 |
| 557 | Fmoc-Tyr(But) | Fmoc-OX-13 | Fmoc-Ser(But) | Fmoc-S35 | 4.0 | 100 | 514 |
| 558 | Fmoc-Lys(Boc) | Fmoc-OX-13 | Fmoc-Ser(But) | Fmoc-S35 | 3.0 | 100 | 479 |
| 559 | Fmoc-D-Lys(Boc) | Fmoc-OX-13 | Fmoc-Ser(But) | Fmoc-S35 | 4.2 | 100 | 479 |
| 560 | Fmoc-Dap(Boc) | Fmoc-OX-13 | Fmoc-Asn(Trt) | Fmoc-S35 | 3.7 | 92 | 464 |
| 561 | Fmoc-D-Dap(Boc) | Fmoc-OX-13 | Fmoc-D-Asn(Trt) | Fmoc-S35 | 3.6 | 100 | 464 |
| 562 | Fmoc-Arg(Pbf) | Fmoc-OX-13 | Fmoc-Phe | Fmoc-S35 | 1.0 | 100 | 567 |
| 563 | Fmoc-D-Arg(Pbf) | Fmoc-OX-13 | Fmoc-D-Phe | Fmoc-S35 | 1.6 | 100 | 567 |
| 564 | Fmoc-Val | Fmoc-OX-13 | Fmoc-Tyr(But) | Fmoc-S35 | 8.3 | 92 | 526 |
| 565 | Fmoc-D-Val | Fmoc-OX-13 | Fmoc-D-Tyr(But) | Fmoc-S35 | 5.8 | 100 | 526 |
| 566 | Fmoc-His(Trt) | Fmoc-OX-13 | Fmoc-Asn(Trt) | Fmoc-S35 | 4.3 | 100 | 515 |
| 567 | Fmoc-D-His(Trt) | Fmoc-OX-13 | Fmoc-Asn(Trt) | Fmoc-S35 | 5.3 | 96 | 515 |
| 568 | Fmoc-Ala | Fmoc-OX-13 | Fmoc-Asn(Trt) | Fmoc-S35 | 2.6 | 100 | 449 |
| 569 | Fmoc-D-Ala | Fmoc-OX-13 | Fmoc-Asn(Trt) | Fmoc-S35 | 2.6 | 100 | 449 |
| 570 | Fmoc-His(Trt) | Fmoc-OX-13 | Fmoc-Ser(But) | Fmoc-S35 | 3.1 | 90 | 488 |
| 571 | Fmoc-D-His(Trt) | Fmoc-OX-13 | Fmoc-Ser(But) | Fmoc-S35 | 4.3 | 100 | 488 |
| 572 | Fmoc-Ala | Fmoc-OX-13 | Fmoc-Ser(But) | Fmoc-S35 | 1.3 | 100 | 422 |
| 573 | Fmoc-D-Ala | Fmoc-OX-13 | Fmoc-Ser(But) | Fmoc-S35 | 2.8 | 100 | 422 |
| 574 | Fmoc-His(Trt) | Fmoc-OX-13 | Fmoc-D-Asn(Trt) | Fmoc-S35 | 5.1 | 100 | 515 |
| 575 | Fmoc-D-His(Trt) | Fmoc-OX-13 | Fmoc-D-Asn(Trt) | Fmoc-S35 | 5.4 | 100 | 515 |
| 576 | Fmoc-Ala | Fmoc-OX-13 | Fmoc-D-Asn(Trt) | Fmoc-S35 | 2.4 | 100 | 449 |
| 577 | Fmoc-D-Ala | Fmoc-OX-13 | Fmoc-D-Asn(Trt) | Fmoc-S35 | 2.1 | 100 | 449 |
| 578 | Fmoc-His(Trt) | Fmoc-OX-13 | Fmoc-D-Ser(But) | Fmoc-S35 | 4.2 | 100 | 488 |
| 579 | Fmoc-D-His(Trt) | Fmoc-OX-13 | Fmoc-D-Ser(But) | Fmoc-S35 | 3.7 | 100 | 488 |
| 580 | Fmoc-Ala | Fmoc-OX-13 | Fmoc-D-Ser(But) | Fmoc-S35 | 2.1 | 100 | 422 |
| 581 | Fmoc-D-Ala | Fmoc-OX-13 | Fmoc-D-Ser(But) | Fmoc-S35 | 1.7 | 100 | 422 |
| 582 | Fmoc-D-Trp(Boc) | Fmoc-OX-13 | Fmoc-Thr(But) | Fmoc-S35 | 3.4 | 100 | 551 |
| 583 | Fmoc-D-Tyr(But) | Fmoc-OX-13 | Fmoc-D-Thr(But) | Fmoc-S35 | 3.6 | 100 | 528 |
| 584 | Fmoc-Trp(Boc) | Fmoc-OX-13 | Fmoc-Thr(But) | Fmoc-S35 | 5.3 | 100 | 551 |
| 585 | Fmoc-Tyr(But) | Fmoc-OX-13 | Fmoc-D-Thr(But) | Fmoc-S35 | 4.0 | 100 | 528 |
| 586 | Fmoc-Lys(Boc) | Fmoc-OX-13 | Fmoc-Thr(But) | Fmoc-S35 | 7.7 | 100 | 493 |
| 587 | Fmoc-D-Lys(Boc) | Fmoc-OX-13 | Fmoc-D-Thr(But) | Fmoc-S35 | 7.6 | 100 | 493 |
| 588 | Fmoc-Phe | Fmoc-OX-13 | Fmoc-Thr(But) | Fmoc-S35 | 7.0 | 88 | 512 |
| 589 | Fmoc-D-Phe | Fmoc-OX-13 | Fmoc-D-Thr(But) | Fmoc-S35 | 3.1 | 100 | 512 |
| 590 | Fmoc-Dap(Boc) | Fmoc-OX-13 | Fmoc-Thr(But) | Fmoc-S35 | 3.9 | 100 | 451 |
| 591 | Fmoc-D-Dap(Boc) | Fmoc-OX-13 | Fmoc-D-Thr(But) | Fmoc-S35 | 1.7 | 100 | 451 |
| 592 | Fmoc-Arg(Pbf) | Fmoc-OX-13 | Fmoc-Thr(But) | Fmoc-S35 | 2.9 | 100 | 521 |
| 593 | Fmoc-D-Arg(Pbf) | Fmoc-OX-13 | Fmoc-D-Thr(But) | Fmoc-S35 | 1.7 | 100 | 521 |
| 594 | Fmoc-Val | Fmoc-OX-13 | Fmoc-Thr(But) | Fmoc-S35 | 7.0 | 100 | 464 |
| 595 | Fmoc-D-Val | Fmoc-OX-13 | Fmoc-D-Thr(But) | Fmoc-S35 | 9.9 | 100 | 464 |

TABLE 2A-continued

| Cpd | BB$_1$ | BB$_2$ | BB$_3$ | BB$_4$ | Wt (mg)[1] | Purity[2] | MS (M + H) |
|---|---|---|---|---|---|---|---|
| 596 | Fmoc-His(Trt) | Fmoc-OX-13 | Fmoc-Thr(But) | Fmoc-S35 | 0.3 | 100 | 502 |
| 597 | Fmoc-D-His(Trt) | Fmoc-OX-13 | Fmoc-D-Thr(But) | Fmoc-S35 | 5.4 | 100 | 502 | na = not available

[1] All syntheses were carried out on the solid phase starting from 70-80 mg of 2-chlorotrityl chloride resin (typical loading 1.0 mmol/g).

[2] Purity is determined by analysis with LC-UV at 220 nm.

TABLE 2B

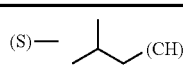

| Cpd | R$_1$ | Q | R$_2$ | R$_3$ | R$_4$ | R$_7$ |
|---|---|---|---|---|---|---|
| 301 | (S)—CH$_3$ | C=O | 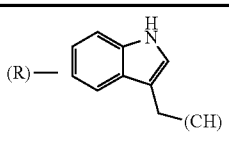 |  | H | 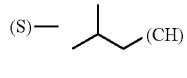 |
| 302 | (S)—H$_2$NOC-(CH) | C=O | 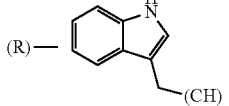 | 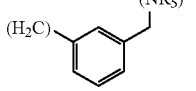 | H | 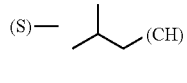 |
| 303 | (R)—CH$_3$ | C=O | 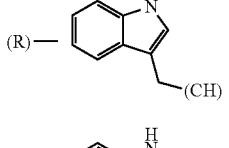 | 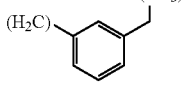 | H | 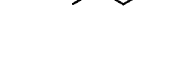 |
| 304 | (R)—H$_2$NOC-(CH) | C=O | 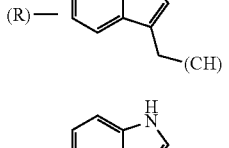 | 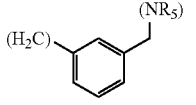 | H |  |
| 305 | (R)—H$_2$NOC-(CH) | C=O | 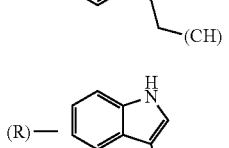 | 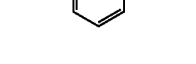 | H | 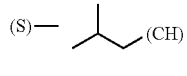 |
| 306 | (R)—HO$_2$C-(CH) | C=O | 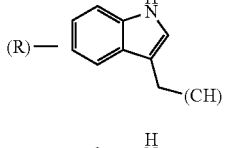 | 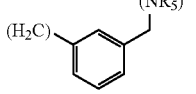 | H | 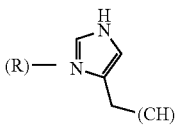 |
| 307 | 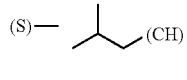 | C=O | 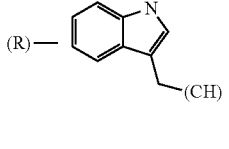 | 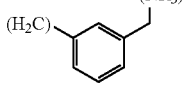 | H | |

TABLE 2B-continued

| Cpd | R₁ | Q | R₂ | R₃ | R₄ | R₇ |
|---|---|---|---|---|---|---|
| 308 | (R)—H₂N—(CH) | C=O | (S)— isobutyl (CH) | (R)— indol-3-ylmethyl (CH) | H | (H₂C)— m-(NR₅)benzyl |
| 309 | (R)— propyl (CH) | C=O | (S)— isobutyl (CH) | (R)— indol-3-ylmethyl (CH) | H | (H₂C)— m-(NR₅)benzyl |
| 310 | (R)— benzyl (CH) | C=O | (S)— isobutyl (CH) | (R)— indol-3-ylmethyl (CH) | H | (H₂C)— m-(NR₅)benzyl |
| 311 | (R)— pyrrolidin-2-yl (HC)(N) | C=O | (S)— isobutyl (CH) | (R)— indol-3-ylmethyl (CH) | H | (H₂C)— m-(NR₅)benzyl |
| 312 | (R)— HO—(CH) | C=O | (S)— isobutyl (CH) | (R)— indol-3-ylmethyl (CH) | H | (H₂C)— m-(NR₅)benzyl |
| 313 | (R)— indol-3-ylmethyl (CH) | C=O | (S)— isobutyl (CH) | (R)— indol-3-ylmethyl (CH) | H | (H₂C)— m-(NR₅)benzyl |
| 314 | (R)— 4-hydroxybenzyl (CH) | C=O | (S)— isobutyl (CH) | (R)— indol-3-ylmethyl (CH) | H | (H₂C)— m-(NR₅)benzyl |
| 315 | (R)— isopropyl (CH) | C=O | (S)— isobutyl (CH) | (R)— indol-3-ylmethyl (CH) | H | (H₂C)— m-(NR₅)benzyl |
| 316 | (S)—H₂NOC—(CH) | C=O | (S)— isobutyl (CH) | (R)— indol-3-ylmethyl (CH) | H | (H₂C)— m-(NR₅)benzyl |

TABLE 2B-continued

| Cpd | R₁ | Q | R₂ | R₃ | R₄ | R₇ |
|---|---|---|---|---|---|---|
| 317 | (S)—HO₂C—(CH) | C=O | (S)—iBu—(CH) | (R)-indol-3-ylmethyl (CH) | H | (H₂C)-3-(NR₅)-benzyl |
| 318 | (S)-imidazol-4-ylmethyl (CH) | C=O | (S)—iBu—(CH) | (R)-indol-3-ylmethyl (CH) | H | (H₂C)-3-(NR₅)-benzyl |
| 319 | (S)—H₂N—(CH₂)₄—(CH) | C=O | (S)—iBu—(CH) | (R)-indol-3-ylmethyl (CH) | H | (H₂C)-3-(NR₅)-benzyl |
| 320 | (S)—Et—(CH) | C=O | (S)—iBu—(CH) | (R)-indol-3-ylmethyl (CH) | H | (H₂C)-3-(NR₅)-benzyl |
| 321 | (S)—benzyl—(CH) | C=O | (S)—iBu—(CH) | (R)-indol-3-ylmethyl (CH) | H | (H₂C)-3-(NR₅)-benzyl |
| 322 | (S)—(HC)-pyrrolidin-2-yl (N) | C=O | (S)—iBu—(CH) | (R)-indol-3-ylmethyl (CH) | H | (H₂C)-3-(NR₅)-benzyl |
| 323 | (S)—HO—CH₂—(CH) | C=O | (S)—iBu—(CH) | (R)-indol-3-ylmethyl (CH) | H | (H₂C)-3-(NR₅)-benzyl |
| 324 | (S)—indol-3-ylmethyl (CH) | C=O | (S)—iBu—(CH) | (R)-indol-3-ylmethyl (CH) | H | (H₂C)-3-(NR₅)-benzyl |
| 325 | (S)—4-HO-benzyl—(CH) | C=O | (S)—iBu—(CH) | (R)-indol-3-ylmethyl (CH) | H | (H₂C)—(R)—(NR₅) |

TABLE 2B-continued

| Cpd | R₁ | Q | R₂ | R₃ | R₄ | R₇ |
|---|---|---|---|---|---|---|
| 326 | (S)—isopropyl(CH) | C=O | (S)—isobutyl(CH) | (R)—indol-3-ylmethyl(CH) | H | (H₂C)—3-aminomethylphenyl(NR₅) |
| 327 | (S)—CH₃ | C=O | (S)—isobutyl(CH) | (R)—4-hydroxybenzyl(CH) | H | (H₂C)—3-aminomethylphenyl(NR₅) |
| 328 | (S)—H₂NOC—(CH) | C=O | (S)—isobutyl(CH) | (R)—4-hydroxybenzyl(CH) | H | (H₂C)—3-aminomethylphenyl(NR₅) |
| 329 | (R)—CH₃ | C=O | (S)—isobutyl(CH) | (R)—4-hydroxybenzyl(CH) | H | (H₂C)—3-aminomethylphenyl(NR₅) |
| 330 | (R)—H₂NOC—(CH) | C=O | (S)—isobutyl(CH) | (R)—4-hydroxybenzyl(CH) | H | (H₂C)—3-aminomethylphenyl(NR₅) |
| 331 | (R)—H₂NOC—(CH) | C=O | (S)—isobutyl(CH) | (R)—4-hydroxybenzyl(CH) | H | (H₂C)—3-aminomethylphenyl(NR₅) |
| 332 | (R)—HO₂C—(CH) | C=O | (S)—isobutyl(CH) | (R)—4-hydroxybenzyl(CH) | H | (H₂C)—3-aminomethylphenyl(NR₅) |
| 333 | (R)—imidazol-4-ylmethyl(CH) | C=O | (S)—isobutyl(CH) | (R)—4-hydroxybenzyl(CH) | H | (H₂C)—3-aminomethylphenyl(NR₅) |
| 334 | (R)—H₂N(CH₂)₄(CH) | C=O | (S)—isobutyl(CH) | (R)—4-hydroxybenzyl(CH) | H | (H₂C)—3-aminomethylphenyl(NR₅) |
| 335 | (R)—propyl(CH) | C=O | (S)—isobutyl(CH) | (R)—4-hydroxybenzyl(CH) | H | (H₂C)—3-aminomethylphenyl(NR₅) |

TABLE 2B-continued

| Cpd | R₁ | Q | R₂ | R₃ | R₄ | R₇ |
|---|---|---|---|---|---|---|
| 336 | (R)—benzyl (CH) | C=O | (S)—isobutyl (CH) | (R)—4-hydroxybenzyl (CH) | H | (H₂C)—3-(NR₅)benzyl |
| 337 | (R)—(HC) pyrrolidinyl (N) | C=O | (S)—isobutyl (CH) | (R)—4-hydroxybenzyl (CH) | H | (H₂C)—3-(NR₅)benzyl |
| 338 | (R)—HO-CH₂-(CH) | C=O | (S)—isobutyl (CH) | (R)—4-hydroxybenzyl (CH) | H | (H₂C)—3-(NR₅)benzyl |
| 339 | (R)—indol-3-ylmethyl (CH) | C=O | (S)—isobutyl (CH) | (R)—4-hydroxybenzyl (CH) | H | (H₂C)—3-(NR₅)benzyl |
| 340 | (R)—4-hydroxybenzyl (CH) | C=O | (S)—isobutyl (CH) | (R)—4-hydroxybenzyl (CH) | H | (H₂C)—3-(NR₅)benzyl |
| 341 | (R)—isopropyl (CH) | C=O | (S)—isobutyl (CH) | (R)—4-hydroxybenzyl (CH) | H | (H₂C)—3-(NR₅)benzyl |
| 342 | (S)—H₂NOC-CH₂CH₂-(CH) | C=O | (S)—isobutyl (CH) | (R)—4-hydroxybenzyl (CH) | H | (H₂C)—3-(NR₅)benzyl |
| 343 | (S)—HO₂C-CH₂CH₂-(CH) | C=O | (S)—isobutyl (CH) | (R)—4-hydroxybenzyl (CH) | H | (H₂C)—3-(NR₅)benzyl |
| 344 | (S)—imidazol-4-ylmethyl (CH) | C=O | (S)—isobutyl (CH) | (R)—4-hydroxybenzyl (CH) | H | (H₂C)—3-(NR₅)benzyl |
| 345 | (S)—H₂N-(CH₂)₄-(CH) | C=O | (S)—isobutyl (CH) | (R)—4-hydroxybenzyl (CH) | H | (H₂C)—3-(NR₅)benzyl |

TABLE 2B-continued

| Cpd | R₁ | Q | R₂ | R₃ | R₄ | R₇ |
|---|---|---|---|---|---|---|
| 346 | (S)-propyl (CH) | C=O | (S)-isobutyl (CH) | (R)-4-hydroxybenzyl (CH) | H | 3-aminomethylbenzyl (H₂C)...(NR₅) |
| 347 | (S)-benzyl (CH) | C=O | (S)-isobutyl (CH) | (R)-4-hydroxybenzyl (CH) | H | 3-aminomethylbenzyl (H₂C)...(NR₅) |
| 348 | (S)-(pyrrolidinyl) (HC) (N) | C=O | (S)-isobutyl (CH) | (R)-4-hydroxybenzyl (CH) | H | 3-aminomethylbenzyl (H₂C)...(NR₅) |
| 349 | (S)-HOCH₂ (CH) | C=O | (S)-isobutyl (CH) | (R)-4-hydroxybenzyl (CH) | H | 3-aminomethylbenzyl (H₂C)...(NR₅) |
| 350 | (S)-(indol-3-ylmethyl) (CH) | C=O | (S)-isobutyl (CH) | (R)-4-hydroxybenzyl (CH) | H | 3-aminomethylbenzyl (H₂C)...(NR₅) |
| 351 | (S)-4-hydroxybenzyl (CH) | C=O | (S)-isobutyl (CH) | (R)-4-hydroxybenzyl (CH) | H | 3-aminomethylbenzyl (H₂C)...(NR₅) |
| 352 | (S)-isopropyl (CH) | C=O | (S)-isobutyl (CH) | (R)-4-hydroxybenzyl (CH) | H | 3-aminomethylbenzyl (H₂C)...(NR₅) |
| 353 | (S)—CH₃ | C=O | (S)-isobutyl (CH) | (S)-(indol-3-ylmethyl) (CH) | H | 3-aminomethylbenzyl (H₂C)...(NR₅) |
| 354 | (S)-H₂NOC-CH₂ (CH) | C=O | (S)-isobutyl (CH) | (S)-(indol-3-ylmethyl) (CH) | H | 3-aminomethylbenzyl (H₂C)...(NR₅) |
| 355 | (R)—CH₃ | C=O | (S)-isobutyl (CH) | (S)-(indol-3-ylmethyl) (CH) | H | 3-aminomethylbenzyl (H₂C)...(NR₅) |

TABLE 2B-continued

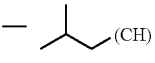

| Cpd | R₁ | Q | R₂ | R₃ | R₄ | R₇ |
|---|---|---|---|---|---|---|
| 356 | (R)—H₂NOC⁀(CH) | C=O | (S)—⋋⋌(CH) | (S)—indol-3-ylmethyl (CH) | H | (H₂C)—C₆H₄—(NR₅) |
| 357 | (R)—H₂NOC⁀(CH) | C=O | (S)—⋋⋌(CH) | (S)—indol-3-ylmethyl (CH) | H | (H₂C)—C₆H₄—(NR₅) |
| 358 | (R)—HO₂C⁀(CH) | C=O | (S)—⋋⋌(CH) | (S)—indol-3-ylmethyl (CH) | H | (H₂C)—C₆H₄—(NR₅) |
| 359 | (R)—imidazol-4-yl-CH₂—(CH) | C=O | (S)—⋋⋌(CH) | (S)—indol-3-ylmethyl (CH) | H | (H₂C)—C₆H₄—(NR₅) |
| 360 | (R)—H₂N⁀⁀(CH) | C=O | (S)—⋋⋌(CH) | (S)—indol-3-ylmethyl (CH) | H | (H₂C)—C₆H₄—(NR₅) |
| 361 | (R)—⋀⋁(CH) | C=O | (S)—⋋⋌(CH) | (S)—indol-3-ylmethyl (CH) | H | (H₂C)—C₆H₄—(NR₅) |
| 362 | (R)—CH₂C₆H₅(CH) | C=O | (S)—⋋⋌(CH) | (S)—indol-3-ylmethyl (CH) | H | (H₂C)—C₆H₄—(NR₅) |
| 363 | (R)—pyrrolidin-2-yl (HC) | C=O | (S)—⋋⋌(CH) | (S)—indol-3-ylmethyl (CH) | H | (H₂C)—C₆H₄—(NR₅) |
| 364 | (R)—HO⁀(CH) | C=O | (S)—⋋⋌(CH) | (S)—indol-3-ylmethyl (CH) | H | (H₂C)—C₆H₄—(NR₅) |

TABLE 2B-continued

| Cpd | R₁ | Q | R₂ | R₃ | R₄ | R₇ |
|---|---|---|---|---|---|---|
| 365 | (R)— 3-(1H-indol-3-yl)methyl (CH) | C=O | (S)— isobutyl (CH) | (S)— 1H-indol-3-ylmethyl (CH) | H | (H₂C)— 3-(NR₅)methyl-phenyl |
| 366 | (R)— 4-hydroxybenzyl (CH) | C=O | (S)— isobutyl (CH) | (S)— 1H-indol-3-ylmethyl (CH) | H | (H₂C)— 3-(NR₅)methyl-phenyl |
| 367 | (R)— isopropyl (CH) | C=O | (S)— isobutyl (CH) | (S)— 1H-indol-3-ylmethyl (CH) | H | (H₂C)— 3-(NR₅)methyl-phenyl |
| 368 | (S)—H₂NOC— (CH) | C=O | (S)— isobutyl (CH) | (S)— 1H-indol-3-ylmethyl (CH) | H | (H₂C)— 3-(NR₅)methyl-phenyl |
| 369 | (S)—HO₂C— (CH) | C=O | (S)— isobutyl (CH) | (S)— 1H-indol-3-ylmethyl (CH) | H | (H₂C)— 3-(NR₅)methyl-phenyl |
| 370 | (S)— 1H-imidazol-4-ylmethyl (CH) | C=O | (S)— isobutyl (CH) | (S)— 1H-indol-3-ylmethyl (CH) | H | (H₂C)— 3-(NR₅)methyl-phenyl |
| 371 | (S)—H₂N— (CH) | C=O | (S)— isobutyl (CH) | (S)— 1H-indol-3-ylmethyl (CH) | H | (H₂C)— 3-(NR₅)methyl-phenyl |
| 372 | (S)— propyl (CH) | C=O | (S)— isobutyl (CH) | (S)— 1H-indol-3-ylmethyl (CH) | H | (H₂C)— 3-(NR₅)methyl-phenyl |
| 373 | (S)— benzyl (CH) | C=O | (S)— isobutyl (CH) | (S)— 1H-indol-3-ylmethyl (CH) | H | (H₂C)— 3-(NR₅)methyl-phenyl |

TABLE 2B-continued

| Cpd | R₁ | Q | R₂ | R₃ | R₄ | R₇ |
|---|---|---|---|---|---|---|
| 374 | (S)-(HC) pyrrolidinyl(N) | C=O | (S)-isobutyl(CH) | (S)-indolylmethyl(CH) | H | (H₂C)-benzyl(NR₅) |
| 375 | (S)-HOCH₂(CH) | C=O | (S)-isobutyl(CH) | (S)-indolylmethyl(CH) | H | (H₂C)-benzyl(NR₅) |
| 376 | (S)-indolylmethyl(CH) | C=O | (S)-isobutyl(CH) | (S)-indolylmethyl(CH) | H | (H₂C)-benzyl(NR₅) |
| 377 | (S)-4-hydroxybenzyl(CH) | C=O | (S)-isobutyl(CH) | (S)-indolylmethyl(CH) | H | (H₂C)-benzyl(NR₅) |
| 378 | (S)-isopropyl(CH) | C=O | (S)-isobutyl(CH) | (S)-indolylmethyl(CH) | H | (H₂C)-benzyl(NR₅) |
| 379 | (S)-CH₃ | C=O | (S)-isobutyl(CH) | (S)-4-hydroxybenzyl(CH) | H | (H₂C)-benzyl(NR₅) |
| 380 | (S)-H₂NOC-(CH) | C=O | (S)-isobutyl(CH) | (S)-4-hydroxybenzyl(CH) | H | (H₂C)-benzyl(NR₅) |
| 381 | (R)-CH₃ | C=O | (S)-isobutyl(CH) | (S)-4-hydroxybenzyl(CH) | H | (H₂C)-benzyl(NR₅) |
| 382 | (R)-H₂NOC-(CH) | C=O | (S)-isobutyl(CH) | (S)-4-hydroxybenzyl(CH) | H | (H₂C)-benzyl(NR₅) |
| 383 | (R)-H₂NOC~(CH) | C=O | (S)-isobutyl(CH) | (S)-4-hydroxybenzyl(CH) | H | (H₂C)-benzyl(NR₅) |

TABLE 2B-continued

| Cpd | R₁ | Q | R₂ | R₃ | R₄ | R₇ |
|---|---|---|---|---|---|---|
| 384 | (R)—HO₂C~(CH) | C=O | (S)—iBu(CH) | (S)—4-HO-C₆H₄-CH₂(CH) | H | (H₂C)-3-(NR₅)-benzyl |
| 385 | (R)-imidazol-4-yl-CH₂(CH) | C=O | (S)—iBu(CH) | (S)—4-HO-C₆H₄-CH₂(CH) | H | (H₂C)-3-(NR₅)-benzyl |
| 386 | (R)—H₂N~(CH) | C=O | (S)—iBu(CH) | (S)—4-HO-C₆H₄-CH₂(CH) | H | (H₂C)-3-(NR₅)-benzyl |
| 387 | (R)—n-Pr(CH) | C=O | (S)—iBu(CH) | (S)—4-HO-C₆H₄-CH₂(CH) | H | (H₂C)-3-(NR₅)-benzyl |
| 388 | (R)—Bn(CH) | C=O | (S)—iBu(CH) | (S)—4-HO-C₆H₄-CH₂(CH) | H | (H₂C)-3-(NR₅)-benzyl |
| 389 | (R)—pyrrolidin-2-yl(HC) | C=O | (S)—iBu(CH) | (S)—4-HO-C₆H₄-CH₂(CH) | H | (H₂C)-3-(NR₅)-benzyl |
| 390 | (S)—HOCH₂(CH) | C=O | (S)—iBu(CH) | (S)—4-HO-C₆H₄-CH₂(CH) | H | (H₂C)-3-(NR₅)-benzyl |
| 391 | (R)—indol-3-yl-CH₂(CH) | C=O | (S)—iBu(CH) | (S)—4-HO-C₆H₄-CH₂(CH) | H | (H₂C)-3-(NR₅)-benzyl |
| 392 | (R)—4-HO-C₆H₄-CH₂(CH) | C=O | (S)—iBu(CH) | (S)—4-HO-C₆H₄-CH₂(CH) | H | (H₂C)-3-(NR₅)-benzyl |
| 393 | (R)—iPr(CH) | C=O | (S)—iBu(CH) | (S)—4-HO-C₆H₄-CH₂(CH) | H | (H₂C)-3-(NR₅)-benzyl |

TABLE 2B-continued

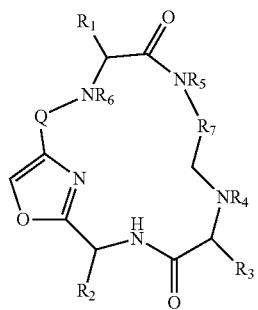

| Cpd | R₁ | Q | R₂ | R₃ | R₄ | R₇ |
|---|---|---|---|---|---|---|
| 394 | (S)—H₂NOC~(CH) | C=O | (S)—iBu(CH) | (S)—4-HO-C₆H₄-CH₂(CH) | H | (H₂C)-3-(NR₅)-C₆H₄-CH₂ |
| 395 | (S)—HO₂C~(CH) | C=O | (S)—iBu(CH) | (S)—4-HO-C₆H₄-CH₂(CH) | H | (H₂C)-3-(NR₅)-C₆H₄-CH₂ |
| 396 | (S)—imidazol-4-yl-CH₂(CH) | C=O | (S)—iBu(CH) | (S)—4-HO-C₆H₄-CH₂(CH) | H | (H₂C)-3-(NR₅)-C₆H₄-CH₂ |
| 397 | (S)—H₂N(CH₂)₄(CH) | C=O | (S)—iBu(CH) | (S)—4-HO-C₆H₄-CH₂(CH) | H | (H₂C)-3-(NR₅)-C₆H₄-CH₂ |
| 398 | (S)—Pr(CH) | C=O | (S)—iBu(CH) | (S)—4-HO-C₆H₄-CH₂(CH) | H | (H₂C)-3-(NR₅)-C₆H₄-CH₂ |
| 399 | (S)—Bn(CH) | C=O | (S)—iBu(CH) | (S)—4-HO-C₆H₄-CH₂(CH) | H | (H₂C)-3-(NR₅)-C₆H₄-CH₂ |
| 400 | (S)—pyrrolidinyl(HC)(N) | C=O | (S)—iBu(CH) | (S)—4-HO-C₆H₄-CH₂(CH) | H | (H₂C)-3-(NR₅)-C₆H₄-CH₂ |
| 401 | (S)—HOCH₂(CH) | C=O | (S)—iBu(CH) | (S)—4-HO-C₆H₄-CH₂(CH) | H | (H₂C)-3-(NR₅)-C₆H₄-CH₂ |
| 402 | (S)—indol-3-yl-CH₂(CH) | C=O | (S)—iBu(CH) | (S)—4-HO-C₆H₄-CH₂(CH) | H | (H₂C)-3-(NR₅)-C₆H₄-CH₂ |
| 403 | (S)—4-HO-C₆H₄-CH₂(CH) | C=O | (S)—iBu(CH) | (S)—4-HO-C₆H₄-CH₂(CH) | H | (H₂C)-3-(NR₅)-C₆H₄-CH₂ |

TABLE 2B-continued

| Cpd | R₁ | Q | R₂ | R₃ | R₄ | R₇ |
|---|---|---|---|---|---|---|
| 404 | (S)—isopropyl(CH) | C=O | (S)—isobutyl(CH) | (S)—4-hydroxybenzyl(CH) | H | (H₂C)—3-(NR₅)methylphenyl |
| 405 | (S)—H₂N-C(=NH)-NH-(CH₂)₃(CH) | C=O | (S)—isobutyl(CH) | (S)—4-hydroxybenzyl(CH) | H | (H₂C)—3-(NR₅)methylphenyl |
| 406 | (S)—H₂N-C(=NH)-NH-(CH₂)₃(CH) | C=O | (S)—isobutyl(CH) | (S)—indol-3-ylmethyl(CH) | H | (H₂C)—3-(NR₅)methylphenyl |
| 407 | (S)—H₂N-C(=NH)-NH-(CH₂)₃(CH) | C=O | (S)—isobutyl(CH) | (S)—4-hydroxybenzyl(CH) | H | (H₂C)—3-(NR₅)methylphenyl |
| 408 | (S)—H₂N-C(=NH)-NH-(CH₂)₃(CH) | C=O | (S)—isobutyl(CH) | (R)—indol-3-ylmethyl(CH) | H | (H₂C)—3-(NR₅)methylphenyl |
| 409 | (R)—H₂N-C(=NH)-NH-(CH₂)₃(CH) | C=O | (S)—isobutyl(CH) | (S)—4-hydroxybenzyl(CH) | H | (H₂C)—3-(NR₅)methylphenyl |
| 410 | (R)—H₂N-C(=NH)-NH-(CH₂)₃(CH) | C=O | (S)—isobutyl(CH) | (S)—indol-3-ylmethyl(CH) | H | (H₂C)—3-(NR₅)methylphenyl |
| 411 | (R)—H₂N-C(=NH)-NH-(CH₂)₃(CH) | C=O | (S)—isobutyl(CH) | (R)—4-hydroxybenzyl(CH) | H | (H₂C)—3-(NR₅)methylphenyl |
| 412 | (R)—H₂N-C(=NH)-NH-(CH₂)₃(CH) | C=O | (S)—isobutyl(CH) | (R)—indol-3-ylmethyl(CH) | H | (H₂C)—3-(NR₅)methylphenyl |
| 413 | (R)—indol-3-ylmethyl(CH) | C=O | (S)—isobutyl(CH) | (S)—H₂N-(CH₂)₄(CH) | H | (H₂C)—piperidin-4-yl(N) |

TABLE 2B-continued

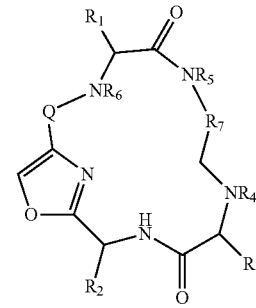

| Cpd | R₁ | Q | R₂ | R₃ | R₄ | R₇ |
|---|---|---|---|---|---|---|
| 414 | (R)—4-hydroxybenzyl (CH) | C=O | (S)—isobutyl (CH) | (S)—H₂N-butyl (CH) | H | (H₂C)-4-piperidinyl (N) |
| 415 | (S)—indol-3-ylmethyl (CH) | C=O | (S)—isobutyl (CH) | (S)—imidazol-4-ylmethyl (CH) | H | (H₂C)-4-piperidinyl (N) |
| 416 | (S)—4-hydroxybenzyl (CH) | C=O | (S)—isobutyl (CH) | (S)—imidazol-4-ylmethyl (CH) | H | (H₂C)-4-piperidinyl (N) |
| 417 | (S)—benzyl (CH) | C=O | (S)—isobutyl (CH) | (S)—indol-3-ylmethyl (CH) | H | (H₂C)-4-piperidinyl (N) |
| 418 | (R)—benzyl (CH) | C=O | (S)—isobutyl (CH) | (S)—indol-3-ylmethyl (CH) | H | (H₂C)-4-piperidinyl (N) |
| 419 | (S)—isopropyl (CH) | C=O | (S)—isobutyl (CH) | (S)—indol-3-ylmethyl (CH) | H | (H₂C)-4-piperidinyl (N) |
| 420 | (R)—isopropyl (CH) | C=O | (S)—isobutyl (CH) | (S)—indol-3-ylmethyl (CH) | H | (H₂C)-4-piperidinyl (N) |
| 421 | (S)—CH₃ | C=O | (S)—isobutyl (CH) | (S)—indol-3-ylmethyl (CH) | H | (H₂C)-4-piperidinyl (N) |
| 422 | (R)—CH₃ | C=O | (S)—isobutyl (CH) | (S)—indol-3-ylmethyl (CH) | H | (H₂C)-4-piperidinyl (N) |

TABLE 2B-continued

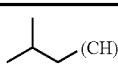

| Cpd | R₁ | Q | R₂ | R₃ | R₄ | R₇ |
|---|---|---|---|---|---|---|
| 423 | (S)— HO⌒(CH) | C=O | (S)—⤴(CH) | (S)—indol-3-ylmethyl(CH) | H | (H₂C)—4-piperidinyl(N) |
| 424 | (R)— HO⌒(CH) | C=O | (S)—⤴(CH) | (S)—indol-3-ylmethyl(CH) | H | (H₂C)—4-piperidinyl(N) |
| 425 | (S)—⤴(CH) | C=O | (S)—⤴(CH) | (S)—indol-3-ylmethyl(CH) | H | (H₂C)—4-piperidinyl(N) |
| 426 | (R)—⤴(CH) | C=O | (S)—⤴(CH) | (S)—indol-3-ylmethyl(CH) | H | (H₂C)—4-piperidinyl(N) |
| 427 | (S)—H₂NOC⌒(CH) | C=O | (S)—⤴(CH) | (S)—indol-3-ylmethyl(CH) | H | (H₂C)—4-piperidinyl(N) |
| 428 | (R)—H₂NOC⌒(CH) | C=O | (S)—⤴(CH) | (S)—indol-3-ylmethyl(CH) | H | (H₂C)—4-piperidinyl(N) |
| 429 | (R)—indol-3-ylmethyl(CH) | C=O | (S)—⤴(CH) | (R)—H₂N⌒⌒⌒(CH) | H | (H₂C)—4-piperidinyl(N) |
| 430 | (R)—4-hydroxybenzyl(CH) | C=O | (S)—⤴(CH) | (R)—H₂N⌒⌒⌒(CH) | H | (H₂C)—4-piperidinyl(N) |
| 431 | (S)—indol-3-ylmethyl(CH) | C=O | (S)—⤴(CH) | (R)—H₂N⌒⌒⌒(CH) | H | (H₂C)—4-piperidinyl(N) |
| 432 | (S)—4-hydroxybenzyl(CH) | C=O | (S)—⤴(CH) | (R)—H₂N⌒⌒⌒(CH) | H | (H₂C)—4-piperidinyl(N) |

TABLE 2B-continued

| Cpd | R₁ | Q | R₂ | R₃ | R₄ | R₇ |
|---|---|---|---|---|---|---|
| 433 | (S)—benzyl (CH) | C=O | (S)—isobutyl (CH) | (R)—H₂N-butyl (CH) | H | (H₂C)-piperidin-4-yl (N) |
| 434 | (R)—benzyl (CH) | C=O | (S)—isobutyl (CH) | (R)—H₂N-butyl (CH) | H | (H₂C)-piperidin-4-yl (N) |
| 435 | (S)—isopropyl (CH) | C=O | (S)—isobutyl (CH) | (R)—indol-3-ylmethyl (CH) | H | (H₂C)-piperidin-4-yl (N) |
| 436 | (R)—isopropyl (CH) | C=O | (S)—isobutyl (CH) | (R)—indol-3-ylmethyl (CH) | H | (H₂C)-piperidin-4-yl (N) |
| 437 | (R)—indol-3-ylmethyl (CH) | CH₂ | (S)—isobutyl (CH) | (R)—H₂NOC-CH₂ (CH) | H | (H₂C)-3-(NR₅)benzyl |
| 438 | (R)—4-HO-benzyl (CH) | CH₂ | (S)—isobutyl (CH) | (R)—H₂NOC-CH₂ (CH) | H | (H₂C)-3-(NR₅)benzyl |
| 439 | (S)—indol-3-ylmethyl (CH) | CH₂ | (S)—isobutyl (CH) | (R)—H₂NOC-CH₂ (CH) | H | (H₂C)-3-(NR₅)benzyl |
| 440 | (S)—4-HO-benzyl (CH) | CH₂ | (S)—isobutyl (CH) | (R)—H₂NOC-CH₂ (CH) | H | (H₂C)-3-(NR₅)benzyl |
| 441 | (R)—indol-3-ylmethyl (CH) | CH₂ | (S)—isobutyl (CH) | (R)—HO-CH₂ (CH) | H | (H₂C)-3-(NR₅)benzyl |
| 442 | (R)—4-HO-benzyl (CH) | CH₂ | (S)—isobutyl (CH) | (R)—HO-CH₂ (CH) | H | (H₂C)-3-(NR₅)benzyl |

TABLE 2B-continued

| Cpd | R₁ | Q | R₂ | R₃ | R₄ | R₇ |
|---|---|---|---|---|---|---|
| 443 | (S)— 1H-indol-3-ylmethyl (CH) | CH₂ | (S)— isobutyl (CH) | (R)— HOCH₂ (CH) | H | (H₂C) 3-(NR₅)-benzyl |
| 444 | (S)— 4-hydroxybenzyl (CH) | CH₂ | (S)— isobutyl (CH) | (R)— HOCH₂ (CH) | H | (H₂C) 3-(NR₅)-benzyl |
| 445 | (S)— benzyl (CH) | CH₂ | (S)— isobutyl (CH) | (S)—H₂NOC-CH₂ (CH) | H | (H₂C) 3-(NR₅)-benzyl |
| 446 | (R)— benzyl (CH) | CH₂ | (S)— isobutyl (CH) | (R)—H₂NOC-CH₂ (CH) | H | (H₂C) 3-(NR₅)-benzyl |
| 447 | (S)—H₂N-(CH₂)₄ (CH) | CH₂ | (S)— isobutyl (CH) | (S)— benzyl (CH) | H | (H₂C) 3-(NR₅)-benzyl |
| 448 | (R)—H₂N-(CH₂)₄ (CH) | CH₂ | (S)— isobutyl (CH) | (R)— benzyl (CH) | H | (H₂C) 3-(NR₅)-benzyl |
| 449 | (S)— HOCH₂ (CH) | CH₂ | (S)— isobutyl (CH) | (S)—CH₃ | H | (H₂C) 3-(NR₅)-benzyl |
| 450 | (R)— HOCH₂ (CH) | CH₂ | (S)— isobutyl (CH) | (R)—CH₃ | H | (H₂C) 3-(NR₅)-benzyl |
| 451 | (S)—CH₃ | CH₂ | (S)— isobutyl (CH) | (S)— 4-hydroxybenzyl (CH) | H | (H₂C) 3-(NR₅)-benzyl |
| 452 | (S)—CH₃ | CH₂ | (S)— isobutyl (CH) | (R)— 4-hydroxybenzyl (CH) | H | (H₂C) 3-(NR₅)-benzyl |

TABLE 2B-continued

| Cpd | R₁ | Q | R₂ | R₃ | R₄ | R₇ |
|---|---|---|---|---|---|---|
| 453 | (R)— indol-3-ylmethyl (CH) | CH₂ | (S)— isobutyl (CH) | (S)—H₂NOC—CH₂—(CH) | H | (H₂C)—3-(NR₅)methyl-phenyl |
| 454 | (R)— 4-hydroxybenzyl (CH) | CH₂ | (S)— isobutyl (CH) | (S)—H₂NOC—CH₂—(CH) | H | (H₂C)—3-(NR₅)methyl-phenyl |
| 455 | (S)— indol-3-ylmethyl (CH) | CH₂ | (S)— isobutyl (CH) | (S)—H₂NOC—CH₂—(CH) | H | (H₂C)—3-(NR₅)methyl-phenyl |
| 456 | (S)— 4-hydroxybenzyl (CH) | CH₂ | (S)— isobutyl (CH) | (S)—H₂NOC—CH₂—(CH) | H | (H₂C)—3-(NR₅)methyl-phenyl |
| 457 | (R)— indol-3-ylmethyl (CH) | CH₂ | (S)— isobutyl (CH) | (S)— HO—CH₂—(CH) | H | (H₂C)—3-(NR₅)methyl-phenyl |
| 458 | (R)— 4-hydroxybenzyl (CH) | CH₂ | (S)— isobutyl (CH) | (S)— HO—CH₂—(CH) | H | (H₂C)—3-(NR₅)methyl-phenyl |
| 459 | (S)— indol-3-ylmethyl (CH) | CH₂ | (S)— isobutyl (CH) | (S)— HO—CH₂—(CH) | H | (H₂C)—3-(NR₅)methyl-phenyl |
| 460 | (S)— 4-hydroxybenzyl (CH) | CH₂ | (S)— isobutyl (CH) | (S)— HO—CH₂—(CH) | H | (H₂C)—3-(NR₅)methyl-phenyl |
| 461 | (S)—H₂N—(CH₂)₄—(CH) | CH₂ | (S)— isobutyl (CH) | (S)— HO—CH₂—(CH) | H | (H₂C)—3-(NR₅)methyl-phenyl |
| 462 | (R)—H₂N—(CH₂)₄—(CH) | CH₂ | (S)— isobutyl (CH) | (S)— HO—CH₂—(CH) | H | (H₂C)—3-(NR₅)methyl-phenyl |

TABLE 2B-continued

| Cpd | R₁ | Q | R₂ | R₃ | R₄ | R₇ |
|---|---|---|---|---|---|---|
| 463 | (S)—benzyl (CH) | CH₂ | (S)—isobutyl (CH) | H | Me | (H₂C)—3-(CH₂NR₅)phenyl |
| 464 | (R)—benzyl (CH) | CH₂ | (S)—isobutyl (CH) | H | Me | (H₂C)—3-(CH₂NR₅)phenyl |
| 465 | (S)—H₂N(CH₂)₃—(CH) | CH₂ | (S)—isobutyl (CH) | H | Me | (H₂C)—3-(CH₂NR₅)phenyl |
| 466 | (R)—H₂N(CH₂)₃—(CH) | CH₂ | (S)—isobutyl (CH) | H | Me | (H₂C)—3-(CH₂NR₅)phenyl |
| 467 | (S)—HOCH₂—(CH) | CH₂ | (S)—isobutyl (CH) | H | Me | (H₂C)—3-(CH₂NR₅)phenyl |
| 468 | (R)—HOCH₂—(CH) | CH₂ | (S)—isobutyl (CH) | H | Me | (H₂C)—3-(CH₂NR₅)phenyl |
| 469 | (S)—CH₃ | CH₂ | (S)—isobutyl (CH) | H | Me | (H₂C)—3-(CH₂NR₅)phenyl |
| 470 | (R)—CH₃ | CH₂ | (S)—isobutyl (CH) | H | Me | (H₂C)—3-(CH₂NR₅)phenyl |
| 471 | (R)—(1H-indol-3-yl)methyl (CH) | CH₂ | (S)—isobutyl (CH) | H | Me | (H₂C)—3-(CH₂NR₅)phenyl |
| 472 | (R)—(4-hydroxyphenyl)methyl (CH) | CH₂ | (S)—isobutyl (CH) | H | Me | (H₂C)—3-(CH₂NR₅)phenyl |

TABLE 2B-continued

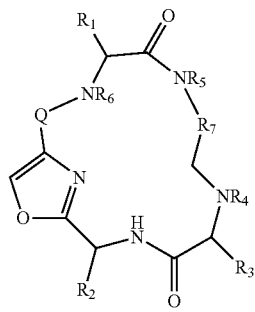

| Cpd | R₁ | Q | R₂ | R₃ | R₄ | R₇ |
|---|---|---|---|---|---|---|
| 473 | (S)— 3-(1H-indol-3-yl)ethyl (CH) | CH₂ | (S)— isobutyl (CH) | H | Me | (H₂C)— 3-(CH₂NR₅)phenyl |
| 474 | (S)— 4-hydroxybenzyl (CH) | CH₂ | (S)— isobutyl (CH) | H | Me | (H₂C)— 3-(CH₂NR₅)phenyl |
| 475 | (S)— H₂N—CH₂—(CH) | CH₂ | (S)— isobutyl (CH) | H | Me | (H₂C)— 3-(CH₂NR₅)phenyl |
| 476 | (R)— H₂N—CH₂—(CH) | CH₂ | (S)— isobutyl (CH) | H | Me | (H₂C)— 3-(CH₂NR₅)phenyl |
| 477 | (S)— H₂N-C(=NH)-NH-(CH₂)₃-(CH) | CH₂ | (S)— isobutyl (CH) | H | Me | (H₂C)— 3-(CH₂NR₅)phenyl |
| 478 | (R)— H₂N-C(=NH)-NH-(CH₂)₃-(CH) | CH₂ | (S)— isobutyl (CH) | H | Me | (H₂C)— 3-(CH₂NR₅)phenyl |
| 479 | (S)— H₂N—CH₂—(CH) | CH₂ | (S)— isobutyl (CH) | (S)—H₂NOC-CH₂-(CH) | H | (H₂C)— 3-(CH₂NR₅)phenyl |
| 480 | (R)— H₂N—CH₂—(CH) | CH₂ | (S)— isobutyl (CH) | (R)—H₂NOC-CH₂-(CH) | H | (H₂C)— 3-(CH₂NR₅)phenyl |
| 481 | (S)— H₂N-C(=NH)-NH-(CH₂)₃-(CH) | CH₂ | (S)— isobutyl (CH) | (S)— benzyl (CH) | H | (H₂C)— 3-(CH₂NR₅)phenyl |
| 482 | (R)— H₂N-C(=NH)-NH-(CH₂)₃-(CH) | CH₂ | (S)— isobutyl (CH) | (R)— benzyl (CH) | H | (H₂C)— 3-(CH₂NR₅)phenyl |

TABLE 2B-continued

| Cpd | R₁ | Q | R₂ | R₃ | R₄ | R₇ |
|-----|----|----|----|----|----|----|
| 483 | (S)—CH(CH₃)₂ (CH) | CH₂ | (S)—iBu (CH) | (S)—4-HO-C₆H₄-CH₂ (CH) | H | (H₂C)—C₆H₄-CH₂—(NR₅) |
| 484 | (R)—CH(CH₃)₂ (CH) | CH₂ | (S)—iBu (CH) | (R)—4-HO-C₆H₄-CH₂ (CH) | H | (H₂C)—C₆H₄-CH₂—(NR₅) |
| 485 | (S)—imidazolyl-CH₂ (CH) | CH₂ | (S)—iBu (CH) | (S)—H₂NOC-CH₂ (CH) | H | (H₂C)—C₆H₄-CH₂—(NR₅) |
| 486 | (R)—imidazolyl-CH₂ (CH) | CH₂ | (S)—iBu (CH) | (S)—H₂NOC-CH₂ (CH) | H | (H₂C)—C₆H₄-CH₂—(NR₅) |
| 487 | (S)—pyrrolidinyl (HC) (N) | CH₂ | (S)—iBu (CH) | (S)—H₂NOC-CH₂ (CH) | H | (H₂C)—C₆H₄-CH₂—(NR₅) |
| 488 | (R)—pyrrolidinyl (HC) (N) | CH₂ | (S)—iBu (CH) | (S)—H₂NOC-CH₂ (CH) | H | (H₂C)—C₆H₄-CH₂—(NR₅) |
| 489 | (S)—imidazolyl-CH₂ (CH) | CH₂ | (S)—iBu (CH) | (S)—HO-CH₂ (CH) | H | (H₂C)—C₆H₄-CH₂—(NR₅) |
| 490 | (R)—imidazolyl-CH₂ (CH) | CH₂ | (S)—iBu (CH) | (S)—HO-CH₂ (CH) | H | (H₂C)—C₆H₄-CH₂—(NR₅) |
| 491 | (S)—pyrrolidinyl (HC) (N) | CH₂ | (S)—iBu (CH) | (S)—HO-CH₂ (CH) | H | (H₂C)—C₆H₄-CH₂—(NR₅) |
| 492 | (R)—pyrrolidinyl (HC) (N) | CH₂ | (S)—iBu (CH) | (S)—HO-CH₂ (CH) | H | (H₂C)—C₆H₄-CH₂—(NR₅) |

TABLE 2B-continued

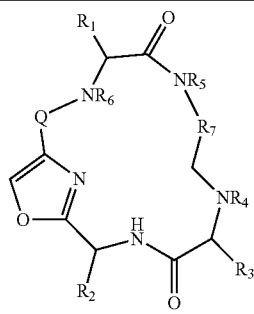

| Cpd | R₁ | Q | R₂ | R₃ | R₄ | R₇ |
|-----|----|----|----|----|----|----|
| 493 | (S)— 1H-imidazol-4-ylmethyl (CH) | CH₂ | (S)— isobutyl (CH) | (R)—H₂NOC-CH₂ (CH) | H | (H₂C)-3-(NR₅)-benzyl |
| 494 | (R)— 1H-imidazol-4-ylmethyl (CH) | CH₂ | (S)— isobutyl (CH) | (R)—H₂NOC-CH₂ (CH) | H | (H₂C)-3-(NR₅)-benzyl |
| 495 | (S)—(HC) pyrrolidin-2-yl (N) | CH₂ | (S)— isobutyl (CH) | (R)—H₂NOC-CH₂ (CH) | H | (H₂C)-3-(NR₅)-benzyl |
| 496 | (R)—(HC) pyrrolidin-2-yl (N) | CH₂ | (S)— isobutyl (CH) | (R)—H₂NOC-CH₂ (CH) | H | (H₂C)-3-(NR₅)-benzyl |
| 497 | (S)— 1H-imidazol-4-ylmethyl (CH) | CH₂ | (S)— isobutyl (CH) | (R)— HO-CH₂ (CH) | H | (H₂C)-3-(NR₅)-benzyl |
| 498 | (R)— 1H-imidazol-4-ylmethyl (CH) | CH₂ | (S)— isobutyl (CH) | (R)— HO-CH₂ (CH) | H | (H₂C)-3-(NR₅)-benzyl |
| 499 | (S)—(HC) pyrrolidin-2-yl (N) | CH₂ | (S)— isobutyl (CH) | (R)— HO-CH₂ (CH) | H | (H₂C)-3-(NR₅)-benzyl |
| 500 | (R)—(HC) pyrrolidin-2-yl (N) | CH₂ | (S)— isobutyl (CH) | (R)— HO-CH₂ (CH) | H | (H₂C)-3-(NR₅)-benzyl |
| 501 | (R)— 1H-indol-3-ylmethyl (CH) | CH₂ | (S)— isobutyl (CH) | (S)— HO-CH(CH₃) (CH) | H | (H₂C)-3-(NR₅)-benzyl |
| 502 | (R)— 4-hydroxybenzyl (CH) | CH₂ | (S)— isobutyl (CH) | (R)— HO-CH(CH₃) (CH) | H | (H₂C)-3-(NR₅)-benzyl |

TABLE 2B-continued

| Cpd | R₁ | Q | R₂ | R₃ | R₄ | R₇ |
|---|---|---|---|---|---|---|
| 503 | (S)—indol-3-yl-ethyl (CH) | CH₂ | (S)—isobutyl (CH) | (S)—HO-CH(CH₃)— (CH) | H | (H₂C)—(3-aminomethyl-phenyl) (NR₅) |
| 504 | (S)—4-hydroxybenzyl (CH) | CH₂ | (S)—isobutyl (CH) | (R)—HO-CH(CH₃)— (CH) | H | (H₂C)—(3-aminomethyl-phenyl) (NR₅) |
| 505 | (S)—H₂N-(CH₂)₄— (CH) | CH₂ | (S)—isobutyl (CH) | (S)—HO-CH(CH₃)— (CH) | H | (H₂C)—(3-aminomethyl-phenyl) (NR₅) |
| 506 | (R)—H₂N-(CH₂)₄— (CH) | CH₂ | (S)—isobutyl (CH) | (R)—HO-CH(CH₃)— (CH) | H | (H₂C)—(3-aminomethyl-phenyl) (NR₅) |
| 507 | (S)—benzyl (CH) | CH₂ | (S)—isobutyl (CH) | (S)—HO-CH(CH₃)— (CH) | H | (H₂C)—(3-aminomethyl-phenyl) (NR₅) |
| 508 | (R)—benzyl (CH) | CH₂ | (S)—isobutyl (CH) | (R)—HO-CH(CH₃)— (CH) | H | (H₂C)—(3-aminomethyl-phenyl) (NR₅) |
| 509 | (S)—H₂N-CH₂— (CH) | CH₂ | (S)—isobutyl (CH) | (S)—HO-CH(CH₃)— (CH) | H | (H₂C)—(3-aminomethyl-phenyl) (NR₅) |
| 510 | (R)—H₂N-CH₂— (CH) | CH₂ | (S)—isobutyl (CH) | (R)—HO-CH(CH₃)— (CH) | H | (H₂C)—(3-aminomethyl-phenyl) (NR₅) |
| 511 | (S)—H₂N-C(=NH)-NH-(CH₂)₃— (CH) | CH₂ | (S)—isobutyl (CH) | (S)—HO-CH(CH₃)— (CH) | H | (H₂C)—(3-aminomethyl-phenyl) (NR₅) |
| 512 | (R)—H₂N-C(=NH)-NH-(CH₂)₃— (CH) | CH₂ | (S)—isobutyl (CH) | (R)—HO-CH(CH₃)— (CH) | H | (H₂C)—(3-aminomethyl-phenyl) (NR₅) |

TABLE 2B-continued

| Cpd | R₁ | Q | R₂ | R₃ | R₄ | R₇ |
|---|---|---|---|---|---|---|
| 513 | (S)—CH(iPr) | CH₂ | (S)—iBu(CH) | (S)—CH(OH)CH₃ | H | 3-(CH₂)C₆H₄(CH₂NR₅) |
| 514 | (R)—CH(iPr) | CH₂ | (S)—iBu(CH) | (R)—CH(OH)CH₃ | H | 3-(CH₂)C₆H₄(CH₂NR₅) |
| 515 | (S)—CH(CH₂-imidazole) | CH₂ | (S)—iBu(CH) | (S)—CH(OH)CH₃ | H | 3-(CH₂)C₆H₄(CH₂NR₅) |
| 516 | (R)—CH(CH₂-imidazole) | CH₂ | (S)—iBu(CH) | (R)—CH(OH)CH₃ | H | 3-(CH₂)C₆H₄(CH₂NR₅) |
| 517 | (S)—CH(pyrrolidine) | CH₂ | (S)—iBu(CH) | (S)—CH((CH₂)₃NHC(NH)NH₂) | H | 3-(CH₂)C₆H₄(CH₂NR₅) |
| 518 | (R)—CH(pyrrolidine) | CH₂ | (S)—iBu(CH) | (S)—CH((CH₂)₃NHC(NH)NH₂) | H | 3-(CH₂)C₆H₄(CH₂NR₅) |
| 519 | (R)—CH(CH₂-indole) | CH₂ | (S)—iBu(CH) | (S)—CH((CH₂)₃NHC(NH)NH₂) | H | 3-(CH₂)C₆H₄(CH₂NR₅) |
| 520 | (R)—CH(CH₂-C₆H₄-OH) | CH₂ | (S)—iBu(CH) | (S)—CH((CH₂)₃NHC(NH)NH₂) | H | 3-(CH₂)C₆H₄(CH₂NR₅) |
| 521 | (S)—CH(CH₂-indole) | CH₂ | (S)—iBu(CH) | (S)—CH((CH₂)₃NHC(NH)NH₂) | H | 3-(CH₂)C₆H₄(CH₂NR₅) |
| 522 | (S)—CH(CH₂-C₆H₄-OH) | CH₂ | (S)—iBu(CH) | (S)—CH((CH₂)₃NHC(NH)NH₂) | H | 3-(CH₂)C₆H₄(CH₂NR₅) |

TABLE 2B-continued

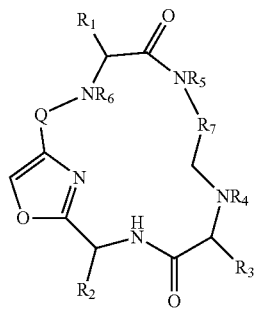

| Cpd | R₁ | Q | R₂ | R₃ | R₄ | R₇ |
|---|---|---|---|---|---|---|
| 523 | (S)—CH₂-phenyl (CH) | CH₂ | (S)—isobutyl (CH) | (S)—guanidinobutyl (CH) | H | (H₂C)-m-phenylene-CH₂(NR₅) |
| 524 | (R)—CH₂-phenyl (CH) | CH₂ | (S)—isobutyl (CH) | (S)—guanidinobutyl (CH) | H | (H₂C)-m-phenylene-CH₂(NR₅) |
| 525 | (S)—iPr (CH) | CH₂ | (S)—isobutyl (CH) | (S)—guanidinobutyl (CH) | H | (H₂C)-m-phenylene-CH₂(NR₅) |
| 526 | (R)—iPr (CH) | CH₂ | (S)—isobutyl (CH) | (S)—guanidinobutyl (CH) | H | (H₂C)-m-phenylene-CH₂(NR₅) |
| 527 | (S)—CH₃ | CH₂ | (S)—isobutyl (CH) | (S)—guanidinobutyl (CH) | H | (H₂C)-m-phenylene-CH₂(NR₅) |
| 528 | (R)—CH₃ | CH₂ | (S)—isobutyl (CH) | (S)—guanidinobutyl (CH) | H | (H₂C)-m-phenylene-CH₂(NR₅) |
| 529 | (S)—HO-CH₂(CH) | CH₂ | (S)—isobutyl (CH) | (S)—guanidinobutyl (CH) | H | (H₂C)-m-phenylene-CH₂(NR₅) |
| 530 | (R)—HO-CH₂(CH) | CH₂ | (S)—isobutyl (CH) | (S)—guanidinobutyl (CH) | H | (H₂C)-m-phenylene-CH₂(NR₅) |
| 531 | (S)—(HC)-pyrrolidinyl(N) | CH₂ | (S)—isobutyl (CH) | (R)—guanidinobutyl (CH) | H | (H₂C)-m-phenylene-CH₂(NR₅) |
| 532 | (R)—(HC)-pyrrolidinyl(N) | CH₂ | (S)—isobutyl (CH) | (R)—guanidinobutyl (CH) | H | (H₂C)-m-phenylene-CH₂(NR₅) |

TABLE 2B-continued

| Cpd | R₁ | Q | R₂ | R₃ | R₄ | R₇ |
|---|---|---|---|---|---|---|
| 533 | (R)— 3-(1H-indol-3-yl)methyl (CH) | CH₂ | (S)— isobutyl (CH) | (R)— 3-guanidinopropyl (CH) | H | (H₂C)— 3-(NR₅)methylphenyl |
| 534 | (R)— 4-hydroxybenzyl (CH) | CH₂ | (S)— isobutyl (CH) | (R)— 3-guanidinopropyl (CH) | H | (H₂C)— 3-(NR₅)methylphenyl |
| 535 | (S)— 3-(1H-indol-3-yl)methyl (CH) | CH₂ | (S)— isobutyl (CH) | (R)— 3-guanidinopropyl (CH) | H | (H₂C)— 3-(NR₅)methylphenyl |
| 536 | (S)— 4-hydroxybenzyl (CH) | CH₂ | (S)— isobutyl (CH) | (R)— 3-guanidinopropyl (CH) | H | (H₂C)— 3-(NR₅)methylphenyl |
| 537 | (S)— benzyl (CH) | CH₂ | (S)— isobutyl (CH) | (R)— 3-guanidinopropyl (CH) | H | (H₂C)— 3-(NR₅)methylphenyl |
| 538 | (R)— benzyl (CH) | CH₂ | (S)— isobutyl (CH) | (R)— 3-guanidinopropyl (CH) | H | (H₂C)— 3-(NR₅)methylphenyl |
| 539 | (S)— isopropyl (CH) | CH₂ | (S)— isobutyl (CH) | (R)— 3-guanidinopropyl (CH) | H | (H₂C)— 3-(NR₅)methylphenyl |
| 540 | (R)— isopropyl (CH) | CH₂ | (S)— isobutyl (CH) | (R)— 3-guanidinopropyl (CH) | H | (H₂C)— 3-(NR₅)methylphenyl |
| 541 | (S)—CH₃ | CH₂ | (S)— isobutyl (CH) | (R)— 3-guanidinopropyl (CH) | H | (H₂C)— 3-(NR₅)methylphenyl |
| 542 | (R)—CH₃ | CH₂ | (S)— isobutyl (CH) | (R)— 3-guanidinopropyl (CH) | H | (H₂C)— 3-(NR₅)methylphenyl |

TABLE 2B-continued

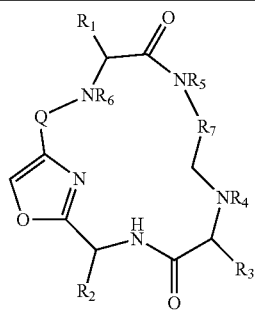

| Cpd | R₁ | Q | R₂ | R₃ | R₄ | R₇ |
|---|---|---|---|---|---|---|
| 543 | (S)—HOCH₂—(CH) | CH₂ | (S)—iBu—(CH) | (R)—H₂N-C(=NH)-NH-(CH₂)₃—(CH) | H | (H₂C)-m-C₆H₄-CH₂-(NR₅) |
| 544 | (R)—HOCH₂—(CH) | CH₂ | (S)—iBu—(CH) | (R)—H₂N-C(=NH)-NH-(CH₂)₃—(CH) | H | (H₂C)-m-C₆H₄-CH₂-(NR₅) |
| 545 | (S)—PhCH₂—(CH) | CH₂ | (S)—iBu—(CH) | (S)—H₂NOC-CH₂—(CH) | H | (H₂C)-4-piperidinyl(N) |
| 546 | (R)—PhCH₂—(CH) | CH₂ | (S)—iBu—(CH) | (R)—H₂NOC-CH₂—(CH) | H | (H₂C)-4-piperidinyl(N) |
| 547 | (S)—H₂N(CH₂)₄—(CH) | CH₂ | (S)—iBu—(CH) | (S)—PhCH₂—(CH) | H | (H₂C)-4-piperidinyl(N) |
| 548 | (S)—HOCH₂—(CH) | CH₂ | (S)—iBu—(CH) | (S)—CH₃ | H | (H₂C)-4-piperidinyl(N) |
| 549 | (R)—HOCH₂—(CH) | CH₂ | (S)—iBu—(CH) | (R)—CH₃ | H | (H₂C)-4-piperidinyl(N) |
| 550 | (S)—CH₃ | CH₂ | (S)—iBu—(CH) | (S)—4-HO-C₆H₄-CH₂—(CH) | H | (H₂C)-4-piperidinyl(N) |
| 551 | (R)—CH₃ | CH₂ | (S)—iBu—(CH) | (R)—4-HO-C₆H₄-CH₂—(CH) | H | (H₂C)-4-piperidinyl(N) |
| 552 | (R)—3-indolyl-CH₂—(CH) | CH₂ | (S)—iBu—(CH) | (S)—H₂NOC-CH₂—(CH) | H | (H₂C)-4-piperidinyl(N) |
| 553 | (R)—4-HO-C₆H₄-CH₂—(CH) | CH₂ | (S)—iBu—(CH) | (S)—H₂NOC-CH₂—(CH) | H | (H₂C)-4-piperidinyl(N) |
| 554 | (S)—3-indolyl-CH₂—(CH) | CH₂ | (S)—iBu—(CH) | (S)—H₂NOC-CH₂—(CH) | H | (H₂C)-4-piperidinyl(N) |
| 555 | (S)—4-HO-C₆H₄-CH₂—(CH) | CH₂ | (S)—iBu—(CH) | (S)—H₂NOC-CH₂—(CH) | H | (H₂C)-4-piperidinyl(N) |

TABLE 2B-continued

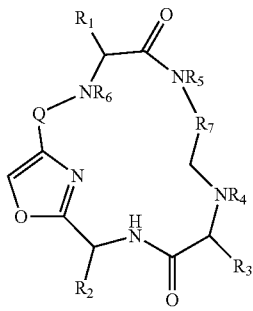

| Cpd | R₁ | Q | R₂ | R₃ | R₄ | R₇ |
|---|---|---|---|---|---|---|
| 556 | (R)—4-hydroxybenzyl(CH) | CH₂ | (S)—isobutyl(CH) | (S)—HOCH₂(CH) | H | (H₂C)-4-piperidinyl(N) |
| 557 | (S)—4-hydroxybenzyl(CH) | CH₂ | (S)—isobutyl(CH) | (S)—HOCH₂(CH) | H | (H₂C)-4-piperidinyl(N) |
| 558 | (S)—H₂N(CH₂)₄(CH) | CH₂ | (S)—isobutyl(CH) | (S)—HOCH₂(CH) | H | (H₂C)-4-piperidinyl(N) |
| 559 | (R)—H₂N(CH₂)₄(CH) | CH₂ | (S)—isobutyl(CH) | (S)—HOCH₂(CH) | H | (H₂C)-4-piperidinyl(N) |
| 560 | (S)—H₂NCH₂(CH) | CH₂ | (S)—isobutyl(CH) | (S)—H₂NOCCH₂(CH) | H | (H₂C)-4-piperidinyl(N) |
| 561 | (R)—H₂NCH₂(CH) | CH₂ | (S)—isobutyl(CH) | (R)—H₂NOCCH₂(CH) | H | (H₂C)-4-piperidinyl(N) |
| 562 | (S)—H₂N-C(=NH)-NH-(CH₂)₃(CH) | CH₂ | (S)—isobutyl(CH) | (S)—benzyl(CH) | H | (H₂C)-4-piperidinyl(N) |
| 563 | (R)—H₂N-C(=NH)-NH-(CH₂)₃(CH) | CH₂ | (S)—isobutyl(CH) | (R)—benzyl(CH) | H | (H₂C)-4-piperidinyl(N) |
| 564 | (S)—isopropyl(CH) | CH₂ | (S)—isobutyl(CH) | (S)—4-hydroxybenzyl(CH) | H | (H₂C)-4-piperidinyl(N) |
| 565 | (R)—isopropyl(CH) | CH₂ | (S)—isobutyl(CH) | (R)—4-hydroxybenzyl(CH) | H | (H₂C)-4-piperidinyl(N) |
| 566 | (S)—imidazol-4-ylmethyl(CH) | CH₂ | (S)—isobutyl(CH) | (S)—H₂NOCCH₂(CH) | H | (H₂C)-4-piperidinyl(N) |
| 567 | (R)—imidazol-4-ylmethyl(CH) | CH₂ | (S)—isobutyl(CH) | (S)—H₂NOCCH₂(CH) | H | (H₂C)-4-piperidinyl(N) |
| 568 | (S)—CH₃ | CH₂ | (S)—isobutyl(CH) | (S)—H₂NOCCH₂(CH) | H | (H₂C)-4-piperidinyl(N) |

US 10,981,931 B2

TABLE 2B-continued

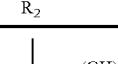

| Cpd | R₁ | Q | R₂ | R₃ | R₄ | R₇ |
|---|---|---|---|---|---|---|
| 569 | (R)—CH₃ | CH₂ | (S)—isobutyl (CH) | (S)—H₂NOC-CH₂-(CH) | H | (H₂C)-piperidinyl(N) |
| 570 | (S)—CH₂-(4-imidazolyl)(CH) | CH₂ | (S)—isobutyl (CH) | (S)—HO-CH₂-(CH) | H | (H₂C)-piperidinyl(N) |
| 571 | (R)—CH₂-(4-imidazolyl)(CH) | CH₂ | (S)—isobutyl (CH) | (S)—HO-CH₂-(CH) | H | (H₂C)-piperidinyl(N) |
| 572 | (S)—CH₃ | CH₂ | (S)—isobutyl (CH) | (S)—HO-CH₂-(CH) | H | (H₂C)-piperidinyl(N) |
| 573 | (R)—CH₃ | CH₂ | (S)—isobutyl (CH) | (S)—HO-CH₂-(CH) | H | (H₂C)-piperidinyl(N) |
| 574 | (S)—CH₂-(4-imidazolyl)(CH) | CH₂ | (S)—isobutyl (CH) | (R)—H₂NOC-CH₂-(CH) | H | (H₂C)-piperidinyl(N) |
| 575 | (R)—CH₂-(4-imidazolyl)(CH) | CH₂ | (S)—isobutyl (CH) | (R)—H₂NOC-CH₂-(CH) | H | (H₂C)-piperidinyl(N) |
| 576 | (S)—CH₃ | CH₂ | (S)—isobutyl (CH) | (R)—H₂NOC-CH₂-(CH) | H | (H₂C)-piperidinyl(N) |
| 577 | (R)—CH₃ | CH₂ | (S)—isobutyl (CH) | (R)—H₂NOC-CH₂-(CH) | H | (H₂C)-piperidinyl(N) |
| 578 | (S)—CH₂-(4-imidazolyl)(CH) | CH₂ | (S)—isobutyl (CH) | (R)—HO-CH₂-(CH) | H | (H₂C)-piperidinyl(N) |
| 579 | (R)—CH₂-(4-imidazolyl)(CH) | CH₂ | (S)—isobutyl (CH) | (R)—HO-CH₂-(CH) | H | (H₂C)-piperidinyl(N) |
| 580 | (S)—CH₃ | CH₂ | (S)—isobutyl (CH) | (R)—HO-CH₂-(CH) | H | (H₂C)-piperidinyl(N) |

TABLE 2B-continued

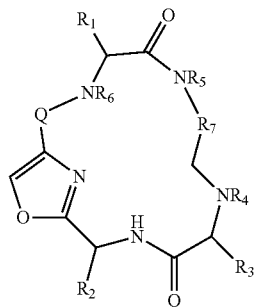

| Cpd | R₁ | Q | R₂ | R₃ | R₄ | R₇ |
|---|---|---|---|---|---|---|
| 581 | (R)—CH₃ | CH₂ | (S)—iBu (CH) | (R)—HOCH₂ (CH) | H | (H₂C)-piperidine(N) |
| 582 | (R)—CH₂-indole (CH) | CH₂ | (S)—iBu (CH) | (S)—HO-CH(CH₃) (CH) | H | (H₂C)-piperidine(N) |
| 583 | (R)—CH₂-C₆H₄-OH (CH) | CH₂ | (S)—iBu (CH) | (R)—HO-CH(CH₃) (CH) | H | (H₂C)-piperidine(N) |
| 584 | (S)—CH₂-indole (CH) | CH₂ | (S)—iBu (CH) | (S)—HO-CH(CH₃) (CH) | H | (H₂C)-piperidine(N) |
| 585 | (S)—CH₂-C₆H₄-OH (CH) | CH₂ | (S)—iBu (CH) | (R)—HO-CH(CH₃) (CH) | H | (H₂C)-piperidine(N) |
| 586 | (S)—H₂N-(CH₂)₄- (CH) | CH₂ | (S)—iBu (CH) | (S)—HO-CH(CH₃) (CH) | H | (H₂C)-piperidine(N) |
| 587 | (R)—H₂N-(CH₂)₄- (CH) | CH₂ | (S)—iBu (CH) | (R)—HO-CH(CH₃) (CH) | H | (H₂C)-piperidine(N) |
| 588 | (S)—CH₂-C₆H₅ (CH) | CH₂ | (S)—iBu (CH) | (S)—HO-CH(CH₃) (CH) | H | (H₂C)-piperidine(N) |
| 589 | (R)—CH₂-C₆H₅ (CH) | CH₂ | (S)—iBu (CH) | (R)—HO-CH(CH₃) (CH) | H | (H₂C)-piperidine(N) |
| 590 | (S)—H₂N-CH₂- (CH) | CH₂ | (S)—iBu (CH) | (S)—HO-CH(CH₃) (CH) | H | (H₂C)-piperidine(N) |
| 591 | (R)—H₂N-CH₂- (CH) | CH₂ | (S)—iBu (CH) | (R)—HO-CH(CH₃) (CH) | H | (H₂C)-piperidine(N) |
| 592 | (S)—H₂N-C(=NH)-NH-(CH₂)₃- (CH) | CH₂ | (S)—iBu (CH) | (S)—HO-CH(CH₃) (CH) | H | (H₂C)-piperidine(N) |
| 593 | (R)—H₂N-C(=NH)-NH-(CH₂)₃- (CH) | CH₂ | (S)—iBu (CH) | (R)—HO-CH(CH₃) (CH) | H | (H₂C)-piperidine(N) |

TABLE 2B-continued

| Cpd | R₁ | Q | R₂ | R₃ | R₄ | R₇ |
|---|---|---|---|---|---|---|
| 594 | (S)—$\diagup$(CH) (isopropyl) | CH₂ | (S)—$\diagup\diagdown$(CH) (isobutyl) | (S)— HO$\diagup$(CH) | H | (H₂C)—piperidine(N) |
| 595 | (R)—$\diagup$(CH) (isopropyl) | CH₂ | (S)—$\diagup\diagdown$(CH) (isobutyl) | (R)— HO$\diagup$(CH) | H | (H₂C)—piperidine(N) |
| 596 | (S)—imidazole-(CH) | CH₂ | (S)—$\diagup\diagdown$(CH) (isobutyl) | (S)— HO$\diagup$(CH) | H | (H₂C)—piperidine(N) |
| 597 | (R)—imidazole-(CH) | CH₂ | (S)—$\diagup\diagdown$(CH) (isobutyl) | (R)— HO$\diagup$(CH) | H | (H₂C)—piperidine(N) |

For all compounds $R_5$=H and $R_6$=H, except for those compounds in which Fmoc-Pro or Fmoc-D-Pro is BB₁ wherein R₁ and (N)R₆ form a cyclic five-membered ring, including the nitrogen atom, as shown for R₁ in Table 2B and those compounds in which BB₄ is Fmoc-S35 wherein (N)R₅ and R₇ are part of a six-membered ring, including the nitrogen atom, as shown for R₇ in Table 2B.

Example 4

Synthesis of a Representative Library of Macrocyclic Compounds of Formula (Ia)

The synthetic scheme presented in Scheme 4 was followed to prepare the library of macrocyclic compounds 601-948 on solid support. The first amino acid building block amino acid (BB₁) was loaded onto the resin (Method 1D), then, after removal of the Fmoc protection (Method 1F), the second amino acid building block (BB₂) attached through amide bond formation (Method 1G). The Fmoc group was cleaved (Method 1F), then the oxazole building block (BB₃) attached by reductive amination (Method 1J) or amide coupling (Method 1G) to extend the intermediate chain. After deprotection (Method 1F), the final building block was then added using reductive amination (Method 1I or 1J) to complete the pre-cyclization intermediate. Deprotection of the N-terminal Fmoc group (Method 1F), cleavage from the resin (Method 1Q), macrocyclization (Method 1R) and removal of the side chain protecting groups (Method 1S) followed by evaporation under reduced pressure gave the crude macrocycle. The results after purification by preparative HPLC (Method 2B) are included in Table 3A, including, for each compound, the amounts obtained, the HPLC purity and the confirmation of identity by MS. The macrocyclic structures are provided in Table 3B.

TABLE 3A

| Cpd | BB₁ | BB₂ | BB₃ | BB₄ | Wt (mg)¹ | Purity² | MS (M + H) |
|---|---|---|---|---|---|---|---|
| 601 | Fmoc-D-Trp(Boc) | Fmoc-Ala | Fmoc-OX-1 | Fmoc-S37 | 4.4 | 100 | 557 |
| 602 | Fmoc-D-Tyr(But) | Fmoc-Ala | Fmoc-OX-1 | Fmoc-S37 | 4.2 | 100 | 534 |
| 603 | Fmoc-Trp(Boc) | Fmoc-Ala | Fmoc-OX-1 | Fmoc-S37 | 7.0 | 97 | 557 |
| 604 | Fmoc-Tyr(But) | Fmoc-Ala | Fmoc-OX-1 | Fmoc-S37 | 6.6 | 100 | 534 |
| 605 | Fmoc-D-Trp(Boc) | Fmoc-Asn(Trt) | Fmoc-OX-1 | Fmoc-S37 | 11.1 | 100 | 600 |
| 606 | Fmoc-D-Tyr(But) | Fmoc-Asn(Trt) | Fmoc-OX-1 | Fmoc-S37 | 16.8 | 100 | 577 |
| 607 | Fmoc-Trp(Boc) | Fmoc-Asn(Trt) | Fmoc-OX-1 | Fmoc-S37 | 19.0 | 100 | 600 |
| 608 | Fmoc-Tyr(But) | Fmoc-Asn(Trt) | Fmoc-OX-1 | Fmoc-S37 | 14.0 | 100 | 577 |
| 609 | Fmoc-D-Trp(Boc) | Fmoc-D-Ala | Fmoc-OX-1 | Fmoc-S37 | 7.7 | 100 | 557 |
| 610 | Fmoc-D-Tyr(But) | Fmoc-D-Ala | Fmoc-OX-1 | Fmoc-S37 | 3.3 | 100 | 534 |
| 611 | Fmoc-Trp(Boc) | Fmoc-D-Ala | Fmoc-OX-1 | Fmoc-S37 | 7.9 | 95 | 557 |
| 612 | Fmoc-Tyr(But) | Fmoc-D-Ala | Fmoc-OX-1 | Fmoc-S37 | 3.0 | 100 | 534 |
| 613 | Fmoc-D-Trp(Boc) | Fmoc-Dap(Boc) | Fmoc-OX-1 | Fmoc-S37 | 5.0 | 100 | 572 |

TABLE 3A-continued

| Cpd | BB$_1$ | BB$_2$ | BB$_3$ | BB$_4$ | Wt (mg)[1] | Purity[2] | MS (M + H) |
|---|---|---|---|---|---|---|---|
| 614 | Fmoc-D-Tyr(But) | Fmoc-Dap(Boc) | Fmoc-OX-1 | Fmoc-S37 | 4.1 | 100 | 549 |
| 615 | Fmoc-Trp(Boc) | Fmoc-Dap(Boc) | Fmoc-OX-1 | Fmoc-S37 | 6.1 | 100 | 572 |
| 616 | Fmoc-Tyr(But) | Fmoc-Dap(Boc) | Fmoc-OX-1 | Fmoc-S37 | 4.9 | 100 | 549 |
| 617 | Fmoc-D-Trp(Boc) | Fmoc-D-Asn(Trt) | Fmoc-OX-1 | Fmoc-S37 | 16.3 | 100 | 600 |
| 618 | Fmoc-D-Tyr(But) | Fmoc-D-Asn(Trt) | Fmoc-OX-1 | Fmoc-S37 | 11.7 | 91 | 577 |
| 619 | Fmoc-Trp(Boc) | Fmoc-D-Asn(Trt) | Fmoc-OX-1 | Fmoc-S37 | 13.6 | 100 | 600 |
| 620 | Fmoc-Tyr(But) | Fmoc-D-Asn(Trt) | Fmoc-OX-1 | Fmoc-S37 | 11.0 | 100 | 577 |
| 621 | Fmoc-D-Trp(Boc) | Fmoc-D-Dap(Boc) | Fmoc-OX-1 | Fmoc-S37 | 7.3 | 100 | 572 |
| 622 | Fmoc-D-Tyr(But) | Fmoc-D-Dap(Boc) | Fmoc-OX-1 | Fmoc-S37 | 5.5 | 100 | 549 |
| 623 | Fmoc-Trp(Boc) | Fmoc-D-Dap(Boc) | Fmoc-OX-1 | Fmoc-S37 | 7.0 | 100 | 572 |
| 624 | Fmoc-Tyr(But) | Fmoc-D-Dap(Boc) | Fmoc-OX-1 | Fmoc-S37 | 7.0 | 100 | 549 |
| 625 | Fmoc-D-Trp(Boc) | Fmoc-D-Gln(Trt) | Fmoc-OX-1 | Fmoc-S37 | 6.7 | 100 | 614 |
| 626 | Fmoc-D-Tyr(But) | Fmoc-D-Gln(Trt) | Fmoc-OX-1 | Fmoc-S37 | 1.7 | 100 | 591 |
| 627 | Fmoc-Trp(Boc) | Fmoc-D-Gln(Trt) | Fmoc-OX-1 | Fmoc-S37 | 10.7 | 100 | 614 |
| 628 | Fmoc-Tyr(But) | Fmoc-D-Gln(Trt) | Fmoc-OX-1 | Fmoc-S37 | 13.6 | 100 | 591 |
| 629 | Fmoc-D-Trp(Boc) | Fmoc-D-Glu(OBut) | Fmoc-OX-1 | Fmoc-S37 | 5.8 | 100 | 615 |
| 630 | Fmoc-D-Tyr(But) | Fmoc-D-Glu(OBut) | Fmoc-OX-1 | Fmoc-S37 | 7.3 | 100 | 592 |
| 631 | Fmoc-Trp(Boc) | Fmoc-D-Glu(OBut) | Fmoc-OX-1 | Fmoc-S37 | 8.5 | 100 | 615 |
| 632 | Fmoc-Tyr(But) | Fmoc-D-Glu(OBut) | Fmoc-OX-1 | Fmoc-S37 | 11.0 | 100 | 592 |
| 633 | Fmoc-D-Trp(Boc) | Fmoc-D-His(Trt) | Fmoc-OX-1 | Fmoc-S37 | 5.4 | 100 | 623 |
| 634 | Fmoc-D-Tyr(But) | Fmoc-D-His(Trt) | Fmoc-OX-1 | Fmoc-S37 | 5.8 | 100 | 600 |
| 635 | Fmoc-Trp(Boc) | Fmoc-D-His(Trt) | Fmoc-OX-1 | Fmoc-S37 | 5.6 | 100 | 623 |
| 636 | Fmoc-Tyr(But) | Fmoc-D-His(Trt) | Fmoc-OX-1 | Fmoc-S37 | 5.9 | 100 | 600 |
| 637 | Fmoc-D-Trp(Boc) | Fmoc-D-Ile | Fmoc-OX-1 | Fmoc-S37 | 6.0 | 99 | 599 |
| 638 | Fmoc-D-Tyr(But) | Fmoc-D-Ile | Fmoc-OX-1 | Fmoc-S37 | 6.5 | 100 | 576 |
| 639 | Fmoc-Trp(Boc) | Fmoc-D-Ile | Fmoc-OX-1 | Fmoc-S37 | 11.2 | 94 | 599 |
| 640 | Fmoc-Tyr(But) | Fmoc-D-Ile | Fmoc-OX-1 | Fmoc-S37 | 7.8 | 100 | 576 |
| 641 | Fmoc-D-Trp(Boc) | Fmoc-D-Lys(Boc) | Fmoc-OX-1 | Fmoc-S37 | 5.0 | 100 | 614 |
| 642 | Fmoc-D-Tyr(But) | Fmoc-D-Lys(Boc) | Fmoc-OX-1 | Fmoc-S37 | 6.0 | 100 | 591 |
| 643 | Fmoc-Trp(Boc) | Fmoc-D-Lys(Boc) | Fmoc-OX-1 | Fmoc-S37 | 6.4 | 100 | 614 |
| 644 | Fmoc-Tyr(But) | Fmoc-D-Lys(Boc) | Fmoc-OX-1 | Fmoc-S37 | 16.0 | 100 | 591 |
| 645 | Fmoc-D-Trp(Boc) | Fmoc-D-Nva | Fmoc-OX-1 | Fmoc-S37 | 5.6 | 100 | 585 |
| 646 | Fmoc-D-Tyr(But) | Fmoc-D-Nva | Fmoc-OX-1 | Fmoc-S37 | 6.1 | 100 | 562 |
| 647 | Fmoc-Trp(Boc) | Fmoc-D-Nva | Fmoc-OX-1 | Fmoc-S37 | 6.1 | 100 | 585 |
| 648 | Fmoc-Tyr(But) | Fmoc-D-Nva | Fmoc-OX-1 | Fmoc-S31 | 1.4 | 100 | 500 |
| 649 | Fmoc-D-Trp(Boc) | Fmoc-D-Phe | Fmoc-OX-1 | Fmoc-S37 | 12.1 | 100 | 633 |
| 650 | Fmoc-D-Tyr(But) | Fmoc-D-Phe | Fmoc-OX-1 | Fmoc-S37 | 9.0 | 100 | 610 |
| 651 | Fmoc-Trp(Boc) | Fmoc-D-Phe | Fmoc-OX-1 | Fmoc-S37 | 8.8 | 100 | 633 |
| 652 | Fmoc-Tyr(But) | Fmoc-D-Phe | Fmoc-OX-1 | Fmoc-S37 | 10.1 | 100 | 610 |
| 653 | Fmoc-D-Trp(Boc) | Fmoc-D-Pro | Fmoc-OX-1 | Fmoc-S37 | 5.5 | 100 | 583 |
| 654 | Fmoc-D-Tyr(But) | Fmoc-D-Pro | Fmoc-OX-1 | Fmoc-S37 | 4.3 | 100 | 560 |
| 655 | Fmoc-Trp(Boc) | Fmoc-D-Pro | Fmoc-OX-1 | Fmoc-S37 | 7.2 | 96 | 583 |
| 656 | Fmoc-Tyr(But) | Fmoc-D-Pro | Fmoc-OX-1 | Fmoc-S37 | 6.3 | 100 | 560 |
| 657 | Fmoc-D-Trp(Boc) | Fmoc-D-Ser(But) | Fmoc-OX-1 | Fmoc-S37 | 8.0 | 100 | 573 |
| 658 | Fmoc-D-Tyr(But) | Fmoc-D-Ser(But) | Fmoc-OX-1 | Fmoc-S37 | 6.0 | 100 | 550 |
| 659 | Fmoc-Trp(Boc) | Fmoc-D-Ser(But) | Fmoc-OX-1 | Fmoc-S37 | 6.1 | 100 | 573 |
| 660 | Fmoc-Tyr(But) | Fmoc-D-Ser(But) | Fmoc-OX-1 | Fmoc-S37 | 6.9 | 100 | 550 |
| 661 | Fmoc-Ala | Fmoc-D-Trp(Boc) | Fmoc-OX-1 | Fmoc-S37 | 9.1 | 100 | 557 |
| 662 | Fmoc-Asn(Trt) | Fmoc-D-Trp(Boc) | Fmoc-OX-1 | Fmoc-S37 | 17.3 | 100 | 600 |
| 663 | Fmoc-Asp(OBut) | Fmoc-D-Trp(Boc) | Fmoc-OX-1 | Fmoc-S37 | 8.1 | 100 | 601 |
| 664 | Fmoc-D-Ala | Fmoc-D-Trp(Boc) | Fmoc-OX-1 | Fmoc-S37 | 9.7 | 100 | 557 |
| 665 | Fmoc-D-Asn(Trt) | Fmoc-D-Trp(Boc) | Fmoc-OX-1 | Fmoc-S37 | 17.4 | 100 | 600 |
| 666 | Fmoc-D-Asp(OBut) | Fmoc-D-Trp(Boc) | Fmoc-OX-1 | Fmoc-S37 | 8.9 | 100 | 601 |
| 667 | Fmoc-D-His(Trt) | Fmoc-D-Trp(Boc) | Fmoc-OX-1 | Fmoc-S37 | 0.3 | 100 | 623 |
| 668 | Fmoc-D-Lys(Boc) | Fmoc-D-Trp(Boc) | Fmoc-OX-1 | Fmoc-S37 | 7.7 | 100 | 614 |
| 669 | Fmoc-D-Nva | Fmoc-D-Trp(Boc) | Fmoc-OX-1 | Fmoc-S37 | 9.6 | 100 | 585 |
| 670 | Fmoc-D-Phe | Fmoc-D-Trp(Boc) | Fmoc-OX-1 | Fmoc-S37 | 10.0 | 100 | 633 |
| 671 | Fmoc-D-Pro | Fmoc-D-Trp(Boc) | Fmoc-OX-1 | Fmoc-S37 | 5.5 | 100 | 583 |
| 672 | Fmoc-D-Ser(But) | Fmoc-D-Trp(Boc) | Fmoc-OX-1 | Fmoc-S37 | 8.9 | 100 | 573 |
| 673 | Fmoc-D-Trp(Boc) | Fmoc-D-Trp(Boc) | Fmoc-OX-1 | Fmoc-S37 | 9.6 | 100 | 672 |
| 674 | Fmoc-D-Tyr(But) | Fmoc-D-Trp(Boc) | Fmoc-OX-1 | Fmoc-S37 | 9.0 | 100 | 649 |
| 675 | Fmoc-D-Val | Fmoc-D-Trp(Boc) | Fmoc-OX-1 | Fmoc-S37 | 8.5 | 100 | 585 |
| 676 | Fmoc-His(Trt) | Fmoc-D-Trp(Boc) | Fmoc-OX-1 | Fmoc-S37 | 9.4 | 100 | 623 |
| 677 | Fmoc-Lys(Boc) | Fmoc-D-Trp(Boc) | Fmoc-OX-1 | Fmoc-S37 | 11.8 | 100 | 614 |
| 678 | Fmoc-Nva | Fmoc-D-Trp(Boc) | Fmoc-OX-1 | Fmoc-S37 | 11.0 | 100 | 585 |
| 679 | Fmoc-Phe | Fmoc-D-Trp(Boc) | Fmoc-OX-1 | Fmoc-S37 | 13.2 | 98 | 633 |
| 680 | Fmoc-Pro | Fmoc-D-Trp(Boc) | Fmoc-OX-1 | Fmoc-S37 | 6.7 | 100 | 583 |
| 681 | Fmoc-Ser(But) | Fmoc-D-Trp(Boc) | Fmoc-OX-1 | Fmoc-S37 | 13.4 | 100 | 573 |
| 682 | Fmoc-Trp(Boc) | Fmoc-D-Trp(Boc) | Fmoc-OX-1 | Fmoc-S37 | 12.6 | 100 | 672 |
| 683 | Fmoc-Tyr(But) | Fmoc-D-Trp(Boc) | Fmoc-OX-1 | Fmoc-S37 | 11.3 | 100 | 649 |
| 684 | Fmoc-Val | Fmoc-D-Trp(Boc) | Fmoc-OX-1 | Fmoc-S37 | 10.5 | 100 | 585 |
| 685 | Fmoc-Ala | Fmoc-D-Tyr(But) | Fmoc-OX-1 | Fmoc-S37 | 9.8 | 100 | 534 |
| 686 | Fmoc-Asn(Trt) | Fmoc-D-Tyr(But) | Fmoc-OX-1 | Fmoc-S37 | 18.8 | 100 | 577 |
| 687 | Fmoc-Asp(OBut) | Fmoc-D-Tyr(But) | Fmoc-OX-1 | Fmoc-S37 | 8.8 | 100 | 578 |
| 688 | Fmoc-D-Ala | Fmoc-D-Tyr(But) | Fmoc-OX-1 | Fmoc-S37 | 9.3 | 100 | 534 |
| 689 | Fmoc-D-Asn(Trt) | Fmoc-D-Tyr(But) | Fmoc-OX-1 | Fmoc-S37 | 16.3 | 100 | 577 |
| 690 | Fmoc-D-Asp(OBut) | Fmoc-D-Tyr(But) | Fmoc-OX-1 | Fmoc-S37 | 11.4 | 100 | 578 |
| 691 | Fmoc-D-His(Trt) | Fmoc-D-Tyr(But) | Fmoc-OX-1 | Fmoc-S37 | 8.9 | 100 | 600 |

TABLE 3A-continued

| Cpd | BB$_1$ | BB$_2$ | BB$_3$ | BB$_4$ | Wt (mg)[1] | Purity[2] | MS (M + H) |
|---|---|---|---|---|---|---|---|
| 692 | Fmoc-D-Lys(Boc) | Fmoc-D-Tyr(But) | Fmoc-OX-1 | Fmoc-S37 | 10.3 | 100 | 591 |
| 693 | Fmoc-D-Nva | Fmoc-D-Tyr(But) | Fmoc-OX-1 | Fmoc-S37 | 6.2 | 100 | 562 |
| 694 | Fmoc-D-Phe | Fmoc-D-Tyr(But) | Fmoc-OX-1 | Fmoc-S37 | 8.5 | 100 | 610 |
| 695 | Fmoc-D-Pro | Fmoc-D-Tyr(But) | Fmoc-OX-1 | Fmoc-S37 | 5.3 | 100 | 560 |
| 696 | Fmoc-D-Ser(But) | Fmoc-D-Tyr(But) | Fmoc-OX-1 | Fmoc-S37 | 11.5 | 100 | 550 |
| 697 | Fmoc-D-Trp(Boc) | Fmoc-D-Tyr(But) | Fmoc-OX-1 | Fmoc-S37 | 8.5 | 100 | 649 |
| 698 | Fmoc-D-Tyr(But) | Fmoc-D-Tyr(But) | Fmoc-OX-1 | Fmoc-S37 | 7.4 | 100 | 626 |
| 699 | Fmoc-D-Val | Fmoc-D-Tyr(But) | Fmoc-OX-1 | Fmoc-S37 | 6.2 | 100 | 562 |
| 700 | Fmoc-His(Trt) | Fmoc-D-Tyr(But) | Fmoc-OX-1 | Fmoc-S37 | 9.5 | 100 | 600 |
| 701 | Fmoc-Lys(Boc) | Fmoc-D-Tyr(But) | Fmoc-OX-1 | Fmoc-S37 | 2.4 | 100 | 591 |
| 702 | Fmoc-Nva | Fmoc-D-Tyr(But) | Fmoc-OX-1 | Fmoc-S37 | 10.4 | 100 | 562 |
| 703 | Fmoc-Phe | Fmoc-D-Tyr(But) | Fmoc-OX-1 | Fmoc-S37 | 8.3 | 100 | 610 |
| 704 | Fmoc-Pro | Fmoc-D-Tyr(But) | Fmoc-OX-1 | Fmoc-S37 | 5.2 | 100 | 560 |
| 705 | Fmoc-Ser(But) | Fmoc-D-Tyr(But) | Fmoc-OX-1 | Fmoc-S37 | 11.6 | 100 | 550 |
| 706 | Fmoc-Trp(Boc) | Fmoc-D-Tyr(But) | Fmoc-OX-1 | Fmoc-S37 | 6.9 | 100 | 649 |
| 707 | Fmoc-Tyr(But) | Fmoc-D-Tyr(But) | Fmoc-OX-1 | Fmoc-S37 | 12.3 | 100 | 626 |
| 708 | Fmoc-Val | Fmoc-D-Tyr(But) | Fmoc-OX-1 | Fmoc-S37 | 10.0 | 100 | 562 |
| 709 | Fmoc-D-Trp(Boc) | Fmoc-D-Val | Fmoc-OX-1 | Fmoc-S37 | 10.6 | 100 | 585 |
| 710 | Fmoc-D-Tyr(But) | Fmoc-D-Val | Fmoc-OX-1 | Fmoc-S37 | 7.1 | 100 | 562 |
| 711 | Fmoc-Trp(Boc) | Fmoc-D-Val | Fmoc-OX-1 | Fmoc-S37 | 8.8 | 92 | 585 |
| 712 | Fmoc-Tyr(But) | Fmoc-D-Val | Fmoc-OX-1 | Fmoc-S37 | 8.0 | 100 | 562 |
| 713 | Fmoc-D-Trp(Boc) | Fmoc-Glu(OBut) | Fmoc-OX-1 | Fmoc-S37 | 6.7 | 100 | 615 |
| 714 | Fmoc-D-Tyr(But) | Fmoc-Glu(OBut) | Fmoc-OX-1 | Fmoc-S37 | 7.7 | 100 | 592 |
| 715 | Fmoc-Trp(Boc) | Fmoc-Glu(OBut) | Fmoc-OX-1 | Fmoc-S37 | 5.1 | 100 | 615 |
| 716 | Fmoc-Tyr(But) | Fmoc-Glu(OBut) | Fmoc-OX-1 | Fmoc-S37 | 6.0 | 100 | 592 |
| 717 | Fmoc-D-Trp(Boc) | Fmoc-Sar | Fmoc-OX-1 | Fmoc-S37 | 5.6 | 100 | 557 |
| 718 | Fmoc-D-Tyr(But) | Fmoc-Sar | Fmoc-OX-1 | Fmoc-S37 | 5.5 | 100 | 534 |
| 719 | Fmoc-Trp(Boc) | Fmoc-Sar | Fmoc-OX-1 | Fmoc-S37 | 5.0 | 100 | 557 |
| 720 | Fmoc-Tyr(But) | Fmoc-Sar | Fmoc-OX-1 | Fmoc-S37 | 5.9 | 100 | 534 |
| 721 | Fmoc-D-Trp(Boc) | Fmoc-His(Trt) | Fmoc-OX-1 | Fmoc-S37 | 9.5 | 100 | 623 |
| 722 | Fmoc-D-Tyr(But) | Fmoc-His(Trt) | Fmoc-OX-1 | Fmoc-S37 | 7.5 | 100 | 600 |
| 723 | Fmoc-Trp(Boc) | Fmoc-His(Trt) | Fmoc-OX-1 | Fmoc-S37 | 5.4 | 100 | 623 |
| 724 | Fmoc-Tyr(But) | Fmoc-His(Trt) | Fmoc-OX-1 | Fmoc-S37 | 6.6 | 100 | 600 |
| 725 | Fmoc-D-Trp(Boc) | Fmoc-Ile | Fmoc-OX-1 | Fmoc-S37 | 9.6 | 96 | 599 |
| 726 | Fmoc-D-Tyr(But) | Fmoc-Ile | Fmoc-OX-1 | Fmoc-S37 | 9.1 | 100 | 576 |
| 727 | Fmoc-Trp(Boc) | Fmoc-Ile | Fmoc-OX-1 | Fmoc-S37 | 5.4 | 100 | 599 |
| 728 | Fmoc-Tyr(But) | Fmoc-Ile | Fmoc-OX-1 | Fmoc-S37 | 5.5 | 100 | 576 |
| 729 | Fmoc-D-Trp(Boc) | Fmoc-Lys(Boc) | Fmoc-OX-1 | Fmoc-S37 | 7.5 | 100 | 614 |
| 730 | Fmoc-D-Tyr(But) | Fmoc-Lys(Boc) | Fmoc-OX-1 | Fmoc-S37 | 9.6 | 100 | 591 |
| 731 | Fmoc-Trp(Boc) | Fmoc-Lys(Boc) | Fmoc-OX-1 | Fmoc-S37 | 6.1 | 100 | 614 |
| 732 | Fmoc-Tyr(But) | Fmoc-Lys(Boc) | Fmoc-OX-1 | Fmoc-S37 | 4.9 | 100 | 591 |
| 733 | Fmoc-D-Trp(Boc) | Fmoc-Nva | Fmoc-OX-1 | Fmoc-S37 | 7.1 | 95 | 585 |
| 734 | Fmoc-D-Tyr(But) | Fmoc-Nva | Fmoc-OX-1 | Fmoc-S37 | 5.8 | 100 | 562 |
| 735 | Fmoc-Trp(Boc) | Fmoc-Nva | Fmoc-OX-1 | Fmoc-S37 | 5.3 | 100 | 585 |
| 736 | Fmoc-Tyr(But) | Fmoc-Nva | Fmoc-OX-1 | Fmoc-S37 | 4.9 | 100 | 562 |
| 737 | Fmoc-D-Trp(Boc) | Fmoc-Phe | Fmoc-OX-1 | Fmoc-S37 | 7.3 | 87 | 633 |
| 738 | Fmoc-D-Tyr(But) | Fmoc-Phe | Fmoc-OX-1 | Fmoc-S37 | 10.7 | 100 | 610 |
| 739 | Fmoc-Trp(Boc) | Fmoc-Phe | Fmoc-OX-1 | Fmoc-S37 | 7.6 | 100 | 633 |
| 740 | Fmoc-Tyr(But) | Fmoc-Phe | Fmoc-OX-1 | Fmoc-S37 | 7.9 | 100 | 610 |
| 741 | Fmoc-D-Trp(Boc) | Fmoc-Pro | Fmoc-OX-1 | Fmoc-S37 | 5.3 | 100 | 583 |
| 742 | Fmoc-D-Tyr(But) | Fmoc-Pro | Fmoc-OX-1 | Fmoc-S37 | 4.1 | 100 | 560 |
| 743 | Fmoc-Trp(Boc) | Fmoc-Pro | Fmoc-OX-1 | Fmoc-S37 | 5.5 | 100 | 583 |
| 744 | Fmoc-Tyr(But) | Fmoc-Pro | Fmoc-OX-1 | Fmoc-S37 | 4.7 | 100 | 560 |
| 745 | Fmoc-D-Trp(Boc) | Fmoc-Ser(But) | Fmoc-OX-1 | Fmoc-S37 | 6.0 | 100 | 573 |
| 746 | Fmoc-D-Tyr(But) | Fmoc-Ser(But) | Fmoc-OX-1 | Fmoc-S37 | 5.9 | 100 | 550 |
| 747 | Fmoc-Trp(Boc) | Fmoc-Ser(But) | Fmoc-OX-1 | Fmoc-S37 | 6.2 | 100 | 573 |
| 748 | Fmoc-Tyr(But) | Fmoc-Ser(But) | Fmoc-OX-1 | Fmoc-S37 | 13.1 | 100 | 550 |
| 749 | Fmoc-Ala | Fmoc-Trp(Boc) | Fmoc-OX-1 | Fmoc-S37 | 6.5 | 100 | 557 |
| 750 | Fmoc-Asn(Trt) | Fmoc-Trp(Boc) | Fmoc-OX-1 | Fmoc-S37 | 12.3 | 100 | 600 |
| 751 | Fmoc-Asp(OBut) | Fmoc-Trp(Boc) | Fmoc-OX-1 | Fmoc-S37 | 6.3 | 100 | 601 |
| 752 | Fmoc-D-Ala | Fmoc-Trp(Boc) | Fmoc-OX-1 | Fmoc-S37 | 7.8 | 100 | 557 |
| 753 | Fmoc-D-Asn(Trt) | Fmoc-Trp(Boc) | Fmoc-OX-1 | Fmoc-S37 | 12.7 | 100 | 600 |
| 754 | Fmoc-D-Asp(OBut) | Fmoc-Trp(Boc) | Fmoc-OX-1 | Fmoc-S37 | 8.3 | 100 | 601 |
| 755 | Fmoc-D-His(Trt) | Fmoc-Trp(Boc) | Fmoc-OX-1 | Fmoc-S37 | 7.3 | 100 | 623 |
| 756 | Fmoc-D-Lys(Boc) | Fmoc-Trp(Boc) | Fmoc-OX-1 | Fmoc-S37 | 11.4 | 100 | 614 |
| 757 | Fmoc-D-Nva | Fmoc-Trp(Boc) | Fmoc-OX-1 | Fmoc-S37 | 9.4 | 100 | 585 |
| 758 | Fmoc-D-Phe | Fmoc-Trp(Boc) | Fmoc-OX-1 | Fmoc-S37 | 9.7 | 100 | 633 |
| 759 | Fmoc-D-Pro | Fmoc-Trp(Boc) | Fmoc-OX-1 | Fmoc-S37 | 4.7 | 100 | 583 |
| 760 | Fmoc-D-Ser(But) | Fmoc-Trp(Boc) | Fmoc-OX-1 | Fmoc-S37 | 10.3 | 100 | 573 |
| 761 | Fmoc-D-Trp(Boc) | Fmoc-Trp(Boc) | Fmoc-OX-1 | Fmoc-S37 | 11.7 | 100 | 672 |
| 762 | Fmoc-D-Tyr(But) | Fmoc-Trp(Boc) | Fmoc-OX-1 | Fmoc-S37 | 10.0 | 100 | 649 |
| 763 | Fmoc-D-Val | Fmoc-Trp(Boc) | Fmoc-OX-1 | Fmoc-S37 | 8.7 | 100 | 585 |
| 764 | Fmoc-His(Trt) | Fmoc-Trp(Boc) | Fmoc-OX-1 | Fmoc-S37 | 6.2 | 100 | 623 |
| 765 | Fmoc-Lys(Boc) | Fmoc-Trp(Boc) | Fmoc-OX-1 | Fmoc-S37 | 7.1 | 100 | 614 |
| 766 | Fmoc-Nva | Fmoc-Trp(Boc) | Fmoc-OX-1 | Fmoc-S37 | 7.0 | 100 | 585 |
| 767 | Fmoc-Phe | Fmoc-Trp(Boc) | Fmoc-OX-1 | Fmoc-S37 | 8.5 | 100 | 633 |
| 768 | Fmoc-Pro | Fmoc-Trp(Boc) | Fmoc-OX-1 | Fmoc-S37 | 6.9 | 100 | 583 |
| 769 | Fmoc-Ser(But) | Fmoc-Trp(Boc) | Fmoc-OX-1 | Fmoc-S37 | 7.6 | 100 | 573 |

TABLE 3A-continued

| Cpd | BB$_1$ | BB$_2$ | BB$_3$ | BB$_4$ | Wt (mg)[1] | Purity[2] | MS (M + H) |
|---|---|---|---|---|---|---|---|
| 770 | Fmoc-Trp(Boc) | Fmoc-Trp(Boc) | Fmoc-OX-1 | Fmoc-S37 | 8.7 | 96 | 672 |
| 771 | Fmoc-Tyr(But) | Fmoc-Trp(Boc) | Fmoc-OX-1 | Fmoc-S37 | 14.5 | 100 | 649 |
| 772 | Fmoc-Val | Fmoc-Trp(Boc) | Fmoc-OX-1 | Fmoc-S37 | 8.3 | 100 | 585 |
| 773 | Fmoc-Ala | Fmoc-Tyr(But) | Fmoc-OX-1 | Fmoc-S37 | 6.3 | 100 | 534 |
| 774 | Fmoc-Asn(Trt) | Fmoc-Tyr(But) | Fmoc-OX-1 | Fmoc-S37 | 14.6 | 100 | 577 |
| 775 | Fmoc-Asp(OBut) | Fmoc-Tyr(But) | Fmoc-OX-1 | Fmoc-S37 | 5.3 | 100 | 578 |
| 776 | Fmoc-D-Ala | Fmoc-Tyr(But) | Fmoc-OX-1 | Fmoc-S37 | 9.1 | 100 | 534 |
| 777 | Fmoc-D-Asn(Trt) | Fmoc-Tyr(But) | Fmoc-OX-1 | Fmoc-S37 | 16.2 | 100 | 577 |
| 778 | Fmoc-D-Asp(OBut) | Fmoc-Tyr(But) | Fmoc-OX-1 | Fmoc-S37 | 9.7 | 100 | 578 |
| 779 | Fmoc-D-His(Trt) | Fmoc-Tyr(But) | Fmoc-OX-1 | Fmoc-S37 | 8.2 | 100 | 600 |
| 780 | Fmoc-D-Lys(Boc) | Fmoc-Tyr(But) | Fmoc-OX-1 | Fmoc-S37 | 12.0 | 100 | 591 |
| 781 | Fmoc-D-Nva | Fmoc-Tyr(But) | Fmoc-OX-1 | Fmoc-S37 | 10.1 | 100 | 562 |
| 782 | Fmoc-D-Phe | Fmoc-Tyr(But) | Fmoc-OX-1 | Fmoc-S37 | 8.7 | 100 | 610 |
| 783 | Fmoc-D-Pro | Fmoc-Tyr(But) | Fmoc-OX-1 | Fmoc-S37 | 6.0 | 100 | 560 |
| 784 | Fmoc-D-Ser(But) | Fmoc-Tyr(But) | Fmoc-OX-1 | Fmoc-S37 | 9.4 | 100 | 550 |
| 785 | Fmoc-D-Trp(Boc) | Fmoc-Tyr(But) | Fmoc-OX-1 | Fmoc-S37 | 8.6 | 95 | 649 |
| 786 | Fmoc-D-Tyr(But) | Fmoc-Tyr(But) | Fmoc-OX-1 | Fmoc-S37 | 8.2 | 100 | 626 |
| 787 | Fmoc-D-Val | Fmoc-Tyr(But) | Fmoc-OX-1 | Fmoc-S37 | 8.5 | 100 | 562 |
| 788 | Fmoc-His(Trt) | Fmoc-Tyr(But) | Fmoc-OX-1 | Fmoc-S37 | 6.6 | 100 | 600 |
| 789 | Fmoc-Lys(Boc) | Fmoc-Tyr(But) | Fmoc-OX-1 | Fmoc-S37 | 9.6 | 100 | 591 |
| 790 | Fmoc-Nva | Fmoc-Tyr(But) | Fmoc-OX-1 | Fmoc-S37 | 6.1 | 100 | 562 |
| 791 | Fmoc-Phe | Fmoc-Tyr(But) | Fmoc-OX-1 | Fmoc-S37 | 7.7 | 100 | 610 |
| 792 | Fmoc-Pro | Fmoc-Tyr(But) | Fmoc-OX-1 | Fmoc-S37 | 10.8 | 100 | 560 |
| 793 | Fmoc-Ser(But) | Fmoc-Tyr(But) | Fmoc-OX-1 | Fmoc-S37 | 15.5 | 100 | 550 |
| 794 | Fmoc-Trp(Boc) | Fmoc-Tyr(But) | Fmoc-OX-1 | Fmoc-S37 | 7.4 | 100 | 649 |
| 795 | Fmoc-Tyr(But) | Fmoc-Tyr(But) | Fmoc-OX-1 | Fmoc-S37 | 5.7 | 100 | 626 |
| 796 | Fmoc-Val | Fmoc-Tyr(But) | Fmoc-OX-1 | Fmoc-S37 | 7.2 | 100 | 562 |
| 797 | Fmoc-D-Trp(Boc) | Fmoc-Val | Fmoc-OX-1 | Fmoc-S37 | 7.4 | 100 | 585 |
| 798 | Fmoc-D-Tyr(But) | Fmoc-Val | Fmoc-OX-1 | Fmoc-S37 | 7.9 | 100 | 562 |
| 799 | Fmoc-Trp(Boc) | Fmoc-Val | Fmoc-OX-1 | Fmoc-S37 | 6.0 | 100 | 585 |
| 800 | Fmoc-Tyr(But) | Fmoc-Val | Fmoc-OX-1 | Fmoc-S37 | 6.1 | 100 | 562 |
| 801 | Fmoc-Arg(Pbf) | Fmoc-Tyr(But) | Fmoc-OX-1 | Fmoc-S37 | 7.7 | 100 | 619 |
| 802 | Fmoc-Arg(Pbf) | Fmoc-Trp(Boc) | Fmoc-OX-1 | Fmoc-S37 | 6.1 | 100 | 642 |
| 803 | Fmoc-Arg(Pbf) | Fmoc-D-Tyr(But) | Fmoc-OX-1 | Fmoc-S37 | 8.4 | 100 | 619 |
| 804 | Fmoc-Arg(Pbf) | Fmoc-D-Trp(Boc) | Fmoc-OX-1 | Fmoc-S37 | 8.1 | 100 | 642 |
| 805 | Fmoc-D-Arg(Pbf) | Fmoc-Tyr(But) | Fmoc-OX-1 | Fmoc-S37 | 7.7 | 100 | 619 |
| 806 | Fmoc-D-Arg(Pbf) | Fmoc-Trp(Boc) | Fmoc-OX-1 | Fmoc-S37 | 5.1 | 100 | 642 |
| 807 | Fmoc-D-Arg(Pbf) | Fmoc-D-Tyr(But) | Fmoc-OX-1 | Fmoc-S37 | 6.5 | 100 | 619 |
| 808 | Fmoc-D-Arg(Pbf) | Fmoc-D-Trp(Boc) | Fmoc-OX-1 | Fmoc-S37 | 6.3 | 100 | 642 |
| 809 | Fmoc-D-Trp(Boc) | Fmoc-Arg(Pbf) | Fmoc-OX-1 | Fmoc-S37 | 11.5 | 100 | 642 |
| 810 | Fmoc-D-Tyr(But) | Fmoc-Arg(Pbf) | Fmoc-OX-1 | Fmoc-S37 | 13.2 | 100 | 619 |
| 811 | Fmoc-Trp(Boc) | Fmoc-Arg(Pbf) | Fmoc-OX-1 | Fmoc-S37 | 5.4 | 100 | 642 |
| 812 | Fmoc-Tyr(But) | Fmoc-Arg(Pbf) | Fmoc-OX-1 | Fmoc-S37 | 8.3 | 100 | 619 |
| 813 | Fmoc-D-Trp(Boc) | Fmoc-D-Arg(Pbf) | Fmoc-OX-1 | Fmoc-S37 | 8.7 | 100 | 642 |
| 814 | Fmoc-D-Tyr(But) | Fmoc-D-Arg(Pbf) | Fmoc-OX-1 | Fmoc-S37 | 8.6 | 100 | 619 |
| 815 | Fmoc-Trp(Boc) | Fmoc-D-Arg(Pbf) | Fmoc-OX-1 | Fmoc-S37 | 12.2 | 100 | 642 |
| 816 | Fmoc-Tyr(But) | Fmoc-D-Arg(Pbf) | Fmoc-OX-1 | Fmoc-S37 | 14.8 | 100 | 619 |
| 817 | Fmoc-D-Asn(Trt) | Fmoc-D-Trp(Boc) | Fmoc-OX-13 | Fmoc-S37 | 10.5 | 100 | 586 |
| 818 | Fmoc-D-Asn(Trt) | Fmoc-D-Tyr(But) | Fmoc-OX-13 | Fmoc-S37 | 12.5 | 92 | 563 |
| 819 | Fmoc-D-Asn(Trt) | Fmoc-Trp(Boc) | Fmoc-OX-13 | Fmoc-S37 | 11.0 | 100 | 586 |
| 820 | Fmoc-D-Asn(Trt) | Fmoc-Tyr(But) | Fmoc-OX-13 | Fmoc-S37 | 11.6 | 100 | 563 |
| 821 | Fmoc-D-Ser(But) | Fmoc-D-Trp(Boc) | Fmoc-OX-13 | Fmoc-S37 | 13.2 | 84 | 559 |
| 822 | Fmoc-D-Ser(But) | Fmoc-D-Tyr(But) | Fmoc-OX-13 | Fmoc-S37 | 15.9 | 100 | 536 |
| 823 | Fmoc-D-Ser(But) | Fmoc-Trp(Boc) | Fmoc-OX-13 | Fmoc-S37 | 16.2 | 100 | 559 |
| 824 | Fmoc-D-Ser(But) | Fmoc-Tyr(But) | Fmoc-OX-13 | Fmoc-S37 | 19.1 | 100 | 536 |
| 825 | Fmoc-Phe | Fmoc-Asn(Trt) | Fmoc-OX-13 | Fmoc-S37 | 3.9 | 100 | 547 |
| 826 | Fmoc-D-Phe | Fmoc-D-Asn(Trt) | Fmoc-OX-13 | Fmoc-S37 | 4.9 | 100 | 547 |
| 827 | Fmoc-Lys(Boc) | Fmoc-Phe | Fmoc-OX-13 | Fmoc-S37 | 2.1 | 100 | 561 |
| 828 | Fmoc-D-Lys(Boc) | Fmoc-D-Phe | Fmoc-OX-13 | Fmoc-S37 | 4.7 | 80 | 561 |
| 829 | Fmoc-Ser(But) | Fmoc-Ala | Fmoc-OX-13 | Fmoc-S37 | 5.3 | 100 | 444 |
| 830 | Fmoc-D-Ser(But) | Fmoc-D-Ala | Fmoc-OX-13 | Fmoc-S37 | 6.2 | 100 | 444 |
| 831 | Fmoc-Ala | Fmoc-Tyr(But) | Fmoc-OX-13 | Fmoc-S37 | 5.2 | 100 | 520 |
| 832 | Fmoc-D-Ala | Fmoc-D-Tyr(But) | Fmoc-OX-13 | Fmoc-S37 | 4.9 | 90 | 520 |
| 833 | Fmoc-D-Trp(Boc) | Fmoc-Asn(Trt) | Fmoc-OX-13 | Fmoc-S37 | 6.1 | 100 | 586 |
| 834 | Fmoc-D-Tyr(But) | Fmoc-Asn(Trt) | Fmoc-OX-13 | Fmoc-S37 | 8.4 | 100 | 563 |
| 835 | Fmoc-Trp(Boc) | Fmoc-Asn(Trt) | Fmoc-OX-13 | Fmoc-S37 | 4.3 | 100 | 586 |
| 836 | Fmoc-Tyr(But) | Fmoc-Asn(Trt) | Fmoc-OX-13 | Fmoc-S37 | 2.9 | 100 | 563 |
| 837 | Fmoc-D-Trp(Boc) | Fmoc-Ser(But) | Fmoc-OX-13 | Fmoc-S37 | 4.8 | 100 | 559 |
| 838 | Fmoc-D-Tyr(But) | Fmoc-Ser(But) | Fmoc-OX-13 | Fmoc-S37 | 5.7 | 100 | 536 |
| 839 | Fmoc-Trp(Boc) | Fmoc-Ser(But) | Fmoc-OX-13 | Fmoc-S37 | 3.2 | 100 | 559 |
| 840 | Fmoc-Tyr(But) | Fmoc-Ser(But) | Fmoc-OX-13 | Fmoc-S37 | 4.8 | 100 | 536 |
| 841 | Fmoc-Lys(Boc) | Fmoc-Ser(But) | Fmoc-OX-13 | Fmoc-S37 | 5.6 | 72 | 501 |
| 842 | Fmoc-D-Lys(Boc) | Fmoc-Ser(But) | Fmoc-OX-13 | Fmoc-S37 | 9.2 | 100 | 501 |
| 843 | Fmoc-Phe | Fmoc-Sar | Fmoc-OX-13 | Fmoc-S37 | 1.0 | na | 504 |
| 844 | Fmoc-D-Phe | Fmoc-Sar | Fmoc-OX-13 | Fmoc-S37 | 1.5 | na | 504 |
| 845 | Fmoc-Lys(Boc) | Fmoc-Sar | Fmoc-OX-13 | Fmoc-S37 | 5.0 | 100 | 485 |
| 846 | Fmoc-D-Lys(Boc) | Fmoc-Sar | Fmoc-OX-13 | Fmoc-S37 | 5.4 | 100 | 485 |
| 847 | Fmoc-Ser(But) | Fmoc-Sar | Fmoc-OX-13 | Fmoc-S37 | 5.0 | 100 | 444 |

TABLE 3A-continued

| Cpd | BB$_1$ | BB$_2$ | BB$_3$ | BB$_4$ | Wt (mg)[1] | Purity[2] | MS (M + H) |
|---|---|---|---|---|---|---|---|
| 848 | Fmoc-D-Ser(But) | Fmoc-Sar | Fmoc-OX-13 | Fmoc-S37 | 5.0 | 100 | 444 |
| 849 | Fmoc-Ala | Fmoc-Sar | Fmoc-OX-13 | Fmoc-S37 | 1.3 | 100 | 428 |
| 850 | Fmoc-D-Ala | Fmoc-Sar | Fmoc-OX-13 | Fmoc-S37 | 1.6 | 100 | 428 |
| 851 | Fmoc-D-Trp(Boc) | Fmoc-Sar | Fmoc-OX-13 | Fmoc-S37 | 1.6 | 86 | 543 |
| 852 | Fmoc-D-Tyr(But) | Fmoc-Sar | Fmoc-OX-13 | Fmoc-S37 | 1.7 | 81 | 520 |
| 853 | Fmoc-Trp(Boc) | Fmoc-Sar | Fmoc-OX-13 | Fmoc-S37 | 0.5 | 100 | 543 |
| 854 | Fmoc-Tyr(But) | Fmoc-Sar | Fmoc-OX-13 | Fmoc-S37 | 0.8 | na | 520 |
| 855 | Fmoc-Dap(Boc) | Fmoc-Sar | Fmoc-OX-13 | Fmoc-S37 | 0.9 | 100 | 443 |
| 856 | Fmoc-D-Dap(Boc) | Fmoc-Sar | Fmoc-OX-13 | Fmoc-S37 | 1.7 | 100 | 443 |
| 857 | Fmoc-Arg(Pbf) | Fmoc-N-Me-D-Phe | Fmoc-OX-13 | Fmoc-S37 | 0.7 | 100 | 603 |
| 858 | Fmoc-D-Arg(Pbf) | Fmoc-N-Me-D-Phe | Fmoc-OX-13 | Fmoc-S37 | 0.6 | na | 603 |
| 859 | Fmoc-Dap(Boc) | Fmoc-Asn(Trt) | Fmoc-OX-13 | Fmoc-S37 | 1.5 | 100 | 486 |
| 860 | Fmoc-D-Dap(Boc) | Fmoc-D-Asn(Trt) | Fmoc-OX-13 | Fmoc-S37 | 1.9 | 100 | 486 |
| 861 | Fmoc-Arg(Pbf) | Fmoc-Phe | Fmoc-OX-13 | Fmoc-S37 | 1.0 | 100 | 589 |
| 862 | Fmoc-D-Arg(Pbf) | Fmoc-D-Phe | Fmoc-OX-13 | Fmoc-S37 | 1.6 | 88 | 589 |
| 863 | Fmoc-Val | Fmoc-Tyr(But) | Fmoc-OX-13 | Fmoc-S37 | 9.5 | 100 | 548 |
| 864 | Fmoc-D-Val | Fmoc-D-Tyr(But) | Fmoc-OX-13 | Fmoc-S37 | 4.1 | 89 | 548 |
| 865 | Fmoc-His(Trt) | Fmoc-Asn(Trt) | Fmoc-OX-13 | Fmoc-S37 | 4.9 | 100 | 537 |
| 866 | Fmoc-D-His(Trt) | Fmoc-Asn(Trt) | Fmoc-OX-13 | Fmoc-S37 | 8.6 | 100 | 537 |
| 867 | Fmoc-Pro | Fmoc-Asn(Trt) | Fmoc-OX-13 | Fmoc-S37 | 6.0 | 100 | 497 |
| 868 | Fmoc-D-Pro | Fmoc-Asn(Trt) | Fmoc-OX-13 | Fmoc-S37 | 4.7 | 100 | 497 |
| 869 | Fmoc-His(Trt) | Fmoc-Ser(But) | Fmoc-OX-13 | Fmoc-S37 | 5.6 | 100 | 510 |
| 870 | Fmoc-D-His(Trt) | Fmoc-Ser(But) | Fmoc-OX-13 | Fmoc-S37 | 8.0 | 100 | 510 |
| 871 | Fmoc-Pro | Fmoc-Ser(But) | Fmoc-OX-13 | Fmoc-S37 | 6.9 | 100 | 470 |
| 872 | Fmoc-D-Pro | Fmoc-Ser(But) | Fmoc-OX-13 | Fmoc-S37 | 3.0 | 100 | 470 |
| 873 | Fmoc-His(Trt) | Fmoc-D-Asn(Trt) | Fmoc-OX-13 | Fmoc-S37 | 5.6 | 100 | 537 |
| 874 | Fmoc-D-His(Trt) | Fmoc-D-Asn(Trt) | Fmoc-OX-13 | Fmoc-S37 | 5.9 | 100 | 537 |
| 875 | Fmoc-Pro | Fmoc-D-Asn(Trt) | Fmoc-OX-13 | Fmoc-S37 | 3.2 | 100 | 497 |
| 876 | Fmoc-D-Pro | Fmoc-D-Asn(Trt) | Fmoc-OX-13 | Fmoc-S37 | 5.9 | 100 | 497 |
| 877 | Fmoc-His(Trt) | Fmoc-D-Ser(But) | Fmoc-OX-13 | Fmoc-S37 | 5.6 | 100 | 510 |
| 878 | Fmoc-D-His(Trt) | Fmoc-D-Ser(But) | Fmoc-OX-13 | Fmoc-S37 | 3.6 | 100 | 510 |
| 879 | Fmoc-Pro | Fmoc-D-Ser(But) | Fmoc-OX-13 | Fmoc-S37 | 6.2 | 100 | 470 |
| 880 | Fmoc-D-Pro | Fmoc-D-Ser(But) | Fmoc-OX-13 | Fmoc-S37 | 7.5 | 100 | 470 |
| 881 | Fmoc-D-Trp(Boc) | Fmoc-Thr(But) | Fmoc-OX-13 | Fmoc-S37 | 11.5 | 100 | 573 |
| 882 | Fmoc-D-Tyr(But) | Fmoc-D-Thr(But) | Fmoc-OX-13 | Fmoc-S37 | 5.4 | 82 | 550 |
| 883 | Fmoc-Trp(Boc) | Fmoc-Thr(But) | Fmoc-OX-13 | Fmoc-S37 | 6.4 | 100 | 573 |
| 884 | Fmoc-Tyr(But) | Fmoc-D-Thr(But) | Fmoc-OX-13 | Fmoc-S37 | 13.6 | 100 | 550 |
| 885 | Fmoc-Lys(Boc) | Fmoc-Thr(But) | Fmoc-OX-13 | Fmoc-S37 | 9.5 | 100 | 515 |
| 886 | Fmoc-D-Lys(Boc) | Fmoc-D-Thr(But) | Fmoc-OX-13 | Fmoc-S37 | 9.2 | 100 | 515 |
| 887 | Fmoc-Phe | Fmoc-Thr(But) | Fmoc-OX-13 | Fmoc-S37 | 5.3 | 100 | 534 |
| 888 | Fmoc-D-Phe | Fmoc-D-Thr(But) | Fmoc-OX-13 | Fmoc-S37 | 5.3 | 91 | 534 |
| 889 | Fmoc-Dap(Boc) | Fmoc-Thr(But) | Fmoc-OX-13 | Fmoc-S37 | 3.6 | 100 | 473 |
| 890 | Fmoc-D-Dap(Boc) | Fmoc-D-Thr(But) | Fmoc-OX-13 | Fmoc-S37 | 5.4 | 100 | 473 |
| 891 | Fmoc-Arg(Pbf) | Fmoc-Thr(But) | Fmoc-OX-13 | Fmoc-S37 | 1.3 | 100 | 543 |
| 892 | Fmoc-D-Arg(Pbf) | Fmoc-D-Thr(But) | Fmoc-OX-13 | Fmoc-S37 | 1.3 | 100 | 543 |
| 893 | Fmoc-Val | Fmoc-Thr(But) | Fmoc-OX-13 | Fmoc-S37 | 3.1 | 100 | 486 |
| 894 | Fmoc-D-Val | Fmoc-D-Thr(But) | Fmoc-OX-13 | Fmoc-S37 | 6.8 | 93 | 486 |
| 895 | Fmoc-His(Trt) | Fmoc-Thr(But) | Fmoc-OX-13 | Fmoc-S37 | 7.7 | 100 | 524 |
| 896 | Fmoc-D-His(Trt) | Fmoc-D-Thr(But) | Fmoc-OX-13 | Fmoc-S37 | 5.6 | 100 | 524 |
| 897 | Fmoc-D-Trp(Boc) | Fmoc-Arg(Pbf) | Fmoc-OX-13 | Fmoc-S37 | 4.4 | 100 | 628 |
| 898 | Fmoc-D-Tyr(But) | Fmoc-Arg(Pbf) | Fmoc-OX-13 | Fmoc-S37 | 5.5 | 100 | 605 |
| 899 | Fmoc-Trp(Boc) | Fmoc-Arg(Pbf) | Fmoc-OX-13 | Fmoc-S37 | 2.4 | 100 | 628 |
| 900 | Fmoc-Tyr(But) | Fmoc-Arg(Pbf) | Fmoc-OX-13 | Fmoc-S37 | 5.0 | 100 | 605 |
| 901 | Fmoc-Phe | Fmoc-Arg(Pbf) | Fmoc-OX-13 | Fmoc-S37 | 2.1 | 100 | 589 |
| 902 | Fmoc-D-Phe | Fmoc-Arg(Pbf) | Fmoc-OX-13 | Fmoc-S37 | 4.1 | 100 | 589 |
| 903 | Fmoc-Val | Fmoc-Arg(Pbf) | Fmoc-OX-13 | Fmoc-S37 | 4.4 | 100 | 541 |
| 904 | Fmoc-D-Val | Fmoc-Arg(Pbf) | Fmoc-OX-13 | Fmoc-S37 | 5.2 | 100 | 541 |
| 905 | Fmoc-Ala | Fmoc-Arg(Pbf) | Fmoc-OX-13 | Fmoc-S37 | 4.0 | 100 | 513 |
| 906 | Fmoc-D-Ala | Fmoc-Arg(Pbf) | Fmoc-OX-13 | Fmoc-S37 | 4.6 | 100 | 513 |
| 907 | Fmoc-Ser(But) | Fmoc-Arg(Pbf) | Fmoc-OX-13 | Fmoc-S37 | 5.7 | 100 | 529 |
| 908 | Fmoc-D-Ser(But) | Fmoc-Arg(Pbf) | Fmoc-OX-13 | Fmoc-S37 | 7.7 | 100 | 529 |
| 909 | Fmoc-D-Trp(Boc) | Fmoc-D-Arg(Pbf) | Fmoc-OX-13 | Fmoc-S37 | 2.6 | 100 | 628 |
| 910 | Fmoc-D-Tyr(But) | Fmoc-D-Arg(Pbf) | Fmoc-OX-13 | Fmoc-S37 | 2.3 | 88 | 605 |
| 911 | Fmoc-Trp(Boc) | Fmoc-D-Arg(Pbf) | Fmoc-OX-13 | Fmoc-S37 | 4.5 | 100 | 628 |
| 912 | Fmoc-Tyr(But) | Fmoc-D-Arg(Pbf) | Fmoc-OX-13 | Fmoc-S37 | 6.9 | 100 | 605 |
| 913 | Fmoc-Phe | Fmoc-D-Arg(Pbf) | Fmoc-OX-13 | Fmoc-S37 | 4.7 | 100 | 589 |
| 914 | Fmoc-D-Phe | Fmoc-D-Arg(Pbf) | Fmoc-OX-13 | Fmoc-S37 | 2.8 | 100 | 589 |
| 915 | Fmoc-Val | Fmoc-D-Arg(Pbf) | Fmoc-OX-13 | Fmoc-S37 | 6.0 | 100 | 541 |
| 916 | Fmoc-D-Val | Fmoc-D-Arg(Pbf) | Fmoc-OX-13 | Fmoc-S37 | 3.1 | 77 | 541 |
| 917 | Fmoc-Ala | Fmoc-D-Arg(Pbf) | Fmoc-OX-13 | Fmoc-S37 | na | na | na |
| 918 | Fmoc-D-Ala | Fmoc-D-Arg(Pbf) | Fmoc-OX-13 | Fmoc-S37 | 2.9 | 97 | 513 |
| 919 | Fmoc-Ser(But) | Fmoc-D-Arg(Pbf) | Fmoc-OX-13 | Fmoc-S37 | 9.1 | 100 | 529 |
| 920 | Fmoc-D-Ser(But) | Fmoc-D-Arg(Pbf) | Fmoc-OX-13 | Fmoc-S37 | 5.5 | 100 | 529 |
| 921 | Fmoc-D-Trp(Boc) | Fmoc-Pro | Fmoc-OX-13 | Fmoc-S37 | 3.1 | 97 | 569 |
| 922 | Fmoc-D-Tyr(But) | Fmoc-Pro | Fmoc-OX-13 | Fmoc-S37 | 2.8 | 78 | 546 |
| 923 | Fmoc-Ser(But) | Fmoc-Pro | Fmoc-OX-13 | Fmoc-S37 | 3.0 | 91 | 470 |
| 924 | Fmoc-D-Ser(But) | Fmoc-Pro | Fmoc-OX-13 | Fmoc-S37 | 6.7 | 100 | 470 |
| 925 | Fmoc-Glu(OBut) | Fmoc-Pro | Fmoc-OX-13 | Fmoc-S37 | 1.4 | na | na |

TABLE 3A-continued

| Cpd | BB$_1$ | BB$_2$ | BB$_3$ | BB$_4$ | Wt (mg)[1] | Purity[2] | MS (M + H) |
|---|---|---|---|---|---|---|---|
| 926 | Fmoc-D-Glu(OBut) | Fmoc-Pro | Fmoc-OX-13 | Fmoc-S37 | 4.2 | 100 | 512 |
| 927 | Fmoc-Trp(Boc) | Fmoc-D-Pro | Fmoc-OX-13 | Fmoc-S37 | 2.9 | 89 | 569 |
| 928 | Fmoc-Tyr(But) | Fmoc-D-Pro | Fmoc-OX-13 | Fmoc-S37 | 2.4 | 89 | 546 |
| 929 | Fmoc-Ser(But) | Fmoc-D-Pro | Fmoc-OX-13 | Fmoc-S37 | 4.5 | 100 | 470 |
| 930 | Fmoc-D-Ser(But) | Fmoc-D-Pro | Fmoc-OX-13 | Fmoc-S37 | 3.0 | 85 | 470 |
| 931 | Fmoc-Gln(Trt) | Fmoc-D-Pro | Fmoc-OX-13 | Fmoc-S37 | 3.9 | 100 | 511 |
| 932 | Fmoc-D-Gln(Trt) | Fmoc-D-Pro | Fmoc-OX-13 | Fmoc-S37 | 1.8 | na | na |
| 933 | Fmoc-Nva | Fmoc-D-Val | Fmoc-OX-3 | Fmoc-S48 | 6.6 | 100 | 610 |
| 934 | Fmoc-Nva | Fmoc-D-Val | Fmoc-OX-2 | Fmoc-S48 | 3.7 | 100 | 610 |
| 935 | Fmoc-D-Nva | Fmoc-D-Val | Fmoc-OX-3 | Fmoc-S48 | 3.0 | 100 | 610 |
| 936 | Fmoc-D-Nva | Fmoc-D-Val | Fmoc-OX-2 | Fmoc-S48 | 4.8 | 100 | 610 |
| 937 | Fmoc-Nva | Fmoc-Val | Fmoc-OX-3 | Fmoc-S48 | 5.3 | 100 | 610 |
| 938 | Fmoc-Nva | Fmoc-Val | Fmoc-OX-2 | Fmoc-S48 | 5.8 | 100 | 610 |
| 939 | Fmoc-Nva | Fmoc-D-Val | Fmoc-OX-3 | Fmoc-S37 | 7.3 | 100 | 532 |
| 940 | Fmoc-Nva | Fmoc-D-Val | Fmoc-OX-2 | Fmoc-S37 | 11.6 | 100 | 532 |
| 941 | Fmoc-D-Nva | Fmoc-D-Val | Fmoc-OX-3 | Fmoc-S37 | 7.0 | 100 | 532 |
| 942 | Fmoc-D-Nva | Fmoc-D-Val | Fmoc-OX-2 | Fmoc-S37 | 7.8 | 100 | 532 |
| 943 | Fmoc-Nva | Fmoc-Val | Fmoc-OX-3 | Fmoc-S37 | 7.0 | 100 | 532 |
| 944 | Fmoc-Nva | Fmoc-Val | Fmoc-OX-2 | Fmoc-S37 | 7.5 | 100 | 532 |
| 945 | Fmoc-D-Nva | Fmoc-Val | Fmoc-OX-3 | Fmoc-S48 | 10.5 | 100 | 610 |
| 946 | Fmoc-D-Nva | Fmoc-Val | Fmoc-OX-2 | Fmoc-S48 | 11.8 | 100 | 610 |
| 947 | Fmoc-D-Nva | Fmoc-Val | Fmoc-OX-3 | Fmoc-S37 | 15.4 | 100 | 532 |
| 948 | Fmoc-D-Nva | Fmoc-Val | Fmoc-OX-2 | Fmoc-S37 | 15.4 | 100 | 532 | na = not available

[1] All syntheses were carried out on the solid phase starting from 70-80 mg of 2-chlorotrityl chloride resin (typical loading 1.0 mmol/g).

[2] Purity is determined by analysis with LC-UV at 220 nm.

TABLE 3B

| Cpd | R₁ | R₂ | R₃ | Q | R₄ | R₆ |
|---|---|---|---|---|---|---|
| 601 | (R)-indol-3-yl-CH₂-(CH) | (S)-CH₃ | H | C=O | (S)-isobutyl-(CH) | 3-(H₂C)-phenyl-(NH) |
| 602 | (R)-4-hydroxyphenyl-CH₂-(CH) | (S)-CH₃ | H | C=O | (S)-isobutyl-(CH) | 3-(H₂C)-phenyl-(NH) |
| 603 | (S)-indol-3-yl-CH₂-(CH) | (S)-CH₃ | H | C=O | (S)-isobutyl-(CH) | 3-(H₂C)-phenyl-(NH) |

TABLE 3B-continued
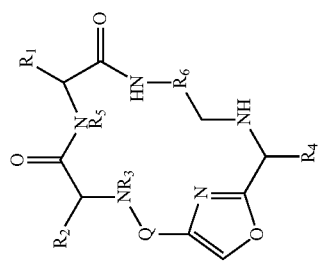
| Cpd | R₁ | R₂ | R₃ | Q | R₄ | R₆ |
|---|---|---|---|---|---|---|
| 604 | (S)- 4-hydroxybenzyl | (S)-CH₃ | H | C=O | (S)- isobutyl | 3-(aminomethyl)benzyl |
| 605 | (R)- indol-3-ylmethyl | (S)- H₂NOC-CH₂CH₂- | H | C=O | (S)- isobutyl | 3-(aminomethyl)benzyl |
| 606 | (R)- 4-hydroxybenzyl | (S)- H₂NOC-CH₂CH₂- | H | C=O | (S)- isobutyl | 3-(aminomethyl)benzyl |
| 607 | (S)- indol-3-ylmethyl | (S)- H₂NOC-CH₂CH₂- | H | C=O | (S)- isobutyl | 3-(aminomethyl)benzyl |

TABLE 3B-continued

| Cpd | R₁ | R₂ | R₃ | Q | R₄ | R₆ |
|---|---|---|---|---|---|---|
| 608 | (S)- CH₂-C₆H₄-OH | (S)- H₂NOC-CH₂- | H | C=O | (S)- isobutyl | 3-(CH₂)-C₆H₄-(NH) |
| 609 | (R)- CH₂-indole | (R)- CH₃ | H | C=O | (S)- isobutyl | 3-(CH₂)-C₆H₄-(NH) |
| 610 | (R)- CH₂-C₆H₄-OH | (R)- CH₃ | H | C=O | (S)- isobutyl | 3-(CH₂)-C₆H₄-(NH) |
| 611 | (S)- CH₂-indole | (R)- CH₃ | H | C=O | (S)- isobutyl | 3-(CH₂)-C₆H₄-(NH) |

TABLE 3B-continued
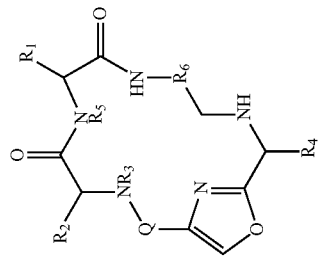
| Cpd | R₁ | R₂ | R₃ | Q | R₄ | R₆ |
|---|---|---|---|---|---|---|
| 612 | (S)-CH₂-C₆H₄-OH | (R)-CH₃ | H | C=O | (S)-CH₂-CH(CH₃)₂ | 3-(H₂C)-C₆H₄-(NH) |
| 613 | (R)-CH₂-(1H-indol-3-yl) | (S)-CH₂-CH₂-NH₂ | H | C=O | (S)-CH₂-CH(CH₃)₂ | 3-(H₂C)-C₆H₄-(NH) |
| 614 | (R)-CH₂-C₆H₄-OH | (S)-CH₂-CH₂-NH₂ | H | C=O | (S)-CH₂-CH(CH₃)₂ | 3-(H₂C)-C₆H₄-(NH) |
| 615 | (S)-CH₂-(1H-indol-3-yl) | (S)-CH₂-CH₂-NH₂ | H | C=O | (S)-CH₂-CH(CH₃)₂ | 3-(H₂C)-C₆H₄-(NH) |

TABLE 3B-continued

| Cpd | R₁ | R₂ | R₃ | Q | R₄ | R₆ |
|---|---|---|---|---|---|---|
| 616 | (S)- 4-hydroxybenzyl | (S)- H₂N-CH₂- | H | C=O | (S)- isobutyl | 3-methylbenzylamine |
| 617 | (R)- indol-3-ylmethyl | (R)- H₂NOC-CH₂- | H | C=O | (S)- isobutyl | 3-methylbenzylamine |
| 618 | (R)- 4-hydroxybenzyl | (R)- H₂NOC-CH₂- | H | C=O | (S)- isobutyl | 3-methylbenzylamine |
| 619 | (S)- indol-3-ylmethyl | (R)- H₂NOC-CH₂- | H | C=O | (S)- isobutyl | 3-methylbenzylamine |

TABLE 3B-continued

| Cpd | R₁ | R₂ | R₃ | Q | R₄ | R₆ |
|---|---|---|---|---|---|---|
| 620 | (S)- 4-hydroxybenzyl | (R)- H₂NOC-CH₂- | H | C=O | (S)- isobutyl | 3-(aminomethyl)benzyl |
| 621 | (R)- indol-3-ylmethyl | (R)- H₂N-CH₂- | H | C=O | (S)- isobutyl | 3-(aminomethyl)benzyl |
| 622 | (R)- 4-hydroxybenzyl | (R)- H₂N-CH₂- | H | C=O | (S)- isobutyl | 3-(aminomethyl)benzyl |
| 623 | (S)- indol-3-ylmethyl | (R)- H₂N-CH₂- | H | C=O | (S)- isobutyl | 3-(aminomethyl)benzyl |

TABLE 3B-continued

| Cpd | R₁ | R₂ | R₃ | Q | R₄ | R₆ |
|---|---|---|---|---|---|---|
| 624 | (S)- 4-hydroxybenzyl | (R)- H₂N-CH₂- | H | C=O | (S)- isobutyl | 3-(aminomethyl)benzyl |
| 625 | (R)- indol-3-ylmethyl | (R)- H₂NOC-(CH₂)₂- | H | C=O | (S)- isobutyl | 3-(aminomethyl)benzyl |
| 626 | (R)- 4-hydroxybenzyl | (R)- H₂NOC-(CH₂)₂- | H | C=O | (S)- isobutyl | 3-(aminomethyl)benzyl |
| 627 | (S)- indol-3-ylmethyl | (R)- H₂NOC-(CH₂)₂- | H | C=O | (S)- isobutyl | 3-(aminomethyl)benzyl |

TABLE 3B-continued

| Cpd | R₁ | R₂ | R₃ | Q | R₄ | R₆ |
|---|---|---|---|---|---|---|
| 628 | (S)- 4-hydroxybenzyl | (R)- H₂NOC-(CH₂)₂- | H | C=O | (S)- isobutyl | 3-(aminomethyl)benzyl |
| 629 | (R)- indol-3-ylmethyl | (R)- HO₂C-(CH₂)₃- | H | C=O | (S)- isobutyl | 3-(aminomethyl)benzyl |
| 630 | (R)- 4-hydroxybenzyl | (R)- HO₂C-(CH₂)₃- | H | C=O | (S)- isobutyl | 3-(aminomethyl)benzyl |
| 631 | (S)- indol-3-ylmethyl | (R)- HO₂C-(CH₂)₃- | H | C=O | (S)- isobutyl | 3-(aminomethyl)benzyl |

TABLE 3B-continued

| Cpd | R₁ | R₂ | R₃ | Q | R₄ | R₆ |
|---|---|---|---|---|---|---|
| 632 | (S)- 4-hydroxybenzyl (CH) | (R)- HO₂C-propyl (CH) | H | C=O | (S)- isobutyl (CH) | 3-(aminomethyl)benzyl (NH)/(H₂C) |
| 633 | (R)- indol-3-ylmethyl (CH) | (R)- imidazol-4-ylmethyl (CH) | H | C=O | (S)- isobutyl (CH) | 3-(aminomethyl)benzyl (NH)/(H₂C) |
| 634 | (R)- 4-hydroxybenzyl (CH) | (R)- imidazol-4-ylmethyl (CH) | H | C=O | (S)- isobutyl (CH) | 3-(aminomethyl)benzyl (NH)/(H₂C) |
| 635 | (S)- indol-3-ylmethyl (CH) | (R)- imidazol-4-ylmethyl (CH) | H | C=O | (S)- isobutyl (CH) | 3-(aminomethyl)benzyl (NH)/(H₂C) |

TABLE 3B-continued

| Cpd | R₁ | R₂ | R₃ | Q | R₄ | R₆ |
|-----|----|----|----|---|----|----|
| 636 | (S)- 4-hydroxybenzyl | (R)- imidazol-4-ylmethyl | H | C=O | (S)- isobutyl | 3-(aminomethyl)benzyl (methyl) |
| 637 | (R)- indol-3-ylmethyl | (R)- sec-butyl | H | C=O | (S)- isobutyl | 3-(aminomethyl)benzyl (methyl) |
| 638 | (R)- 4-hydroxybenzyl | (R)- sec-butyl | H | C=O | (S)- isobutyl | 3-(aminomethyl)benzyl (methyl) |
| 639 | (S)- indol-3-ylmethyl | (R)- sec-butyl | H | C=O | (S)- isobutyl | 3-(aminomethyl)benzyl (methyl) |

TABLE 3B-continued

| Cpd | R₁ | R₂ | R₃ | Q | R₄ | R₆ |
|---|---|---|---|---|---|---|
| 640 | (S)- 4-hydroxybenzyl | (R)- isobutyl | H | C=O | (S)- isobutyl | 3-(methyl)benzyl (NH) |
| 641 | (R)- indol-3-ylmethyl | (R)- 4-aminobutyl | H | C=O | (S)- isobutyl | 3-(methyl)benzyl (NH) |
| 642 | (R)- 4-hydroxybenzyl | (R)- 4-aminobutyl | H | C=O | (S)- isobutyl | 3-(methyl)benzyl (NH) |
| 643 | (S)- indol-3-ylmethyl | (R)- 4-aminobutyl | H | C=O | (S)- isobutyl | 3-(methyl)benzyl (NH) |

TABLE 3B-continued
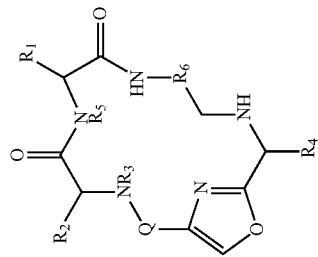
| Cpd | R1 | R2 | R3 | Q | R4 | R6 |
|---|---|---|---|---|---|---|
| 644 | (S)- 4-hydroxybenzyl | (R)- H2N-(CH2)4- | H | C=O | (S)- isobutyl | 3-(aminomethyl)benzyl |
| 645 | (R)- indol-3-ylmethyl-CH2 | (R)- (CH2)3-CH3 | H | C=O | (S)- isobutyl | 3-(aminomethyl)benzyl |
| 646 | (S)- 4-hydroxybenzyl | (R)- (CH2)3-CH3 | H | C=O | (S)- isobutyl | 3-(aminomethyl)benzyl |
| 647 | (S)- indol-3-ylmethyl-CH2 | (R)- (CH2)3-CH3 | H | C=O | (S)- isobutyl | 3-(aminomethyl)benzyl |

TABLE 3B-continued

| Cpd | R₁ | R₂ | R₃ | Q | R₄ | R₆ |
|-----|----|----|----|---|----|----|
| 648 | (S)- 4-hydroxybenzyl (CH₂) | (R)- n-butyl (CH₂) | H | C=O | (S)- isobutyl (CH) | (R)- 1-methyl-2-aminoethyl (CH₂)(NH), (H₂C) |
| 649 | (R)- indol-3-ylmethyl (CH₂) | (R)- benzyl (CH₂) | H | C=O | (S)- isobutyl (CH) | 3-(aminomethyl)benzyl (NH)(H₂C) |
| 650 | (R)- 4-hydroxybenzyl (CH₂) | (R)- benzyl (CH₂) | H | C=O | (S)- isobutyl (CH) | 3-(aminomethyl)benzyl (NH)(H₂C) |
| 651 | (S)- indol-3-ylmethyl (CH₂) | (R)- benzyl (CH₂) | H | C=O | (S)- isobutyl (CH) | 3-(aminomethyl)benzyl (NH)(H₂C) |

TABLE 3B-continued

| Cpd | R₁ | R₂ | R₃ | Q | R₄ | R₆ |
|---|---|---|---|---|---|---|
| 652 | (S)- 4-hydroxybenzyl | (R)- benzyl | H | C=O | (S)- isobutyl | 3-(aminomethyl)benzyl |
| 653 | (R)- indol-3-ylmethyl | (R)- pyrrolidinyl | H | C=O | (S)- isobutyl | 3-(aminomethyl)benzyl |
| 654 | (R)- 4-hydroxybenzyl | (R)- pyrrolidinyl | H | C=O | (S)- isobutyl | 3-(aminomethyl)benzyl |
| 655 | (R)- indol-3-ylmethyl | (R)- pyrrolidinyl | H | C=O | (S)- isobutyl | 3-(aminomethyl)benzyl |

TABLE 3B-continued

| Cpd | R₁ | R₂ | R₃ | Q | R₄ | R₆ |
|---|---|---|---|---|---|---|
| 656 | (S)- 4-hydroxybenzyl | (R)- pyrrolidinyl-CH | H | C=O | (S)- isobutyl | 3-methylbenzyl-NH |
| 657 | (R)- indol-3-yl-CH₂ | (R)- HO-CH₂-CH | H | C=O | (S)- isobutyl | 3-methylbenzyl-NH |
| 658 | (R)- 4-hydroxybenzyl | (R)- HO-CH₂-CH | H | C=O | (S)- isobutyl | 3-methylbenzyl-NH |
| 659 | (S)- indol-3-yl-CH₂ | (R)- HO-CH₂-CH | H | C=O | (S)- isobutyl | 3-methylbenzyl-NH |

TABLE 3B-continued

| Cpd | R₁ | R₂ | R₃ | Q | R₄ | R₆ |
|-----|----|----|----|---|----|----|
| 660 | (S)- 4-hydroxybenzyl | (R)- HOCH₂- | H | C=O | (S)- isobutyl | 3-(aminomethyl)benzyl (NH/CH₂) |
| 661 | (S)-CH₃ | (R)- indol-3-ylmethyl | H | C=O | (S)- isobutyl | 3-(aminomethyl)benzyl (NH/CH₂) |
| 662 | (S)- H₂NOC-CH₂- | (R)- indol-3-ylmethyl | H | C=O | (S)- isobutyl | 3-(aminomethyl)benzyl (NH/CH₂) |
| 663 | (S)- HO₂C-CH₂- | (R)- indol-3-ylmethyl | H | C=O | (S)- isobutyl | 3-(aminomethyl)benzyl (NH/CH₂) |

TABLE 3B-continued

| Cpd | R₁ | R₂ | R₃ | Q | R₄ | R₆ |
|---|---|---|---|---|---|---|
| 664 | (R)—CH₃ | (R)- indol-3-ylmethyl (CH) | H | C=O | (S)- isobutyl (CH) | 3-(aminomethyl)benzyl (NH)(H₂C) |
| 665 | (R)- H₂NOC-CH₂- (CH) | (R)- indol-3-ylmethyl (CH) | H | C=O | (S)- isobutyl (CH) | 3-(aminomethyl)benzyl (NH)(H₂C) |
| 666 | (R)- HO₂C-CH₂- (CH) | (R)- indol-3-ylmethyl (CH) | H | C=O | (S)- isobutyl (CH) | 3-(aminomethyl)benzyl (NH)(H₂C) |
| 667 | (R)- 1H-imidazol-4-ylmethyl (CH) | (R)- indol-3-ylmethyl (CH) | H | C=O | (S)- isobutyl (CH) | 3-(aminomethyl)benzyl (NH)(H₂C) |

TABLE 3B-continued

| Cpd | R₁ | R₂ | R₃ | Q | R₄ | R₆ |
|---|---|---|---|---|---|---|
| 668 | (R)- H₂N-(CH₂)₄-(CH) | (R)- indol-3-yl-CH₂-(CH) | H | C=O | (S)- isobutyl-(CH) | 3-(H₂C)-C₆H₄-(NH) |
| 669 | (R)- propyl-(CH) | (R)- indol-3-yl-CH₂-(CH) | H | C=O | (S)- isobutyl-(CH) | 3-(H₂C)-C₆H₄-(NH) |
| 670 | (R)- benzyl-(CH) | (R)- indol-3-yl-CH₂-(CH) | H | C=O | (S)- isobutyl-(CH) | 3-(H₂C)-C₆H₄-(NH) |

TABLE 3B-continued
| Cpd | R₁ | R₂ | R₃ | Q | R₄ | R₆ |
|---|---|---|---|---|---|---|
| 671 |  |  | H | C=O |  |  |
| 672 |  |  | H | C=O |  |  |
| 673 |  |  | H | C=O |  |  |
| 674 |  |  | H | C=O |  |  |

TABLE 3B-continued
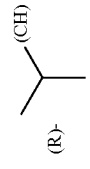
| Cpd | R₁ | R₂ | R₃ | Q | R₄ | R₆ |
|---|---|---|---|---|---|---|
| 675 | (R)- isopropyl (CH) | (R)- indol-3-ylmethyl (CH) | H | C=O | (S)- isobutyl (CH) | 3-(methyl)benzyl (NH)(H₂C) |
| 676 | (S)- imidazol-4-ylmethyl (CH) | (R)- indol-3-ylmethyl (CH) | H | C=O | (S)- isobutyl (CH) | 3-(methyl)benzyl (NH)(H₂C) |
| 677 | (S)- 4-aminobutyl H₂N (CH) | (R)- indol-3-ylmethyl (CH) | H | C=O | (S)- isobutyl (CH) | 3-(methyl)benzyl (NH)(H₂C) |

TABLE 3B-continued
| Cpd | R₁ | R₂ | R₃ | Q | R₄ | R₆ |
|---|---|---|---|---|---|---|
| 678 | (S)-n-propyl (CH) | (R)-indolylmethyl (CH) | H | C=O | (S)-isobutyl (CH) | 3-methylbenzyl (NH)(H₂C) |
| 679 | (S)-benzyl (CH) | (R)-indolylmethyl (CH) | H | C=O | (S)-isobutyl (CH) | 3-methylbenzyl (NH)(H₂C) |
| 680 | (S)-pyrrolidinylmethyl (N)(HC) | (R)-indolylmethyl (CH) | H | C=O | (S)-isobutyl (CH) | 3-methylbenzyl (NH)(H₂C) |
| 681 | (S)-hydroxymethyl HO-(CH) | (R)-indolylmethyl (CH) | H | C=O | (S)-isobutyl (CH) | 3-methylbenzyl (NH)(H₂C) |

TABLE 3B-continued

| Cpd | R₁ | R₂ | R₃ | Q | R₄ | R₆ |
|---|---|---|---|---|---|---|
| 682 | (S)-CH₂-indol-3-yl | (R)-CH₂-indol-3-yl | H | C=O | (S)-isobutyl | 3-(aminomethyl)benzyl (CH₂-C₆H₄-CH₂NH) |
| 683 | (S)-CH₂-(4-hydroxyphenyl) | (R)-CH₂-indol-3-yl | H | C=O | (S)-isobutyl | 3-(aminomethyl)benzyl |
| 684 | (S)-isobutyl | (R)-CH₂-indol-3-yl | H | C=O | (S)-isobutyl | 3-(aminomethyl)benzyl |
| 685 | (S)-CH₃ | (R)-CH₂-(4-hydroxyphenyl) | H | C=O | (S)-isobutyl | 3-(aminomethyl)benzyl |

TABLE 3B-continued

| Cpd | R₁ | R₂ | R₃ | Q | R₄ | R₆ |
|---|---|---|---|---|---|---|
| 686 | (S)- H₂NOC—(CH) | (R)- HO-C₆H₄-CH₂ (CH) | H | C=O | (S)- isobutyl (CH) | 3-(H₂C)-C₆H₄-(NH) |
| 687 | (S)- HO₂C—(CH) | (R)- HO-C₆H₄-CH₂ (CH) | H | C=O | (S)- isobutyl (CH) | 3-(H₂C)-C₆H₄-(NH) |
| 688 | (R)—CH₃ | (R)- HO-C₆H₄-CH₂ (CH) | H | C=O | (S)- isobutyl (CH) | 3-(H₂C)-C₆H₄-(NH) |
| 689 | (R)- H₂NOC—(CH) | (R)- HO-C₆H₄-CH₂ (CH) | H | C=O | (S)- isobutyl (CH) | 3-(H₂C)-C₆H₄-(NH) |

TABLE 3B-continued
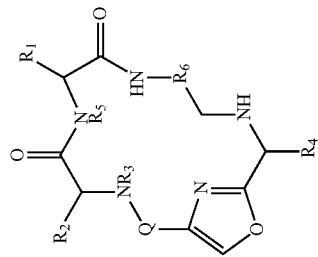
| Cpd | R₁ | R₂ | R₃ | Q | R₄ | R₆ |
|---|---|---|---|---|---|---|
| 690 | (R)- HO₂C-(CH) | (R)- HO-C₆H₄-CH₂-(CH) | H | C=O | (S)- isobutyl (CH) | 3-(H₂C)-C₆H₄-(NH) |
| 691 | (R)- imidazolyl-CH₂-(CH) | (R)- HO-C₆H₄-CH₂-(CH) | H | C=O | (S)- isobutyl (CH) | 3-(H₂C)-C₆H₄-(NH) |
| 692 | (R)- H₂N-(CH₂)₄-(CH) | (R)- HO-C₆H₄-CH₂-(CH) | H | C=O | (S)- isobutyl (CH) | 3-(H₂C)-C₆H₄-(NH) |
| 693 | (R)- n-propyl-(CH) | (R)- HO-C₆H₄-CH₂-(CH) | H | C=O | (S)- isobutyl (CH) | 3-(H₂C)-C₆H₄-(NH) |

TABLE 3B-continued

| Cpd | R₁ | R₂ | R₃ | Q | R₄ | R₆ |
|---|---|---|---|---|---|---|
| 694 | (R)-benzyl | (R)-4-hydroxybenzyl (CH) | H | C=O | (S)-isobutyl (CH) | 3-(aminomethyl)benzyl (NH)(H₂C) |
| 695 | (R)-pyrrolidin-2-yl (HC)(N) | (R)-4-hydroxybenzyl (CH) | H | C=O | (S)-isobutyl (CH) | 3-(aminomethyl)benzyl (NH)(H₂C) |
| 696 | (R)-2-hydroxyethyl (CH)(HO) | (R)-4-hydroxybenzyl (CH) | H | C=O | (S)-isobutyl (CH) | 3-(aminomethyl)benzyl (NH)(H₂C) |
| 697 | (R)-(1H-indol-3-yl)methyl (CH) | (R)-4-hydroxybenzyl (CH) | H | C=O | (S)-isobutyl (CH) | 3-(aminomethyl)benzyl (NH)(H₂C) |

TABLE 3B-continued

| Cpd | R₁ | R₂ | R₃ | Q | R₄ | R₆ |
|-----|-----|-----|-----|-----|-----|-----|
| 698 | (R)- 4-hydroxybenzyl (CH) | (R)- 4-hydroxybenzyl (CH) | H | C=O | (S)- isobutyl (CH) | 3-(H₂C)-phenyl-(NH) |
| 699 | (R)- isopropyl (CH) | (R)- 4-hydroxybenzyl (CH) | H | C=O | (S)- isobutyl (CH) | 3-(H₂C)-phenyl-(NH) |
| 700 | (S)- imidazolylmethyl (CH) | (R)- 4-hydroxybenzyl (CH) | H | C=O | (S)- isobutyl (CH) | 3-(H₂C)-phenyl-(NH) |
| 701 | (S)- 4-aminobutyl (CH) | (R)- 4-hydroxybenzyl (CH) | H | C=O | (S)- isobutyl (CH) | 3-(H₂C)-phenyl-(NH) |

TABLE 3B-continued

| Cpd | R₁ | R₂ | R₃ | Q | R₄ | R₆ |
|---|---|---|---|---|---|---|
| 702 | (S)-propyl(CH) | (R)-4-hydroxybenzyl(CH) | H | C=O | (S)-isobutyl(CH) | 3-methylbenzyl(NH)(H₂C) |
| 703 | (S)-benzyl(CH) | (R)-4-hydroxybenzyl(CH) | H | C=O | (S)-isobutyl(CH) | 3-methylbenzyl(NH)(H₂C) |
| 704 | (S)-pyrrolidinyl(HC)(N) | (R)-4-hydroxybenzyl(CH) | H | C=O | (S)-isobutyl(CH) | 3-methylbenzyl(NH)(H₂C) |
| 705 | (S)-hydroxyethyl(CH)(HO) | (R)-4-hydroxybenzyl(CH) | H | C=O | (S)-isobutyl(CH) | 3-methylbenzyl(NH)(H₂C) |

TABLE 3B-continued

| Cpd | R₁ | R₂ | R₃ | Q | R₄ | R₆ |
|---|---|---|---|---|---|---|
| 706 | (S)-CH₂-indol-3-yl | (R)-CH₂-C₆H₄-4-OH | H | C=O | (S)-CH₂-CH(CH₃)₂ | 3-(CH₂NH)-C₆H₄-CH₃ |
| 707 | (R)-CH₂-C₆H₄-4-OH | (R)-CH₂-C₆H₄-4-OH | H | C=O | (S)-CH₂-CH(CH₃)₂ | 3-(CH₂NH)-C₆H₄-CH₃ |
| 708 | (S)-CH-CH(CH₃)₂ | (R)-CH₂-C₆H₄-4-OH | H | C=O | (S)-CH₂-CH(CH₃)₂ | 3-(CH₂NH)-C₆H₄-CH₃ |
| 709 | (R)-CH₂-indol-3-yl | (R)-CH-CH(CH₃)₂ | H | C=O | (S)-CH₂-CH(CH₃)₂ | 3-(CH₂NH)-C₆H₄-CH₃ |

TABLE 3B-continued

| Cpd | R₁ | R₂ | R₃ | Q | R₄ | R₆ |
|---|---|---|---|---|---|---|
| 710 | (R)- 4-hydroxybenzyl (CH) | (R)- isobutyl (CH) | H | C=O | (S)- isobutyl (CH) | 3-(aminomethyl)benzyl (NH)(H₂C) |
| 711 | (S)- (1H-indol-3-yl)methyl (CH) | (R)- isobutyl (CH) | H | C=O | (S)- isobutyl (CH) | 3-(aminomethyl)benzyl (NH)(H₂C) |
| 712 | (R)- 4-hydroxybenzyl (CH) | (R)- isobutyl (CH) | H | C=O | (S)- isobutyl (CH) | 3-(aminomethyl)benzyl (NH)(H₂C) |
| 713 | (R)- (1H-indol-3-yl)methyl (CH) | (S)- HO₂C-(CH) | H | C=O | (S)- isobutyl (CH) | 3-(aminomethyl)benzyl (NH)(H₂C) |

TABLE 3B-continued

| Cpd | R₁ | R₂ | R₃ | Q | R₄ | R₆ |
|---|---|---|---|---|---|---|
| 714 | (R)- 4-hydroxybenzyl (CH) | (S)- HO₂C-propyl (CH) | H | C=O | (S)- isobutyl (CH) | 3-methylbenzyl (NH)(H₂C) |
| 715 | (S)- indol-3-ylmethyl (CH) | (S)- HO₂C-propyl (CH) | H | C=O | (S)- isobutyl (CH) | 3-methylbenzyl (NH)(H₂C) |
| 716 | (S)- 4-hydroxybenzyl (CH) | (S)- HO₂C-propyl (CH) | H | C=O | (S)- isobutyl (CH) | 3-methylbenzyl (NH)(H₂C) |
| 717 | (R)- indol-3-ylmethyl (CH) | H | Me | C=O | (S)- isobutyl (CH) | 3-methylbenzyl (NH)(H₂C) |

TABLE 3B-continued

| Cpd | R₁ | R₂ | R₃ | Q | R₄ | R₆ |
|---|---|---|---|---|---|---|
| 718 | (R)- 4-hydroxybenzyl (CH) | H | Me | C=O | (S)- isobutyl (CH) | 3-(aminomethyl)benzyl (NH)(H₂C) |
| 719 | (S)- indol-3-ylmethyl (CH) | H | Me | C=O | (S)- isobutyl (CH) | 3-(aminomethyl)benzyl (NH)(H₂C) |
| 720 | (S)- 4-hydroxybenzyl (CH) | H | Me | C=O | (S)- isobutyl (CH) | 3-(aminomethyl)benzyl (NH)(H₂C) |
| 721 | (R)- indol-3-ylmethyl (CH) | (S)- imidazol-4-ylmethyl (CH) | H | C=O | (S)- isobutyl (CH) | 3-(aminomethyl)benzyl (NH)(H₂C) |

TABLE 3B-continued

| Cpd | R₁ | R₂ | R₃ | Q | R₄ | R₆ |
|---|---|---|---|---|---|---|
| 722 | (R)- 4-hydroxybenzyl (CH) | (S)- 4-imidazolylmethyl (CH) | H | C=O | (S)- isobutyl (CH) | 3-(aminomethyl)benzyl with (H₂C) and (NH) |
| 723 | (S)- 3-indolylmethyl (CH) | (S)- 4-imidazolylmethyl (CH) | H | C=O | (S)- isobutyl (CH) | 3-(aminomethyl)benzyl with (H₂C) and (NH) |
| 724 | (S)- 4-hydroxybenzyl (CH) | (S)- 4-imidazolylmethyl (CH) | H | C=O | (S)- isobutyl (CH) | 3-(aminomethyl)benzyl with (H₂C) and (NH) |
| 725 | (R)- 3-indolylmethyl (CH) | (S)- sec-butyl (CH) | H | C=O | (S)- isobutyl (CH) | 3-(aminomethyl)benzyl with (H₂C) and (NH) |

TABLE 3B-continued

| Cpd | R₁ | R₂ | R₃ | Q | R₄ | R₆ |
|---|---|---|---|---|---|---|
| 726 | (R)- 4-hydroxybenzyl | (S)- isobutyl | H | C=O | (S)- isobutyl | 3-(aminomethyl)benzyl |
| 727 | (R)- indol-3-ylmethyl | (S)- isobutyl | H | C=O | (S)- isobutyl | 3-(aminomethyl)benzyl |
| 728 | (S)- 4-hydroxybenzyl | (S)- isobutyl | H | C=O | (S)- isobutyl | 3-(aminomethyl)benzyl |
| 729 | (R)- indol-3-ylmethyl | (S)- 4-aminobutyl | H | C=O | (S)- isobutyl | 3-(aminomethyl)benzyl |

TABLE 3B-continued

| Cpd | R₁ | R₂ | R₃ | Q | R₄ | R₆ |
|---|---|---|---|---|---|---|
| 730 | (R)- 4-hydroxybenzyl | (S)- H₂N-(CH₂)₄- | H | C=O | (S)- isobutyl | 3-(aminomethyl)benzyl |
| 731 | (S)- indol-3-ylmethyl | (S)- H₂N-(CH₂)₄- | H | C=O | (S)- isobutyl | 3-(aminomethyl)benzyl |
| 732 | (S)- 4-hydroxybenzyl | (S)- H₂N-(CH₂)₄- | H | C=O | (S)- isobutyl | 3-(aminomethyl)benzyl |
| 733 | (R)- indol-3-ylmethyl | (S)- n-butyl | H | C=O | (S)- isobutyl | 3-(aminomethyl)benzyl |

TABLE 3B-continued

| Cpd | R₁ | R₂ | R₃ | Q | R₄ | R₆ |
|-----|----|----|----|----|----|-----|
| 734 | (R)- 4-hydroxybenzyl (CH) | (S)- n-butyl (CH) | H | C=O | (S)- isobutyl (CH) | 3-methylbenzyl (NH)(H₂C) |
| 735 | (S)- indol-3-ylmethyl (CH) | (S)- n-butyl (CH) | H | C=O | (S)- isobutyl (CH) | 3-methylbenzyl (NH)(H₂C) |
| 736 | (S)- 4-hydroxybenzyl (CH) | (S)- n-butyl (CH) | H | C=O | (S)- isobutyl (CH) | 3-methylbenzyl (NH)(H₂C) |
| 737 | (R)- indol-3-ylmethyl (CH) | (S)- benzyl (CH) | H | C=O | (S)- isobutyl (CH) | 3-methylbenzyl (NH)(H₂C) |

TABLE 3B-continued

| Cpd | R₁ | R₂ | R₃ | Q | R₄ | R₆ |
|---|---|---|---|---|---|---|
| 738 | (R)- 4-hydroxybenzyl (CH) | (S)- benzyl (CH) | H | C=O | (S)- isobutyl (CH) | 3-(aminomethyl)benzyl (NH)/(H₂C) |
| 739 | (S)- indol-3-ylmethyl (CH) | (S)- benzyl (CH) | H | C=O | (S)- isobutyl (CH) | 3-(aminomethyl)benzyl (NH)/(H₂C) |
| 740 | (S)- 4-hydroxybenzyl (CH) | (S)- benzyl (CH) | H | C=O | (S)- isobutyl (CH) | 3-(aminomethyl)benzyl (NH)/(H₂C) |
| 741 | (R)- indol-3-ylmethyl (CH) | (S)- pyrrolidinyl (HC/N) | H | C=O | (S)- isobutyl (CH) | 3-(aminomethyl)benzyl (NH)/(H₂C) |

TABLE 3B-continued

| Cpd | R₁ | R₂ | R₃ | Q | R₄ | R₆ |
|---|---|---|---|---|---|---|
| 742 | (R)- 4-hydroxybenzyl | (S)- pyrrolidinyl-CH | H | C=O | (S)- isobutyl | 3-(aminomethyl)benzyl |
| 743 | (S)- indol-3-yl-CH₂ | (S)- pyrrolidinyl-CH | H | C=O | (S)- isobutyl | 3-(aminomethyl)benzyl |
| 744 | (S)- 4-hydroxybenzyl | (S)- pyrrolidinyl-CH | H | C=O | (S)- isobutyl | 3-(aminomethyl)benzyl |
| 745 | (R)- indol-3-yl-CH₂ | (S)- HOCH₂ | H | C=O | (S)- isobutyl | 3-(aminomethyl)benzyl |

TABLE 3B-continued

| Cpd | R₁ | R₂ | R₃ | Q | R₄ | R₆ |
|-----|-----|-----|-----|-----|-----|-----|
| 746 | (R)-4-hydroxybenzyl (CH) | (S)-2-hydroxyethyl (CH) HO | H | C=O | (S)-isobutyl (CH) | 3-(aminomethyl)benzyl (NH)/(H₂C) |
| 747 | (S)-indol-3-ylmethyl (CH) | (S)-2-hydroxyethyl (CH) HO | H | C=O | (S)-isobutyl (CH) | 3-(aminomethyl)benzyl (NH)/(H₂C) |
| 748 | (S)-4-hydroxybenzyl (CH) | (S)-2-hydroxyethyl (CH) HO | H | C=O | (S)-isobutyl (CH) | 3-(aminomethyl)benzyl (NH)/(H₂C) |
| 749 | (S)—CH₃ | (S)-indol-3-ylmethyl (CH) | H | C=O | (S)-isobutyl (CH) | 3-(aminomethyl)benzyl (NH)/(H₂C) |

TABLE 3B-continued

| Cpd | R₁ | R₂ | R₃ | Q | R₄ | R₆ |
|---|---|---|---|---|---|---|
| 750 | (S)- H₂NOC-CH₂- | (S)- indol-3-ylmethyl | H | C=O | (S)- isobutyl | 3-(aminomethyl)benzyl |
| 751 | (S)- HO₂C-CH₂- | (R)- indol-3-ylmethyl | H | C=O | (S)- isobutyl | 3-(aminomethyl)benzyl |
| 752 | (R)-CH₃ | (R)- indol-3-ylmethyl | H | C=O | (S)- isobutyl | 3-(aminomethyl)benzyl |
| 753 | (R)- H₂NOC-CH₂- | (S)- indol-3-ylmethyl | H | C=O | (S)- isobutyl | 3-(aminomethyl)benzyl |

TABLE 3B-continued
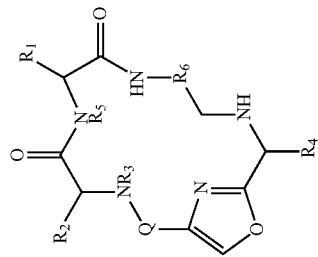
| Cpd | R₁ | R₂ | R₃ | Q | R₄ | R₆ |
|---|---|---|---|---|---|---|
| 754 | (R)- HO₂C—(CH) | (S)- indol-3-ylmethyl (CH) | H | C=O | (S)- isobutyl (CH) | 3-(aminomethyl)benzyl (NH)/(H₂C) |
| 755 | (R)- imidazol-4-ylmethyl (CH) | (S)- indol-3-ylmethyl (CH) | H | C=O | (S)- isobutyl (CH) | 3-(aminomethyl)benzyl (NH)/(H₂C) |
| 756 | (R)- H₂N—(CH) (aminobutyl) | (S)- indol-3-ylmethyl (CH) | H | C=O | (S)- isobutyl (CH) | 3-(aminomethyl)benzyl (NH)/(H₂C) |

TABLE 3B-continued

| Cpd | R₁ | R₂ | R₃ | Q | R₄ | R₆ |
|---|---|---|---|---|---|---|
| 757 | (R)- propyl (CH) | (S)- indol-3-ylmethyl (CH) | H | C=O | (S)- isobutyl (CH) | 3-(H₂C)-phenyl-(NH) |
| 758 | (R)- benzyl (CH) | (S)- indol-3-ylmethyl (CH) | H | C=O | (S)- isobutyl (CH) | 3-(H₂C)-phenyl-(NH) |
| 759 | (R)- pyrrolidin-2-yl (CH)(N) | (S)- indol-3-ylmethyl (CH) | H | C=O | (S)- isobutyl (CH) | 3-(H₂C)-phenyl-(NH) |
| 760 | (R)- hydroxyethyl (CH) | (S)- indol-3-ylmethyl (CH) | H | C=O | (S)- isobutyl (CH) | 3-(H₂C)-phenyl-(NH) |

TABLE 3B-continued

| Cpd | R₁ | R₂ | R₃ | Q | R₄ | R₆ |
|---|---|---|---|---|---|---|
| 761 | (R)-indol-3-ylmethyl-(CH) | (S)-indol-3-ylmethyl-(CH) | H | C=O | (S)-isobutyl-(CH) | 3-(aminomethyl)benzyl (NH)(H₂C) |
| 762 | (R)-4-hydroxybenzyl-(CH) | (S)-indol-3-ylmethyl-(CH) | H | C=O | (S)-isobutyl-(CH) | 3-(aminomethyl)benzyl (NH)(H₂C) |
| 763 | (R)-isopropyl-(CH) | (S)-indol-3-ylmethyl-(CH) | H | C=O | (S)-isobutyl-(CH) | 3-(aminomethyl)benzyl (NH)(H₂C) |

TABLE 3B-continued

| Cpd | R₁ | R₂ | R₃ | Q | R₄ | R₆ |
|---|---|---|---|---|---|---|
| 764 | (S)- imidazolyl-CH₂-(CH) | (S)- indol-3-yl-CH₂-(CH) | H | C=O | (S)- isobutyl-(CH) | 3-(H₂C)-phenyl-CH₂-(NH) |
| 765 | (S)- H₂N-(CH₂)₄-(CH) | (S)- indol-3-yl-CH₂-(CH) | H | C=O | (S)- isobutyl-(CH) | 3-(H₂C)-phenyl-CH₂-(NH) |
| 766 | (S)- propyl-(CH) | (S)- indol-3-yl-CH₂-(CH) | H | C=O | (S)- isobutyl-(CH) | 3-(H₂C)-phenyl-CH₂-(NH) |
| 767 | (S)- benzyl-(CH) | (S)- indol-3-yl-CH₂-(CH) | H | C=O | (S)- isobutyl-(CH) | 3-(H₂C)-phenyl-CH₂-(NH) |

TABLE 3B-continued
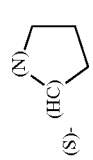
| Cpd | R₁ | R₂ | R₃ | Q | R₄ | R₆ |
|---|---|---|---|---|---|---|
| 768 | 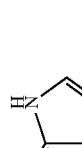 |  | H | C=O | 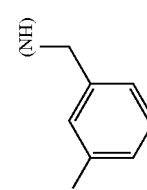 | 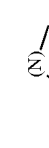 |
| 769 |  |  | H | C=O | 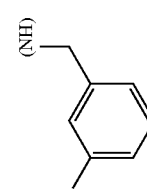 |  |
| 770 |  |  | H | C=O | 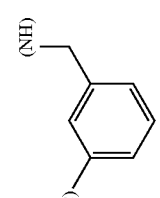 | |

TABLE 3B-continued

| Cpd | R₁ | R₂ | R₃ | Q | R₄ | R₆ |
|---|---|---|---|---|---|---|
| 771 | (S)- CH₂-C₆H₄-OH | (S)- CH₂-indol-3-yl | H | C=O | (S)- isobutyl | 3-(aminomethyl)benzyl |
| 772 | (S)- isobutyl | (S)- CH₂-indol-3-yl | H | C=O | (S)- isobutyl | 3-(aminomethyl)benzyl |
| 773 | (S)- CH₃ | (S)- CH₂-C₆H₄-OH | H | C=O | (S)- isobutyl | 3-(aminomethyl)benzyl |
| 774 | (S)- CH₂-CONH₂ | (S)- CH₂-C₆H₄-OH | H | C=O | (S)- isobutyl | 3-(aminomethyl)benzyl |

TABLE 3B-continued

| Cpd | R₁ | R₂ | R₃ | Q | R₄ | R₆ |
|---|---|---|---|---|---|---|
| 775 | (S)-HO₂C-(CH₂)- | (S)-4-hydroxybenzyl-(CH₂)- | H | C=O | (S)-isobutyl-(CH)- | 3-(aminomethyl)benzyl (NH) |
| 776 | (R)-CH₃ | (S)-4-hydroxybenzyl-(CH₂)- | H | C=O | (S)-isobutyl-(CH)- | 3-(aminomethyl)benzyl (NH) |
| 777 | (R)-H₂NOC-(CH₂)- | (S)-4-hydroxybenzyl-(CH₂)- | H | C=O | (S)-isobutyl-(CH)- | 3-(aminomethyl)benzyl (NH) |
| 778 | (R)-HO₂C-(CH₂)- | (S)-4-hydroxybenzyl-(CH₂)- | H | C=O | (S)-isobutyl-(CH)- | 3-(aminomethyl)benzyl (NH) |

TABLE 3B-continued

| Cpd | R₁ | R₂ | R₃ | Q | R₄ | R₆ |
|---|---|---|---|---|---|---|
| 779 | (R)- imidazol-4-ylmethyl (CH) | (S)- 4-hydroxybenzyl (CH) | H | C=O | (S)- isobutyl (CH) | 3-methylbenzyl-NH (NH) |
| 780 | (R)- 4-aminobutyl (CH) | (S)- 4-hydroxybenzyl (CH) | H | C=O | (S)- isobutyl (CH) | 3-methylbenzyl-NH (NH) |
| 781 | (R)- propyl (CH) | (S)- 4-hydroxybenzyl (CH) | H | C=O | (S)- isobutyl (CH) | 3-methylbenzyl-NH (NH) |
| 782 | (R)- benzyl (CH) | (S)- 4-hydroxybenzyl (CH) | H | C=O | (S)- isobutyl (CH) | 3-methylbenzyl-NH (NH) |

TABLE 3B-continued

| Cpd | R₁ | R₂ | R₃ | Q | R₄ | R₆ |
|---|---|---|---|---|---|---|
| 783 | (R)-pyrrolidin-2-yl-CH | (S)-4-hydroxybenzyl (CH) | H | C=O | (S)-isobutyl (CH) | 3-methylbenzyl (NH) |
| 784 | (R)-2-hydroxyethyl (CH) | (S)-4-hydroxybenzyl (CH) | H | C=O | (S)-isobutyl (CH) | 3-methylbenzyl (NH) |
| 785 | (R)-(1H-indol-3-yl)methyl (CH) | (S)-4-hydroxybenzyl (CH) | H | C=O | (S)-isobutyl (CH) | 3-methylbenzyl (NH) |
| 786 | (R)-4-hydroxybenzyl (CH) | (S)-4-hydroxybenzyl (CH) | H | C=O | (S)-isobutyl (CH) | 3-methylbenzyl (NH) |

TABLE 3B-continued

| Cpd | R₁ | R₂ | R₃ | Q | R₄ | R₆ |
|---|---|---|---|---|---|---|
| 787 | (R)- isobutyl | (S)- 4-hydroxybenzyl | H | C=O | (S)- isobutyl | 3-(aminomethyl)benzyl |
| 788 | (S)- 1H-imidazol-4-ylmethyl | (S)- 4-hydroxybenzyl | H | C=O | (S)- isobutyl | 3-(aminomethyl)benzyl |
| 789 | (S)- 4-aminobutyl | (S)- 4-hydroxybenzyl | H | C=O | (S)- isobutyl | 3-(aminomethyl)benzyl |
| 790 | (S)- n-propyl | (S)- 4-hydroxybenzyl | H | C=O | (S)- isobutyl | 3-(aminomethyl)benzyl |

TABLE 3B-continued

| Cpd | R1 | R2 | R3 | Q | R4 | R6 |
|---|---|---|---|---|---|---|
| 791 | (S)-CH2-phenyl | (S)-CH2-(4-hydroxyphenyl) | H | C=O | (S)-CH2-CH(CH3)2 | 3-(CH3)-benzyl-NH |
| 792 | (S)-pyrrolidine | (S)-CH2-(4-hydroxyphenyl) | H | C=O | (S)-CH2-CH(CH3)2 | 3-(CH3)-benzyl-NH |
| 793 | (S)-CH2-OH | (S)-CH2-(4-hydroxyphenyl) | H | C=O | (S)-CH2-CH(CH3)2 | 3-(CH3)-benzyl-NH |
| 794 | (S)-CH2-(1H-indol-3-yl) | (S)-CH2-(4-hydroxyphenyl) | H | C=O | (S)-CH2-CH(CH3)2 | 3-(CH3)-benzyl-NH |

TABLE 3B-continued

| Cpd | R₁ | R₂ | R₃ | Q | R₄ | R₆ |
|---|---|---|---|---|---|---|
| 795 | (S)-4-hydroxybenzyl (CH) | (S)-4-hydroxybenzyl (CH) | H | C=O | (S)-isobutyl (CH) | 3-(aminomethyl)benzyl (NH)(H₂C) |
| 796 | (S)-isopropyl (CH) | (S)-4-hydroxybenzyl (CH) | H | C=O | (S)-isobutyl (CH) | 3-(aminomethyl)benzyl (NH)(H₂C) |
| 797 | (R)-1H-indol-3-ylmethyl (CH) | (S)-isopropyl (CH) | H | C=O | (S)-isobutyl (CH) | 3-(aminomethyl)benzyl (NH)(H₂C) |
| 798 | (R)-4-hydroxybenzyl (CH) | (S)-isopropyl (CH) | H | C=O | (S)-isobutyl (CH) | 3-(aminomethyl)benzyl (NH)(H₂C) |

TABLE 3B-continued

| Cpd | R₁ | R₂ | R₃ | Q | R₄ | R₆ |
|---|---|---|---|---|---|---|
| 799 | (S)-CH₂-indole | (S)-CH(CH₃)₂ | H | C=O | (S)-CH₂CH(CH₃)₂ | 3-(CH₂NH)-phenyl-CH₃ |
| 800 | (S)-CH₂-(4-hydroxyphenyl) | (S)-CH(CH₃)₂ | H | C=O | (S)-CH₂CH(CH₃)₂ | 3-(CH₂NH)-phenyl-CH₃ |
| 801 | (S)-(CH₂)₃NHC(=NH)NH₂ | (S)-CH₂-(4-hydroxyphenyl) | H | C=O | (S)-CH₂CH(CH₃)₂ | 3-(CH₂NH)-phenyl-CH₃ |
| 802 | (S)-(CH₂)₃NHC(=NH)NH₂ | (S)-CH₂-indole | H | C=O | (S)-CH₂CH(CH₃)₂ | 3-(CH₂NH)-phenyl-CH₃ |

TABLE 3B-continued

| Cpd | R₁ | R₂ | R₃ | Q | R₄ | R₆ |
|---|---|---|---|---|---|---|
| 803 | (S)- arginine sidechain | (R)- tyrosine sidechain | H | C=O | (S)- isobutyl | 3-methylbenzylamine |
| 804 | (S)- arginine sidechain | (S)- tryptophan sidechain | H | C=O | (S)- isobutyl | 3-methylbenzylamine |
| 805 | (R)- arginine sidechain | (S)- tyrosine sidechain | H | C=O | (S)- isobutyl | 3-methylbenzylamine |
| 806 | (R)- arginine sidechain | (S)- tryptophan sidechain | H | C=O | (S)- isobutyl | 3-methylbenzylamine |

TABLE 3B-continued

| Cpd | R₁ | R₂ | R₃ | Q | R₄ | R₆ |
|---|---|---|---|---|---|---|
| 807 | (R)-(CH)-CH₂CH₂CH₂NHC(=NH)NH₂ | (R)-(CH)-CH₂-C₆H₄-OH | H | C=O | (S)-(CH)-CH₂CH(CH₃)₂ | 3-(H₂C)-C₆H₄-(NH) |
| 808 | (R)-(CH)-CH₂CH₂CH₂NHC(=NH)NH₂ | (R)-(CH)-CH₂-indol-3-yl | H | C=O | (S)-(CH)-CH₂CH(CH₃)₂ | 3-(H₂C)-C₆H₄-(NH) |
| 809 | (R)-(CH)-CH₂-indol-3-yl | (S)-(CH)-CH₂CH₂CH₂NHC(=NH)NH₂ | H | C=O | (S)-(CH)-CH₂CH(CH₃)₂ | 3-(H₂C)-C₆H₄-(NH) |
| 810 | (R)-(CH)-CH₂-C₆H₄-OH | (S)-(CH)-CH₂CH₂CH₂NHC(=NH)NH₂ | H | C=O | (S)-(CH)-CH₂CH(CH₃)₂ | 3-(H₂C)-C₆H₄-(NH) |

TABLE 3B-continued

| Cpd | R₁ | R₂ | R₃ | Q | R₄ | R₆ |
|---|---|---|---|---|---|---|
| 811 | (S)-indol-3-ylmethyl-(CH) | (S)-[H₂N-C(=NH)-NH-(CH₂)₃]-(CH) | H | C=O | (S)-isobutyl-(CH) | 3-(aminomethyl)benzyl (H₂C)-phenyl-(NH) |
| 812 | (S)-4-hydroxybenzyl-(CH) | (S)-[H₂N-C(=NH)-NH-(CH₂)₄]-(CH) | H | C=O | (S)-isobutyl-(CH) | 3-(aminomethyl)benzyl |
| 813 | (R)-indol-3-ylmethyl-(CH) | (R)-[H₂N-C(=NH)-NH-(CH₂)₄]-(CH) | H | C=O | (S)-isobutyl-(CH) | 3-(aminomethyl)benzyl |
| 814 | (R)-4-hydroxybenzyl-(CH) | (R)-[H₂N-C(=NH)-NH-(CH₂)₄]-(CH) | H | C=O | (S)-isobutyl-(CH) | 3-(aminomethyl)benzyl |

TABLE 3B-continued

| Cpd | R₁ | R₂ | R₃ | Q | R₄ | R₆ |
|---|---|---|---|---|---|---|
| 815 | (S)- 1H-indol-3-ylmethyl (CH) | (R)- 4-guanidinobutyl (CH) | H | C=O | (S)- isobutyl (CH) | 3-(aminomethyl)benzyl (NH)(H₂C) |
| 816 | (S)- 4-hydroxybenzyl (CH) | (R)- 4-guanidinobutyl (CH) | H | C=O | (S)- isobutyl (CH) | 3-(aminomethyl)benzyl (NH)(H₂C) |
| 817 | (R)- H₂NOC-CH₂- (CH) | (R)- 1H-indol-3-ylmethyl (CH) | H | CH₂ | (S)- isobutyl (CH) | 3-(aminomethyl)benzyl (NH)(H₂C) |
| 818 | (R)- H₂NOC-CH₂- (CH) | (R)- 4-hydroxybenzyl (CH) | H | CH₂ | (S)- isobutyl (CH) | 3-(aminomethyl)benzyl (NH)(H₂C) |

TABLE 3B-continued
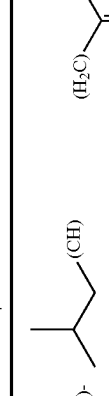
| Cpd | R₁ | R₂ | R₃ | Q | R₄ | R₆ |
|-----|----|----|----|---|----|----|
| 819 | (R)- H₂NOC—(CH) | (S)- indol-3-ylmethyl | H | CH₂ | (S)- isobutyl | 3-(CH₂NH)-benzyl |
| 820 | (R)- H₂NOC—(CH) | (S)- 4-hydroxybenzyl | H | CH₂ | (S)- isobutyl | 3-(CH₂NH)-benzyl |
| 821 | (R)- HO—(CH) | (R)- indol-3-ylmethyl | H | CH₂ | (S)- isobutyl | 3-(CH₂NH)-benzyl |
| 822 | (R)- HO—(CH) | (R)- 4-hydroxybenzyl | H | CH₂ | (S)- isobutyl | 3-(CH₂NH)-benzyl |

TABLE 3B-continued

| Cpd | R₁ | R₂ | R₃ | Q | R₄ | R₆ |
|---|---|---|---|---|---|---|
| 823 | (R)- HO-CH₂-(CH) | (S)- indol-3-ylmethyl-(CH) | H | CH₂ | (S)- isobutyl-(CH) | 3-(H₂C)-phenyl-CH₂-(NH) |
| 824 | (R)- HO-CH₂-(CH) | (S)- 4-hydroxybenzyl-(CH) | H | CH₂ | (S)- isobutyl-(CH) | 3-(H₂C)-phenyl-CH₂-(NH) |
| 825 | (S)- benzyl-(CH) | (S)- H₂NOC-CH₂-(CH) | H | CH₂ | (S)- isobutyl-(CH) | 3-(H₂C)-phenyl-CH₂-(NH) |
| 826 | (R)- benzyl-(CH) | (S)- H₂NOC-CH₂-(CH) | H | CH₂ | (S)- isobutyl-(CH) | 3-(H₂C)-phenyl-CH₂-(NH) |

TABLE 3B-continued
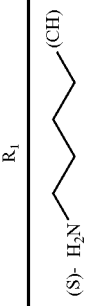
| Cpd | R₁ | R₂ | R₃ | Q | R₄ | R₆ |
|---|---|---|---|---|---|---|
| 827 | (S)- H₂N—(CH)— | (S)- —(CH)—C₆H₅ | H | CH₂ | (S)- —(CH)—CH₂CH(CH₃)₂ | 3-(CH₂)-C₆H₄-(NH) |
| 828 | (R)- H₂N—(CH)— | (R)- —(CH)—C₆H₅ | H | CH₂ | (S)- —(CH)—CH₂CH(CH₃)₂ | 3-(CH₂)-C₆H₄-(NH) |
| 829 | (S)- HO—(CH)— | (S)- —CH₃ | H | CH₂ | (S)- —(CH)—CH₂CH(CH₃)₂ | 3-(CH₂)-C₆H₄-(NH) |
| 830 | (R)- HO—(CH)— | (R)- —CH₃ | H | CH₂ | (S)- —(CH)—CH₂CH(CH₃)₂ | 3-(CH₂)-C₆H₄-(NH) |

TABLE 3B-continued

| Cpd | R1 | R2 | R3 | Q | R4 | R6 |
|---|---|---|---|---|---|---|
| 831 | (S)—CH3 | (S)- 4-hydroxybenzyl | H | CH2 | (S)- isobutyl (CH) | 3-(aminomethyl)benzyl (NH)(H2C) |
| 832 | (R)—CH3 | (R)- 4-hydroxybenzyl | H | CH2 | (S)- isobutyl (CH) | 3-(aminomethyl)benzyl (NH)(H2C) |
| 833 | (R)- indol-3-ylmethyl (CH) | (S)- H2NOC-CH2CH2 (CH) | H | CH2 | (S)- isobutyl (CH) | 3-(aminomethyl)benzyl (NH)(H2C) |
| 834 | (R)- 4-hydroxybenzyl (CH) | (S)- H2NOC-CH2CH2 (CH) | H | CH2 | (S)- isobutyl (CH) | 3-(aminomethyl)benzyl (NH)(H2C) |

TABLE 3B-continued

| Cpd | R₁ | R₂ | R₃ | Q | R₄ | R₆ |
|---|---|---|---|---|---|---|
| 835 | (S)- indol-3-ylmethyl (CH) | (S)- H₂NOC-CH₂- (CH) | H | CH₂ | (S)- isobutyl (CH) | 3-(aminomethyl)benzyl |
| 836 | (S)- 4-hydroxybenzyl (CH) | (S)- H₂NOC-CH₂- (CH) | H | CH₂ | (S)- isobutyl (CH) | 3-(aminomethyl)benzyl |
| 837 | (R)- indol-3-ylmethyl (CH) | (S)- HOCH₂- (CH) | H | CH₂ | (S)- isobutyl (CH) | 3-(aminomethyl)benzyl |
| 838 | (R)- 4-hydroxybenzyl (CH) | (S)- HOCH₂- (CH) | H | CH₂ | (S)- isobutyl (CH) | 3-(aminomethyl)benzyl |

TABLE 3B-continued

| Cpd | R₁ | R₂ | R₃ | Q | R₄ | R₆ |
|---|---|---|---|---|---|---|
| 839 | (S)- 1H-indol-3-ylmethyl (CH) | (S)- HOCH₂ (CH) | H | CH₂ | (S)- isobutyl (CH) | 3-(H₂C)-phenyl-(NH) |
| 840 | (S)- 4-hydroxybenzyl (CH) | (S)- HOCH₂ (CH) | H | CH₂ | (S)- isobutyl (CH) | 3-(H₂C)-phenyl-(NH) |
| 841 | (S)- H₂N-(CH₂)₄- (CH) | (S)- HOCH₂ (CH) | H | CH₂ | (S)- isobutyl (CH) | 3-(H₂C)-phenyl-(NH) |
| 842 | (R)- H₂N-(CH₂)₄- (CH) | (S)- HOCH₂ (CH) | H | CH₂ | (S)- isobutyl (CH) | 3-(H₂C)-phenyl-(NH) |

TABLE 3B-continued

| Cpd | R₁ | R₂ | R₃ | Q | R₄ | R₆ |
|---|---|---|---|---|---|---|
| 843 | (S)- benzyl | H | Me | CH₂ | (S)- isobutyl | 3-(aminomethyl)benzyl (NH/H₂C) |
| 844 | (R)- benzyl | H | Me | CH₂ | (S)- isobutyl | 3-(aminomethyl)benzyl (NH/H₂C) |
| 845 | (S)- H₂N-(CH₂)₄- | H | Me | CH₂ | (S)- isobutyl | 3-(aminomethyl)benzyl (NH/H₂C) |
| 846 | (R)- H₂N-(CH₂)₄- | H | Me | CH₂ | (S)- isobutyl | 3-(aminomethyl)benzyl (NH/H₂C) |

TABLE 3B-continued

| Cpd | R₁ | R₂ | R₃ | Q | R₄ | R₆ |
|---|---|---|---|---|---|---|
| 847 | (S)- HO—(CH)— | H | Me | CH₂ | (S)- isobutyl (CH) | 3-(H₂C)-benzyl (NH) |
| 848 | (R)- HO—(CH)— | H | Me | CH₂ | (S)- isobutyl (CH) | 3-(H₂C)-benzyl (NH) |
| 849 | (S)—CH₃ | H | Me | CH₂ | (S)- isobutyl (CH) | 3-(H₂C)-benzyl (NH) |
| 850 | (R)—CH₃ | H | Me | CH₂ | (S)- isobutyl (CH) | 3-(H₂C)-benzyl (NH) |

TABLE 3B-continued

| Cpd | R₁ | R₂ | R₃ | Q | R₄ | R₆ |
|---|---|---|---|---|---|---|
| 851 | (R)- 1H-indol-3-ylmethyl (CH) | H | Me | CH₂ | (S)- isobutyl (CH) | 3-(aminomethyl)benzyl (NH)(H₂C) |
| 852 | (R)- 4-hydroxybenzyl (CH) | H | Me | CH₂ | (S)- isobutyl (CH) | 3-(aminomethyl)benzyl (NH)(H₂C) |
| 853 | (S)- 1H-indol-3-ylmethyl (CH) | H | Me | CH₂ | (S)- isobutyl (CH) | 3-(aminomethyl)benzyl (NH)(H₂C) |
| 854 | (S)- 4-hydroxybenzyl (CH) | H | Me | CH₂ | (S)- isobutyl (CH) | 3-(aminomethyl)benzyl (NH)(H₂C) |

TABLE 3B-continued

| Cpd | R₁ | R₂ | R₃ | Q | R₄ | R₆ |
|---|---|---|---|---|---|---|
| 855 | (S)- H₂N-CH₂-CH₂- | H | Me | CH₂ | (S)- isobutyl | 3-(aminomethyl)benzyl (NH/H₂C) |
| 856 | (R)- H₂N-CH₂-CH₂- | H | Me | CH₂ | (S)- isobutyl | 3-(aminomethyl)benzyl (NH/H₂C) |
| 857 | (S)- guanidinopropyl | (R)- benzyl | Me | CH₂ | (S)- isobutyl | 3-(aminomethyl)benzyl (NH/H₂C) |
| 858 | (R)- guanidinopropyl | (R)- benzyl | Me | CH₂ | (S)- isobutyl | 3-(aminomethyl)benzyl (NH/H₂C) |

TABLE 3B-continued

| Cpd | R₁ | R₂ | R₃ | Q | R₄ | R₆ |
|---|---|---|---|---|---|---|
| 859 | (S)- H₂N-CH₂-CH₂- (CH) | (S)- H₂NOC-CH₂- (CH) | H | CH₂ | (S)- isobutyl (CH) | 3-methylbenzyl-NH |
| 860 | (R)- H₂N-CH₂-CH₂- (CH) | (R)- H₂NOC-CH₂- (CH) | H | CH₂ | (S)- isobutyl (CH) | 3-methylbenzyl-NH |
| 861 | (S)- guanidino-butyl (CH) | (S)- benzyl (CH) | H | CH₂ | (S)- isobutyl (CH) | 3-methylbenzyl-NH |
| 862 | (R)- guanidino-butyl (CH) | (R)- benzyl (CH) | H | CH₂ | (S)- isobutyl (CH) | 3-methylbenzyl-NH |

TABLE 3B-continued

| Cpd | R₁ | R₂ | R₃ | Q | R₄ | R₆ |
|---|---|---|---|---|---|---|
| 863 | (S)-isopropyl (CH) | (S)-4-hydroxybenzyl (CH) | H | CH₂ | (S)-isobutyl (CH) | 3-(aminomethyl)benzyl (NH)(H₂C) |
| 864 | (R)-isopropyl (CH) | (R)-4-hydroxybenzyl (CH) | H | CH₂ | (S)-isobutyl (CH) | 3-(aminomethyl)benzyl (NH)(H₂C) |
| 865 | (S)-(1H-imidazol-4-yl)methyl (CH) | (S)-H₂NOC-CH₂- (CH) | H | CH₂ | (S)-isobutyl (CH) | 3-(aminomethyl)benzyl (NH)(H₂C) |
| 866 | (R)-(1H-imidazol-4-yl)methyl (CH) | (S)-H₂NOC-CH₂- (CH) | H | CH₂ | (S)-isobutyl (CH) | 3-(aminomethyl)benzyl (NH)(H₂C) |

TABLE 3B-continued

| Cpd | R₁ | R₂ | R₃ | Q | R₄ | R₆ |
|---|---|---|---|---|---|---|
| 867 | (S)-pyrrolidine | (S)- H₂NOC-CH₂-(CH) | H | CH₂ | (S)- isobutyl (CH) | 3-(H₂C)-benzyl (NH) |
| 868 | (R)-pyrrolidine | (S)- H₂NOC-CH₂-(CH) | H | CH₂ | (S)- isobutyl (CH) | 3-(H₂C)-benzyl (NH) |
| 869 | (S)-imidazolylmethyl (CH) | (S)- HO-CH₂-(CH) | H | CH₂ | (S)- isobutyl (CH) | 3-(H₂C)-benzyl (NH) |
| 870 | (R)-imidazolylmethyl (CH) | (S)- HO-CH₂-(CH) | H | CH₂ | (S)- isobutyl (CH) | 3-(H₂C)-benzyl (NH) |

TABLE 3B-continued

| Cpd | R₁ | R₂ | R₃ | Q | R₄ | R₆ |
|-----|-----|-----|-----|-----|-----|-----|
| 871 | (S)- pyrrolidine (CH) | (S)- HO-(CH) | H | CH₂ | (S)- isobutyl (CH) | 3-(H₂C)-benzyl (NH) |
| 872 | (R)- pyrrolidine (CH) | (S)- HO-(CH) | H | CH₂ | (S)- isobutyl (CH) | 3-(H₂C)-benzyl (NH) |
| 873 | (S)- imidazole-CH₂ (CH) | (R)- H₂NOC-(CH) | H | CH₂ | (S)- isobutyl (CH) | 3-(H₂C)-benzyl (NH) |
| 874 | (R)- imidazole-CH₂ (CH) | (R)- H₂NOC-(CH) | H | CH₂ | (S)- isobutyl (CH) | 3-(H₂C)-benzyl (NH) |

TABLE 3B-continued

| Cpd | R₁ | R₂ | R₃ | Q | R₄ | R₆ |
|---|---|---|---|---|---|---|
| 875 | (S)- pyrrolidinyl-CH | (R)- H₂NOC-CH₂-(CH) | H | CH₂ | (S)- isobutyl (CH) | 3-(H₂C)-phenyl-(NH) |
| 876 | (S)- pyrrolidinyl-CH | (R)- H₂NOC-CH₂-(CH) | H | CH₂ | (S)- isobutyl (CH) | 3-(H₂C)-phenyl-(NH) |
| 877 | (S)- imidazolyl-CH₂-(CH) | (R)- HO-CH₂-(CH) | H | CH₂ | (S)- isobutyl (CH) | 3-(H₂C)-phenyl-(NH) |
| 878 | (R)- imidazolyl-CH₂-(CH) | (R)- HO-CH₂-(CH) | H | CH₂ | (S)- isobutyl (CH) | 3-(H₂C)-phenyl-(NH) |

TABLE 3B-continued
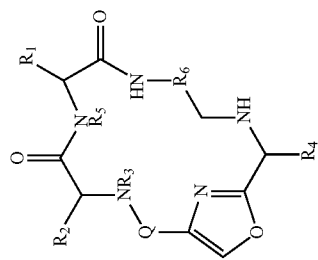
| Cpd | R₁ | R₂ | R₃ | Q | R₄ | R₆ |
|---|---|---|---|---|---|---|
| 879 | (S)-pyrrolidinylmethyl | (R)-HOCH₂- | H | CH₂ | (S)-isobutyl | 3-(aminomethyl)phenyl |
| 880 | (R)-pyrrolidinylmethyl | (R)-HOCH₂- | H | CH₂ | (S)-isobutyl | 3-(aminomethyl)phenyl |
| 881 | (R)-indol-3-ylmethyl | (S)-HO-CH(CH₃)- | H | CH₂ | (S)-isobutyl | 3-(aminomethyl)phenyl |
| 882 | (R)-4-hydroxybenzyl | (R)-HO-CH(CH₃)- | H | CH₂ | (S)-isobutyl | 3-(aminomethyl)phenyl |

TABLE 3B-continued

| Cpd | R₁ | R₂ | R₃ | Q | R₄ | R₆ |
|---|---|---|---|---|---|---|
| 883 | (R)- 1H-indol-3-yl-CH₂-(CH) | (R)- HO-CH(CH₃)- (CH) | H | CH₂ | (S)- isobutyl (CH) | 3-(H₃C)-C₆H₄-CH₂-(NH) |
| 884 | (S)- 4-HO-C₆H₄-CH₂-(CH) | (R)- HO-CH(CH₃)- (CH) | H | CH₂ | (S)- isobutyl (CH) | 3-(H₃C)-C₆H₄-CH₂-(NH) |
| 885 | (S)- H₂N-(CH₂)₄-(CH) | (R)- HO-CH(CH₃)- (CH) | H | CH₂ | (S)- isobutyl (CH) | 3-(H₃C)-C₆H₄-CH₂-(NH) |
| 886 | (R)- H₂N-(CH₂)₄-(CH) | (R)- HO-CH(CH₃)- (CH) | H | CH₂ | (S)- isobutyl (CH) | 3-(H₃C)-C₆H₄-CH₂-(NH) |

TABLE 3B-continued

| Cpd | R₁ | R₂ | R₃ | Q | R₄ | R₆ |
|---|---|---|---|---|---|---|
| 887 | (S)-benzyl | (R)-CH(OH)CH₃ | H | CH₂ | (S)-isobutyl | 3-(aminomethyl)benzyl |
| 888 | (R)-benzyl | (R)-CH(OH)CH₃ | H | CH₂ | (S)-isobutyl | 3-(aminomethyl)benzyl |
| 889 | (S)-CH(CH₂NH₂) | (R)-CH(OH)CH₃ | H | CH₂ | (S)-isobutyl | 3-(aminomethyl)benzyl |
| 890 | (R)-CH(CH₂NH₂) | (R)-CH(OH)CH₃ | H | CH₂ | (S)-isobutyl | 3-(aminomethyl)benzyl |

TABLE 3B-continued

| Cpd | R₁ | R₂ | R₃ | Q | R₄ | R₆ |
|---|---|---|---|---|---|---|
| 891 | (S)- H₂N-C(=NH)-NH-(CH₂)₃-(CH) | (R)- HO-(CH)-CH₃ | H | CH₂ | (S)- isobutyl (CH) | 3-(CH₂)-C₆H₄-(NH) |
| 892 | (R)- H₂N-C(=NH)-NH-(CH₂)₃-(CH) | (R)- HO-(CH)-CH₃ | H | CH₂ | (S)- isobutyl (CH) | 3-(CH₂)-C₆H₄-(NH) |
| 893 | (S)- isopropyl (CH) | (S)- HO-(CH)-CH₃ | H | CH₂ | (S)- isobutyl (CH) | 3-(CH₂)-C₆H₄-(NH) |
| 894 | (R)- isopropyl (CH) | (R)- HO-(CH)-CH₃ | H | CH₂ | (S)- isobutyl (CH) | 3-(CH₂)-C₆H₄-(NH) |

TABLE 3B-continued

| Cpd | R₁ | R₂ | R₃ | Q | R₄ | R₆ |
|---|---|---|---|---|---|---|
| 895 | (S)- histidine sidechain | (S)- hydroxypropyl | H | CH₂ | (S)- isobutyl | 3-(aminomethyl)benzyl |
| 896 | (R)- histidine sidechain | (R)- hydroxypropyl | H | CH₂ | (S)- isobutyl | 3-(aminomethyl)benzyl |
| 897 | (R)- tryptophan sidechain | (S)- arginine sidechain | H | CH₂ | (S)- isobutyl | 3-(aminomethyl)benzyl |
| 898 | (R)- tyrosine sidechain | (S)- arginine sidechain | H | CH₂ | (S)- isobutyl | 3-(aminomethyl)benzyl |

TABLE 3B-continued

| Cpd | R₁ | R₂ | R₃ | Q | R₄ | R₆ |
|---|---|---|---|---|---|---|
| 899 | (S)- indol-3-yl-CH₂-CH(CH) | (S)- -(CH₂)₄-NH-C(=NH)-NH₂ (CH) | H | CH₂ | (S)- isobutyl (CH) | 3-(CH₂)-phenyl-CH₂-(NH) |
| 900 | (S)- 4-hydroxyphenyl-CH₂-CH(CH) | (S)- -(CH₂)₄-NH-C(=NH)-NH₂ (CH) | H | CH₂ | (S)- isobutyl (CH) | 3-(CH₂)-phenyl-CH₂-(NH) |
| 901 | (S)- phenyl-CH₂-CH(CH) | (S)- -(CH₂)₄-NH-C(=NH)-NH₂ (CH) | H | CH₂ | (S)- isobutyl (CH) | 3-(CH₂)-phenyl-CH₂-(NH) |
| 902 | (R)- phenyl-CH₂-CH(CH) | (S)- -(CH₂)₄-NH-C(=NH)-NH₂ (CH) | H | CH₂ | (S)- isobutyl (CH) | 3-(CH₂)-phenyl-CH₂-(NH) |

TABLE 3B-continued

| Cpd | R₁ | R₂ | R₃ | Q | R₄ | R₆ |
|---|---|---|---|---|---|---|
| 903 | (S)-iPr (CH) | (S)-(CH₂)₃NHC(=NH)NH₂ (CH) | H | CH₂ | (S)-iBu (CH) | 3-(CH₂NH)-benzyl |
| 904 | (R)-iPr (CH) | (S)-(CH₂)₃NHC(=NH)NH₂ (CH) | H | CH₂ | (S)-iBu (CH) | 3-(CH₂NH)-benzyl |
| 905 | (S)-CH₃ | (S)-(CH₂)₃NHC(=NH)NH₂ (CH) | H | CH₂ | (S)-iBu (CH) | 3-(CH₂NH)-benzyl |
| 906 | (R)-CH₃ | (S)-(CH₂)₃NHC(=NH)NH₂ (CH) | H | CH₂ | (S)-iBu (CH) | 3-(CH₂NH)-benzyl |

TABLE 3B-continued

| Cpd | R₁ | R₂ | R₃ | Q | R₄ | R₆ |
|---|---|---|---|---|---|---|
| 907 | (S)- HO-CH₂-CH₂- (CH) | (S)- H₂N-C(=NH)-NH-(CH₂)₃-(CH) | H | CH₂ | (S)- isobutyl (CH) | 3-(aminomethyl)benzyl (NH)(H₂C) |
| 908 | (R)- HO-CH₂-CH₂- (CH) | (S)- H₂N-C(=NH)-NH-(CH₂)₃-(CH) | H | CH₂ | (S)- isobutyl (CH) | 3-(aminomethyl)benzyl (NH)(H₂C) |
| 909 | (R)- indol-3-ylmethyl (CH) | (R)- H₂N-C(=NH)-NH-(CH₂)₃-(CH) | H | CH₂ | (S)- isobutyl (CH) | 3-(aminomethyl)benzyl (NH)(H₂C) |
| 910 | (R)- 4-hydroxybenzyl (CH) | (R)- H₂N-C(=NH)-NH-(CH₂)₃-(CH) | H | CH₂ | (S)- isobutyl (CH) | 3-(aminomethyl)benzyl (NH)(H₂C) |

TABLE 3B-continued

| Cpd | R₁ | R₂ | R₃ | Q | R₄ | R₆ |
|---|---|---|---|---|---|---|
| 911 | (S)-(CH)-CH₂-indole | (R)-(CH)-(CH₂)₃-NH-C(NH)-NH₂ | H | CH₂ | (S)-(CH)-CH₂-CH(CH₃)₂ | 3-(H₂C)-C₆H₄-(NH) |
| 912 | (S)-(CH)-CH₂-(4-hydroxyphenyl) | (R)-(CH)-(CH₂)₃-NH-C(NH)-NH₂ | H | CH₂ | (S)-(CH)-CH₂-CH(CH₃)₂ | 3-(H₂C)-C₆H₄-(NH) |
| 913 | (S)-(CH)-CH₂-phenyl | (R)-(CH)-(CH₂)₃-NH-C(NH)-NH₂ | H | CH₂ | (S)-(CH)-CH₂-CH(CH₃)₂ | 3-(H₂C)-C₆H₄-(NH) |
| 914 | (R)-(CH)-CH₂-phenyl | (R)-(CH)-(CH₂)₃-NH-C(NH)-NH₂ | H | CH₂ | (S)-(CH)-CH₂-CH(CH₃)₂ | 3-(H₂C)-C₆H₄-(NH) |

TABLE 3B-continued
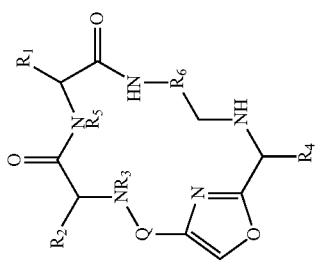
| Cpd | R₁ | R₂ | R₃ | Q | R₄ | R₆ |
|---|---|---|---|---|---|---|
| 915 | (S)-iPr | (R)-(CH₂)₃NHC(=NH)NH₂ | H | CH₂ | (S)-iBu | 3-(aminomethyl)benzyl |
| 916 | (R)-iPr | (R)-(CH₂)₃NHC(=NH)NH₂ | H | CH₂ | (S)-iBu | 3-(aminomethyl)benzyl |
| 917 | (S)-CH₃ | (R)-(CH₂)₃NHC(=NH)NH₂ | H | CH₂ | (S)-iBu | 3-(aminomethyl)benzyl |
| 918 | (R)-CH₃ | (R)-(CH₂)₃NHC(=NH)NH₂ | H | CH₂ | (S)-iBu | 3-(aminomethyl)benzyl |

TABLE 3B-continued

| Cpd | R₁ | R₂ | R₃ | Q | R₄ | R₆ |
|---|---|---|---|---|---|---|
| 919 | (S)- CH₂CH₂OH | (R)- (CH₂)₃NHC(=NH)NH₂ | H | CH₂ | (S)- CH₂CH(CH₃)₂ | 3-(aminomethyl)benzyl |
| 920 | (R)- CH₂CH₂OH | (R)- (CH₂)₃NHC(=NH)NH₂ | H | CH₂ | (S)- CH₂CH(CH₃)₂ | 3-(aminomethyl)benzyl |
| 921 | (R)- CH₂-(1H-indol-3-yl) | (S)- pyrrolidin-2-yl-CH₂ | H | CH₂ | (S)- CH₂CH(CH₃)₂ | 3-(aminomethyl)benzyl |
| 922 | (R)- CH₂-(4-hydroxyphenyl) | (S)- pyrrolidin-2-yl-CH₂ | H | CH₂ | (S)- CH₂CH(CH₃)₂ | 3-(aminomethyl)benzyl |

TABLE 3B-continued

| Cpd | R₁ | R₂ | R₃ | Q | R₄ | R₆ |
|---|---|---|---|---|---|---|
| 923 | (S)- HO-(CH)- | (S)- pyrrolidine-(HC)- | H | CH₂ | (S)- isobutyl-(CH) | 3-(H₂C)-phenyl-(NH) |
| 924 | (R)- HO-(CH)- | (S)- pyrrolidine-(HC)- | H | CH₂ | (S)- isobutyl-(CH) | 3-(H₂C)-phenyl-(NH) |
| 925 | (S)- HO₂C-(CH)- | (S)- pyrrolidine-(HC)- | H | CH₂ | (S)- isobutyl-(CH) | 3-(H₂C)-phenyl-(NH) |
| 926 | (R)- HO₂C-(CH)- | (S)- pyrrolidine-(HC)- | H | CH₂ | (S)- isobutyl-(CH) | 3-(H₂C)-phenyl-(NH) |

TABLE 3B-continued

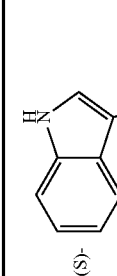

| Cpd | R₁ | R₂ | R₃ | Q | R₄ | R₆ |
|---|---|---|---|---|---|---|
| 927 | (S)- indol-3-ylmethyl-(CH) | (R)-pyrrolidin-2-yl-(HC) | H | CH₂ | (S)-isobutyl-(CH) | 3-(aminomethyl)benzyl (NH/H₂C) |
| 928 | (R)-4-hydroxybenzyl-(CH) | (R)-pyrrolidin-2-yl-(HC) | H | CH₂ | (S)-isobutyl-(CH) | 3-(aminomethyl)benzyl (NH/H₂C) |
| 929 | (S)-hydroxymethyl-(CH) HO- | (R)-pyrrolidin-2-yl-(HC) | H | CH₂ | (S)-isobutyl-(CH) | 3-(aminomethyl)benzyl (NH/H₂C) |
| 930 | (R)-hydroxymethyl-(CH) HO- | (R)-pyrrolidin-2-yl-(HC) | H | CH₂ | (S)-isobutyl-(CH) | 3-(aminomethyl)benzyl (NH/H₂C) |

TABLE 3B-continued

| Cpd | R₁ | R₂ | R₃ | Q | R₄ | R₆ |
|-----|----|----|----|---|----|----|
| 931 | (S)- H₂NOC-(CH)-propyl | (R)-pyrrolidine-(HC)- | H | CH₂ | (S)-isobutyl | 3-(H₂C)-benzyl-(NH) |
| 932 | (R)- H₂NOC-(CH)-propyl | (R)-pyrrolidine-(HC)- | H | CH₂ | (S)-isobutyl | 3-(H₂C)-benzyl-(NH) |
| 933 | (S)-(CH)-propyl | (R)-isopropyl-(CH) | H | C=O | (R)-benzyl-(CH) | 2-(H₂C)O-, 2-(HN)CH₂CH₂O-, 5-F-phenyl |

TABLE 3B-continued
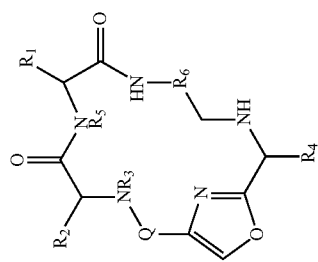
| Cpd | R₁ | R₂ | R₃ | Q | R₄ | R₆ |
|---|---|---|---|---|---|---|
| 934 | (S)-(CH)-propyl | (R)-(CH)-isopropyl | H | C=O | (S)-(CH)-benzyl | (HN)-(CH₂)-2-(2-ethoxy-5-fluorophenoxy)ethyl |
| 935 | (R)-(CH)-propyl | (R)-(CH)-isopropyl | H | C=O | (R)-(CH)-benzyl | (HN)-(CH₂)-2-(2-ethoxy-5-fluorophenoxy)ethyl |

TABLE 3B-continued
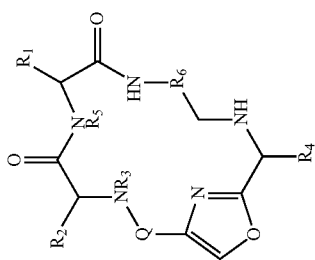
| Cpd | R$_1$ | R$_2$ | NR$_3$ | R$_3$ | Q | R$_4$ | R$_6$ |
|---|---|---|---|---|---|---|---|
| 936 | (R)- propyl (CH) | (R)- isobutyl (CH) | | H | C=O | (S)- benzyl (CH) | 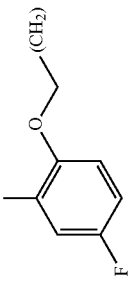 |
| 937 | (S)- propyl (CH) | (S)- isobutyl (CH) | | H | C=O | (R)- benzyl (CH) | 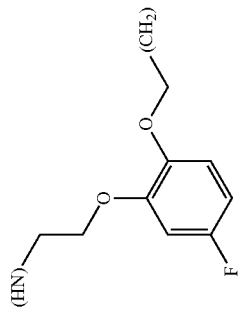 |

TABLE 3B-continued
| Cpd | R₁ | R₂ | R₃ | Q | R₄ | R₆ |
|---|---|---|---|---|---|---|
| 938 | (S)- 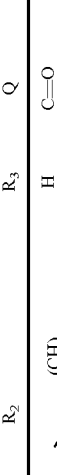 (CH) | (S)- 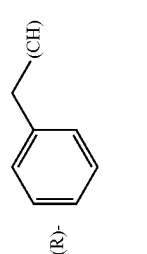 (CH) | H | C=O | (S)- 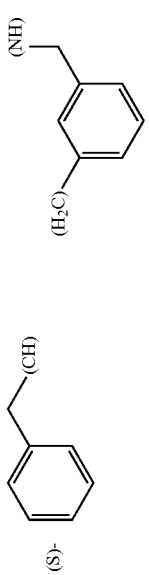 (CH) |  |
| 939 | (S)- 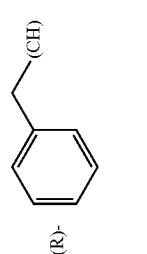 (CH) | (R)- 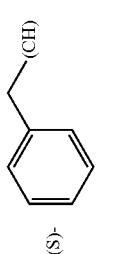 (CH) | H | C=O | (R)-  (CH) | 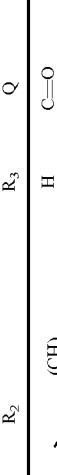 |
| 940 | (S)- 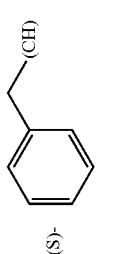 (CH) | (R)-  (CH) | H | C=O | (S)- 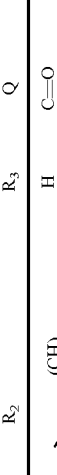 (CH) | 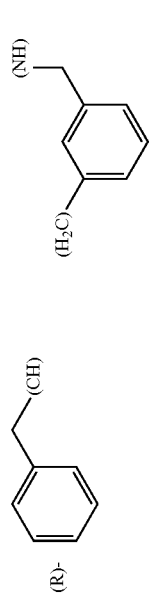 |

TABLE 3B-continued

| Cpd | R₁ | R₂ | R₃ | Q | R₄ | R₆ |
|---|---|---|---|---|---|---|
| 941 | (R)-propyl (CH) | (R)-isopropyl (CH) | H | C=O | (R)-benzyl (CH) | 3-(CH₂)-phenyl-(NH) |
| 942 | (R)-propyl (CH) | (R)-isopropyl (CH) | H | C=O | (S)-benzyl (CH) | 3-(CH₂)-phenyl-(NH) |
| 943 | (S)-propyl (CH) | (S)-isopropyl (CH) | H | C=O | (R)-benzyl (CH) | 3-(CH₂)-phenyl-(NH) |
| 944 | (S)-propyl (CH) | (S)-isopropyl (CH) | H | C=O | (S)-benzyl (CH) | 3-(CH₂)-phenyl-(NH) |

TABLE 3B-continued

| Cpd | R$_1$ | R$_2$ | R$_3$ | Q | R$_4$ | R$_6$ |
|---|---|---|---|---|---|---|
| 945 | (R)-, (CH), propyl | (S)-, (CH), isopropyl | H | C=O | (R)-, (CH), benzyl | (HN)-CH$_2$-(2-(2-hydroxyethoxy)-5-fluorophenoxy) ethyl |
| 946 | (R)-, (CH), propyl | (S)-, (CH), isopropyl | H | C=O | (S)-, (CH), benzyl | (HN)-CH$_2$-(2-(2-hydroxyethoxy)-5-fluorophenoxy) ethyl |
| 947 | (R)-, (CH), propyl | (S)-, (CH), isopropyl | H | C=O | (R)-, (CH), benzyl | (NH)-CH$_2$-phenyl-CH$_2$- |

TABLE 3B-continued
| Cpd | R₁ | R₂ | R₃ | Q | R₄ | R₆ |
|---|---|---|---|---|---|---|
| 948 | (R)- 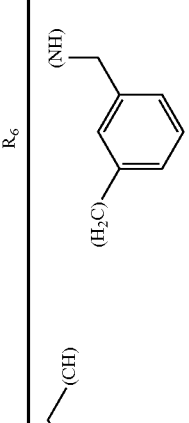 (CH) | (S)- 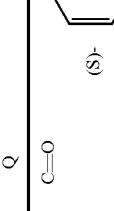 (CH) | H | C=O | (S)- 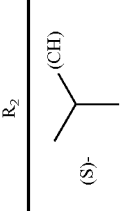 (CH) | 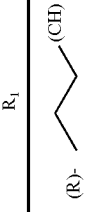 (NH) |

For all compounds $R_5$=H, except for those compounds in which Fmoc-Pro or Fmoc-D-Pro is the $BB_1$ component wherein $R_1$ and $(N)R_5$ form a five-membered ring, including the nitrogen atom, as shown for $R_1$ in Table 3B. Similarly, compounds in which $BB_2$ is Fmoc-Pro or Fmoc-D-Pro have $(N)R_3$ and $R_2$ are part of a five-membered ring, including the nitrogen atom, as shown for a combined $R_2$-$R_3$ in Table 3B.

Example 5

Synthesis of a Representative Library of Macrocyclic Compounds of Formula (Ie)

The series of synthetic schemes in Schemes 5, 6 and 7 were employed for the solid phase construction of macrocyclic compounds 1001-1065, 1066-1142 and 1143-1189, respectively. For all of the compounds, the first amino acid building block amino acid ($BB_1$) was loaded onto the resin (Method 1D). For compounds 1001-1065 and 1143-1189, the second amino acid building block ($BB_2$) was attached through peptide coupling (Method 1G) following Fmoc deprotection (Method 1F). $BB_2$ was added using reductive amination (Method 1I or 1J) for the remaining compounds (1066-1142). For this latter set of macrocycles (1066-1142), as well as compounds 1001-1065, the third building block ($BB_3$) was installed after Fmoc deprotection (Method 1F) via amide bond formation (Method 1G), while for 1143-1189, reductive amination (Method 1I or 1J) was employed for $BB_3$. After Fmoc removal ((Method 1F), addition of the oxazole building block ($BB_4$) for all compounds was performed using reductive amination (Method 1J) or amide bond formation (Method 1G). With each scheme, deprotection of the Fmoc moiety (Method 1F), resin cleavage (Method 1Q), macrocycle formation (Method 1R) and removal of the side chain protection (Method 1S) were followed by evaporation in vacuo to yield the crude macrocycle. Upon purification by preparative HPLC (Method 2B), the desired macrocyclic library compounds were obtained. For each macrocycle, the quantities, purity (HPLC) and identity conformation (MS) are presented in Table 4A, with the structures shown in Tables 4B, 4C and 4D.

TABLE 4A

| Cpd | $BB_1$ | $BB_2$ | $BB_3$ | $BB_4$ | Wt (mg)[1] | Purity[2] | MS (M + H) |
|---|---|---|---|---|---|---|---|
| 1001 | Fmoc-D-Asn(Trt) | Fmoc-D-Trp(Boc) | Fmoc-Lys(Boc) | Fmoc-OX-13 | 19.8 | 100 | 595 |
| 1002 | Fmoc-D-Asn(Trt) | Fmoc-D-Tyr(But) | Fmoc-Lys(Boc) | Fmoc-OX-13 | 16.9 | 100 | 572 |
| 1003 | Fmoc-D-Asn(Trt) | Fmoc-Trp(Boc) | Fmoc-Lys(Boc) | Fmoc-OX-13 | 20.7 | 88 | 595 |
| 1004 | Fmoc-D-Asn(Trt) | Fmoc-Tyr(But) | Fmoc-Lys(Boc) | Fmoc-OX-13 | 25.6 | 100 | 572 |
| 1005 | Fmoc-D-Ser(But) | Fmoc-D-Trp(Boc) | Fmoc-Lys(Boc) | Fmoc-OX-13 | 17.4 | 100 | 568 |
| 1006 | Fmoc-D-Ser(But) | Fmoc-D-Tyr(But) | Fmoc-Lys(Boc) | Fmoc-OX-13 | 9.7 | 100 | 545 |
| 1007 | Fmoc-D-Ser(But) | Fmoc-Trp(Boc) | Fmoc-Lys(Boc) | Fmoc-OX-13 | 25.9 | 100 | 568 |
| 1008 | Fmoc-D-Ser(But) | Fmoc-Tyr(But) | Fmoc-Lys(Boc) | Fmoc-OX-13 | 23.6 | 100 | 545 |
| 1009 | Fmoc-Lys(Boc) | Fmoc-Ser(But) | Fmoc-Asp(OBut) | Fmoc-OX-13 | 15.1 | 100 | 497 |
| 1010 | Fmoc-D-Asn(Trt) | Fmoc-D-Trp(Boc) | Fmoc-D-Lys(Boc) | Fmoc-OX-13 | 13.5 | 100 | 595 |
| 1011 | Fmoc-D-Asn(Trt) | Fmoc-D-Tyr(But) | Fmoc-D-Lys(Boc) | Fmoc-OX-13 | 9.6 | 82 | 572 |
| 1012 | Fmoc-D-Asn(Trt) | Fmoc-Trp(Boc) | Fmoc-D-Lys(Boc) | Fmoc-OX-13 | 12.5 | 100 | 595 |
| 1013 | Fmoc-D-Asn(Trt) | Fmoc-Tyr(But) | Fmoc-D-Lys(Boc) | Fmoc-OX-13 | 11.2 | 100 | 572 |
| 1014 | Fmoc-D-Ser(But) | Fmoc-D-Trp(Boc) | Fmoc-D-Lys(Boc) | Fmoc-OX-13 | 13.2 | 100 | 568 |
| 1015 | Fmoc-D-Ser(But) | Fmoc-D-Tyr(But) | Fmoc-D-Lys(Boc) | Fmoc-OX-13 | 10.7 | 100 | 545 |
| 1016 | Fmoc-D-Ser(But) | Fmoc-Trp(Boc) | Fmoc-D-Lys(Boc) | Fmoc-OX-13 | 21.4 | 97 | 568 |
| 1017 | Fmoc-D-Ser(But) | Fmoc-Tyr(But) | Fmoc-D-Lys(Boc) | Fmoc-OX-13 | 19.3 | 100 | 545 |
| 1018 | Fmoc-Asn(Trt) | Fmoc-D-Trp(Boc) | Fmoc-Lys(Boc) | Fmoc-OX-13 | 10.9 | 100 | 595 |
| 1019 | Fmoc-Asn(Trt) | Fmoc-D-Tyr(But) | Fmoc-Lys(Boc) | Fmoc-OX-13 | 20.8 | 100 | 572 |
| 1020 | Fmoc-Asn(Trt) | Fmoc-Trp(Boc) | Fmoc-Lys(Boc) | Fmoc-OX-13 | 4.0 | 92 | 595 |
| 1021 | Fmoc-Asn(Trt) | Fmoc-Tyr(But) | Fmoc-Lys(Boc) | Fmoc-OX-13 | 3.3 | 78 | 572 |
| 1022 | Fmoc-Ser(But) | Fmoc-D-Trp(Boc) | Fmoc-Lys(Boc) | Fmoc-OX-13 | 26.4 | 100 | 568 |
| 1023 | Fmoc-Ser(But) | Fmoc-D-Tyr(But) | Fmoc-Lys(Boc) | Fmoc-OX-13 | 23.0 | 100 | 545 |
| 1024 | Fmoc-Ser(But) | Fmoc-Trp(Boc) | Fmoc-Lys(Boc) | Fmoc-OX-13 | 9.0 | 85 | 568 |
| 1025 | Fmoc-Ser(But) | Fmoc-Tyr(But) | Fmoc-Lys(Boc) | Fmoc-OX-13 | 8.7 | 77 | 545 |
| 1026 | Fmoc-Pro | Fmoc-D-Trp(Boc) | Fmoc-Lys(Boc) | Fmoc-OX-13 | 11.5 | 100 | 578 |
| 1027 | Fmoc-D-Pro | Fmoc-D-Tyr(But) | Fmoc-Lys(Boc) | Fmoc-OX-13 | 5.7 | 93 | 555 |
| 1028 | Fmoc-Pro | Fmoc-Trp(Boc) | Fmoc-Lys(Boc) | Fmoc-OX-13 | 3.0 | 100 | 578 |
| 1029 | Fmoc-D-Pro | Fmoc-Tyr(But) | Fmoc-Lys(Boc) | Fmoc-OX-13 | 24.2 | 100 | 555 |
| 1030 | Fmoc-Pro | Fmoc-D-Trp(Boc) | Fmoc-D-Lys(Boc) | Fmoc-OX-13 | 4.5 | 85 | 578 |
| 1031 | Fmoc-D-Pro | Fmoc-D-Tyr(But) | Fmoc-D-Lys(Boc) | Fmoc-OX-13 | 7.3 | 100 | 555 |
| 1032 | Fmoc-Pro | Fmoc-Trp(Boc) | Fmoc-D-Lys(Boc) | Fmoc-OX-13 | 3.0 | 100 | 578 |
| 1033 | Fmoc-D-Pro | Fmoc-Tyr(But) | Fmoc-D-Lys(Boc) | Fmoc-OX-13 | 26.4 | 100 | 555 |
| 1034 | Fmoc-D-Trp(Boc) | Fmoc-Sar | Fmoc-Lys(Boc) | Fmoc-OX-13 | 2.9 | 100 | 552 |
| 1035 | Fmoc-D-Tyr(But) | Fmoc-Sar | Fmoc-Lys(Boc) | Fmoc-OX-13 | 9.7 | 100 | 529 |
| 1036 | Fmoc-Trp(Boc) | Fmoc-Sar | Fmoc-Lys(Boc) | Fmoc-OX-13 | 12.0 | 100 | 552 |
| 1037 | Fmoc-Tyr(But) | Fmoc-Sar | Fmoc-Lys(Boc) | Fmoc-OX-13 | 18.4 | 100 | 529 |
| 1038 | Fmoc-Phe | Fmoc-Sar | Fmoc-Lys(Boc) | Fmoc-OX-13 | 13.5 | 100 | 513 |
| 1039 | Fmoc-D-Phe | Fmoc-Sar | Fmoc-Lys(Boc) | Fmoc-OX-13 | 6.8 | 100 | 513 |
| 1040 | Fmoc-Val | Fmoc-Sar | Fmoc-Lys(Boc) | Fmoc-OX-13 | 21.8 | 100 | 465 |
| 1041 | Fmoc-D-Val | Fmoc-Sar | Fmoc-Lys(Boc) | Fmoc-OX-13 | 12.9 | 100 | 465 |
| 1042 | Fmoc-Ala | Fmoc-Sar | Fmoc-Lys(Boc) | Fmoc-OX-13 | 11.6 | 100 | 437 |
| 1043 | Fmoc-D-Ala | Fmoc-Sar | Fmoc-Lys(Boc) | Fmoc-OX-13 | 6.6 | 100 | 437 |
| 1044 | Fmoc-Ser(But) | Fmoc-Sar | Fmoc-Lys(Boc) | Fmoc-OX-13 | 17.1 | 100 | 453 |
| 1045 | Fmoc-D-Ser(But) | Fmoc-Sar | Fmoc-Lys(Boc) | Fmoc-OX-13 | 13.8 | 100 | 453 |
| 1046 | Fmoc-Leu | Fmoc-Sar | Fmoc-Lys(Boc) | Fmoc-OX-13 | 15.0 | 100 | 479 |
| 1047 | Fmoc-D-Leu | Fmoc-Sar | Fmoc-Lys(Boc) | Fmoc-OX-13 | 7.9 | 100 | 479 |
| 1048 | Fmoc-Glu(OBut) | Fmoc-Sar | Fmoc-Lys(Boc) | Fmoc-OX-13 | 11.8 | 100 | 495 |
| 1049 | Fmoc-D-Glu(OBut) | Fmoc-Sar | Fmoc-Lys(Boc) | Fmoc-OX-13 | 5.7 | 100 | 495 |
| 1050 | Fmoc-D-Trp(Boc) | Fmoc-Sar | Fmoc-D-Lys(Boc) | Fmoc-OX-13 | 8.8 | 100 | 552 |
| 1051 | Fmoc-D-Tyr(But) | Fmoc-Sar | Fmoc-D-Lys(Boc) | Fmoc-OX-13 | 11.6 | 100 | 529 |

TABLE 4A-continued

| Cpd | BB$_1$ | BB$_2$ | BB$_3$ | BB$_4$ | Wt (mg)[1] | Purity[2] | MS (M + H) |
|---|---|---|---|---|---|---|---|
| 1052 | Fmoc-Trp(Boc) | Fmoc-Sar | Fmoc-D-Lys(Boc) | Fmoc-OX-13 | 3.6 | 100 | 552 |
| 1053 | Fmoc-Tyr(But) | Fmoc-Sar | Fmoc-D-Lys(Boc) | Fmoc-OX-13 | 8.1 | 98 | 529 |
| 1054 | Fmoc-Phe | Fmoc-Sar | Fmoc-D-Lys(Boc) | Fmoc-OX-13 | 8.7 | 100 | 513 |
| 1055 | Fmoc-D-Phe | Fmoc-Sar | Fmoc-D-Lys(Boc) | Fmoc-OX-13 | 8.6 | 100 | 513 |
| 1056 | Fmoc-Val | Fmoc-Sar | Fmoc-D-Lys(Boc) | Fmoc-OX-13 | 16.8 | 100 | 465 |
| 1057 | Fmoc-D-Val | Fmoc-Sar | Fmoc-D-Lys(Boc) | Fmoc-OX-13 | 14.7 | 100 | 465 |
| 1058 | Fmoc-Ala | Fmoc-Sar | Fmoc-D-Lys(Boc) | Fmoc-OX-13 | 4.3 | 100 | 437 |
| 1059 | Fmoc-D-Ala | Fmoc-Sar | Fmoc-D-Lys(Boc) | Fmoc-OX-13 | 10.2 | 100 | 437 |
| 1060 | Fmoc-Ser(But) | Fmoc-Sar | Fmoc-D-Lys(Boc) | Fmoc-OX-13 | 16.8 | 100 | 453 |
| 1061 | Fmoc-D-Ser(But) | Fmoc-Sar | Fmoc-D-Lys(Boc) | Fmoc-OX-13 | 15.0 | 100 | 453 |
| 1062 | Fmoc-Leu | Fmoc-Sar | Fmoc-D-Lys(Boc) | Fmoc-OX-13 | 9.6 | 100 | 479 |
| 1063 | Fmoc-D-Leu | Fmoc-Sar | Fmoc-D-Lys(Boc) | Fmoc-OX-13 | 12.5 | 100 | 479 |
| 1064 | Fmoc-Glu(OBut) | Fmoc-Sar | Fmoc-D-Lys(Boc) | Fmoc-OX-13 | 5.8 | 100 | 495 |
| 1065 | Fmoc-D-Glu(OBut) | Fmoc-Sar | Fmoc-D-Lys(Boc) | Fmoc-OX-13 | 7.8 | 100 | 495 |
| 1066 | Fmoc-D-Asn(Trt) | Fmoc-S30 | Fmoc-Trp(Boc) | Fmoc-OX-13 | 6.0 | 100 | 524 |
| 1067 | Fmoc-Asn(Trt) | Fmoc-S30 | Fmoc-Trp(Boc) | Fmoc-OX-13 | 4.0 | 100 | 524 |
| 1068 | Fmoc-D-His(Trt) | Fmoc-S30 | Fmoc-Trp(Boc) | Fmoc-OX-13 | 1.5 | 100 | 547 |
| 1069 | Fmoc-His(Trt) | Fmoc-S30 | Fmoc-Trp(Boc) | Fmoc-OX-13 | 1.4 | 100 | 547 |
| 1070 | Fmoc-D-Ser(But) | Fmoc-S30 | Fmoc-Trp(Boc) | Fmoc-OX-13 | 3.8 | 100 | 497 |
| 1071 | Fmoc-Ser(But) | Fmoc-S30 | Fmoc-Trp(Boc) | Fmoc-OX-13 | 3.1 | 100 | 497 |
| 1072 | Fmoc-D-Lys(Boc) | Fmoc-S30 | Fmoc-Trp(Boc) | Fmoc-OX-13 | 4.1 | 100 | 538 |
| 1073 | Fmoc-Lys(Boc) | Fmoc-S30 | Fmoc-Trp(Boc) | Fmoc-OX-13 | 5.1 | 100 | 538 |
| 1074 | Fmoc-D-Trp(Boc) | Fmoc-S30 | Fmoc-Lys(Boc) | Fmoc-OX-13 | 2.0 | 100 | 538 |
| 1075 | Fmoc-D-Tyr(But) | Fmoc-S30 | Fmoc-Lys(Boc) | Fmoc-OX-13 | 3.0 | 100 | 515 |
| 1076 | Fmoc-Trp(Boc) | Fmoc-S30 | Fmoc-Lys(Boc) | Fmoc-OX-13 | 1.9 | 99 | 538 |
| 1077 | Fmoc-Tyr(But) | Fmoc-S30 | Fmoc-Lys(Boc) | Fmoc-OX-13 | 3.5 | 100 | 515 |
| 1078 | Fmoc-Phe | Fmoc-S30 | Fmoc-Lys(Boc) | Fmoc-OX-13 | 3.6 | 100 | 499 |
| 1079 | Fmoc-D-Phe | Fmoc-S30 | Fmoc-Lys(Boc) | Fmoc-OX-13 | 4.6 | 93 | 499 |
| 1080 | Fmoc-Val | Fmoc-S30 | Fmoc-Tyr(But) | Fmoc-OX-13 | 1.3 | 88 | 486 |
| 1081 | Fmoc-D-Val | Fmoc-S30 | Fmoc-Tyr(But) | Fmoc-OX-13 | 0.3 | 100 | 486 |
| 1082 | Fmoc-Ala | Fmoc-S30 | Fmoc-Tyr(But) | Fmoc-OX-13 | 0.6 | 100 | 458 |
| 1083 | Fmoc-D-Ala | Fmoc-S30 | Fmoc-Tyr(But) | Fmoc-OX-13 | 1.2 | 100 | 458 |
| 1084 | Fmoc-Ser(But) | Fmoc-S30 | Fmoc-Tyr(But) | Fmoc-OX-13 | 2.6 | 100 | 474 |
| 1085 | Fmoc-D-Ser(But) | Fmoc-S30 | Fmoc-Tyr(But) | Fmoc-OX-13 | 2.7 | 100 | 474 |
| 1086 | Fmoc-Leu | Fmoc-S30 | Fmoc-Tyr(But) | Fmoc-OX-13 | 1.4 | 100 | 500 |
| 1087 | Fmoc-D-Leu | Fmoc-S30 | Fmoc-Tyr(But) | Fmoc-OX-13 | 1.3 | 100 | 500 |
| 1088 | Fmoc-Glu(OBut) | Fmoc-S30 | Fmoc-Tyr(But) | Fmoc-OX-13 | na | na | na |
| 1089 | Fmoc-D-Glu(OBut) | Fmoc-S30 | Fmoc-Tyr(But) | Fmoc-OX-13 | 0.8 | 80 | 516 |
| 1090 | Fmoc-D-Trp(Boc) | Fmoc-S30 | Fmoc-D-Lys(Boc) | Fmoc-OX-13 | 2.1 | 100 | 538 |
| 1091 | Fmoc-D-Tyr(But) | Fmoc-S30 | Fmoc-D-Lys(Boc) | Fmoc-OX-13 | 3.7 | 100 | 515 |
| 1092 | Fmoc-Trp(Boc) | Fmoc-S30 | Fmoc-D-Lys(Boc) | Fmoc-OX-13 | 1.5 | 76 | 538 |
| 1093 | Fmoc-Tyr(But) | Fmoc-S30 | Fmoc-D-Lys(Boc) | Fmoc-OX-13 | 2.0 | 78 | 515 |
| 1094 | Fmoc-Phe | Fmoc-S30 | Fmoc-D-Lys(Boc) | Fmoc-OX-13 | 3.3 | na | na |
| 1095 | Fmoc-D-Phe | Fmoc-S30 | Fmoc-D-Lys(Boc) | Fmoc-OX-13 | 2.9 | 100 | 499 |
| 1096 | Fmoc-Val | Fmoc-S30 | Fmoc-D-Tyr(But) | Fmoc-OX-13 | 0.5 | 100 | 486 |
| 1097 | Fmoc-D-Val | Fmoc-S30 | Fmoc-D-Tyr(But) | Fmoc-OX-13 | 1.7 | 100 | 486 |
| 1098 | Fmoc-Ala | Fmoc-S30 | Fmoc-D-Tyr(But) | Fmoc-OX-13 | 1.4 | na | na |
| 1099 | Fmoc-D-Ala | Fmoc-S30 | Fmoc-D-Tyr(But) | Fmoc-OX-13 | 0.9 | 100 | 458 |
| 1100 | Fmoc-Ser(But) | Fmoc-S30 | Fmoc-D-Tyr(But) | Fmoc-OX-13 | 1.8 | 100 | 474 |
| 1101 | Fmoc-D-Ser(But) | Fmoc-S30 | Fmoc-D-Tyr(But) | Fmoc-OX-13 | 2.6 | 100 | 474 |
| 1102 | Fmoc-Leu | Fmoc-S30 | Fmoc-D-Tyr(But) | Fmoc-OX-13 | 0.6 | 100 | 500 |
| 1103 | Fmoc-D-Leu | Fmoc-S30 | Fmoc-D-Tyr(But) | Fmoc-OX-13 | 1.6 | 89 | 500 |
| 1104 | Fmoc-Glu(OBut) | Fmoc-S30 | Fmoc-D-Tyr(But) | Fmoc-OX-13 | 3.3 | 100 | 516 |
| 1105 | Fmoc-D-Glu(OBut) | Fmoc-S30 | Fmoc-D-Tyr(But) | Fmoc-OX-13 | 0.4 | 77 | 516 |
| 1106 | Fmoc-Trp(Boc) | Fmoc-S31 | Fmoc-D-Lys(Boc) | Fmoc-OX-13 | 0.5 | 45 | 538 |
| 1107 | Fmoc-Tyr(But) | Fmoc-S31 | Fmoc-D-Lys(Boc) | Fmoc-OX-13 | 0.9 | 70 | 515 |
| 1108 | Fmoc-Ser(But) | Fmoc-S31 | Fmoc-D-Lys(Boc) | Fmoc-OX-13 | 1.2 | 100 | 439 |
| 1109 | Fmoc-D-Ser(But) | Fmoc-S31 | Fmoc-D-Lys(Boc) | Fmoc-OX-13 | 2.6 | 100 | 439 |
| 1110 | Fmoc-D-Trp(Boc) | Fmoc-S35 | Fmoc-Lys(Boc) | Fmoc-OX-13 | 2.3 | 100 | 578 |
| 1111 | Fmoc-D-Tyr(But) | Fmoc-S35 | Fmoc-Lys(Boc) | Fmoc-OX-13 | 1.6 | 100 | 555 |
| 1112 | Fmoc-Trp(Boc) | Fmoc-S35 | Fmoc-His(Trt) | Fmoc-OX-13 | 0.9 | na | na |
| 1113 | Fmoc-Tyr(But) | Fmoc-S35 | Fmoc-His(Trt) | Fmoc-OX-13 | 0.8 | na | na |
| 1114 | Fmoc-Phe | Fmoc-S35 | Fmoc-Trp(Boc) | Fmoc-OX-13 | 0.9 | 88 | 597 |
| 1115 | Fmoc-D-Phe | Fmoc-S35 | Fmoc-Trp(Boc) | Fmoc-OX-13 | 0.7 | 70 | 597 |
| 1116 | Fmoc-Val | Fmoc-S35 | Fmoc-Trp(Boc) | Fmoc-OX-13 | 1.0 | 64 | 549 |
| 1117 | Fmoc-D-Val | Fmoc-S35 | Fmoc-Trp(Boc) | Fmoc-OX-13 | 1.5 | 76 | 549 |
| 1118 | Fmoc-Ala | Fmoc-S35 | Fmoc-Trp(Boc) | Fmoc-OX-13 | 1.1 | 72 | 521 |
| 1119 | Fmoc-D-Ala | Fmoc-S35 | Fmoc-Trp(Boc) | Fmoc-OX-13 | 1.3 | 69 | 521 |
| 1120 | Fmoc-Ser(But) | Fmoc-S35 | Fmoc-Trp(Boc) | Fmoc-OX-13 | 0.8 | 70 | 537 |
| 1121 | Fmoc-D-Ser(But) | Fmoc-S35 | Fmoc-Trp(Boc) | Fmoc-OX-13 | 1.0 | 56 | 537 |
| 1122 | Fmoc-Leu | Fmoc-S35 | Fmoc-Trp(Boc) | Fmoc-OX-13 | 1.1 | 89 | 563 |
| 1123 | Fmoc-D-Leu | Fmoc-S35 | Fmoc-Trp(Boc) | Fmoc-OX-13 | 1.3 | 87 | 563 |
| 1124 | Fmoc-Glu(OBut) | Fmoc-S35 | Fmoc-Trp(Boc) | Fmoc-OX-13 | 0.7 | 45 | 579 |
| 1125 | Fmoc-D-Glu(OBut) | Fmoc-S35 | Fmoc-Trp(Boc) | Fmoc-OX-13 | 0.4 | na | na |
| 1126 | Fmoc-D-Trp(Boc) | Fmoc-S35 | Fmoc-D-Lys(Boc) | Fmoc-OX-13 | 3.7 | 100 | 578 |
| 1127 | Fmoc-D-Tyr(But) | Fmoc-S35 | Fmoc-D-Lys(Boc) | Fmoc-OX-13 | 3.5 | 100 | 555 |
| 1128 | Fmoc-Trp(Boc) | Fmoc-S35 | Fmoc-D-Lys(Boc) | Fmoc-OX-13 | 2.0 | 100 | 578 |
| 1129 | Fmoc-Tyr(But) | Fmoc-S35 | Fmoc-D-Lys(Boc) | Fmoc-OX-13 | 3.2 | 60 | 555 |

TABLE 4A-continued

| Cpd | BB$_1$ | BB$_2$ | BB$_3$ | BB$_4$ | Wt (mg)[1] | Purity[2] | MS (M + H) |
|---|---|---|---|---|---|---|---|
| 1130 | Fmoc-Phe | Fmoc-S35 | Fmoc-D-Lys(Boc) | Fmoc-OX-13 | 3.4 | 47 | 539 |
| 1131 | Fmoc-D-Phe | Fmoc-S35 | Fmoc-D-Lys(Boc) | Fmoc-OX-13 | 2.6 | 100 | 539 |
| 1132 | Fmoc-Val | Fmoc-S35 | Fmoc-D-Trp(Boc) | Fmoc-OX-13 | 1.5 | 79 | 549 |
| 1133 | Fmoc-D-Val | Fmoc-S35 | Fmoc-D-Trp(Boc) | Fmoc-OX-13 | 1.5 | 100 | 549 |
| 1134 | Fmoc-Ala | Fmoc-S35 | Fmoc-D-Trp(Boc) | Fmoc-OX-13 | 1.1 | 64 | 521 |
| 1135 | Fmoc-D-Ala | Fmoc-S35 | Fmoc-D-Trp(Boc) | Fmoc-OX-13 | na | na | na |
| 1136 | Fmoc-Ser(But) | Fmoc-S35 | Fmoc-D-Trp(Boc) | Fmoc-OX-13 | 1.6 | 81 | 537 |
| 1137 | Fmoc-D-Ser(But) | Fmoc-S35 | Fmoc-D-Trp(Boc) | Fmoc-OX-13 | 2.0 | 82 | 537 |
| 1138 | Fmoc-Leu | Fmoc-S35 | Fmoc-D-Trp(Boc) | Fmoc-OX-13 | 1.3 | 100 | 563 |
| 1139 | Fmoc-D-Leu | Fmoc-S35 | Fmoc-D-Trp(Boc) | Fmoc-OX-13 | 1.9 | 100 | 563 |
| 1140 | Fmoc-Glu(OBut) | Fmoc-S35 | Fmoc-D-Trp(Boc) | Fmoc-OX-13 | 1.2 | na | na |
| 1141 | Fmoc-D-Glu(OBut) | Fmoc-S35 | Fmoc-D-Trp(Boc) | Fmoc-OX-13 | 1.0 | 73 | 579 |
| 1142 | Fmoc-Ser(But) | Fmoc-S30 | Fmoc-Trp(Boc) | Fmoc-OX-1 | 0.6 | 77 | 511 |
| 1143 | Fmoc-D-Trp(Boc) | Fmoc-N-Me-Ser(But) | Fmoc-S37 | Fmoc-OX-13 | na | na | na |
| 1144 | Fmoc-D-Tyr(But) | Fmoc-N-Me-Ser(But) | Fmoc-S37 | Fmoc-OX-13 | na | na | na |
| 1145 | Fmoc-Trp(Boc) | Fmoc-N-Me-Ser(But) | Fmoc-S37 | Fmoc-OX-13 | na | na | na |
| 1146 | Fmoc-Tyr(But) | Fmoc-N-Me-Ser(But) | Fmoc-S37 | Fmoc-OX-13 | na | na | na |
| 1147 | Fmoc-D-Trp(Boc) | Fmoc-Ser(But) | Fmoc-S37 | Fmoc-OX-13 | 3.4 | 100 | 559 |
| 1148 | Fmoc-D-Tyr(But) | Fmoc-Ser(But) | Fmoc-S37 | Fmoc-OX-13 | 4.3 | 100 | 536 |
| 1149 | Fmoc-Trp(Boc) | Fmoc-Ser(But) | Fmoc-S37 | Fmoc-OX-13 | 1.8 | 100 | 559 |
| 1150 | Fmoc-Tyr(But) | Fmoc-Ser(But) | Fmoc-S37 | Fmoc-OX-13 | 5.2 | 100 | 536 |
| 1151 | Fmoc-D-Trp(Boc) | Fmoc-Lys(Boc) | Fmoc-S37 | Fmoc-OX-13 | 0.6 | 100 | 600 |
| 1152 | Fmoc-D-Tyr(But) | Fmoc-Lys(Boc) | Fmoc-S37 | Fmoc-OX-13 | 0.8 | 66 | 577 |
| 1153 | Fmoc-Trp(Boc) | Fmoc-Lys(Boc) | Fmoc-S37 | Fmoc-OX-13 | 0.2 | 100 | 600 |
| 1154 | Fmoc-Tyr(But) | Fmoc-Lys(Boc) | Fmoc-S37 | Fmoc-OX-13 | 0.2 | 100 | 577 |
| 1155 | Fmoc-D-Trp(Boc) | Fmoc-D-Lys(Boc) | Fmoc-S37 | Fmoc-OX-13 | 0.5 | 100 | 600 |
| 1156 | Fmoc-D-Tyr(But) | Fmoc-Pro | Fmoc-S37 | Fmoc-OX-13 | 0.7 | 100 | 577 |
| 1157 | Fmoc-Trp(Boc) | Fmoc-D-Lys(Boc) | Fmoc-S37 | Fmoc-OX-13 | 0.3 | 100 | 600 |
| 1158 | Fmoc-Tyr(But) | Fmoc-D-Lys(Boc) | Fmoc-S37 | Fmoc-OX-13 | 4.2 | 100 | 577 |
| 1159 | Fmoc-Lys(Boc) | Fmoc-Phe | Fmoc-S37 | Fmoc-OX-13 | na | na | na |
| 1160 | Fmoc-Lys(Boc) | Fmoc-D-Phe | Fmoc-S37 | Fmoc-OX-13 | 0.3 | 100 | 561 |
| 1161 | Fmoc-D-Lys(Boc) | Fmoc-Phe | Fmoc-S37 | Fmoc-OX-13 | 1.5 | 100 | 561 |
| 1162 | Fmoc-D-Lys(Boc) | Fmoc-D-Phe | Fmoc-S37 | Fmoc-OX-13 | 2.6 | 90 | 561 |
| 1163 | Fmoc-Lys(Boc) | Fmoc-D-Trp(Boc) | Fmoc-S37 | Fmoc-OX-13 | 0.6 | 100 | 600 |
| 1164 | Fmoc-Lys(Boc) | Fmoc-D-Tyr(But) | Fmoc-S37 | Fmoc-OX-13 | 0.5 | 100 | 577 |
| 1165 | Fmoc-D-Lys(Boc) | Fmoc-Trp(Boc) | Fmoc-S37 | Fmoc-OX-13 | 0.5 | 100 | 600 |
| 1166 | Fmoc-D-Lys(Boc) | Fmoc-N-Me-D-Phe | Fmoc-S37 | Fmoc-OX-13 | na | na | na |
| 1167 | Fmoc-Asp(OBut) | Fmoc-N-Me-D-Phe | Fmoc-S37 | Fmoc-OX-13 | na | na | na |
| 1168 | Fmoc-Asp(OBut) | Fmoc-D-Tyr(But) | Fmoc-S37 | Fmoc-OX-13 | na | na | na |
| 1169 | Fmoc-D-Asp(OBut) | Fmoc-Trp(Boc) | Fmoc-S37 | Fmoc-OX-13 | 0.2 | 100 | 587 |
| 1170 | Fmoc-D-Asp(OBut) | Fmoc-Tyr(But) | Fmoc-S37 | Fmoc-OX-13 | 0.1 | 100 | 564 |
| 1171 | Fmoc-Ser(But) | Fmoc-Phe | Fmoc-S37 | Fmoc-OX-13 | na | na | na |
| 1172 | Fmoc-Ser(But) | Fmoc-D-Phe | Fmoc-S37 | Fmoc-OX-13 | na | na | na |
| 1173 | Fmoc-D-Ser(But) | Fmoc-Phe | Fmoc-S37 | Fmoc-OX-13 | 1.1 | 100 | 520 |
| 1174 | Fmoc-D-Ser(But) | Fmoc-D-Phe | Fmoc-S37 | Fmoc-OX-13 | 0.7 | 100 | 520 |
| 1175 | Fmoc-Ser(But) | Fmoc-D-Trp(Boc) | Fmoc-S37 | Fmoc-OX-13 | 3.5 | na | na |
| 1176 | Fmoc-Ser(But) | Fmoc-D-Tyr(But) | Fmoc-S37 | Fmoc-OX-13 | 0.8 | 100 | 536 |
| 1177 | Fmoc-D-Ser(But) | Fmoc-Trp(Boc) | Fmoc-S37 | Fmoc-OX-13 | na | na | na |
| 1178 | Fmoc-D-Ser(But) | Fmoc-Tyr(But) | Fmoc-S37 | Fmoc-OX-13 | 1.5 | 100 | 536 |
| 1179 | Fmoc-D-Trp(Boc) | Fmoc-Sar | Fmoc-S37 | Fmoc-OX-13 | na | na | na |
| 1180 | Fmoc-D-Tyr(But) | Fmoc-Sar | Fmoc-S37 | Fmoc-OX-13 | na | na | na |
| 1181 | Fmoc-Asp(OBut) | Fmoc-Sar | Fmoc-S37 | Fmoc-OX-13 | na | na | na |
| 1182 | Fmoc-D-Asp(OBut) | Fmoc-Sar | Fmoc-S37 | Fmoc-OX-13 | na | na | na |
| 1183 | Fmoc-Lys(Boc) | Fmoc-Sar | Fmoc-S37 | Fmoc-OX-13 | 0.9 | 100 | 485 |
| 1184 | Fmoc-D-Lys(Boc) | Fmoc-Sar | Fmoc-S37 | Fmoc-OX-13 | 2.7 | 100 | 485 |
| 1185 | Fmoc-Asp(OBut) | Fmoc-Sar | Fmoc-S37 | Fmoc-OX-13 | na | 100 | na |
| 1186 | Fmoc-D-Asp(OBut) | Fmoc-Sar | Fmoc-S37 | Fmoc-OX-13 | 0.8 | 100 | 472 |
| 1187 | Fmoc-Ser(But) | Fmoc-Sar | Fmoc-S37 | Fmoc-OX-13 | na | na | na |
| 1188 | Fmoc-D-Ser(But) | Fmoc-Sar | Fmoc-S37 | Fmoc-OX-13 | 2.6 | 100 | 444 |
| 1189 | Fmoc-Ser(But) | Fmoc-Lys(Boc) | Fmoc-S30 | Fmoc-OX-1 | 9.7 | 100 | 453 | na = not available

[1]All syntheses were carried out on the solid phase starting from 70-80 mg of 2-chlorotrityl chloride resin (typical loading 1.0 mmol/g).

[2]Purity is determined by analysis with LC-UV at 220 nm.

TABLE 4B

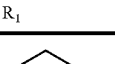

| Cpd | R₁ | R₂ | R₃ | R₄ | Q | R₅ |
|---|---|---|---|---|---|---|
| 1001 | (R)- H₂NOC—(CH) | (R)- indol-3-ylmethyl—(CH) | H | (S)- H₂N(CH₂)₄—(CH) | CH₂ | (S)- isobutyl—(CH) |
| 1002 | (R)- H₂NOC—(CH) | (R)- 4-HO-benzyl—(CH) | H | (S)- H₂N(CH₂)₄—(CH) | CH₂ | (S)- isobutyl—(CH) |
| 1003 | (R)- H₂NOC—(CH) | (S)- indol-3-ylmethyl—(CH) | H | (S)- H₂N(CH₂)₄—(CH) | CH₂ | (S)- isobutyl—(CH) |
| 1004 | (R)- H₂NOC—(CH) | (S)- 4-HO-benzyl—(CH) | H | (S)- H₂N(CH₂)₄—(CH) | CH₂ | (S)- isobutyl—(CH) |
| 1005 | (R)- HO—(CH) | (R)- indol-3-ylmethyl—(CH) | H | (S)- H₂N(CH₂)₄—(CH) | CH₂ | (S)- isobutyl—(CH) |
| 1006 | (R)- HO—(CH) | (R)- 4-HO-benzyl—(CH) | H | (S)- H₂N(CH₂)₄—(CH) | CH² | (S)- isobutyl—(CH) |
| 1007 | (R)- HO—(CH) | (S)- indol-3-ylmethyl—(CH) | H | (S)- H₂N(CH₂)₄—(CH) | CH₂ | (S)- isobutyl—(CH) |
| 1008 | (R)- HO—(CH) | (S)- 4-HO-benzyl—(CH) | H | (S)- H₂N(CH₂)₄—(CH) | CH₂ | (S)- isobutyl—(CH) |
| 1009 | (S)- H₂N(CH₂)₄—(CH) | (S)- HO—(CH) | H | (S)- H₂N(CH₂)₄—(CH) | CH₂ | (S)- isobutyl—(CH) |
| 1010 | (R)- H₂NOC—(CH) | (R)- indol-3-ylmethyl—(CH) | H | (R)- H₂N(CH₂)₄—(CH) | CH₂ | (S)- isobutyl—(CH) |
| 1011 | (R)- H₂NOC—(CH) | (R)- 4-HO-benzyl—(CH) | H | (R)- H₂N(CH₂)₄—(CH) | CH₂ | (S)- isobutyl—(CH) |

TABLE 4B-continued

| Cpd | R₁ | R₂ | R₃ | R₄ | Q | R₅ |
|---|---|---|---|---|---|---|
| 1012 | (R)- H₂NOC-(CH) | (S)- indol-3-ylmethyl-(CH) | H | (R)- H₂N-butyl-(CH) | CH₂ | (S)- isobutyl-(CH) |
| 1013 | (R)- H₂NOC-(CH) | (S)- 4-hydroxybenzyl-(CH) | H | (R)- H₂N-butyl-(CH) | CH₂ | (S)- isobutyl-(CH) |
| 1014 | (R)- HO-(CH) | (R)- indol-3-ylmethyl-(CH) | H | (R)- H₂N-butyl-(CH) | CH₂ | (S)- isobutyl-(CH) |
| 1015 | (R)- HO-(CH) | (R)- 4-hydroxybenzyl-(CH) | H | (R)- H₂N-butyl-(CH) | CH₂ | (S)- isobutyl-(CH) |
| 1016 | (R)- HO-(CH) | (S)- indol-3-ylmethyl-(CH) | H | (R)- H₂N-butyl-(CH) | CH₂ | (S)- isobutyl-(CH) |
| 1017 | (R)- HO-(CH) | (S)- 4-hydroxybenzyl-(CH) | H | (R)- H₂N-butyl-(CH) | CH₂ | (S)- isobutyl-(CH) |
| 1018 | (S)- H₂NOC-(CH) | (R)- indol-3-ylmethyl-(CH) | H | (S)- H₂N-butyl-(CH) | CH₂ | (S)- isobutyl-(CH) |
| 1019 | (S)- H₂NOC-(CH) | (R)- 4-hydroxybenzyl-(CH) | H | (S)- H₂N-butyl-(CH) | CH₂ | (S)- isobutyl-(CH) |
| 1020 | (S)- H₂NOC-(CH) | (S)- indol-3-ylmethyl-(CH) | H | (S)- H₂N-butyl-(CH) | CH₂ | (S)- isobutyl-(CH) |
| 1021 | (S)- H₂NOC-(CH) | (S)- 4-hydroxybenzyl-(CH) | H | (S)- H₂N-butyl-(CH) | CH₂ | (S)- isobutyl-(CH) |
| 1022 | (S)- HO-(CH) | (R)- indol-3-ylmethyl-(CH) | H | (S)- H₂N-butyl-(CH) | CH₂ | (S)- isobutyl-(CH) |

TABLE 4B-continued

| Cpd | R₁ | R₂ | R₃ | R₄ | Q | R₅ |
|---|---|---|---|---|---|---|
| 1023 | (S)- HO-CH₂-(CH) | (R)- 4-HO-C₆H₄-CH₂-(CH) | H | (S)- H₂N-(CH₂)₄-(CH) | CH₂ | (S)- isobutyl-(CH) |
| 1024 | (S)- HO-CH₂-(CH) | (S)- 3-indolyl-CH₂-(CH) | H | (S)- H₂N-(CH₂)₄-(CH) | CH₂ | (S)- isobutyl-(CH) |
| 1025 | (S)- HO-CH₂-(CH) | (S)- 4-HO-C₆H₄-CH₂-(CH) | H | (S)- H₂N-(CH₂)₄-(CH) | CH₂ | (S)- isobutyl-(CH) |
| 1026 | (S)- pyrrolidinyl-(HC) | (R)- 3-indolyl-CH₂-(CH) | H | (S)- H₂N-(CH₂)₄-(CH) | CH₂ | (S)- isobutyl-(CH) |
| 1027 | (R)- pyrrolidinyl-(HC) | (R)- 4-HO-C₆H₄-CH₂-(CH) | H | (S)- H₂N-(CH₂)₄-(CH) | CH₂ | (S)- isobutyl-(CH) |
| 1028 | (S)- pyrrolidinyl-(HC) | (S)- 3-indolyl-CH₂-(CH) | H | (S)- H₂N-(CH₂)₄-(CH) | CH₂ | (S)- isobutyl-(CH) |
| 1029 | (R)- pyrrolidinyl-(HC) | (S)- 4-HO-C₆H₄-CH₂-(CH) | H | (S)- H₂N-(CH₂)₄-(CH) | CH₂ | (S)- isobutyl-(CH) |
| 1030 | (S)- pyrrolidinyl-(HC) | (R)- 3-indolyl-CH₂-(CH) | H | (S)- H₂N-(CH₂)₄-(CH) | CH₂ | (S)- isobutyl-(CH) |
| 1031 | (S)- pyrrolidinyl-(HC) | (R)- 4-HO-C₆H₄-CH₂-(CH) | H | (S)- H₂N-(CH₂)₄-(CH) | CH₂ | (S)- isobutyl-(CH) |
| 1032 | (S)- pyrrolidinyl-(HC) | (S)- 3-indolyl-CH₂-(CH) | H | (R)- H₂N-(CH₂)₄-(CH) | CH₂ | (S)- isobutyl-(CH) |
| 1033 | (R)- pyrrolidinyl-(HC) | (S)- 4-HO-C₆H₄-CH₂-(CH) | H | (R)- H₂N-(CH₂)₄-(CH) | CH₂ | (S)- isobutyl-(CH) |

TABLE 4B-continued

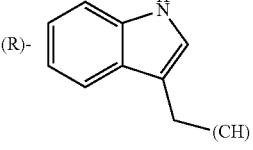

| Cpd | R₁ | R₂ | R₃ | R₄ | Q | R₅ |
|---|---|---|---|---|---|---|
| 1034 | (R)-indol-3-ylmethyl-(CH) | H | Me | (S)-H₂N-(CH₂)₄-(CH) | CH₂ | (S)-isobutyl-(CH) |
| 1035 | (R)-4-hydroxybenzyl-(CH) | H | Me | (S)-H₂N-(CH₂)₄-(CH) | CH₂ | (S)-isobutyl-(CH) |
| 1036 | (S)-indol-3-ylmethyl-(CH) | H | Me | (S)-H₂N-(CH₂)₄-(CH) | CH₂ | (S)-isobutyl-(CH) |
| 1037 | (S)-4-hydroxybenzyl-(CH) | H | Me | (S)-H₂N-(CH₂)₄-(CH) | CH₂ | (S)-isobutyl-(CH) |
| 1038 | (S)-benzyl-(CH) | H | Me | (S)-H₂N-(CH₂)₄-(CH) | CH₂ | (S)-isobutyl-(CH) |
| 1039 | (R)-benzyl-(CH) | H | Me | (S)-H₂N-(CH₂)₄-(CH) | CH₂ | (S)-isobutyl-(CH) |
| 1040 | (S)-isopropyl-(CH) | H | Me | (S)-H₂N-(CH₂)₄-(CH) | CH₂ | (S)-isobutyl-(CH) |
| 1041 | (R)-isopropyl-(CH) | H | Me | (S)-H₂N-(CH₂)₄-(CH) | CH₂ | (S)-isobutyl-(CH) |
| 1042 | (S)-CH₃ | H | Me | (S)-H₂N-(CH₂)₄-(CH) | CH₂ | (S)-isobutyl-(CH) |
| 1043 | (R)-CH₃ | H | Me | (S)-H₂N-(CH₂)₄-(CH) | CH₂ | (S)-isobutyl-(CH) |
| 1044 | (S)-HO-CH₂-(CH) | H | Me | (S)-H₂N-(CH₂)₄-(CH) | CH₂ | (S)-isobutyl-(CH) |

TABLE 4B-continued

| Cpd | R₁ | R₂ | R₃ | R₄ | Q | R₅ |
|---|---|---|---|---|---|---|
| 1045 | (R)- HOCH₂-(CH) | H | Me | (S)- H₂N-(CH₂)₄-(CH) | CH₂ | (S)- iBu-(CH) |
| 1046 | (S)- iBu-(CH) | H | Me | (S)- H₂N-(CH₂)₄-(CH) | CH₂ | (S)- iBu-(CH) |
| 1047 | (S)- iBu-(CH) | H | Me | (S)- H₂N-(CH₂)₄-(CH) | CH₂ | (S)- iBu-(CH) |
| 1048 | (S)- HO₂C-(CH₂)₂-(CH) | H | Me | (S)- H₂N-(CH₂)₄-(CH) | CH₂ | (S)- iBu-(CH) |
| 1049 | (R)- HO₂C-(CH₂)₂-(CH) | H | Me | (S)- H₂N-(CH₂)₄-(CH) | CH₂ | (S)- iBu-(CH) |
| 1050 | (R)- indol-3-yl-CH₂-(CH) | H | Me | (R)- H₂N-(CH₂)₄-(CH) | CH₂ | (S)- iBu-(CH) |
| 1051 | (R)- 4-HO-C₆H₄-CH₂-(CH) | H | Me | (R)- H₂N-(CH₂)₄-(CH) | CH₂ | (S)- iBu-(CH) |
| 1052 | (S)- indol-3-yl-CH₂-(CH) | H | Me | (R)- H₂N-(CH₂)₄-(CH) | CH₂ | (S)- iBu-(CH) |
| 1053 | (S)- 4-HO-C₆H₄-CH₂-(CH) | H | Me | (R)- H₂N-(CH₂)₄-(CH) | CH₂ | (S)- iBu-(CH) |
| 1054 | (S)- Ph-CH₂-(CH) | H | Me | (R)- H₂N-(CH₂)₄-(CH) | CH₂ | (S)- iBu-(CH) |
| 1055 | (R)- Ph-CH₂-(CH) | H | Me | (R)- H₂N-(CH₂)₄-(CH) | CH₂ | (S)- iBu-(CH) |

TABLE 4B-continued

[Structure: cyclic peptide with R1, R2, R3, R4, R5, R6, Q substituents on an oxazole-containing macrocycle]

| Cpd | R1 | R2 | R3 | R4 | Q | R5 |
|---|---|---|---|---|---|---|
| 1056 | (S)-isopropyl (CH) | H | Me | (R)-H2N-(CH2)3-(CH) | CH2 | (S)-isobutyl (CH) |
| 1057 | (R)-isopropyl (CH) | H | Me | (R)-H2N-(CH2)3-(CH) | CH2 | (S)-isobutyl (CH) |
| 1058 | (S)-CH3 | H | Me | (R)-H2N-(CH2)3-(CH) | CH2 | (S)-isobutyl (CH) |
| 1059 | (R)-CH3 | H | Me | (R)-H2N-(CH2)3-(CH) | CH2 | (S)-isobutyl (CH) |
| 1060 | (S)-HO-CH2-(CH) | H | Me | (R)-H2N-(CH2)3-(CH) | CH2 | (S)-isobutyl (CH) |
| 1061 | (R)-HO-CH2-(CH) | H | Me | (R)-H2N-(CH2)3-(CH) | CH2 | (S)-isobutyl (CH) |
| 1062 | (S)-isobutyl (CH) | H | Me | (R)-H2N-(CH2)3-(CH) | CH2 | (S)-isobutyl (CH) |
| 1063 | (R)-isobutyl (CH) | H | Me | (R)-H2N-(CH2)3-(CH) | CH2 | (S)-isobutyl (CH) |
| 1064 | (S)-HO2C-(CH2)2-(CH) | H | Me | (R)-H2N-(CH2)3-(CH) | CH2 | (S)-isobutyl (CH) |
| 1065 | (S)-HO2C-CH2-(CH) | H | Me | (R)-H2N-(CH2)3-(CH) | CH2 | (S)-isobutyl (CH) |

For all compounds R₆=H, except for those compounds in which Fmoc-Pro or Fmoc-D-Pro is the BB₁ component wherein R₁ and (N)R₆ form a five-membered ring, including the nitrogen atom, as shown for R₁ in compounds 1026-1033 in Table 4B.

TABLE 4C

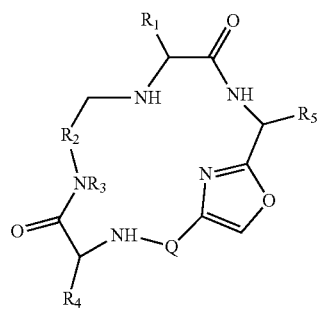

| Cpd | R₁ | R₂ | R₃ | R₄ | Q | R₅ |
|---|---|---|---|---|---|---|
| 1066 | (R)- H₂NOC—(CH) | (H₂C)—(NR₃) | Me | (S)- indol-3-ylmethyl (CH) | CH₂ | (S)- isobutyl (CH) |
| 1067 | (S)- H₂NOC—(CH) | (H₂C)—(NR₃) | Me | (S)- indol-3-ylmethyl (CH) | CH₂ | (S)- isobutyl (CH) |
| 1068 | (R)- imidazol-4-ylmethyl (CH) | (H₂C)—(NR₃) | Me | (S)- indol-3-ylmethyl (CH) | CH₂ | (S)- isobutyl (CH) |
| 1069 | (S)- imidazol-4-ylmethyl (CH) | (H₂C)—(NR₃) | Me | (S)- indol-3-ylmethyl (CH) | CH₂ | (S)- isobutyl (CH) |
| 1070 | (R)- HO—CH₂—(CH) | (H₂C)—(NR₃) | Me | (S)- indol-3-ylmethyl (CH) | CH₂ | (S)- isobutyl (CH) |
| 1071 | (S)- HO—CH₂—(CH) | (H₂C)—(NR₃) | Me | (S)- indol-3-ylmethyl (CH) | CH₂ | (S)- isobutyl (CH) |
| 1072 | (R)- H₂N—(CH₂)₄—(CH) | (H₂C)—(NR₃) | Me | (S)- indol-3-ylmethyl (CH) | CH₂ | (S)- isobutyl (CH) |

TABLE 4C-continued

| Cpd | R₁ | R₂ | R₃ | R₄ | Q | R₅ |
|---|---|---|---|---|---|---|
| 1073 | (S)- H₂N-(CH₂)₄-(CH) | (H₂C)₂-(NR₃) | Me | (S)- indol-3-yl-CH₂-(CH) | CH₂ | (S)- isobutyl-(CH) |
| 1074 | (R)- indol-3-yl-CH₂-(CH) | (H₂C)₂-(NR₃) | Me | (S)- H₂N-(CH₂)₄-(CH) | CH₂ | (S)- isobutyl-(CH) |
| 1075 | (R)- 4-HO-C₆H₄-CH₂-(CH) | (H₂C)₂-(NR₃) | Me | (S)- H₂N-(CH₂)₄-(CH) | CH₂ | (S)- isobutyl-(CH) |
| 1076 | (S)- indol-3-yl-CH₂-(CH) | (H₂C)₂-(NR₃) | Me | (S)- H₂N-(CH₂)₄-(CH) | CH₂ | (S)- isobutyl-(CH) |
| 1077 | (S)- 4-HO-C₆H₄-CH₂-(CH) | (H₂C)₂-(NR₃) | Me | (S)- H₂N-(CH₂)₄-(CH) | CH₂ | (S)- isobutyl-(CH) |
| 1078 | (S)- PhCH₂-(CH) | (H₂C)₂-(NR₃) | Me | (S)- H₂N-(CH₂)₄-(CH) | CH₂ | (S)- isobutyl-(CH) |
| 1079 | (R)- PhCH₂-(CH) | (H₂C)₂-(NR₃) | Me | (S)- H₂N-(CH₂)₄-(CH) | CH₂ | (S)- isobutyl-(CH) |
| 1080 | (S)- iPr-(CH) | (H₂C)₂-(NR₃) | Me | (S)- 4-HO-C₆H₄-CH₂-(CH) | CH₂ | (S)- isobutyl-(CH) |
| 1081 | (R)- iPr-(CH) | (H₂C)₂-(NR₃) | Me | (S)- 4-HO-C₆H₄-CH₂-(CH) | CH₂ | (S)- isobutyl-(CH) |
| 1082 | (S)-CH₃ | (H₂C)₂-(NR₃) | Me | (S)- 4-HO-C₆H₄-CH₂-(CH) | CH₂ | (S)- isobutyl-(CH) |

TABLE 4C-continued

| Cpd | R₁ | R₂ | R₃ | R₄ | Q | R₅ |
|---|---|---|---|---|---|---|
| 1083 | (R)-CH₃ | (H₂C)~(NR₃) | Me | (S)- 4-HO-C₆H₄-CH₂-(CH) | CH₂ | (S)- iBu-(CH) |
| 1084 | (S)- HOCH₂-(CH) | (H₂C)~(NR₃) | Me | (S)- 4-HO-C₆H₄-CH₂-(CH) | CH₂ | (S)- iBu-(CH) |
| 1085 | (R)- HOCH₂-(CH) | (H₂C)~(NR₃) | Me | (S)- 4-HO-C₆H₄-CH₂-(CH) | CH₂ | (S)- iBu-(CH) |
| 1086 | (S)- iBu-(CH) | (H₂C)~(NR₃) | Me | (S)- 4-HO-C₆H₄-CH₂-(CH) | CH₂ | (S)- iBu-(CH) |
| 1087 | (R)- iBu-(CH) | (H₂C)~(NR₃) | Me | (S)- 4-HO-C₆H₄-CH₂-(CH) | CH₂ | (S)- iBu-(CH) |
| 1088 | (S)- HO₂C-CH₂CH₂-(CH) | (H₂C)~(NR₃) | Me | (S)- 4-HO-C₆H₄-CH₂-(CH) | CH₂ | (S)- iBu-(CH) |
| 1089 | (R)- HO₂C-CH₂CH₂-(CH) | (H₂C)~(NR₃) | Me | (S)- 4-HO-C₆H₄-CH₂-(CH) | CH₂ | (S)- iBu-(CH) |
| 1090 | (R)- indol-3-yl-CH₂-(CH) | (H₂C)~(NR₃) | Me | (R)- H₂N-(CH₂)₃-(CH) | CH₂ | (S)- iBu-(CH) |
| 1091 | (R)- 4-HO-C₆H₄-CH₂-(CH) | (H₂C)~(NR₃) | Me | (R)- H₂N-(CH₂)₃-(CH) | CH₂ | (S)- iBu-(CH) |
| 1092 | (S)- indol-3-yl-CH₂-(CH) | (H₂C)~(NR₃) | Me | (R)- H₂N-(CH₂)₃-(CH) | CH₂ | (S)- iBu-(CH) |
| 1093 | (S)- 4-HO-C₆H₄-CH₂-(CH) | (H₂C)~(NR₃) | Me | (R)- H₂N-(CH₂)₃-(CH) | CH₂ | (S)- iBu-(CH) |

TABLE 4C-continued

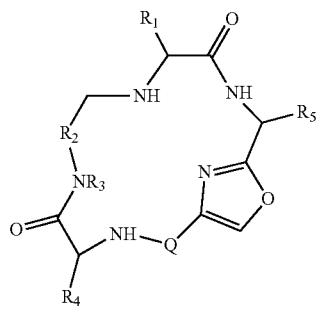

| Cpd | R₁ | R₂ | R₃ | R₄ | Q | R₅ |
|---|---|---|---|---|---|---|
| 1094 | (S)-benzyl (CH) | (H₂C)—(NR₃) | Me | (R)- H₂N-butyl (CH) | CH₂ | (S)-isobutyl (CH) |
| 1095 | (R)-benzyl (CH) | (H₂C)—(NR₃) | Me | (R)- H₂N-butyl (CH) | CH₂ | (S)-isobutyl (CH) |
| 1096 | (S)-isopropyl (CH) | (H₂C)—(NR₃) | Me | (R)- 4-HO-benzyl (CH) | CH₂ | (S)-isobutyl (CH) |
| 1097 | (R)-isopropyl (CH) | (H₂C)—(NR₃) | Me | (R)- 4-HO-benzyl (CH) | CH₂ | (S)-isobutyl (CH) |
| 1098 | (S)-CH₃ | (H₂C)—(NR₃) | Me | (R)- 4-HO-benzyl (CH) | CH₂ | (S)-isobutyl (CH) |
| 1099 | (R)-CH₃ | (H₂C)—(NR₃) | Me | (R)- 4-HO-benzyl (CH) | CH₂ | (S)-isobutyl (CH) |
| 1100 | (S)- HO-CH₂ (CH) | (H₂C)—(NR₃) | Me | (R)- 4-HO-benzyl (CH) | CH₂ | (S)-isobutyl (CH) |
| 1101 | (R)- HO-CH₂ (CH) | (H₂C)—(NR₃) | Me | (R)- 4-HO-benzyl (CH) | CH₂ | (S)-isobutyl (CH) |
| 1102 | (S)-isobutyl (CH) | (H₂C)—(NR₃) | Me | (R)- 4-HO-benzyl (CH) | CH₂ | (S)-isobutyl (CH) |
| 1103 | (R)-isobutyl (CH) | (H₂C)—(NR₃) | Me | (R)- 4-HO-benzyl (CH) | CH₂ | (S)-isobutyl (CH) |
| 1104 | (S)- HO₂C-CH₂CH₂ (CH) | (H₂C)—(NR₃) | Me | (R)- 4-HO-benzyl (CH) | CH₂ | (S)-isobutyl (CH) |
| 1105 | (R)- HO₂C-CH₂CH₂ (CH) | (H₂C)—(NR₃) | Me | (R)- 4-HO-benzyl (CH) | CH₂ | (S)-isobutyl (CH) |

TABLE 4C-continued

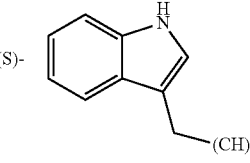

| Cpd | R$_1$ | R$_2$ | R$_3$ | R$_4$ | Q | R$_5$ |
|---|---|---|---|---|---|---|
| 1106 | (S)- indol-3-ylmethyl (CH) | (H$_2$C)—(NR$_3$) | H | (R)- H$_2$N—(CH) butyl | CH$_2$ | (S)- isobutyl (CH) |
| 1107 | (S)- 4-hydroxybenzyl (CH) | (H$_2$C)—(NR$_3$) | H | (R)- H$_2$N—(CH) butyl | CH$_2$ | (S)- isobutyl (CH) |
| 1108 | (S)- HO—(CH) | (H$_2$C)—(NR$_3$) | H | (R)- H$_2$N—(CH) butyl | CH$_2$ | (S)- isobutyl (CH) |
| 1109 | (R)- HO—(CH) | (H$_2$C)—(NR$_3$) | H | (R)- H$_2$N—(CH) butyl | CH$_2$ | (S)- isobutyl (CH) |
| 1110 | (R)- indol-3-ylmethyl (CH) | (N)—(CH$_2$) piperidinyl | | (S)- H$_2$N—(CH) butyl | CH$_2$ | (S)- isobutyl (CH) |
| 1111 | (R)- 4-hydroxybenzyl (CH) | (N)—(CH$_2$) piperidinyl | | (S)- H$_2$N—(CH) butyl | CH$_2$ | (S)- isobutyl (CH) |
| 1112 | (S)- indol-3-ylmethyl (CH) | (N)—(CH$_2$) piperidinyl | | (S)- imidazol-4-ylmethyl (CH) | CH$_2$ | (S)- isobutyl (CH) |
| 1113 | (S)- 4-hydroxybenzyl (CH) | (N)—(CH$_2$) piperidinyl | | (S)- imidazol-4-ylmethyl (CH) | CH$_2$ | (S)- isobutyl (CH) |
| 1114 | (S)- benzyl (CH) | (N)—(CH$_2$) piperidinyl | | (S)- indol-3-ylmethyl (CH) | CH$_2$ | (S)- isobutyl (CH) |

TABLE 4C-continued

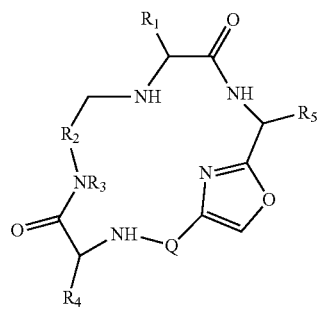

| Cpd | R₁ | R₂ | R₃ | R₄ | Q | R₅ |
|---|---|---|---|---|---|---|
| 1115 | (R)- benzyl (CH) | (N)- piperidin-4-yl (CH₂) | | (S)- indol-3-ylmethyl (CH) | CH₂ | (S)- isobutyl (CH) |
| 1116 | (S)- isopropyl (CH) | (N)- piperidin-4-yl (CH₂) | | (S)- indol-3-ylmethyl (CH) | CH₂ | (S)- isobutyl (CH) |
| 1117 | (R)- isopropyl (CH) | (N)- piperidin-4-yl (CH₂) | | (S)- indol-3-ylmethyl (CH) | CH₂ | (S)- isobutyl (CH) |
| 1118 | (S)-CH₃ | (N)- piperidin-4-yl (CH₂) | | (S)- indol-3-ylmethyl (CH) | CH₂ | (S)- isobutyl (CH) |
| 1119 | (R)-CH₃ | (N)- piperidin-4-yl (CH₂) | | (S)- indol-3-ylmethyl (CH) | CH₂ | (S)- isobutyl (CH) |
| 1120 | (S)- HOCH₂ (CH) | (N)- piperidin-4-yl (CH₂) | | (S)- indol-3-ylmethyl (CH) | CH₂ | (S)- isobutyl (CH) |
| 1121 | (R)- HOCH₂ (CH) | (N)- piperidin-4-yl (CH₂) | | (S)- indol-3-ylmethyl (CH) | CH₂ | (S)- isobutyl (CH) |
| 1122 | (S)- isobutyl (CH) | (N)- piperidin-4-yl (CH₂) | | (S)- indol-3-ylmethyl (CH) | CH₂ | (S)- isobutyl (CH) |
| 1123 | (R)- isobutyl (CH) | (N)- piperidin-4-yl (CH₂) | | (S)- indol-3-ylmethyl (CH) | CH₂ | (S)- isobutyl (CH) |

TABLE 4C-continued

| Cpd | R₁ | R₂ | R₃ | R₄ | Q | R₅ |
|---|---|---|---|---|---|---|
| 1124 | (S)- HO₂C—(CH₂)₂—(CH) | (N-piperidine)—(CH₂) | | (S)- indol-3-yl-CH₂—(CH) | CH₂ | (S)- isobutyl—(CH) |
| 1125 | (R)- HO₂C—(CH₂)₂—(CH₂) | (N-piperidine)—(CH₂) | | (S)- indol-3-yl-CH₂—(CH) | CH₂ | (S)- isobutyl—(CH) |
| 1126 | (R)- indol-3-yl-CH₂—(CH) | (N-piperidine)—(CH₂) | | (R)- H₂N—(CH₂)₃—(CH) | CH₂ | (S)- isobutyl—(CH) |
| 1127 | (R)- 4-HO-C₆H₄-CH₂—(CH) | (N-piperidine)—(CH₂) | | (R)- H₂N—(CH₂)₃—(CH) | CH₂ | (S)- isobutyl—(CH) |
| 1128 | (S)- indol-3-yl-CH₂—(CH) | (N-piperidine)—(CH₂) | | (R)- H₂N—(CH₂)₃—(CH) | CH₂ | (S)- isobutyl—(CH) |
| 1129 | (S)- 4-HO-C₆H₄-CH₂—(CH) | (N-piperidine)—(CH₂) | | (R)- H₂N—(CH₂)₃—(CH) | CH₂ | (S)- isobutyl—(CH) |
| 1130 | (S)- C₆H₅-CH₂—(CH) | (N-piperidine)—(CH₂) | | (R)- H₂N—(CH₂)₃—(CH) | CH₂ | (S)- isobutyl—(CH) |
| 1131 | (R)- C₆H₅-CH₂—(CH) | (N-piperidine)—(CH₂) | | (R)- H₂N—(CH₂)₃—(CH) | CH₂ | (S)- isobutyl—(CH) |
| 1132 | (S)- isopropyl—(CH) | (N-piperidine)—(CH₂) | | (R)- indol-3-yl-CH₂—(CH) | CH₂ | (S)- isobutyl—(CH) |

TABLE 4C-continued

| Cpd | R₁ | R₂ | R₃ | R₄ | Q | R₅ |
|---|---|---|---|---|---|---|
| 1133 | (R)-isopropyl (CH) | (N)-piperidinyl-(CH₂) | | (R)-indol-3-ylmethyl (CH) | CH₂ | (S)-isobutyl (CH) |
| 1134 | (S)-CH₃ | (N)-piperidinyl-(CH₂) | | (R)-indol-3-ylmethyl (CH) | CH₂ | (S)-isobutyl (CH) |
| 1135 | (R)-CH₃ | (N)-piperidinyl-(CH₂) | | (R)-indol-3-ylmethyl (CH) | CH₂ | (S)-isobutyl (CH) |
| 1136 | (S)-HOCH₂ (CH) | (N)-piperidinyl-(CH₂) | | (R)-indol-3-ylmethyl (CH) | CH2 | (S)-isobutyl (CH) |
| 1137 | (R)-HOCH₂ (CH) | (N)-piperidinyl-(CH₂) | | (R)-indol-3-ylmethyl (CH) | CH₂ | (S)-isobutyl (CH) |
| 1138 | (S)-isobutyl (CH) | (N)-piperidinyl-(CH₂) | | (R)-indol-3-ylmethyl (CH) | CH₂ | (S)-isobutyl (CH) |
| 1139 | (R)-isobutyl (CH) | (N)-piperidinyl-(CH₂) | | (R)-indol-3-ylmethyl (CH) | CH₂ | (S)-isobutyl (CH) |
| 1140 | (S)-HO₂C(CH₂)₂ | (N)-piperidinyl-(CH₂) | | (R)-indol-3-ylmethyl (CH) | CH₂ | (S)-isobutyl (CH) |
| 1141 | (R)-HO₂C(CH₂)₂ | (N)-piperidinyl-(CH₂) | | (R)-indol-3-ylmethyl (CH) | CH₂ | (S)-isobutyl (CH) |

TABLE 4C-continued

| Cpd | R₁ | R₂ | R₃ | R₄ | Q | R₅ |
|---|---|---|---|---|---|---|
| 1142 | (S)- HO―(CH) | (H₂C)―(NR₃) | Me | (S)- indol-3-ylmethyl (CH) | C=O | (S)- isobutyl (CH) |

For compounds 1110-1141, in which BB₂ is Fmoc-S35, (N)R₃ and R₂ form part of a six-membered ring, including the nitrogen atom, as shown for the combined R₂-R₃ in Table 4C.

TABLE 4D

| Cpd | R₁ | R₂ | R₃ | R₄ | Q | R₆ |
|---|---|---|---|---|---|---|
| 1143 | (R)- indol-3-ylmethyl (CH) | (S)- HO―(CH) | Me | (H₂C)―(NR₅) phenyl | CH₂ | (S)- isobutyl (CH) |
| 1144 | (R)- 4-hydroxybenzyl (CH) | (S)- HO―(CH) | Me | (H₂C)―(NR₅) phenyl | CH₂ | (S)- isobutyl (CH) |
| 1145 | (S)- indol-3-ylmethyl (CH) | (S)- HO―(CH) | Me | (H₂C)―(NR₅) phenyl | CH₂ | (S)- isobutyl (CH) |
| 1146 | (S)- 4-hydroxybenzyl (CH) | (S)- HO―(CH) | Me | (H₂C)―(NR₅) phenyl | CH₂ | (S)- isobutyl (CH) |

TABLE 4D-continued

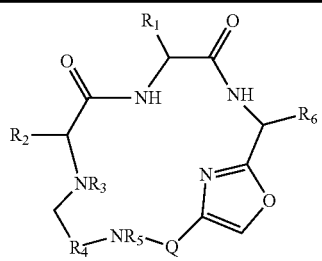

| Cpd | R₁ | R₂ | R₃ | R₄ | Q | R₆ |
|---|---|---|---|---|---|---|
| 1147 | (R)- 1H-indol-3-ylmethyl (CH) | (S)- HO-CH₂-(CH) | H | (H₂C)-3-benzyl-(NR₅) | CH₂ | (S)- isobutyl (CH) |
| 1148 | (R)- 4-hydroxybenzyl (CH) | (S)- HO-CH₂-(CH) | H | (H₂C)-3-benzyl-(NR₅) | CH₂ | (S)- isobutyl (CH) |
| 1149 | (S)- 1H-indol-3-ylmethyl (CH) | (S)- HO-CH₂-(CH) | H | (H₂C)-3-benzyl-(NR₅) | CH₂ | (S)- isobutyl (CH) |
| 1150 | (S)- 4-hydroxybenzyl (CH) | (S)- HO-CH₂-(CH) | H | (H₂C)-3-benzyl-(NR₅) | CH₂ | (S)- isobutyl (CH) |
| 1151 | (R)- 1H-indol-3-ylmethyl (CH) | (S)-H₂N-(CH₂)₃-(CH) | H | (H₂C)-3-benzyl-(NR₅) | CH₂ | (S)- isobutyl (CH) |
| 1152 | (R)- 4-hydroxybenzyl (CH) | (S)-H₂N-(CH₂)₃-(CH) | H | (H₂C)-3-benzyl-(NR₅) | CH₂ | (S)- isobutyl (CH) |
| 1153 | (S)- 1H-indol-3-ylmethyl (CH) | (S)-H₂N-(CH₂)₃-(CH) | H | (H₂C)-3-benzyl-(NR₅) | CH₂ | (S)- isobutyl (CH) |
| 1154 | (S)- 4-hydroxybenzyl (CH) | (S)-H₂N-(CH₂)₃-(CH) | H | (H₂C)-3-benzyl-(NR₅) | CH₂ | (S)- isobutyl (CH) |
| 1155 | (R)- 1H-indol-3-ylmethyl (CH) | (R)-H₂N-(CH₂)₃-(CH) | H | (H₂C)-3-benzyl-(NR₅) | CH₂ | (S)- isobutyl (CH) |

TABLE 4D-continued

| Cpd | R₁ | R₂ | R₃ | R₄ | Q | R₆ |
|---|---|---|---|---|---|---|
| 1156 | (R)- 4-hydroxybenzyl (CH) | (S)- pyrrolidine (HC) (N) | | (H₂C) 3-substituted benzyl (NR₅) | CH₂ | (S)- isobutyl (CH) |
| 1157 | (S)- indol-3-ylmethyl (CH) | (R)- H₂N-(CH₂)₄-(CH) | H | (H₂C) 3-substituted benzyl (NR₅) | CH₂ | (S)- isobutyl (CH) |
| 1158 | (S)- 4-hydroxybenzyl (CH) | (R)- H₂N-(CH₂)₄-(CH) | H | (H₂C) 3-substituted benzyl (NR₅) | CH₂ | (S)- isobutyl (CH) |
| 1159 | (S)- H₂N-(CH₂)₄-(CH) | (S)- benzyl (CH) | H | (H₂C) 3-substituted benzyl (NR₅) | CH₂ | (S)- isobutyl (CH) |
| 1160 | (S)- H₂N-(CH₂)₄-(CH) | (R)- benzyl (CH) | H | (H₂C) 3-substituted benzyl (NR₅) | CH₂ | (S)- isobutyl (CH) |
| 1161 | (R)- H₂N-(CH₂)₄-(CH) | (S)- benzyl (CH) | H | (H₂C) 3-substituted benzyl (NR₅) | CH₂ | (S)- isobutyl (CH) |
| 1162 | (R)- H₂N-(CH₂)₄-(CH) | (R)- benzyl (CH) | H | (H₂C) 3-substituted benzyl (NR₅) | CH₂ | (S)- isobutyl (CH) |
| 1163 | (S)- H₂N-(CH₂)₄-(CH) | (R)- indol-3-ylmethyl (CH) | H | (H₂C) 3-substituted benzyl (NR₅) | CH₂ | (S)- isobutyl (CH) |
| 1164 | (S)- H₂N-(CH₂)₄-(CH) | (R)- 4-hydroxybenzyl (CH) | H | (H₂C) 3-substituted benzyl (NR₅) | CH₂ | (S)- isobutyl (CH) |
| 1165 | (R)- H₂N-(CH₂)₄-(CH) | (S)- indol-3-ylmethyl (CH) | H | (H₂C) 3-substituted benzyl (NR₅) | CH₂ | (S)- isobutyl (CH) |

TABLE 4D-continued

| Cpd | R₁ | R₂ | R₃ | R₄ | Q | R₆ |
|---|---|---|---|---|---|---|
| 1166 | (R)- H₂N-(CH₂)₄-(CH) | (R)- benzyl-(CH) | Me | (H₂C)-m-C₆H₄-CH₂-(NR₅) | CH₂ | (S)- isobutyl-(CH) |
| 1167 | (S)- HO₂C-CH₂-(CH) | (R)- benzyl-(CH) | Me | (H₂C)-m-C₆H₄-CH₂-(NR₅) | CH₂ | (S)- isobutyl-(CH) |
| 1168 | (S)- HO₂C-CH₂-(CH) | (R)- 4-HO-benzyl-(CH) | H | (H₂C)-m-C₆H₄-CH₂-(NR₅) | CH₂ | (S)- isobutyl-(CH) |
| 1169 | (R)- HO₂C-CH₂-(CH) | (S)- indol-3-ylmethyl-(CH) | H | (H₂C)-m-C₆H₄-CH₂-(NR₅) | CH₂ | (S)- isobutyl-(CH) |
| 1170 | (R)- HO₂C-CH₂-(CH) | (S)- 4-HO-benzyl-(CH) | H | (H₂C)-m-C₆H₄-CH₂-(NR₅) | CH₂ | (S)- isobutyl-(CH) |
| 1171 | (S)- HO-CH₂-(CH) | (S)- benzyl-(CH) | H | (H₂C)-m-C₆H₄-CH₂-(NR₅) | CH₂ | (S)- isobutyl-(CH) |
| 1172 | (S)- HO-CH₂-(CH) | (R)- benzyl-(CH) | H | (H₂C)-m-C₆H₄-CH₂-(NR₅) | CH₂ | (S)- isobutyl-(CH) |
| 1173 | (R)- HO-CH₂-(CH) | (S)- benzyl-(CH) | H | (H₂C)-m-C₆H₄-CH₂-(NR₅) | CH₂ | (S)- isobutyl-(CH) |
| 1174 | (R)- HO-CH₂-(CH) | (R)- benzyl-(CH) | H | (H₂C)-m-C₆H₄-CH₂-(NR₅) | CH₂ | (S)- isobutyl-(CH) |
| 1175 | (S)- HO-CH₂-(CH) | (R)- indol-3-ylmethyl-(CH) | H | (H₂C)-m-C₆H₄-CH₂-(NR₅) | CH₂ | (S)- isobutyl-(CH) |
| 1176 | (S)- HO-CH₂-(CH) | (R)- 4-HO-benzyl-(CH) | H | (H₂C)-m-C₆H₄-CH₂-(NR₅) | CH₂ | (S)- isobutyl-(CH) |

TABLE 4D-continued

| Cpd | R₁ | R₂ | R₃ | R₄ | Q | R₆ |
|---|---|---|---|---|---|---|
| 1177 | (R)- HO—(CH) | (S)- indol-3-ylmethyl (CH) | H | (H₂C)-C₆H₄-(NR₅) (meta) | CH₂ | (S)- isobutyl (CH) |
| 1178 | (R)- HO—(CH) | (S)- 4-hydroxybenzyl (CH) | H | (H₂C)-C₆H₄-(NR₅) | CH₂ | (S)- isobutyl (CH) |
| 1179 | (R)- indol-3-ylmethyl (CH) | H | Me | (H₂C)-C₆H₄-(NR₅) | CH₂ | (S)- isobutyl (CH) |
| 1180 | (R)- 4-hydroxybenzyl (CH) | H | Me | (H₂C)-C₆H₄-(NR₅) | CH₂ | (S)- isobutyl (CH) |
| 1181 | (S)- indol-3-ylmethyl (CH) | H | Me | (H₂C)-C₆H₄-(NR₅) | CH₂ | (S)- isobutyl (CH) |
| 1182 | (S)- 4-hydroxybenzyl (CH) | H | Me | (H₂C)-C₆H₄-(NR₅) | CH₂ | (S)- isobutyl (CH) |
| 1183 | (S)- H₂N-(CH₂)₃-(CH) | H | Me | (H₂C)-C₆H₄-(NR₅) | CH₂ | (S)- isobutyl (CH) |
| 1184 | (S)- H₂N-(CH₂)₃-(CH) | H | Me | (H₂C)-C₆H₄-(NR₅) | CH₂ | (S)- isobutyl (CH) |
| 1185 | (S)- HO₂C-(CH) | H | Me | (H₂C)-C₆H₄-(NR₅) | CH₂ | (S)- isobutyl (CH) |
| 1186 | (R)- HO₂C-(CH) | H | Me | (H₂C)-C₆H₄-(NR₅) | CH₂ | (S)- isobutyl (CH) |

TABLE 4D-continued

| Cpd | R₁ | R₂ | R₃ | R₄ | Q | R₆ |
|---|---|---|---|---|---|---|
| 1187 | (S)- HO$\diagdown$(CH) | H | Me | (H₂C)$\diagdown$C₆H₄$\diagdown$(NR₅) | CH₂ | (S)- $\diagdown$(CH) isobutyl |
| 1188 | (R)- HO$\diagdown$(CH) | H | Me | (H₂C)$\diagdown$C₆H₄$\diagdown$(NR₅) | CH₂ | (S)- $\diagdown$(CH) isobutyl |
| 1189 | (R)- HO$\diagdown$(CH) | (S)- H₂N$\diagdown\diagdown\diagdown$(CH) | H | (H₂C)$\diagdown$(NR₅) | C=O | (S)- $\diagdown$(CH) isobutyl |

For all compounds, $R_5$=H, except for compound 1189 wherein $R_5$=CH₃. For compound 1156 in which Fmoc-Pro is the BB₂ component, R₂ and (N)R₃ form a cyclic five-membered ring, including the nitrogen atom, as shown for the combined R₂-R₃ in Table 4D.

Example 6

Synthesis of a Representative Library of Macrocyclic Compounds of Formula (Id)

The synthetic scheme depicted in Scheme 8 was used to synthesize the library of macrocyclic compounds 1201-1334 on solid support. The first amino acid building block amino acid (BB₁) was attached to the resin (Method 1D), then, after Fmoc deprotection (Method 1F), the second building block (BB₂) was added through amide bond formation (Method 1G) or reductive amination (Method 1I or 1J). The N-protection was cleaved (Method 1F) and the oxazole building block (BB₃) attached by reductive amination (Method 1J) or amide coupling (Method 1G) to give the macrocycle precursor scaffold. The crude product was obtained after sequential removal of the Fmoc (Method 1F), acidic cleavage from the resin (Method 1Q), cyclization (Method 1R) and cleavage of the side chain protecting groups (Method 1S) followed by concentration in vacuo. The purified macrocycles obtained after preparative HPLC (Method 2B are presented in Table 5A with the amounts, purity and confirmation of identity. Structures of the individual compounds in the library are provided in Table 5B.

TABLE 5A

| Cpd | BB₁ | BB₂ | BB₃ | Wt (mg)[1] | Purity[2] | MS (M + H) |
|---|---|---|---|---|---|---|
| 1201 | Fmoc-D-His(Trt) | Fmoc-D-Trp(Boc) | Fmoc-OX-13 | 11.7 | 100 | 490 |
| 1202 | Fmoc-D-His(Trt) | Fmoc-D-Tyr(But) | Fmoc-OX-13 | 11.3 | 100 | 467 |
| 1203 | Fmoc-D-His(Trt) | Fmoc-Trp(Boc) | Fmoc-OX-13 | 10.5 | 100 | 490 |
| 1204 | Fmoc-D-His(Trt) | Fmoc-Tyr(But) | Fmoc-OX-13 | 12.7 | 100 | 467 |
| 1205 | Fmoc-D-Lys(Boc) | Fmoc-D-Trp(Boc) | Fmoc-OX-13 | 14.3 | 100 | 481 |
| 1206 | Fmoc-D-Lys(Boc) | Fmoc-D-Tyr(But) | Fmoc-OX-13 | 17.4 | 100 | 458 |
| 1207 | Fmoc-D-Lys(Boc) | Fmoc-Trp(Boc) | Fmoc-OX-13 | 8.8 | 100 | 481 |
| 1208 | Fmoc-D-Lys(Boc) | Fmoc-Tyr(But) | Fmoc-OX-13 | 10.7 | 100 | 458 |
| 1209 | Fmoc-Phe | Fmoc-Asn(Trt) | Fmoc-OX-13 | 2.8 | 97 | 428 |
| 1210 | Fmoc-D-Phe | Fmoc-D-Asn(Trt) | Fmoc-OX-13 | 6.8 | 95 | 428 |
| 1211 | Fmoc-Lys(Boc) | Fmoc-Phe | Fmoc-OX-13 | 2.8 | 100 | 442 |
| 1212 | Fmoc-D-Lys(Boc) | Fmoc-D-Phe | Fmoc-OX-13 | 10.9 | 90 | 442 |
| 1213 | Fmoc-Ser(But) | Fmoc-Ala | Fmoc-OX-13 | 10.3 | 100 | 325 |
| 1214 | Fmoc-D-Ser(But) | Fmoc-D-Ala | Fmoc-OX-13 | 8.6 | 100 | 325 |
| 1215 | Fmoc-Ala | Fmoc-Tyr(But) | Fmoc-OX-13 | 3.4 | 100 | 401 |
| 1216 | Fmoc-D-Ala | Fmoc-D-Tyr(But) | Fmoc-OX-13 | 12.2 | 100 | 401 |
| 1217 | Fmoc-D-Trp(Boc) | Fmoc-Asn(Trt) | Fmoc-OX-13 | 7.9 | 100 | 467 |
| 1218 | Fmoc-D-Tyr(But) | Fmoc-Asn(Trt) | Fmoc-OX-13 | 10.6 | 100 | 444 |
| 1219 | Fmoc-Trp(Boc) | Fmoc-Asn(Trt) | Fmoc-OX-13 | 2.8 | 100 | 467 |
| 1220 | Fmoc-Tyr(But) | Fmoc-Asn(Trt) | Fmoc-OX-13 | 5.1 | 100 | 444 |
| 1221 | Fmoc-D-Trp(Boc) | Fmoc-Ser(But) | Fmoc-OX-13 | 4.9 | 95 | 440 |
| 1222 | Fmoc-D-Tyr(But) | Fmoc-Ser(But) | Fmoc-OX-13 | 7.3 | 100 | 417 |
| 1223 | Fmoc-Trp(Boc) | Fmoc-Ser(But) | Fmoc-OX-13 | 3.2 | 96 | 440 |

TABLE 5A-continued

| Cpd | BB$_1$ | BB$_2$ | BB$_3$ | Wt (mg)[1] | Purity[2] | MS (M + H) |
|---|---|---|---|---|---|---|
| 1224 | Fmoc-Tyr(But) | Fmoc-Ser(But) | Fmoc-OX-13 | 5.8 | 97 | 417 |
| 1225 | Fmoc-Lys(Boc) | Fmoc-Ser(But) | Fmoc-OX-13 | 2.9 | 100 | 382 |
| 1226 | Fmoc-D-Lys(Boc) | Fmoc-Ser(But) | Fmoc-OX-13 | 7.4 | 100 | 382 |
| 1227 | Fmoc-Phe | Fmoc-Sar | Fmoc-OX-13 | 1.0 | 100 | 385 |
| 1228 | Fmoc-D-Phe | Fmoc-Sar | Fmoc-OX-13 | 1.4 | 100 | 385 |
| 1229 | Fmoc-Lys(Boc) | Fmoc-Sar | Fmoc-OX-13 | 3.0 | 100 | 366 |
| 1230 | Fmoc-D-Lys(Boc) | Fmoc-Sar | Fmoc-OX-13 | 2.5 | 100 | 366 |
| 1231 | Fmoc-Ser(But) | Fmoc-Sar | Fmoc-OX-13 | 2.3 | 100 | 325 |
| 1232 | Fmoc-D-Ser(But) | Fmoc-Sar | Fmoc-OX-13 | 2.9 | 100 | 325 |
| 1233 | Fmoc-Ala | Fmoc-Sar | Fmoc-OX-13 | 0.5 | 100 | 309 |
| 1234 | Fmoc-D-Ala | Fmoc-Sar | Fmoc-OX-13 | 0.7 | 100 | 309 |
| 1235 | Fmoc-D-Trp(Boc) | Fmoc-Sar | Fmoc-OX-13 | 0.9 | 100 | 424 |
| 1236 | Fmoc-D-Tyr(But) | Fmoc-Sar | Fmoc-OX-13 | 1.6 | 85 | 401 |
| 1237 | Fmoc-Trp(Boc) | Fmoc-Sar | Fmoc-OX-13 | 1.0 | 100 | 424 |
| 1238 | Fmoc-Tyr(But) | Fmoc-Sar | Fmoc-OX-13 | 1.1 | 100 | 401 |
| 1239 | Fmoc-Dap(Boc) | Fmoc-Sar | Fmoc-OX-13 | 0.5 | 100 | 324 |
| 1240 | Fmoc-D-Dap(Boc) | Fmoc-Sar | Fmoc-OX-13 | 0.6 | 100 | 324 |
| 1241 | Fmoc-Arg(Pbf) | Fmoc-Sar | Fmoc-OX-13 | na | na | na |
| 1242 | Fmoc-D-Arg(Pbf) | Fmoc-Sar | Fmoc-OX-13 | 0.9 | 100 | 394 |
| 1243 | Fmoc-Dap(Boc) | Fmoc-Asn(Trt) | Fmoc-OX-13 | 1.7 | 100 | 367 |
| 1244 | Fmoc-D-Dap(Boc) | Fmoc-D-Asn(Trt) | Fmoc-OX-13 | 3.2 | 100 | 367 |
| 1245 | Fmoc-Arg(Pbf) | Fmoc-Phe | Fmoc-OX-13 | 2.7 | 100 | 470 |
| 1246 | Fmoc-D-Arg(Pbf) | Fmoc-D-Phe | Fmoc-OX-13 | 8.7 | 97 | 470 |
| 1247 | Fmoc-Val | Fmoc-Tyr(But) | Fmoc-OX-13 | 0.8 | 100 | 429 |
| 1248 | Fmoc-D-Val | Fmoc-D-Tyr(But) | Fmoc-OX-13 | 14.7 | 96 | 429 |
| 1249 | Fmoc-His(Trt) | Fmoc-Asn(Trt) | Fmoc-OX-13 | 3.0 | 100 | 418 |
| 1250 | Fmoc-D-His(Trt) | Fmoc-Asn(Trt) | Fmoc-OX-13 | 7.0 | 96 | 418 |
| 1251 | Fmoc-His(Trt) | Fmoc-Ser(But) | Fmoc-OX-13 | 4.5 | 100 | 391 |
| 1252 | Fmoc-D-His(Trt) | Fmoc-Ser(But) | Fmoc-OX-13 | 11.4 | 100 | 391 |
| 1253 | Fmoc-His(Trt) | Fmoc-D-Asn(Trt) | Fmoc-OX-13 | 9.1 | 100 | 418 |
| 1254 | Fmoc-D-His(Trt) | Fmoc-D-Asn(Trt) | Fmoc-OX-13 | 4.5 | 100 | 418 |
| 1255 | Fmoc-His(Trt) | Fmoc-D-Ser(But) | Fmoc-OX-13 | 2.6 | 100 | 391 |
| 1256 | Fmoc-D-His(Trt) | Fmoc-D-Ser(But) | Fmoc-OX-13 | 8.3 | 100 | 391 |
| 1257 | Fmoc-D-Trp(Boc) | Fmoc-Thr(But) | Fmoc-OX-13 | 3.1 | 100 | 454 |
| 1258 | Fmoc-D-Tyr(But) | Fmoc-D-Thr(But) | Fmoc-OX-13 | 13.8 | 100 | 431 |
| 1259 | Fmoc-Trp(Boc) | Fmoc-Thr(But) | Fmoc-OX-13 | 1.7 | 88 | 454 |
| 1260 | Fmoc-Tyr(But) | Fmoc-D-Thr(But) | Fmoc-OX-13 | 4.7 | 100 | 431 |
| 1261 | Fmoc-Lys(Boc) | Fmoc-Thr(But) | Fmoc-OX-13 | 1.7 | 100 | 396 |
| 1262 | Fmoc-D-Lys(Boc) | Fmoc-D-Thr(But) | Fmoc-OX-13 | 22.6 | 100 | 396 |
| 1263 | Fmoc-Phe | Fmoc-Thr(But) | Fmoc-OX-13 | 0.4 | 100 | 415 |
| 1264 | Fmoc-D-Phe | Fmoc-D-Thr(But) | Fmoc-OX-13 | 13.3 | 98 | 415 |
| 1265 | Fmoc-Dap(Boc) | Fmoc-Thr(But) | Fmoc-OX-13 | 2.2 | 100 | 354 |
| 1266 | Fmoc-D-Dap(Boc) | Fmoc-D-Thr(But) | Fmoc-OX-13 | 11.0 | 100 | 354 |
| 1267 | Fmoc-Arg(Pbf) | Fmoc-Thr(But) | Fmoc-OX-13 | 1.2 | 100 | 424 |
| 1268 | Fmoc-D-Arg(Pbf) | Fmoc-D-Thr(But) | Fmoc-OX-13 | 3.9 | 100 | 424 |
| 1269 | Fmoc-Val | Fmoc-Thr(But) | Fmoc-OX-13 | 1.1 | 100 | 367 |
| 1270 | Fmoc-D-Val | Fmoc-D-Thr(But) | Fmoc-OX-13 | 11.5 | 97 | 367 |
| 1271 | Fmoc-His(Trt) | Fmoc-Thr(But) | Fmoc-OX-13 | 10.4 | 100 | 405 |
| 1272 | Fmoc-D-His(Trt) | Fmoc-D-Thr(But) | Fmoc-OX-13 | 16.4 | 100 | 405 |
| 1273 | Fmoc-D-Trp(Boc) | Fmoc-Arg(Pbf) | Fmoc-OX-13 | 1.1 | 100 | 509 |
| 1274 | Fmoc-D-Tyr(But) | Fmoc-Arg(Pbf) | Fmoc-OX-13 | 4.3 | 100 | 486 |
| 1275 | Fmoc-Trp(Boc) | Fmoc-Arg(Pbf) | Fmoc-OX-13 | 1.5 | 100 | 509 |
| 1276 | Fmoc-Tyr(But) | Fmoc-Arg(Pbf) | Fmoc-OX-13 | 4.3 | 100 | 486 |
| 1277 | Fmoc-Phe | Fmoc-Arg(Pbf) | Fmoc-OX-13 | 3.2 | 100 | 470 |
| 1278 | Fmoc-D-Phe | Fmoc-Arg(Pbf) | Fmoc-OX-13 | 1.8 | 100 | 470 |
| 1279 | Fmoc-Val | Fmoc-Arg(Pbf) | Fmoc-OX-13 | na | na | na |
| 1280 | Fmoc-D-Val | Fmoc-Arg(Pbf) | Fmoc-OX-13 | 8.9 | 100 | 422 |
| 1281 | Fmoc-Ala | Fmoc-Arg(Pbf) | Fmoc-OX-13 | 3.7 | 100 | 394 |
| 1282 | Fmoc-D-Ala | Fmoc-Arg(Pbf) | Fmoc-OX-13 | 1.2 | 100 | 394 |
| 1283 | Fmoc-Ser(But) | Fmoc-Arg(Pbf) | Fmoc-OX-13 | 13.6 | 100 | 410 |
| 1284 | Fmoc-D-Ser(But) | Fmoc-Arg(Pbf) | Fmoc-OX-13 | 6.4 | 100 | 410 |
| 1285 | Fmoc-D-Trp(Boc) | Fmoc-D-Arg(Pbf) | Fmoc-OX-13 | 3.5 | 100 | 509 |
| 1286 | Fmoc-D-Tyr(But) | Fmoc-D-Arg(Pbf) | Fmoc-OX-13 | 15.5 | 100 | 486 |
| 1287 | Fmoc-Trp(Boc) | Fmoc-D-Arg(Pbf) | Fmoc-OX-13 | 2.4 | 100 | 509 |
| 1288 | Fmoc-Tyr(But) | Fmoc-D-Arg(Pbf) | Fmoc-OX-13 | 5.6 | 100 | 486 |
| 1289 | Fmoc-Phe | Fmoc-D-Arg(Pbf) | Fmoc-OX-13 | 4.5 | 100 | 470 |
| 1290 | Fmoc-D-Phe | Fmoc-D-Arg(Pbf) | Fmoc-OX-13 | 8.9 | 100 | 470 |
| 1291 | Fmoc-Val | Fmoc-D-Arg(Pbf) | Fmoc-OX-13 | 4.8 | 100 | 422 |
| 1292 | Fmoc-D-Val | Fmoc-D-Arg(Pbf) | Fmoc-OX-13 | 14.3 | 100 | 422 |
| 1293 | Fmoc-Ala | Fmoc-D-Arg(Pbf) | Fmoc-OX-13 | 3.0 | 100 | 394 |
| 1294 | Fmoc-D-Ala | Fmoc-D-Arg(Pbf) | Fmoc-OX-13 | 8.0 | 100 | 394 |
| 1295 | Fmoc-Ser(But) | Fmoc-D-Arg(Pbf) | Fmoc-OX-13 | 3.6 | 100 | 410 |
| 1296 | Fmoc-D-Ser(But) | Fmoc-D-Arg(Pbf) | Fmoc-OX-13 | 6.2 | 100 | 410 |
| 1297 | Fmoc-D-Trp(Boc) | Fmoc-Dap(Boc) | Fmoc-OX-13 | 2.1 | 100 | 439 |
| 1298 | Fmoc-D-Tyr(But) | Fmoc-Dap(Boc) | Fmoc-OX-13 | 3.7 | 100 | 416 |
| 1299 | Fmoc-Trp(Boc) | Fmoc-Dap(Boc) | Fmoc-OX-13 | 2.5 | 81 | 439 |
| 1300 | Fmoc-Tyr(But) | Fmoc-Dap(Boc) | Fmoc-OX-13 | 0.7 | 81 | 416 |
| 1301 | Fmoc-Phe | Fmoc-Dap(Boc) | Fmoc-OX-13 | 2.4 | 73 | 400 |

TABLE 5A-continued

| Cpd | BB$_1$ | BB$_2$ | BB$_3$ | Wt (mg)[1] | Purity[2] | MS (M + H) |
|---|---|---|---|---|---|---|
| 1302 | Fmoc-D-Phe | Fmoc-Dap(Boc) | Fmoc-OX-13 | 1.9 | 100 | 400 |
| 1303 | Fmoc-Val | Fmoc-Dap(Boc) | Fmoc-OX-13 | 0.9 | na | na |
| 1304 | Fmoc-D-Val | Fmoc-Dap(Boc) | Fmoc-OX-13 | 2.1 | 95 | 352 |
| 1305 | Fmoc-Ala | Fmoc-Dap(Boc) | Fmoc-OX-13 | 3.5 | 74+ | 324 |
| 1306 | Fmoc-D-Ala | Fmoc-Dap(Boc) | Fmoc-OX-13 | 4.1 | 100 | 324 |
| 1307 | Fmoc-Ser(But) | Fmoc-Dap(Boc) | Fmoc-OX-13 | 2.2 | 100 | 340 |
| 1308 | Fmoc-D-Ser(But) | Fmoc-Dap(Boc) | Fmoc-OX-13 | 5.3 | 100 | 340 |
| 1309 | Fmoc-D-Trp(Boc) | Fmoc-D-Dap(Boc) | Fmoc-OX-13 | 4.4 | 86 | 439 |
| 1310 | Fmoc-D-Tyr(But) | Fmoc-D-Dap(Boc) | Fmoc-OX-13 | 7.2 | 100 | 416 |
| 1311 | Fmoc-Trp(Boc) | Fmoc-D-Dap(Boc) | Fmoc-OX-13 | 2.2 | 80 | 439 |
| 1312 | Fmoc-Tyr(But) | Fmoc-D-Dap(Boc) | Fmoc-OX-13 | 3.2 | 70+ | 416 |
| 1313 | Fmoc-Phe | Fmoc-D-Dap(Boc) | Fmoc-OX-13 | 4.1 | 57 | 400 |
| 1314 | Fmoc-D-Phe | Fmoc-D-Dap(Boc) | Fmoc-OX-13 | 5.1 | 100 | 400 |
| 1315 | Fmoc-Val | Fmoc-D-Dap(Boc) | Fmoc-OX-13 | 3.3 | 61 | 352 |
| 1316 | Fmoc-D-Val | Fmoc-D-Dap(Boc) | Fmoc-OX-13 | 5.3 | 100 | 352 |
| 1317 | Fmoc-Ala | Fmoc-D-Dap(Boc) | Fmoc-OX-13 | 3.5 | 67 | 324 |
| 1318 | Fmoc-D-Ala | Fmoc-D-Dap(Boc) | Fmoc-OX-13 | 6.5 | 100 | 324 |
| 1319 | Fmoc-Ser(But) | Fmoc-D-Dap(Boc) | Fmoc-OX-13 | 4.2 | 74+ | 340 |
| 1320 | Fmoc-D-Ser(But) | Fmoc-D-Dap(Boc) | Fmoc-OX-13 | 5.9 | 100 | 340 |
| 1321 | Fmoc-Leu | Fmoc-D-Dap(Boc) | Fmoc-OX-13 | 1.1 | 100 | 366 |
| 1322 | Fmoc-D-Leu | Fmoc-D-Dap(Boc) | Fmoc-OX-13 | 0.9 | 100 | 366 |
| 1323 | Fmoc-Ser(But) | Fmoc-S31 | Fmoc-OX-13 | 0.8 | 100 | 311 |
| 1324 | Fmoc-D-Ser(But) | Fmoc-S31 | Fmoc-OX-13 | 0.8 | 100 | 311 |
| 1325 | Fmoc-D-Trp(Boc) | Fmoc-S31 | Fmoc-OX-13 | 0.9 | 100 | 410 |
| 1326 | Fmoc-D-Tyr(But) | Fmoc-S31 | Fmoc-OX-13 | 2.5 | 100 | 387 |
| 1327 | Fmoc-Trp(Boc) | Fmoc-S31 | Fmoc-OX-13 | 1.0 | 100 | 410 |
| 1328 | Fmoc-Tyr(But) | Fmoc-S31 | Fmoc-OX-13 | 0.9 | 100 | 387 |
| 1329 | Fmoc-Phe | Fmoc-S31 | Fmoc-OX-13 | 1.9 | 100 | 371 |
| 1330 | Fmoc-D-Phe | Fmoc-S31 | Fmoc-OX-13 | 1.8 | 100 | 371 |
| 1331 | Fmoc-Dap(Boc) | Fmoc-S31 | Fmoc-OX-13 | 0.8 | 100 | 310 |
| 1332 | Fmoc-D-Dap(Boc) | Fmoc-S31 | Fmoc-OX-13 | 0.3 | 100 | 310 |
| 1333 | Fmoc-Lys(Boc) | Fmoc-S31 | Fmoc-OX-13 | 1.2 | 100 | 352 |
| 1334 | Fmoc-D-Lys(Boc) | Fmoc-S31 | Fmoc-OX-13 | 2.6 | 100 | 352 | na = not available

[1] All syntheses were carried out on the solid phase starting from 70-80 mg of 2-chlorotrityl chloride resin (typical loading 1.0 mmol/g).
[2] Purity is determined by analysis with LC-UV at 220 nm.

TABLE 5B

| Cpd | R$_1$ | Q$_1$ | R$_2$ | R$_3$ | Q$_2$ | R$_4$ |
|---|---|---|---|---|---|---|
| 1201 | (R)-imidazol-4-ylmethyl-(CH) | C=O | (Q$_1$)-(NR$_3$) indol-3-ylmethyl | H | CH$_2$ | (S)-isobutyl-(CH) |
| 1202 | (R)-imidazol-4-ylmethyl-(CH) | C=O | (Q$_1$)-(NR$_3$) 4-hydroxybenzyl | H | CH$_2$ | (S)-isobutyl-(CH) |

TABLE 5B-continued

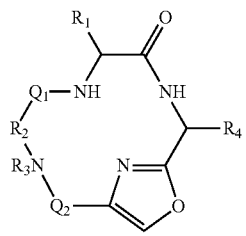

| Cpd | R₁ | Q₁ | R₂ | R₃ | Q₂ | R₄ |
|---|---|---|---|---|---|---|
| 1203 | (R)- 1H-imidazol-4-ylmethyl (CH) | C=O | (Q₁),(NR₃) 3-(1H-indol-3-yl)propyl | H | CH₂ | (S)- isobutyl (CH) |
| 1204 | (R)- 1H-imidazol-4-ylmethyl (CH) | C=O | (Q₁),(NR₃) 4-hydroxybenzyl | H | CH₂ | (S)- isobutyl (CH) |
| 1205 | (R)- H₂N-(CH₂)₄- (CH) | C=O | (Q₁),(NR₃) 3-(1H-indol-3-yl)methyl | H | CH₂ | (S)- isobutyl (CH) |
| 1206 | (R)- H₂N-(CH₂)₄- (CH) | C=O | (Q₁),(NR₃) 4-hydroxybenzyl | H | CH₂ | (S)- isobutyl (CH) |
| 1207 | (R)- H₂N-(CH₂)₄- (CH) | C=O | (Q₁),(NR₃) 3-(1H-indol-3-yl)methyl | H | CH₂ | (S)- isobutyl (CH) |
| 1208 | (R)- H₂N-(CH₂)₄- (CH) | C=O | (Q₁),(NR₃) 4-hydroxybenzyl | H | CH₂ | (S)- isobutyl (CH) |

TABLE 5B-continued

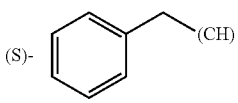

| Cpd | R₁ | Q₁ | R₂ | R₃ | Q₂ | R₄ |
|---|---|---|---|---|---|---|
| 1209 | (S)- benzyl (CH) | C=O | (Q₁)(NR₃)CH-CH₂-CONH₂ | H | CH₂ | (S)- isobutyl (CH) |
| 1210 | (R)- benzyl (CH) | C=O | (Q₁)(NR₃)CH-CH₂-CONH₂ | H | CH₂ | (S)- isobutyl (CH) |
| 1211 | (S)- H₂N-(CH₂)₄-(CH) | C=O | (Q₁)(NR₃)CH-CH₂-Ph | H | CH₂ | (S)- isobutyl (CH) |
| 1212 | (R)- H₂N-(CH₂)₄-(CH) | C=O | (Q₁)(NR₃)CH-CH₂-Ph | H | CH₂ | (S)- isobutyl (CH) |
| 1213 | (S)- HO-CH₂-(CH) | C=O | (Q₁)(NR₃)CH-CH₃ | H | CH₂ | (S)- isobutyl (CH) |
| 1214 | (R)- HO-CH₂-(CH) | C=O | (Q₁)(NR₃)CH-CH₃ | H | CH₂ | (S)- isobutyl (CH) |
| 1215 | (S)-CH₃ | C=O | (Q₁)(NR₃)CH-CH₂-C₆H₄-OH | H | CH₂ | (S)- isobutyl (CH) |
| 1216 | (R)-CH₃ | C=O | (Q₁)(NR₃)CH-CH₂-C₆H₄-OH | H | CH₂ | (S)- isobutyl (CH) |
| 1217 | (R)- indol-3-ylmethyl (CH) | C=O | (Q₁)(NR₃)CH-CH₂-CONH₂ | H | CH₂ | (S)- isobutyl (CH) |

TABLE 5B-continued
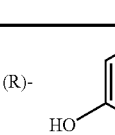
| Cpd | R₁ | Q₁ | R₂ | R₃ | Q₂ | R₄ |
|---|---|---|---|---|---|---|
| 1218 | (R)- 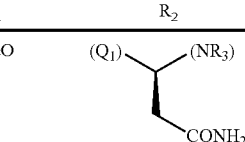 | C=O | (Q₁)─⟨(NR₃)⟩─CONH₂ | H | CH₂ | (S)- 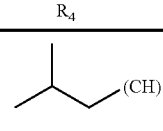 |
| 1219 | (S)- 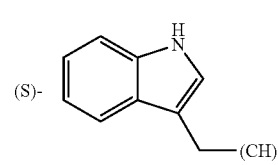 | C=O | (Q₁)─⟨(NR₃)⟩─CONH₂ | H | CH₂ | (S)- 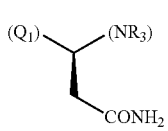 |
| 1220 | (S)- 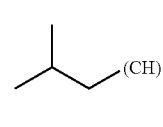 | C=O | (Q₁)─⟨(NR₃)⟩─CONH₂ | H | CH₂ | (S)- 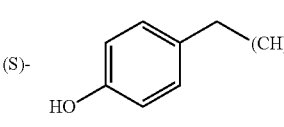 |
| 1221 | (R)- 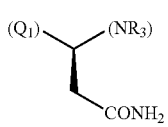 | C=O | (Q₁)─⟨(NR₃)⟩─OH | H | CH₂ | (S)- 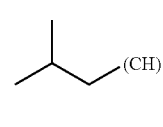 |
| 1222 | (R)- 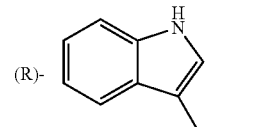 | C=O | (Q₁)─⟨(NR₃)⟩─OH | H | CH₂ | (S)- 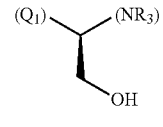 |
| 1223 | (S)- 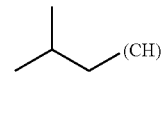 | C=O | (Q₁)─⟨(NR₃)⟩─OH | H | CH₂ | (S)- 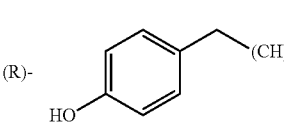 |
| 1224 | (S)- 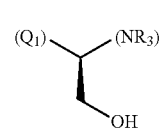 | C=O | (Q₁)─⟨(NR₃)⟩─OH | H | CH₂ | (S)- 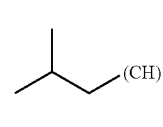 |
| 1225 | (S)- 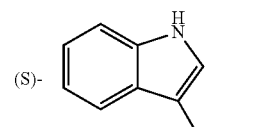 | C=O | (Q₁)─⟨(NR₃)⟩─OH | H | CH₂ | (S)- 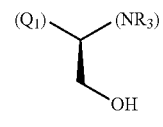 |
| 1226 | (R)- 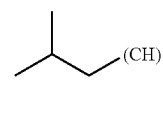 | C=O | (Q₁)─⟨(NR₃)⟩─OH | H | CH₂ | (S)- 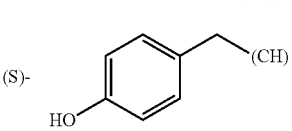 |
| 1227 | (S)- 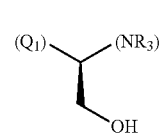 | C=O | (Q₁)─(NR₃) | Me | CH₂ | (S)- 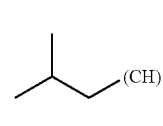 |

TABLE 5B-continued

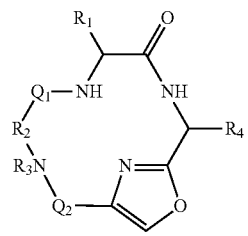

| Cpd | R₁ | Q₁ | R₂ | R₃ | Q₂ | R₄ |
|---|---|---|---|---|---|---|
| 1228 | (R)- benzyl (CH) | C=O | (Q₁)—CH₂CH₂—(NR₃) | Me | CH₂ | (S)- isobutyl (CH) |
| 1229 | (S)- H₂N-(CH₂)₄-(CH) | C=O | (Q₁)—CH₂CH₂—(NR₃) | Me | CH₂ | (S)- isobutyl (CH) |
| 1230 | (R)- H₂N-(CH₂)₄-(CH) | C=O | (Q₁)—CH₂CH₂—(NR₃) | Me | CH₂ | (S)- isobutyl (CH) |
| 1231 | (S)- HO-CH₂-(CH) | C=O | (Q₁)—CH₂CH₂—(NR₃) | Me | CH₂ | (S)- isobutyl (CH) |
| 1232 | (R)- HO-CH₂-(CH) | C=O | (Q₁)—CH₂CH₂—(NR₃) | Me | CH₂ | (S)- isobutyl (CH) |
| 1233 | (S)-CH₃ | C=O | (Q₁)—CH₂CH₂—(NR₃) | Me | CH₂ | (S)- isobutyl (CH) |
| 1234 | (R)-CH₃ | C=O | (Q₁)—CH₂CH₂—(NR₃) | Me | CH₂ | (S)- isobutyl (CH) |
| 1235 | (R)- indol-3-ylmethyl (CH) | C=O | (Q₁)—CH₂CH₂—(NR₃) | Me | CH₂ | (S)- isobutyl (CH) |
| 1236 | (R)- 4-hydroxybenzyl (CH) | C=O | (Q₁)—CH₂CH₂—(NR₃) | Me | CH₂ | (S)- isobutyl (CH) |
| 1237 | (S)- indol-3-ylmethyl (CH) | C=O | (Q₁)—CH₂CH₂—(NR₃) | Me | CH₂ | (S)- isobutyl (CH) |
| 1238 | (S)- 4-hydroxybenzyl (CH) | C=O | (Q₁)—CH₂CH₂—(NR₃) | Me | CH₂ | (S)- isobutyl (CH) |
| 1239 | (S)- H₂N-CH₂-(CH) | C=O | (Q₁)—CH₂CH₂—(NR₃) | Me | CH₂ | (S)- isobutyl (CH) |

TABLE 5B-continued

[Structure: macrocycle with R₁-CH-C(=O)-NH-CH(R₄)-oxazole, Q₁-NH, R₂-N(R₃)-Q₂ connections]

| Cpd | R₁ | Q₁ | R₂ | R₃ | Q₂ | R₄ |
|---|---|---|---|---|---|---|
| 1240 | (R)- H₂N–(CH)– | C=O | (Q₁)–(NR₃) | Me | CH₂ | (S)- isobutyl-(CH)– |
| 1241 | (S)- H₂N-C(=NH)-NH-(CH₂)₃-(CH)– | C=O | (Q₁)–(NR₃) | Me | CH₂ | (S)- isobutyl-(CH)– |
| 1242 | (R)- H₂N-C(=NH)-NH-(CH₂)₃-(CH)– | C=O | (Q₁)–(NR₃) | Me | CH₂ | (S)- isobutyl-(CH)– |
| 1243 | (S)- H₂N–(CH)– | C=O | (Q₁)–(CH)(NR₃), CH₂CONH₂ | H | CH₂ | (S)- isobutyl-(CH)– |
| 1244 | (R)- H₂N–(CH)– | C=O | (Q₁)–(CH)(NR₃), CH₂CONH₂ | H | CH₂ | (S)- isobutyl-(CH)– |
| 1245 | (S)- H₂N-C(=NH)-NH-(CH₂)₃-(CH)– | C=O | (Q₁)–(CH)(NR₃), CH₂-Ph | H | CH₂ | (S)- isobutyl-(CH)– |
| 1246 | (R)- H₂N-C(=NH)-NH-(CH₂)₃-(CH)– | C=O | (Q₁)–(CH)(NR₃), CH₂-Ph | H | CH₂ | (S)- isobutyl-(CH)– |
| 1247 | (S)- iPr-(CH)– | C=O | (Q₁)–(CH)(NR₃), CH₂-C₆H₄-OH | H | CH₂ | (S)- isobutyl-(CH)– |
| 1248 | (R)- iPr-(CH)– | C=O | (Q₁)–(CH)(NR₃), CH₂-C₆H₄-OH | H | CH₂ | (S)- isobutyl-(CH)– |

TABLE 5B-continued

| Cpd | R₁ | Q₁ | R₂ | R₃ | Q₂ | R₄ |
|---|---|---|---|---|---|---|
| 1249 | (S)- imidazolyl-CH₂ | C=O | (Q₁)-CH(NR₃)-CH₂-CONH₂ | H | CH₂ | (S)- isobutyl-CH |
| 1250 | (R)- imidazolyl-CH₂ | C=O | (Q₁)-CH(NR₃)-CH₂-CONH₂ | H | CH₂ | (S)- isobutyl-CH |
| 1251 | (S)- imidazolyl-CH₂ | C=O | (Q₁)-CH(NR₃)-CH₂-OH | H | CH₂ | (S)- isobutyl-CH |
| 1252 | (R)- imidazolyl-CH₂ | C=O | (Q₁)-CH(NR₃)-CH₂-OH | H | CH₂ | (S)- isobutyl-CH |
| 1253 | (S)- imidazolyl-CH₂ | C=O | (Q₁)-CH(NR₃)-CH₂-CONH₂ | H | CH₂ | (S)- isobutyl-CH |
| 1254 | (R)- imidazolyl-CH₂ | C=O | (Q₁)-CH(NR₃)-CH₂-CONH₂ | H | CH₂ | (S)- isobutyl-CH |
| 1255 | (S)- imidazolyl-CH₂ | C=O | (Q₁)-CH(NR₃)-CH₂-OH | H | CH₂ | (S)- isobutyl-CH |
| 1256 | (R)- imidazolyl-CH₂ | C=O | (Q₁)-CH(NR₃)-CH₂-OH | H | CH₂ | (S)- isobutyl-CH |

TABLE 5B-continued

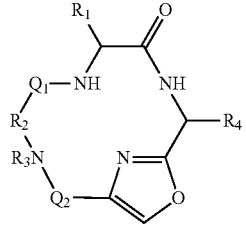

| Cpd | R₁ | Q₁ | R₂ | R₃ | Q₂ | R₄ |
|---|---|---|---|---|---|---|
| 1257 | (R)- 1H-indol-3-ylmethyl (CH) | C=O | (Q₁)–CH(CH₃)–CH(NR₃)–OH | H | CH₂ | (S)- isobutyl (CH) |
| 1258 | (R)- 4-hydroxybenzyl (CH) | C=O | (Q₁)–CH(CH₃)–CH(NR₃)–OH | H | CH₂ | (S)- isobutyl (CH) |
| 1259 | (S)- 1H-indol-3-ylmethyl (CH) | C=O | (Q₁)–CH(CH₃)–CH(NR₃)–OH | H | CH₂ | (S)- isobutyl (CH) |
| 1260 | (S)- 4-hydroxybenzyl (CH) | C=O | (Q₁)–CH(CH₃)–CH(NR₃)–OH | H | CH₂ | (S)- isobutyl (CH) |
| 1261 | (S)- H₂N-(CH₂)₄-(CH) | C=O | (Q₁)–CH(CH₃)–CH(NR₃)–OH | H | CH₂ | (S)- isobutyl (CH) |
| 1262 | (R)- H₂N-(CH₂)₄-(CH) | C=O | (Q₁)–CH(CH₃)–CH(NR₃)–OH | H | CH₂ | (S)- isobutyl (CH) |
| 1263 | (S)- benzyl (CH) | C=O | (Q₁)–CH(CH₃)–CH(NR₃)–OH | H | CH₂ | (S)- isobutyl (CH) |
| 1264 | (R)- benzyl (CH) | C=O | (Q₁)–CH(CH₃)–CH(NR₃)–OH | H | CH₂ | (S)- isobutyl (CH) |
| 1265 | (S)- H₂N-CH₂-(CH) | C=O | (Q₁)–CH(CH₃)–CH(NR₃)–OH | H | CH₂ | (S)- isobutyl (CH) |
| 1266 | (R)- H₂N-CH₂-(CH) | C=O | (Q₁)–CH(CH₃)–CH(NR₃)–OH | H | CH₂ | (S)- isobutyl (CH) |

TABLE 5B-continued

| Cpd | R₁ | Q₁ | R₂ | R₃ | Q₂ | R₄ |
|---|---|---|---|---|---|---|
| 1267 | (S)- H₂N-C(=NH)-NH-(CH₂)₃-(CH) | C=O | (Q₁)-CH(NR₃)-CH(OH)-CH₃ | H | CH₂ | (S)- (CH₃)₂CH-CH₂-(CH) |
| 1268 | (R)- H₂N-C(=NH)-NH-(CH₂)₃-(CH) | C=O | (Q₁)-CH(NR₃)-CH(OH)-CH₃ | H | CH₂ | (S)- (CH₃)₂CH-CH₂-(CH) |
| 1269 | (S)- isobutyl-(CH) | C=O | (Q₁)-CH(NR₃)-CH(OH)-CH₃ | H | CH₂ | (S)- (CH₃)₂CH-CH₂-(CH) |
| 1270 | (R)- isobutyl-(CH) | C=O | (Q₁)-CH(NR₃)-CH(OH)-CH₃ | H | CH₂ | (S)- (CH₃)₂CH-CH₂-(CH) |
| 1271 | (S)- imidazol-4-yl-CH₂-(CH) | C=O | (Q₁)-CH(NR₃)-CH(OH)-CH₃ | H | CH₂ | (S)- (CH₃)₂CH-CH₂-(CH) |
| 1272 | (R)- imidazol-4-yl-CH₂-(CH) | C=O | (Q₁)-CH(NR₃)-CH(OH)-CH₃ | H | CH₂ | (S)- (CH₃)₂CH-CH₂-(CH) |
| 1273 | (R)- indol-3-yl-CH₂-(CH) | C=O | (Q₁)-CH(NR₃)-(CH₂)₃-NH-C(=NH)-NH₂ | H | CH₂ | (S)- (CH₃)₂CH-CH₂-(CH) |
| 1274 | (R)- 4-HO-C₆H₄-CH₂-(CH) | C=O | (Q₁)-CH(NR₃)-(CH₂)₃-NH-C(=NH)-NH₂ | H | CH₂ | (S)- (CH₃)₂CH-CH₂-(CH) |
| 1275 | (S)- indol-3-yl-CH₂-(CH) | C=O | (Q₁)-CH(NR₃)-(CH₂)₃-NH-C(=NH)-NH₂ | H | CH₂ | (S)- (CH₃)₂CH-CH₂-(CH) |

TABLE 5B-continued

| Cpd | R₁ | Q₁ | R₂ | R₃ | Q₂ | R₄ |
|---|---|---|---|---|---|---|
| 1276 | (S)- 4-hydroxybenzyl (CH) | C=O | (Q₁)-(NR₃)-(CH₂)₃-NH-C(=NH)NH₂ | H | CH₂ | (S)- isobutyl (CH) |
| 1277 | (S)- benzyl (CH) | C=O | (Q₁)-(NR₃)-(CH₂)₃-NH-C(=NH)NH₂ | H | CH₂ | (S)- isobutyl (CH) |
| 1278 | (R)- benzyl (CH) | C=O | (Q₁)-(NR₃)-(CH₂)₃-NH-C(=NH)NH₂ | H | CH₂ | (S)- isobutyl (CH) |
| 1279 | (S)- isopropyl (CH) | C=O | (Q₁)-(NR₃)-(CH₂)₃-NH-C(=NH)NH₂ | H | CH₂ | (S)- isobutyl (CH) |
| 1280 | (R)- isopropyl (CH) | C=O | (Q₁)-(NR₃)-(CH₂)₃-NH-C(=NH)NH₂ | H | CH₂ | (S)- isobutyl (CH) |
| 1281 | (S)-CH₃ | C=O | (Q₁)-(NR₃)-(CH₂)₃-NH-C(=NH)NH₂ | H | CH₂ | (S)- isobutyl (CH) |
| 1282 | (R)-CH₃ | C=O | (Q₁)-(NR₃)-(CH₂)₃-NH-C(=NH)NH₂ | H | CH₂ | (S)- isobutyl (CH) |
| 1283 | (S)- HOCH₂ (CH) | C=O | (Q₁)-(NR₃)-(CH₂)₃-NH-C(=NH)NH₂ | H | CH₂ | (S)- isobutyl (CH) |
| 1284 | (R)- HOCH₂ (CH) | C=O | (Q₁)-(NR₃)-(CH₂)₃-NH-C(=NH)NH₂ | H | CH₂ | (S)- isobutyl (CH) |
| 1285 | (R)- 1H-indol-3-ylmethyl (CH) | C=O | (Q₁)-(NR₃)-(CH₂)₃-NH-C(=NH)NH₂ | H | CH₂ | (S)- isobutyl (CH) |

TABLE 5B-continued

| Cpd | R₁ | Q₁ | R₂ | R₃ | Q₂ | R₄ |
|---|---|---|---|---|---|---|
| 1286 | (R)- 4-hydroxybenzyl (CH) | C=O | (Q₁)-(S)-CH(NR₃)-(CH₂)₃-NH-C(=NH)NH₂ | H | CH₂ | (S)- isobutyl (CH) |
| 1287 | (S)- indol-3-ylmethyl (CH) | C=O | (Q₁)-(S)-CH(NR₃)-(CH₂)₃-NH-C(=NH)NH₂ | H | CH₂ | (S)- isobutyl (CH) |
| 1288 | (S)- 4-hydroxybenzyl (CH) | C=O | (Q₁)-(S)-CH(NR₃)-(CH₂)₃-NH-C(=NH)NH₂ | H | CH₂ | (S)- isobutyl (CH) |
| 1289 | (S)- benzyl (CH) | C=O | (Q₁)-(S)-CH(NR₃)-(CH₂)₃-NH-C(=NH)NH₂ | H | CH₂ | (S)- isobutyl (CH) |
| 1290 | (R)- benzyl (CH) | C=O | (Q₁)-(S)-CH(NR₃)-(CH₂)₃-NH-C(=NH)NH₂ | H | CH₂ | (S)- isobutyl (CH) |
| 1291 | (S)- isopropyl (CH) | C=O | (Q₁)-(S)-CH(NR₃)-(CH₂)₃-NH-C(=NH)NH₂ | H | CH₂ | (S)- isobutyl (CH) |
| 1292 | (R)- isopropyl (CH) | C=O | (Q₁)-(S)-CH(NR₃)-(CH₂)₃-NH-C(=NH)NH₂ | H | CH₂ | (S)- isobutyl (CH) |
| 1293 | (S)-CH₃ | C=O | (Q₁)-(S)-CH(NR₃)-(CH₂)₃-NH-C(=NH)NH₂ | H | CH₂ | (S)- isobutyl (CH) |
| 1294 | (R)-CH₃ | C=O | (Q₁)-(S)-CH(NR₃)-(CH₂)₃-NH-C(=NH)NH₂ | H | CH₂ | (S)- isobutyl (CH) |

TABLE 5B-continued

![structure with R1, Q1, R2, R3, NH, NH, R4, oxazole ring, Q2]

| Cpd | R₁ | Q₁ | R₂ | R₃ | Q₂ | R₄ |
|---|---|---|---|---|---|---|
| 1295 | (S)- HO—(CH)— | C=O | (Q₁)—[(S)]—(NR₃), —CH₂CH₂CH₂—NH—C(=NH)NH₂ | H | CH₂ | (S)- isobutyl-(CH) |
| 1296 | (R)- HO—(CH)— | C=O | (Q₁)—[(R)]—(NR₃), —CH₂CH₂CH₂—NH—C(=NH)NH₂ | H | CH₂ | (S)- isobutyl-(CH) |
| 1297 | (R)- indol-3-ylmethyl-(CH) | C=O | (Q₁)—(NR₃), —CH₂—NH₂ | H | CH₂ | (S)- isobutyl-(CH) |
| 1298 | (R)- 4-HO-benzyl-(CH) | C=O | (Q₁)—(NR₃), —CH₂—NH₂ | H | CH₂ | (S)- isobutyl-(CH) |
| 1299 | (S)- indol-3-ylmethyl-(CH) | C=O | (Q₁)—(NR₃), —CH₂—NH₂ | H | CH₂ | (S)- isobutyl-(CH) |
| 1300 | (S)- 4-HO-benzyl-(CH) | C=O | (Q₁)—(NR₃), —CH₂—NH₂ | H | CH₂ | (S)- isobutyl-(CH) |
| 1301 | (S)- benzyl-(CH) | C=O | (Q₁)—(NR₃), —CH₂—NH₂ | H | CH₂ | (S)- isobutyl-(CH) |
| 1302 | (R)- benzyl-(CH) | C=O | (Q₁)—(NR₃), —CH₂—NH₂ | H | CH₂ | (S)- isobutyl-(CH) |
| 1303 | (S)- isopropyl-(CH) | C=O | (Q₁)—(NR₃), —CH₂—NH₂ | H | CH₂ | (S)- isobutyl-(CH) |
| 1304 | (R)- isopropyl-(CH) | C=O | (Q₁)—(NR₃), —CH₂—NH₂ | H | CH₂ | (S)- isobutyl-(CH) |

TABLE 5B-continued

| Cpd | R₁ | Q₁ | R₂ | R₃ | Q₂ | R₄ |
|---|---|---|---|---|---|---|
| 1305 | (S)-CH₃ | C=O | (Q₁)—CH(NR₃)—CH₂NH₂ | H | CH₂ | (S)-CH(CH₂CH(CH₃)₂) |
| 1306 | (R)-CH₃ | C=O | (Q₁)—CH(NR₃)—CH₂NH₂ | H | CH₂ | (S)-CH(CH₂CH(CH₃)₂) |
| 1307 | (S)-HOCH₂—(CH) | C=O | (Q₁)—CH(NR₃)—CH₂NH₂ | H | CH₂ | (S)-CH(CH₂CH(CH₃)₂) |
| 1308 | (R)-HOCH₂—(CH) | C=O | (Q₁)—CH(NR₃)—CH₂NH₂ | H | CH₂ | (S)-CH(CH₂CH(CH₃)₂) |
| 1309 | (R)-indol-3-ylmethyl(CH) | C=O | (Q₁)—CH(NR₃)—CH₂NH₂ | H | CH₂ | (S)-CH(CH₂CH(CH₃)₂) |
| 1310 | (R)-4-HO-C₆H₄-CH₂(CH) | C=O | (Q₁)—CH(NR₃)—CH₂NH₂ | H | CH₂ | (S)-CH(CH₂CH(CH₃)₂) |
| 1311 | (S)-indol-3-ylmethyl(CH) | C=O | (Q₁)—CH(NR₃)—CH₂NH₂ | H | CH₂ | (S)-CH(CH₂CH(CH₃)₂) |
| 1312 | (S)-4-HO-C₆H₄-CH₂(CH) | C=O | (Q₁)—CH(NR₃)—CH₂NH₂ | H | CH₂ | (S)-CH(CH₂CH(CH₃)₂) |
| 1313 | (S)-C₆H₅-CH₂(CH) | C=O | (Q₁)—CH(NR₃)—CH₂NH₂ | H | CH₂ | (S)-CH(CH₂CH(CH₃)₂) |
| 1314 | (R)-C₆H₅-CH₂(CH) | C=O | (Q₁)—CH(NR₃)—CH₂NH₂ | H | CH₂ | (S)-CH(CH₂CH(CH₃)₂) |

TABLE 5B-continued

| Cpd | R₁ | Q₁ | R₂ | R₃ | Q₂ | R₄ |
|---|---|---|---|---|---|---|
| 1315 | (S)-isopropyl(CH) | C=O | (Q₁)-CH(NR₃)-CH₂-NH₂ | H | CH₂ | (S)-isobutyl(CH) |
| 1316 | (R)-isopropyl(CH) | C=O | (Q₁)-CH(NR₃)-CH₂-NH₂ | H | CH₂ | (S)-isobutyl(CH) |
| 1317 | (S)-CH₃ | C=O | (Q₁)-CH(NR₃)-CH₂-NH₂ | H | CH₂ | (S)-isobutyl(CH) |
| 1318 | (R)-CH₃ | C=O | (Q₁)-CH(NR₃)-CH₂-NH₂ | H | CH₂ | (S)-isobutyl(CH) |
| 1319 | (S)-HOCH₂(CH) | C=O | (Q₁)-CH(NR₃)-CH₂-NH₂ | H | CH₂ | (S)-isobutyl(CH) |
| 1320 | (R)-HOCH₂(CH) | C=O | (Q₁)-CH(NR₃)-CH₂-NH₂ | H | CH₂ | (S)-isobutyl(CH) |
| 1321 | (S)-isobutyl(CH) | C=O | (Q₁)-CH(NR₃)-CH₂-NH₂ | H | CH₂ | (S)-isobutyl(CH) |
| 1322 | (R)-isobutyl(CH) | C=O | (Q₁)-CH(NR₃)-CH₂-NH₂ | H | CH₂ | (S)-isobutyl(CH) |
| 1323 | (S)-HOCH₂(CH) | CH₂ | (Q₁)-CH(NR₃)-CH₂-NH₂ | H | CH₂ | (S)-isobutyl(CH) |
| 1324 | (R)-HOCH₂(CH) | CH₂ | (Q₁)-CH(NR₃)-CH₂-NH₂ | H | CH₂ | (S)-isobutyl(CH) |
| 1325 | (R)-indol-3-ylmethyl(CH) | CH₂ | (Q₁)-CH(NR₃)-CH₂-NH₂ | H | CH₂ | (S)-isobutyl(CH) |

TABLE 5B-continued

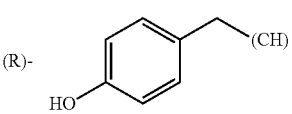

| Cpd | R₁ | Q₁ | R₂ | R₃ | Q₂ | R₄ |
|---|---|---|---|---|---|---|
| 1326 | (R)- 4-hydroxybenzyl (CH) | CH₂ | (Q₁)-CH(NR₃)- | H | CH₂ | (S)- isobutyl (CH) |
| 1327 | (S)- indol-3-ylmethyl (CH) | CH₂ | (Q₁)-CH(NR₃)- | H | CH₂ | (S)- isobutyl (CH) |
| 1328 | (S)- 4-hydroxybenzyl (CH) | CH₂ | (Q₁)-CH(NR₃)- | H | CH₂ | (S)- isobutyl (CH) |
| 1329 | (S)- benzyl (CH) | CH₂ | (Q₁)-CH(NR₃)- | H | CH₂ | (S)- isobutyl (CH) |
| 1330 | (R)- benzyl (CH) | CH₂ | (Q₁)-CH(NR₃)- | H | CH₂ | (S)- isobutyl (CH) |
| 1331 | (S)- H₂N-CH₂-(CH) | CH₂ | (Q₁)-CH(NR₃)- | H | CH₂ | (S)- isobutyl (CH) |
| 1332 | (R)- H₂N-CH₂-(CH) | CH₂ | (Q₁)-CH(NR₃)- | H | CH₂ | (S)- isobutyl (CH) |
| 1333 | (S)- H₂N-(CH₂)₄-(CH) | CH₂ | (Q₁)-CH(NR₃)- | H | CH₂ | (S)- isobutyl (CH) |
| 1334 | (R)- H₂N-(CH₂)₄-(CH) | CH₂ | (Q₁)-CH(NR₃)- | H | CH₂ | (S)- isobutyl (CH) |

Example 7

High Throughput Screening Assay for Identification of Hepatitis C Virus NS3 Protease Inhibitors Infection with hepatitis C virus (HCV) is a major global health concern causing chronic hepatitis, liver cirrhosis and hepatocellular carcinoma. The non-structural viral proteins are cleaved from a precursor protein by the HCV NS3 serine protease that requires the adjacent NS4A cofactor. The NS3 protease plays a vital role in protein processing as it directs proteolytic cleavages at the NS3/4A, NS4A/4B, NS4B/5A, and NS5A/5B junctions and is thus essential for replication and infectivity of the virus.

To identify new HCV NS3 protease inhibitors, a scintillation proximity assay (SPA) optimized for HTS is conducted as described in the literature (J. Biomol. Screen. 2000, 5, 153-158). The buffer used for the assay is 62.5 mM HEPES (pH 7.5), 30 mM dithiothreitol, 18.75% (v/v) glycerol, 0.062% (v/v) Triton X-100. HCV NS3 protease is activated by incubation with the NS4A cofactor (1000:1 cofactor:protease ratio) in assay buffer for 5 min at ambient temperature with mild agitation. Assays are conducted in 96 or 384-well microtiter plates with 50 µL assay buffer, 15 nM dual biotin and tritium-labelled protease substrate (biotin-DRMEECASHLPYK[propionyl-$^3$H]—NH$_2$), 6 mM biotinyl-protease substrate, 25 nM HCV NS3 protease, 25 µM NS4A cofactor peptide (HKKKGSWIVGRIILSG-NH2), and library test compound in 2.5 µL DMSO. Reaction is initiated by the addition of 10 µL of the enzyme and cofactor. The plates are incubated for 30 min at ambient temperature with gentle agitation, then stopped by the addition of 100 µL of an appropriate stop solution (for example, streptavidin-coated YSi-SPA beads in PBS). Measurement of the radioactivity bound to the SPA beads is performed with an appropriate microplate scintillation counter (typically using a 1 min count time). Data thus obtained are analyzed using an appropriate software package, for example GraphPad Prism (La Jolla, Calif.).

Example 8

High Throughput Screening Assay for Identification of 5-Hydroxytryptamine Receptor Subtype 2A (5-HT$_{2A}$) Inverse Agonists The majority of clinically important antipsychotic agents have been found, in addition to their antagonistic action at dopamine D2 receptors, to be potent inverse agonists at the 5-HT$_{2A}$ receptor. For the identification of new such CNS therapeutic agents, the receptor selection and amplification assay as described in the literature (J. Pharm. Exp. Ther. 2001, 299, 268-276) is conducted.
Cell Culture In preparation for the assay, appropriate cells (NIH-3T3 or other) are grown to 70-80% confluence in roller bottles or standard 96-well tissue culture plates in Dulbecco's modified essential media (DMEM) supplemented with 10% calf serum and 1% PSG (penicillin/streptomycin/glutamine. Transfection of cells with plasmid DNAs (cloned receptor) using standard methods for 12-16 h (o/n) followed. Co-expression of Gq was used to augment 5-HT$_{2A}$ receptor constitutive activity. If in plates, assays are performed with 1 to 50 ng/well cloned receptor and 20 ng/well β-galactosidase plasmid DNA. To assist with the 5-HT$_{2A}$ constitutive activity, 4-20 ng/well of G$_q$ protein were also added. After transfection in roller bottles, the cells were trypsinized, harvested and frozen, or could be immediately used in the assay.
Assay For the assay, cells were placed (or rapidly thawed, if previously forzen) in DMEM with 0.5% calf serum and 2% cyto-sf3 (Kemp Biotechnologies, Frederick, Md., USA), then added to the assay plates (typically 96- or 384-well) containing test compounds from the library, negative controls or positive controls (ritanserin). Alternatively, after the o/n transfection in plates, medium was replaced with serum-free DMEM containing 2% cyto-sf3 and 1% PSG and one (or more) concentrations of test library compounds or controls. In all cases, cells were grown in a humidified atmosphere with 5% ambient CO$_2$ for 4-6 d. After removal of the medium, β-galactosidase activity in the plates is measured using standard methods, for example adding o-nitrophenyl β-D-galactopyranoside in phosphate buffered saline. The resulting colorimetric reaction was then measured using a spectrophotometric plate reader at the wavelength appropriate for the β-galactosidase method employed (420 nm for the example). Analysis of data is done using an appropriate software package, for example GraphPad Prism.

Example 9

Cell-Based High Throughput Screening Assay for Identification of Inhibitors of p53-MDM2 Interaction The p53 transcription factor is a potent tumor suppressor that regulates expression of a variety of genes responsible for DNA repair, differentiation, cell cycle inhibition and apoptosis. The function of p53 is suppressed by the MDM2 oncoprotein through direct inhibition of its transcriptional activity and also enhancement of its degradation via the ubiquitin-proteosome pathway. Many human tumors over-express MDM2 and effectively impair p53-mediated apoptosis. Hence, stabilization of p53 through inhibiting the p53-MDM2 interaction offers an approach for cancer chemotherapy. For the identification of such inhibitors, the validated cell-based assay as described in the literature is employed (J. Biomol. Screen. 2011, 16, 450-456). This is based upon mammalian two-hybrid technology utilizing a dual luciferase reporter system to eliminate false hits from cytotoxicity to the compounds.
Cell Culture Appropriate cells (for example HEK293, U2OS, MDA-MB-435) were obtained from ATCC (Manassas, Va., USA) and maintained in DMEM with 10% fetal bovine serum (FBS), 100 mg/L penicillin, and 100 mg/L streptomycin at 37° C. in a humidified atmosphere of 5% CO$_2$. About 1×10$^6$ cells were combined with plasmids (2-4 µg) in transfection buffer (200 µL), and electroporation executed for transient transfection.
Assay A mammalian two-hybrid system (Stratagene, La Jolla, Calif.) was utilized for the cell-based assay developed for assessing the p53-MDM2 interaction. To effect this strategy, full-length p53 or MDM2 were inserted at the C-terminus of the DNA binding domain (BD) of GAL4 or the transcriptional activation domain (AD) of NFκB. Interaction of p53 and MDM2 brings the two domains (BD and AD) into proximity and thereby activates the downstream firefly luciferase reporter gene. Specifically, into the pCMV-AD and pCMV-BD vectors were cloned full-length cDNAs encoding human p53 and MDM2 in-frame with AD or BD at the N terminus. For single-luciferase analysis, cells were co-transfected with pCMV-AD-MDM2 (or -p53), pCMV-BD-p53 (or -MDM2), and the pFR-Luc firefly luciferase reporter plasmid at an equivalent ratio of 1:1:1. While for dual-luciferase analysis, an internal control, the pRL-TK plasmid encoding a *renilla* luciferase, was included. After transfection, seeding of cells is performed at a density of approximately 3×10$^4$ cells per well onto microplate (96 wells). The library test compounds at various concentrations are added 16 h post-transfection. Luciferase activities were measured after an additional 24 h using the Dual-Glo Luciferase system (Promega, Madison, Wis., USA) and an appropriate multiplate reader. Compounds are typically initially screened at a single concentration of 10 µM, 20 µM or 50 µM, then a dose-response curve obtained for those compounds found to be hits as defined below. In each 96-well plate, eight wells were used as positive controls (10 µM known inhibitor, for example nutilin-3, in 1% DMSO) and another eight wells as negative controls (1% DMSO). The luciferase activity was normalized to 100% and 0 in the wells treated with DMSO and known inhibitor, respectively.

The compounds causing the luciferase activity to reduce to less than 30% could be considered as "hits" in the primary screening, although other values can also be selected. GraphPad Prism software, or other appropriate package, is used to analyze data and perform nonlinear regression analyses to generate dose-response curves and calculate $IC_{50}$ values.

Example 10

Synthesis of a Representative Library of Macrocyclic Compounds of Formulae (Ia), (Ib), (Ic), (Id) and (Ie)

The synthetic scheme depicted in Scheme 8 was used to synthesize the library of macrocyclic compounds 1335-1383 on solid support except that $BB_1$ was Fmoc-$NR_5$—$CHR_1$—$CO_2H$. The first amino acid building block amino acid ($BB_1$) was attached to the resin (Method 1D), then, after Fmoc deprotection (Method 1F), the second building block ($BB_2$) was added through amide bond formation (Method 1G) or reductive amination (Method 1I or 1J). The N-protection was cleaved (Method 1F) and the oxazole building block ($BB_3$) attached by reductive amination (Method 1J) or amide coupling (Method 1G) to give the macrocycle precursor scaffold. The crude product was obtained after sequential removal of the Fmoc (Method 1F), acidic cleavage from the resin (Method 1Q), cyclization (Method 1R) and cleavage of the side chain protecting groups (Method 1S) followed by concentration in vacuo. For compounds 1343, 1365 and 1377, prior to macrocyclization, the N-methyl group on $BB_3$ (add $R_6$ in place of H) is installed by the series of reactions described in Method 1P using methanol as the alcohol component. The purified macrocycles obtained after preparative HPLC (Method 2B) are presented in Table 6A with the amounts, purity and confirmation of identity. Structures of the individual compounds in the library are provided in Table 6B.

TABLE 6A

| Cpd | $BB_1$ | $BB_2$ | $BB_3$ | Wt (mg)[1] | Purity[2] | MS (M + H) |
|---|---|---|---|---|---|---|
| 1335 | Fmoc-Glu(OBut) | Fmoc-D-Tyr(But) | Fmoc-OX-13 | 3.3 | 100 | 459 |
| 1336 | Fmoc-Leu | Fmoc-D-Tyr(But) | Fmoc-OX-13 | 1.0 | 100 | 443 |
| 1337 | Fmoc-Ser(But) | Fmoc-D-Dap(Boc) | Fmoc-OX-16 | 10.3 | 100 | 340 |
| 1338 | Fmoc-Ser(But) | Fmoc-Dap(Boc) | Fmoc-OX-16 | 10.2 | 100 | 340 |
| 1339 | Fmoc-D-Ser(But) | Fmoc-Dap(Boc) | Fmoc-OX-16 | 5.0 | 100 | 340 |
| 1340 | Fmoc-D-Ser(But) | Fmoc-D-Dap(Boc) | Fmoc-OX-16 | 7.3 | 100 | 340 |
| 1341 | Fmoc-N-Me-Ser(But) | Fmoc-D-Dap(Boc) | Fmoc-OX-13 | 5.4 | 90 | 354 |
| 1342 | Fmoc-Ser(But) | Fmoc-N-Me-D-Dap(Boc) | Fmoc-OX-13 | 2.0 | 100 | 354 |
| 1343 | Fmoc-Ser(But) | Fmoc-D-Dap(Boc) | Fmoc-OX-13 | 6.0 | 100 | 354 |
| 1344 | Fmoc-Thr(But) | Fmoc-D-Dap(Boc) | Fmoc-OX-13 | 5.2 | 100 | 354 |
| 1345 | Fmoc-Asp(OBut) | Fmoc-D-Dap(Boc) | Fmoc-OX-13 | 0.8 | 100 | 368 |
| 1346 | Fmoc-Asn(Trt) | Fmoc-D-Dap(Boc) | Fmoc-OX-13 | 2.5 | 100 | 367 |
| 1347 | Fmoc-Tyr(But) | Fmoc-D-Dap(Boc) | Fmoc-OX-13 | 3.9 | 72 | 416 |
| 1348 | Fmoc-Dap(Boc) | Fmoc-D-Ser(But) | Fmoc-OX-13 | 3.5 | 100 | 340 |
| 1349 | Fmoc-Ser(But) | Fmoc-D-Dab(Boc) | Fmoc-OX-13 | 7.0 | 100 | 354 |
| 1350 | Fmoc-Ser(But) | Fmoc-D-Orn(Boc) | Fmoc-OX-13 | 7.7 | 100 | 368 |
| 1351 | Fmoc-Ser(But) | Fmoc-D-Lys(Boc) | Fmoc-OX-13 | 6.7 | 100 | 382 |
| 1352 | Fmoc-Ser(But) | Fmoc-D-Ser(But) | Fmoc-OX-13 | 5.5 | 100 | 341 |
| 1353 | Fmoc-Ser(But) | Fmoc-D-Ala | Fmoc-OX-13 | 5.3 | 100 | 325 |
| 1354 | Fmoc-Ser(But) | Fmoc-D-Asn(Trt) | Fmoc-OX-13 | 8.6 | 100 | 368 |
| 1355 | Fmoc-Ser(But) | Fmoc-D-Dap(Boc) | Fmoc-OX-33 | 6.2 | 93 | 340 |
| 1356 | Fmoc-Ser(But) | Fmoc-D-Dap(Boc) | Fmoc-OX-32 | 3.0 | 100 | 340 |
| 1357 | Fmoc-Ser(But) | Fmoc-D-Dap(Boc) | Fmoc-OX-31 | na | na | na |
| 1358 | Fmoc-D-Tyr(But) | Fmoc-D-Lys(Boc) | Fmoc-OX-13 | 18.3 | 100 | 458 |
| 1359 | Fmoc-Tyr(But) | Fmoc-Lys(Boc) | Fmoc-OX-13 | 1.7 | 100 | 458 |
| 1360 | Fmoc-D-Tyr(But) | Fmoc-D-Lys(Boc) | Fmoc-OX-16 | 1.8 | 100 | 458 |
| 1361 | Fmoc-Tyr(But) | Fmoc-D-Lys(Boc) | Fmoc-OX-16 | 7.6 | 100 | 458 |
| 1362 | Fmoc-D-Tyr(But) | Fmoc-Lys(Boc) | Fmoc-OX-16 | 2.8 | 100 | 458 |
| 1363 | Fmoc-Tyr(But) | Fmoc-Lys(Boc) | Fmoc-OX-16 | 8.8 | 100 | 458 |
| 1364 | Fmoc-D-Tyr(But) | Fmoc-NMe-D-Lys(Boc) | Fmoc-OX-13 | 3.5 | 100 | 472 |
| 1365 | Fmoc-D-Tyr(But) | Fmoc-D-Lys(Boc) | Fmoc-OX-13 | 6.5 | 100 | 472 |
| 1366 | Fmoc-D-Tyr(But) | Fmoc-D-Orn(Boc) | Fmoc-OX-13 | 5.6 | 100 | 444 |
| 1367 | Fmoc-D-Tyr(But) | Fmoc-D-Dab(Boc) | Fmoc-OX-13 | 4.9 | 100 | 430 |
| 1368 | Fmoc-D-Tyr(But) | Fmoc-D-Lys(Boc) | Fmoc-OX-33 | 9.9 | 100 | 458 |
| 1369 | Fmoc-D-Tyr(But) | Fmoc-D-Lys(Boc) | Fmoc-OX-31 | 5.1 | 100 | 416 |
| 1370 | Fmoc-D-Tyr(But) | Fmoc-D-Lys(Boc) | Fmoc-OX-32 | 7.1 | 100 | 458 |
| 1371 | Fmoc-Tyr(But) | Fmoc-Arg(Pbf) | Fmoc-OX-16 | 4.8 | 100 | 486 |
| 1372 | Fmoc-D-Tyr(But) | Fmoc-Arg(Pbf) | Fmoc-OX-16 | 2.7 | 100 | 486 |
| 1373 | Fmoc-Tyr(But) | Fmoc-D-Arg(Pbf) | Fmoc-OX-16 | 2.6 | 100 | 486 |
| 1374 | Fmoc-D-Tyr(But) | Fmoc-D-Arg(Pbf) | Fmoc-OX-16 | 1.3 | 100 | 486 |
| 1375 | Fmoc-N-Me-Tyr(But) | Fmoc-Arg(Pbf) | Fmoc-OX-13 | na | na | na |
| 1376 | Fmoc-Tyr(But) | Fmoc-N-Me-Arg(Pbf) | Fmoc-OX-13 | na | na | na |
| 1377 | Fmoc-Tyr(But) | Fmoc-Arg(Pbf) | Fmoc-OX-13 | 2.3 | 100 | 500 |
| 1378 | Fmoc-Arg(Pbf) | Fmoc-Tyr(But) | Fmoc-OX-13 | 1.6 | 100 | 486 |
| 1379 | Fmoc-Tyr(But) | Fmoc-Orn(Boc) | Fmoc-OX-13 | 3.7 | 100 | 444 |
| 1380 | Fmoc-Tyr(But) | Fmoc-Arg(Pbf) | Fmoc-OX-1 | 9.4 | 100 | 500 |
| 1381 | Fmoc-Tyr(But) | Fmoc-Arg(Pbf) | Fmoc-OX-31 | na | na | na |
| 1382 | Fmoc-Tyr(But) | Fmoc-Arg(Pbf) | Fmoc-OX-32 | 1.9 | 100 | 486 |
| 1383 | Fmoc-Tyr(But) | Fmoc-Arg(Pbf) | Fmoc-OX-33 | 4.0 | 100 | 486 | na = not available
[1]All syntheses were carried out on the solid phase starting from 70-80 mg of 2-chlorotrityl chloride resin (typical loading 1.0 mmol/g).
[2]Purity is determined by analysis with LC-UV at 220 nm.

TABLE 6B
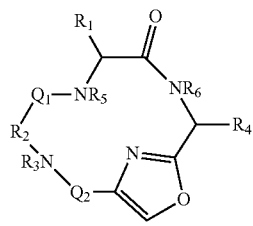
| Cpd | R₁ | Q₁ | R₂ | R₃ | Q₂ | R₄ |
|---|---|---|---|---|---|---|
| 1335 | (S)- HO₂C—(CH) | C=O | (Q₁)—(NR₃), CH₂-C₆H₄-OH | H | CH₂ | (S)- iBu-(CH) |
| 1336 | (S)- iBu-(CH) | C=O | (Q₁)—(NR₃), CH₂-C₆H₄-OH | H | CH₂ | (S)- iBu-(CH) |
| 1337 | (S)- HO—(CH) | C=O | (Q₁)—(NR₃), CH₂-NH₂ | H | CH₂ | (R)- iBu-(CH) |
| 1338 | (S)- HO—(CH) | C=O | (Q₁)—(NR₃), CH₂-NH₂ | H | CH₂ | (R)- iBu-(CH) |
| 1339 | (R)- HO—(CH) | C=O | (Q₁)—(NR₃), CH₂-NH₂ | H | CH₂ | (R)- iBu-(CH) |
| 1340 | (R)- HO—(CH) | C=O | (Q₁)—(NR₃), CH₂-NH₂ | H | CH₂ | (R)- iBu-(CH) |
| 1341 | (S)- HO—(CH) | C=O | (Q₁)—(NR₃), CH₂-NH₂ | H | CH₂ | (S)- iBu-(CH) |
| 1342 | (S)- HO—(CH) | C=O | (Q₁)—(NR₃), CH₂-NH₂ | Me | CH₂ | (S)- iBu-(CH) |
| 1343 | (S)- HO—(CH) | C=O | (Q₁)—(NR₃), CH₂-NH₂ | H | CH₂ | (S)- iBu-(CH) |

TABLE 6B-continued

| Cpd | R₁ | Q₁ | R₂ | R₃ | Q₂ | R₄ |
|---|---|---|---|---|---|---|
| 1344 | (S)- HO-CH(CH₃)- | C=O | (Q₁)-CH(NR₃)-CH₂-NH₂ | H | CH₂ | (S)- isobutyl (CH) |
| 1345 | (S)- HO₂C-CH₂-(CH) | C=O | (Q₁)-CH(NR₃)-CH₂-NH₂ | H | CH₂ | (S)- isobutyl (CH) |
| 1346 | (S)- H₂NOC-CH₂-(CH) | C=O | (Q₁)-CH(NR₃)-CH₂-NH₂ | H | CH₂ | (S)- isobutyl (CH) |
| 1347 | (S)- 4-HO-C₆H₄-CH₂-(CH) | C=O | (Q₁)-CH(NR₃)-CH₂-NH₂ | H | CH₂ | (S)- isobutyl (CH) |
| 1348 | (S)- H₂N-CH₂-(CH) | C=O | (Q₁)-CH(NR₃)-CH₂-OH | H | CH₂ | (S)- isobutyl (CH) |
| 1349 | (S)- HO-CH₂-(CH) | C=O | (Q₁)-CH(NR₃)-CH₂-CH₂-NH₂ | H | CH₂ | (S)- isobutyl (CH) |
| 1350 | (S)- HO-CH₂-(CH) | C=O | (Q₁)-CH(NR₃)-(CH₂)₃-NH₂ | H | CH₂ | (S)- isobutyl (CH) |
| 1351 | (S)- HO-CH₂-(CH) | C=O | (Q₁)-CH(NR₃)-(CH₂)₄-NH₂ | H | CH₂ | (S)- isobutyl (CH) |
| 1352 | (S)- HO-CH₂-(CH) | C=O | (Q₁)-CH(NR₃)-CH₂-OH | H | CH₂ | (S)- isobutyl (CH) |
| 1353 | (S)- HO-CH₂-(CH) | C=O | (Q₁)-CH(NR₃)-CH₃ | H | CH₂ | (S)- isobutyl (CH) |
| 1354 | (S)- HO-CH₂-(CH) | C=O | (Q₁)-CH(NR₃)-CH₂-CONH₂ | H | CH₂ | (S)- isobutyl (CH) |

TABLE 6B-continued

| Cpd | R$_1$ | Q$_1$ | R$_2$ | R$_3$ | Q$_2$ | R$_4$ |
|---|---|---|---|---|---|---|
| 1355 | (S)- HO―(CH) | C=O | (Q$_1$)―(NR$_3$) with NH$_2$ | H | CH$_2$ | (S)- isobutyl (CH) |
| 1356 | (S)- HO―(CH) | C=O | (Q$_1$)―(NR$_3$) with NH$_2$ | H | CH$_2$ | (S)- n-butyl (CH) |
| 1357 | (S)- HO―(CH) | C=O | (Q$_1$)―(NR$_3$) with NH$_2$ | H | CH$_2$ | (S)-CH$_3$ |
| 1358 | (R)- 4-HO-C$_6$H$_4$-CH$_2$-(CH) | C=O | (Q$_1$)―(NR$_3$) lysine side chain | H | CH$_2$ | (S)- isobutyl (CH) |
| 1359 | (S)- 4-HO-C$_6$H$_4$-CH$_2$-(CH) | C=O | (Q$_1$)―(NR$_3$) lysine side chain | H | CH$_2$ | (S)- isobutyl (CH) |
| 1360 | (R)- 4-HO-C$_6$H$_4$-CH$_2$-(CH) | C=O | (Q$_1$)―(NR$_3$) lysine side chain | H | CH$_2$ | (R)- isobutyl (CH) |
| 1361 | (S)- 4-HO-C$_6$H$_4$-CH$_2$-(CH) | C=O | (Q$_1$)―(NR$_3$) lysine side chain | H | CH$_2$ | (R)- isobutyl (CH) |
| 1362 | (R)- 4-HO-C$_6$H$_4$-CH$_2$-(CH) | C=O | (Q$_1$)―(NR$_3$) lysine side chain | H | CH$_2$ | (R)- isobutyl (CH) |
| 1363 | (S)- 4-HO-C$_6$H$_4$-CH$_2$-(CH) | C=O | (Q$_1$)―(NR$_3$) lysine side chain | H | CH$_2$ | (R)- isobutyl (CH) |
| 1364 | (R)- 4-HO-C$_6$H$_4$-CH$_2$-(CH) | C=O | (Q$_1$)―(NR$_3$) lysine side chain | Me | CH$_2$ | (S)- isobutyl (CH) |
| 1365 | (R)- 4-HO-C$_6$H$_4$-CH$_2$-(CH) | C=O | (Q$_1$)―(NR$_3$) lysine side chain | H | CH$_2$ | (S)- isobutyl (CH) |

TABLE 6B-continued

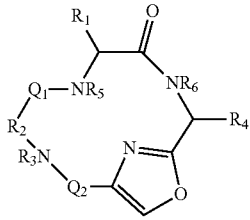

| Cpd | R₁ | Q₁ | R₂ | R₃ | Q₂ | R₄ |
|---|---|---|---|---|---|---|
| 1366 | (R)- 4-HO-C₆H₄-CH₂-(CH) | C=O | (Q₁)-(NR₃)-CH(CH₂CH₂CH₂NH₂) | H | CH₂ | (S)- isobutyl-(CH) |
| 1367 | (R)- 4-HO-C₆H₄-CH₂-(CH) | C=O | (Q₁)-(NR₃)-CH(CH₂NH₂) | H | CH₂ | (S)- isobutyl-(CH) |
| 1368 | (R)- 4-HO-C₆H₄-CH₂-(CH) | C=O | (Q₁)-(NR₃)-CH(CH₂CH₂CH₂CH₂NH₂) | H | CH₂ | (S)- isopropyl-(CH) |
| 1369 | (R)- 4-HO-C₆H₄-CH₂-(CH) | C=O | (Q₁)-(NR₃)-CH(CH₂CH₂CH₂CH₂NH₂) | H | CH₂ | (S)-CH₃ |
| 1370 | (R)- 4-HO-C₆H₄-CH₂-(CH) | C=O | (Q₁)-(NR₃)-CH(CH₂CH₂CH₂CH₂NH₂) | H | CH₂ | (S)- n-butyl-(CH) |
| 1371 | (S)- 4-HO-C₆H₄-CH₂-(CH) | C=O | (Q₁)-(NR₃)-CH(CH₂CH₂CH₂NHC(=NH)NH₂) | H | CH₂ | (R)- isobutyl-(CH) |
| 1372 | (R)- 4-HO-C₆H₄-CH₂-(CH) | C=O | (Q₁)-(NR₃)-CH(CH₂CH₂CH₂NHC(=NH)NH₂) | H | CH₂ | (R)- isobutyl-(CH) |
| 1373 | (S)- 4-HO-C₆H₄-CH₂-(CH) | C=O | (Q₁)-(NR₃)-CH(CH₂CH₂CH₂NHC(=NH)NH₂) | H | CH₂ | (R)- isobutyl-(CH) |
| 1374 | (R)- 4-HO-C₆H₄-CH₂-(CH) | C=O | (Q₁)-(NR₃)-CH(CH₂CH₂CH₂NHC(=NH)NH₂) | H | CH₂ | (R)- isobutyl-(CH) |
| 1375 | (S)- 4-HO-C₆H₄-CH₂-(CH) | C=O | (Q₁)-(NR₃)-CH(CH₂CH₂CH₂NHC(=NH)NH₂) | H | CH₂ | (S)- isobutyl-(CH) |

TABLE 6B-continued

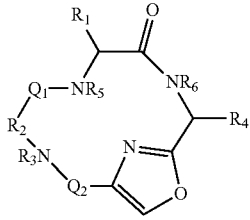

| Cpd | R₁ | Q₁ | R₂ | R₃ | Q₂ | R₄ |
|---|---|---|---|---|---|---|
| 1376 | (S)- 4-hydroxybenzyl (CH) | C=O | (Q₁)-CH(NR₃)-CH₂CH₂CH₂-NH-C(=NH)NH₂ | Me | CH₂ | (S)-isobutyl (CH) |
| 1377 | (S)- 4-hydroxybenzyl (CH) | C=O | (Q₁)-CH(NR₃)-CH₂CH₂CH₂-NH-C(=NH)NH₂ | H | CH₂ | (S)-isobutyl (CH) |
| 1378 | (S)- H₂N-C(=NH)-NH-(CH₂)₃- (CH) | C=O | (Q₁)-CH(NR₃)-CH₂-C₆H₄-OH | H | CH₂ | (S)-isobutyl (CH) |
| 1379 | (S)- 4-hydroxybenzyl (CH) | C=O | (Q₁)-CH(NR₃)-CH₂CH₂CH₂-NH₂ | H | CH₂ | (S)-isobutyl (CH) |
| 1380 | (S)- 4-hydroxybenzyl (CH) | C=O | (Q₁)-CH(NR₃)-CH₂CH₂CH₂-NH-C(=NH)NH₃ | H | C=O | (S)-isobutyl (CH) |
| 1381 | (S)- 4-hydroxybenzyl (CH) | C=O | (Q₁)-CH(NR₃)-CH₂CH₂CH₂-NH-C(=NH)NH₃ | H | CH₂ | (S)-CH₃ |
| 1382 | (S)- 4-hydroxybenzyl (CH) | C=O | (Q₁)-CH(NR₃)-CH₂CH₂CH₂-NH-C(=NH)NH₃ | H | CH₂ | (S)-n-butyl (CH) |
| 1383 | (S)- 4-hydroxybenzyl (CH) | C=O | (Q₁)-CH(NR₃)-CH₂CH₂CH₂-NH-C(=NH)NH₃ | H | CH₂ | (S)-isobutyl (CH) |

For all compounds $R_5$ and $R_6$=H, except for compounds 1341 and 1375 in which $R_5$=CH₃ and compounds 1343, 1365 and 1377 in which $R_6$=CH₃.

For further library diversification, the synthetic scheme presented in Scheme 3 was followed to prepare macrocyclic compounds 1384-1414 on solid support, except for a modification in the attachment of BB₄ related to compounds 1399-1400 noted below. The first amino acid building block amino acid (BB₁) was loaded onto the resin (Method 1D), then, after removal of the Fmoc protection (Method 1F), the oxazole building block (BB₂) attached through amide bond formation (Method 1G) or reductive amination (Method 1J). The next amino acid building block (BB₃) was coupled (Method 1G) after Fmoc-deprotection (Method 1F) to extend the intermediate chain, then the last building block component (BB₄) added using reductive amination (Method 1I or 1J) to complete the cyclization precursor. N-Terminal Fmoc deprotection (Method 1F), macrocyclization (Method 1R) and removal of side chain protecting groups (Method 1S) gave the crude product after evaporation under reduced pressure. The quantities of each macrocycle obtained, their HPLC purity and confirmation of their identity by mass spectrometry (MS) after purification by preparative HPLC (Method 2B) are included in Table 6C. Individual compound structures are provided in Table 6D.

For compounds 1399-1400 only, amide bond formation (Method 1G) was utilized to attach $BB_4$, which results in a carbonyl in the structure rather than a methylene. Also, for compounds 1404 and 1407, $BB_4$ is added via a Mitsunobu reaction using Method 1L. For compound 1392, the N-methyl group on $BB_2$ (add $R_8$ in place of H) is installed prior to the addition of $BB_3$ by the series of reactions described in Method 1P using methanol as the alcohol component. Likewise, for compounds 1406, 1407 and 1409, prior to macrocyclization, the N-methyl group on $BB_4$ ($R_5$) is installed by the series of reactions described in Method 1P using methanol as the alcohol component.

TABLE 6C

| Cpd | $BB_1$ | $BB_2$ | $BB_3$ | $BB_4$ | Wt (mg)[1] | Purity[2] | MS (M + H) |
|---|---|---|---|---|---|---|---|
| 1001 | Fmoc-D-Asn(Trt) | Fmoc-D-Trp(Boc) | Fmoc-Lys(Boc) | Fmoc-OX-13 | 19.8 | 100 | 594 |
| 1002 | Fmoc-D-Asn(Trt) | Fmoc-D-Tyr(But) | Fmoc-Lys(Boc) | Fmoc-OX-13 | 16.9 | 100 | 571 |
| 1003 | Fmoc-D-Asn(Trt) | Fmoc-Trp(Boc) | Fmoc-Lys(Boc) | Fmoc-OX-13 | 20.7 | 88 | 594 |
| 1384 | Fmoc-Trp(Boc) | Fmoc-OX-13 | Fmoc-Ser(But) | Fmoc-S35 | 0.8 | 100 | 593 |
| 1385 | Fmoc-D-Tyr(But) | Fmoc-OX-13 | Fmoc-D-Lys(Boc) | Fmoc-S30 | 9.3 | 100 | 515 |
| 1386 | Fmoc-Trp(Boc) | Fmoc-OX-1 | Fmoc-Lys(Boc) | Fmoc-S35 | 3.9 | 100 | 592 |
| 1387 | Fmoc-Trp(Boc) | Fmoc-OX-4 | Fmoc-D-Lys(Boc) | Fmoc-S35 | 1.7 | 100 | 592 |
| 1388 | Fmoc-D-Trp(Boc) | Fmoc-OX-4 | Fmoc-D-Lys(Boc) | Fmoc-S35 | 4.5 | 100 | 592 |
| 1389 | Fmoc-D-Trp(Boc) | Fmoc-OX-4 | Fmoc-Lys(Boc) | Fmoc-S35 | 1.1 | 100 | 592 |
| 1390 | Fmoc-Trp(Boc) | Fmoc-OX-4 | Fmoc-Lys(Boc) | Fmoc-S35 | 3.5 | 100 | 592 |
| 1391 | Fmoc-N-Me-Trp(Boc) | Fmoc-OX-1 | Fmoc-D-Lys(Boc) | Fmoc-S35 | na | na | na |
| 1392 | Fmoc-Trp(Boc) | Fmoc-OX-1 | Fmoc-D-Lys(Boc) | Fmoc-S35 | 2.1 | 100 | 606 |
| 1393 | Fmoc-Ala | Fmoc-OX-1 | Fmoc-D-Lys(Boc) | Fmoc-S35 | 3.1 | 100 | 477 |
| 1394 | Fmoc-Trp(Boc) | Fmoc-OX-19 | Fmoc-D-Lys(Boc) | Fmoc-S35 | 2.4 | 100 | 550 |
| 1395 | Fmoc-Trp(Boc) | Fmoc-OX-20 | Fmoc-D-Lys(Boc) | Fmoc-S35 | 2.1 | 100 | 592 |
| 1396 | Fmoc-Trp(Boc) | Fmoc-OX-21 | Fmoc-D-Lys(Boc) | Fmoc-S35 | 0.9 | 100 | 592 |
| 1397 | Fmoc-Trp(Boc) | Fmoc-OX-13 | Fmoc-D-Lys(Boc) | Fmoc-S35 | 10.2 | 100 | 578 |
| 1398 | Fmoc-Trp(Boc) | Fmoc-OX-16 | Fmoc-D-Lys(Boc) | Fmoc-S35 | 13.8 | 100 | 578 |
| 1399 | Fmoc-Trp(Boc) | Fmoc-OX-13 | Fmoc-D-Lys(Boc) | Fmoc-4-Pip* | 7.0 | 100 | 592 |
| 1400 | Fmoc-Trp(Boc) | Fmoc-OX-1 | Fmoc-D-Lys(Boc) | Fmoc-4-Pip* | 8.5 | 97 | 606 |
| 1401 | Fmoc-Trp(Boc) | Fmoc-OX-1 | Fmoc-D-Lys(Boc) | Fmoc-(S)-SP1** | 4.8 | 100 | 578 |
| 1402 | Fmoc-Trp(Boc) | Fmoc-OX-1 | Fmoc-D-Lys(Boc) | Fmoc-(R)-SP1** | 6.0 | 100 | 578 |
| 1403 | Fmoc-D-Lys(Boc) | Fmoc-OX-1 | Fmoc-Trp(Boc) | Fmoc-S35 | 2.7 | 100 | 592 |
| 1404 | Fmoc-Trp(Boc) | Fmoc-OX-1 | Fmoc-D-Lys(Boc) | Fmoc-S9 | 19.0 | 100 | 582 |
| 1405 | Fmoc-Trp(Boc) | Fmoc-OX-1 | Fmoc-D-Lys(Boc) | Fmoc-S6b*** | na | na | 566 |
| 1406 | Fmoc-Trp(Boc) | Fmoc-OX-1 | Fmoc-D-Lys(Boc) | Fmoc-S6b*** | 32.5 | 100 | 580 |
| 1407 | Fmoc-Trp(Boc) | Fmoc-OX-1 | Fmoc-D-Lys(Boc) | Fmoc-S9 | 24.7 | 100 | 596 |
| 1408 | Fmoc-Trp(Boc) | Fmoc-OX-1 | Fmoc-D-Lys(Boc) | Fmoc-S33 | na | na | 552 |
| 1409 | Fmoc-Trp(Boc) | Fmoc-OX-1 | Fmoc-D-Lys(Boc) | Fmoc-S33 | na | na | 566 |
| 1410 | Fmoc-Trp(Boc) | Fmoc-OX-1 | Fmoc-D-Arg(Pbf) | Fmoc-S35 | 1.1 | 55 | 620 |
| 1411 | Fmoc-Trp(Boc) | Fmoc-OX-1 | Fmoc-D-Orn(Boc) | Fmoc-S35 | 2.4 | 100 | 578 |
| 1412 | Fmoc-Trp(Boc) | Fmoc-OX-1 | Fmoc-D-Dab(Boc) | Fmoc-S35 | 0.6 | na | 564 |
| 1413 | Fmoc-Trp(Boc) | Fmoc-OX-1 | Fmoc-D-Gln(Trt) | Fmoc-S35 | 0.6 | 100 | 592 |
| 1414 | Fmoc-Trp(Boc) | Fmoc-OX-1 | Fmoc-D-Arg(Pbf) | Fmoc-S35 | 0.3 | 100 | 620 | na = not available

[1]All syntheses were carried out on the solid phase starting from 70-80 mg of 2-chlorotrityl chloride resin (typical loading 1.0 mmol/g).

[2]Purity is determined by analysis with LC-UV at 220 nm.

* Fmoc-Pip is (commercially available, Sigma-Aldrich Cat. No. 09777).

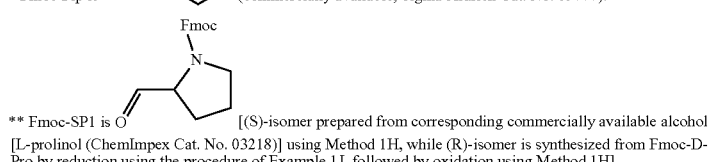

** Fmoc-SP1 is    [(S)-isomer prepared from corresponding commercially available alcohol [L-prolinol (ChemImpex Cat. No. 03218)] using Method 1H, while (R)-isomer is synthesized from Fmoc-D-Pro by reduction using the procedure of Example 1J, followed by oxidation using Method 1H].

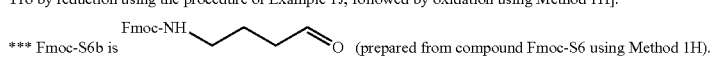

*** Fmoc-S6b is    (prepared from compound Fmoc-S6 using Method 1H).

TABLE 6D

| Cpd | R₁ | Q | R₂ | R₃ |
|---|---|---|---|---|
| 1384 | (S)- indol-3-ylmethyl (CH) | CH₂ | (S)- isobutyl (CH) | (S)- tert-butoxymethyl (CH) |
| 1385 | (R)- 4-hydroxybenzyl (CH) | CH₂ | (S)- isobutyl (CH) | (R)- H₂N-(CH₂)₄-(CH) |
| 1386 | (S)- indol-3-ylmethyl (CH) | C=O | (S)- isobutyl (CH) | (S)- H₂N-(CH₂)₄-(CH) |
| 1387 | (S)- indol-3-ylmethyl (CH) | C=O | (R)- isobutyl (CH) | (R)- H₂N-(CH₂)₄-(CH) |
| 1388 | (R)- indol-3-ylmethyl (CH) | C=O | (R)- isobutyl (CH) | (R)- H₂N-(CH₂)₄-(CH) |
| 1389 | (R)- indol-3-ylmethyl (CH) | C=O | (R)- isobutyl (CH) | (S)- H₂N-(CH₂)₄-(CH) |
| 1390 | (S)- indol-3-ylmethyl (CH) | C=O | (R)- isobutyl (CH) | (S)- H₂N-(CH₂)₄-(CH) |

TABLE 6D-continued

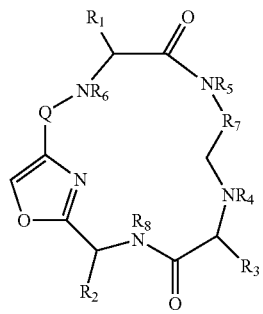

| | R1 | Q | R3 | R2 (NR4 side) |
|---|---|---|---|---|
| 1391 | (S)- indol-3-ylmethyl (CH) | C=O | (S)- isobutyl (CH) | (R)- H2N-butyl (CH) |
| 1392 | (S)- indol-3-ylmethyl (CH) | C=O | (S)- isopropyl (CH) | (R)- H2N-butyl (CH) |
| 1393 | (S)-CH3 | C=O | (S)- isobutyl (CH) | (R)- H2N-butyl (CH) |
| 1394 | (S)- indol-3-ylmethyl (CH) | C=O | (S)-CH3 | (R)- H2N-butyl (CH) |
| 1395 | (S)- indol-3-ylmethyl (CH) | C=O | (S)- n-butyl (CH) | (R)- H2N-butyl (CH) |
| 1396 | (S)- indol-3-ylmethyl (CH) | C=O | (S)- isobutyl (CH) | (R)- H2N-butyl (CH) |
| 1397 | (S)- indol-3-ylmethyl (CH) | CH2 | (S)- isobutyl (CH) | (R)- H2N-butyl (CH) |
| 1398 | (S)- indol-3-ylmethyl (CH) | CH2 | (R)- isobutyl (CH) | (R)- H2N-butyl (CH) |

TABLE 6D-continued

| | | | | |
|---|---|---|---|---|
| 1399 | (S)- [indole-CH2-(CH)] | CH2 | (S)- [isobutyl-(CH)] | (R)- H2N-(CH2)4-(CH) |
| 1400 | (S)- [indole-CH2-(CH)] | C=O | (S)- [isobutyl-(CH)] | (R)- H2N-(CH2)4-(CH) |
| 1401 | (S)- [indole-CH2-(CH)] | C=O | (S)- [isobutyl-(CH)] | (R)- H2N-(CH2)4-(CH) |
| 1402 | (S)- [indole-CH2-(CH)] | C=O | (S)- [isobutyl-(CH)] | (R)- H2N-(CH2)4-(CH) |
| 1403 | D-Lys | C=O | (S)- [isobutyl-(CH)] | (S)- [indole-CH2-(CH)] |
| 1404 | (S)- [indole-CH2-(CH)] | C=O | (S)- [isobutyl-(CH)] | (R)- H2N-(CH2)4-(CH) |
| 1405 | (S)- [indole-CH2-(CH)] | C=O | (S)- [isobutyl-(CH)] | (R)- H2N-(CH2)4-(CH) |

TABLE 6D-continued
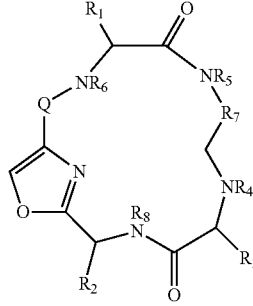
| 1406 | 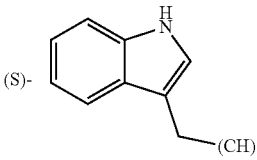 (S)- | C=O | (S)- 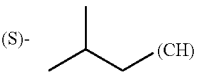 (CH) | (R)-  (CH) |
| 1407 | 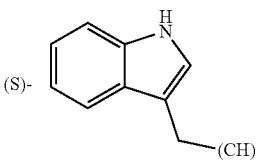 (S)- | C=O | (S)- 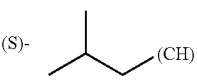 (CH) | (R)-  (CH) |
| 1408 | 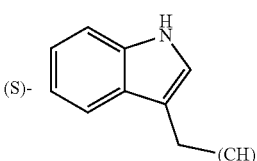 (S)- | C=O | (S)- 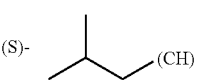 (CH) | (R)- 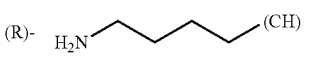 (CH) |
| 1409 | 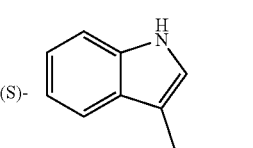 (S)- | C=O | (S)-  (CH) | (R)- 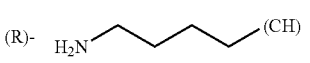 (CH) |
| 1410 | 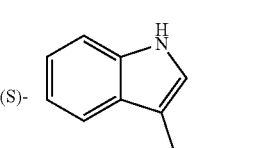 (S)- | C=O | (S)-  (CH) | (R)- 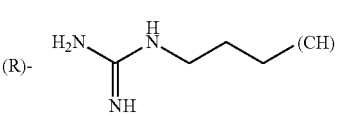 (CH) |
| 1411 | 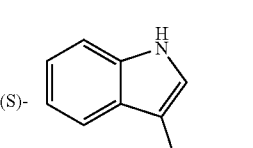 (S)- | C=O | (S)-  (CH) | (R)- 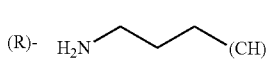 (CH) |
| 1412 | 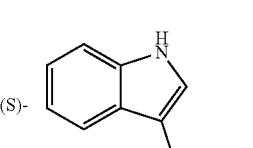 (S)- | C=O | (S)-  (CH) | (R)- 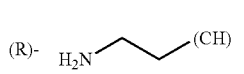 (CH) |

TABLE 6D-continued
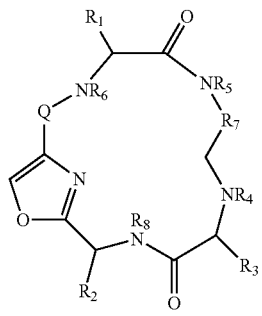
| | | | | |
|---|---|---|---|---|
| 1413 | 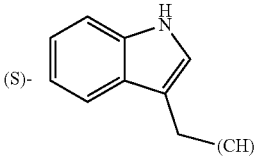 (S)-...(CH) | C=O | (S)- 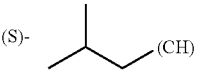(CH) | (R)- H₂NOC...(CH) |
| 1414 | 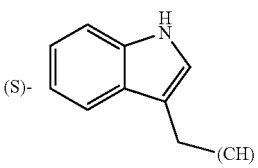 (S)-...(CH) | C=O | (S)- 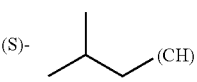(CH) | (R)- 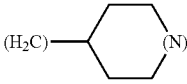(CH) |
| Cpd | R₅ | R₇ |
|---|---|---|
| 1384 | | (H₂C)-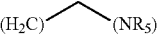(N) |
| 1385 | Me | (H₂C)-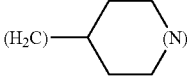(NR₅) |
| 1386 | | (H₂C)-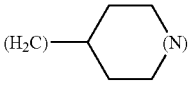(N) |
| 1387 | | (H₂C)-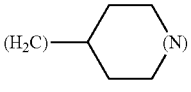(N) |
| 1388 | | (H₂C)-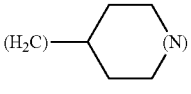(N) |
| 1389 | | (H₂C)-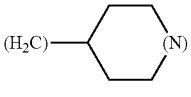(N) |
| 1390 | | (H₂C)-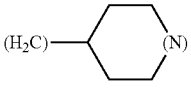(N) |
| 1391 | | (H₂C)-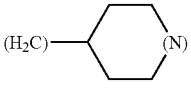(N) |
| 1392 | | (H₂C)-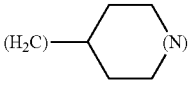(N) |
| 1393 | | (H₂C)-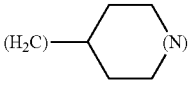(N) |

TABLE 6D-continued

| # | R | Group |
|---|---|---|
| 1394 | | (H₂C)—piperidine(N) |
| 1395 | | (H₂C)—piperidine(N) |
| 1396 | | (H₂C)—piperidine(N) |
| 1397 | | (H₂C)—piperidine(N) |
| 1398 | | (H₂C)—piperidine(N) |
| 1399 | | (S)- (OC)—piperidine(N) |
| 1400 | | (S)- (OC)—piperidine(N) |
| 1401 | | (S)- (H₂C)—pyrrolidine(N) |
| 1402 | | (R)- (H₂C)—pyrrolidine(N) |
| 1403 | | (H₂C)—piperidine(N) |
| 1404 | H | (H₂C)—O—(CH₂CH₂)—(NR₅) |
| 1405 | H | (H₂C)—(CH₂)₃—(NR₅) |
| 1406 | Me | (H₂C)—(CH₂)₃—(NR₅) |

TABLE 6D-continued

| | | | |
|---|---|---|---|
| 1407 | Me | | (H₂C)—O—(NR₅) |
| 1408 | H | | (H₂C)—/\—(NR₅) |
| 1409 | Me | | (H₂C)—/\—(NR₅) |
| 1410 | | | (H₂C)—piperidine(N) |
| 1411 | | | (H₂C)—piperidine(N) |
| 1412 | | | (H₂C)—piperidine(N) |
| 1413 | | | (H₂C)—piperidine(N) |
| 1414 | | | (H₂C)—piperidine(N) |

For all compounds, $R_4$, $R_6$ and $R_8$=H, except for compound 1391, where $R_6$=CH$_3$ and compound 1392, where $R_8$=CH$_3$ For the compounds in which BB$_4$ is Fmoc-S35 or Fmoc-Pip, (N)R$_7$ and R$_5$ form part of a six-membered ring, including the nitrogen atom, as shown for the combined R$_5$-R$_7$ in Table 6B. Likewise, for the compounds in which BB$_4$ is Fmoc-(S)—SP1 or Fmoc-(R)—SP1, (N)R$_7$ and R$_5$ form part of a five-membered ring, including the nitrogen atom, as shown for the combined R$_5$-R$_7$ in Table 6D For compounds 1399-1400, a carbonyl group (C=O) replaces the methylene group (CH$_2$) between NR$_4$ and R$_7$ in the macrocycle structure.

In addition, the synthetic scheme presented in Scheme 4 was followed to prepare macrocyclic compounds 1415-1416 on solid support, except that BB$_4$ was Fmoc-NR$_7$—R$_6$—CHO. The first amino acid building block amino acid (BB$_1$) was loaded onto the resin (Method 1D), then, after removal of the Fmoc protection (Method 1F), the second amino acid building block (BB$_2$) attached through amide bond formation (Method 1G). The Fmoc group was cleaved (Method 1F), then the oxazole building block (BB$_3$) attached by reductive amination (Method 1J) or amide coupling (Method 1G) to extend the intermediate chain. After deprotection (Method 1F), the final building block was then added using reductive amination (Method 1I or 1J) to complete the pre-cyclization intermediate. Deprotection of the N-terminal Fmoc group (Method 1F), cleavage from the resin (Method 1Q), macrocyclization (Method 1R) and removal of the side chain protecting groups (Method 1S) followed by evaporation under reduced pressure gave the crude macrocycle. The results after purification by preparative HPLC (Method 2B) are included in Table 6E, including, for each compound, the amounts obtained, the HPLC purity and the confirmation of identity by MS. The macrocyclic structures are provided in Table 6F.

TABLE 6E

| Cpd | BB₁ | BB₂ | BB₃ | BB₄ | Wt (mg)[1] | Purity[2] | MS (M + H) |
|---|---|---|---|---|---|---|---|
| 1415 | Fmoc-Trp(Boc) | Fmoc-D-Lys(Boc) | Fmoc-OX-13 | Fmoc-(S)-SP1 | 2.3 | 100 | 564 |
| 1416 | Fmoc-Trp(Boc) | Fmoc-D-Lys(Boc) | Fmoc-OX-13 | Fmoc-(R)-SP1 | 6.2 | 100 | 564 |

[1] All syntheses were carried out on the solid phase starting from 70-80 mg of 2-chlorotrityl chloride resin (typical loading 1.0 mmol/g).
[2] Purity is determined by analysis with LC-UV at 220 nm.

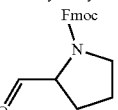

*Fmoc-SP1 is [structure shown]  [(S)-isomer prepared from corresponding commercially available alcohol [L-prolinol (ChemImpex Cat. No. 03218)] using Method 1H, while (R)-isomer is synthesized from Fmoc-D-Pro by reduction using the procedure of Example 1J, followed by oxidation using Method 1H].

TABLE 6F

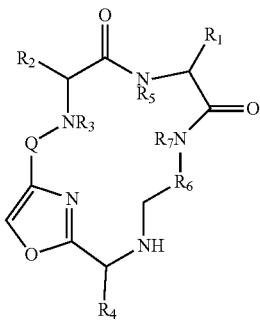

| Cpd | R₁ | R₂ | R₃ | Q | R₄ | R₆—R₇ |
|---|---|---|---|---|---|---|
| 1415 | (S)-indol-3-ylmethyl (CH) | (R)- H₂N-(CH₂)₄-(CH) | H | CH₂ | (S)- isobutyl (CH) | (S)- (H₂C)-pyrrolidine (N) |
| 1416 | (S)-indol-3-ylmethyl (CH) | (R)- H₂N-(CH₂)₄-(CH) | H | CH₂ | (S)- isobutyl (CH) | (R)- (H₂C)-pyrrolidine (N) |

For both compounds, R₆ and (N)R₇ form a five-membered ring, including the nitrogen atom, as shown for R₆-R₇ in Table 6F.

For the addition of still further diverse compounds in the library, the series of synthetic schemes in Schemes 5, 6 and 7 were employed for the solid phase construction of macrocyclic compounds 1417-1440, 1441 and 1442-1465, respectively, except that in Scheme 5, BB₃ was Fmoc-NR₇—CHR₄—CO₂H. For all of the compounds, the first amino acid building block amino acid (BB₁) was loaded onto the resin (Method 1D). For compounds 1417-1440 and 1442-1465, the second amino acid building block (BB₂) was attached through peptide coupling (Method 1G) following Fmoc deprotection (Method 1F). BB₂ was added using reductive amination (Method 1I or 1J) for compound 1441. For compounds 1417-1441, the third building block (BB₃) was installed after Fmoc deprotection (Method 1F) via amide bond formation (Method 1G), while for 1442-1465, reductive amination (Method 1I or 1J) was employed for BB₃. After Fmoc removal ((Method 1F), addition of the oxazole building block (BB₄) for all compounds was performed using reductive amination (Method 1J) or amide bond formation (Method 1G). With each scheme, deprotection of the Fmoc moiety (Method 1F), resin cleavage (Method 1Q), macrocycle formation (Method 1R) and removal of the side chain protection (Method 1S) were followed by evaporation in vacuo to yield the crude macrocycle. Upon purification by preparative HPLC (Method 2B), the desired macrocyclic library compounds were obtained. For each macrocycle, the quantities, purity (HPLC) and identity conformation (MS) are presented in Table 6G, with the structures shown in Tables 6H, 6I and 6J. For compounds 1425-1427, the N-methyl group on BB₂ (R₃) is installed prior to the addition of BB₃ by the series of reactions described in Method 1P using methanol as the alcohol component. Likewise, for compound 1423, prior to macrocyclization, the N-methyl group on BB₄ (add R₈ in place of H) is installed by the series of reactions described in Method 1P using methanol as the alcohol component

TABLE 6G

| Cpd | BB$_1$ | BB$_2$ | BB$_3$ | BB$_4$ | Wt (mg)[1] | Purity[2] | MS (M + H) |
|---|---|---|---|---|---|---|---|
| 1417 | Fmoc-D-Tyr(But) | Fmoc-S30 | Fmoc-D-Lys(Boc) | Fmoc-OX-16 | 0.8 | 80 | 515 |
| 1418 | Fmoc-Tyr(But) | Fmoc-S30 | Fmoc-D-Lys(Boc) | Fmoc-OX-16 | 1.5 | 100 | 515 |
| 1419 | Fmoc-D-Tyr(But) | Fmoc-S30 | Fmoc-Lys(Boc) | Fmoc-OX-16 | 1.3 | 100 | 515 |
| 1420 | Fmoc-Tyr(But) | Fmoc-S30 | Fmoc-Lys(Boc) | Fmoc-OX-16 | 1.6 | 100 | 515 |
| 1421 | Fmoc-D-N-Me-Tyr(But) | Fmoc-S30 | Fmoc-D-Lys(Boc) | Fmoc-OX-13 | 1.2 | 100 | 529 |
| 1422 | Fmoc-D-Tyr(But) | Fmoc-S30 | Fmoc-D-N-Me-Lys(Boc) | Fmoc-OX-13 | 0.6 | 100 | 529 |
| 1423 | Fmoc-D-Tyr(But) | Fmoc-S30 | Fmoc-D-Lys(Boc) | Fmoc-OX-13 | 1.2 | 100 | 529 |
| 1424 | Fmoc-D-Tyr(But) | Fmoc-S29 | Fmoc-D-Lys(Boc) | Fmoc-OX-13 | 1.4 | 100 | 501 |
| 1425 | Fmoc-D-Tyr(But) | Fmoc-S33 | Fmoc-D-Lys(Boc) | Fmoc-OX-13 | 1.3 | 100 | 529 |
| 1426 | Fmoc-D-Tyr(But) | Fmoc-(S)-S31 | Fmoc-D-Lys(Boc) | Fmoc-OX-13 | 2.0 | 100 | 529 |
| 1427 | Fmoc-D-Tyr(But) | Fmoc-(R)-S31 | Fmoc-D-Lys(Boc) | Fmoc-OX-13 | 1.5 | 100 | 529 |
| 1428 | Fmoc-D-Tyr(But) | Fmoc-S30 | Fmoc-D-Orn(Boc) | Fmoc-OX-13 | 1.2 | 100 | 501 |
| 1429 | Fmoc-D-Tyr(But) | Fmoc-S30 | Fmoc-D-Dab(Boc) | Fmoc-OX-13 | 1.0 | 100 | 487 |
| 1430 | Fmoc-D-Tyr(But) | Fmoc-S30 | Fmoc-D-Dab(Boc) | Fmoc-OX-13 | 1.3 | 100 | 473 |
| 1431 | Fmoc-D-Tyr(But) | Fmoc-S30 | Fmoc-D-Asn(Trt) | Fmoc-OX-13 | 1.4 | 100 | 501 |
| 1432 | Fmoc-D-Tyr(But) | Fmoc-S30 | Fmoc-D-Gln(Trt) | Fmoc-OX-13 | na | na | na |
| 1433 | Fmoc-D-Tyr(But) | Fmoc-S30 | Fmoc-D-Tyr(But) | Fmoc-OX-13 | 2.9 | 91 | 515 |
| 1434 | Fmoc-D-Tyr(But) | Fmoc-S30 | Fmoc-D-Lys(Boc) | Fmoc-OX-33 | 1.7 | 100 | 515 |
| 1435 | Fmoc-D-Tyr(But) | Fmoc-S30 | Fmoc-D-Lys(Boc) | Fmoc-OX-31 | 1.1 | 100 | 473 |
| 1436 | Fmoc-D-Tyr(But) | Fmoc-S30 | Fmoc-D-Lys(Boc) | Fmoc-OX-32 | 1.0 | 100 | 515 |
| 1437 | Fmoc-Trp(Boc) | Fmoc-S35 | Fmoc-D-Lys(Boc) | Fmoc-OX-13 | 1.3 | 100 | 592 |
| 1438 | Fmoc-Pro | Fmoc-(S)-SP2* | Fmoc-D-Lys(Boc) | Fmoc-OX-13 | 1.1 | 100 | 564 |
| 1439 | Fmoc-Pro | Fmoc-(R)-SP2* | Fmoc-D-Lys(Boc) | Fmoc-OX-13 | na | na | na |
| 1440 | Fmoc-D-Tyr(But) | Fmoc-S30 | Fmoc-D-Lys(Boc) | Fmoc-OX-16 | 0.5 | 100 | 515 |
| 1441 | Fmoc-Tyr(But) | Fmoc-Arg(Pbf) | Fmoc-S29 | Fmoc-OX-13 | na | na | na |
| 1442 | Fmoc-D-Asn(Trt) | Fmoc-Trp(Boc) | Fmoc-Lys(Boc) | Fmoc-OX-13 | 2.7 | 100 | 595 |
| 1443 | Fmoc-D-Asn(Trt) | Fmoc-Tyr(But) | Fmoc-Lys(Boc) | Fmoc-OX-13 | 10.5 | 98 | 572 |
| 1444 | Fmoc-D-Pro | Fmoc-Trp(Boc) | Fmoc-D-Lys(Boc) | Fmoc-OX-13 | 10.5 | 100 | 578 |
| 1445 | Fmoc-D-Pro | Fmoc-Trp(Boc) | Fmoc-Lys(Boc) | Fmoc-OX-13 | 9.0 | 100 | 578 |
| 1446 | Fmoc-D-Pro | Fmoc-D-Trp(Boc) | Fmoc-D-Lys(Boc) | Fmoc-OX-13 | 10.2 | 100 | 578 |
| 1447 | Fmoc-D-Pro | Fmoc-D-Trp(Boc) | Fmoc-Lys(Boc) | Fmoc-OX-13 | 2.0 | 100 | 578 |
| 1448 | Fmoc-Pro | Fmoc-Trp(Boc) | Fmoc-D-Lys(Boc) | Fmoc-OX-16 | 3.1 | 100 | 578 |
| 1449 | Fmoc-Pro | Fmoc-Trp(Boc) | Fmoc-Lys(Boc) | Fmoc-OX-16 | 9.9 | 100 | 578 |
| 1450 | Fmoc-Pro | Fmoc-D-Trp(Boc) | Fmoc-D-Lys(Boc) | Fmoc-OX-16 | 14.0 | 100 | 578 |
| 1451 | Fmoc-Pro | Fmoc-D-Trp(Boc) | Fmoc-Lys(Boc) | Fmoc-OX-16 | 9.3 | 100 | 578 |
| 1452 | Fmoc-D-Pro | Fmoc-Trp(Boc) | Fmoc-D-Lys(Boc) | Fmoc-OX-16 | 8.0 | 100 | 578 |
| 1453 | Fmoc-D-Pro | Fmoc-Trp(Boc) | Fmoc-Lys(Boc) | Fmoc-OX-16 | 10.2 | 100 | 578 |
| 1454 | Fmoc-D-Pro | Fmoc-D-Trp(Boc) | Fmoc-D-Lys(Boc) | Fmoc-OX-16 | 2.4 | 100 | 578 |
| 1455 | Fmoc-D-Pro | Fmoc-D-Trp(Boc) | Fmoc-Lys(Boc) | Fmoc-OX-16 | 2.2 | 100 | 578 |
| 1456 | Fmoc-Pro | Fmoc-Trp(Boc) | Fmoc-D-Lys(Boc) | Fmoc-OX-1 | na | na | na |
| 1457 | Fmoc-N-Me-Ala | Fmoc-Trp(Boc) | Fmoc-D-Lys(Boc) | Fmoc-OX-13 | 6.2 | 100 | 566 |
| 1458 | Fmoc-Pro | Fmoc-Ala | Fmoc-D-Lys(Boc) | Fmoc-OX-13 | 2.1 | 80 | 463 |
| 1459 | Fmoc-Pro | Fmoc-Trp(But) | Fmoc-D-Lys(Boc) | Fmoc-OX-13 | 2.5 | 100 | 555 |
| 1460 | Fmoc-Pro | Fmoc-Phe | Fmoc-D-Lys(Boc) | Fmoc-OX-13 | 1.0 | 100 | 539 |
| 1461 | Fmoc-Pro | Fmoc-Trp(Boc) | Fmoc-D-Orn(Boc) | Fmoc-OX-13 | 2.3 | 100 | 564 |
| 1462 | Fmoc-Pro | Fmoc-Trp(Boc) | Fmoc-D-Arg(Pbf) | Fmoc-OX-13 | 2.2 | 100 | 606 |
| 1463 | Fmoc-Pro | Fmoc-Trp(Boc) | Fmoc-D-Lys(Boc) | Fmoc-OX-31 | 1.2 | 100 | 536 |
| 1464 | Fmoc-Pro | Fmoc-Trp(Boc) | Fmoc-D-Lys(Boc) | Fmoc-OX-32 | 1.8 | 100 | 578 |
| 1465 | Fmoc-Pro | Fmoc-Trp(Boc) | Fmoc-D-Lys(Boc) | Fmoc-OX-33 | 1.5 | 100 | 578 | na = not available

[1] All syntheses were carried out on the solid phase starting from 70-80 mg of 2-chlorotrityl chloride resin (typical loading 1.0 mmol/g).

[2] Purity is determined by analysis with LC-UV at 220 nm.

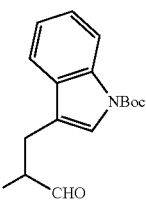

* Fmoc-SP2 is Fmoc-HN   CHO   [(S)-isomer prepared from Fmoc-Trp(Boc), while (R)-isomer is synthesized from Fmoc-D-Trp(Boc), by first reduction using the procedure of Example 1J, followed by oxidation using Method 1H].

TABLE 6H

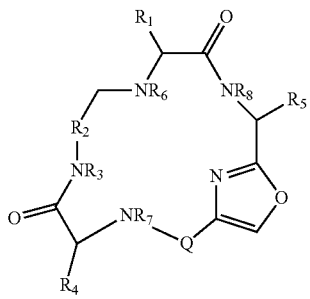

| Cpd | R₁ | R₂ | R₃ | R₄ |
|---|---|---|---|---|
| 1417 | (R)- 4-HO-C₆H₄-CH₂-(CH) | (H₂C)-CH₂-(NR₃) | Me | (R)- H₂N-(CH₂)₃-(CH) |
| 1418 | (S)- 4-HO-C₆H₄-CH₂-(CH) | (H₂C)-CH₂-(NR₃) | Me | (R)- H₂N-(CH₂)₃-(CH) |
| 1419 | (R)- 4-HO-C₆H₄-CH₂-(CH) | (H₂C)-CH₂-(NR₃) | Me | (S)- H₂N-(CH₂)₃-(CH) |
| 1420 | (S)- 4-HO-C₆H₄-CH₂-(CH) | (H₂C)-CH₂-(NR₃) | Me | (S)- H₂N-(CH₂)₃-(CH) |
| 1421 | (R)- 4-HO-C₆H₄-CH₂-(CH) | (H₂C)-CH₂-(NR₃) | Me | (R)- H₂N-(CH₂)₃-(CH) |
| 1422 | (R)- 4-HO-C₆H₄-CH₂-(CH) | (H₂C)-CH₂-(NR₃) | Me | (R)- H₂N-(CH₂)₃-(CH) |
| 1423 | (R)- 4-HO-C₆H₄-CH₂-(CH) | (H₂C)-CH₂-(NR₃) | Me | (R)- H₂N-(CH₂)₃-(CH) |
| 1424 | (R)- 4-HO-C₆H₄-CH₂-(CH) | (H₂C)-CH₂-(NR₃) | H | (R)- H₂N-(CH₂)₃-(CH) |
| 1425 | (R)- 4-HO-C₆H₄-CH₂-(CH) | (H₂C)-(CH₂)₂-(NR₃) | Me | (R)- H₂N-(CH₂)₃-(CH) |
| 1426 | (R)- 4-HO-C₆H₄-CH₂-(CH) | (H₂C)-CH(Me)-(NR₃) (α) | Me | (R)- H₂N-(CH₂)₃-(CH) |
| 1427 | (R)- 4-HO-C₆H₄-CH₂-(CH) | (H₂C)-CH(Me)-(NR₃) (β) | Me | (R)- H₂N-(CH₂)₃-(CH) |

TABLE 6H-continued
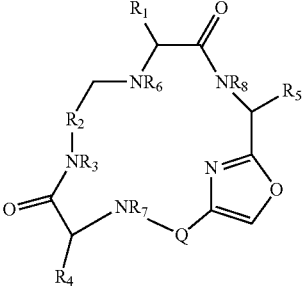
| | | | | |
|---|---|---|---|---|
| 1428 | (R)- HO-C6H4-CH2-(CH) | (H2C)-(NR3) | Me | (R)- H2N-(CH2)3-(CH) |
| 1429 | (R)- HO-C6H4-CH2-(CH) | (H2C)-(NR3) | Me | (R)- H2N-(CH2)2-(CH) |
| 1430 | (R)- HO-C6H4-CH2-(CH) | (H2C)-(NR3) | Me | (R)- H2N-CH2-(CH) |
| 1431 | (R)- HO-C6H4-CH2-(CH) | (H2C)-(NR3) | Me | (R)- H2NOC-CH2-(CH) |
| 1432 | (R)- HO-C6H4-CH2-(CH) | (H2C)-(NR3) | Me | (R)- H2NOC-(CH2)2-(CH) |
| 1433 | (R)- H2N-(CH2)4-(CH) | (H2C)-(NR3) | Me | (R)- HO-C6H4-CH2-(CH) |
| 1434 | (R)- HO-C6H4-CH2-(CH) | (H2C)-(NR3) | Me | (R)- H2N-(CH2)4-(CH) |
| 1435 | (R)- HO-C6H4-CH2-(CH) | (H2C)-(NR3) | Me | (R)- H2N-(CH2)4-(CH) |
| 1436 | (R)- HO-C6H4-CH2-(CH) | (H2C)-(NR3) | Me | (R)- H2N-(CH2)4-(CH) |
| 1437 | (S)- indol-3-yl-CH2-(CH) | (H2C)-piperidin-4-yl-(N) | | (R)- H2N-(CH2)4-(CH) |

TABLE 6H-continued
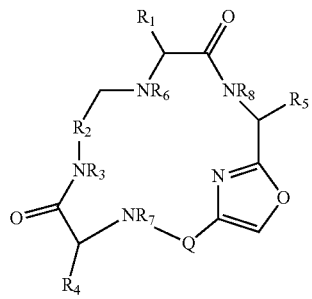
| | | | | | |
|---|---|---|---|---|---|
| 1438 | (S)- (HC)—(N) pyrrolidine | (S)- CH2-indole-NBoc with (NR3) | H | (R)- H2N—(CH) pentyl | |
| 1439 | (S)- (HC)—(N) pyrrolidine | (S)- CH2-indole-NBoc with (NR3) | H | (R)- H2N—(CH) pentyl | |
| 1440 | (R)- (CH)-CH2-C6H4-OH | (H2C)—(NR3) | CH3 | (R)- H2N—(CH) pentyl | |
| Cpd | Q | R5 |
|---|---|---|
| 1417 | CH2 | (R)- isobutyl (CH) |
| 1418 | CH2 | (R)- isobutyl (CH) |
| 1419 | CH2 | (R)- isobutyl (CH) |
| 1420 | CH2 | (R)- isobutyl (CH) |
| 1421 | CH2 | (S)- isobutyl (CH) |
| 1422 | CH2 | (S)- isobutyl (CH) |
| 1423 | CH2 | (S)- isobutyl (CH) |
| 1424 | CH2 | (S)- isobutyl (CH) |

TABLE 6H-continued

| | | | |
|---|---|---|---|
| 1425 | CH$_2$ | (S)- | isobutyl (CH) |
| 1426 | CH$_2$ | (S)- | isobutyl (CH) |
| 1427 | CH$_2$ | (S)- | isobutyl (CH) |
| 1428 | CH$_2$ | (S)- | isobutyl (CH) |
| 1429 | CH$_2$ | (S)- | isobutyl (CH) |
| 1430 | CH$_2$ | (S)- | isobutyl (CH) |
| 1431 | CH$_2$ | (S)- | isobutyl (CH) |
| 1432 | CH$_2$ | (S)- | isobutyl (CH) |
| 1433 | CH$_2$ | (S)- | isobutyl (CH) |
| 1434 | CH$_2$ | (S)- | sec-butyl (CH) |
| 1435 | CH$_2$ | | (S)-CH$_3$ |
| 1436 | CH$_2$ | (S)- | n-pentyl (CH) |
| 1437 | C=O | (S)- | isobutyl (CH) |

TABLE 6H-continued

[Structure: macrocycle with R1, R2, R3, R4, R5, NR6, NR7, NR8, Q, oxazole]

| Cpd | R2 | R5 |
|---|---|---|
| 1438 | CH₂ | (S)- isobutyl (CH) |
| 1439 | CH₂ | (S)- isobutyl (CH) |
| 1440 | CH₂ | (R)- isobutyl (CH) |

For all compounds, R₆, R₇ and R₈=H, except for compound 1421, where R₆=CH₃, compound 1422, where R₇=CH₃ and compound 1423, where R₈=CH₃. In addition, for those compounds (1438-1439) in which Fmoc-Pro is the BB₁ component, R₁ and (N)R₆ form part of a five-membered ring, including the nitrogen atom, as shown for R₁ in Table 6H.

For compound 1437, in which BB₂ is Fmoc-S35, R₂ and (N)R₃ form part of a six-membered ring, including the nitrogen atom, as shown for the combined R₂-R₃ in Table 6H.

TABLE 6I

[Structure: macrocycle with R1, R2, R3, R4, R5, R6, Q, oxazole, NH groups]

| Cpd | R₁ | R₂ | R₃ | R₄ | Q | R₆ |
|---|---|---|---|---|---|---|
| 1441 | (S)- 4-hydroxybenzyl (CH) | (S)- H₂N-C(=NH)-NH-(CH₂)₃- (CH) | H | (H₂C)-(NR₅) | CH₂ | (S)- isobutyl (CH) |

In addition for this compound, R₅=H.

TABLE 6J

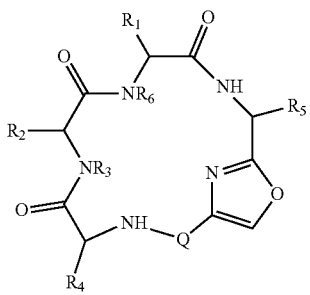

| Cpd | R₁ | R₂ | R₃ | R₄ |
|---|---|---|---|---|
| 1442 | (R)- H₂NOC―(CH) | (S)- indol-3-ylmethyl―(CH) | H | (S)- H₂N―(CH) |
| 1443 | (R)- H₂NOC―(CH) | (S)- 4-hydroxybenzyl―(CH) | H | (S)- H₂N―(CH) |
| 1444 | (R)- pyrrolidin-2-yl (HC) | (S)- indol-3-ylmethyl―(CH) | H | (R)- H₂N―(CH) |
| 1445 | (R)- pyrrolidin-2-yl (HC) | (S)- indol-3-ylmethyl―(CH) | H | (S)- H₂N―(CH) |
| 1446 | (R)- pyrrolidin-2-yl (HC) | (R)- indol-3-ylmethyl―(CH) | H | (R)- H₂N―(CH) |
| 1447 | (R)- pyrrolidin-2-yl (HC) | (R)- indol-3-ylmethyl―(CH) | H | (S)- H₂N―(CH) |
| 1448 | (S)- pyrrolidin-2-yl (HC) | (S)- indol-3-ylmethyl―(CH) | H | (S)- H₂N―(CH) |
| 1449 | (S)- pyrrolidin-2-yl (HC) | (S)- indol-3-ylmethyl―(CH) | H | (S)- H₂N―(CH) |

TABLE 6J-continued
| | R2 | R1 | R5 | R4 |
|---|---|---|---|---|
| 1450 | (S)- 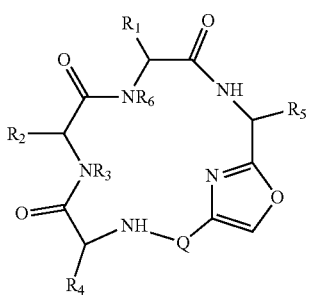 | (R)- 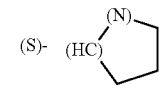 | H | (R)- 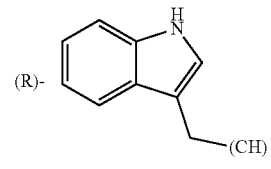 |
| 1451 | (S)- 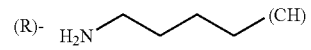 | (R)- 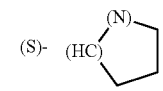 | H | (S)- 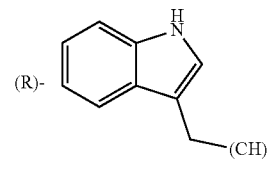 |
| 1452 | (R)- 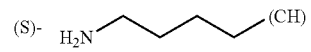 | (S)- 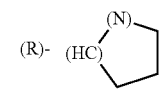 | H | (R)- 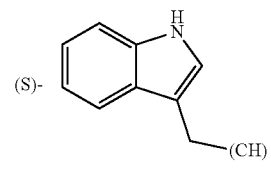 |
| 1453 | (R)- 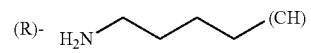 | (S)- 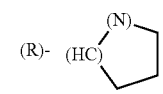 | H | (S)- 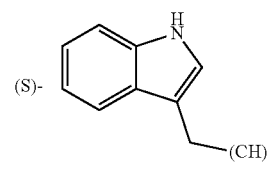 |
| 1454 | (R)- 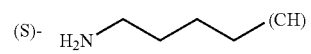 | (R)- 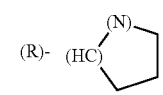 | H | (R)- 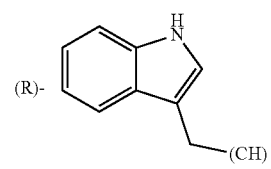 |
| 1455 | (R)- 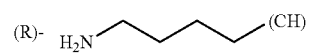 | (R)- 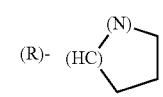 | H | (S)-  |
| 1456 | (S)- 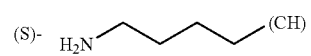 | (S)- 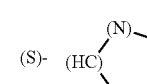 | H | (R)-  |
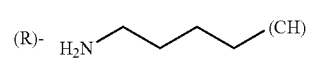

TABLE 6J-continued

| # | R2 | R1 | R5 | R4 |
|---|---|---|---|---|
| 1457 | (S)-CH₃ | (S)- indol-3-yl-(CH) | H | (R)- H₂N-(CH₂)₄-(CH) |
| 1458 | (S)- pyrrolidin-2-yl (HC) | (S)-CH₃ | H | (R)- H₂N-(CH₂)₄-(CH) |
| 1459 | (S)- pyrrolidin-2-yl (HC) | (S)- 4-hydroxybenzyl (CH) | H | (R)- H₂N-(CH₂)₄-(CH) |
| 1460 | (S)- pyrrolidin-2-yl (HC) | (S)- benzyl (CH) | H | (R)- H₂N-(CH₂)₄-(CH) |
| 1461 | (S)- pyrrolidin-2-yl (HC) | (S)- indol-3-yl-(CH) | H | (R)- H₂N-(CH₂)₃-(CH) |
| 1462 | (S)- pyrrolidin-2-yl (HC) | (S)- indol-3-yl-(CH) | H | (R)- guanidino-(CH₂)₃-(CH) |
| 1463 | (S)- pyrrolidin-2-yl (HC) | (S)- indol-3-yl-(CH) | H | (R)- H₂N-(CH₂)₄-(CH) |
| 1464 | (S)- pyrrolidin-2-yl (HC) | (S)- indol-3-yl-(CH) | H | (R)- H₂N-(CH₂)₄-(CH) |

TABLE 6J-continued
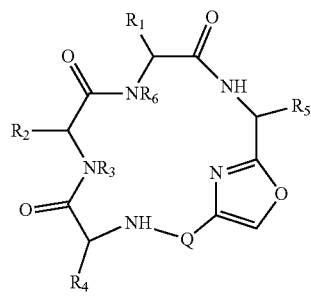
| | | | | | Cpd | Q | R₅ |
|---|---|---|---|---|---|---|---|
| 1465 | (S)- (N)(HC) pyrrolidine (CH) | (S)- indolyl-CH₂ (CH) | H | (R)- H₂N-butyl (CH) | | | |
| | | | | | 1442 | CH₂ | (S)- isobutyl (CH) |
| | | | | | 1443 | CH₂ | (S)- isobutyl (CH) |
| | | | | | 1444 | CH₂ | (S)- isobutyl (CH) |
| | | | | | 1445 | CH₂ | (S)- isobutyl (CH) |
| | | | | | 1446 | CH₂ | (S)- isobutyl (CH) |
| | | | | | 1447 | CH₂ | (S)- isobutyl (CH) |
| | | | | | 1448 | CH₂ | (R)- isobutyl (CH) |
| | | | | | 1449 | CH₂ | (R)- isobutyl (CH) |
| | | | | | 1450 | CH₂ | (R)- isobutyl (CH) |
| | | | | | 1451 | CH₂ | (R)- isobutyl (CH) |
| | | | | | 1452 | CH₂ | (R)- isobutyl (CH) |
| | | | | | 1453 | CH₂ | (R)- isobutyl (CH) |

TABLE 6J-continued

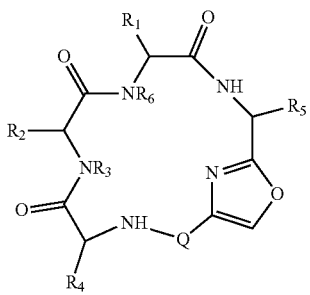

| | | | |
|---|---|---|---|
| 1454 | CH$_2$ | (R)- | 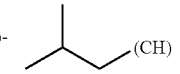 |
| 1455 | CH$_2$ | (R)- | 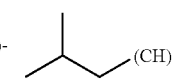 |
| 1456 | C=O | (S)- | 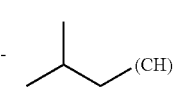 |
| 1457 | CH$_2$ | (S)- | 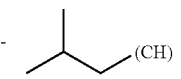 |
| 1458 | CH$_2$ | (S)- | 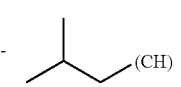 |
| 1459 | CH$_2$ | (S)- | 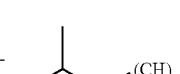 |
| 1460 | CH$_2$ | (S)- | 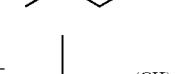 |
| 1461 | CH$_2$ | (S)- | 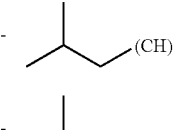 |
| 1462 | CH$_2$ | (S)- | 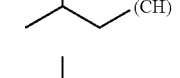 |
| 1463 | CH$_2$ | (S)-CH$_3$ | |
| 1464 | CH$_2$ | (S)- | 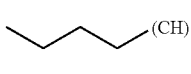 |
| 1465 | CH$_2$ | (S)- | 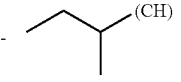 |

For all compounds, R$_6$=H, except for compound 1457, where R$_6$=CH$_3$, and for those compounds in which Fmoc-Pro or Fmoc-D-Pro is the BB$_1$ component, wherein R$_1$ and (N)R$_6$ form part of a five-membered ring, including the nitrogen atom, as shown for R$_1$ in Table 6J.

Lastly, the synthetic scheme presented in Scheme 2 was followed to prepare the macrocyclic compounds 1466-1467 on solid support, except that BB$_3$ was Fmoc-NR$_5$—CHR$_4$—CHO and was attached using different chemistry. The oxazole amino acid (BB$_1$) was loaded onto the resin (Method 1D), then the next two building blocks (BB$_2$, BB$_3$) attached via coupling (Method 1G) and reductive amination (Method 1I or 1J), respectively, each after removal of the Fmoc protection (Method 1F) on the preceding building block. The final building block (BB$_4$) was attached using reductive amination (Method 1I or 1J) followed by selective N-terminal deprotection (Method 1F) and macrocyclization (Method 1R). The side chain protecting groups were then removed (Method 1S) and the resulting crude product purified by preparative HPLC (Method 2B). The amounts of each macrocycle obtained, their HPLC purity and confirmation of their identity by mass spectrometry (MS) are provided in Table 6K. The individual structures of the compounds thus prepared are presented in Table 6L.

TABLE 6K

| Cpd | BB₁ | BB₂ | BB₃ | BB₄ | Wt (mg)[1] | Purity[2] | MS (M + H) |
|---|---|---|---|---|---|---|---|
| 1466 | Fmoc-OX-1 | Fmoc-D-Lys(Boc) | Fmoc-S35 | Fmoc-(S)-SP2* | 2.0 | 100 | 578 |
| 1467 | Fmoc-OX-1 | Fmoc-D-Lys(Boc) | Fmoc-S35 | Fmoc-(R)-SP2* | 1.6 | 100 | 578 |

[1]All syntheses were carried out on the solid phase starting from 70-80 mg of chlorotrityl chloride resin (typical loading 1.0 mmol/g).

[2]Purity is determined by analysis with LC-UV at 220 nm.

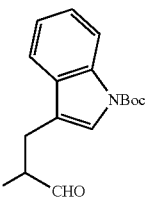

*Fmoc-SP2 is Fmoc-HN—CHO [(S)-isomer prepared from Fmoc-Trp(Boc), while (R)-isomer is synthesized from Fmoc-D-Trp(Boc), by first reduction using the procedure of Example 1J, followed by oxidation using Method 1H].

TABLE 6L

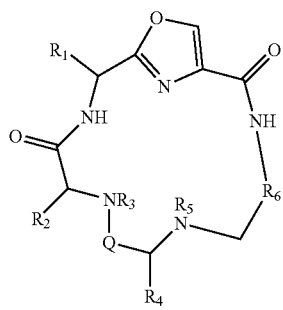

| Cpd | R₁ | R₂ | R₃ | Q | R₄—R₅ | R₆ |
|---|---|---|---|---|---|---|
| 1466 | (S)-isobutyl (CH) | (R)-H₂N-(CH₂)₄-(CH) | H | CH₂ | (Q)-piperidin-4-yl(N) | (S)-CH₂-CH(NR₇)-CH₂-(3-indolyl-NBoc) |
| 1467 | (S)-isobutyl (CH) | (R)-H₂N-(CH₂)₄-(CH) | H | CH₂ | (Q)-piperidin-4-yl(N) | (S)-CH₂-CH(NR₇)-CH₂-(3-indolyl-NBoc) |

For both compounds, $R_4$ and $(N)R_5$ form part of a six-membered ring, including the nitrogen atom, as shown for combined $R_4$-$R_5$ in Table 6L.

Scheme 1

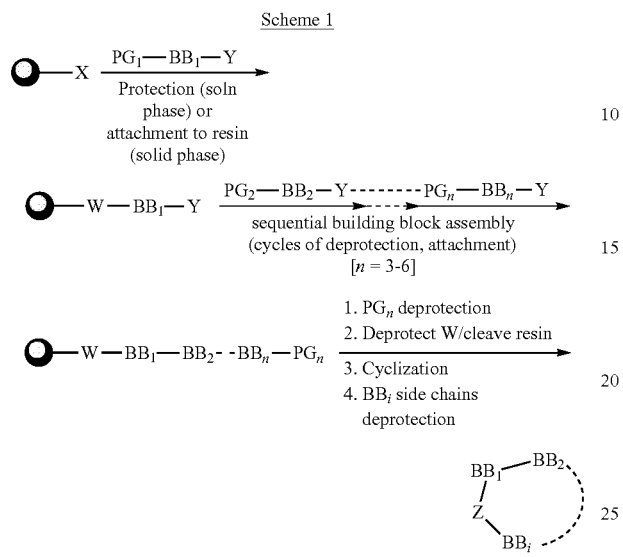

◯—X = polymer with reactive site for solid phase; appropriate protecting group for solution phase; this approach typically starts with the fully protected $BB_1$ and does not require the first reaction shown $BB_i$ = multifunctional building blocks (for example: amino acids, hydroxy acids, amino alcohols, diamines, diols, etc.)
$PG_i$ = protecting group
X, Y = reactive functional groups
W, Z = functional group resulting from reaction (attachment, cyclization)

Scheme 2

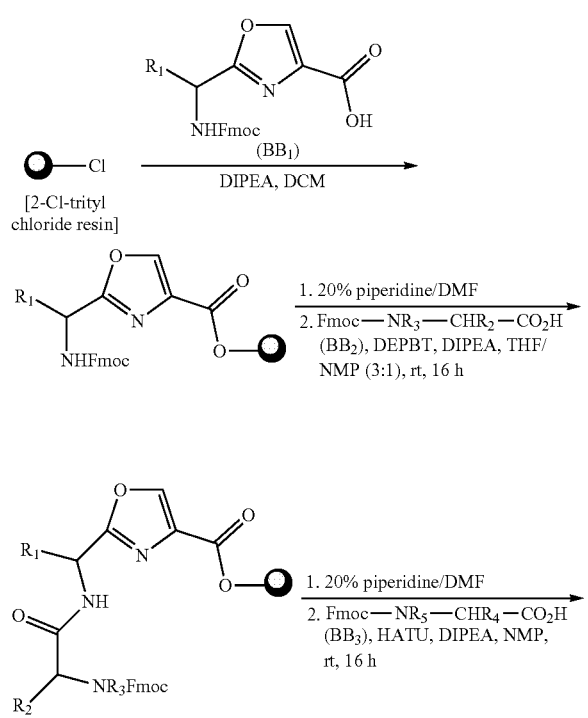

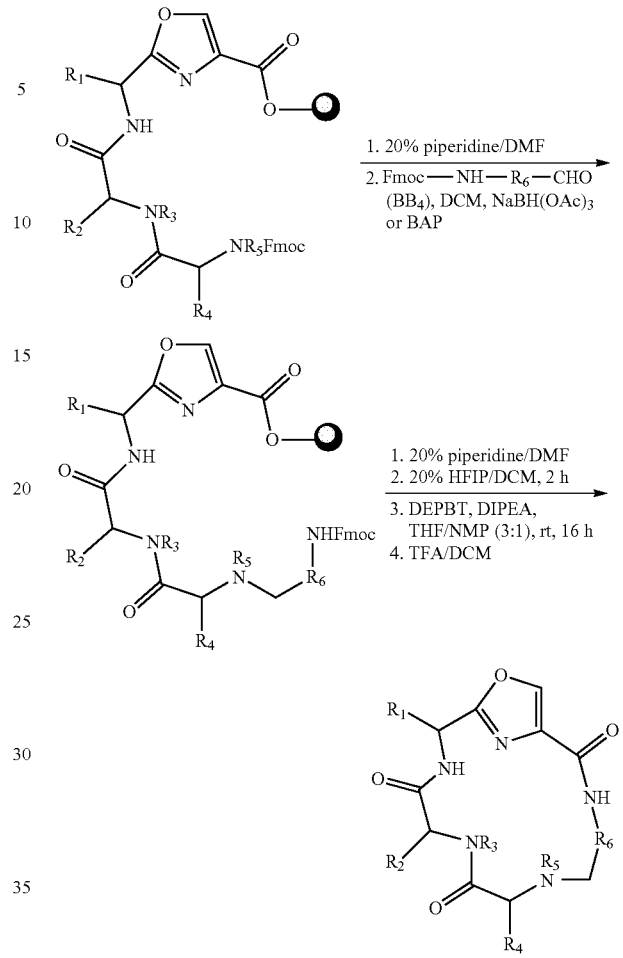

Scheme 3

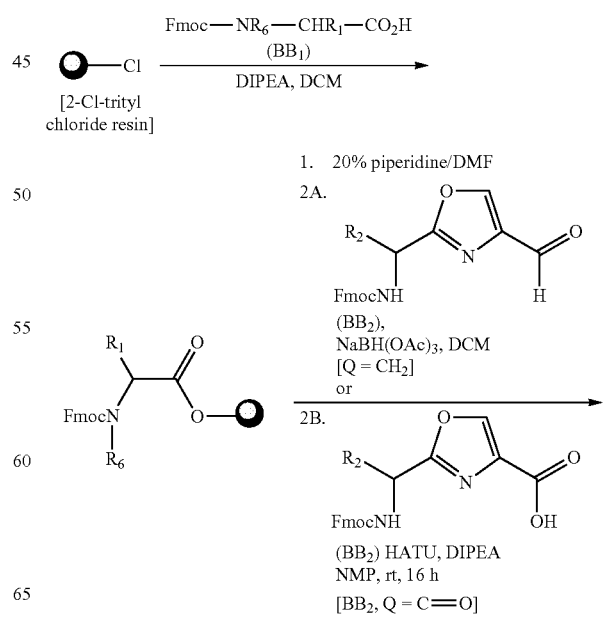

611
-continued

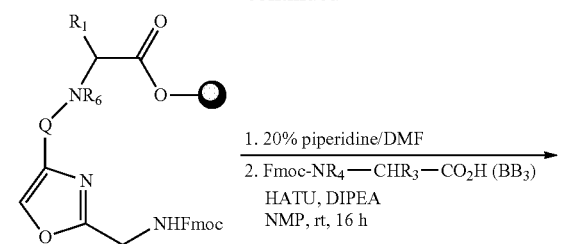

1. 20% piperidine/DMF
2. Fmoc-NR$_4$—CHR$_3$—CO$_2$H (BB$_3$)
   HATU, DIPEA
   NMP, rt, 16 h

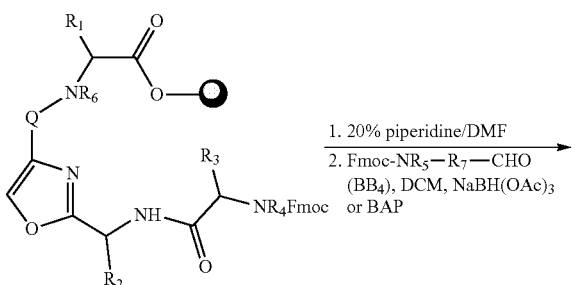

1. 20% piperidine/DMF
2. Fmoc-NR$_5$—R$_7$—CHO (BB$_4$), DCM, NaBH(OAc)$_3$ or BAP

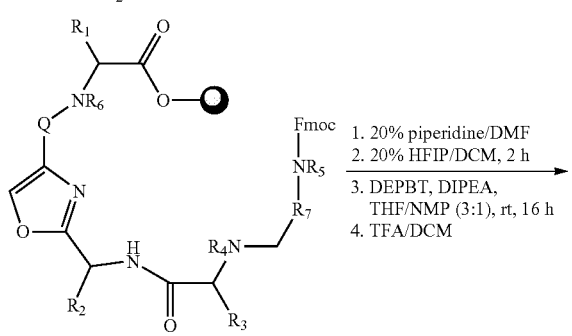

1. 20% piperidine/DMF
2. 20% HFIP/DCM, 2 h
3. DEPBT, DIPEA, THF/NMP (3:1), rt, 16 h
4. TFA/DCM

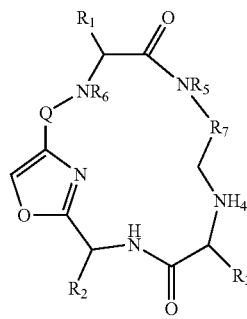

Scheme 4

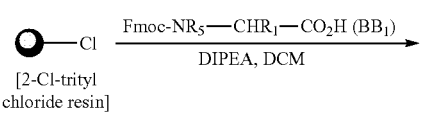

Fmoc-NR$_5$—CHR$_1$—CO$_2$H (BB$_1$)
DIPEA, DCM

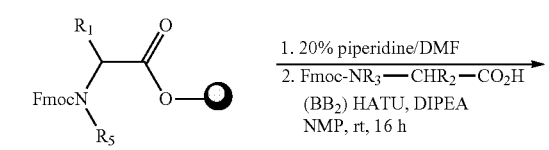

1. 20% piperidine/DMF
2. Fmoc-NR$_3$—CHR$_2$—CO$_2$H (BB$_2$) HATU, DIPEA NMP, rt, 16 h

612
-continued 1. 20% piperidine/DMF

2A. 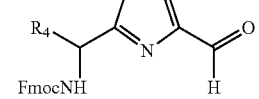
(BB$_3$), NaBH(OAc)$_3$, DCM [Q = CH$_2$]
or

2B. 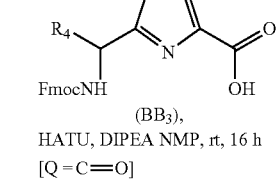
(BB$_3$), HATU, DIPEA NMP, rt, 16 h [Q = C=O]

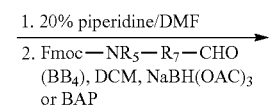

1. 20% piperidine/DMF
2. Fmoc—NR$_5$—R$_7$—CHO (BB$_4$), DCM, NaBH(OAc)$_3$ or BAP

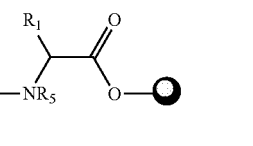

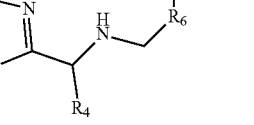

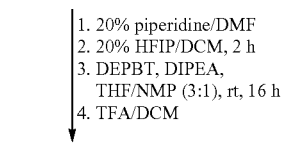

1. 20% piperidine/DMF
2. 20% HFIP/DCM, 2 h
3. DEPBT, DIPEA, THF/NMP (3:1), rt, 16 h
4. TFA/DCM

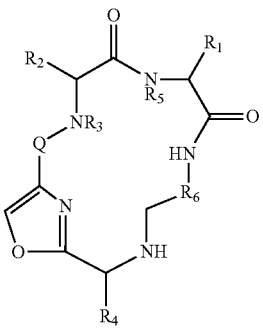

Scheme 5
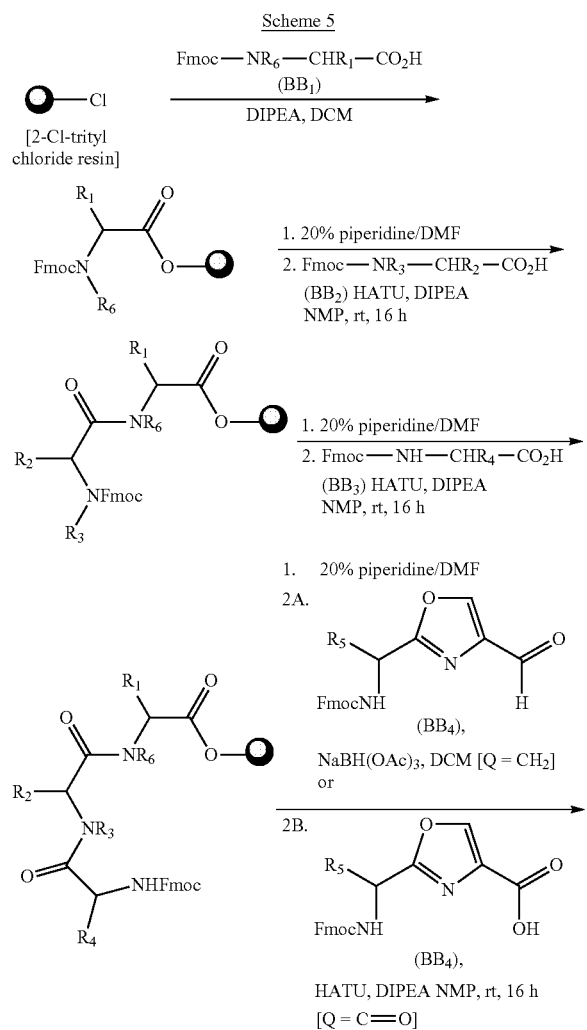
Scheme 6
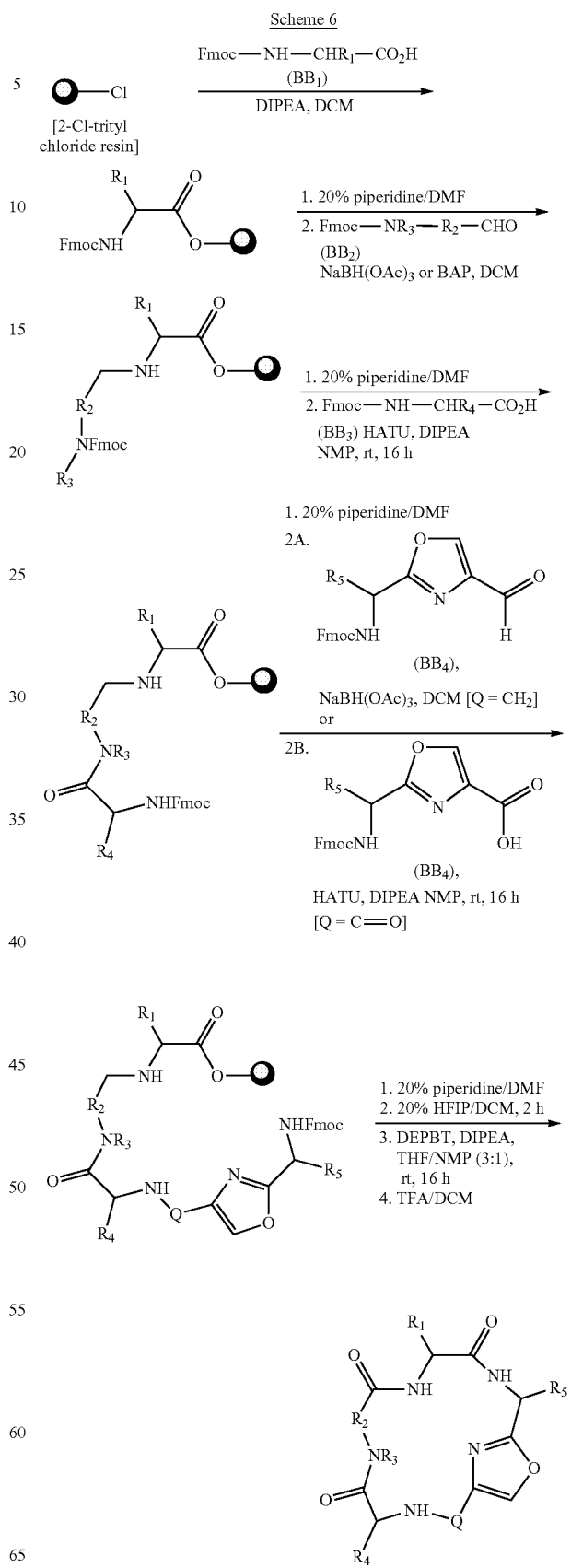

Scheme 7

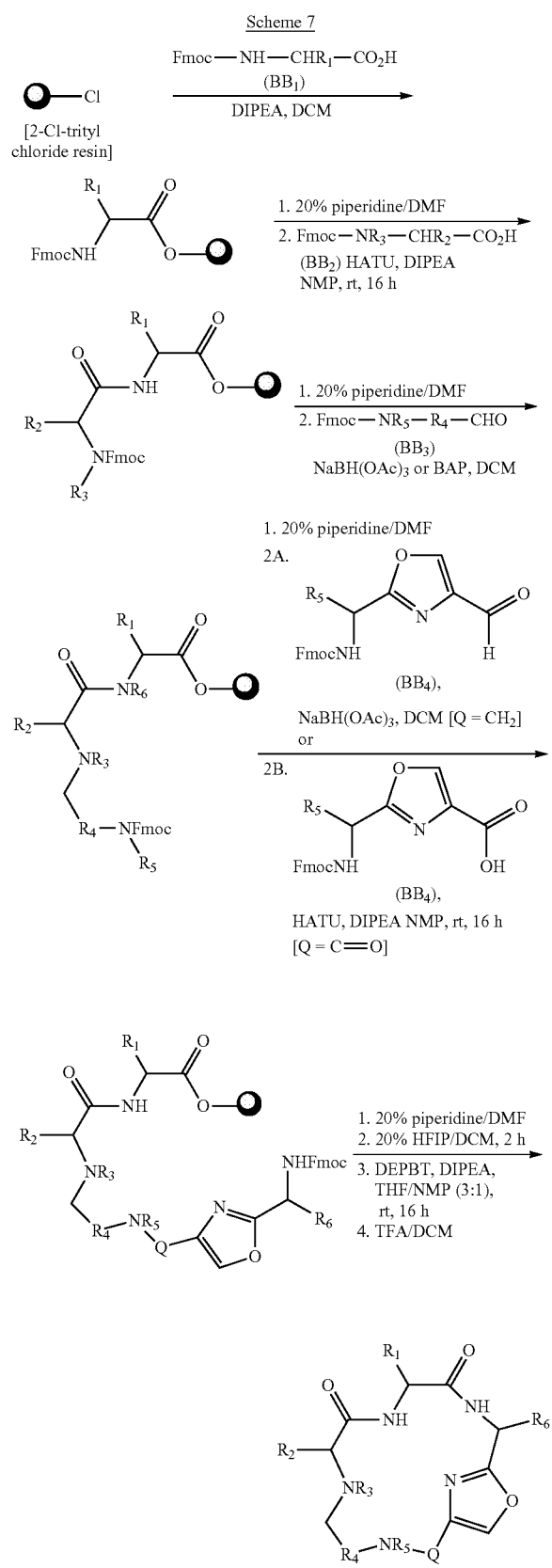

Scheme 8

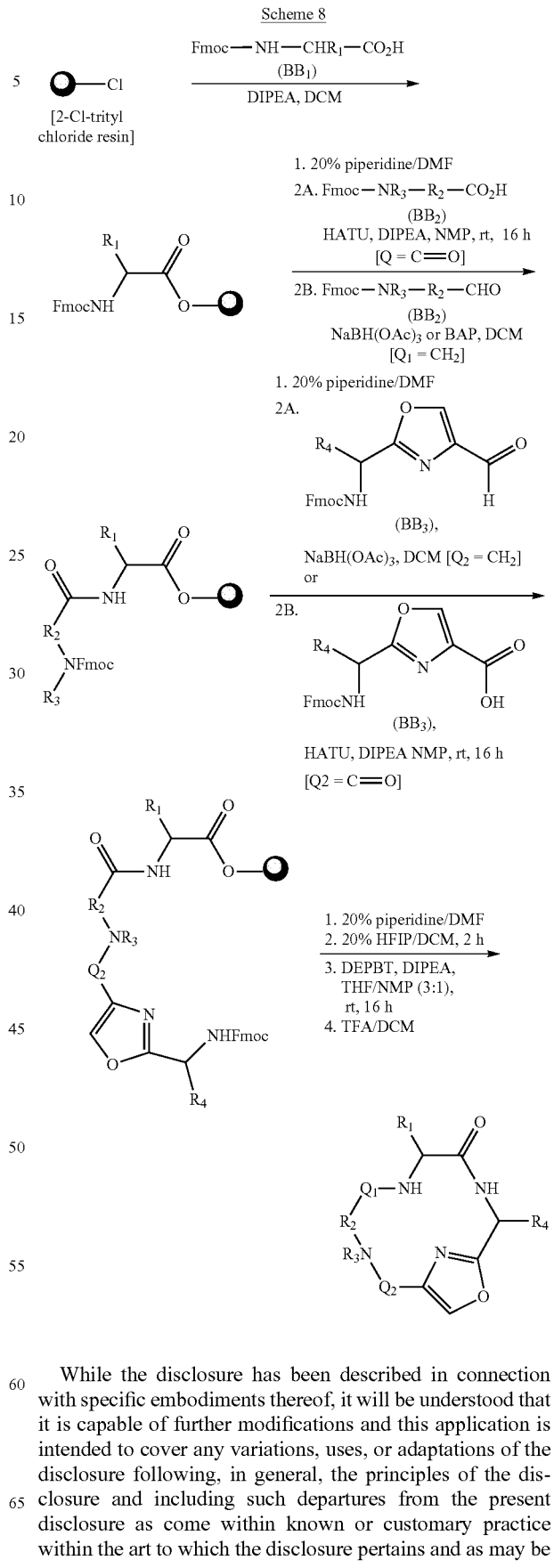

While the disclosure has been described in connection with specific embodiments thereof, it will be understood that it is capable of further modifications and this application is intended to cover any variations, uses, or adaptations of the disclosure following, in general, the principles of the disclosure and including such departures from the present disclosure as come within known or customary practice within the art to which the disclosure pertains and as may be applied to the essential features hereinbefore set forth, and as follows in the scope of the appended claims.

What is claimed is:

1. A process of preparing a library comprising at least two macrocyclic compounds selected from the group consisting of compounds of formula (Ia), formula (Ib), formula (Ic), formula (Id), formula (Ie) and salts thereof:

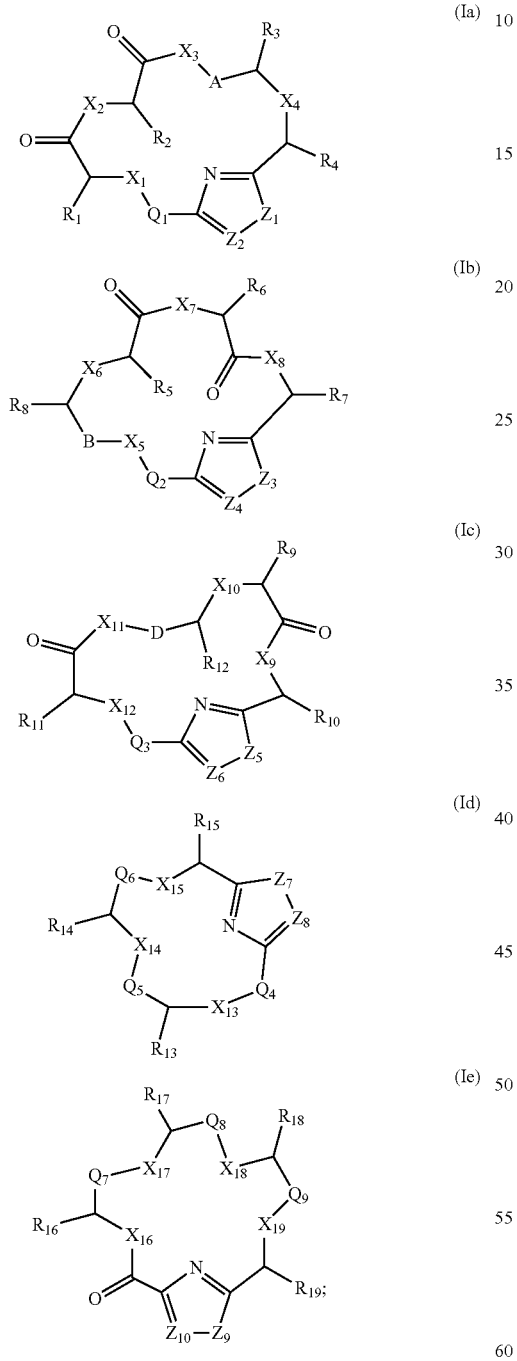

wherein:

$Q_1$, $Q_2$, $Q_3$, $Q_4$, $Q_5$, $Q_6$, $Q_7$, $Q_8$ and $Q_9$ are independently selected from the group consisting of $CH_2$ or $C=O$, wherein in formula (Id) at least one of $Q_4$, $Q_5$ and $Q_6$ is $CH_2$ and wherein in formula (Ie) at least one of $Q_7$, $Q_8$ and $Q_9$ is $CH_2$;

$X_1$, $X_5$, $X_{12}$, $X_{13}$, $X_{14}$, $X_{15}$, $X_{17}$, $X_{18}$ and $X_{19}$ are, when $Q_1$, $Q_2$, $Q_3$, $Q_4$, $Q_5$, $Q_6$, $Q_7$, $Q_8$ and $Q_9$, respectively, are $C=O$, independently selected from the group consisting of O and $NR_{20a}$, where $R_{20a}$ is selected from the group consisting of hydrogen, $C_1$-$C_{20}$ alkyl, $C_3$-$C_{15}$ cycloalkyl, $C_2$-$C_{14}$ heterocycle, $C_6$-$C_{15}$ aryl, $C_4$-$C_{14}$ heteroaryl, sulfonyl and $C_1$-$C_6$ alkyl substituted with hydroxy, alkoxy, amino, mercapto, carboxy, carboxyalkyl, carboxyaryl, amido, amidino, guanidino, $C_3$-$C_{14}$ cycloalkyl, $C_2$-$C_{14}$ heterocycle, $C_6$-$C_{15}$ aryl or $C_4$-$C_{14}$ heteroaryl;

when $X_1$, $X_{12}$, $X_{13}$, $X_{14}$, $X_{15}$, $X_{17}$, $X_{18}$ or $X_{19}$ are $NR_{20a}$; $X_1$, $X_{12}$, $X_{13}$, $X_{14}$, $X_{15}$, $X_{17}$, $X_{18}$ and $X_{19}$ can also form an optionally substituted four, five, six or seven-membered ring together with, respectively, $R_1$, $R_{11}$, $R_{13}$, $R_{14}$, $R_{15}$, $R_{17}$, $R_{18}$ and $R_{19}$;

when $Q_1$, $Q_2$, $Q_3$, $Q_4$, $Q_5$, $Q_6$, $Q_7$, $O_8$ and $Q_9$, are $CH_2$; $X_1$, $X_5$, $X_{12}$, $X_{13}$, $X_{14}$, $X_{15}$, $X_{17}$, $X_{18}$ and $X_{19}$, respectively, can also be independently selected from the group consisting of $S(O)_{q1}$ and $NR_{20b}$, where q1 is 0-2; and $R_{20b}$ is selected from the group consisting of formyl, acyl, amino acyl, amido, amidino, carboxyalkyl, carboxyaryl and sulfonamido, and that $X_5$ can also be N and form, together with B, an optionally substituted four, five, six or seven-membered ring;

$X_2$, $X_3$, $X_7$, $X_8$, $X_9$, $X_{11}$ and $X_{16}$ are independently selected from the group consisting of O and $NR_{21}$, where $R_{21}$ is selected from the group consisting of hydrogen, $C_1$-$C_{20}$ alkyl, $C_3$-$C_{15}$ cycloalkyl, $C_2$-$C_{14}$ heterocycle, $C_6$-$C_{15}$ aryl, $C_4$-$C_{14}$ heteroaryl, sulfonyl and $C_1$-$C_6$ alkyl substituted with hydroxy, alkoxy, amino, mercapto, carboxy, carboxyalkyl, carboxyaryl, amido, amidino, guanidino, $C_3$-$C_{15}$ cycloalkyl, $C_2$-$C_{14}$ heterocycle, $C_6$-$C_{15}$ aryl or $C_4$-$C_{14}$ heteroaryl, when $X_2$, $X_7$, $X_8$, $X_9$ or $X_{16}$ are $NR_{21}$, $X_2$, $X_7$, $X_8$, $X_9$ and $X_{16}$ can also form an optionally substituted four, five, six or seven-membered ring together with, respectively, $R_2$, $R_6$, $R_7$, $R_{10}$ and $R_{16}$, and wherein $X_3$ and $X_8$ can also independently be N and form, together with A and D, respectively, an optionally substituted four, five, six or seven-membered ring;

$X_4$, $X_6$ and $X_{10}$ are independently selected from the group consisting of O, $S(O)_{q2}$ and $NR_{22}$, where q2 is 0-2 and $R_{22}$ is selected from the group consisting of hydrogen, $C_1$-$C_{20}$ alkyl, $C_3$-$C_{15}$ cycloalkyl, $C_2$-$C_{14}$ heterocycle, $C_6$-$C_{15}$ aryl, $C_4$-$C_{14}$ heteroaryl, formyl, acyl, amino acyl, carboxyalkyl, carboxyaryl, amido, amidino, sulfonyl, sulfonamido and $C_1$-$C_6$ alkyl substituted with hydroxy, alkoxy, amino, mercapto, carboxy, carboxyalkyl, carboxyaryl, amido, amidino, guanidino, $C_3$-$C_{15}$ cycloalkyl, $C_2$-$C_{14}$ heterocycle, $C_6$-$C_{15}$ aryl or $C_4$-$C_{14}$ heteroaryl, when $X_4$ or $X_6$ are $NR_{22}$, $X_4$ and $X_6$ can also form an optionally substituted four, five, six or seven-membered ring together with, respectively, $R_4$ and $R_5$;

$Z_1$, $Z_3$, $Z_5$, $Z_7$ and $Z_9$ are independently selected from the group consisting of O, S and $NR_{23}$ where $R_{23}$ is selected from the group consisting of hydrogen, $C_1$-$C_{20}$ alkyl, $C_3$-$C_{15}$ cycloalkyl, $C_2$-$C_{14}$ heterocycle, $C_6$-$C_{15}$ aryl, $C_4$-$C_{14}$ heteroaryl, formyl, acyl, amino acyl, carboxyalkyl, carboxyaryl, amido, amidino, sulfonyl, sulfonamido and $C_1$-$C_8$ alkyl substituted with $C_3$-$C_{15}$ cycloalkyl, $C_6$-$C_{15}$ aryl, or $C_4$-$C_{14}$ heteroaryl;

$Z_2$, $Z_4$, $Z_6$, $Z_8$ and $Z_{10}$ are independently selected from the group consisting of N, $N^+$—$O^-$ and $CR_{24}$ where $R_{24}$ is selected from the group consisting of hydrogen, halogen, amino, nitro, carboxy, carboxyalkyl, carboxyaryl, trifluoromethyl, $C_1$-$C_{20}$ alkyl, $C_3$-$C_{15}$ cycloalkyl, $C_2$-$C_{14}$ heterocycle, $C_6$-$C_{15}$ aryl and $C_4$-$C_{14}$ heteroaryl;

$R_1$, $R_2$, $R_4$, $R_5$, $R_6$, $R_7$, $R_9$, $R_{10}$, $R_{11}$, $R_{13}$, $R_{14}$, $R_{15}$, $R_{16}$, $R_{17}$, $R_{18}$ and $R_{19}$ are independently selected from the group consisting of:

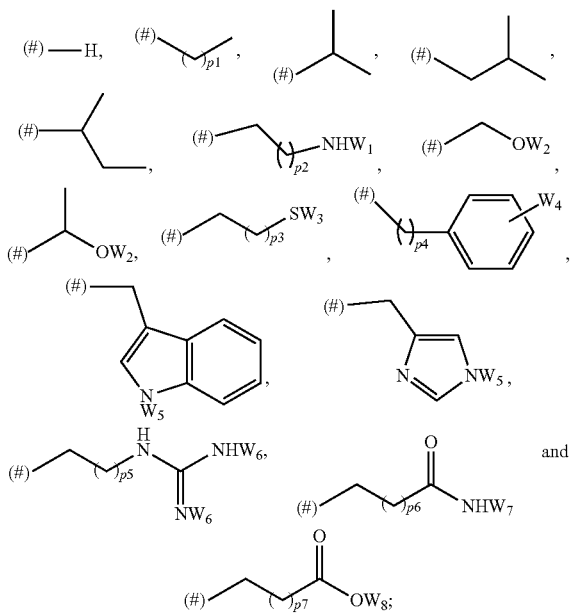

where (#) indicates the site of bonding of the group to the remainder of the structure; p1, p2, p3, p4 and p5 are independently 0-5; p6 and p7 are independently 0-6;

$W_1$ is selected from the group consisting of hydrogen, $C_1$-$C_{20}$ alkyl, $C_3$-$C_{15}$ cycloalkyl, $C_2$-$C_{14}$ heterocycle, $C_6$-$C_{15}$ aryl, $C_4$-$C_{14}$ heteroaryl, formyl, acyl, amino acyl, amido, carboxyalkyl, carboxyaryl, amidino, sulfonyl, sulfonamido and $C_1$-$C_8$ alkyl substituted with $C_3$-$C_1$ cycloalkyl, $C_6$-$C_{15}$ aryl or $C_4$-$C_{14}$ heteroaryl;

$W_2$ is selected from the group consisting of hydrogen, $C_1$-$C_{20}$ alkyl, $C_3$-$C_{15}$ cycloalkyl, $C_2$-$C_{14}$ heterocycle, $C_6$-$C_{15}$ aryl, $C_4$-$C_{14}$ heteroaryl, acyl, amino acyl and $C_1$-$C_8$ alkyl substituted with $C_3$-$C_{15}$ cycloalkyl, $C_6$-$C_{15}$ aryl or $C_4$-$C_{14}$ heteroaryl;

$W_3$ and $W_8$ are independently selected from the group consisting of hydrogen $C_1$-$C_{20}$ alkyl $C_3$-$C_{15}$ cycloalkyl $C_2$-$C_{14}$ heterocycle $C_6$-$C_{15}$ aryl $C_4$-$C_{14}$ heteroaryl and $C_1$-$C_8$ alkyl substituted with $C_3$-$C_{15}$ cycloalkyl, $C_6$-$C_{15}$ aryl or $C_4$-$C_{14}$ heteroaryl;

$W_4$ is selected from the group consisting of hydrogen, halogen, trifluoromethyl, hydroxy and methyl;

$W_5$ is selected from the group consisting of hydrogen, $C_1$-$C_{20}$ alkyl, $C_3$-$C_{15}$ cycloalkyl, $C_2$-$C_{14}$ heterocycle, $C_6$-$C_{15}$ aryl, $C_4$-$C_{14}$ heteroaryl, formyl, acyl, carboxyalkyl, carboxyaryl, amido, amidino, sulfonyl, sulfonamido and $C_1$-$C_8$ alkyl substituted with $C_3$-$C_{15}$ cycloalkyl, $C_6$-$C_{15}$ aryl or $C_4$-$C_{14}$ heteroaryl;

$W_6$ is selected from the group consisting of hydrogen, $C_1$-$C_{20}$ alkyl, $C_3$-$C_{15}$ cycloalkyl, $C_2$-$C_{14}$ heterocycle, $C_6$-$C_{15}$ aryl, $C_4$-$C_{14}$ heteroaryl, acyl, carboxyalkyl, carboxyaryl, amido and sulfonyl; and $W_7$ is selected from the group consisting of hydrogen, $C_1$-$C_{20}$ alkyl, $C_3$-$C_{15}$ cycloalkyl, $C_2$-$C_{14}$ heterocycle, $C_6$-$C_{15}$ aryl, $C_4$-$C_{14}$ heteroaryl, sulfonyl and $C_1$-$C_8$ alkyl substituted with $C_3$-$C_{15}$ cycloalkyl, $C_6$-$C_{15}$ aryl or $C_4$-$C_{14}$ heteroaryl;

wherein $R_1$, $R_{11}$, $R_{13}$, $R_{14}$, $R_{15}$, $R_{17}$, $R_{18}$ and $R_{19}$, when $X_1$, $X_{12}$, $X_{13}$, $X_{14}$, $X_{15}$, $X_{17}$, $X_{18}$ or $X_{19}$ are $NR_{20a}$, can also form an optionally substituted four, five, six or seven-membered ring together with $NR_{20a}$;

wherein $R_2$, $R_6$, $R_7$, $R_{10}$ and $R_{16}$, when $X_2$, $X_7$, $X_8$, $X_9$ or $X_{16}$, respectively, are $NR_{21}$, can also form an optionally substituted four, five, six or seven-membered ring together with $NR_{21}$, wherein $R_4$ and $R_5$, when $X_4$ or $X_6$, respectively, are $NR_{22}$, can also form an optionally substituted four, five, six or seven-membered ring together with $NR_{22}$;

$R_3$, $R_8$ and $R_{12}$ are independently selected from the group consisting of hydrogen, $C_1$-$C_6$ alkyl and $C_6$-$C_{15}$ aryl; and A, B and D are independently selected from the group consisting of:

(X)—$(CH_2)_{n1a}$—(C), (X)—$(CH_2)_{n1b}$—$X_{20}$—$(CH_2)_{n1c}$—(C),

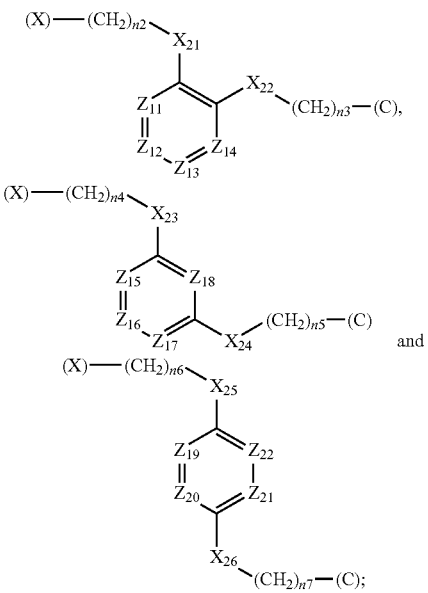

when $X_3$, $X_5$, or $X_8$ is N; A, B and D, respectively, can also be independently selected from the group consisting of:

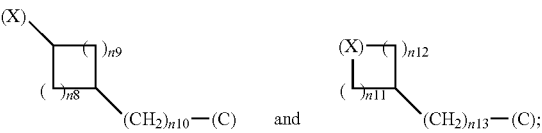

wherein n1a is 0-5; n1b and n1c are independently 1-3; n2, n3, n4, n5, n6, n7, n10 and n13 are independently 0-4 n8, n9, n11 and n12 are independently 0-4, wherein the sum of n8 and n9 is at least 2, and wherein the sum of n11 and n12 is at least 2;

$X_{20}$ is selected from the group consisting of O, $NR_{26}$, CH=CH and C≡C, where $R_{26}$ is selected from the group consisting of hydrogen, $C_1$-$C_4$ alkyl, acyl and sulfonyl;

$X_{21}$, $X_{22}$, $X_{23}$, $X_{24}$, $X_{25}$ and $X_{26}$ are independently selected from the group consisting of $(CH_2)_{m1}$, O, $S(O)_{q3}$ and $NR_{27}$, where m1 is 0-4, q3 is 0-2 and $R_{27}$ is selected from the group consisting of hydrogen, $C_1$-$C_4$ alkyl, acyl and sulfonyl;

$Z_{11}$, $Z_{12}$, $Z_{13}$, $Z_{14}$, $Z_{15}$, $Z_{16}$, $Z_{17}$, $Z_{18}$, $Z_{19}$, $Z_{20}$, $Z_{21}$ and $Z_{22}$ are independently selected from the group consisting of N, $N^+$—$O^-$ and $CR_{28}$, where $R_{28}$ is selected from the group consisting of hydrogen, hydroxy, alkoxy, amino, amido, amidino, guanidino, halogen, cyano, nitro, carboxy, carboxyalkyl, carboxyaryl, trifluoromethyl, $C_1$-$C_{20}$ alkyl, $C_3$-$C_{15}$ cycloalkyl, $C_2$-$C_{14}$ heterocycle, $C_6$-$C_{15}$ aryl, $C_4$-$C_{14}$ heteroaryl, wherein in the group of $Z_{11}$, $Z_{12}$, $Z_{13}$ and $Z_{14}$, three or less within that group are N; wherein in the group of $Z_{15}$, $Z_{16}$, $Z_{17}$ and $Z_{18}$, three or less within that group are N; and wherein in the group of $Z_{19}$, $Z_{20}$, $Z_{21}$ and $Z_{22}$, three or less within that group are N; and (X) indicates the site or sites of bonding to $X_3$ of formula (Ia) for A, to $X_5$ of formula (Ib) for B, and to $X_{11}$ of formula (Ic) for D, and (C) indicates the site of bonding to $CHR_3$ of formula (Ia) for A, to $CHR_8$ of formula (Ib) for B and to $CHR_{12}$ of formula (Ic) for D, the process comprising:

synthesis of the individual multifunctional, protected building blocks;

assembly of from three to six building blocks in a sequential manner with cycles of selective deprotection of a reactive functionality followed by attachment, wherein one of the building blocks contains an oxazole, thiazole or imidazole ring;

selective deprotection of two reactive functional groups of the assembled building block structure followed by cyclization;

removal of all remaining protecting groups from the cyclized products; and optionally, purification.

2. The process of claim 1, further comprising distribution of the final macrocycle compounds into a format suitable for screening.

3. The process of claim 1 wherein the assembly of the building blocks is conducted on solid phase.

4. The process of claim 1, wherein the attachment of each individual building block is performed using a reaction independently selected from amide bond formation, reductive amination, Mitsunobu reaction and its variants, and nucleophilic substitution.

* * * * *